US012790352B2

(12) United States Patent
Barlaam et al.

(10) Patent No.: US 12,790,352 B2
(45) **Date of Patent: *Nov. 10, 2026**

(54) 2,6,9-TRISUBSTITUTED PURINES

(71) Applicant: ASTRAZENECA AB, Södertälje (SE)

(72) Inventors: Bernard Barlaam, Cambridge (GB); Michael Bodnarchuk, Cambridge (GB); Avipsa Ghosh, Waltham, MA (US); Frederick Goldberg, Cambridge (GB); Sudhir Hande, Waltham, MA (US); Phillip Lichtor, Waltham, MA (US); Kun Song, Waltham, MA (US); Qibin Su, Waltham, MA (US); Reem Telmesani, Waltham, MA (US); James Sheppeck, Waltham, MA (US)

(73) Assignee: AstraZeneca AB, Södertälje (SE)

( * ) Notice: Subject to any disclaimer, the term of this patent is extended or adjusted under 35 U.S.C. 154(b) by 351 days.

This patent is subject to a terminal disclaimer.

(21) Appl. No.: 18/541,006

(22) Filed: Dec. 15, 2023

(65) Prior Publication Data

US 2024/0247001 A1 Jul. 25, 2024

Related U.S. Application Data

(60) Provisional application No. 63/387,734, filed on Dec. 16, 2022.

(51) Int. Cl.
*C07D 519/00* (2006.01)
*A61K 31/52* (2006.01)
*A61P 31/00* (2006.01)
*C07D 487/04* (2006.01)

(52) U.S. Cl.
CPC ............ *C07D 519/00* (2013.01); *A61K 31/52* (2013.01); *A61P 31/00* (2018.01); *C07D 487/04* (2013.01)

(58) Field of Classification Search
CPC .. C07D 519/00; C07D 487/04; C07D 473/16; C07D 473/34; A61K 31/52; A61P 31/00; A61P 35/00
See application file for complete search history.

(56) References Cited

U.S. PATENT DOCUMENTS

| | | | |
|---|---|---|---|
| 6,790,958 | B2 | 9/2004 | Lum et al. |
| 2006/0009642 | A1 | 1/2006 | Ding et al. |
| 2009/0253717 | A1 | 10/2009 | Brown et al. |
| 2018/0000814 | A1 | 1/2018 | Hacia et al. |

FOREIGN PATENT DOCUMENTS

| | | | |
|---|---|---|---|
| CN | 113024563 | A | 6/2021 |
| CN | 116813621 | A | 9/2023 |
| EP | 0853084 | A2 | 7/1998 |
| EP | 3505517 | A1 | 7/2019 |
| EP | 3967691 | A1 | 3/2022 |
| JP | 2006056879 | A | 3/2006 |
| KR | 101893879 | B1 | 9/2018 |
| WO | 9308206 | A1 | 4/1993 |
| WO | 9507921 | A1 | 3/1995 |
| WO | 9733590 | A1 | 9/1997 |
| WO | 9733591 | A1 | 9/1997 |
| WO | 9805335 | A1 | 2/1998 |
| WO | 9924449 | A2 | 5/1999 |
| WO | WO 99/43675 | | 9/1999 |
| WO | 9967262 | A1 | 12/1999 |
| WO | 0044750 | A1 | 8/2000 |
| WO | 0049018 | A1 | 8/2000 |
| WO | 0071543 | A1 | 11/2000 |
| WO | 0119788 | A2 | 3/2001 |
| WO | 0164642 | A2 | 9/2001 |

(Continued)

OTHER PUBLICATIONS

Adapta™ Screening Protocol and Assay Conditions (Revised Jan. 23, 2018 version) available at http://assets[dot]thermofisher[dot]com/TFS-Assets/BID/Methods-&-Protocols/20180123_SSBK_Adapta_Customer_Protocol_and_Assay Conditions[dot]pdf.

(Continued)

*Primary Examiner* — Kamal A Saeed
*Assistant Examiner* — Meghan C Heasley
(74) *Attorney, Agent, or Firm* — Arnold & Porter Kaye Scholer LLP

(57) ABSTRACT

Compounds having the structure of Formula (I):

(I)

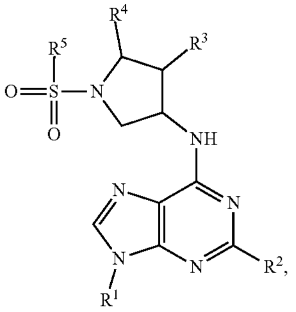

and pharmaceutically acceptable salts thereof, wherein $R^1$, $R^2$, $R^3$, $R^4$, and $R^5$ are as defined in the specification; pharmaceutical compositions comprising such compounds and salts; use of such compounds and salts to treat or prevent cyclin-dependent kinase 2 (CDK2)-mediated conditions; kits comprising such compounds and salts; and methods for manufacturing such compounds and salts.

21 Claims, 23 Drawing Sheets

(56) References Cited

FOREIGN PATENT DOCUMENTS

| | | | |
|---|---|---|---|
| WO | 0242303 | A2 | 5/2002 |
| WO | 03031405 | A2 | 4/2003 |
| WO | 03031406 | A2 | 4/2003 |
| WO | 2004002990 | A2 | 1/2004 |
| WO | 2004069185 | A2 | 8/2004 |
| WO | 2005016528 | A2 | 2/2005 |
| WO | 2005020892 | A2 | 3/2005 |
| WO | 2005110410 | A2 | 11/2005 |
| WO | 2006125211 | A1 | 11/2006 |
| WO | 2007015064 | A1 | 2/2007 |
| WO | 2007028022 | A2 | 3/2007 |
| WO | 2007110649 | A2 | 10/2007 |
| WO | 2008012555 | A2 | 1/2008 |
| WO | 2008094737 | A2 | 8/2008 |
| WO | 2008122767 | A2 | 10/2008 |
| WO | 2008154642 | A2 | 12/2008 |
| WO | 2009001097 | A2 | 12/2008 |
| WO | 2009034386 | A1 | 3/2009 |
| WO | 2009129094 | A2 | 10/2009 |
| WO | 2010009155 | A2 | 1/2010 |
| WO | 2010111406 | A2 | 9/2010 |
| WO | 2010118367 | A2 | 10/2010 |
| WO | 2010151797 | A2 | 12/2010 |
| WO | 2011119869 | A1 | 9/2011 |
| WO | 2012009649 | A1 | 1/2012 |
| WO | 2012019093 | A1 | 2/2012 |
| WO | 2012052540 | A1 | 4/2012 |
| WO | 2012142498 | A2 | 10/2012 |
| WO | 2013036869 | A2 | 3/2013 |
| WO | 2013123335 | A1 | 8/2013 |
| WO | 2014075393 | A1 | 5/2014 |
| WO | 2014127350 | A1 | 8/2014 |
| WO | 2014160197 | A1 | 10/2014 |
| WO | 2014172616 | A2 | 10/2014 |
| WO | 2014189830 | A1 | 11/2014 |
| WO | 2016011394 | A1 | 1/2016 |
| WO | 2016160617 | A2 | 10/2016 |
| WO | 2018036414 | A1 | 3/2018 |
| WO | 2018200527 | A1 | 11/2018 |
| WO | 2018203099 | A1 | 11/2018 |
| WO | 2019195056 | A1 | 10/2019 |
| WO | 2020051207 | A2 | 3/2020 |
| WO | 2020096948 | A1 | 5/2020 |
| WO | 2020118194 | A1 | 6/2020 |
| WO | 2020157652 | A2 | 8/2020 |
| WO | 2020172324 | A1 | 8/2020 |
| WO | 2020181050 | A1 | 9/2020 |
| WO | 2020215998 | A1 | 10/2020 |
| WO | 2021003084 | A1 | 1/2021 |
| WO | 2021030537 | A1 | 2/2021 |
| WO | 2021183970 | A1 | 9/2021 |
| WO | 2021205363 | A1 | 10/2021 |
| WO | 2021226137 | A1 | 11/2021 |
| WO | 2021236650 | A1 | 11/2021 |
| WO | 2022063106 | A1 | 3/2022 |
| WO | 2022073469 | A1 | 4/2022 |
| WO | 2022164928 | A2 | 8/2022 |
| WO | 2022164931 | A2 | 8/2022 |
| WO | 2022164933 | A2 | 8/2022 |
| WO | 2022266190 | A1 | 12/2022 |
| WO | 2023278326 | A1 | 1/2023 |

OTHER PUBLICATIONS

LanthaScreen™ Eu Kinase Binding Assay Screening Protocol and Assay Conditions (Revised Jan. 23, 2018 version) available at http://assets[dot] Thermofisher[dot]com/TFS-Assets/BID/Methods-&-Protocols/20180123_SSBK_LanthaScreen_Binding Customer Protocol and Assay Conditions[dot]pdf.

Williamson, et al., "Evaluation of the Disconnect between Hepatocyte and Microsome Intrinsic Clearance and In Vitro In Vivo Extrapolation Performance," *Drug Metab Dispos.*, 48(11), pp. 1137-1146 (Nov. 2020) (Amsterdam, The Netherlands).

Z-LYTE™ Screening Protocol and Assay Conditions (Revised Jan. 23, 2018 version) available at http://assets[dot]thermofisher[dot]com/TFS-Assets/BID/Methods-&-Protocols/20180123_SSBK_Customer_Protocol_and_Assay_Conditions[dot]pdf.

Denz C.R., et al., "Targeting the Cell Cycle with AZD8421, a Potent and Highly Selective CDK2 Inhibitor", 2024 AACR Poster, Apr. 7, 2024, 1 page.

Denz C.R., "First Disclosure of AZD8421, a Highly Selective CDK2 Inhibitor to Address Resistance to CDK4/6 Inhibitors in Breast and CCNE1-high Cancers", 2024 AACR Presentation, Apr. 7, 2024, pp. 1-18.

Frame S., et al., "Fadraciclib (CYC065), a Novel CDK Inhibitor, Targets Key Pro-survival and Oncogenic Pathways in Cancer", PLoS One, vol. 15, No. 7: e0234103, Jul. 9, 2020, pp. 1-31.

Fulp A., et al., "Diphenyl Purine Derivatives as Peripherally Selective Cannabinoid Receptor 1 Antagonists", Journal of Medicinal Chemistry, vol. 55, No. 22, 2012, pp. 10022-10032.

Gray N S., et al., "Exploiting Chemical Libraries, Structure, and Genomics in the Search for Kinase Inhibitors", Science, American Association for the Advancement of Science, vol. 281, Jul. 24, 1998, pp. 533-538, XP002211200, ISSN: 0036-8075, DOI: 10.1126/SCIENCE.281.5376.533 abstract, purvalanol B in Fig. 1D, p. 534, col. 3, paragraph 2.

Guo Y., et al., "Design, Synthesis and Biological Evaluation of Purine-based Derivatives as Novel JAK2/BRD4 (BD2) Dual Target Inhibitors", Bioorganic Chemistry, vol. 132, 106386, 2023, 5 pages.

International Search Report and Written Opinion for International Application No. PCT/IB2023/062789, mailed Mar. 14, 2024, 16 Pages.

Knutsen L.J.S., et al., "The Synthesis and Biochemical Evaluation of New A1 Selective Adenosine Receptor Agonists Containing 6-Hydrazinopurine Moieties", Bioorganic Medicinal Chemistry Letters, vol. 3, No. 12, 1993, pp. 2661-2666.

Martinez C S., et al., "Cyclin Dependent Kinase (CDK) Inhibitors as Anticancer Drugs: Recent Advances (2015-2019)", Bio Organic Medicinal Chemistry Letters, Elsevier, Amsterdam, NL, vol. 29, No. 20, Aug. 26, 2019, XP085831668, pp. 1-18, ISSN: 0960-894X, DOI: 10.1016/J.BMCL.2019.126637, Compound NU-6300 in Fig. 8, Compound 5 in Fig. 11, Compound 8 in Fig. 13, soliciclib in Fig. 16 and compound CYC-065 = fadraciclib in Fig. 16, p. 11, right-hand column, paragraph 2 p. 15, left-hand column paragraph 2.

Park S.J., et al., "Synthesis and Biological Evaluation of N9-cis-cyclobutylpurine Derivatives for Use as Cyclin-dependent Kinase (CDK) Inhibitors", Bioorganic Medicinal Chemistry Letters, vol. 27, No. 18, 2017, pp. 4399-4404.

Reznickova E., et al., "2,6,9-Trisubstituted Purines as CRK3 Kinase Inhibitors with Antileishmanial Activity in Vitro", Bioorganic Medicinal Chemistry Letters, vol. 25, No. 11, Jun. 1, 2015, pp. 2298-2301.

Registry No. 1523571-84-7 (Jan. 2014).

Search Report dated Sep. 17, 2025, issued in ROC Taiwan Patent Appln. No. 112148944 (translation).

EFFECT OF CDK2 INHIBITION ON CELL CYCLE PHASE IN OVCAR3 CELL LINE (COMPOUND 6)

EFFECT OF CDK2 INHIBITION ON CELL CYCLE PHASE IN OVCAR3 CELL LINE (COMPOUND 20)

WESTERN BLOT FOR pRB AND pSerII IN OVCAR3 CELL LINE (COMPOUND 20)

FIG. 3A

COMBINATION SIGNAL HEATMAP (% INHIBITION OF GROWTH SIGNAL)
IN PALBOCICLIB RESISTANT MCF7-PC1 CELL LINE (COMPOUND 6/PALBOCICLIB)

| COMPOUND 6 \ Palbociclib | 0 | 0.017 | 0.033 | 0.167 | 0.333 | 1 |
|---|---|---|---|---|---|---|
| 1 | 86 | 89 | 86 | 83 | 97 | 100 |
| 0.333 | 31 | 43 | 57 | 83 | 94 | 100 |
| 0.167 | 23 | 30 | 43 | 64 | 90 | 99 |
| 0.033 | 10 | 10 | 29 | 56 | 68 | 88 |
| 0.017 | 21 | 12 | 22 | 54 | 61 | 81 |
| 0 | -5 | 15 | 16 | 41 | 49 | 71 |

FIG. 3B

COMBINATION SIGNAL HEATMAP (% INHIBITION OF GROWTH SIGNAL)
IN PALBOCICLIB RESISTANT MCF7-PC1 CELL LINE (COMPOUND 6/ABEMACICLIB)

| COMPOUND 6 | | | | | | |
|---|---|---|---|---|---|---|
| 1 | 85 | 85 | 83 | 97 | 99 | 100 |
| 0.333 | 26 | 67 | 79 | 96 | 99 | 100 |
| 0.167 | 25 | 53 | 67 | 92 | 99 | 100 |
| 0.033 | 6 | 24 | 45 | 69 | 89 | 98 |
| 0.017 | 20 | 34 | 34 | 71 | 77 | 97 |
| 0 | -10 | 30 | 24 | 53 | 68 | 86 |
| | 0 | 0.017 | 0.033 | 0.167 | 0.333 | 1 |

Abemaciclib

FIG. 3C

COMBINATION SIGNAL HEATMAP (% INHIBITION OF GROWTH SIGNAL)
IN PALBOCICLIB RESISTANT MCF7-PC1 CELL LINE (COMPOUND 20/PALBOCICLIB)

| COMPOUND 20 \ Palbociclib | 0 | 0.033 | 0.167 | 0.333 | 1.667 | 3.333 |
|---|---|---|---|---|---|---|
| 3.333 | 96 | 94 | 88 | 97 | 100 | 99 |
| 1.667 | 84 | 87 | 89 | 95 | 100 | 99 |
| 0.333 | 32 | 37 | 68 | 81 | 98 | 99 |
| 0.167 | 14 | 29 | 57 | 70 | 99 | 100 |
| 0.033 | -2 | 13 | 50 | 62 | 76 | 89 |
| 0 | 8 | 8 | 37 | 51 | 65 | 70 |

FIG. 4A

COMBINATION SIGNAL HEATMAP (% INDUCTION OF SENESCENCE)
IN PALBOCICLIB RESISTANT MCF7-PC1 CELL LINE (COMPOUND 6/PALBOCICLIB)

| COMPOUND 6 \ Palbociclib | 0 | 0.01 | 0.04 | 0.11 | 0.33 | 1 |
|---|---|---|---|---|---|---|
| 1 | 38 | 52 | 64 | 73 | 78 | 101 |
| 0.33 | 25 | 39 | 48 | 66 | 71 | 85 |
| 0.11 | 2 | 19 | 34 | 56 | 64 | 71 |
| 0.04 | 5 | 13 | 21 | 28 | 37 | 55 |
| 0.01 | 0 | 8 | 16 | 21 | 38 | 55 |
| 0 | 0 | 3 | 10 | 16 | 33 | 45 |

FIG. 4B

COMBINATION SIGNAL HEATMAP (% INDUCTION OF SENESCENCE)
IN PALBOCICLIB RESISTANT MCF7-PC1 CELL LINE (COMPOUND 6/ABEMACICLIB)

| COMPOUND 6 \ Abemaciclib | 0 | 0.01 | 0.04 | 0.11 | 0.33 | 1 |
|---|---|---|---|---|---|---|
| 1 | 45 | 54 | 58 | 68 | 76 | 100 |
| 0.33 | 19 | 32 | 39 | 49 | 67 | 85 |
| 0.11 | 9 | 20 | 27 | 35 | 50 | 72 |
| 0.04 | 6 | 14 | 20 | 29 | 45 | 72 |
| 0.01 | 2 | 9 | 15 | 25 | 46 | 74 |
| 0 | 2 | 4 | 7 | 17 | 41 | 75 |

FIG. 5A

COMBINATION SIGNAL HEATMAP (% INDUCTION OF SENESCENCE) IN MCF7 CELL LINE (COMPOUND 6/PALBOCICLIB)

| COMPOUND 6 \ Palbociclib | 0 | 0.01 | 0.04 | 0.11 | 0.33 | 1 |
|---|---|---|---|---|---|---|
| 1 | 32 | 36 | 68 | 79 | 79 | 81 |
| 0.33 | 37 | 44 | 66 | 80 | 81 | 84 |
| 0.11 | 34 | 37 | 51 | 79 | 85 | 88 |
| 0.04 | 12 | 32 | 41 | 63 | 82 | 97 |
| 0.01 | 13 | 27 | 34 | 50 | 74 | 88 |
| 0 | 6 | 10 | 25 | 46 | 57 | 60 |

FIG. 5B

COMBINATION SIGNAL HEATMAP (% INDUCTION OF SENESCENCE) IN MCF7 CELL LINE (COMPOUND 6/ABEMACICLIB)

| COMPOUND 6 \ Abemaciclib | 0 | 0.01 | 0.04 | 0.11 | 0.33 | 1 |
|---|---|---|---|---|---|---|
| 1 | 16 | 46 | 44 | 47 | 60 | 81 |
| 0.33 | 10 | 41 | 47 | 50 | 54 | 64 |
| 0.11 | 13 | 27 | 32 | 42 | 53 | 73 |
| 0.04 | 10 | 20 | 28 | 40 | 52 | 74 |
| 0.01 | 8 | 17 | 27 | 42 | 57 | 79 |
| 0 | 5 | 10 | 24 | 42 | 74 | 100 |

FIG. 6

COMBINATION SIGNAL HEATMAP (% INDUCTION OF SENESCENCE) IN OVCAR3 CELL LINE (COMPOUND 6/PALBOCICLIB)

| COMPOUND 6 \ Palbociclib | 0 | 0.01 | 0.04 | 0.11 | 0.33 | 1 |
|---|---|---|---|---|---|---|
| 1 | 78 | 90 | 76 | 75 | 78 | 80 |
| 0.33 | 40 | 49 | 40 | 40 | 44 | 37 |
| 0.11 | 11 | 16 | 12 | 11 | 14 | 9 |
| 0.04 | 3 | 5 | 4 | 3 | 5 | 2 |
| 0.01 | 1 | 2 | 3 | 1 | 2 | 1 |
| 0 | 0 | 1 | 2 | 0 | 0 | 1 |

EFFECT OF TREATMENT ON BODY WEIGHT IN OVCAR3
HUMAN OVARIAN CANCER XENOGRAFT MOUSE MODEL (COMPOUND 6/PALBOCICLIB)

EFFECT OF TREAMENT ON TUMOR VOLUME IN OVCAR3
HUMAN OVARIAN CANCER XENOGRAFT MOUSE MODEL (COMPOUND 6/PALBOCICLIB)

EFFECT OF TREATMENT ON PRB LEVELS IN MCF7-PC1 HUMAN PALBOCICLIB RESISTANT ER+ BREAST CANCER XENOGRAFT MOUSE MODEL (COMPOUND 6/PALBOCICLIB)

EFFECT OF TREATMENT ON TUMOR VOLUME IN CTG-3298 HUMAN CDK4/6 RESISTANT ER+ BREAST CANCER XENOGRAFT MOUSE MODEL (COMPOUND 6/PALBOCICLIB)

EFFECT OF TREATMENT ON pRB LEVELS IN CTG-3298 HUMAN CDK4/6 RESISTANT ER+ BREAST CANCER XENOGRAFT MOUSE MODEL (COMPOUND 6/PALBOCICLIB)

EFFECT OF TREATMENT ON pHH3 LEVELS IN CTG-3298 HUMAN CDK4/6 RESISTANT ER+ BREAST CANCER XENOGRAFT MOUSE MODEL (COMPOUND 6)

EFFECT OF TREATMENT ON pRB LEVELS IN T47D P1 HUMAN CDK4/6 RESISTANT ER+ BREAST CANCER CANCER XENOGRAFT MOUSE MODEL (COMPOUND 6/PALBOCICLIB)

EFFECT OF TREATMENT ON TUMOR VOLUME IN CTG-3283 HUMAN CDK4/6 RESISTANT ER+ BREAST CANCER XENOGRAFT MOUSE MODEL (COMPOUND 6/PALBOCICLIB)

EFFECT OF TREATMENT ON pRB LEVELS IN CTG-3283 HUMAN CDK4/6 RESISTANT ER+ BREAST CANCER XENOGRAFT MOUSE MODEL (COMPOUND 6/PALBOCICLIB)

2,6,9-TRISUBSTITUTED PURINES

CROSS-REFERENCE TO RELATED APPLICATIONS

This application claims the priority benefit of U.S. Provisional Application No. 63/387,734 filed on Dec. 16, 2022, which is incorporated by reference in its entirety for all purposes.

FIELD

The present disclosure relates generally to 2,6,9-trisubstituted purines and pharmaceutically acceptable salts thereof. The specification further relates to pharmaceutical compositions comprising such compounds and salts; use of such compounds and salts to treat or prevent cyclin-dependent kinase 2 (CDK2)-mediated conditions; kits comprising such compounds and salts; and methods for manufacturing such compounds and salts.

BACKGROUND

Cyclin-dependent kinases (CDKs), including CDK2, are serine/threonine protein kinases involved in cell cycle regulation. CDK2 drives the progression of cells into the S- and M-phases of the cell cycle. Overexpression of CDK2 is associated with abnormal regulation of the cell-cycle and tumor growth in multiple cancer types. The monomeric form of CDK2 is inactive, but is activated when it forms a heterodimeric complex with one of its two regulatory partners, Cyclin A or Cyclin E. Cyclin E binding to CDK2 in the late G1 phase of the cell cycle is required for the transition from the G1 to S phase of the cell cycle. Cyclin A binding to CDK2 is then required to progress through the S phase of the cell cycle. The activated CDK2-cyclin A/E complex governs the phosphorylation of a wide range of transcription factors that modulate a variety of oncogenic signaling pathways impacting cell cycle progression. CDK2 activation also leads to hyperphosphorylation and inactivation of the retinoblastoma protein (pRB), a tumor suppressor protein that helps maintain cells in a quiescent state (i.e., the G0 phase of the cell cycle).

Overexpression of the CCNE1 gene, which produces Cyclin E, occurs in many tumor cells causing those cells to become dependent on CDK2 and Cyclin E. Abnormal Cyclin E activity has been observed, for example, in solid tumor cancers such as breast, ovarian, lung, colorectal, gastric, endometrial, and bone cancers, and in blood cancers such as leukemia and lymphoma. In addition, amplification and/or overexpression of Cyclin E has been reported as a potential mechanism of resistance to CDK4/6 therapies in ER-positive HER2-negative breast cancer. Likewise, abnormal expression of Cyclin A is associated with chromosomal instability and tumor proliferation while inhibition of cyclin A leads to decreased tumor growth.

Inhibition of CDK2 activity is presently an unexploited therapeutic approach for treating cancer and other diseases associated with CDK2 activity. Despite significant efforts, no approved pharmacological agents that inhibit CDK2 activity generally, or that inhibit CDK2 activity specifically, are currently available. Efforts to identify such inhibitors have been challenging, in part, due to two major hurdles. First, the mechanism of CDK2 degradation remains poorly understood. Second, the CDK2 inhibitors developed to date generally lack the requisite specificity or otherwise exhibit off-target CDK-driven toxicities. Sequence and structure similarity among the various CDKs are generally high and the similarities among the CDK binding sites render most CDK2 inhibitors either poorly specific and/or highly toxic. Accordingly, there is a need for CDK2 inhibitors, particularly CDK2 inhibitors that have pharmacologically appropriate properties, including selectivity, that are suitable for administration to a subject in need of such treatment. The present disclosure addresses this large unmet need by providing such compounds together with corresponding pharmaceutical compositions and methods for the treatment of cancers and other CDK2-mediated conditions.

SUMMARY

In one aspect, the present disclosure provides compounds having the structure of Formula (I):

(I)

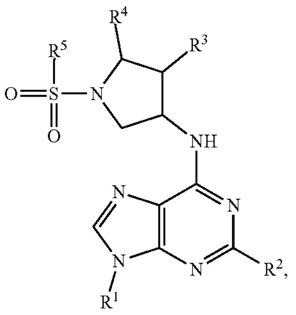

or a pharmaceutically acceptable salt thereof, wherein:

$R^1$ is selected from the group consisting of $C_{1-6}$-alkyl, halo-$C_{1-6}$-alkyl, and cyclopropyl;

$R^2$ is selected from the group consisting of —$NHR^6$,

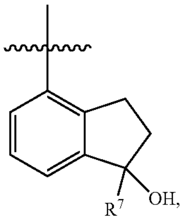

and

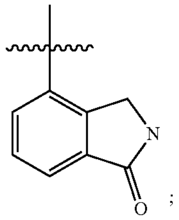

;

one of $R^3$ and $R^4$ is hydrogen and the other of $R^3$ and $R^4$ is selected from the group consisting of hydrogen, halogen, $C_{1-3}$-alkyl, halo-$C_{1-3}$-alkyl, and $C_{1-3}$-alkoxy;

$R^5$ is selected from the group consisting of $C_{1-6}$-alkyl, $C_{3-6}$-cycloalkyl, —$NR^8R^9$, pyrazolyl, and imidazolyl; wherein the $C_{1-6}$-alkyl and $C_{3-6}$-cycloalkyl are optionally substituted with one or more substituents independently selected from halogen and $C_{1-3}$-alkoxy; and the pyrazolyl and imidazolyl are optionally substituted with one or more substituents independently selected from $C_{1-3}$-alkyl;

$R^6$ is $C_{1-10}$-alkyl or

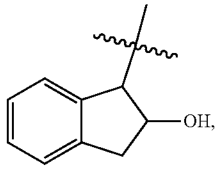 [SMILES: *C1c2ccccc2CC1O]

wherein the $C_{1-10}$-alkyl is substituted with hydroxy or oxo, and is optionally substituted with one or more substituents independently selected from the group consisting of halogen, $C_{3-6}$-cycloalkyl, and tetrahydrofuranyl;

$R^7$ is hydrogen or $C_{1-3}$-alkyl;

$R^8$ is hydrogen; and $R^9$ is selected from the group consisting of hydrogen, $C_{1-6}$-alkyl, $C_{3-6}$-cycloalkyl, $C_{1-6}$-alkoxy-$C_{1-6}$-alkyl, tetrahydrofuranyl, and 1,4-dioxanyl-$C_{1-3}$-alkyl; wherein the $C_{1-6}$-alkyl, $C_{3-6}$-cycloalkyl, $C_{1-6}$-alkoxy-$C_{1-6}$-alkyl, tetrahydrofuranyl, and 1,4-dioxanyl-$C_{1-3}$-alkyl are optionally substituted with one or more substituents independently selected from halogen; or $R^8$ and $R^9$ together with the nitrogen atom to which they are attached form a 4-, 5-, or 6-membered saturated monocyclic ring wherein the remaining ring atoms are carbon atoms, and wherein the monocyclic ring is optionally substituted with one or more substituents independently selected from halogen.

In another aspect, the present disclosure provides pharmaceutical compositions comprising a therapeutically-effective amount of a compound having the structure of Formula (I), or a pharmaceutically acceptable salt thereof, and a pharmaceutically acceptable carrier.

In another aspect, the present disclosure provides methods for treating or preventing a CDK2-mediated condition in a subject suffering from or susceptible to the CDK2-mediated condition by administering to the subject a therapeutically effective amount of a compound having the structure of Formula (I), or pharmaceutically acceptable salt thereof. In one aspect, the condition is cancer. In another aspect, the condition is a cancer characterized by amplification or overexpression of the cyclin E1 (CCNE1) gene and/or the cyclin E2 (CCNE2) gene.

In another aspect, the present disclosure provides compounds having the structure of Formula (I), or pharmaceutically acceptable salts thereof, for use as a medicament for treating or preventing a CDK2-mediated condition.

In another aspect, the present disclosure provides use of compounds having the structure of Formula (I), or pharmaceutically acceptable salts thereof, for the manufacture of a medicament for treating or preventing a CDK2-mediated condition.

In another aspect, the present disclosure provides methods for treating or preventing a CDK2-mediated condition in a subject suffering from or susceptible to the CDK2-mediated condition by administering to a subject a therapeutically effective amount of a compound having the structure of Formula (I), or pharmaceutically acceptable salt thereof, and a second pharmacological agent. In one aspect, the second pharmacological agent is a CDK4/6 inhibitor.

In another aspect, the present disclosure provides kits comprising a compound having the structure of Formula (I), or pharmaceutically acceptable salt thereof. In one aspect, the kit further comprises a second pharmacological agent.

In another aspect, the present disclosure provides methods for preparing compounds having the structure of Formula (I), or pharmaceutically acceptable salts thereof.

BRIEF DESCRIPTION OF THE DRAWINGS

FIG. 1A corresponds to treatment with the compound of Example 6. FIG. 1B corresponds to treatment with the compound of Example 20.

FIG. 2 illustrates Western blots (pRB) for OVCAR3 cells after treatment with a CDK2 inhibitor.

FIG. 3A illustrates a combination signal heatmap (% inhibition of growth signal) for palbociclib resistant MCF7-PC1 cells after treatment with a CDK2 inhibitor (the compound of Example 6), a CDK4/6 inhibitor (palbociclib), or a combination of a CDK2 inhibitor (the compound of Example 6) and a CDK4/6 inhibitor (palbociclib).

FIG. 3B illustrates a combination signal heatmap (% inhibition of growth signal) for palbociclib resistant MCF7-PC1 cells after treatment with a CDK2 inhibitor (the compound of Example 6), a CDK4/6 inhibitor (abemaciclib), or a combination of a CDK2 inhibitor (the compound of Example 6) and a CDK4/6 inhibitor (abemaciclib).

FIG. 3C illustrates a combination signal heatmap (% inhibition of growth signal) for palbociclib resistant MCF7-PC1 cells after treatment with a CDK2 inhibitor (the compound of Example 20), a CDK4/6 inhibitor (palbociclib), or a combination of a CDK2 inhibitor (the compound of Example 20) and a CDK4/6 inhibitor (palbociclib).

FIG. 4A illustrates a combination signal heatmap (% induction of senescence) for palbociclib resistant MCF7-PC1 cells after treatment with a CDK2 inhibitor (the compound of Example 6), a CDK4/6 inhibitor (palbociclib), or a combination of a CDK2 inhibitor (the compound of Example 6) and a CDK4/6 inhibitor (palbociclib).

FIG. 4B illustrates a combination signal heatmap (% induction of senescence) for palbociclib resistant MCF7-PC1 cells after treatment with a CDK2 inhibitor (the compound of Example 6), a CDK4/6 inhibitor (abemaciclib), or a combination of a CDK2 inhibitor (the compound of Example 6) and a CDK4/6 inhibitor (abemaciclib).

FIG. 5A illustrates a combination signal heatmap (% induction of senescence) for MCF7 cells after treatment with a CDK2 inhibitor (the compound of Example 6), a CDK4/6 inhibitor (palbociclib), or a combination of a CDK2 inhibitor (the compound of Example 6) and a CDK4/6 inhibitor (palbociclib).

FIG. 5B illustrates a combination signal heatmap (% induction of senescence) for MCF7 cells after treatment with a CDK2 inhibitor (the compound of Example 6), a CDK4/6 inhibitor (abemaciclib), or a combination of a CDK2 inhibitor (the compound of Example 6) and a CDK4/6 inhibitor (abemaciclib).

FIG. 6 illustrates a combination signal heatmap (% induction of senescence) for OVAR3 cells after treatment with a CDK2 inhibitor (the compound of Example 6), a CDK4/6 inhibitor (palbociclib), or a combination of a CDK2 inhibitor (the compound of Example 6), and a CDK4/6 inhibitor (palbociclib).

DETAILED DESCRIPTION

Figure 1A:
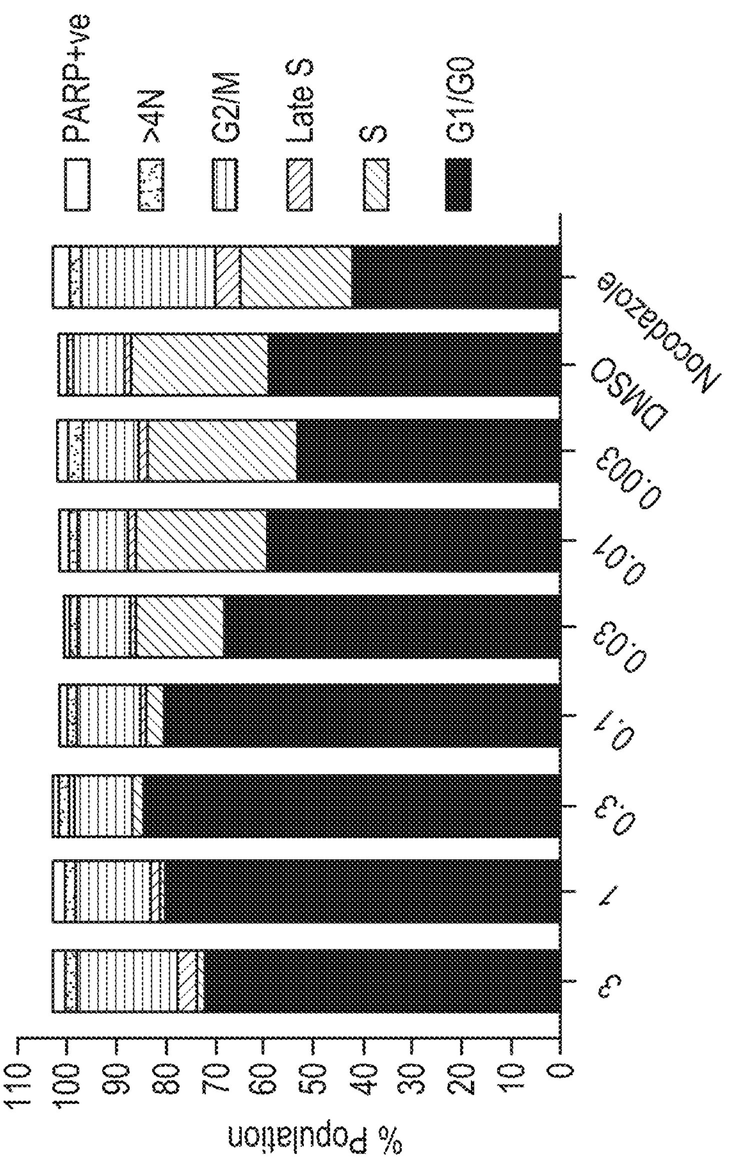
FIGS. 1A and 1B illustrate the effect on cell cycle phase in OVCAR3 cells of treatment with a CDK2 inhibitor.

Many embodiments are detailed throughout the specification and will be apparent to a reader skilled in the art. The specification is not to be interpreted as being limited to any particular embodiment(s) described herein.

I. Definitions

With respect to the embodiments disclosed in this specification, the following terms have the meanings set forth below:

Reference to "a" or "an" means "one or more." Throughout, the plural and singular should be treated as interchangeable, other than the indication of number.

Unless the context requires otherwise, the words "comprise" or "comprises" or "comprising" are used on the basis and clear understanding that they are to be interpreted inclusively, rather than exclusively, and that Applicants intend each of those words to be so interpreted in construing this patent, including the claims below.

The term "halogen" (alone or in combination with another term(s)) means a fluorine radical (which may be depicted as —F), chlorine radical (which may be depicted as —Cl), bromine radical (which may be depicted as —Br), or iodine radical (which may be depicted as —I).

The term "hydroxy" (alone or in combination with another term(s)) means —OH.

The term "oxo" (alone or in combination with another term(s)) means an oxo radical, and may be depicted as =O.

The term "alkyl" (alone or in combination with another term(s)) means a straight or branched chain saturated hydrocarbyl substituent (i.e., a substituent containing only carbon and hydrogen). Alkyl typically contains from 1 to about 20 carbon atoms, more typically from 1 to about 10 carbon atoms, even more typically from 1 to about 8 carbon atoms, and still even more typically from 1 to about 6 carbon atoms. Examples of such substituents include methyl, ethyl, propyl (including n-propyl and isopropyl), butyl (including n-butyl, isobutyl, sec-butyl, and tert-butyl), pentyl (including n-pentyl, iso-amyl, and 2,2-dimethylpropyl), and hexyl.

The term "cycloalkyl" (alone or in combination with another term(s)) means a saturated carbocyclyl substituent containing from 3 to about 14 carbon ring atoms, more typically from 3 to about 12 carbon ring atoms, and even more typically from 3 to about 8 carbon ring atoms. A cycloalkyl includes a single carbon ring, which typically contains from 3 to 6 carbon ring atoms. Examples of single-ring cycloalkyls include cyclopropyl, cyclobutyl, cyclopentyl, and cyclohexyl.

The term "alkoxy" (alone or in combination with another term(s)) means an alkylether substituent, i.e., alkyl-O—. Examples of alkoxy include methoxy ($CH_3$—O—), ethoxy, n-propoxy, iso-propoxy, n-butoxy, iso-butoxy, sec-butoxy, and tert-butoxy. Thus, for example, the term "alkoxyalkyl" (alone or in combination with another term(s)) means alkyl substituted with alkoxy such as "methoxymethyl" which may be depicted as:

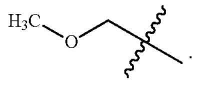

The prefix "halo" indicates that the substituent to which the prefix is attached is substituted with one or more independently selected halogen radicals. For example, haloalkyl means an alkyl substituent wherein at least one hydrogen radical is replaced with a halogen radical. Where more than one hydrogen is replaced with a halogen, the halogens may be the identical or different. Examples of haloalkyls include fluoromethyl, difluoromethyl, trifluoromethyl, difluoroethyl, 1,1,1-trifluoroethyl, pentafluoroethyl, difluoropropyl, heptafluoropropyl chloromethyl, dichloromethyl, trichloromethyl, difluorochloromethyl, dichlorofluoromethyl, and dichloropropyl. Similarly, "haloalkoxy" means an alkoxy substituent wherein at least one hydrogen radical is replaced by a halogen radical. Where more than one hydrogen is replaced with a halogen, the halogens may be the identical or different. Examples of haloalkoxy substituents include fluoromethoxy, difluoromethoxy, trifluoromethoxy (also known as "perfluoromethyloxy"), 1,1,1-trifluoroethoxy, and chloromethoxy.

In some instances, the number of carbon atoms in a substituent (e.g., alkyl, cycloalkyl, etc.) is indicated by the prefix "Cx-y-", wherein x is the minimum and y is the maximum number of carbon atoms in the substituent. Thus, for example, "$C_{1-6}$-alkyl" refers to an alkyl substituent containing from 1 to 6 carbon atoms. Illustrating further, $C_{3-6}$-cycloalkyl refers to a cycloalkyl substituent containing from 3 to 6 carbon ring atoms.

A substituent is "substitutable" if it comprises at least one carbon or nitrogen atom that is bonded to one or more hydrogen atoms. Thus, for example, hydrogen, halogen, and cyano do not fall within this definition.

If a substituent is described as being "substituted", a non-hydrogen radical is in the place of a hydrogen radical on a carbon or nitrogen of the substituent. Thus, for example, a substituted alkyl substituent is an alkyl substituent wherein at least one non-hydrogen radical is in the place of a hydrogen radical on the alkyl substituent. To illustrate, monofluoroalkyl is alkyl substituted with a fluoro radical, and difluoroalkyl is alkyl substituted with two fluoro radicals. It should be recognized that if there are more than one substitutions on a substituent, each non-hydrogen radical may be identical or different (unless otherwise stated).

If a substituent is described as being "optionally substituted", the substituent may be either (1) not substituted, or (2) substituted. If a carbon of a substituent is described as being optionally substituted with one or more of a list of substituents, one or more of the hydrogens on the carbon (to the extent there are any) may separately and/or together be replaced with an independently selected optional substituent. If a nitrogen of a substituent is described as being optionally substituted with one or more of a list of substituents, one or more of the hydrogens on the nitrogen (to the extent there are any) may each be replaced with an independently selected optional substituent.

If substituents are described as being "independently selected" from a group, each substituent is selected independent of the other. Each substituent therefore may be identical to or different from the other substituent(s).

The term "pharmaceutically acceptable" is used adjectivally in this specification to mean that the modified noun is appropriate for use as a pharmaceutical product or as a part of a pharmaceutical product. For example, "pharmaceutically acceptable salts" are salts that are suitable for use in mammals, particularly humans, and include salts with an inorganic base, organic base, inorganic acid, organic acid, or basic or acidic amino acid that are suitable for use in mammals, particularly humans.

A "therapeutically effective amount" refers to an amount of a compound being administered that will relieve to some extent one or more of the symptoms of the condition being treated, or otherwise provide a beneficial or desired result with respect to that condition. Where the pharmacological agent is being administered to treat cancer, a therapeutically effective amount refers, for example, to an amount that has the effect of (1) reducing the size of the tumor, (2) inhibiting (that is, slowing to some extent, preferably stopping) tumor metastasis, (3) inhibiting to some extent (that is, slowing to some extent, preferably stopping) tumor growth or tumor invasiveness, (4) relieving to some extent (or, preferably, eliminating) one or more signs or symptoms associated with the cancer, (5) decreasing the dose of other medications required to treat the disease, (6) enhancing the effect of another medication, and/or (7) delaying the progression of the disease in a patient.

The terms "treat," "treating," and "treatment" are readily understood by an ordinarily skilled physician and, with respect to treatment of a particular condition, can include (1) diminishing the extent or cause of the condition being treated, and/or (2) alleviating or ameliorating one or more symptoms associated with that condition. Treatment of a subject having or diagnosed with cancer can include, for example, reducing the number of cancer cells, reducing tumor size, reducing the rate of cancer cell infiltration into peripheral organs, reducing the rate of tumor metastases or tumor growth, or otherwise reversing, alleviating, or inhibiting the progress of the cancer.

II. Compounds

A. Compounds of Formula (I)

In one embodiment, the present disclosure provides compounds having the structure of Formula (I):

(I)

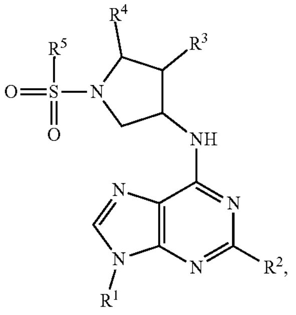

and pharmaceutically acceptable salts thereof, wherein:

$R^1$ is selected from the group consisting of $C_{1-6}$-alkyl, halo-$C_{1-6}$-alkyl, and cyclopropyl;

$R^2$ is selected from the group consisting of —$NHR^6$,

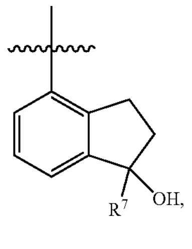

and

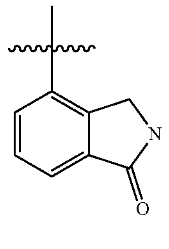

;

one of $R^3$ and $R^4$ is hydrogen and the other of $R^3$ and $R^4$ is selected from the group consisting of hydrogen, halogen, $C_{1-3}$-alkyl, halo-$C_{1-3}$-alkyl, and $C_{1-3}$-alkoxy;

$R^5$ is selected from the group consisting of $C_{1-6}$-alkyl, $C_{3-6}$-cycloalkyl, —$NR^8R^9$, pyrazolyl, and imidazolyl; wherein the $C_{1-6}$-alkyl and $C_{3-6}$-cycloalkyl are optionally substituted with one or more substituents independently selected from halogen and $C_{1-3}$-alkoxy; and the pyrazolyl and imidazolyl are optionally substituted with one or more substituents independently selected from $C_{1-3}$-alkyl;

$R^6$ is $C_{1-10}$-alkyl or

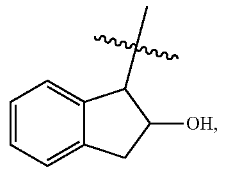 [SMILES: *C1c2ccccc2CC1O]

wherein the $C_{1-10}$-alkyl is substituted with hydroxy or oxo, and is optionally substituted with one or more substituents independently selected from the group consisting of halogen, $C_{3-6}$-cycloalkyl, and tetrahydrofuranyl;

$R^7$ is hydrogen or $C_{1-3}$-alkyl;

$R^8$ is hydrogen; and $R^9$ is selected from the group consisting of hydrogen, $C_{1-6}$-alkyl, $C_{3-6}$-cycloalkyl, $C_{1-6}$-alkoxy-$C_{1-6}$-alkyl, tetrahydrofuranyl, and 1,4-dioxanyl-$C_{1-3}$-alkyl; wherein the $C_{1-6}$-alkyl, $C_{3-6}$-cycloalkyl, $C_{1-6}$-alkoxy-$C_{1-6}$-alkyl, tetrahydrofuranyl, and 1,4-dioxanyl-$C_{1-3}$-alkyl are optionally substituted with one or more substituents independently selected from halogen; or $R^8$ and $R^9$ together with the nitrogen atom to which they are attached form a 4-, 5-, or 6-membered saturated monocyclic ring wherein the remaining ring atoms are carbon atoms, and wherein the monocyclic ring is optionally substituted with one or more substituents independently selected from halogen.

In some embodiments, the present disclosure provides compounds of Formula (I) having the structure of Formula (I-A):

(I-A)

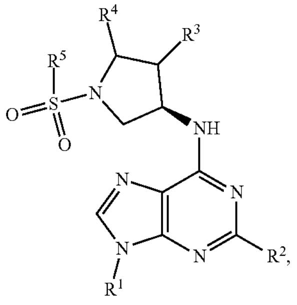

and pharmaceutically acceptable salts thereof, wherein $R^1$, $R^2$, $R^3$, $R^4$, and $R^5$ are as previously defined.

$R^1$ Substituents

In some embodiments, the present disclosure provides compounds having the structure of Formula (I) or Formula (I-A), and pharmaceutically acceptable salts thereof, wherein $R^1$ is selected from the group consisting of $C_{1-3}$-alkyl, halo-$C_{1-3}$-alkyl, and cyclopropyl. In one aspect, $R^1$ is selected from the group consisting of $C_{1-3}$-alkyl and halo-$C_{1-3}$-alkyl. In another aspect, $R^1$ is selected from the group consisting of methyl, ethyl, isopropyl, fluoromethyl, and difluoromethyl. In another aspect, $R^1$ is selected from the group consisting of ethyl and isopropyl. In another aspect, $R^1$ is $C_{1-3}$-alkyl. In another aspect, $R^1$ is methyl. In another aspect, $R^1$ is ethyl. In another aspect, $R^1$ is n-propyl. In another aspect, $R^1$ is isopropyl. In another aspect, $R^1$ is halo-$C_{1-3}$-alkyl. In another aspect, $R^1$ is fluoro-$C_{1-3}$-alkyl. In another aspect, $R^1$ is selected from the group consisting of fluoromethyl and difluoromethyl. In another aspect, $R^1$ is fluoromethyl. In another aspect, $R^1$ is difluoromethyl. In another aspect, $R^1$ is cyclopropyl.

$R^2$ Substituents

In some embodiments, the present disclosure provides compounds having the structure of Formula (I) or Formula (I-A), and pharmaceutically acceptable salts thereof, wherein $R^2$ is —$NHR^6$.

In some embodiments, $R^2$ is —$NHR^6$ and $R^6$ is $C_{1-10}$-alkyl, wherein the $C_{1-10}$-alkyl is substituted with hydroxy, and is optionally substituted with one or more substituents independently selected from the group consisting of halogen, $C_{3-6}$-cycloalkyl, and tetrahydrofuranyl. In one aspect, $R^6$ is $C_{2-6}$-alkyl, wherein the $C_{2-6}$-alkyl is substituted with hydroxy, and is optionally substituted with one or more substituents independently selected from the group consisting of halogen, $C_{3-6}$-cycloalkyl, and tetrahydrofuranyl. In another aspect, $R^6$ is $C_{1-10}$-alkyl, wherein the $C_{1-10}$-alkyl is substituted with hydroxy, and is optionally substituted with one or more substituents independently selected from the group consisting of fluoro, cyclopropyl, and tetrahydrofuranyl. In another aspect, $R^6$ is $C_{2-6}$-alkyl, wherein the $C_{2-6}$-alkyl is substituted with hydroxy, and is optionally substituted with one or more substituents independently selected from the group consisting of fluoro, cyclopropyl, and tetrahydrofuranyl. In another aspect, $R^6$ is $C_{1-10}$-alkyl, wherein the $C_{1-10}$-alkyl is substituted with hydroxy, and is optionally substituted with one or more substituents independently selected from the group consisting of fluoro and cyclopropyl. In another aspect, $R^6$ is $C_{2-6}$-alkyl, wherein the $C_{2-6}$-alkyl is substituted with hydroxy, and is optionally substituted with one or more substituents independently selected from the group consisting of fluoro and cyclopropyl.

In some embodiments, the present disclosure provides compounds having the structure of Formula (I) or Formula (I-A), and pharmaceutically acceptable salts thereof, wherein $R^2$ is —$NHR^6$ and $R^6$ is $C_{1-10}$-alkyl, wherein the $C_{1-10}$-alkyl is substituted with hydroxy. In one aspect, $R^6$ is $C_{2-6}$-alkyl, wherein the $C_{2-6}$-alkyl is substituted with hydroxy. In another aspect, $R^6$ is $C_4$-alkyl, wherein the $C_4$-alkyl is substituted with hydroxy. In another aspect, $R^6$ is $C_5$-alkyl, wherein the $C_5$-alkyl is substituted with hydroxy. In another aspect, $R^6$ is $C_6$-alkyl, wherein the $C_6$-alkyl is substituted with hydroxy. In another aspect, $R^6$ is

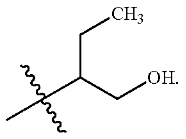 [SMILES: *C(CC)CO]

In another aspect, $R^6$ is selected from the group consisting of

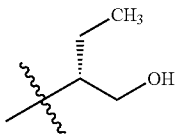

and

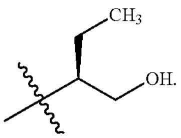

In another aspect, $R^6$ is

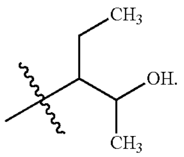 [SMILES: *C(CC)C(C)O]

In another aspect, $R^6$ is selected from the group consisting of

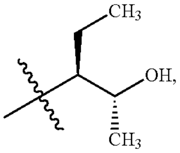

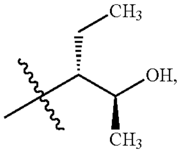

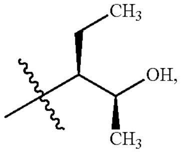

and

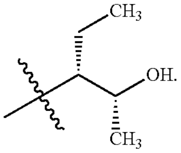

In another aspect, $R^6$ is

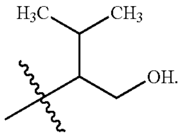 [SMILES: *C(CO)C(C)C]

In another aspect, Re is selected from the group consisting of

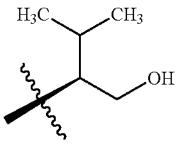

and

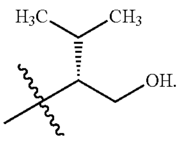

In some embodiments, the present disclosure provides compounds having the structure of Formula (I) or Formula (I-A), and pharmaceutically acceptable salts thereof, wherein $R^2$ is —$NHR^6$ and $R^6$ is $C_{1-10}$-alkyl, wherein the $C_{1-10}$-alkyl is substituted with hydroxy and one or more halogen. In one aspect, $R^6$ is $C_{2-6}$-alkyl, wherein the $C_{2-6}$-alkyl is substituted with hydroxy and one or more halogen. In another aspect, $R^6$ is $C_4$-alkyl, wherein the $C_4$-alkyl is substituted with hydroxy and one or more halogen. In another aspect, $R^6$ is $C_5$-alkyl, wherein the $C_5$-alkyl is substituted with hydroxy and one or more halogen. In another aspect, $R^6$ is $C_6$-alkyl, wherein the $C_6$-alkyl is substituted with hydroxy and one or more halogen. In further aspects, the halogen is fluoro. In another aspect, $R^6$ is

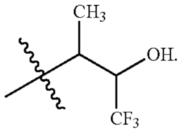

In another aspect, $R^6$ is

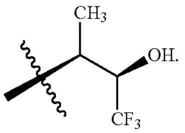

In another aspect, $R^6$ is

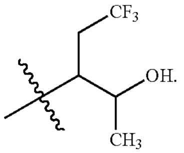

In another aspect, $R^6$ is

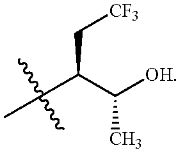 [SMILES: *[C@@H](CC(F)(F)F)[C@@H](C)O]

In some embodiments, the present disclosure provides compounds having the structure of Formula (I) or Formula (I-A), and pharmaceutically acceptable salts thereof, wherein $R^2$ is —$NHR^6$ and $R^6$ is $C_{1-10}$-alkyl, wherein the $C_{1-10}$-alkyl is substituted with hydroxy and $C_{3-6}$-cycloalkyl. In one aspect, $R^6$ is $C_{2-6}$-alkyl, wherein the $C_{2-6}$-alkyl is substituted with hydroxy and $C_{3-6}$-cycloalkyl. In another aspect, $R^6$ is $C_2$-alkyl, wherein the $C_2$-alkyl is substituted with hydroxy and $C_{3-6}$-cycloalkyl. In another aspect, $R^6$ is $C_3$-alkyl, wherein the $C_3$-alkyl is substituted with hydroxy and $C_{3-6}$-cycloalkyl.

In some embodiments, the present disclosure provides compounds having the structure of Formula (I) or Formula (I-A), and pharmaceutically acceptable salts thereof, wherein $R^2$ is —$NHR^6$ and $R^6$ is $C_{1-10}$-alkyl, wherein the $C_{1-10}$-alkyl is substituted with hydroxy and cyclopropyl. In one aspect, $R^6$ is $C_{2-6}$-alkyl, wherein the $C_{2-6}$-alkyl is substituted with hydroxy and cyclopropyl. In another aspect, $R^6$ is $C_2$-alkyl, wherein the $C_2$-alkyl is substituted with hydroxy and cyclopropyl. In another aspect, $R^6$ is $C_3$-alkyl, wherein the $C_3$-alkyl is substituted with hydroxy and cyclopropyl. In another aspect, $R^6$ is

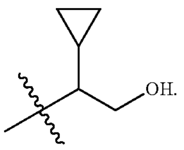 [SMILES: *C(CO)C1CC1]

In another aspect, $R^6$ is selected from the group consisting of:

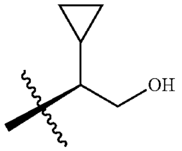
and
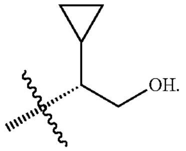

In another aspect, $R^6$ is

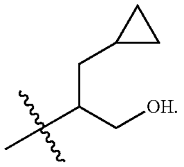 [SMILES: *C(CO)CC1CC1]

In another aspect, $R^6$ is selected from the group consisting of:

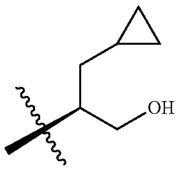
and
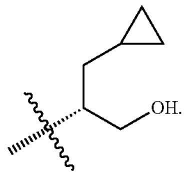

In some embodiments, the present disclosure provides compounds having the structure of Formula (I) or Formula (I-A), and pharmaceutically acceptable salts thereof, wherein $R^2$ is —NHR$^6$ and $R^6$ is $C_{1-10}$-alkyl, wherein the $C_{1-10}$-alkyl is substituted with hydroxy and cyclopentyl. In one aspect, $R^6$ is $C_{2-6}$-alkyl, wherein the $C_{2-6}$-alkyl is substituted with hydroxy and cyclopentyl. In another aspect, $R^6$ is $C_2$-alkyl, wherein the $C_2$-alkyl is substituted with hydroxy and cyclopentyl. In another aspect, $R^6$ is $C_3$-alkyl, wherein the $C_3$-alkyl is substituted with hydroxy and cyclopentyl. In another aspect, $R^6$ is

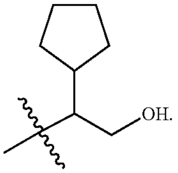 [SMILES: *C(CO)C1CCCC1]

In another aspect, $R^6$ is

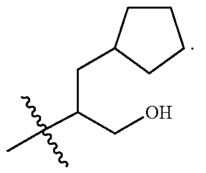 [SMILES: *C(CO)CC1CCCC1]

In some embodiments, the present disclosure provides compounds having the structure of Formula (I) or Formula (I-A), and pharmaceutically acceptable salts thereof, wherein $R^2$ is —NHR$^6$ and $R^6$ is $C_{1-10}$-alkyl, wherein the $C_{1-10}$-alkyl is substituted with hydroxy and tetrahydrofuranyl. In one aspect, $R^6$ is $C_{2-6}$-alkyl, wherein the $C_{2-6}$-alkyl is substituted with hydroxy and tetrahydrofuranyl. In another aspect, $R^6$ is $C_2$-alkyl, wherein the $C_2$-alkyl is substituted with hydroxy and tetrahydrofuranyl. In another aspect, $R^6$ is $C_3$-alkyl, wherein the $C_3$-alkyl is substituted with hydroxy and tetrahydrofuranyl. In another aspect, $R^6$ is

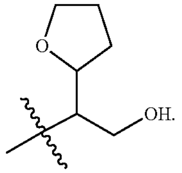 [SMILES: *C(CO)C1CCCO1]

In another aspect, $R^6$ is

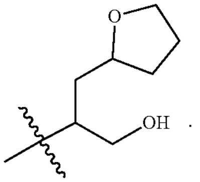 [SMILES: *C(CO)CC1CCCO1]

In some embodiments, the present disclosure provides compounds having the structure of Formula (I) or Formula (I-A), and pharmaceutically acceptable salts thereof, wherein $R^2$ is —NHR$^6$ and $R^6$ is

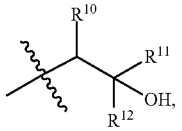

wherein $R^{10}$ is selected from the group consisting of $C_{1-3}$-alkyl, halo-$C_{1-3}$-alkyl, $C_{3-6}$-cycloalkyl, $C_{3-6}$-cycloalkyl-$C_{1-3}$-alkyl, and tetrahydrofuranyl; $R^{11}$ is selected from the group consisting of hydrogen and $C_{1-3}$-alkyl; and $R^{12}$ is selected from the group consisting of hydrogen, $C_{1-3}$-alkyl, and halo-$C_{1-3}$-alkyl. For clarity, the initial definition of $R^6$ previously set forth for the broadest embodiment of compounds having the structure of Formula (I) further limits the combinations of $R^{10}$, $R^{11}$, and $R^{12}$ substituents that can be selected. In one aspect, $R^{10}$ is selected from the group consisting of $C_{1-3}$-alkyl and halo-$C_{1-3}$-alkyl; $R^{11}$ is selected from the group consisting of hydrogen and $C_{1-3}$-alkyl; and $R^{12}$ is selected from the group consisting of hydrogen, $C_{1-3}$-alkyl, and halo-$C_1$-3-alkyl. In another aspect, $R^{10}$ is selected from the group consisting of $C_{3-6}$-cycloalkyl, $C_{3-6}$-cycloalkyl-$C_{1-3}$-alkyl, and tetrahydrofuranyl; $R^{11}$ is selected from the group consisting of hydrogen and $C_{1-3}$-alkyl; and $R^{12}$ is selected from the group consisting of hydrogen, $C_{1-3}$-alkyl, and halo-$C_{1-3}$-alkyl. In another aspect, $R^{10}$ is selected from the group consisting of methyl, ethyl, fluoroethyl, cyclopropyl, cyclopropylmethyl, cyclopentyl, and tetrahydrofuranyl; $R^{11}$ is selected from the group consisting of hydrogen and methyl; and $R^{12}$ is selected from the group consisting of hydrogen, methyl, and trifluoromethyl. In another aspect, $R^{10}$ is selected from the group consisting of methyl, ethyl, and fluoroethyl; $R^{11}$ is selected from the group consisting of hydrogen and methyl; and $R^{12}$ is selected from the group consisting of hydrogen, methyl, and trifluoromethyl. In another aspect, $R^{10}$ is methyl; $R^{11}$ is selected from the group consisting of hydrogen and methyl; and $R^{12}$ is selected from the group consisting of hydrogen, methyl, and trifluoromethyl. In another aspect, $R^{10}$ is ethyl; $R^{11}$ is selected from the group consisting of hydrogen and methyl; and $R^{12}$ is selected from the group consisting of hydrogen, methyl, and trifluoromethyl. In another aspect, $R^{10}$ is fluoroethyl; $R^{11}$ is selected from the group consisting of hydrogen and methyl; and $R^{12}$ is selected from the group consisting of hydrogen, methyl, and trifluoromethyl. In another aspect, $R^{10}$ is selected from the group consisting of cyclopropyl and cyclopropylmethyl; $R^{11}$ is selected from the group consisting of hydrogen and methyl; and $R^{12}$ is selected from the group consisting of hydrogen and methyl. In another aspect, $R^{10}$ is cyclohexyl; $R^{11}$ is selected from the group consisting of hydrogen and methyl; and $R^{12}$ is selected from the group consisting of hydrogen and methyl. In another aspect, $R^{10}$ is tetrahydrofuranyl; $R^{11}$ is selected from the group consisting of hydrogen and methyl; and $R^{12}$ is selected from the group consisting of hydrogen and methyl. In another aspect, $R^6$ is

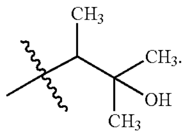

In another aspect, $R^6$ is selected from the group consisting of:

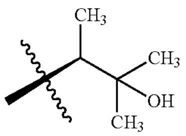
and
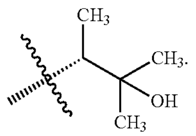

In another aspect, $R^6$ is

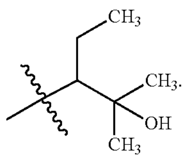 [SMILES: *C(CC)C(C)(C)O]

In another aspect, $R^6$ is selected from the group consisting of:

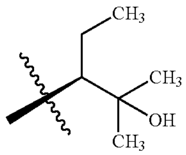
and
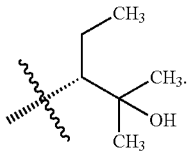

In some embodiments, the present disclosure provides compounds having the structure of Formula (I) or Formula (I-A), and pharmaceutically acceptable salts thereof, wherein $R^2$ is —$NHR^6$ and $R^6$ is $C_{1-10}$-alkyl, wherein the $C_{1-10}$-alkyl is substituted with oxo, and is optionally substituted with one or more substituents independently selected from the group consisting of halogen, $C_{3-6}$-cycloalkyl, and tetrahydrofuranyl. In one aspect, $R^6$ is $C_{2-5}$-alkyl, wherein the $C_{2-5}$-alkyl is substituted with oxo, and is optionally substituted with one or more substituents independently selected from the group consisting of halogen, $C_{3-6}$-cycloalkyl, and tetrahydro-furanyl. In another aspect, $R^6$ is $C_{1-10}$-alkyl, wherein the $C_{1-10}$-alkyl is substituted with oxo. In another aspect, $R^6$ is $C_{1-5}$-alkyl, wherein the $C_{2-5}$-alkyl is substituted with oxo. In another aspect, $R^6$ is

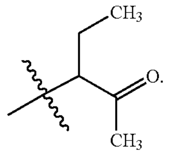 [SMILES: *C(CC)C(C)=O]

In another aspect, $R^6$ is selected from the group consisting of:

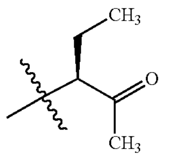
and
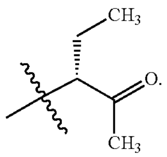

In some embodiments, the present disclosure provides compounds having the structure of Formula (I) or Formula (I-A), and pharmaceutically acceptable salts thereof, wherein $R^2$ is —$NHR^6$ and $R^6$ is

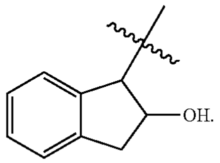 [SMILES: *C1c2ccccc2CC1O]

In some embodiments, the present disclosure provides compounds having the structure of Formula (I) or Formula (I-A), and pharmaceutically acceptable salts thereof, wherein $R^2$ is

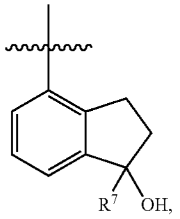

wherein $R^7$ is hydrogen or $C_{1-3}$-alkyl. In another aspect, $R^7$ is hydrogen or methyl. In another aspect, $R^7$ is hydrogen. In another aspect, $R^7$ is methyl.

In some embodiments, the present disclosure provides compounds having the structure of Formula (I) or Formula (I-A), and pharmaceutically acceptable salts thereof, wherein $R^2$ is

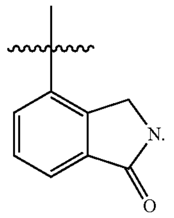

R^3 and R^4 Substituents

In some embodiments, the present disclosure provides compounds having the structure of Formula (I) or Formula (I-A), and pharmaceutically acceptable salts thereof, wherein $R^3$ is selected from the group consisting of hydrogen, halogen, $C_{1-3}$-alkyl, halo-$C_{1-3}$-alkyl, and $C_{1-3}$-alkoxy, and $R^4$ is hydrogen. In another aspect, $R^3$ is selected from the group consisting of hydrogen, fluoro, methyl, and methoxy, and $R^4$ is hydrogen. In another aspect, $R^3$ is selected from the group consisting of hydrogen, methyl, and fluoro, and $R^4$ is hydrogen. In another aspect, $R^3$ is fluoro and $R^4$ is hydrogen. In another aspect, $R^3$ is methyl and $R^4$ is hydrogen.

In some embodiments, the present disclosure provides compounds having the structure of Formula (I) or Formula (I-A), and pharmaceutically acceptable salts thereof, wherein $R^3$ is hydrogen and $R^4$ is selected from the group consisting of hydrogen, halogen, $C_{1-3}$-alkyl, halo-$C_{1-3}$-alkyl, and $C_{1-3}$-alkoxy. In one aspect, $R^3$ is hydrogen and $R^4$ is selected from the group consisting of hydrogen, fluoro, methyl, and methoxy. In another aspect, $R^3$ is hydrogen and $R^4$ is selected from the group consisting of hydrogen and methyl. In another aspect, $R^3$ is hydrogen and $R^4$ is methyl.

In some embodiments, the present disclosure provides compounds having the structure of Formula (I) or Formula (I-A), and pharmaceutically acceptable salts thereof, wherein $R^3$ and $R^4$ are each hydrogen.

$R^5$ Substituents

In some embodiments, the present disclosure provides compounds having the structure of Formula (I) or Formula (I-A), and pharmaceutically acceptable salts thereof, wherein $R^5$ is selected from the group consisting of $C_{1-6}$-alkyl, $C_{3-6}$-cycloalkyl, and —$NR^8R^9$; wherein the $C_{1-6}$-alkyl and $C_{3-6}$-cycloalkyl are optionally substituted with one or more substituents independently selected from halogen and $C_{1-3}$-alkoxy. In one aspect, $R^5$ is selected from the group consisting of $C_{1-3}$-alkyl, $C_{3-6}$-cycloalkyl, and —$NR^8R^9$; wherein the $C_{1-3}$-alkyl and $C_{3-6}$-cycloalkyl are optionally substituted with one or more substituents independently selected from halogen and $C_{1-3}$-alkoxy.

In some embodiments, the present disclosure provides compounds having the structure of Formula (I) or Formula (I-A), and pharmaceutically acceptable salts thereof, wherein $R^5$ is selected from the group consisting of $C_{1-6}$-alkyl and $C_{3-6}$-cycloalkyl; wherein the $C_{1-6}$-alkyl and $C_{3-6}$-cycloalkyl are optionally substituted with one or more substituents independently selected from halogen and $C_{1-3}$-alkoxy.

In some embodiments, the present disclosure provides compounds having the structure of Formula (I) or Formula (I-A), and pharmaceutically acceptable salts thereof, wherein $R^5$ is $C_1$-6-alkyl, wherein the $C_{1-6}$-alkyl is optionally substituted with one or more substituents independently selected from halogen and $C_{1-3}$-alkoxy. In one aspect, $R^5$ is $C_{1-3}$-alkyl, wherein the $C_{1-3}$-alkyl is optionally substituted with one or more substituents independently selected from halogen and $C_{1-3}$-alkoxy. In another aspect, $R^5$ is methyl, wherein the methyl is optionally substituted with one or more substituents independently selected from halogen and $C_{1-3}$-alkoxy. In another aspect, $R^5$ is ethyl, wherein the ethyl is optionally substituted with one or more substituents independently selected from halogen and $C_{1-3}$-alkoxy. In another aspect, $R^5$ is propyl, wherein the propyl is optionally substituted with one or more substituents independently selected from halogen and $C_{1-3}$-alkoxy. In further aspects, the halogen is fluoro and the $C_{1-3}$-alkoxy is methoxy.

In some embodiments, the present disclosure provides compounds having the structure of Formula (I) or Formula (I-A), and pharmaceutically acceptable salts thereof, wherein $R^5$ is $C_{3-6}$-cycloalkyl, wherein the $C_{3-6}$-cycloalkyl is optionally substituted with one or more substituents independently selected from halogen and $C_{1-3}$-alkoxy. In one aspect, $R^5$ is cyclopropyl, wherein the cyclopropyl is optionally substituted with one or more substituents independently selected from halogen and $C_{1-3}$-alkoxy. In another aspect, $R^5$ is cyclobutyl, wherein the cyclobutyl is optionally substituted with one or more substituents independently selected from halogen and $C_{1-3}$-alkoxy. In another aspect, $R^5$ is cyclopentyl, wherein the cyclopentyl is optionally substituted with one or more substituents independently selected from halogen and $C_{1-3}$-alkoxy. In another aspect, $R^5$ is cyclohexyl, wherein the cyclohexyl is optionally substituted with one or more substituents independently selected from halogen and $C_{1-3}$-alkoxy. In further aspects, the halogen is fluoro. In further aspects, the $C_{1-3}$-alkoxy is methoxy. In further aspects, the halogen is fluoro and the $C_{1-3}$-alkoxy is methoxy.

In some embodiments, the present disclosure provides compounds having the structure of Formula (I) or Formula (I-A), and pharmaceutically acceptable salts thereof, wherein $R^5$ is selected from the group consisting of pyrazolyl and imidazolyl, wherein the pyrazolyl and imidazolyl are optionally substituted with one or more substituents independently selected from $C_{1-3}$-alkyl. In one aspect, $R^5$ is selected from the group consisting of pyrazolyl and imidazolyl, wherein the pyrazolyl and imidazolyl are optionally substituted with one or more methyl. In another aspect, $R^5$ is pyrazolyl, wherein the pyrazolyl is optionally substituted with one or more substituents independently selected from $C_{1-3}$-alkyl. In another aspect, $R^5$ is pyrazolyl, wherein the pyrazolyl is optionally substituted with one or more methyl. In another aspect, $R^5$ is imidazolyl, wherein the imidazolyl is optionally substituted with one or more substituents independently selected from $C_{1-3}$-alkyl. In another aspect, $R^5$ is imidazolyl, wherein the imidazolyl is optionally substituted with one or more methyl.

In some embodiments, the present disclosure provides compounds having the structure of Formula (I) or Formula (I-A), and pharmaceutically acceptable salts thereof, wherein $R^5$ is selected from the group consisting of methyl, fluoromethyl, trifluoromethyl, methoxyethyl, cyclopropyl, imidazolyl, pyrazolyl, methylimidazolyl, and methylpyrazolyl.

In some embodiments, the present disclosure provides compounds having the structure of Formula (I) or Formula (I-A), and pharmaceutically acceptable salts thereof, wherein $R^5$ is —$NR^8R^9$; $R^8$ is hydrogen; and $R^9$ is selected from the group consisting of hydrogen, $C_{1-6}$-alkyl, $C_{3-6}$-cycloalkyl, $C_{1-6}$-alkoxy-$C_{1-6}$-alkyl, tetrahydrofuranyl, and 1,4-dioxanyl-$C_{1-3}$-alkyl; wherein the $C_{1-6}$-alkyl, $C_{3-6}$-cycloalkyl, $C_{1-6}$-alkoxy-$C_{1-6}$-alkyl, tetrahydrofuranyl, and 1,4-dioxanyl-$C_{1-3}$-alkyl are optionally substituted with one or more substituents independently selected from halogen. In one aspect, $R^9$ is selected from the group consisting of hydrogen, $C_{1-3}$-alkyl, $C_{3-6}$-cycloalkyl, $C_{1-3}$-alkoxy-$C_{1-3}$-alkyl, tetrahydrofuranyl, and 1,4-dioxanyl-$C_{1-3}$-alkyl; wherein the $C_{1-3}$-alkyl, $C_{3-6}$-cycloalkyl, $C_{1-3}$-alkoxy-$C_{1-3}$-alkyl, tetrahydrofuranyl, and 1,4-dioxanyl-$C_{1-3}$-alkyl are optionally substituted with one or more substituents independently selected from halogen. In another aspect, $R^9$ is selected from the group consisting of hydrogen, $C_{1-3}$-alkyl, tetrahydrofuranyl, and 1,4-dioxanyl-$C_{1-3}$-alkyl; wherein the $C_{1-3}$-alkyl is optionally substituted with one or more substituents independently selected from halogen. In further aspects, the halogen is fluoro.

In some embodiments, the present disclosure provides compounds having the structure of Formula (I) or Formula (I-A), and pharmaceutically acceptable salts thereof, wherein $R^5$ is —$NR^8R^9$; $R^8$ is hydrogen; and $R^9$ is hydrogen.

In some embodiments, the present disclosure provides compounds having the structure of Formula (I) or Formula (I-A), and pharmaceutically acceptable salts thereof, wherein $R^5$ is —$NR^8R^9$; $R^8$ is hydrogen; and $R^9$ is $C_{1-6}$-alkyl, wherein the $C_{1-6}$-alkyl is optionally substituted with one or more substituents independently selected from halogen. In one aspect, $R^9$ is $C_{1-3}$-alkyl, wherein the $C_{1-3}$-alkyl is optionally substituted with one or more substituents independently selected from halogen. In another aspect, $R^9$ is methyl, wherein the methyl is optionally substituted with one or more substituents independently selected from halogen. In another aspect, $R^9$ is ethyl, wherein the ethyl is optionally substituted with one or more substituents independently selected from halogen. In another aspect, $R^9$ is propyl, wherein the propyl is optionally substituted with one or more substituents independently selected from halogen. In further aspects, the halogen is fluoro.

In some embodiments, the present disclosure provides compounds having the structure of Formula (I) or Formula (I-A), and pharmaceutically acceptable salts thereof, wherein $R^5$ is —$NR^8R^9$; $R^8$ is hydrogen; and $R^9$ is $C_{3-6}$-cycloalkyl, wherein the $C_{3-6}$-cycloalkyl is optionally substituted with one or more substituents independently selected from halogen. In one aspect, $R^9$ is cyclopropyl, wherein the cyclopropyl is optionally substituted with one or more substituents independently selected from halogen. In another aspect, $R^9$ is cyclobutyl, wherein the cyclobutyl is optionally substituted with one or more substituents independently selected from halogen. In another aspect, $R^9$ is cyclopentyl, wherein the cyclopentyl is optionally substituted with one or more substituents independently selected from halogen. In another aspect, $R^9$ is cyclohexyl, wherein the cyclohexyl is optionally substituted with one or more substituents independently selected from halogen. In further aspects, the halogen is fluoro.

In some embodiments, the present disclosure provides compounds having the structure of Formula (I) or Formula (I-A), and pharmaceutically acceptable salts thereof, wherein $R^5$ is —$NR^8R^9$; $R^8$ is hydrogen; and $R^9$ is $C_{1-6}$-alkoxy-$C_{1-6}$-alkyl, wherein the $C_{1-6}$-alkoxy-$C_{1-6}$-alkyl is optionally substituted with one or more substituents independently selected from halogen. In one aspect, $R^9$ is $C_{1-3}$-alkoxy-$C_{1-3}$-alkyl, wherein the $C_{1-3}$-alkoxy-$C_{1-3}$-alkyl is optionally substituted with one or more substituents independently selected from halogen. In another aspect, $R^9$ is methoxy-$C_{1-3}$-alkyl, wherein the methoxy-$C_{1-3}$-alkyl is optionally substituted with one or more substituents independently selected from halogen. In another aspect, $R^9$ is methoxymethyl, wherein the methoxymethyl is optionally substituted with one or more substituents independently selected from halogen. In another aspect, $R^9$ is methoxyethyl, wherein the methoxyethyl is optionally substituted with one or more substituents independently selected from halogen. In further aspects, the halogen is fluoro.

In some embodiments, the present disclosure provides compounds having the structure of Formula (I) or Formula (I-A), and pharmaceutically acceptable salts thereof, wherein $R^5$ is —$NR^8R^9$; $R^8$ is hydrogen; and $R^9$ is selected from the group consisting of tetrahydrofuranyl and 1,4-dioxanyl-$C_{1-3}$-alkyl; wherein the tetrahydrofuranyl, and 1,4-dioxanyl-$C_{1-3}$-alkyl are optionally substituted with one or more substituents independently selected from halogen. In one aspect, $R^9$ is tetrahydrofuranyl. In another aspect, $R^9$ is 1,4-dioxanyl-$C_{1-3}$-alkyl. In another aspect, $R^9$ is 1,4-dioxanylmethyl. In further aspects, the halogen is fluoro.

In some embodiments, the present disclosure provides compounds having the structure of Formula (I) or Formula (I-A), and pharmaceutically acceptable salts thereof, wherein $R^5$ is —$NR^8R^9$; and $R^8$ and $R^9$ together with the nitrogen atom to which they are attached form a 4-, 5-, or 6-membered saturated monocyclic ring wherein the remaining ring atoms are carbon atoms, and wherein the monocyclic ring is optionally substituted with one or more substituents independently selected from halogen. In one aspect, $R^8$ and $R^9$ together with the nitrogen atom to which they are attached form a 4-membered saturated monocyclic ring wherein the remaining ring atoms are carbon atoms, and wherein the monocyclic ring is optionally substituted with one or more substituents independently selected from halogen. In another aspect, $R^8$ and $R^9$ together with the nitrogen atom to which they are attached form a 5-membered saturated monocyclic ring wherein the remaining ring atoms are carbon atoms, and wherein the monocyclic ring is optionally substituted with one or more substituents independently selected from halogen. In another aspect, $R^8$ and $R^9$ together with the nitrogen atom to which they are attached form a 6-membered saturated monocyclic ring wherein the remaining ring atoms are carbon atoms, and wherein the monocyclic ring is optionally substituted with one or more substituents independently selected from halogen. In further aspects, the halogen is fluoro.

In some embodiments, the present disclosure provides compounds having the structure of Formula (I) or Formula (I-A), and pharmaceutically acceptable salts thereof, wherein $R^5$ is —$NR^8R^9$; $R^8$ is hydrogen; and $R^9$ is selected from the group consisting of hydrogen, methyl, ethyl, difluoroethyl, trifluoroethyl, tetrahydrofuranyl, and 1,4-dioxanylmethyl; or $R^8$ and $R^9$ together with the nitrogen atom to which they are attached form an azetidinyl ring, and wherein the azetidinyl ring is optionally substituted with one or more substituents independently selected from halogen. In further aspects, the halogen is fluoro. In another aspect, $R^5$ is —$NR^8R^9$; $R^8$ is hydrogen; and $R^9$ is selected from the group consisting of methyl, ethyl, difluoroethyl, trifluoroethyl, tetrahydrofuranyl, and 1,4-dioxanylmethyl.

B. Additional Embodiments

In some embodiments, the present disclosure provides compounds of Formula (I), and pharmaceutically acceptable salts thereof, wherein the compound has a structure selected from the structures of Formulae I-1 through I-117 set out in Table 1:

TABLE 1
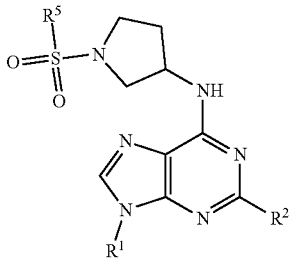
(I-1)
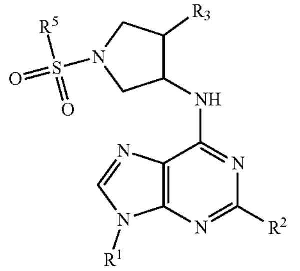
(I-2)
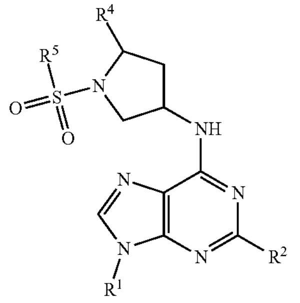
(I-3)
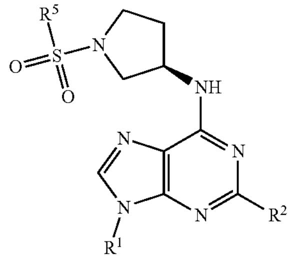
(I-4)
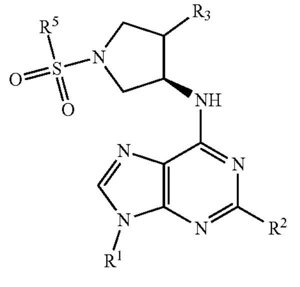
(I-5)
TABLE 1-continued
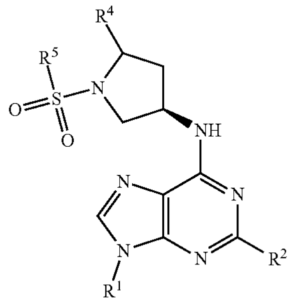
(I-6)
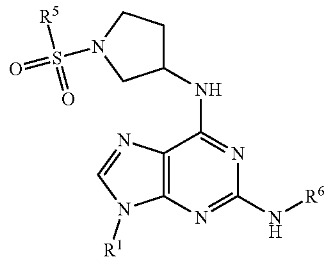
(I-7)
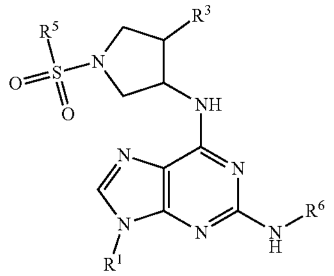
(I-8)
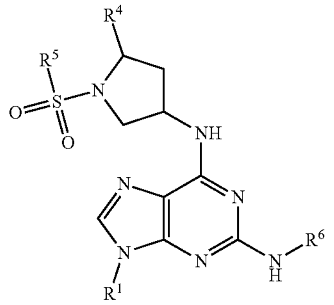
(I-9)
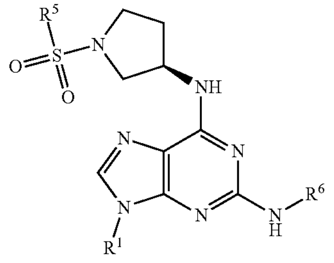
(I-10)

TABLE 1-continued
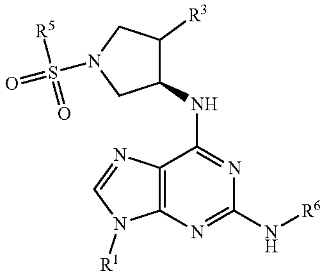
(I-11)
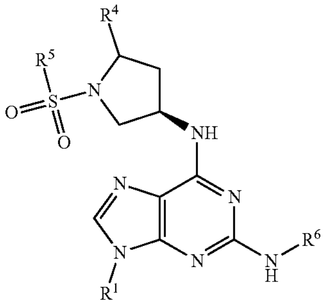
(I-12)
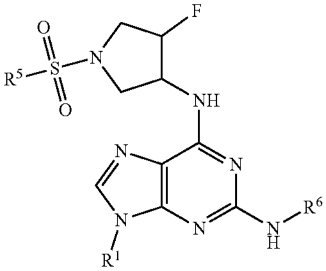
(I-13)
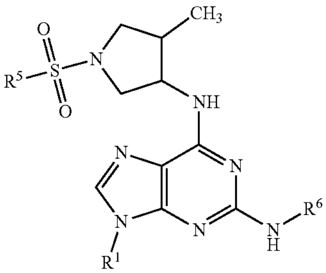
(I-14)
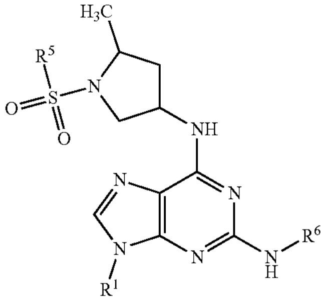
(I-15)
TABLE 1-continued
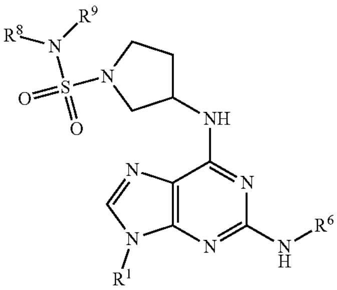
(I-16)
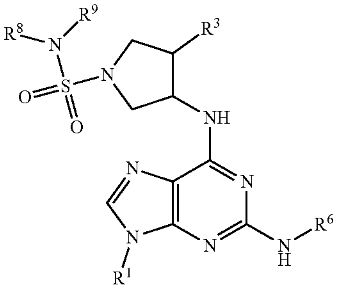
(I-17)
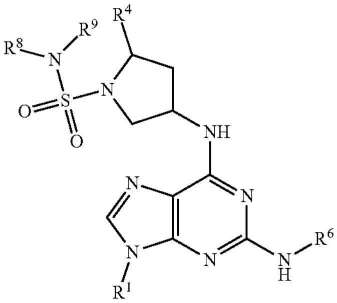
(I-18)
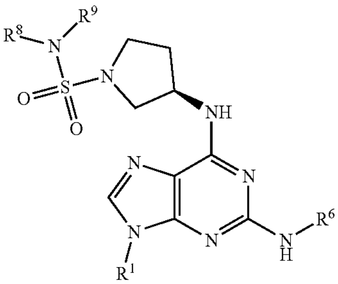
(I-19)
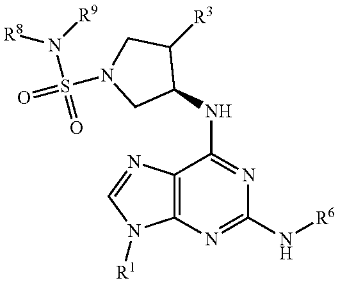
(I-20)

TABLE 1-continued
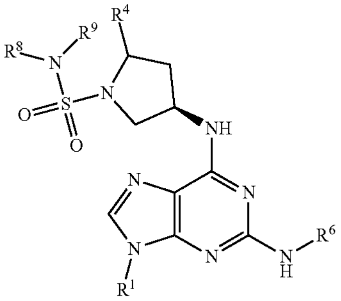
(I-21)
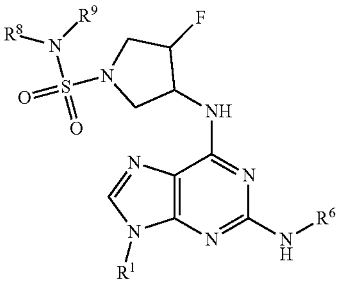
(I-22)
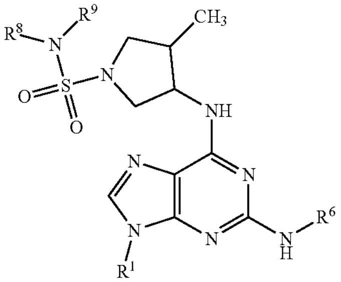
(I-23)
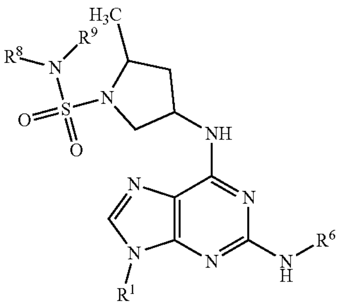
(I-24)
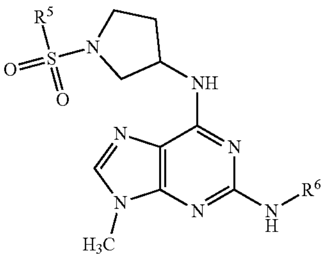
(I-25)
TABLE 1-continued
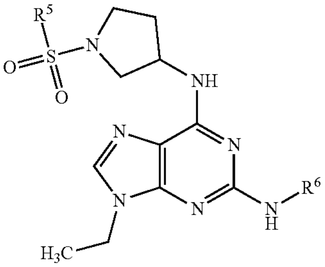
(I-26)
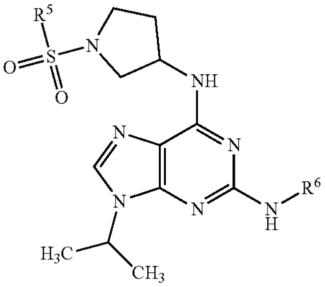
(I-27)
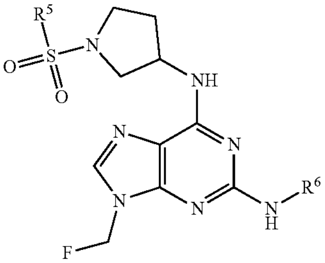
(I-28)
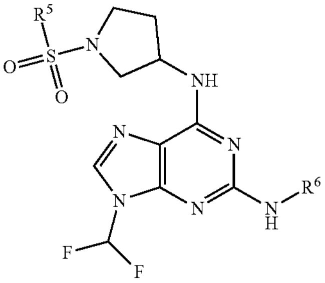
(I-29)
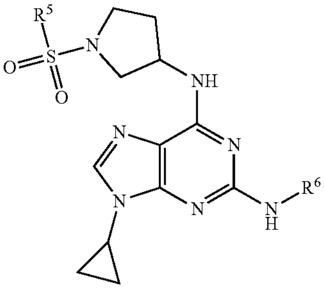
(I-30)

TABLE 1-continued
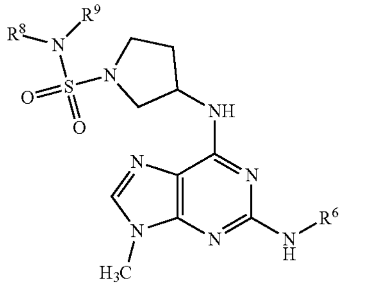
(I-31)
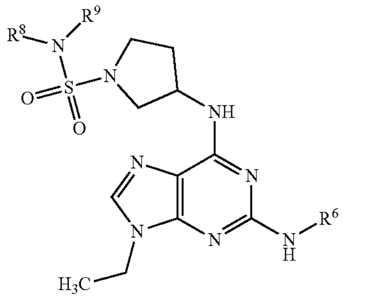
(I-32)
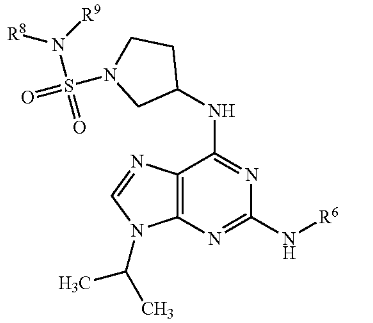
(I-33)
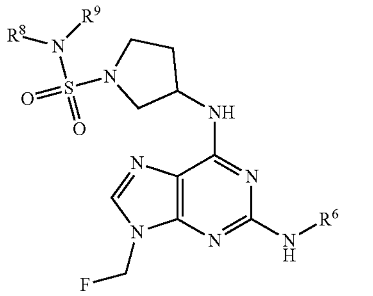
(I-34)
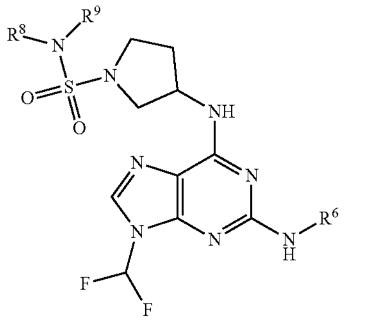
(I-35)
TABLE 1-continued
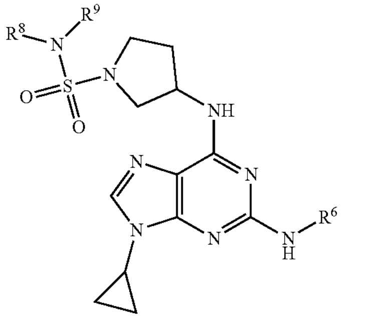
(I-36)
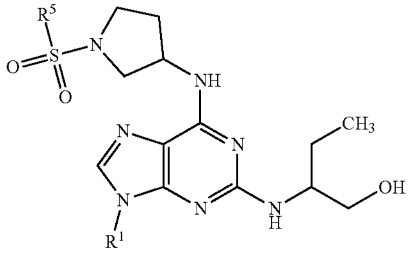
(I-37)
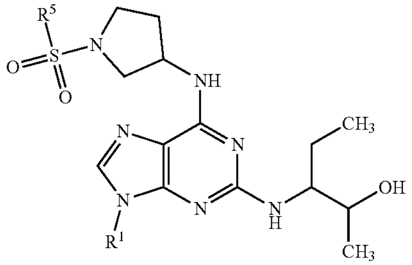
(I-38)
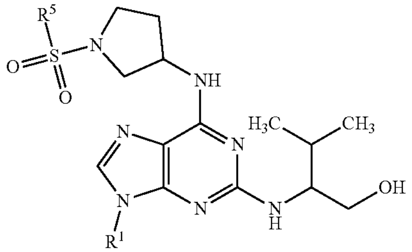
(I-39)
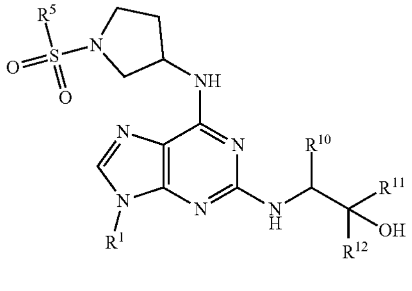
(I-40)

TABLE 1-continued
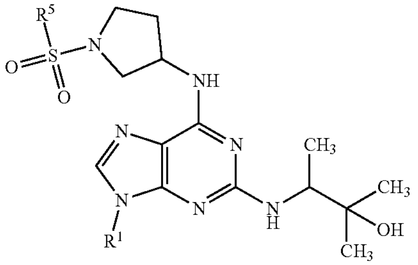
(I-41)
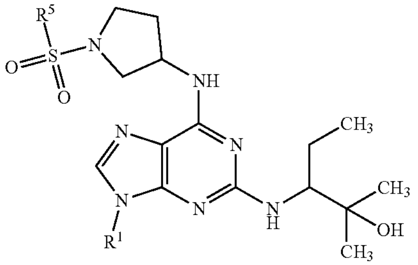
(I-42)
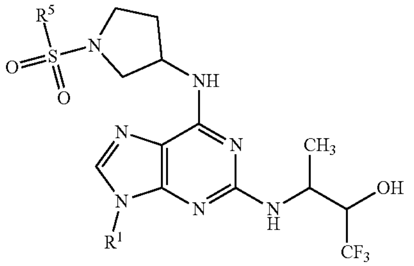
(I-43)
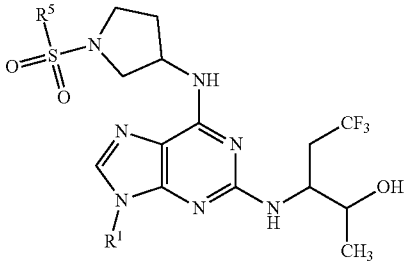
(I-44)
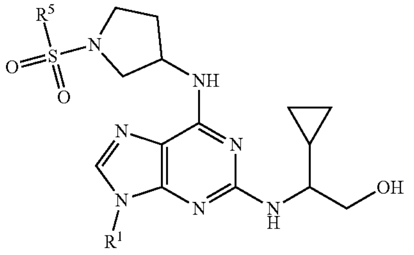
(I-45)
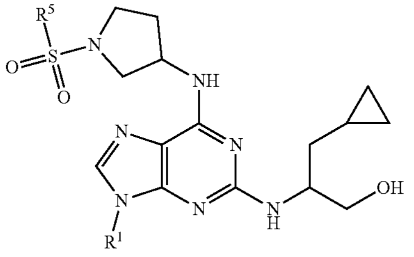
(I-46)
TABLE 1-continued
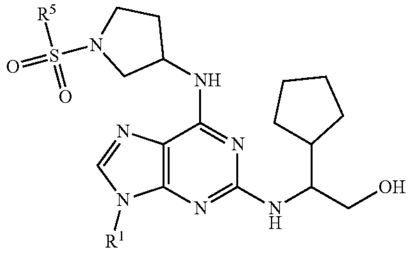
(I-47)
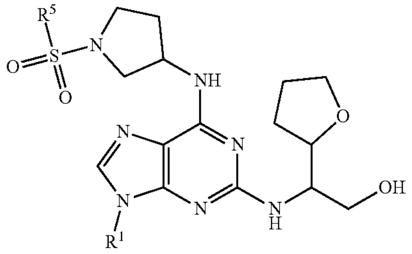
(I-48)
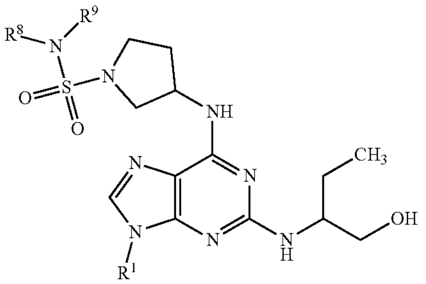
(I-49)
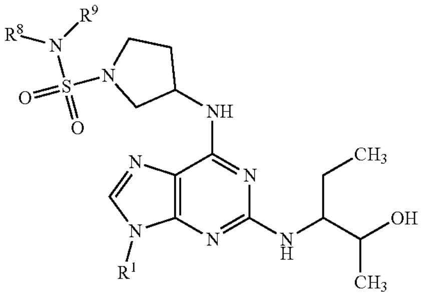
(I-50)
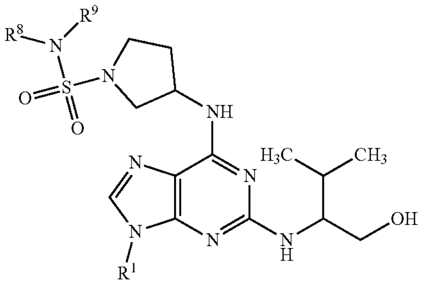
(I-51)

TABLE 1-continued
(I-52)
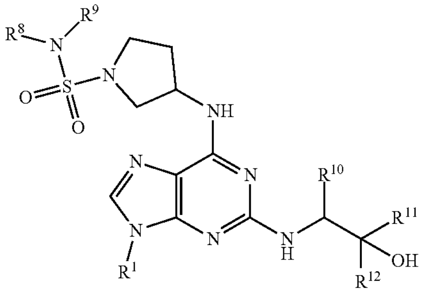
(I-53)
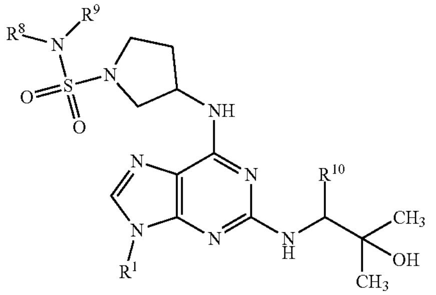
(I-54)
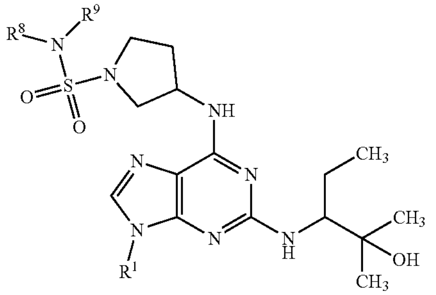
(I-55)
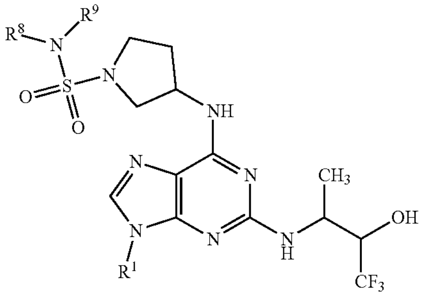
(I-56)
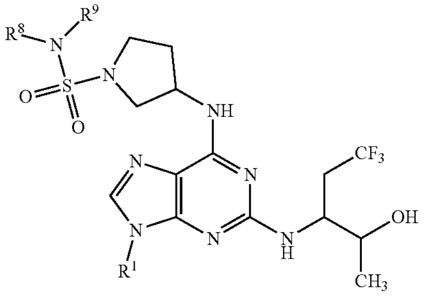
TABLE 1-continued
(I-57)
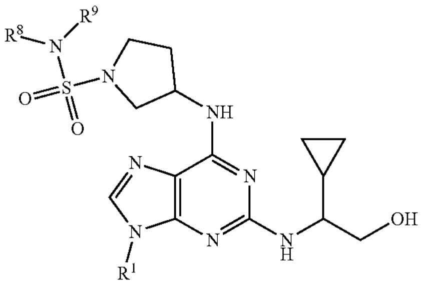
(I-58)
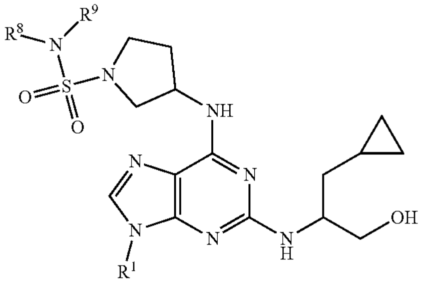
(I-59)
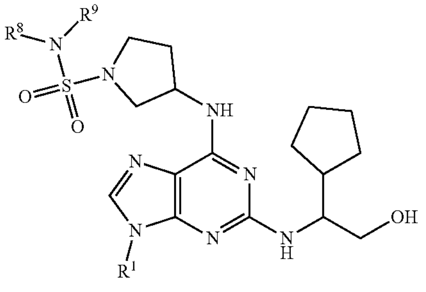
(I-60)
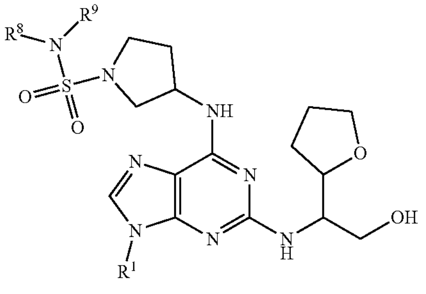
(I-61)
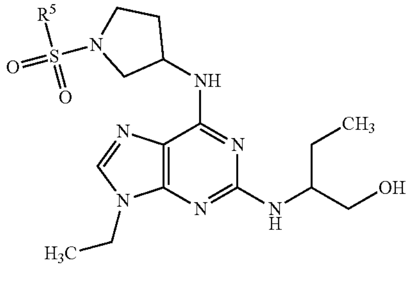

TABLE 1-continued
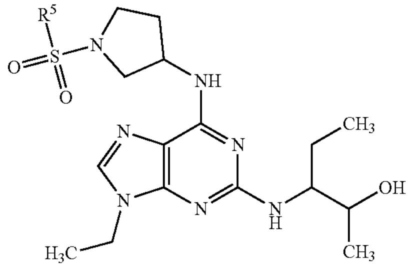
(I-62)
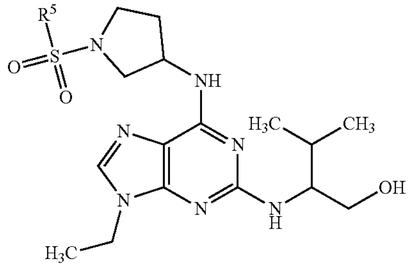
(I-63)
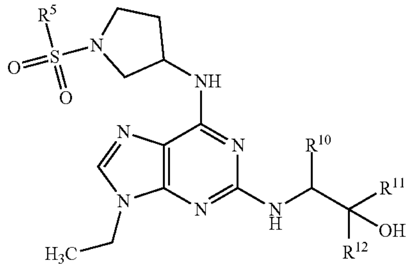
(I-64)
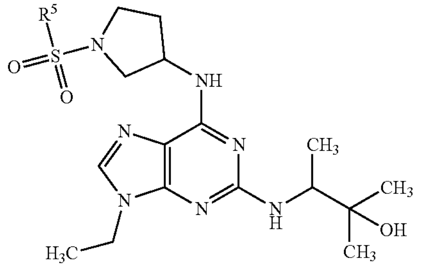
(I-65)
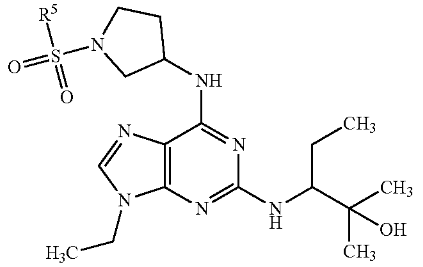
(I-66)
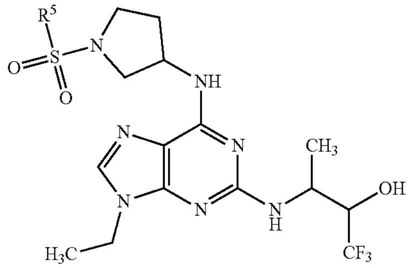
(I-67)
TABLE 1-continued
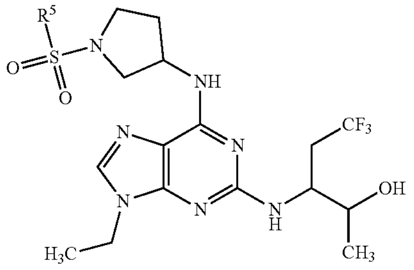
(I-68)
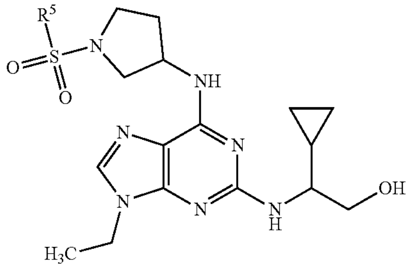
(I-69)
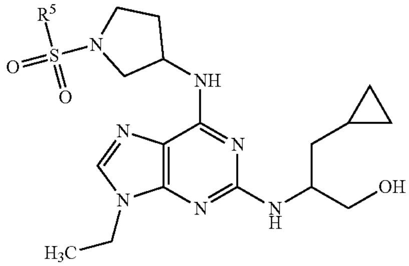
(I-70)
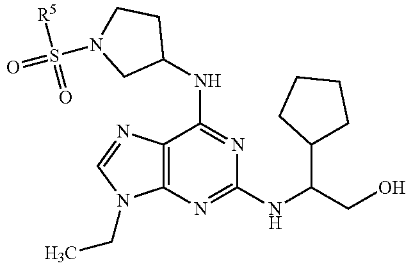
(I-71)
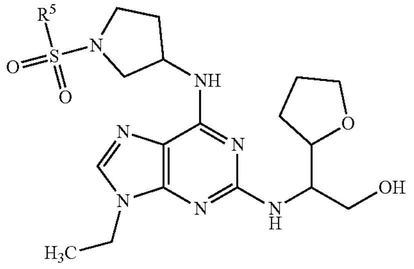
(I-72)

TABLE 1-continued
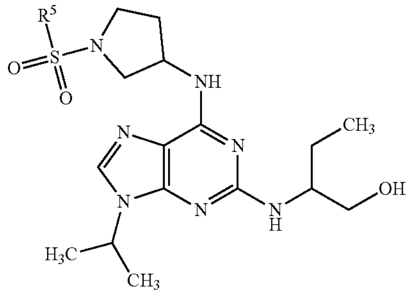
(I-73)
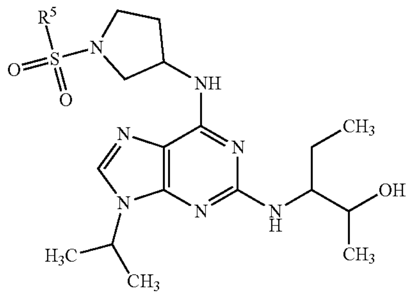
(I-74)
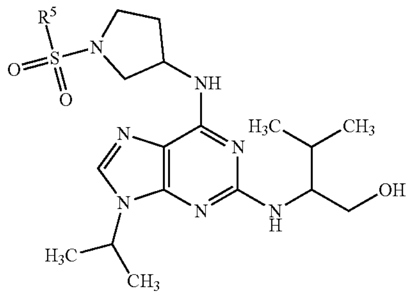
(I-75)
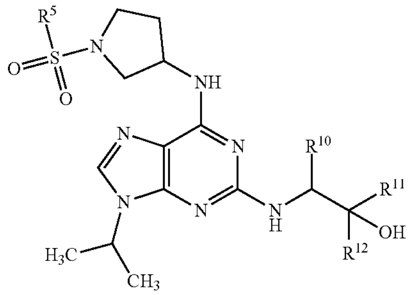
(I-76)
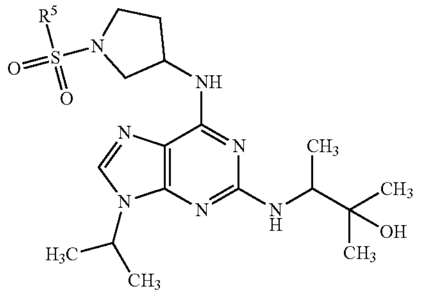
(I-77)
TABLE 1-continued
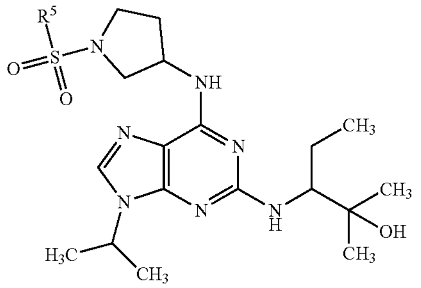
(I-78)
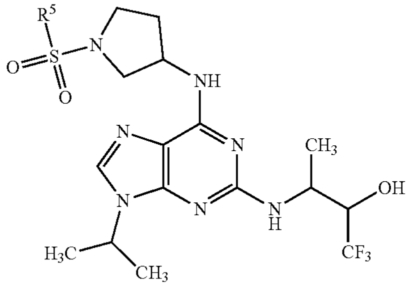
(I-79)
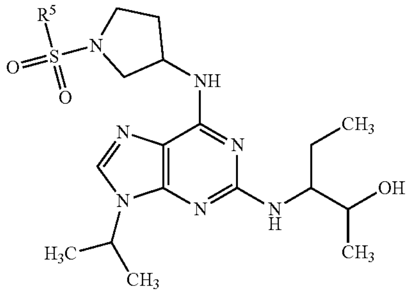
(I-80)
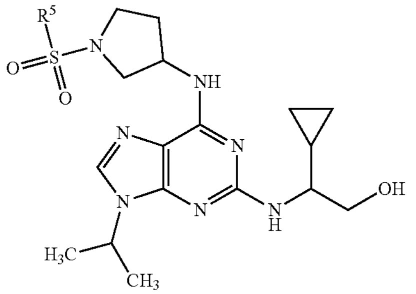
(I-81)
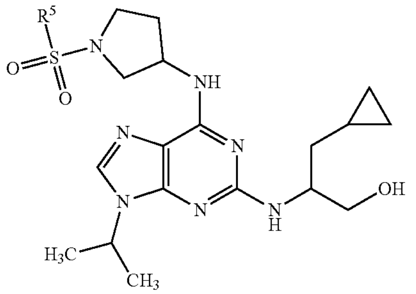
(I-82)

TABLE 1-continued
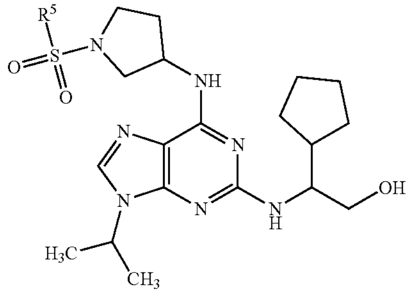
(I-83)
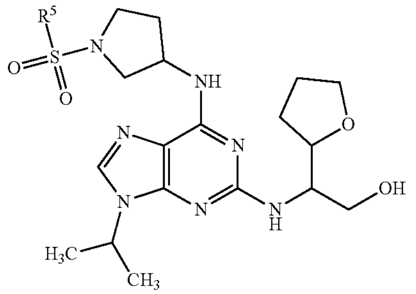
(I-84)
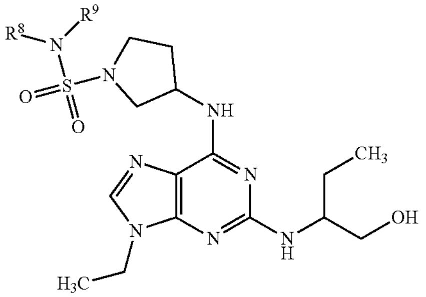
(I-85)
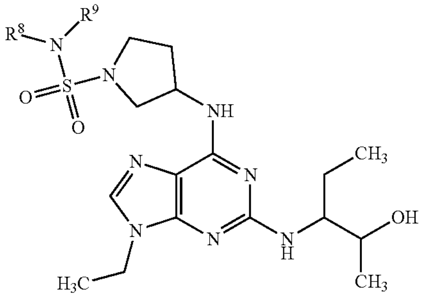
(I-86)
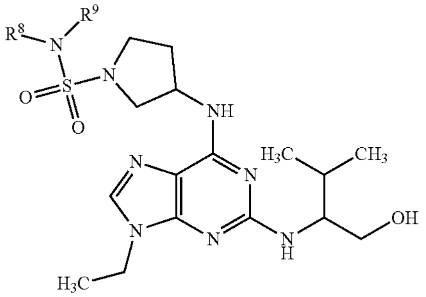
(I-87)
TABLE 1-continued
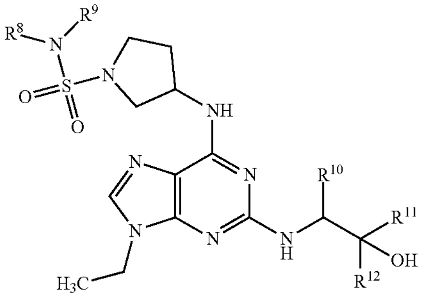
(I-88)
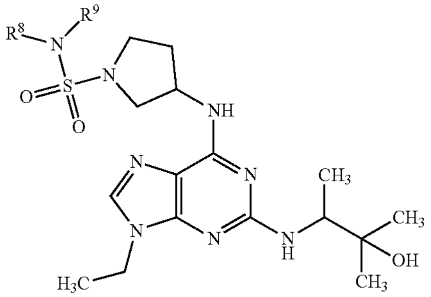
(I-89)
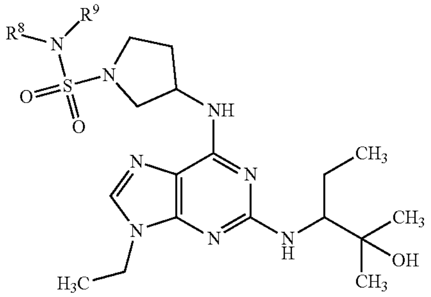
(I-90)
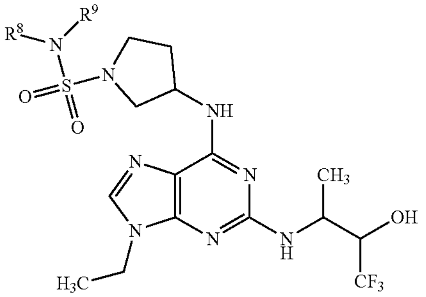
(I-91)
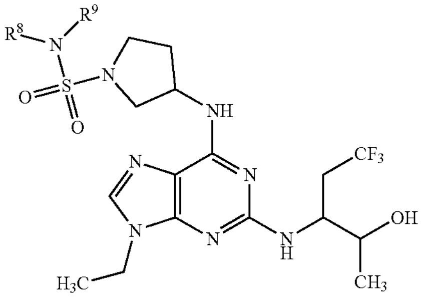
(I-92)

TABLE 1-continued
(I-93)
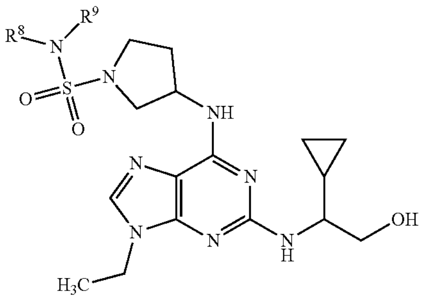
(I-94)
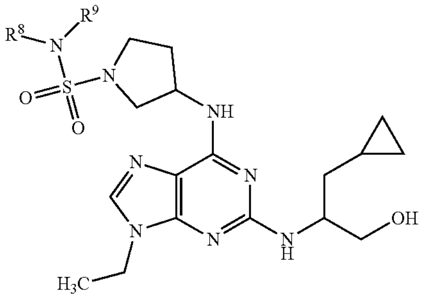
(I-95)
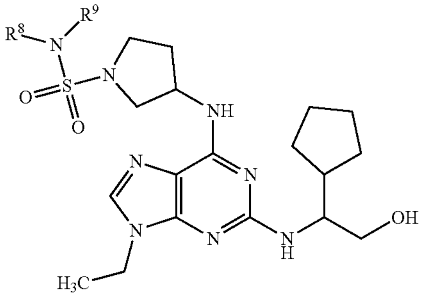
(I-96)
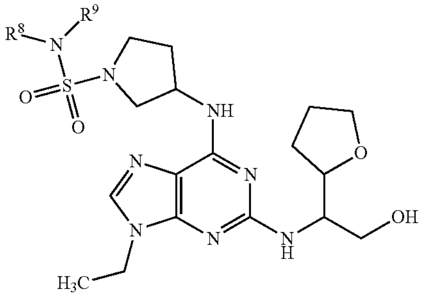
(I-97)
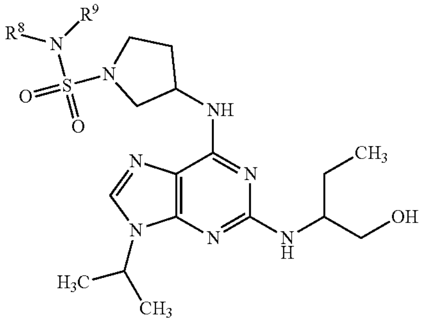
TABLE 1-continued
(I-98)
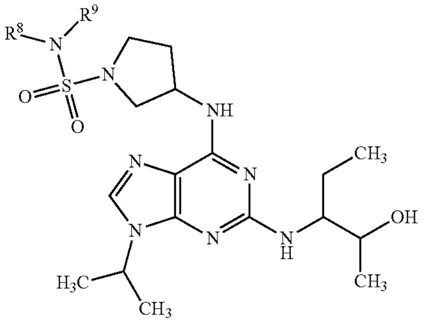
(I-99)
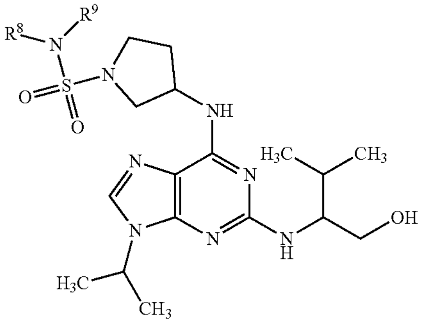
(I-100)
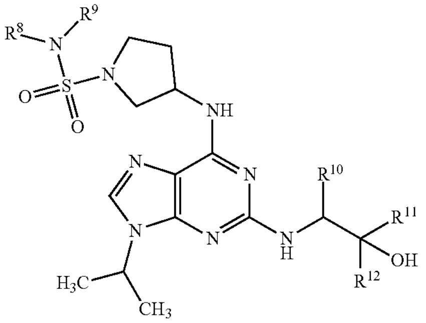
(I-101)
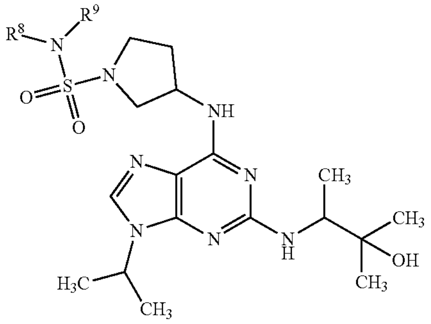
(I-102)
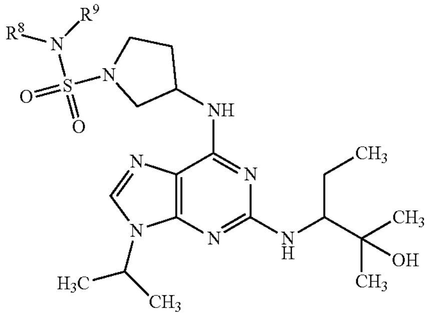

TABLE 1-continued
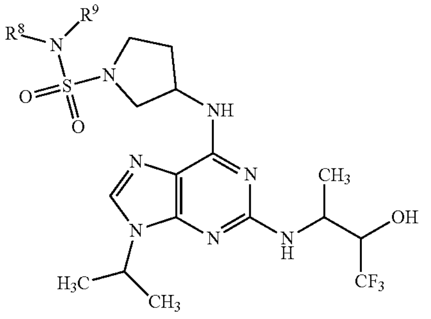
(I-103)
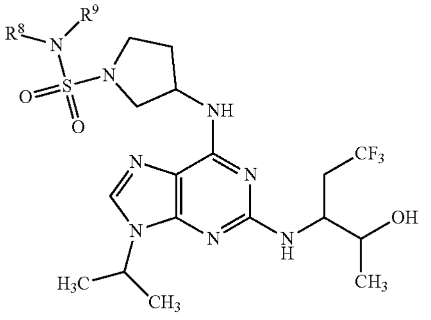
(I-104)
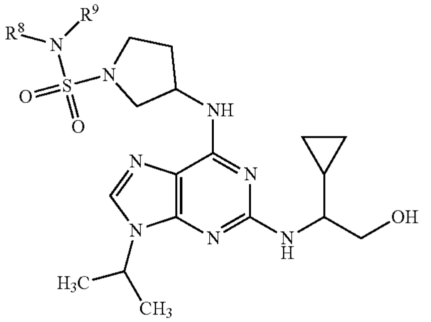
(I-105)
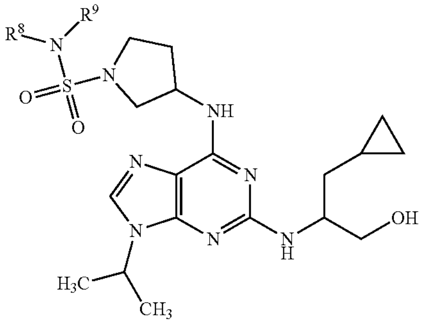
(I-106)
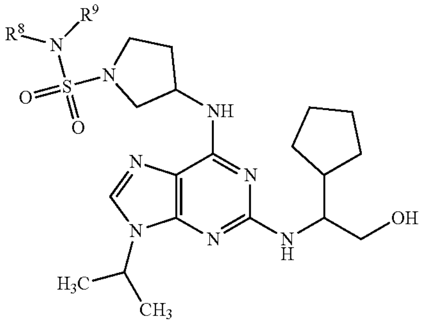
(I-107)
TABLE 1-continued
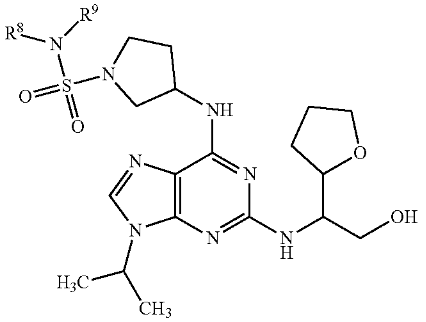
(I-108)
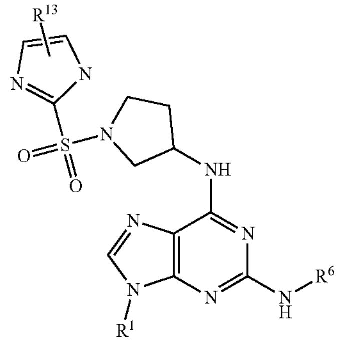
(I-109)
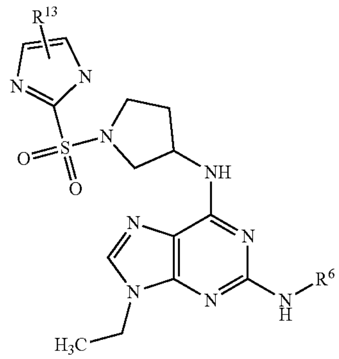
(I-110)
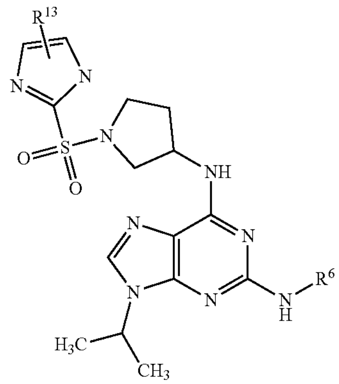
(I-111)

TABLE 1-continued

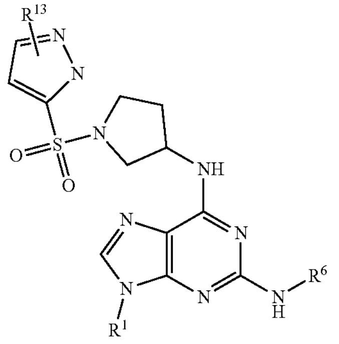

(I-112)

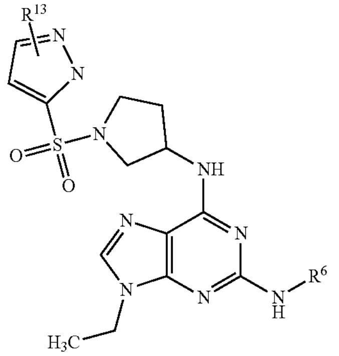

(I-113)

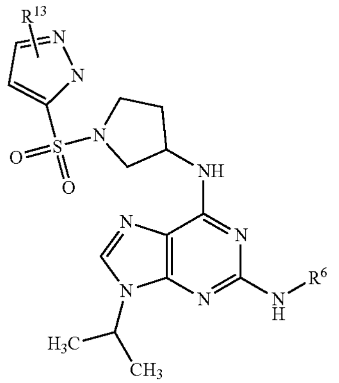

(I-114)

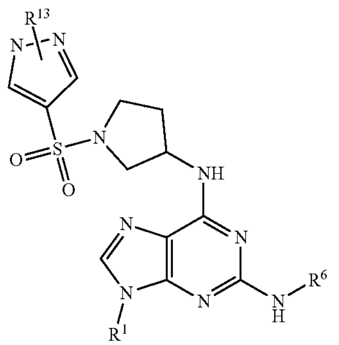

(I-115)

TABLE 1-continued

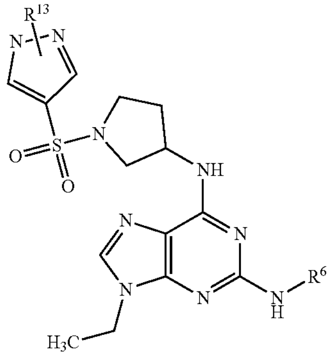

(I-116)

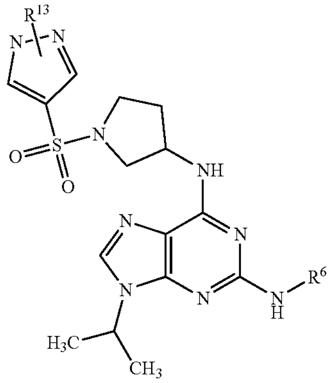

(I-117)

wherein, as applicable:

$R^1$ is selected from the group consisting of $C_{1-6}$-alkyl, halo-$C_{1-6}$-alkyl, and cyclopropyl;

$R^2$ is selected from the group consisting of —$NHR^6$,

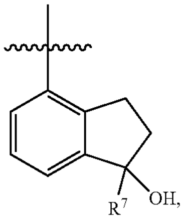

and

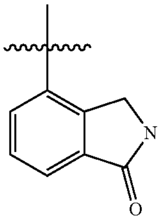

;

one of $R^3$ and $R^4$ is hydrogen and the other of $R^3$ and $R^4$ is selected from the group consisting of hydrogen, halogen, $C_{1-3}$-alkyl, halo-$C_{1-3}$-alkyl, and $C_{1-3}$-alkoxy;

$R^5$ is selected from the group consisting of $C_{1-6}$-alkyl, $C_{3-6}$-cycloalkyl, —$NR^8R^9$, pyrazolyl, and imidazolyl; wherein the $C_{1-6}$-alkyl and $C_{3-6}$-cycloalkyl are optionally substituted with one or more substituents independently selected from halogen and $C_{1-3}$-alkoxy; and the pyrazolyl and imidazolyl are optionally substituted with one or more substituents independently selected from $C_{1-3}$-alkyl;

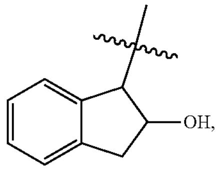 [SMILES: *C1c2ccccc2CC1O]

$R^6$ is $C_{1-10}$-alkyl or wherein the $C_{1-10}$-alkyl is substituted with hydroxy or oxo, and is optionally substituted with one or more substituents independently selected from the group consisting of halogen, $C_{3-6}$-cycloalkyl, and tetrahydrofuranyl;

$R^7$ is hydrogen or $C_{1-3}$-alkyl;

$R^8$ is hydrogen;

$R^9$ is selected from the group consisting of hydrogen, $C_{1-6}$-alkyl, $C_{3-6}$-cycloalkyl, $C_{1-6}$-alkoxy-$C_{1-6}$-alkyl, tetrahydrofuranyl, and 1,4-dioxanyl-$C_{1-3}$-alkyl; wherein the $C_{1-6}$-alkyl, $C_{3-6}$-cycloalkyl, $C_{1-6}$-alkoxy-$C_{1-6}$-alkyl, tetrahydrofuranyl, and 1,4-dioxanyl-$C_{1-3}$-alkyl are optionally substituted with one or more substituents independently selected from halogen; or $R^8$ and $R^9$ together with the nitrogen atom to which they are attached form a 4-, 5-, or 6-membered saturated monocyclic ring wherein the remaining ring atoms are carbon atoms, and wherein the monocyclic ring is optionally substituted with one or more substituents independently selected from halogen;

$R^{10}$ is selected from the group consisting of $C_{1-3}$-alkyl, halo-$C_{1-3}$-alkyl, $C_{3-6}$-cycloalkyl, $C_{3-6}$-cycloalkyl-$C_{1-3}$-alkyl, and tetrahydrofuranyl;

$R^{11}$ is selected from the group consisting of hydrogen and $C_{1-3}$-alkyl;

$R^{12}$ is selected from the group consisting of hydrogen, $C_{1-3}$-alkyl, and halo-$C_{1-3}$-alkyl; and $R^{13}$ is selected from the group consisting of hydrogen and $C_{1-3}$-alkyl.

In some embodiments, the present disclosure provides compounds of Formula (I), and pharmaceutically acceptable salts thereof, wherein, as applicable:

$R^1$ is selected from the group consisting of $C_{1-3}$-alkyl, halo-$C_{1-3}$-alkyl, and cyclopropyl;

$R^2$ is —$NHR^6$;

$R^3$ is hydrogen and $R^4$ is selected from the group consisting of hydrogen and $C_{1-3}$-alkyl; or $R^4$ is hydrogen and $R^3$ is selected from the group consisting of hydrogen, halogen, and $C_{1-3}$-alkyl;

$R^5$ is selected from the group consisting of $C_{1-6}$-alkyl, $C_{3-6}$-cycloalkyl, —$NR^8R^9$, pyrazolyl, and imidazolyl; wherein the $C_{1-6}$-alkyl and $C_{3-6}$-cycloalkyl are optionally substituted with one or more substituents independently selected from halogen and $C_{1-3}$-alkoxy; and the pyrazolyl and imidazolyl are optionally substituted with one or more substituents independently selected from $C_{1-3}$-alkyl;

$R^6$ is $C_{1-10}$-alkyl, wherein the $C_{1-10}$-alkyl is substituted with hydroxy, and is optionally substituted with one or more substituents independently selected from the group consisting of halogen, $C_{3-6}$-cycloalkyl, and tetrahydrofuranyl;

$R^8$ is hydrogen;

$R^9$ is selected from the group consisting of hydrogen, $C_{1-3}$-alkyl, tetrahydrofuranyl, and 1,4-dioxanyl-$C_{1-3}$-alkyl; wherein the $C_{1-3}$-alkyl, tetrahydrofuranyl, and 1,4-dioxanyl-$C_{1-3}$-alkyl are optionally substituted with one or more substituents independently selected from halogen; or $R^8$ and $R^9$ together with the nitrogen atom to which they are attached form an azetidinyl ring, and wherein the azetidinyl ring is optionally substituted with one or more substituents independently selected from halogen;

$R^{10}$ is selected from the group consisting of $C_{1-3}$-alkyl, halo-$C_{1-3}$-alkyl, $C_{3-6}$-cycloalkyl, $C_{3-6}$-cycloalkyl-$C_{1-3}$-alkyl, and tetrahydrofuranyl;

$R^{11}$ is selected from the group consisting of hydrogen and $C_{1-3}$-alkyl;

$R^{12}$ is selected from the group consisting of hydrogen, $C_{1-3}$-alkyl, and halo-$C_{1-3}$-alkyl; and $R^{13}$ is selected from the group consisting of hydrogen and $C_{1-3}$-alkyl.

In one aspect, the compound has a structure selected from the structures of Formulae I-1 through I-117 set out in Table 1.

In some embodiments, the present disclosure provides compounds of Formula (I), and pharmaceutically acceptable salts thereof, wherein, as applicable:

$R^1$ is selected from the group consisting of $C_{1-3}$-alkyl and fluoro-$C_{1-3}$-alkyl;

$R^2$ is —$NHR^6$;

$R^3$ is hydrogen and $R^4$ is selected from the group consisting of hydrogen and methyl; or $R^4$ is hydrogen and $R^3$ is selected from the group consisting of hydrogen, fluoro, and methyl;

$R^5$ is selected from the group consisting of $C_{1-3}$-alkyl, $C_{3-6}$-cycloalkyl, —$NR^8R^9$, pyrazolyl, and imidazolyl; wherein the $C_{1-6}$-alkyl and $C_{3-6}$-cycloalkyl are optionally substituted with one or more substituents independently selected from fluoro and methoxy; and the pyrazolyl and imidazolyl are optionally substituted with one or more methyl;

$R^6$ is $C_{2-6}$-alkyl, wherein the $C_{2-6}$-alkyl is substituted with hydroxy, and is optionally substituted with one or more substituents independently selected from the group consisting of fluoro, $C_{3-6}$-cycloalkyl, and tetrahydrofuranyl;

$R^8$ is hydrogen;

$R^9$ is selected from the group consisting of hydrogen, $C_{1-3}$-alkyl, tetrahydrofuranyl, and 1,4-dioxanylmethyl; wherein the $C_{1-3}$-alkyl, tetrahydrofuranyl, and 1,4-dioxanylmethyl are optionally substituted with one or more substituents independently selected from halogen;

$R^{10}$ is selected from the group consisting of $C_{1-3}$-alkyl, fluoro-$C_{1-3}$-alkyl, $C_{3-6}$-cycloalkyl, $C_{3-6}$-cycloalkylmethyl, and tetrahydrofuranyl;

$R^{11}$ is selected from the group consisting of hydrogen and $C_{1-3}$-alkyl;

$R^{12}$ is selected from the group consisting of hydrogen, $C_{1-3}$-alkyl, and halo-$C_{1-3}$-alkyl; and $R^{13}$ is selected from the group consisting of hydrogen and $C_{1-3}$-alkyl.

In one aspect, the compound has a structure selected from the structures of Formulae I-1 through I-117 set out in Table 1.

In some embodiments, the present disclosure provides compounds of Formula (I), and pharmaceutically acceptable salts thereof, wherein, as applicable:

$R^1$ is selected from the group consisting of $C_{1-3}$-alkyl and fluoro-$C_{1-3}$-alkyl;

$R^2$ is —$NHR^6$;

$R^3$ is selected from the group consisting of hydrogen and fluoro;

$R^4$ is hydrogen;

$R^5$ is selected from the group consisting of $C_{1-3}$-alkyl, cyclopropyl, —$NR^8R^9$, pyrazolyl, and imidazolyl; wherein the $C_{1-6}$-alkyl and cyclopropyl are optionally substituted with one or more substituents independently selected from fluoro and methoxy; and the pyrazolyl and imidazolyl are optionally substituted with one or more methyl;

$R^6$ is $C_{2-6}$-alkyl, wherein the $C_{2-6}$-alkyl is substituted with hydroxy, and is optionally substituted with one or more substituents independently selected from the group consisting of fluoro, $C_{3-6}$-cycloalkyl, and tetrahydrofuranyl;

$R^8$ is hydrogen;

$R^9$ is selected from the group consisting of hydrogen, $C_{1-3}$-alkyl, tetrahydrofuranyl, and 1,4-dioxanylmethyl; wherein the $C_{1-3}$-alkyl, tetrahydrofuranyl, and 1,4-dioxanylmethyl are optionally substituted with one or more fluoro;

$R^{10}$ is selected from the group consisting of methyl, ethyl, fluoroethyl, cyclopropyl, cyclopropylmethyl, cyclopentyl, and tetrahydrofuranyl;

$R^{11}$ is selected from the group consisting of hydrogen and methyl; and $R^{12}$ is selected from the group consisting of hydrogen, methyl, and fluoromethyl.

In one aspect, the compound has a structure selected from the structures of Formulae I-1 through I-117 set out in Table 1.

In some embodiments, the present disclosure provides compounds of Formula (I), and pharmaceutically acceptable salts thereof, wherein, as applicable:

$R^1$ is selected from the group consisting of methyl, ethyl, isopropyl, fluoromethyl, and difluoromethyl;

$R^2$ is —$NHR^6$;

$R^3$ and $R^4$ are hydrogen;

$R^5$ is selected from the group consisting of methyl, fluoromethyl, trifluoromethyl, methoxyethyl, cyclopropyl, —$NR^8R^9$, imidazolyl, pyrazolyl, methylimidazolyl, and methylpyrazolyl;

$R^6$ is $C_{2-6}$-alkyl, wherein the $C_{2-6}$-alkyl is substituted with hydroxy, and is optionally substituted with one or more substituents independently selected from the group consisting of fluoro, $C_{3-6}$-cycloalkyl, and tetrahydrofuranyl;

$R^8$ is hydrogen;

$R^9$ is selected from the group consisting of of hydrogen, methyl, ethyl, difluoroethyl, trifluoroethyl, tetrahydrofuranyl, and 1,4-dioxanylmethyl;

$R^{10}$ is selected from the group consisting of methyl, ethyl, fluoroethyl, cyclopropyl, cyclopropylmethyl, cyclopentyl, and tetrahydrofuranyl;

$R^{11}$ is selected from the group consisting of hydrogen and methyl; and $R^{12}$ is selected from the group consisting of hydrogen, methyl, and fluoromethyl.

In one aspect, the compound has a structure selected from the structures of Formulae I-1 through I-117 set out in Table 1.

In some embodiments, the present disclosure provides compounds of Formula (I), and pharmaceutically acceptable salts thereof, wherein the compound has the structure of Formula (I-61):

(I-61)

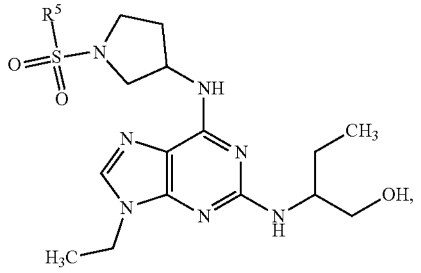

and wherein $R^5$ is as defined in any of the embodiments disclosed in this specification.

In some embodiments, the present disclosure provides compounds of Formula (I), and pharmaceutically acceptable salts thereof, wherein the compound has the structure of Formula (I-62)

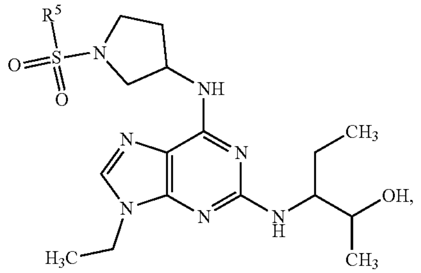

and wherein $R^5$ is as defined in any of the embodiments disclosed in this specification.

In some embodiments, the present disclosure provides compounds of Formula (I), and pharmaceutically acceptable salts thereof, wherein the compound has the structure of Formula (I-63):

(I-63)

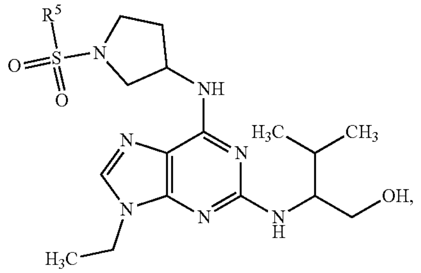

and wherein $R^5$ is as defined in any of the embodiments disclosed in this specification.

In some embodiments, the present disclosure provides compounds of Formula (I), and pharmaceutically acceptable salts thereof, wherein the compound has the structure of Formula (I-64):

(I-64)

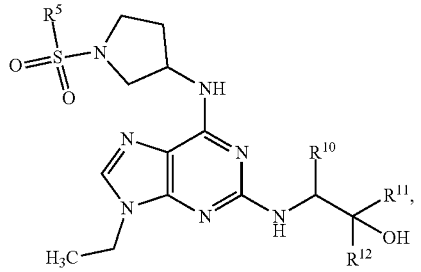

and wherein $R^5$, $R^{10}$, $R^{11}$, and $R^{12}$ are as defined in any of the embodiments disclosed in this specification.

In some embodiments, the present disclosure provides compounds of Formula (I), and pharmaceutically acceptable salts thereof, wherein the compound has the structure of Formula (I-65)

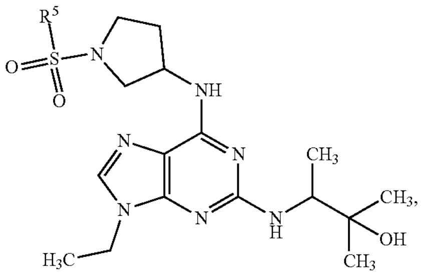

and wherein $R^5$ is as defined in any of the embodiments disclosed in this specification.

In some embodiments, the present disclosure provides compounds of Formula (I), and pharmaceutically acceptable salts thereof, wherein the compound has the structure of Formula (I-66):

(I-66)

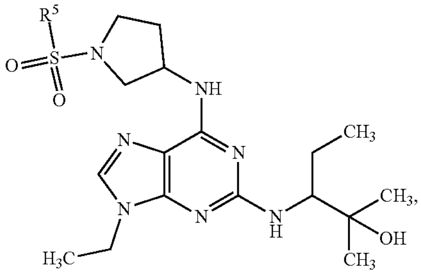

and wherein $R^5$ is as defined in any of the embodiments disclosed in this specification.

In some embodiments, the present disclosure provides compounds of Formula (I), and pharmaceutically acceptable salts thereof, wherein the compound has the structure of Formula (I-67):

(I-67)

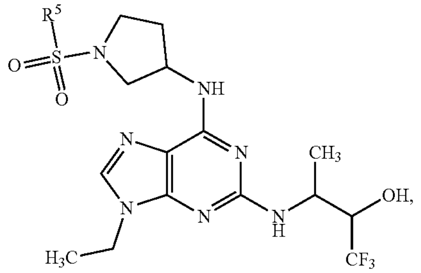

and wherein $R^5$ is as defined in any of the embodiments disclosed in this specification.

In some embodiments, the present disclosure provides compounds of Formula (I), and pharmaceutically acceptable salts thereof, wherein the compound has the structure of Formula (I-68):

(I-68)

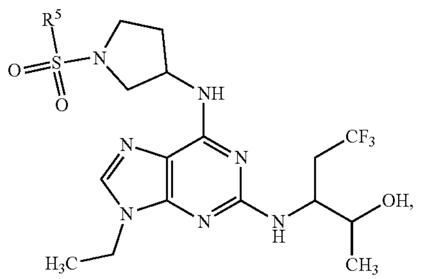

and wherein $R^5$ is as defined in any of the embodiments disclosed in this specification.

In some embodiments, the present disclosure provides compounds of Formula (I), and pharmaceutically acceptable salts thereof, wherein the compound has the structure of Formula (I-69):

(I-69)

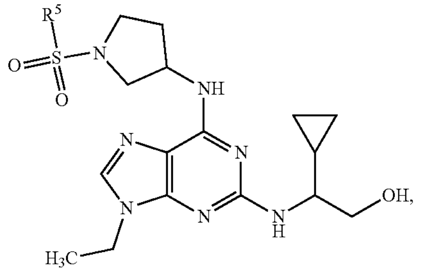

and wherein $R^5$ is as defined in any of the embodiments disclosed in this specification.

In some embodiments, the present disclosure provides compounds of Formula (I), and pharmaceutically acceptable salts thereof, wherein the compound has the structure of Formula (I-70):

(I-70)

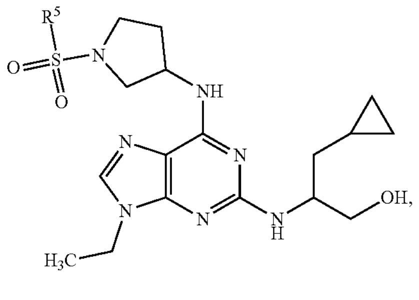

and wherein $R^5$ is as defined in any of the embodiments disclosed in this specification.

In some embodiments, the present disclosure provides compounds of Formula (I), and pharmaceutically acceptable salts thereof, wherein the compound has the structure of Formula (I-71):

(I-71)

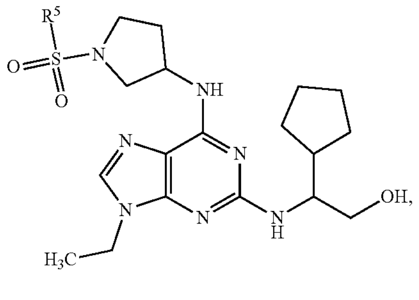

and wherein $R^5$ is as defined in any of the embodiments disclosed in this specification.

In some embodiments, the present disclosure provides compounds of Formula (I), and pharmaceutically acceptable salts thereof, wherein the compound has the structure of Formula (I-72):

(I-72)

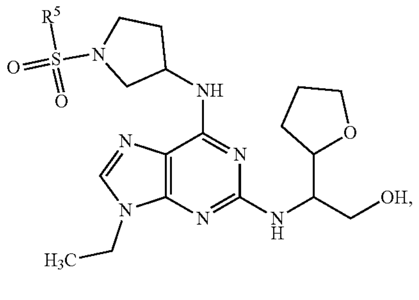

and wherein $R^5$ is as defined in any of the embodiments disclosed in this specification.

In some embodiments, the present disclosure provides compounds of Formula (I), and pharmaceutically acceptable salts thereof, wherein the compound has the structure of Formula (I-73):

(I-73)

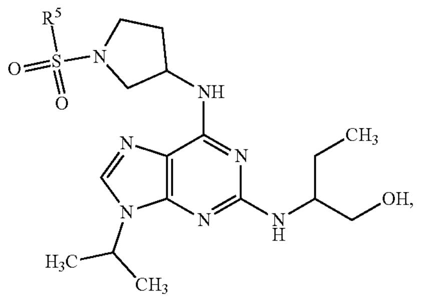

and wherein $R^5$ is as defined in any of the embodiments disclosed in this specification.

In some embodiments, the present disclosure provides compounds of Formula (I), and pharmaceutically acceptable salts thereof, wherein the compound has the structure of Formula (I-74):

(I-74)

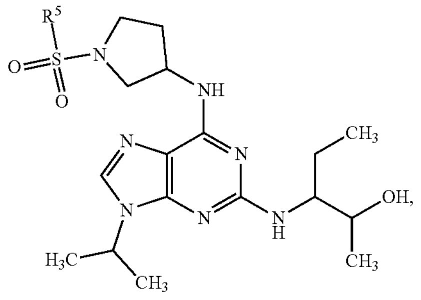

and wherein $R^5$ is as defined in any of the embodiments disclosed in this specification.

In some embodiments, the present disclosure provides compounds of Formula (I), and pharmaceutically acceptable salts thereof, wherein the compound has the structure of Formula (I-75):

(I-75)

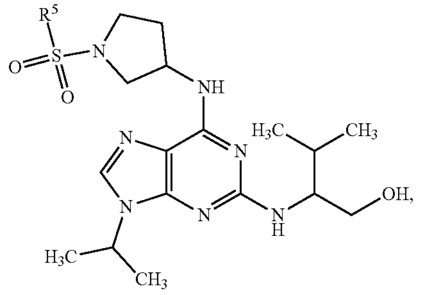

and wherein $R^5$ is as defined in any of the embodiments disclosed in this specification.

In some embodiments, the present disclosure provides compounds of Formula (I), and pharmaceutically acceptable salts thereof, wherein the compound has the structure of Formula (I-76):

(I-76)

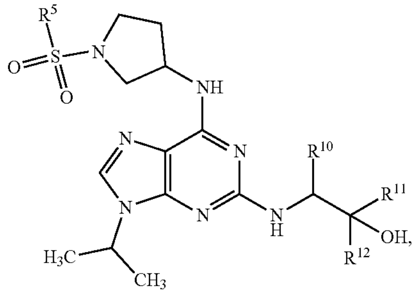

and wherein $R^5$, $R^{10}$, $R^{11}$, and $R^{12}$ are as defined in any of the embodiments disclosed in this specification.

In some embodiments, the present disclosure provides compounds of Formula (I), and pharmaceutically acceptable salts thereof, wherein the compound has the structure of Formula (I-77):

(I-77)

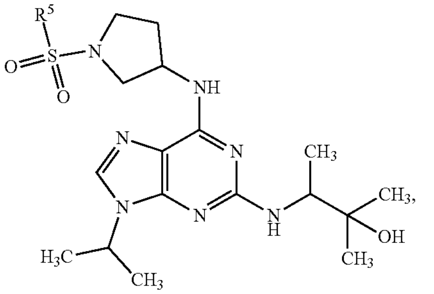

and wherein $R^5$ is as defined in any of the embodiments disclosed in this specification.

In some embodiments, the present disclosure provides compounds of Formula (I), and pharmaceutically acceptable salts thereof, wherein the compound has the structure of Formula (I-78):

(I-78)

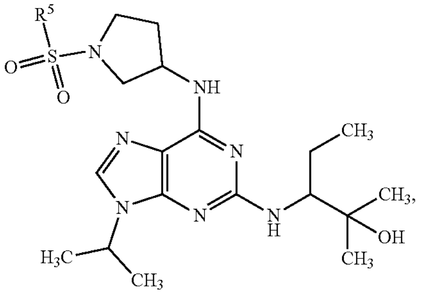

and wherein $R^5$ is as defined in any of the embodiments disclosed in this specification.

In some embodiments, the present disclosure provides compounds of Formula (I), and pharmaceutically acceptable salts thereof, wherein the compound has the structure of Formula (I-79):

(I-79)

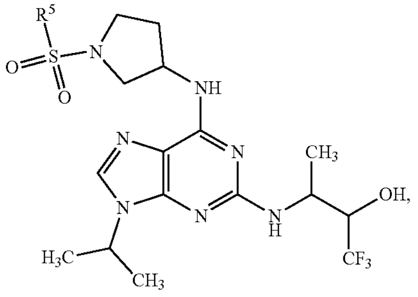

and wherein $R^5$ is as defined in any of the embodiments disclosed in this specification.

In some embodiments, the present disclosure provides compounds of Formula (I), and pharmaceutically acceptable salts thereof, wherein the compound has the structure of Formula (I-80):

(I-80)

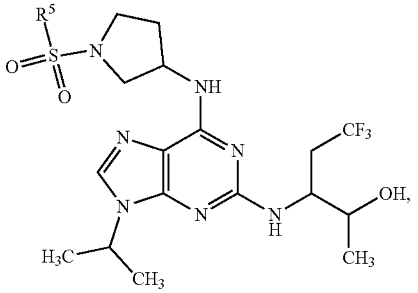

and wherein $R^5$ is as defined in any of the embodiments disclosed in this specification.

In some embodiments, the present disclosure provides compounds of Formula (I), and pharmaceutically acceptable salts thereof, wherein the compound has the structure of Formula (I-81):

(I-81)

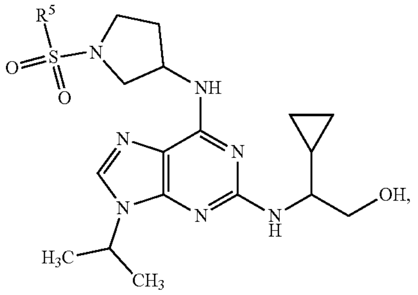

and wherein $R^5$ is as defined in any of the embodiments disclosed in this specification.

In some embodiments, the present disclosure provides compounds of Formula (I), and pharmaceutically acceptable salts thereof, wherein the compound has the structure of Formula (I-82):

(I-82)

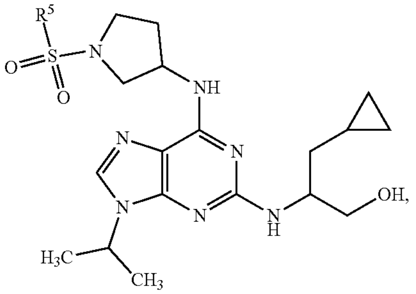

and wherein $R^5$ is as defined in any of the embodiments disclosed in this specification.

In some embodiments, the present disclosure provides compounds of Formula (I), and pharmaceutically acceptable salts thereof, wherein the compound has the structure of Formula (I-83):

(I-83)

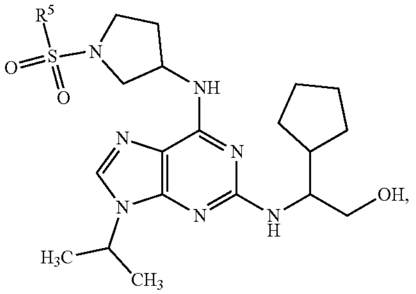

and wherein $R^5$ is as defined in any of the embodiments disclosed in this specification.

In some embodiments, the present disclosure provides compounds of Formula (I), and pharmaceutically acceptable salts thereof, wherein the compound has the structure of Formula (I-84):

(I-84)

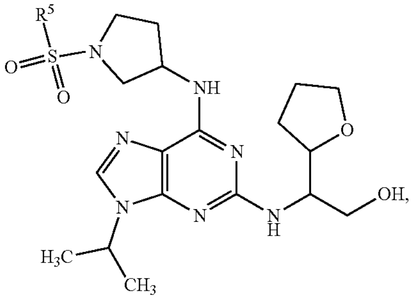

and wherein $R^5$ is as defined in any of the embodiments disclosed in this specification.

In some embodiments, the present disclosure provides compounds of Formula (I), and pharmaceutically acceptable salts thereof, wherein the compound has a structure selected from the structures of Formulae I-1 through I-117 set out in Table 1, and wherein, as applicable, $R^5$ is $C_{1-3}$-alkyl, wherein the $C_{1-3}$-alkyl is optionally substituted with one or more substituents independently selected from fluoro and $C_{1-3}$-alkoxy.

In some embodiments, the present disclosure provides compounds of Formula (I), and pharmaceutically acceptable salts thereof, wherein the compound has a structure selected from the structures of Formulae I-1 through I-117 set out in Table 1, and wherein, as applicable, $R^5$ is $C_{3-6}$-cycloalkyl, wherein the $C_{3-6}$-cycloalkyl is optionally substituted with one or more fluoro substituents. In one aspect, $R^5$ is cyclopropyl, wherein the cyclopropyl is optionally substituted with one or more fluoro substituents. In another aspect, $R^5$ is cyclobutyl, wherein the cyclobutyl is optionally substituted with one or more fluoro substituents. In another aspect, $R^5$ is cyclopentyl, wherein the cyclopentyl is optionally substituted with one or more fluoro substituents. In another aspect, $R^5$ is cyclohexyl, wherein the cyclohexyl is optionally substituted with one or more fluoro substituents.

In some embodiments, the present disclosure provides compounds of Formula (I), and pharmaceutically acceptable salts thereof, wherein the compound has a structure selected from the structures of Formulae I-1 through I-117 set out in Table 1, and wherein, as applicable, $R^5$ is pyrazolyl, wherein the pyrazolyl is optionally substituted with one or more substituents independently selected from $C_{1-3}$-alkyl. In one aspect, $R^5$ is pyrazolyl, wherein the pyrazolyl is optionally substituted with one or more methyl.

In some embodiments, the present disclosure provides compounds of Formula (I), and pharmaceutically acceptable salts thereof, wherein the compound has a structure selected from the structures of Formulae I-1 through I-117 set out in Table 1, and wherein, as applicable, $R^5$ is imidazolyl, wherein the imidazolyl is optionally substituted with one or more substituents independently selected from $C_{1-3}$-alkyl. In one aspect, $R^5$ is imidazolyl, wherein the imidazolyl is optionally substituted with one or more methyl.

In some embodiments, the present disclosure provides compounds of Formula (I), and pharmaceutically acceptable salts thereof, wherein the compound has a structure selected from the structures of Formulae I-1 through I-117 set out in Table 1, and wherein, as applicable, $R^5$ is —$NR^8R^9$. In one aspect, $R^9$ is $C_{1-3}$-alkyl, wherein the $C_{1-3}$-alkyl is optionally substituted with one or more fluoro substituents. In another aspect, $R^9$ is tetrahydrofuranyl. In another aspect, $R^9$ is 1,4-dioxanyl-$C_{1-3}$-alkyl. In another aspect, $R^9$ is 1,4-dioxanylmethyl.

In some embodiments, the present disclosure provides compounds of Formula (I), and pharmaceutically acceptable salts thereof, wherein the compound is selected from the group consisting of:

(S)-3-((9-ethyl-2-(1-oxoisoindolin-4-yl)-9H-purin-6-yl)amino)-N-methylpyrrolidine-1-sulfonamide [Example 1];

(S)-3-((9-ethyl-2-((R)-1-hydroxy-2,3-dihydro-1H-inden-4-yl)-9H-purin-6-yl)amino)-N-methylpyrrolidine-1-sulfonamide [Example 2];

(S)-3-((9-ethyl-2-((R*)-1-hydroxy-1-methyl-2,3-dihydro-1H-inden-4-yl)-9H-purin-6-yl)-amino)-N-methylpyrrolidine-1-sulfonamide [Example 3];

(S)-3-((9-ethyl-2-(((2R,3S)-2-hydroxypentan-3-yl)amino)-9H-purin-6-yl)amino)-N-(2,2,2-trifluoroethyl)pyrrolidine-1-sulfonamide [Example 4];

(S)—N-(2,2-difluoroethyl)-3-((9-ethyl-2-(((2R,3S)-2-hydroxypentan-3-yl)amino)-9H-purin-6-yl)amino)pyrrolidine-1-sulfonamide [Example 5];

(S)—N-ethyl-3-((9-ethyl-2-(((2R,3S)-2-hydroxypentan-3-yl)amino)-9H-purin-6-yl)amino)pyrrolidine-1-sulfonamide [Example 6];

(S)—N-ethyl-3-((9-ethyl-2-(((S)-2-oxopentan-3-yl)amino)-9H-purin-6-yl)amino)-pyrrolidine-1-sulfonamide [Example 7];

(S)—N-ethyl-3-((9-ethyl-2-(((2S,3S)-2-hydroxypentan-3-yl)amino)-9H-purin-6-yl)-amino)pyrrolidine-1-sulfonamide [Example 8];

(S)-3-((9-ethyl-2-(((2R,3S)-2-hydroxypentan-3-yl)amino)-9H-purin-6-yl)amino)pyrrolidine-1-sulfonamide [Example 9];

(S)-3-((9-ethyl-2-(((S)-2-oxopentan-3-yl)amino)-9H-purin-6-yl)amino)pyrrolidine-1-sulfonamide [Example 10];

(S)—N-ethyl-3-((9-ethyl-2-(((2S,3R)-2-hydroxypentan-3-yl)amino)-9H-purin-6-yl)-amino)pyrrolidine-1-sulfonamide [Example 11];

(S)—N-ethyl-3-((9-ethyl-2-(((R)-2-oxopentan-3-yl)amino)-9H-purin-6-yl)amino)pyrrolidine-1-sulfonamide [Example 12];

(S)—N-ethyl-3-((9-ethyl-2-(((2R,3R)-2-hydroxypentan-3-yl)amino)-9H-purin-6-yl)amino)pyrrolidine-1-sulfonamide [Example 13];

(S)-3-((2-(((R)-1-cyclopropyl-2-hydroxyethyl)amino)-9-(difluoromethyl)-9H-purin-6-yl)-amino)-N-ethylpyrrolidine-1-sulfonamide [Example 14];

2-cyclopentyl-2-((9-isopropyl-6-(((S)-1-(methylsulfonyl)pyrrolidin-3-yl)amino)-9H-purin-2-yl)amino)ethan-1-ol [Example 15];

2-((9-isopropyl-6-(((S)-1-(methylsulfonyl)pyrrolidin-3-yl)amino)-9H-purin-2-yl)amino)-2-(tetrahydrofuran-2-yl)ethan-1-ol [Example 16];

(R)-2-((6-(((3R*,4R*)-1-((1H-imidazol-2-yl)sulfonyl)-4-fluoropyrrolidin-3-yl)amino)-9-ethyl-9H-purin-2-yl)amino)-2-cyclopropylethan-1-ol [Example 17];

(S)-3-((2-(((2S,3R)-1,3-dihydroxybutan-2-yl)amino)-9-ethyl-9H-purin-6-yl)amino)-N—((R)-tetrahydrofuran-3-yl)pyrrolidine-1-sulfonamide [Example 18];

(S)-3-((2-(((R)-1-cyclopropyl-2-hydroxyethyl)amino)-9-methyl-9H-purin-6-yl)amino)-N-ethylpyrrolidine-1-sulfonamide [Example 19];

(R)-2-((9-isopropyl-6-(((S)-1-(methylsulfonyl)pyrrolidin-3-yl)-amino)-9H-purin-2-yl)-amino)-3-methylbutan-1-ol [Example 20];

(S)-3-((9-ethyl-2-(((3S,4R)-1,1,1-trifluoro-4-hydroxypentan-3-yl-)-amino)-9H-purin-6-yl)amino)-N-methylpyrrolidine-1-sulfonamide [Example 21];

(S)-3-((9-ethyl-2-(((2R,3S)-2-hydroxypentan-3-yl)amino)-9H-purin-6-yl)amino)-N—((S)-tetrahydrofuran-3-yl)pyrrolidine-1-sulfonamide [Example 22];

(S)—N—(((S)-1,4-dioxan-2-yl)methyl)-3-((9-ethyl-2-(((2R,3S)-2-hydroxypentan-3-yl)-amino)-9H-purin-6-yl)amino)pyrrolidine-1-sulfonamide [Example 23];

(2R,3S)-3-((9-ethyl-6-(((S)-1-((3-fluoroazetidin-1-yl)sulfonyl)pyrrolidin-3-yl)amino)-9H-purin-2-yl)amino)pentan-2-ol [Example 24];

(S)—N—(((R)-1,4-dioxan-2-yl)methyl)-3-((9-ethyl-2-(((2R,3S)-2-hydroxypentan-3-yl)-amino)-9H-purin-6-yl)amino)pyrrolidine-1-sulfonamide [Example 25];

(3R*,4R*)-3-((2-(((R)-1-cyclopropyl-2-hydroxyethyl)amino)-9-methyl-9H-purin-6-yl)-amino)-N-ethyl-4-fluoropyrrolidine-1-sulfonamide [Example 26];

(R)-2-(6-((S)-1-(cyclopropylsulfonyl)pyrrolidin-3-yl)amino)-9-isopropyl-9H-purin-2-ylamino)-3-methylbutan-1-ol [Example 27];

(R)-2-(9-ethyl-6-((S)-1-(methylsulfonyl)pyrrolidin-3-yl)amino)-9H-purin-2-yl)amino)-3-methylbutan-1-ol [Example 28];

(R)-2-(9-cyclopropyl-6-(((S)-1-(methylsulfonyl)pyrrolidin-3-yl-amino)-9H-purin-2-yl)amino)-3-methylbutan-1-ol [Example 29];

(R)-2-cyclopropyl-2-((9-isopropyl-6-(((S)-1-(methylsulfonyl)-pyrrolidin-3-yl)amino)-9H-purin-2-yl)amino)ethanol [Example 30];

(2R,3S)-3-((9-isopropyl-6-(((S)-1-(1-methyl-1H-pyrazol-4-yl-sulfonyl)pyrrolidin-3-yl)amino)-9H-purin-2-yl)amino)pentan-2-ol [Example 31];

(2R,3S)-3-((9-isopropyl-6-(((S)-1-(1-methyl-1H-imidazol-4-yl-sulfonyl)pyrrolidin-3-yl)amino)-9H-purin-2-yl)amino)pentan-2-ol [Example 32];

(R)-2-((6-(((3R,4R)-4-fluoro-1-(methylsulfonyl)pyrrolidin-3-yl)amino)-9-isopropyl-9H-purin-2-yl)amino)-3-methylbutan-1-ol [Example 33];

(R)-2-((9-isopropyl-6-(((3S,5R)-5-methyl-1-(methylsulfonyl)-pyrrolidin-3-yl)amino)-9H-purin-2-yl)amino)-3-methylbutan-1-ol [Example 34];

(R)-2-((9-isopropyl-6-(((3S,5S)-5-methyl-1-(methylsulfonyl)-pyrrolidin-3-yl)amino)-9H-purin-2-yl)amino)-3-methylbutan-1-ol [Example 35];

(R)-2-((9-isopropyl-6-(((3S,4R)-4-methyl-1-(methylsulfonyl)-pyrrolidin-3-yl)amino)-9H-purin-2-yl)amino)-3-methylbutan-1-ol [Example 36];

(2R,3S)-3-((9-isopropyl-6-(((3S,5R)-5-methyl-1-(methylsulfonyl)-pyrrolidin-3-yl)amino)-9H-purin-2-yl)amino)pentan-2-ol [Example 37];

(R)-2-((9-ethyl-6-(((S)-1-(methylsulfonyl)pyrrolidin-3-yl)amino)-9H-purin-2-yl)amino)butan-1-ol [Example 38];

(R)-2-cyclopropyl-2-((9-ethyl-6-(((S)-1-(methylsulfonyl)pyrrolidin-3-yl)amino)-9H-purin-2-yl)amino)ethanol [Example 39];

(R)-2-((9-ethyl-6-(((S)-1-(2,2,2-trifluoroethylsulfonyl)pyrrolidin-3-yl)amino)-9H-purin-2-yl)amino)-3-methylbutan-1-ol [Example 40];

(R)-2-((6-(((S)-1-(cyclopropylsulfonyl)pyrrolidin-3-yl)amino)-9-ethyl-9H-purin-2-yl)amino)-3-methylbutan-1-ol [Example 41];

(R)-2-((9-ethyl-6-(((S)-1-((2-methoxyethyl)sulfonyl)pyrrolidin-3-yl)amino)-9H-purin-2-yl)amino)-3-methylbutan-1-ol [Example 42];

(R)-2-((9-ethyl-6-(((S)-1-(fluoromethylsulfonyl)pyrrolidin-3-yl)amino)-9H-purin-2-yl)amino)-3-methylbutan-1-ol [Example 43];

(S)-3-((9-ethyl-2-(((2R,3S)-2-hydroxypentan-3-yl)amino)-9H-purin-6-yl)amino)-N-methylpyrrolidine-1-sulfonamide [Example 44];

(S)-3-((9-ethyl-2-(((S)-2-oxopentan-3-yl)amino)-9H-purin-6-yl)amino)-N-methylpyrrolidine-1-sulfonamide [Example 45];

(S)-3-((9-ethyl-2-(((S)-2-hydroxy-2-methylpentan-3-yl)amino)-9H-purin-6-yl)amino)-N-methylpyrrolidine-1-sulfonamide [Example 46];

(S)-3-((9-ethyl-2-(((S)-2-hydroxy-2-methylpentan-3-yl)amino)-9H-purin-6-yl)amino)-N-methylpyrrolidine-1-sulfonamide [Example 47];

(S)-3-((9-ethyl-2-(((S)-1-hydroxybutan-2-yl)amino)-9H-purin-6-yl)amino)-N-methylpyrrolidine-1-sulfonamide [Example 48];

(S)-3-((9-ethyl-2-(((2R*,3S*)-4,4,4-trifluoro-3-hydroxybutan-2-yl)amino)-9H-purin-6-yl)amino)-N-methylpyrrolidine-1-sulfonamide [Examples 49/50];

(S)-3-((9-ethyl-2-(((1R,2S)-2-hydroxy-2,3-dihydro-1H-inden-1-yl)amino)-9H-purin-6-yl)amino)-N-methylpyrrolidine-1-sulfonamide [Example 51];

(3R*,4R*)-3-((9-ethyl-2-(((2R,3S)-2-hydroxypentan-3-yl)amino)-9H-purin-6-yl)amino)-4-fluoro-N-methylpyrrolidine-1-sulfonamide [Example 52];

(S)—N-ethyl-3-((2-(((2R,3S)-2-hydroxypentan-3-yl)amino)-9-methyl-9H-purin-6-yl)amino)pyrrolidine-1-sulfonamide [Example 53];

(S)-3-((9-(fluoromethyl)-2-(((2R,3S)-2-hydroxypentan-3-yl)amino)-9H-purin-6-yl)amino)-N-methylpyrrolidine-1-sulfonamide [Example 54];

(S)-3-((9-(difluoromethyl)-2-(((2R,3S)-2-hydroxypentan-3-yl)amino)-9H-purin-6-yl)amino)-N-methylpyrrolidine-1-sulfonamide [Example 55];

(2R,3S)-3-((6-(((3R*,4R*)-1-((1H-imidazol-2-yl)sulfonyl)-4-fluoropyrrolidin-3-yl)-amino)-9-methyl-9H-purin-2-yl)amino)pentan-2-ol [Example 56];

(2R,3S)-3-((6-(((3R*,4R*)-1-((1H-imidazol-2-yl)sulfonyl)-4-fluoropyrrolidin-3-yl)-amino)-9-(difluoromethyl)-9H-purin-2-yl)amino)-1,1,1-trifluorobutan-2-ol [Example 57];

(S)-3-((2-(((R*)-1-cyclopropyl-3-hydroxypropan-2-yl)amino)-9-ethyl-9H-purin-6-yl)-amino)-N-ethylpyrrolidine-1-sulfonamide [Example 58];

(S)—N-ethyl-3-((9-ethyl-2-(((R*)-3-hydroxy-3-methylbutan-2-yl)-amino)-9H-purin-6-yl)amino)pyrrolidine-1-sulfonamide [Example 59];

(S)—N-ethyl-3-((3-ethyl-5-(((2R,3S)-2-hydroxypentan-3-yl)amino)-3H-imidazo[4,5-b]pyridin-7-yl)amino)pyrrolidine-1-sulfonamide [Example 60];

(R)-2-((6-(((3R*,4R*)-1-((1H-imidazol-2-yl)sulfonyl)-4-fluoro-pyrrolidin-3-yl)amino)-9-(difluoromethyl)-9H-purin-2-yl)amino)-2-cyclopropylethan-1-ol [Example 61]; and (2R,3S)-3-((6-(((S)-1-((1H-pyrazol-5-yl)sulfonyl)pyrrolidin-3-yl)amino)-9-ethyl-9H-purin-2-yl)amino)pentan-2-ol [Example 62].

C. Combination of Embodiments

Any embodiment of the compounds described in the present disclosure can be combined with any other suitable embodiment described herein to provide additional embodiments. For example, where one embodiment individually or collectively describes possible groups for $R^1$, $R^2$, $R^3$, $R^4$, and/or $R^5$ and a separate embodiment describes possible groups for $R^5$, it is understood that these embodiments can be combined to provide an additional embodiment describing the possible groups described for $R^1$, $R^3$, $R^4$, and/or $R^5$ together with the possible groups described for $R^5$. In other words, for any of the embodiments of the compounds described in the present disclosure, the $R^5$ substituent can be as defined in any of the embodiments of $R^5$ described in this specification.

D. Further Embodiments

In some embodiments, the compounds of the present disclosure have an $IC_{50}$ value for CDK2 inhibition below about 200 nM as measured in the NanoBRET assay described in Example 63 below. In one aspect, the $IC_{50}$ value is below about 150 nM. In another aspect, the $IC_{50}$ value is below about 100 nM. In another aspect, the $IC_{50}$ value is below about 50 nM. In another aspect, the $IC_{50}$ value is below about 25 nM.

In some embodiments, the compounds of the present disclosure have an $IC_{50}$ value for NPM phosphorylation inhibition below about 1 μM as measured in the pNPM phosphorylation assay described in Example 64 below. In one aspect, the $IC_{50}$ value in the assay is below about 750 nM. In another aspect, the $IC_{50}$ value in the assay is below about 500 nM. In another aspect, the $IC_{50}$ value in the assay is below about 250 nM. In another aspect, the $IC_{50}$ value in the assay is below about 100 nM.

In some embodiments, the compounds of the present disclosure are selective inhibitors of CDK2, i.e., they have a lower inhibitory constant (e.g., Ki or $IC_{50}$) for CDK2 relative to other enzymatic targets. Compounds that are selective CDK2 inhibitors generally will have an improved safety profile, improved dosing schedule, and/or enhanced overall efficacy relative to non-selective CDK2 inhibitors. In one aspect, the compounds have an inhibitory constant for CDK2 that is at least 10 times lower than the corresponding inhibitory constant for at least one of CDK1, CDK4, CDK6, and/or CDK9. In another aspect, the compounds have an inhibitory constant for CDK2 that is at least 10 times lower than the corresponding inhibitory constant for at least two of CDK1, CDK4, CDK6, and/or CDK9. In another aspect, the compounds have an inhibitory constant for CDK2 that is at least 10 times lower than the corresponding inhibitory constant for at least three of CDK1, CDK4, CDK6, and/or CDK9. In another aspect, the compounds have an inhibitory constant for CDK2 that is at least 10 times lower than the corresponding inhibitory constant for CDK1, CDK4, CDK6, and CDK9.

In some embodiments, the compounds of the present disclosure are at least about 5 times more selective for CDK2 relative to CDK1 as measured in the NanoBRET assay described in Example 63 below. In one aspect, the compounds are at least about 10 times more selective for CDK2 relative to CDK1. In another aspect, the compounds have an $IC_{50}$ value for CDK1 inhibition greater than about 0.1 μM. In another aspect, the compounds have an $IC_{50}$ value for CDK1 inhibition greater than about 0.2 μM. In another aspect, the compounds have an $IC_{50}$ value for CDK1 greater than about 0.3 μM.

In some embodiments, the compounds of the present disclosure are at least about 30 times more selective for CDK2 relative to CDK4 as measured in the NanoBRET assay described in Example 63 below. In one aspect, the compounds are at least about 100 times more selective for CDK2 relative to CDK4. In another aspect, the compounds are at least about 500 times more selective for CDK2 relative to CDK4. In another aspect, the compounds have an $IC_{50}$ value for CDK4 inhibition greater than about 0.7 μM. In another aspect, the compounds have an $IC_{50}$ value for CDK4 inhibition greater than about 1.0 μM. In another aspect, the compounds have an $IC_{50}$ value for CDK4 inhibition greater than about 5.0 μM.

In some embodiments, the compounds of the present disclosure are at least about 100 times more selective for CDK2 relative to CDK9 as measured in POLR2A Ser2 phosphorylation assay described in Example 65 below. In one aspect, the compounds are at least about 100 times more selective for CDK2 relative to CDK9. In another aspect, the compounds are at least about 500 times more selective for CDK2 relative to CDK9. In another aspect, the compounds are at least about 1000 times more selective for CDK2 relative to CDK9. In another aspect, the compounds have an $IC_{50}$ value in the assay greater than about 1.0 μM. In another aspect, the compounds have an $IC_{50}$ value in the assay greater than about 5.0 μM. In another aspect, the compounds have an $IC_{50}$ value in the assay greater than about 10.0 μM.

In some embodiments, the compounds of the present disclosure inhibit MCF7 cellular proliferation as measured in the EdU assay described in Example 66 below. In one aspect, the compounds have an $IC_{50}$ value in the assay below about 2.0 μM. In another aspect, the $IC_{50}$ value is below about 1.0 μM. In another aspect, the $IC_{50}$ value is below about 750 nM. In another aspect, the $IC_{50}$ value is below about 500 nM.

In some embodiments, the compounds of the present disclosure inhibit OVCAR3 cellular proliferation as measured in the EdU assay described in Example 66 below. In one aspect, the compounds have an $IC_{50}$ value in the assay below about 1.0 μM. In another aspect, the $IC_{50}$ value is below about 750 nM. In another aspect, the $IC_{50}$ value is below about 500 nM. In another aspect, the $IC_{50}$ value is below about 250 nM.

In some embodiments, the compounds of the present disclosure have a pharmaceutically acceptable metabolic stability measured as described for the human liver microsomes (HLM) assay reported in Example 83 below. In one aspect, the compounds have an HLM $CL_{int}$ value less than about 300 μL/min/mg. In another aspect, the HLM $CL_{int}$ value is less than about 200 μL/min/mg. In another aspect, the HLM $CL_{int}$ value is less than about 100 μL/min/mg. In another aspect, the HLM $CL_{int}$ value is less than about 50 μL/min/mg.

E. Salts

The compounds of the present disclosure may exist in salt form or in non-salt form (i.e., as a free base), and the present disclosure covers both salt forms and non-salt forms. The compounds may form acid addition salts or base addition salts. In general, an acid addition salt can be prepared using various inorganic or organic acids. Such salts can typically be formed by, for example, mixing the compound with an acid (e.g., a stoichiometric amount of an acid) using various methods known in the art. This mixing may occur in water, an organic solvent (e.g., ether, ethyl acetate, ethanol, methanol, isopropanol, or acetonitrile), or an aqueous/organic mixture. In another aspect, the acid addition salts are, for example, trifluoroacetate, formate, acetate or hydrochloric. In general, a base addition salt can be prepared using various inorganic or organic bases, for example an alkali or alkaline earth metal salt such as a sodium, calcium or magnesium salt, or other metal salts, such as potassium or zinc, or an ammonium salt, or a salt with an organic base such as methylamine, dimethylamine, trimethylamine, piperidine or morpholine. The skilled person will be aware of the general principles and techniques of preparing pharmaceutical salts, such as those described in, for example, *J. Pharm. Sci.* 1977 66, 1. Examples of pharmaceutically acceptable salts are also described in "Handbook of Pharmaceutical Salts: Properties, Selection, and Use" by Stahl and Wermuth (Wiley-VCH, Weinheim, Germany, 2002).

F. Isomers

The compounds and salts of the present disclosure may exist in one or more geometrical, optical, enantiomeric, and diastereomeric forms, including, but not limited to, cis- and trans-forms, E- and Z-forms, and R-, S- and meso-forms. Unless otherwise stated a reference to a particular compound includes all such isomeric forms, including racemic and other mixtures thereof. Where appropriate such isomers can be separated from their mixtures by the application or adaptation of known methods (e.g., chromatographic techniques and recrystallisation techniques). Where appropriate such isomers can be prepared by the application or adaptation of known methods. In some embodiments, a single stereoisomer is obtained by isolating it from a mixture of isomers (e.g., a racemate) using, for example, chiral chromatographic separation. In other embodiments, a single stereoisomer is obtained through direct synthesis from, for example, a chiral starting material.

A particular enantiomer of a compound described herein may be more active than other enantiomers of the same compound. In one embodiment, the compound, or a pharmaceutically acceptable salt thereof, is a single enantiomer being in an enantiomeric excess (% ee) of ≥90, ≥95%, ≥96%, ≥97, ≥98% or ≥99%. In one aspect, the single enantiomer is present in an enantiomeric excess (% ee) of ≥99%.

In another embodiment, the present disclosure relates to a pharmaceutical composition comprising a compound, or a pharmaceutically acceptable salt thereof, which is a single enantiomer being in an enantiomeric excess (% ee) of ≥90, ≥95%, ≥96%, ≥97, ≥98% or ≥99%, or a pharmaceutically acceptable salt thereof, in association with one or more pharmaceutically acceptable excipients. In one aspect, the single enantiomer is present in an enantiomeric excess (% ee) of ≥99%.

G. Additional Forms

The compounds and salts of the present disclosure may exist in various tautomeric forms and the specification encompasses all such tautomeric forms. "Tautomers" are structural isomers that exist in equilibrium resulting from the migration of a hydrogen atom.

The compounds of the present disclosure, and pharmaceutically acceptable salts thereof, may exist as solvates (such as a hydrates) as well as unsolvated forms, and the present specification covers all such solvates.

The compounds of the present disclosure, and pharmaceutically acceptable salts thereof, may exist in crystalline or amorphous form, and the present specification covers all such forms.

Compounds and salts of the present disclosure may be isotopically-labeled (or "radio-labeled"). In that instance, one or more atoms are replaced by an atom having an atomic mass or mass number different from the atomic mass or mass number typically found in nature. The specification encompasses isotopically-labelled forms of compounds disclosed herein. Examples of isotopes that may be incorporated include $^{2}H$ (also written as "D" for deuterium), $^{3}H$ (also written as "T" for tritium), $^{11}C$, $^{13}C$, $^{14}C$, $^{13}N$, $^{15}N$, $^{15}O$, $^{17}O$, $^{18}O$ and $^{36}Cl$. The isotope that is used will depend on the specific application of that radio-labeled derivative. For example, for in vitro receptor labeling and competition assays, $^{3}H$ or $^{14}C$ are often useful. For radio-imaging applications, $^{11}C$ is often useful. In some embodiments, the radionuclide is $^{3}H$. In some embodiments, the radionuclide is $^{14}C$. In some embodiments, the radionuclide is $^{11}C$.

H. Intermediates

In some embodiments, the present disclosure provides additional compounds that are useful as intermediates for preparing the compounds of the present disclosure, and pharmaceutically acceptable salts thereof.

III. Methods of Use

The compounds of the present disclosure, and pharmaceutically acceptable salts thereof, are inhibitors of cyclin-dependent kinase 2 (CDK2) activity.

In some embodiments, therefore, the present disclosure provides a method for treating or preventing a CDK2-mediated condition in a subject suffering from or susceptible to the CDK2-mediated condition by administering to the subject a therapeutically effective amount of a compound of Formula I, or a pharmaceutically acceptable salt thereof.

In some embodiments, the present disclosure provides a method for inhibiting CDK2 activity in a subject suffering from or susceptible to the CDK2-mediated condition by administering to the subject a therapeutically effective amount of a compound of the present disclosure, or a pharmaceutically acceptable salt thereof.

In some embodiments, the present disclosure provides a method for treating a cancer in a subject suffering from or susceptible to the cancer by administering to the subject a therapeutically effective amount of a compound of the present disclosure, or a pharmaceutically acceptable salt thereof. In one aspect, the cancer is a solid tumor cancer. In another aspect the cancer is a hematological cancer. In another aspect, the cancer is mediated, in whole or in part, by CDK2.

In some embodiments, the present disclosure provides a method for treating a cancer characterized by amplification or overexpression of the cyclin E (CCNE) gene in a subject suffering from or susceptible to the cancer by administering to the subject a therapeutically effective amount of a compound of the present disclosure, or a pharmaceutically acceptable salt thereof. In one aspect, the cancer is characterized by amplification or overexpression of CCNE1. In another aspect, the cancer is characterized by amplification or overexpression of CCNE2. In another aspect, the cancer is characterized by amplification or overexpression of CCNE1 and CCNE2. In another aspect, the cancer is a solid tumor cancer characterized by amplification or overexpression of CCNE1 and/or CCNE2. In another aspect, the solid tumor cancer is selected from the group consisting of breast cancer, ovarian cancer, endometrial cancer, and lung cancer. In another aspect, the solid tumor cancer is breast cancer or ovarian cancer. In another aspect the cancer is a hematological cancer characterized by amplification or overexpression of CCNE1 and/or CCNE2.

In some embodiments, the present disclosure provides a method for treating or preventing a solid tumor cancer in a subject suffering from or susceptible to the cancer by administering to the subject a therapeutically effective amount of a compound of the present disclosure, or a pharmaceutically acceptable salt thereof, wherein the solid tumor cancer is selected from the group consisting of breast cancer, ovarian cancer, endometrial cancer, cervical cancer, uterine cancer, gastric cancer, prostate cancer, bladder cancer, lung cancer, esophageal cancer, head and neck cancer, kidney cancer, liver cancer, pancreatic cancer, thyroid cancer, colorectal cancer, and skin cancer. In one aspect, the solid tumor cancer is selected from the group consisting of breast cancer, ovarian cancer, endometrial cancer, cervical cancer, lung cancer, colorectal cancer, and skin cancer. In another aspect, the solid tumor cancer is selected from the group consisting of breast cancer, ovarian cancer, endometrial cancer, and lung cancer. In another aspect, the solid tumor cancer is breast cancer or ovarian cancer.

In some embodiments, the cancer is breast cancer. In one aspect, the breast cancer is selected from the group consisting of hormone receptor positive (HR+) breast cancer, hormone receptor negative (HR−) breast cancer, and triple negative breast cancer. In another aspect, the breast cancer is HR+ HER2− breast cancer. In another aspect, the breast cancer is a chemotherapy-resistant breast cancer. In another aspect, the breast cancer is a radiotherapy-resistant breast cancer. In another aspect, the breast cancer is characterized by amplification or overexpression of CCNE1 and/or CCNE2. In another aspect, the breast cancer is an advanced or metastatic breast cancer. In another aspect, the subject suffering from breast cancer was previously treated with a CDK4/6 inhibitor.

In some embodiments, the cancer is ovarian cancer. In one aspect, the ovarian cancer is platinum-sensitive or platinum-resistant ovarian cancer. In another aspect, the ovarian cancer is characterized by amplification or overexpression of CCNE1 and/or CCNE2. In another aspect, the cancer is epithelial ovarian cancer. In another aspect, the ovarian cancer is serous ovarian cancer. In another aspect, the ovarian cancer is high-grade serous ovarian cancer (HGSOC). In another aspect, the ovarian cancer is an advanced or metastatic ovarian cancer. In another aspect, the ovarian cancer is metastatic high-grade serous ovarian cancer (HGSOC). In another aspect, the subject suffering from ovarian cancer was previously treated with a platinum-based chemotherapy.

In some embodiments, the cancer the condition is lung cancer. In one aspect, the lung cancer is small cell lung cancer (SCLC). In another aspect, the lung cancer is non-small cell lung cancer (NSCLC). In another aspect, the non-small cell lung cancer (NSCLC) is squamous cell carcinoma. In another aspect, the non-small cell lung cancer (NSCLC) is adenocarcinoma. In another aspect, the non-small cell lung cancer (NSCLC) is large-cell carcinoma.

In some embodiments, the present disclosure provides a method for treating or preventing a hematological cancer in a subject suffering from or susceptible to the cancer by administering to the subject a therapeutically effective amount of a compound of the present disclosure, or a pharmaceutically acceptable salt thereof, wherein the hematological cancer is selected from the group consisting of non-Hodgkin's lymphoma, leukemia, multiple myeloma (MM), and myelodysplastic syndrome (MDS). In one aspect, the hematological cancer is non-Hodgkin's lymphoma (NHL). In another aspect, the non-Hodgkin's lymphoma (NHL) is selected from diffuse large B-cell lymphoma (DLBCL), follicular lymphoma, mantle cell lymphoma (MCL), and marginal zone lymphoma. In another aspect, the hematological cancer is leukemia. In another aspect, the leukemia is selected from the group consisting of acute lymphoblastic leukemia (ALL), acute myelogenous leukemia (AML), chronic lymphocytic leukemia (CLL), and chronic myeloid leukemia (CML). In another aspect, the hematological cancer is multiple myeloma (MM). In another aspect, the hematological cancer is myelodysplastic syndrome (MDS).

In some embodiments, the compound of the present disclosure, or a pharmaceutically acceptable salt thereof, is administered as first line therapy.

In some embodiments, the compound of the present disclosure, or a pharmaceutically acceptable salt thereof, is administered as second line (or later) therapy.

In some embodiments, the subject to whom a therapeutically effective amount of a compound of the present disclosure, or a pharmaceutically acceptable salt thereof, is administered exhibits a partial response (PR) in response to such treatment.

In some embodiments, the subject to whom a therapeutically effective amount of a compound of the present disclosure, or a pharmaceutically acceptable salt thereof, is administered exhibits a complete response (CR) in response to such treatment.

In some embodiments, the subject to whom a therapeutically effective amount of a compound of the present disclosure, or a pharmaceutically acceptable salt thereof, is administered exhibits an improved progression free survival (PFS) in response to such treatment.

In some embodiments, the subject to whom a therapeutically effective amount of a compound of the present disclosure, or a pharmaceutically acceptable salt thereof, is administered exhibits an improved overall survival (OR) in response to such treatment.

PR, CR, PFS, and OR can be assessed, for example, in accordance with RECIST (Response Evaluation Criteria in Solid Tumours) guidelines (version 1.1).

The subject treated typically will be a human or non-human mammal, particularly a human. Suitable subjects can also include domestic or wild animals; companion animals (including dogs, cats, and the like); livestock (including horses, cows and other ruminants, pigs, poultry, rabbits, and the like); primates (including monkeys such as rhesus monkeys, cynomolgus (also known as crab-eating or long-tailed) monkeys, marmosets, tamarins, chimpanzees, macaques, and the like); and rodents (including rats, mice, gerbils, guinea pigs, and the like).

In some embodiments, the present disclosure provides the compounds of the present disclosure, or pharmaceutically acceptable salts thereof, for use as medicaments for treating a cancer mediated, in whole or in part, by CDK2.

In some embodiments, the present disclosure provides for the use of the compounds of the present disclosure, or pharmaceutically acceptable salts thereof, for treating a cancer mediated, in whole or in part, by CDK2.

In some embodiments, the present disclosure provides for the use of the compounds of the present disclosure, or pharmaceutically acceptable salts thereof, for the manufacture of medicaments for treating a cancer mediated, in whole or in part, by CDK2.

IV. Combination Therapies and Fixed-Dose Combinations

The compounds and pharmaceutically acceptable salts of the present disclosure may be used in the methods described above as either as single pharmacological agents or in combination with other pharmacological agents or techniques. Such combination therapies may be achieved by way of the simultaneous, sequential, or separate dosing of the individual components of the treatment. These combination therapies (and corresponding combination products) employ the compounds and pharmaceutically acceptable salts of the present disclosure within the dosage ranges described in this application and the other pharmacological agent(s), typically within its approved dosage range(s).

In some embodiments, the present disclosure provides a combination suitable for use in the treatment of a cancer mediated, in whole or in part, by CDK2, wherein the combination comprises a compound of the present disclosure, or a pharmaceutically acceptable salt thereof, and a cyclin-dependent kinase 4/6 (CDK4/6) inhibitor. In one aspect, the CDK4/6 inhibitor is selected from the group consisting of palbociclib, abemaciclib, ribociclib, lerociclib (G1T38), trilaciclib (GIT28), dalpiciclib (SHR-6390), and BPI-16350. In another aspect, the CDK4/6 inhibitor is selected from the group consisting of palbociclib, abemaciclib, ribociclib, and dalpiciclib. In another aspect, the CDK4/6 inhibitor is palbociclib. In another aspect, the CDK4/6 inhibitor is abemaciclib. In another aspect, the CDK4/6 inhibitor is ribociclib. In another aspect, the CDK4/6 inhibitor is dalpiciclib.

In some embodiments, the present disclosure provides a combination suitable for use in the treatment of a cancer mediated, in whole or in part, by CDK2, wherein the combination comprises a compound of the present disclosure, or a pharmaceutically acceptable salt thereof, and endocrine therapy. In one aspect, the cancer is breast cancer.

In some embodiments, the present disclosure provides a combination suitable for use in the treatment of a cancer mediated, in whole or in part, by CDK2, wherein the combination comprises a compound of the present disclosure, or a pharmaceutically acceptable salt thereof, and an aromatase inhibitor. In one aspect, the aromatase inhibitor is selected from the group consisting of anastrozole, letrozole, exemestane, vorozole, formestane, and fadrozole. In another aspect, the combination further comprises everolimus. In another aspect, the cancer is breast cancer.

In some embodiments, the present disclosure provides a combination suitable for use in the treatment of a cancer mediated, in whole or in part, by CDK2, wherein the combination comprises a compound of the present disclosure, or a pharmaceutically acceptable salt thereof, and a selective estrogen receptor degrader (SERD). In one aspect, the SERD is selected from the group consisting of fulvestrant, giredestrant (GDC-9545), amcenestrant (SAR439859), camizestrant (AZD9833), rintodestrant (GIT48), imlunestrant (LY3484356), elacestrant (RAD-1901), taragarestrant (D-0502), OP1250 (Olema), LSZ102 (Novartis), ZN-c5 (Zentalis), and SHR9549 (Jiangsu Hengrui Medicine). In another aspect, the SERD is selected from the group consisting of fulvestrant, giredestrant, camizestrant, imlunestrant, and elacestrant. In another aspect, the SERD is fulvestrant. In another aspect, the SERD is fulvestrant and the combination administered further comprises alpelisib. In another aspect, the SERD is camizestrant (AZD9833). In another aspect, the SERD is camizestrant and the combination administered further comprises alpelisib. In another aspect, the cancer is breast cancer.

In some embodiments, the present disclosure provides a combination suitable for use in the treatment of a cancer mediated, in whole or in part, by CDK2, wherein the combination comprises a compound of the present disclosure, or a pharmaceutically acceptable salt thereof; a selective estrogen receptor degrader (SERD); and a cyclin-dependent kinase 4/6 (CDK4/6) inhibitor. In one aspect, the SERD is selected from the group consisting of fulvestrant, giredestrant (GDC-9545), amcenestrant (SAR439859), camizestrant (AZD9833), rintodestrant (G1T48), imlunestrant (LY3484356), elacestrant (RAD-1901), taragarestrant (D-0502), OP1250 (Olema), LSZ102 (Novartis), ZN-c5 (Zentalis), and SHR9549 (Jiangsu Hengrui Medicine); and the CDK4/6 inhibitor is selected from the group consisting of palbociclib, abemaciclib, ribociclib, lerociclib (G1T38), trilaciclib (G1T28), dalpiciclib (SHR-6390), and BPI-16350. In another aspect, the SERD is selected from the group consisting of fulvestrant, giredestrant, camizestrant, imlunestrant, and elacestrant; and the CDK4/6 inhibitor is selected from the group consisting of palbociclib, abemaciclib, ribociclib, and dalpiciclib. In another aspect, the SERD is selected from the group consisting of fulvestrant and camizestrant; and the CDK4/6 inhibitor is selected from the group consisting of palbociclib, abemaciclib, and ribociclib. In another aspect, the SERD is camizestrant; and the CDK4/6 inhibitor is selected from the group consisting of palbociclib, abemaciclib, and ribociclib. In another aspect, the cancer is breast cancer.

In some embodiments, the present disclosure provides a combination suitable for use in the treatment of a cancer mediated, in whole or in part, by CDK2, wherein the combination comprises a compound of the present disclosure, or a pharmaceutically acceptable salt thereof, and a PROTAC estrogen receptor degrader (PROTAC ER Degrader). In one aspect, the PROTAC ER Degrader is vepdegestrant. In another aspect, the cancer is breast cancer.

In some embodiments, the present disclosure provides a combination suitable for use in the treatment of a cancer mediated, in whole or in part, by CDK2, wherein the combination comprises a compound of the present disclosure, or a pharmaceutically acceptable salt thereof, and a selective estrogen receptor modulator (SERM). In one aspect, the SERM is selected from the group consisting of anordrin, bazedoxifene, broparestrol, clomifene, cyclofenil, lasofoxifene, ormeloxifene, ospemifene, raloxifene, tamoxifen, and toremifene. In another aspect, the SERM is tamoxifen. In another aspect, the SERM is toremifene. In another aspect, the SERM is selected from the group consisting of acolbifene, afimoxifene, enclomifene, endoxifen, and zuclomifene. In another aspect, the SERM is selected from the group consisting of arzoxifene, brilanestrant, clomifenoxide, droloxifene, etacstil, fispemifene, idoxifene, levormeloxifene, miproxifene, nafoxidine, nitromifene, panomifene, pipendoxifene, trioxifene, zindoxifene, GW-7604 (Glaxo Wellcome), and NNC 45-0095 (Novo Nordisk). In another aspect, the cancer is breast cancer.

In some embodiments, the present disclosure provides a combination suitable for use in the treatment of a cancer mediated, in whole or in part, by CDK2, wherein the combination comprises a compound of the present disclosure, or a pharmaceutically acceptable salt thereof, and an anti-HER2 agent. In one aspect, the anti-HER2 agent is an anti-HER2 monoclonal antibody. In another aspect, the anti-HER2 monoclonal antibody is trastuzumab or pertuzumab. In another aspect, the cancer is breast cancer.

In some embodiments, the present disclosure provides a combination suitable for use in the treatment of a cancer mediated, in whole or in part, by CDK2, wherein the combination comprises a compound of the present disclosure, or a pharmaceutically acceptable salt thereof, and a poly ADP ribose polymerase (PARP) inhibitor. In one aspect, the PARP inhibitor is selected from the group consisting of olaparib, rucaparib, niraparib, talazoparib, and AZD5305 (CAS No. 2589531-76-8). In another aspect, the PARP inhibitor is olaparib. In another aspect, the PARP inhibitor is AZD5305. In another aspect, the cancer is breast cancer. In another aspect, the cancer is ovarian cancer.

In some embodiments, the present disclosure provides a combination suitable for use in the treatment of a cancer mediated, in whole or in part, by CDK2, wherein the combination comprises a compound of the present disclosure, or a pharmaceutically acceptable salt thereof, and a Protein kinase B (Akt) inhibitor. In one aspect, the Akt inhibitor is selected from the group consisting of capivasertib (AZD5363) and ipatasertib (RG7440). In another aspect, the Akt inhibitor is capivasertib. In another aspect, the Akt inhibitor is ipatasertib. In another aspect, the cancer is breast cancer.

In some embodiments, the present disclosure provides a combination suitable for use in the treatment of a cancer mediated, in whole or in part, by CDK2, wherein the combination comprises a compound of the present disclosure, or a pharmaceutically acceptable salt thereof, and radiotherapy.

In some embodiments, the present disclosure provides a combination suitable for use in the treatment of a cancer mediated, in whole or in part, by CDK2, wherein the combination comprises a compound of the present disclosure, or a pharmaceutically acceptable salt thereof, and chemotherapy.

In some embodiments, the present disclosure provides a combination suitable for use in the treatment of breast cancer, wherein the combination comprises a compound of the present disclosure, or a pharmaceutically acceptable salt thereof, and chemotherapy. In one aspect, chemotherapy comprises administration of a combination of cyclophosphamide and doxorubicin ("AC"). In another aspect, chemotherapy comprises administration of a combination of cyclophosphamide, doxorubicin, and a taxane such as paclitaxel or docetaxel ("CAT"). In another aspect, chemotherapy comprises administration of a combination of cyclophosphamide, methotrexate, and fluorouracil (or "CMF").

In some embodiments, the present disclosure provides a combination suitable for use in the treatment of ovarian cancer, wherein the combination comprises a compound of the present disclosure, or a pharmaceutically acceptable salt thereof, and chemotherapy. In one aspect, chemotherapy comprises administration of one or more chemotherapeutics selected from the group consisting of cisplatin, carboplatin, paclitaxel, docetaxel, topotecan, doxorubicin, epirubicin, and gemcitabine. In another aspect, chemotherapy comprises administration of a combination of carboplatin and either doxorubicin, gemcitabine, paclitaxel, or docetaxel. In another aspect, chemotherapy comprises administration of a combination of carboplatin and either paclitaxel or docetaxel. In another aspect, chemotherapy comprises administration of topotecan. In another aspect, chemotherapy comprises administration a combination of bleomycin, etoposide, and cisplatin (BEP). In another aspect, chemotherapy comprises administration of vincristine, dactinomycin, and cyclophosphamide (VAC). In another aspect, chemotherapy comprises administration of combination of paclitaxel, gemcitabine, and oxaliplatin.

V. Pharmaceutical Compositions

The compounds of the present disclosure, and pharmaceutically acceptable salts thereof, may be administered as pharmaceutical compositions, comprising one or more pharmaceutically acceptable excipients. Therefore, in some embodiments the present disclosure provides pharmaceutical compositions comprising a compound of the present disclosure, or a pharmaceutically acceptable salt thereof, and at least one pharmaceutically acceptable excipient.

The excipient(s) selected for inclusion in a particular composition will depend on factors such as the mode of administration and the form of the composition provided. Suitable pharmaceutically acceptable excipients are well known to persons skilled in the art and are described, for example, in the Handbook of Pharmaceutical Excipients, Sixth Edition, Pharmaceutical Press, edited by Rowe, Ray C; Sheskey, Paul J; Quinn, Marian. Pharmaceutically acceptable excipients may function as, for example, adjuvants, diluents, carriers, stabilisers, flavourings, colorants, fillers, binders, disintegrants, lubricants, glidants, thickening agents and coating agents. As persons skilled in the art will appreciate, certain pharmaceutically acceptable excipients may serve more than one function and may serve alternative functions depending on how much of the excipient is present in the composition and what other excipients are present in the composition.

The compositions may be in a form suitable for oral use (for example as tablets, lozenges, hard or soft capsules, aqueous or oily suspensions, emulsions, dispersible powders or granules, syrups or elixirs), for topical use (for example as creams, ointments, gels, or aqueous or oily solutions or suspensions), for administration by inhalation (for example as a finely divided powder or a liquid aerosol), for administration by insufflation (for example as a finely divided powder) or for parenteral administration (for example as a sterile aqueous or oily solution for intravenous, subcutaneous or intramuscular dosing), or as a suppository for rectal dosing. The compositions may be obtained by conventional procedures using conventional pharmaceutical excipients, well known in the art. Thus, compositions intended for oral use may contain, for example, one or more coloring, sweetening, flavoring and/or preservative agents.

The total daily dose will necessarily be varied depending upon the subject treated, the particular route of administration, any therapies being co-administered, and the severity of the illness being treated, and may include single or multiple doses. Specific dosages can be adjusted, for example, depending upon the condition being treated; the age, body weight, general health condition, sex, and diet of the subject; administration routes; dose intervals; excretion rate; and other drugs being co-administered to the subject. An ordinarily skilled physician provided with the disclosure of the present application will be able to determine appropriate dosages and regimens for administration of the therapeutic agent to the subject, and to adjust such dosages and regimens as necessary during the course of treatment, in accordance with methods well-known in the therapeutic arts. The compound of the present disclosure, or a pharmaceutically acceptable salt thereof, typically will be administered to a warm-blooded animal at a unit dose within the range 2.5 to 5000 $mg/m^2$ body area of the animal, or approximately 0.05 to 100 mg/kg, and this normally provides a therapeutically effective dose.

In some embodiments, the present disclosure provides pharmaceutical compositions for use in therapy, comprising a compound of the present disclosure, or a pharmaceutically acceptable salt thereof, and at least one pharmaceutically acceptable excipient.

In some embodiments, the present disclosure provides pharmaceutical compositions for use in the treatment of a CDK2-mediated condition, comprising a compound of the present disclosure, or a pharmaceutically acceptable salt thereof, and at least one pharmaceutically acceptable excipient. In further aspects, the CDK2-mediated condition is selected from those conditions disclosed in this specification. In one aspect, the CDK2-mediated condition is breast cancer. In another aspect, the CDK2-mediated condition is ovarian cancer. In another aspect, the CDK2-mediated condition is endometrial cancer. In another aspect, the CDK2-mediated condition is lung cancer.

VI. Kits

The present disclosure further provides kits comprising a unit dosage form comprising a compound of the present disclosure, or a pharmaceutically acceptable salt thereof, contained within a packaging material and a label or package insert which indicates that the unit dosage form can be used for treating one or more of the previously described conditions.

In some embodiments, the kit comprises a unit dosage form comprising a compound of the present disclosure, or a pharmaceutically acceptable salt thereof, contained within a packaging material and a label or package insert which indicates that the pharmaceutical composition can be used for treating a CDK2-mediated condition. In further aspects, the CDK2-mediated condition is selected from those conditions disclosed in this specification. In one aspect, the CDK2-mediated condition is breast cancer. In another aspect, the CDK2-mediated condition is ovarian cancer. In another aspect, the CDK2-mediated condition is endometrial cancer. In another aspect, the CDK2-mediated condition is lung cancer.

In some embodiments, kit comprises: (a) a first unit dosage form comprising a compound of the present disclosure, or a pharmaceutically acceptable salt thereof; (b) a second unit dosage form comprising a pharmacological agent selected from the group consisting of CDK4/6 inhibitors, aromatase inhibitors, selective estrogen receptor degraders, PROTAC estrogen receptor degraders, selective estrogen receptor modulators, anti-HER2 agents, poly ADP ribose polymerase inhibitors, and Protein kinase B inhibitors; (c) a container means for containing said first and second dosage forms; and (d) a label or package insert which indicates that the first unit dosage form and second unit dosage form can be used for treating a CDK2-mediated condition. In one aspect, the second unit dosage form comprises a CDK4/6 inhibitor.

VII. Methods of Preparation

The present disclosure further provides processes for the preparation of the compounds of the present disclosure, and pharmaceutically acceptable salts thereof. Reaction Schemes 1 to 8 illustrate synthetic routes to these compounds wherein, unless otherwise stated, $R^1$, $R^2$, $R^3$, $R^4$, $R^5$, $R^6$, $R^7$, $R^8$, $R^9$, $R^{10}$, $R^{11}$, $R^{12}$, and $R^{13}$ are as defined in Formula (I). One of skill in the art will appreciate that these methods are representative and are not inclusive of all possible methods for preparing the compounds of the present disclosure.

SCHEME 1

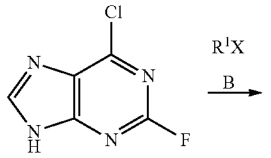

A

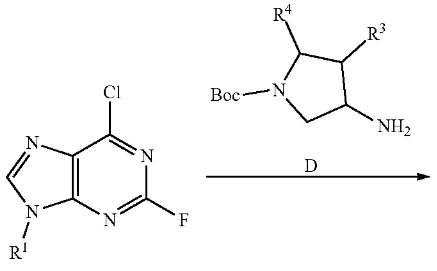

C

-continued

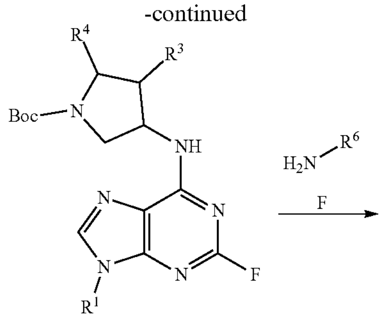

E

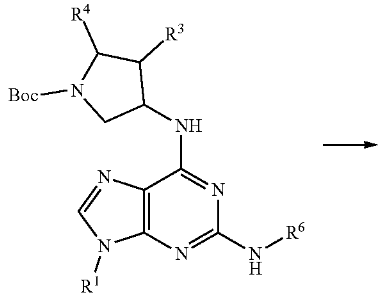

G

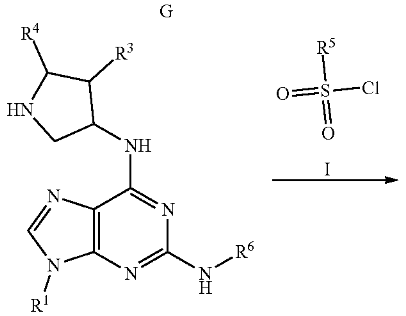

G

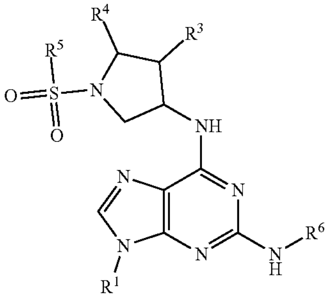

(I)

Scheme 1 illustrates synthetic routes to certain compounds of formula (I). A compound of formula A may be reacted with a compound of formula B (X are leaving groups such as I, Br, etc.) to give a compound of formula C. The reaction may be performed in the presence of a base (typically an inorganic base such as $K_2CO_3$, NaH, etc.) using a solvent (such as DMSO), and at temperatures typically ranging from 0° C. to 60° C.

A compound of formula C may be reacted with an amine of formula D to give a compound of formula E. The reaction may be performed in the presence of a base (typically an organic base such as DIPEA) using a solvent (such as ethanol), and at temperatures typically ranging from 0° C. to 80° C.

A compound of formula E may be reacted with an amine of formula F to give a compound of formula G. The reaction may be performed in the presence of a base (typically an organic base such as DIPEA) using a solvent (such as n-butanol, DMF, DMSO, NMP, 3-ethyl-3-pentanol, or mixtures thereof), and at a temperature typically ranging from 80° C. to 160° C.

A compound of formula G may be transformed into a compound of formula H by deprotection of Boc using a suitable reagent (such as 4 M HCl in 1,4-dioxane) in a solvent (such as DCM), and at 23° C.

A compound of formula H may be reacted with a compound of formula I to give a compound of formula (I). The reaction may be performed in the presence of a base (typically an organic base such as TEA, DIPEA etc.) using a solvent (such as DCM), and at temperatures typically ranging from −78° C. to 23° C.

SCHEME 2

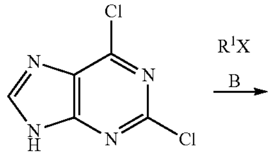

J

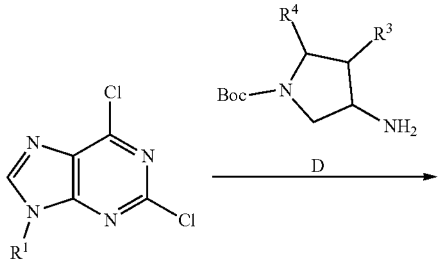

K

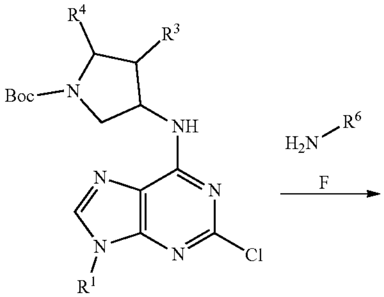

L

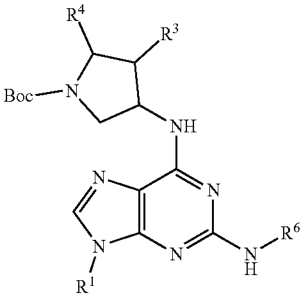

G

Scheme 2 illustrates synthetic routes to certain compounds of formula G. A compound of formula J may be reacted with a compound of formula B (X are leaving groups such as I, Br, etc.) to give a compound of formula K. The reaction may be performed in the presence of a base (typically an inorganic base such as $K_2CO_3$, NaH, etc.) using a solvent (such as DMSO), and at temperatures typically ranging from 0° C. to 60° C.

A compound of formula K may be reacted with an amine of formula D to give a compound of formula L. The reaction may be performed in the presence of a base (typically an organic base such as DIPEA) using a solvent (such as ethanol), and at temperatures typically ranging from 0° C. to 80° C.

A compound of formula L may be reacted with an amine of formula F to give a compound of formula G. The reaction may be performed in the presence of a base (typically an organic base such as DIPEA), using a solvent (such as n-butanol, DMF, DMSO, NMP, 3-ethyl-3-pentanol, or mixtures thereof), and at a temperature typically ranging from 80° C. to 160° C.

SCHEME 3

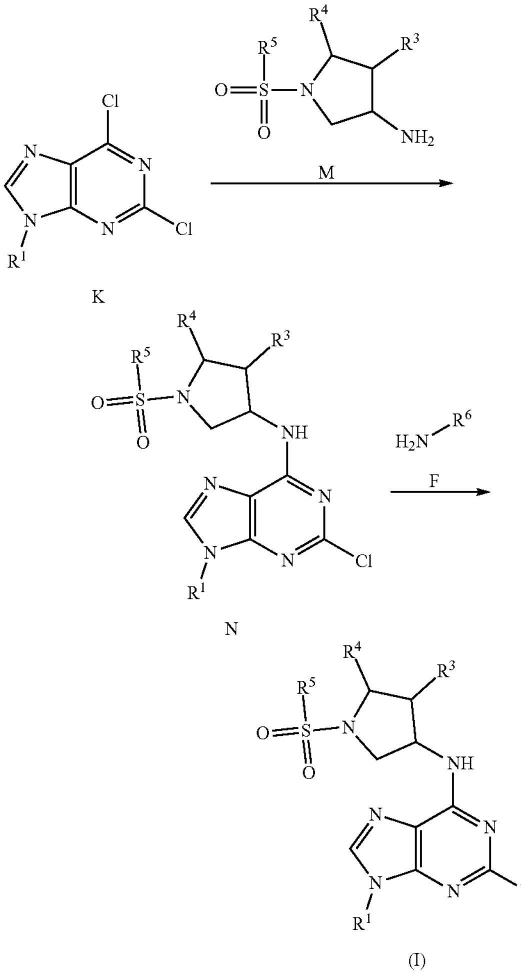

Scheme 3 illustrates synthetic routes to certain compounds of formula (I). A compound of formula K may be reacted with an amine of formula M to give a compound of formula N. The reaction may be performed in the presence of a base (typically an organic base such as DIPEA) using a solvent (such as ethanol), and at temperatures typically ranging from 0° C. to 80° C.

A compound of formula N may be reacted with an amine of formula F to give a compound of formula (I). The reaction may be performed in the presence of a base (typically an organic base such as DIPEA) using a solvent (such as n-butanol, DMF, DMSO, NMP, 3-ethyl-3-pentanol, or mixtures thereof), and at a temperature typically ranging from 80° C. to 160° C.

SCHEME 4

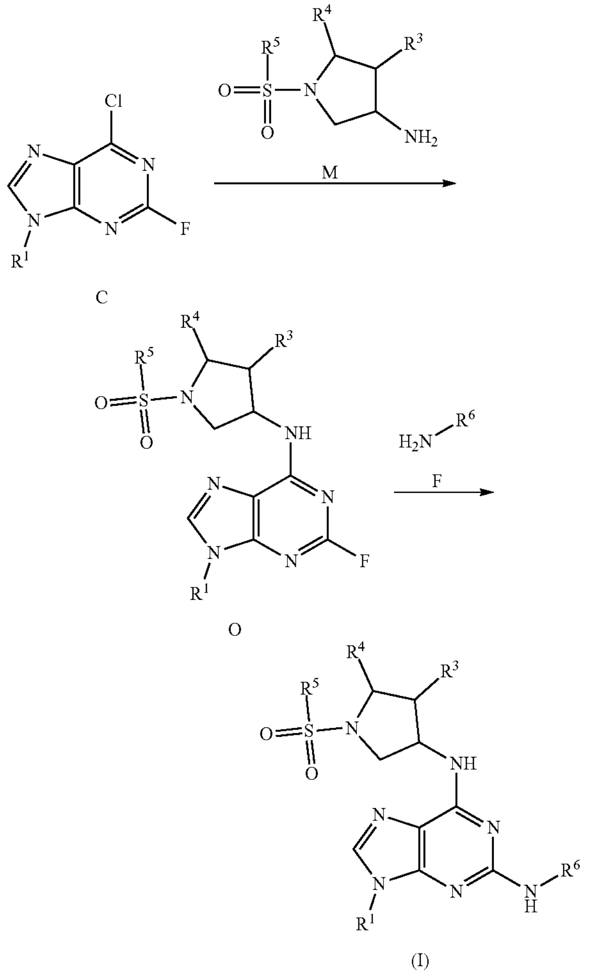

Scheme 4 illustrates synthetic routes to certain compounds of formula (I). A compound of formula C may be reacted with an amine of formula M to give a compound of formula O. The reaction may be performed in the presence of a base (typically an organic base such as DIPEA) using a solvent (such as ethanol), and at temperatures typically ranging from 0° C. to 80° C.

A compound of formula O may be reacted with an amine of formula F to give a compound of formula (I). The reaction may be performed in the presence of a base (typically an organic base such as DIPEA) using a solvent (such as n-butanol, DMF, DMSO, NMP, 3-ethyl-3-pentanol, or mixtures thereof), and at a temperature typically ranging from 80° C. to 160° C.

SCHEME 5

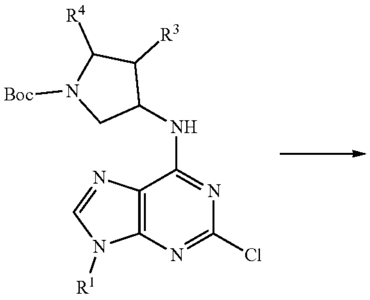

L

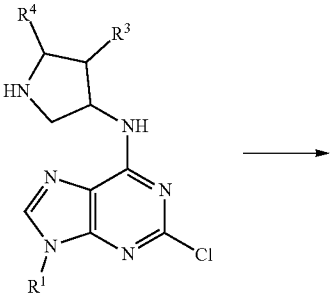

P

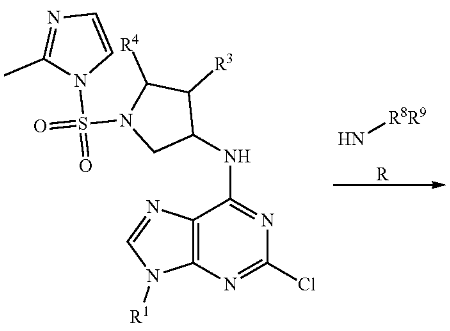

Q

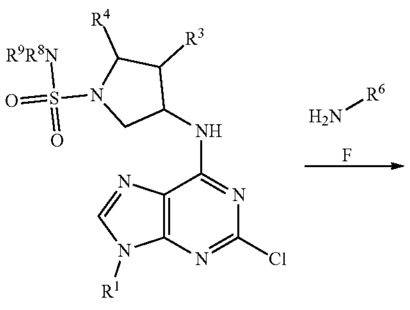

S

-continued

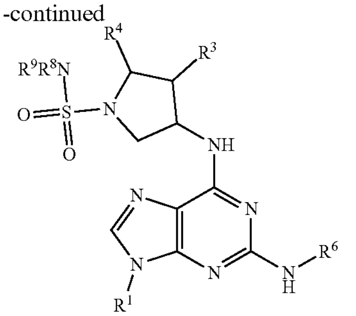

T

Scheme 5 illustrates synthetic routes to certain compounds of formula T. A compound of formula L may be transformed into a compound of formula P by deprotection of Boc using a suitable reagent (such as 4 M HCl in 1,4-dioxane) in a solvent (such as DCM), and at 23° C.

A compound of formula P may be reacted with 2,3-dimethyl-1-((2-methyl-1H-imidazol-1-yl)sulfonyl)-1H-imidazol-3-ium trifluoromethanesulfonate to give a compound of formula Q. The reaction may be performed using a solvent (such as acetonitrile, THF, etc.), and at 23° C.

A compound of formula Q may be reacted with an amine of formula R to give a compound of formula S. The reaction may be performed in the presence of methyl trifluoromethanesulfonate, using a solvent (such as DCM, acetonitrile, etc.), and at temperatures typically ranging from −20° C. to 70° C.

A compound of formula S may be reacted with an amine of formula F to give a compound of formula T. The reaction may be catalyzed with a suitable Pd-precatalyst (such as $Pd(OAc)_2$) and phosphine ligand (e.g., BrettPhos) in the presence of a base (such as $Cs_2CO_3$) using a suitable solvent (such as t-BuOH), and at temperatures typically ranging from 80° C. to 100° C.

SCHEME 6

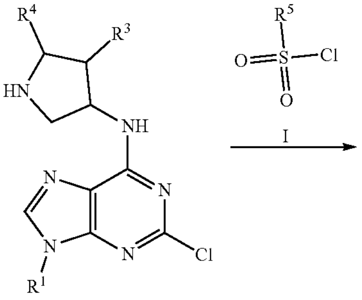

P

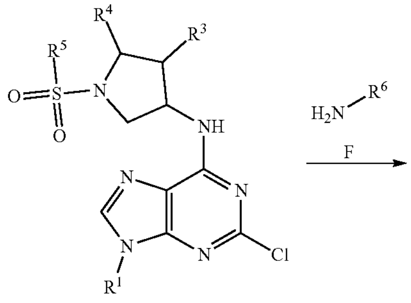

U

-continued

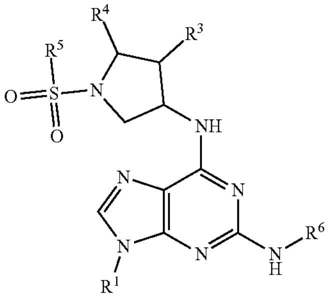

(I)

Scheme 6 illustrates synthetic routes to certain compounds of formula (I). A compound of formula P may be reacted with a compound of formula I to give a compound of formula U. The reaction may be performed in the presence of a base (typically an organic base such as TEA, DIPEA, etc.) using a solvent (such as DCM), and at temperatures typically ranging from −78° C. to 23° C.

A compound of formula U may be reacted with an amine of formula F to give a compound of formula (I). The reaction may be catalyzed with a suitable Pd-catalyst (such as Pd-PEPPSI-IPentCl o-picoline (2-methylpyridine)) in the presence of a base (such as NatBuO) using a suitable solvent (such as 1,4-dioxane), and at temperatures typically ranging from 80° C. to 120° C.

SCHEME 7

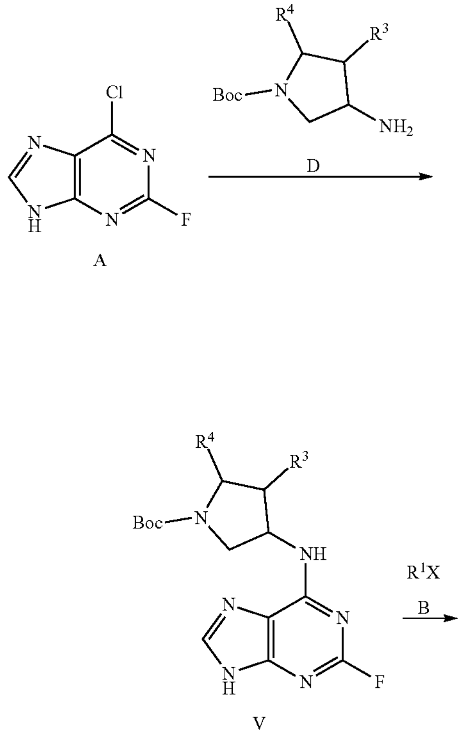

A

V

-continued

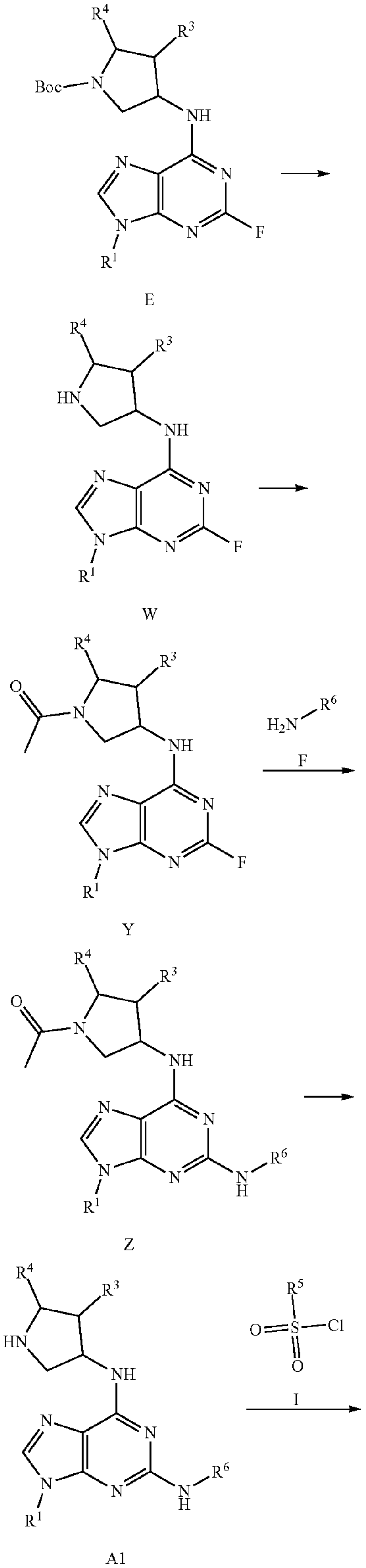

E

W

Y

Z

A1

-continued

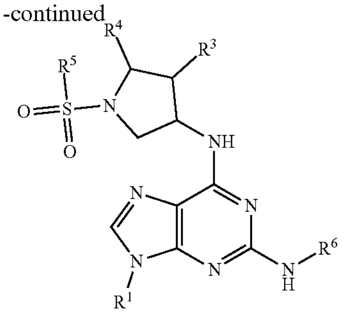

(I)

Scheme 7 illustrates synthetic routes to certain compounds of formula (I). A compound of formula A may be reacted with an amine of formula D to give a compound of formula V. The reaction may be performed in the presence of a base (typically an organic base such as DIPEA) using a solvent (such as tert-amyl alcohol), and at 100° C.

A compound of formula V may be reacted with a compound of formula B to give a compound of formula E. The reaction may be performed in the presence of a base (typically an inorganic base such as $K_2CO_3$) using a solvent (such as DMSO), and at temperatures typically ranging from 0° C. to 60° C.

A compound of formula E may be transformed into a compound of formula W by deprotection of Boc using a suitable reagent (such as 4 M HCl in 1,4-dioxane) in a solvent (such as DCM), and at 23° C.

A compound of formula W may be transformed into a compound of formula Y using a suitable reagent ($Ac_2O$) in the presence of base (such as TEA) in a solvent (such as DCM), and at 23° C.

A compound of formula Y may be reacted with an amine of formula F to give a compound of formula Z. The reaction may be performed in the presence of a base (typically an organic base such as DIPEA) using a solvent (such as 3-ethyl-3-pentanol), and at 160° C.

A compound of formula Z may be transformed into a compound of formula A1, using a suitable reagent (such as LiOH) in a solvent (such as an ethanol:water mixture), and at 80° C.

A compound of formula A1 may be reacted with a compound of formula I to give a compound of formula (I). The reaction may be performed in the presence of a base (typically an organic base such as TEA, DIPEA, etc.) using a solvent (such as DCM), and at temperatures typically ranging from −78° C. to 23° C.

SCHEME 8

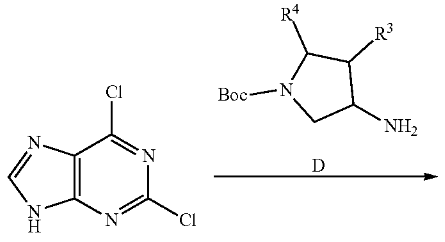

J

-continued

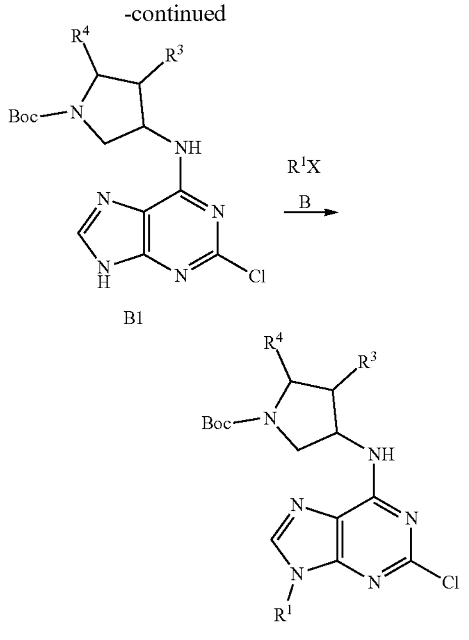

B1

L

Scheme 8 illustrates synthetic routes to certain compounds of formula L. A compound of formula J may be reacted with an amine of formula D to give a compound of formula B1. The reaction may be performed in the presence of a base (typically an organic base such as DIPEA), using a solvent (such as IPA), and at 100° C.

A compound of formula B1 may be reacted with a compound of formula B to give a compound of formula L. The reaction may be performed in the presence of a base (typically an inorganic base such as $K_2CO_3$) using a solvent (such as DMSO), and at temperatures typically ranging from 0° C. to 80° C.

It is understood that organic reactions described herein are performed according to laboratory practice known to person skilled in the art. It is understood that some of the reactions described herein may optionally be performed in different orders than laid out herein. It is understood that chiral isomers of compounds herein can be resolved at any stage in the synthetic process using chiral resolving agents described in the literature and known to person skilled in the art, or chiral chromatography methods described in the literature and known to person skilled in the art, or as described further in the Examples.

It is further understood that additional protective groups may optionally be needed in some of the steps described above, and it is further understood that a deprotection step therefore optionally may be performed, using method described in the literature and known to person skilled in the art. The protection and deprotection of functional groups is described in "*Protective Groups in Organic Synthesis*" 3$^{rd}$ Ed, T. W. Greene and P. G. M. Wutz, Wiley-Interscience (1999), which publication is incorporated herein by reference.

VIII. EXAMPLES

The following descriptions of experiments, procedures, examples, and intermediates are intended to exemplify embodiments of the disclosure. They are in no way intended to be limiting. Other compounds of this disclosure may be prepared using the methods illustrated in these examples, either alone or in combination with techniques generally known in the art.

A. General Conditions

Unless Otherwise Stated:

$^1H$ NMR spectra were obtained using a Bruker 300 MHz, 400 MHZ, or 500 MHz spectrometer at 27° C. unless otherwise noted. Chemical shifts are expressed in parts per million (ppm, units) and are referenced to the residual mono-$^1H$ isotopologue of the solvent ($CHCl_3$: 7.24 ppm; $CHDCl_2$: 5.32 ppm; $CD_3S(=O)CD_2H$: 2.49 ppm). Coupling constants are given in units of hertz (Hz). Splitting patterns describe apparent multiplicities and are designated as s (singlet), d (doublet), t (triplet), q (quartet), m (multiplet) and br s (broad singlet).

LC-MS was carried out using a Waters UPLC fitted with a Waters SQD mass spectrometer or Shimadzu LC-20AD LC-20XR LC-30AD with a Shimadzu 2020 mass spectrometer. Reported molecular ions correspond to $[M+H]^+$ unless otherwise noted. For molecules with multiple isotopic patterns (Br, Cl, etc.) the reported value is the one obtained for the lowest isotope mass unless otherwise specified.

Flash chromatography was performed using straight phase flash chromatography on a SPI™ Purification system from Biotage™, CombiFlash® Rf from ISCO, or on a Gilson system from Thermo Fisher using normal phase silica FLASH+™ (40M, 25M or 12 M) or SNAP™ KP-Sil Cartridges (340, 100, 50 or 10), Flash Column silica-CS columns from Agela, with C18-flash columns or standard flash chromatography. In general, all solvents used were commercially available and of analytical grade. Anhydrous solvents were routinely used for reactions. Phase Separators used in the examples are ISOLUTE® Phase Separator columns. The intermediates and examples named below were named using ACD/Name 12.01 from Advanced Chemistry Development, Inc. (ACD/Labs). The starting materials were obtained from commercial sources or made via literature routes.

In general, Examples and Intermediate compounds are named using ChemDraw Professional version 21.0.0.28 from PerkinElmer. ChemDraw Professional version 21.0.0.28 generates the names of chemical structures using the Cahn-Ingold-Prelog (CIP) rules for stereochemistry and follows IUPAC rules as closely as possible when generating chemical names. Stereoisomers are differentiated from each other by stereodescriptors cited in names and assigned in accordance with the CIP rules:

(a) ChemDraw has optionally used labels in the graphical representation of stereocenters such as '&' and 'or' to describe the configuration of the stereochemical centers present in the structure. In general, chemical structures of Examples and Intermediates containing the label '&' at a stereocenter means the configuration of such Example or Intermediate at that stereocenter is a mixture of both (R) and (S); and a label 'or' means the configuration of such Example or Intermediate at that stereocenter is either (S) or (R). Absolute, unspecified, '&', and 'or' stereocenters can all be present in a single structure.

(b) In general, for structures of Examples and Intermediates where all of the stereocenters are designated as '&', the structure is named with a "rac-" prefix. For structures of Examples and Intermediates where all of the stereocenters are designated as 'or', the structure is named with a "rel-" prefix.

(c) In general, Examples and Intermediate compounds are named using the descriptors (RS) and (SR) to denote general '&' centers for chemical structures with multiple chiral centers where only some are designated as '&'. The descriptors (R*) and (S*) are used to denote the general 'or' centers for chemical structures with multiple chiral centers where only some are designated as 'or'.

(d) In general, the label "Isomer 1" corresponds to the first eluted isomer, and "Isomer 2" corresponds to the second eluted isomer, on a given chiral HPLC column and eluent, and are used to distinguish two isomers containing one or more stereocenters with absolute unknown configuration at one or more stereocenters.

In addition to those mentioned above, the following abbreviations have been used:

ACN=acetonitrile;
$Ac_2O$=acetic anhydride;
AcOH=acetic acid;
aq.=aqueous;
BINAP=2,2'-bis(diphenylphosphino)-1,1'-binaphthyl;
Boc=t-butyloxycarbonyl;
$Boc_2O$=di-tert-butyl dicarbonate;
cataCXium® A Pd G3=[(Di(1-adamantyl)-butylphosphine)-2-(2'-amino-1,1'-biphenyl)]-palladium(II) methanesulfonate;
$CDCl_3$=deuterated chloroform;
$CD_3OD$=deuterated methanol;
$CH_3NO_2$=nitromethane;
$CO_2$=carbon dioxide;
$Cs_2CO_3$=cesium carbonate;
DCE=1,2-dichloroethane;
DCM=dichloromethane;
DEA=diethylamine;
DEAD=diethyl azodicarboxylate;
Dess-martin periodinane=1,1,1-Tris(acetyloxy)-1,1-dihydro-1,2-benziodoxol-3-(1H)-one;
DIEA=N,N-diisopropylethylamine;
DMAP=2,6-dimethylaminopyridine;
DMF=N,N-dimethylformamide;
DMSO=dimethylsulfoxide;
DMSO-$d_6$=deuterated dimethylsulfoxide;
DIAD=Di-isopropyl (E)-diazene-1,2-dicarboxylate;
DIBAL-H=diisobutylaluminium hydride;
DSC=differential scanning calorimetry;
DTAD=Di-tert-butyl (E)-diazene-1,2-dicarboxylate;
EDC=N-(3-Dimethylaminopropyl)-N'-ethylcarbodiimide;
ee=enantiomeric excess;
eq=equivalent;
ESI=electrospray ionization;
$Et_2O$=diethyl ether;
EtOAc=ethyl acetate;
$E_2O$=diethyl ether;
EtOH=ethanol;
FA=formic acid;
h=hour(s);
HATU=(dimethylamino)-N,N-dimethyl(3-oxido-1H-[1,2,3]triazolo[4,5-b]pyridinyl)-methaniminium hexafluorophosphate;
HBr=hydrobromic acid;
HCl=hydrochloric acid;
$H_2O$=water;
$H_2O_2$=hydrogen peroxide;
HOBt=1-hydroxybenzotriazole;
HP=high pressure;
IPA or iPrOH=isopropanol;

IPAmine=Isopropylamine;
$KHSO_4$=potassium bisulfate;
LAH=lithium aluminium hydride;
LC=liquid chromatography;
LC-MS/MS=liquid chromatography with tandem mass spectrometry
$LiClO_4$=lithium perchlorate;
LiOH=lithium hydroxide;
mCPBA=meta-chloroperoxybenzoic acid;
MeCN or $CH_3CN$=acetonitrile;
MeMgBr=methyl magnesium bromide;
$MeNO_2$=nitromethane;
MeOH=methanol;
$MgSO_4$=magnesium sulfate;
min=minute(s);
mmol=millimole;
MP carbonate=tetraalkylammonium carbonate, polymer-bound, 2.5-3.5 mmol/g loading;
MS=mass spectrometry;
MTBE=methyl tert-butyl ether;
$Na_2CO_3$=sodium carbonate;
NaCl=sodium chloride;
NaH=sodium hydride;
$NaHCO_3$=sodium bicarbonate;
$Na_2SO_4$=sodium sulfate;
$NH_3$=ammonia;
$NH_4Cl$=ammonium chloride;
$NH_4HCO_3$=ammonium bicarbonate;
NMP=N-methyl-2-pyrrolidone;
NMR=nuclear magnetic resonance;
Pd/C=Palladium on carbon;
$PdCl_2$(dppf)=1,1'-bis(di-tert-butylphosphino)ferrocene palladium dichloride;
$Pd_2dba_3$=tris(dibenzylideneacetone)dipalladium (0);
$Pd(OH)_2$=palladium hydroxide;
Pd-PEPPSI-IPentCl o-picoline (2-methylpyridine) pre-catalyst=(SP-4-1)-[1,3-BIs[2,6-bis(1-ethylpropyl)phenyl]-4,5-dichloro-1,3-dihydro-2H-imidazol-2-ylidene]dichloro(2-methylpyridine)palladium;
PE=Petroleum ether;
$PPh_3$=triphenylphosphine;
rt=room temperature;
Rt or RT=retention time;
Ruphos Pd G3=(2-Dicyclohexylphosphino-2',6'-diisopropoxy-1,1'-biphenyl)[2-(2'-amino-1,1'biphenyl)]palladium(II) methanesulfonate;
sat=saturated;
SFC=supercritical fluid chromatography;
$SOCl_2$=thionyl chloride;
TBAF=tetrabutyl ammonium fluoride;
tBuBrettPhos=2-(Di-tert-butylphosphino)-2',4',6'-triisopropyl-3,6-dimethoxy-1,1'-biphenyl;
tBuBrettPhos Pd $G_3$=[(2-Di-tert-butylphosphino-3,6-dimethoxy-2',4',6'-triisopropyl-1,1'-biphenyl)-2-(2'-amino-1,1'-biphenyl)]palladium(II) methanesulfonate;
tBuOH=tert-butanol;
TEA=triethylamine;
TFA=trifluoroacetic acid;
THF=tetrahydrofuran;
TLC=thin layer chromatography;
TMS=trimethylsilyl;
$T_3P$=2,4,6-tripropyl-1,3,5,2,4,6-trioxatriphosphinane 2,4,6-trioxide; and
UPLC=Ultra-performance liquid chromatography

B. Compounds

Example 1: (S)-3-((9-ethyl-2-(1-oxoisoindolin-4-yl)-9H-purin-6-yl)amino)-N-methylpyrrolidine-1-sulfonamide

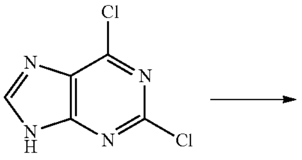

Intermediate 1

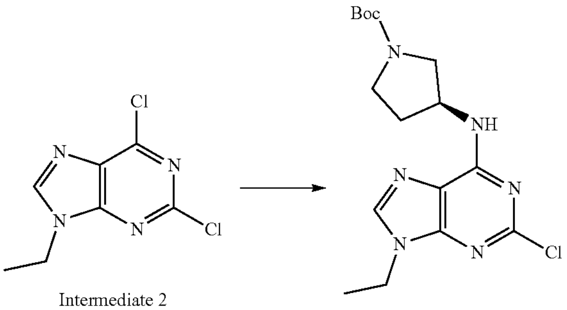

Intermediate 2

Intermediate 3

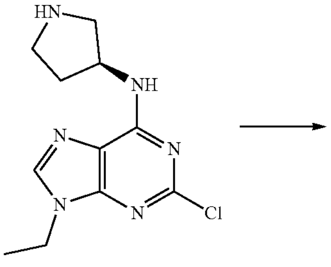

Intermediate 4

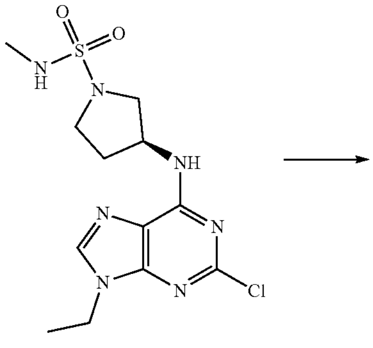

Intermediate 5

-continued

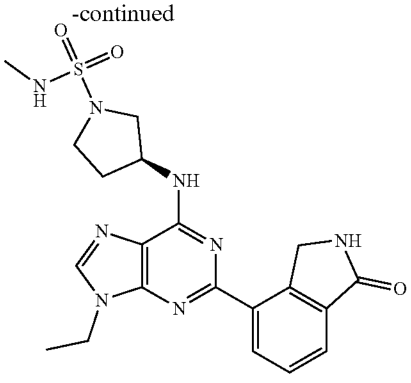

Example 1

Intermediate 2: 2,6-dichloro-9-ethyl-9H-purine 2,6-Dichloro-9H-purine (Intermediate 1, 15.10 g, 79.89 mmol) and potassium carbonate (13.80 g, 99.87 mmol) were suspended in DMSO (67.1 mL) and treated with iodoethane (7.10 ml, 87.88 mmol) under nitrogen. The reaction was stirred at room temperature over the weekend. The reaction was diluted with water, adjusted to pH 7 with acetic acid, and extracted with EtOAc. The combined organic extracts were washed with brine, dried over sodium sulfate, filtered, and the filtrate concentrated under reduced pressure. The resulting residue was purified by flash silica chromatography, elution gradient 0 to 100% EtOAc in hexanes. Product fractions were concentrated under reduced pressure to afford 2,6-dichloro-9-ethyl-9H-purine (Intermediate 2, 10.40 g, 60.0%) as a white solid. $^1$H NMR (500 MHZ, DMSO-$d_6$) 1.43 (3H, t), 4.27 (2H, q), 8.75 (1H, s); m/z (ES$^+$) $[M+H]^+$=217.

Intermediate 3: tert-butyl (S)-3-((2-chloro-9-ethyl-9H-purin-6-yl)amino)-pyrrolidine-1-carboxylate 2,6-Dichloro-9-ethyl-9H-purine (Intermediate 2, 5.69 g, 26.21 mmol) and tert-butyl (S)-3-aminopyrrolidine-1-carboxylate (5.85 g, 30.15 mmol) were dissolved in ethanol (100 mL) under nitrogen, cooled to 0 C, then N,N-diisopropylethylamine (13.74 ml, 78.64 mmol) was added dropwise. The reaction was warmed to rt, stirred for 2 days. The solvent was removed under reduced pressure and the residue was dissolved in EtOAc and washed with water. The aqueous layer was re-extracted with EtOAc. The combined organic layers were washed with brine, dried over magnesium sulfate, filtered and concentrated under reduced pressure to yield tert-butyl (S)-3-((2-chloro-9-ethyl-9H-purin-6-yl)amino)pyrrolidine-1-carboxylate as a white solid (Intermediate 3, 8.00 g, 83%). $^1$H NMR (500 MHZ, DMSO-$d_6$) 1.32-1.47 (12H, m), 1.86-2.09 (1H, m), 2.08-2.25 (1H, m), 3.15-3.27 (1H, m), 3.35-3.41 (1H, m), 3.41-3.51 (1H, m), 3.60 (1H, br dd), 4.15 (2H, q), 4.50-4.70 (1H, m), 8.22 (1H, s), 8.49 (1H, br s). m/z (ES$^-$) $[M-H]^-$=365.

Intermediate 4: (S)-2-chloro-9-ethyl-N-(pyrrolidin-3-yl)-9H-purin-6-amine hydrochloride In a 30 mL scintillation vial was added tert-butyl (S)-3-((2-chloro-9-ethyl-9H-purin-6-yl)amino)pyrrolidine-1-carboxylate (Intermediate 3, 1.029 g, 2.80 mmol), dichloromethane (10 mL) and hydrogen chloride (3.51 ml, 14.02 mmol) (4 M solution in 1,4-dioxane). The vial was sealed and stirred at rt for 3 h. The reaction mixture was filtered, ppt washed with DCM and dried under vacuum to obtain a white solid as product (S)-2-chloro-9-ethyl-N-(pyrrolidin-3-yl)-9H-purin-6-amine. HCl (Intermediate 4, 0.850 g, 100%); m/z (ES$^+$) $[M+H]^+$=267.

Intermediate 5: (S)-3-((2-chloro-9-ethyl-9H-purin-6-yl)amino)-N-methylpyrrolidine-1-sulfonamide (S)-2-chloro-9-ethyl-N-(pyrrolidin-3-yl)-9H-purin-6-amine. HCl (Intermediate 4, 0.850 g, 2.80 mmol) was weighed in a 40 mL scintillation vial, added dichloromethane (30 mL) and triethylamine (1.943 ml, 14.02 mmol). The reaction was cooled to −40° C. A solution of methylsulfamoyl chloride (0.454 g, 3.36 mmol) in dichloromethane (5 mL) was added to the reaction mixture, stirred for 1 h and then warmed to RT. The reaction was quenched by addition of aq. solution of $NaHCO_3$ solution. The organic layer was separated, dried over $Na_2SO_4$, and concentrated under vacuum. The resulting white solid was purified by flash silica chromatography using 0-10% MeOH in DCM to yield (S)-3-((2-chloro-9-ethyl-9H-purin-6-yl)amino)-N-methylpyrrolidine-1-sulfonamide (Intermediate 5, 0.442 g, 43.8%) as a white solid. $^1$H NMR (500 MHZ, Dichloromethane-$d_2$) 1.52 (3H, t), 2.04-2.22 (1H, m), 2.42 (1H, dq), 2.79 (3H, d), 3.36-3.48 (2H, m), 3.61 (1H, dt), 3.70 (1H, dd), 4.22 (2H, q), 4.74-5.13 (1H, m), 5.44 (1H, br s), 6.55 (1H, br s), 7.80 (1H, s). m/z (ES$^+$) $[M+H]^+$=360.

Example 1: (S)-3-((9-ethyl-2-(1-oxoisoindolin-4-yl)-9H-purin-6-yl)amino)-N-methylpyrrolidine-1-sulfonamide

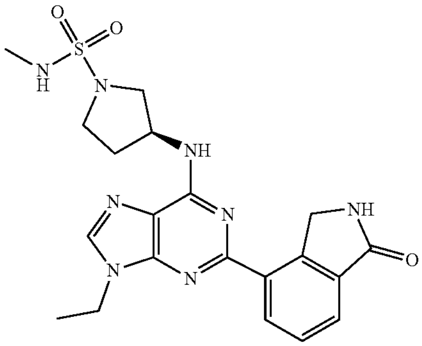 [SMILES: CCn1cnc2c(N[C@H]3CCN(S(=O)(=O)NC)C3)nc(-c3cccc4c3CNC4=O)nc21]

(S)-3-((2-chloro-9-ethyl-9H-purin-6-yl)amino)-N-methylpyrrolidine-1-sulfonamide (Intermediate 5, 50 mg, 0.14 mmol), 4-(4,4,5,5-tetramethyl-1,3,2-dioxaborolan-2-yl) isoindolin-1-one (54.0 mg, 0.21 mmol), cesium carbonate (136 mg, 0.42 mmol) and cataCXium® A Pd $G_3$ (10.12 mg, 0.01 mmol) were weighed in a 20 mL scintillation vial, evacuated, filled with $N_2$, and sealed. 1,4-dioxane (2 mL) and water (0.500 mL) were added. The reaction vial was placed on a heating block pre-heated to 100° C. and stirred for 16 h. The reaction mixture was cooled, quenched with brine and attempted to extract with DCM (solid precipitated out), added DCM:MeOH mixture (resulted in clear biphasic mixture). The organic layer was separated, dried over $Na_2SO_4$ and concentrated under vacuum over silica gel. The resulting solid was purified by flash silica chromatography using 0-10% MeOH in DCM to yield a light brown solid.

The brown solid was further purified by flash C18 chromatography using 0-100% ACN in water (0.1% $NH_4OH$) to yield (S)-3-((9-ethyl-2-(1-oxoisoindolin-4-yl)-9H-purin-6-yl)amino)-N-methylpyrrolidine-1-sulfonamide (Example 1, 0.040 g, 63.1%). $^1$H NMR (500 MHz, DMSO-$d_6$) 1.50 (3H, t), 2.12-2.22 (1H, m), 2.28-2.36 (1H, m), 2.57 (3H, d), 3.23-3.30 (2H, m), 3.43-3.51 (1H, m), 3.65 (1H, dd), 4.29 (2H, q), 4.87-4.98 (3H, m), 7.03 (1H, q), 7.64 (1H, t), 7.78 (1H, dd), 8.11 (1H, br s), 8.27 (1H, s), 8.62-8.73 (2H, m). m/z ($ES^+$) $[M+H]^+$=457.

Example 2: (S)-3-((9-ethyl-2-((R)-1-hydroxy-2,3-dihydro-1H-inden-4-yl)-9H-purin-6-yl)amino)-N-methylpyrrolidine-1-sulfonamide

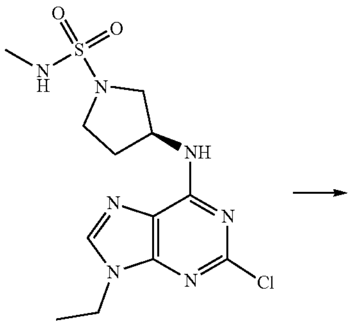

Intermediate 5

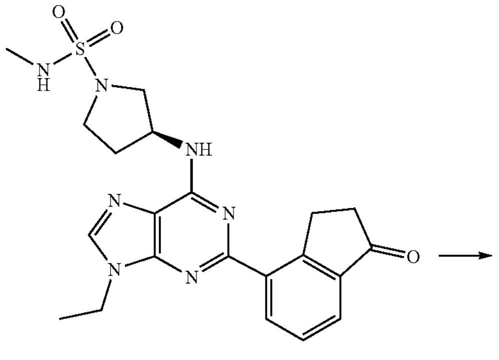

Intermediate 6

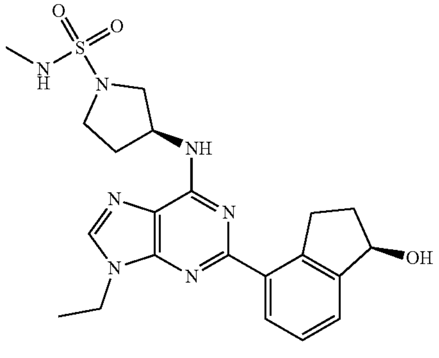

Example 2

Intermediate 6: (S)-3-((9-ethyl-2-(1-oxo-2,3-dihydro-1H-inden-4-yl)-9H-purin-6-yl)amino)-N-methylpyrrolidine-1-sulfonamide (S)-3-((2-chloro-9-ethyl-9H-purin-6-yl)amino)-N-methylpyrrolidine-1-sulfonamide (Intermediate 5, 50 mg, 0.14 mmol), 4-(4,4,5,5-tetramethyl-1,3,2-dioxaborolan-2-yl)-2,3-dihydro-1H-inden-1-one (43.0 mg, 0.17 mmol), cesium carbonate (136 mg, 0.42 mmol) and cataCXium® A Pd $G_3$ (10.12 mg, 0.01 mmol) were weighed in a 20 mL scintillation vial, evacuated, filled with $N_2$, sealed, added 1,4-dioxane (2 mL) and water (0.500 mL). The reaction vial was placed in a heating block pre-heated to 100° C. and stirred for 16 h. The reaction mixture was cooled, quenched with brine and attempted to extract with DCM (solid precipitated out), added DCM:MeOH mixture. The organic layer was separated, dried over $Na_2SO_4$ and concentrated under vacuum over silica gel. The resulting solid was purified by flash silica chromatography using 0-10% MeOH in DCM to obtain an off-white solid. The above solid was further purified by flash C18 chromatography using 0-100% ACN in water (0.1% $NH_4OH$) to yield (S)-3-((9-ethyl-2-(1-oxo-2,3-dihydro-1H-inden-4-yl)-9H-purin-6-yl)amino)-N-methylpyrrolidine-1-sulfonamide (Intermediate 6, 0.050 g, 79%) as a white solid. $^1$H NMR (500 MHz, DMSO-$d_6$) 1.49 (3H, t), 2.15-2.37 (2H, m), 2.53-2.59 (3H, m), 2.61-2.72 (2H, m), 3.09-3.26 (2H, m), 3.34-3.49 (1H, m), 3.63-3.72 (3H, m), 4.28 (2H, q), 4.87 (1H, br s), 7.02 (1H, br s), 7.58 (1H, t), 7.74 (1H, d), 7.96-8.16 (1H, m), 8.27 (1H, s), 8.61-8.68 (1H, m). m/z ($ES^+$) $[M+H]^+$=456.

Example 2: (S)-3-((9-ethyl-2-((R)-1-hydroxy-2,3-dihydro-1H-inden-4-yl)-9H-purin-6-yl)amino)-N-methylpyrrolidine-1-sulfonamide

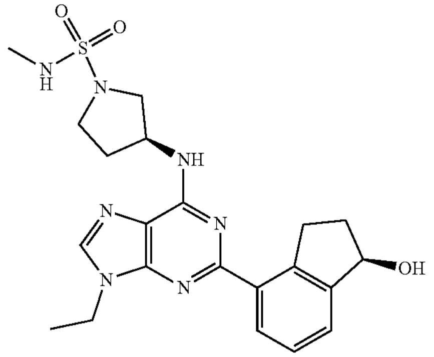 [SMILES: CCn1cnc2c(N[C@H]3CCN(S(=O)(=O)NC)C3)nc(-c3cccc4c3CC[C@H]4O)nc21]

(S)-3-((9-Ethyl-2-(1-oxo-2,3-dihydro-1H-inden-4-yl)-9H-purin-6-yl)amino)-N-methylpyrrolidine-1-sulfonamide (Intermediate 6, 44 mg, 0.10 mmol) was added to a 20 ml vial and added methanol (1 mL). Sodium tetrahydroborate (7.31 mg, 0.19 mmol) was added to the reaction mixture at room temperature, stirred for 1 h. The reaction was concentrated and quenched with sat. aq. $NH_4Cl$. The reaction was extracted with DCM, and the combined organic layers were dried over $Mg_2SO_4$, filtered and concentrated under vacuum. The crude product containing mixture of diastereomers was purified by chiral SFC (Whelk-O 4.6 mm×100 mm 5 μm column) using MeOH with 0.2% $NH_4OH$ to yield (S)-3-((9-ethyl-2-((R)-1-hydroxy-2,3-dihydro-1H-inden-4-yl)-9H-purin-6-yl)amino)-N-methylpyrrolidine-1-sulfonamide (Example 2, Isomer 1, 14.00 mg, 31.7%) $^1$H NMR (500 MHZ, DMSO-$d_6$) 1.47 (3H, t), 1.76-1.84 (1H, m), 2.07-2.21 (1H, m), 2.23-2.38 (2H, m), 2.60 (3H, s), 3.16-3.25 (2H, m), 3.38-3.56 (3H, m), 3.63 (1H, dd), 4.25 (2H, q), 4.86 (1H, br s), 5.09 (1H, br s), 5.21 (1H, br d), 7.02 (1H, br s), 7.32 (1H, t), 7.42 (1H, d), 7.93 (1H, br s), 8.15 (1H, br d), 8.22 (1H, s). m/z ($ES^+$) $[M+H]^+$=458; and (S)-3-((9-ethyl-2-((S)-1-hydroxy-2,3-dihydro-1H-inden-4-yl)-9H-purin-6-yl)amino)-N-methylpyrrolidine-1-sulfonamide (Isomer 2, 14.00 mg, 31.7%).

Example 3: (S)-3-((9-ethyl-2-((R*)-1-hydroxy-1-methyl-2,3-dihydro-1H-inden-4-yl)-9H-purin-6-yl)amino)-N-methylpyrrolidine-1-sulfonamide

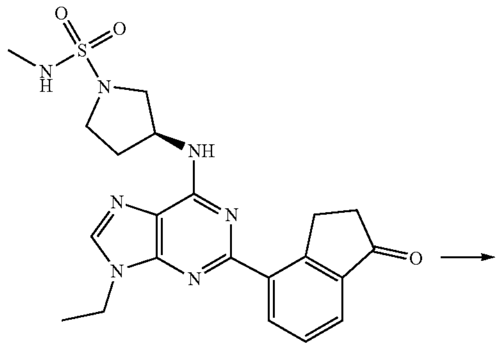

Intermediate 6

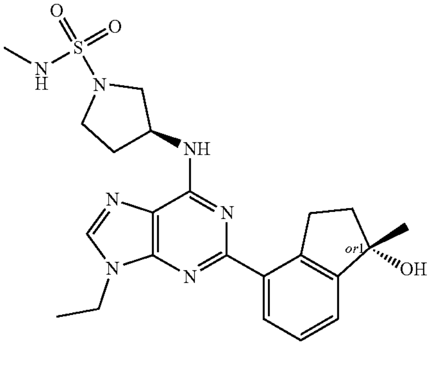

Example 3

(S)-3-((9-Ethyl-2-(1-oxo-2,3-dihydro-1H-inden-4-yl)-9H-purin-6-yl)amino)-N-methylpyrrolidine-1-sulfonamide (Intermediate 6, 0.040 g, 0.09 mmol) was weighed in a 20 mL scintillation vial, evacuated, filled with $N_2$, sealed, added tetrahydrofuran (2 mL). The reaction vial was cooled to 0° C. and methylmagnesium bromide (0.146 ml, 0.44 mmol, 1 M solution in $Et_2O$) was added dropwise and stirred for 1.5 h. Additional 2 equiv of MeMgBr was added and stirred for 1.5 h. The reaction mixture was quenched with brine and extracted with DCM. The organic layer was separated, dried over $Na_2SO_4$, concentrated. The crude product containing mixture of diastereomers was purified by chiral SFC (Whelk-O 4.6 mm×100 mm 5 μm column) using MeOH with 0.2% $NH_4OH$ to yield (S)-3-((9-ethyl-2-((R*)-1-hydroxy-1-methyl-2,3-dihydro-1H-inden-4-yl)-9H-purin-6-yl)amino)-N-methylpyrrolidine-1-sulfonamide (Example 3, Isomer 1, 0.013 g, 30.2%); $^1H$ NMR (500 MHz, DMSO-$d_6$) 1.41-1.50 (6H, m), 2.07 (2H, t), 2.11-2.20 (1H, m), 2.22-2.36 (1H, m), 2.56 (3H, s), 3.17-3.29 (2H, m), 3.40-3.55 (3H, m), 3.63 (1H, dd), 4.24 (2H, q), 4.99 (2H, br s), 6.84-7.15 (1H, m), 7.30-7.40 (2H, m), 7.93 (1H, br s), 8.14 (1H, br d), 8.22 (1H, s). m/z ($ES^+$) $[M+H]^+$=472; and Isomer 2 (0.012 g, 29.0%).

Example 4: (S)-3-((9-ethyl-2-(((2R,3S)-2-hydroxypentan-3-yl)amino)-9H-purin-6-yl)amino)-N-(2,2,2-trifluoroethyl)pyrrolidine-1-sulfonamide

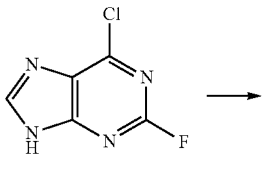

Intermediate 7

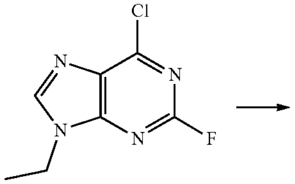

Intermediate 8

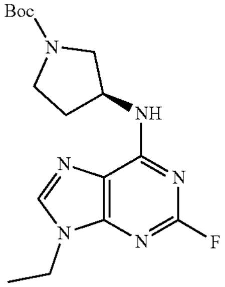

Intermediate 9

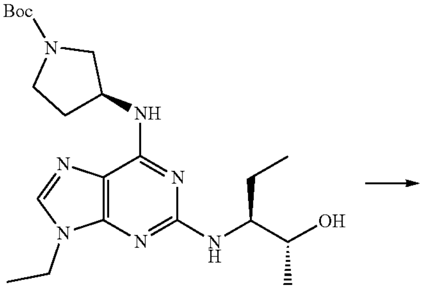

Intermediate 10

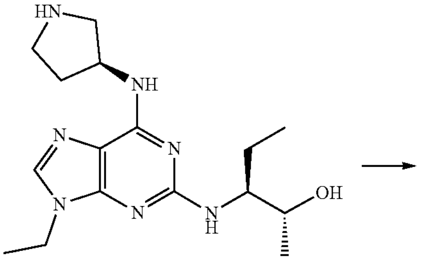

Intermediate 11

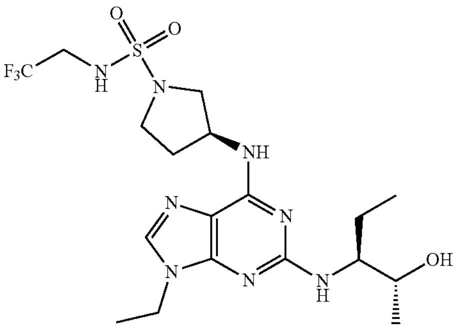

Example 4

Intermediate 8: 6-chloro-9-ethyl-2-fluoro-9H-purine

Iodoethane (5.15 ml, 63.75 mmol) was added to a stirred suspension of 6-chloro-2-fluoro-9H-purine (Intermediate 7, 10 g, 57.96 mmol) and potassium carbonate (10.01 g, 72.44 mmol) in DMSO (52.8 mL) at 23° C. The resulting suspension was stirred at 23° C. for 20 h. The reaction was diluted with water, adjusted to pH 7-8 with glacial acetic acid and then extracted with ethyl acetate. The combined organic layer was washed with brine, dried over sodium sulfate, filtered, and concentrated. The resulting residue was purified by flash silica chromatography, elution gradient 0 to 100% EtOAc in hexanes. Product fractions were concentrated to afford 6-chloro-9-ethyl-2-fluoro-9H-purine (Intermediate 8, 7.00 g, 60.2%) 1H NMR (Chloroform-d, 300 MHz) δ 1.58 (3H, t), 4.31 (2H, q), 8.11 (1H, s); m/z ($ES^+$) $[M+H]^+$=201; and 6-chloro-7-ethyl-2-fluoro-7H-purine, both as off-white solids.

Intermediate 9: tert-butyl (S)-3-((9-ethyl-2-fluoro-9H-purin-6-yl)amino)-pyrrolidine-1-carboxylate 6-Chloro-9-ethyl-2-fluoro-9H-purine (Intermediate 8, 2.30 g, 11.47 mmol) and tert-butyl (S)-3-aminopyrrolidine-1-carboxylate (2.093 g, 11.24 mmol) was dissolved in DMF (15 mL) under nitrogen, cooled to 0° C., then added N,N-diisopropylethylamine (4.01 ml, 22.93 mmol) dropwise. The reaction was warmed to 80° C., stirred for 1 h. The solvent was removed under reduced pressure and the white residue was purified by flash silica chromatography, elution gradient 50 to 100% EtOAc in hexanes, then 15% MeOH in DCM. Product fractions were concentrated under reduced pressure to afford tert-butyl (S)-3-((9-ethyl-2-fluoro-9H-purin-6-yl) amino)pyrrolidine-1-carboxylate (Intermediate 9, 2.37 g, 59.1%) as a white solid. 1H NMR (300 MHz, DMSO-$d_6$) δ 1.37-1.45 (12H, m), 2.00 (1H, s), 2.14 (1H, s), 3.16-3.31 (2H, m), 3.38-3.66 (2H, m), 4.12 (2H, q), 4.58 (1H, s), 8.18 (1H, s), 8.56 (1H, s). m/z ($ES^+$) [M+H]+=351.

Intermediate 10: tert-butyl (S)-3-((9-ethyl-2-(((2R, 3S)-2-hydroxypentan-3-yl)-amino)-9H-purin-6-yl) amino)pyrrolidine-1-carboxylate tert-Butyl (S)-3-((9-ethyl-2-fluoro-9H-purin-6-yl)amino) pyrrolidine-1-carboxylate (Intermediate 9, 0.903 g, 2.58 mmol), (2R,3S)-3-aminopentan-2-ol (0.857 ml, 7.73 mmol), and DIEA (1.350 ml, 7.73 mmol) were dissolved in n-butanol (6.13 mL)/dimethylsulfoxide (0.613 mL) and the reaction was heated at 100° C. The reaction was stirred at 100° C. for 65 h, then continued at 120° C. for an additional 16 h. The reaction was concentrated and purified by flash C18 chromatography, elution gradient 0 to 100% acetonitrile in water (containing 0.1% formic acid additive) to yield tert-butyl (S)-3-((9-ethyl-2-(((2R,3S)-2-hydroxypentan-3-yl) amino)-9H-purin-6-yl)amino)pyrrolidine-1-carboxylate (Intermediate 10, 0.700 g, 62.7%) as a white solid. m/z ($ES^+$) $[M+H]^+$=434.

Intermediate 11: (2R,3S)-3-((9-ethyl-6-(((S)-pyrrolidin-3-yl)amino)-9H-purin-2-yl)amino)pentan-2-ol hydrochloride In a scintillation vial was added tert-butyl (S)-3-((9-ethyl-2-(((2R,3S)-2-hydroxypentan-3-yl)amino)-9H-purin-6-yl) amino)pyrrolidine-1-carboxylate (Intermediate 10, 0.240 g, 0.55 mmol), dichloromethane (3 mL) and hydrogen chloride (0.692 ml, 2.77 mmol) (4 M solution in 1,4-dioxane). The vial was sealed and stirred at rt for 16 h. The reaction mixture was concentrated under vacuum to obtain (2R,3S)-3-((9-ethyl-6-(((S)-pyrrolidin-3-yl)amino)-9H-purin-2-yl) amino)pentan-2-ol. HCl (Intermediate 11, 0.205 g, 100%) as a white solid. m/z ($ES^+$) $[M+H]^+$=334.

Example 4: (S)-3-((9-ethyl-2-(((2R,3S)-2-hydroxypentan-3-yl)amino)-9H-purin-6-yl)amino)-N-(2,2,2-trifluoroethyl)pyrrolidine-1-sulfonamide

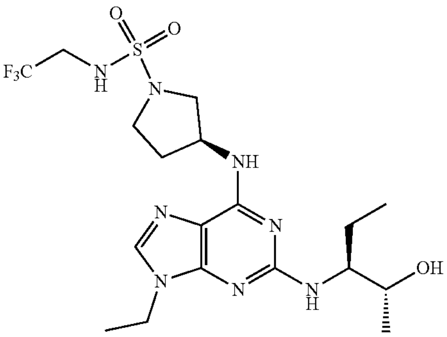 [SMILES: CC[C@H](Nc1nc(N[C@H]2CCN(S(=O)(=O)NCC(F)(F)F)C2)c2ncn(CC)c2n1)[C@@H](C)O]

(2R,3S)-3-((9-ethyl-6-(((S)-pyrrolidin-3-yl)amino)-9H-purin-2-yl)amino)pentan-2-ol hydrochloride (Intermediate 11, 94 mg, 0.25 mmol) was weighed in a scintillation vial, added dichloromethane (5 mL) and triethylamine (195 µl, 1.40 mmol) and the reaction was cooled to 0° C. (2,2,2-Trifluoroethyl)sulfamoyl chloride (55.2 mg, 0.28 mmol) was added to the reaction mixture and stirred for 30 min. The reaction mixture was concentrated and purified by flash C18 chromatography using 0-100% ACN in water (0.1% $NH_4OH$) followed by SFC purification to yield (S)-3-((9-ethyl-2-(((2R,3S)-2-hydroxypentan-3-yl)amino)-9H-purin-6-yl)amino)-N-(2,2,2-trifluoroethyl)pyrrolidine-1-sulfonamide (Example 4, 40 mg, 0.081 mmol, 31.8%). $^1H$ NMR (500 MHZ, DMSO-$d_6$) 0.86 (3H, t), 1.06 (3H, d), 1.30-1.43 (4H, m), 1.69 (1H, ddd), 2.00-2.09 (1H, m), 2.17-2.24 (1H, m), 2.52-2.57 (1H, m), 3.13-3.30 (1H, m), 3.37-3.45 (1H, m), 3.57 (1H, dd), 3.61-3.68 (1H, m), 3.72-3.80 (3H, m), 3.99 (2H, q), 4.56-4.76 (2H, m), 5.89-6.03 (1H, m), 7.29-7.46 (1H, m), 7.74 (1H, s), 8.03 (1H, br s); 19F NMR (471 MHz, DMSO-$d_6$)-71.28 (3F, s). m/z ($ES^+$) $[M+H]^+$=495.

Example 5: (S)—N-(2,2-difluoroethyl)-3-((9-ethyl-2-(((2R,3S)-2-hydroxypentan-3-yl)amino)-9H-purin-6-yl)amino)pyrrolidine-1-sulfonamide

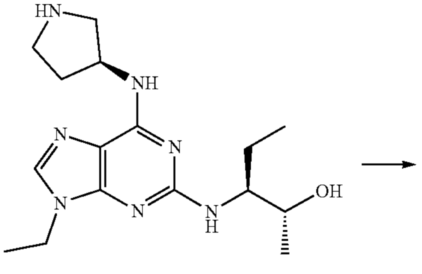

Intermediate 11

-continued

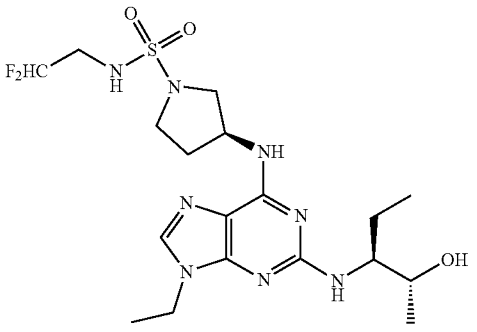

Example 5

-continued

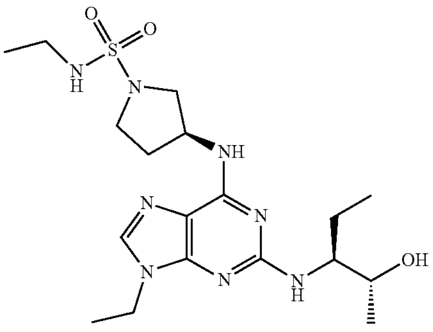

Example 6

(2R,3S)-3-((9-ethyl-6-(((S)-pyrrolidin-3-yl)amino)-9H-purin-2-yl)amino)pentan-2-ol hydrochloride (Intermediate 11, 80 mg, 0.22 mmol) was weighed in a 20 mL scintillation vial, added dichloromethane (5 mL) and triethylamine (165 µl, 1.19 mmol), and the reaction was cooled to 0° C. (2,2-Difluoroethyl)sulfamoyl chloride (42.7 mg, 0.24 mmol) was added to the reaction mixture and stirred for 30 min. The reaction mixture was concentrated and purified by flash C18 chromatography followed by SFC to yield (S)—N-(2,2-difluoroethyl)-3-((9-ethyl-2-(((2R,3S)-2-hydroxypentan-3-yl)amino)-9H-purin-6-yl)amino)pyrrolidine-1-sulfonamide (Example 5, 0.031 g, 30.1%). $^1$H NMR (500 MHz, DMSO-$d_6$) 0.86 (3H, t), 1.06 (3H, d), 1.30-1.43 (4H, m), 1.64-1.77 (1H, m), 1.98-2.12 (1H, m), 2.15-2.26 (1H, m), 3.11-3.29 (3H, m), 3.34-3.43 (3H, m), 3.56 (1H, dd), 3.61-3.69 (1H, m), 3.77 (1H, tdd), 3.99 (2H, q), 4.56-4.77 (1H, m), 5.91-6.13 (2H, m), 7.26-7.48 (1H, m), 7.65-7.79 (2H, m). 19F NMR (471 MHZ, DMSO-$d_6$)-122.03 (2F, s). m/z (ES$^+$) [M+H]$^+$=477.

Example 6: (S)—N-ethyl-3-((9-ethyl-2-(((2R,3S)-2-hydroxypentan-3-yl)amino)-9H-purin-6-yl)amino) pyrrolidine-1-sulfonamide

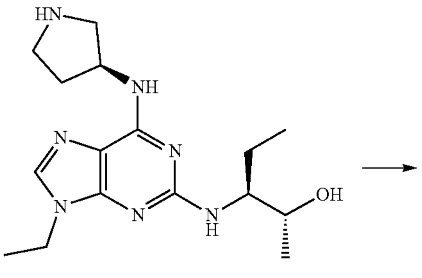

Intermediate 11

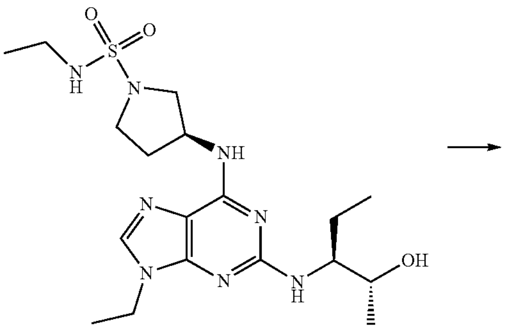

Example 6

(2R,3S)-3-((9-ethyl-6-(((S)-pyrrolidin-3-yl)amino)-9H-purin-2-yl)amino)pentan-2-ol. HCl (Intermediate 11, 0.482 g, 1.30 mmol) was weighed in a 40 mL scintillation vial, added dichloromethane (20 mL) and triethylamine (0.903 ml, 6.52 mmol), reaction was cooled to −78° C. Ethylsulfamoyl chloride (0.177 g, 1.17 mmol) was added to the reaction mixture and stirred for 2 h. Additional ethylsulfamoyl chloride (0.030 g, 0.20 mmol) was added and stirred for 1 h. The reaction was quenched with aq. $NaHCO_3$ solution, warmed to 25° C., stirred for 15 mins, extracted with DCM, organic layer separated, dried over $MgSO_4$ and concentrated to yield a white foam. The solid was purified by flash silica chromatography using 0-20% MeOH in DCM to yield (S)—N-ethyl-3-((9-ethyl-2-(((2R,3S)-2-hydroxypentan-3-yl)amino)-9H-purin-6-yl)amino)pyrrolidine-1-sulfonamide (Example 6, 0.302 g, 52.6%). $^1$H NMR (400 MHZ, DMSO-$d_6$) 0.86 (3H, t), 0.97-1.1 (6H, m), 1.27-1.49 (4H, m), 1.69 (1H, ddd), 2.05 (1H, dt), 2.20 (1H, td), 2.95 (2H, qd), 3.09 (1H, dd), 3.21 (1H, dt), 3.33-3.42 (1H, m), 3.54 (1H, dd), 3.58-3.66 (1H, m), 3.71-3.82 (1H, m), 3.98 (2H, q), 4.64 (2H, s), 5.96 (1H, s), 6.93-7.62 (2H, m), 7.73 (1H, s); m/z (ES$^+$) [M+H]$^+$=441.

Example 7: (S)—N-ethyl-3-((9-ethyl-2-(((S)-2-oxopentan-3-yl)amino)-9H-purin-6-yl)amino)pyrrolidine-1-sulfonamide -continued

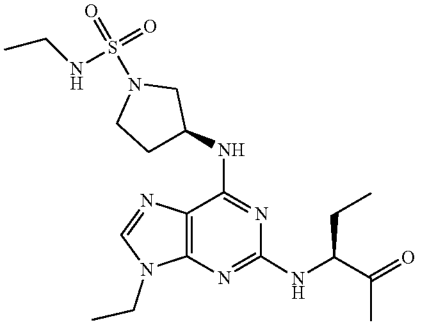

Example 7

3-Oxo-115-benzo[d][1,2]iodaoxole-1,1,1(3H)-triyl triacetate (42.4 mg, 0.10 mmol) was added to (S)—N-ethyl-3-((9-ethyl-2-(((2R,3S)-2-hydroxypentan-3-yl)amino)-9H-purin-6-yl)amino)pyrrolidine-1-sulfonamide (Example 6, 40 mg, 0.09 mmol) in dichloromethane (0.5 mL). The resulting mixture was stirred at 25° C. for 16 h. The reaction mixture was concentrated and purified by flash C18 chromatography using 0-100% ACN in $H_2O$ to yield (S)—N-ethyl-3-((9-ethyl-2-(((S)-2-oxopentan-3-yl)amino)-9H-purin-6-yl)amino)pyrrolidine-1-sulfonamide (Example 7, 0.026 g, 64.3%). $^1$H NMR (500 MHz, DMSO-$d_6$) 0.92 (3H, t), 1.07 (3H, t), 1.34 (3H, t), 1.61-1.78 (2H, m), 1.95-2.19 (5H, m), 2.92-3.01 (2H, m), 3.10 (1H, dd), 3.17-3.29 (2H, m), 3.33-3.40 (1H, m), 3.52 (1H, dd), 3.96-4.05 (2H, m), 4.05-4.15 (1H, m), 6.67-6.89 (1H, m), 7.08 (1H, br t), 7.42-7.57 (1H, m), 7.78 (1H, s). m/z ($ES^+$) $[M+H]^+$=439.

Example 8: (S)—N-ethyl-3-((9-ethyl-2-(((2S,3S)-2-hydroxypentan-3-yl)amino)-9H-purin-6-yl)amino)pyrrolidine-1-sulfonamide

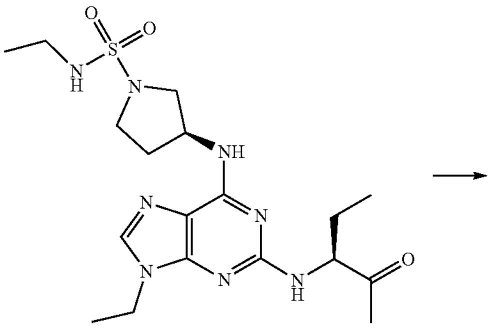

Example 7

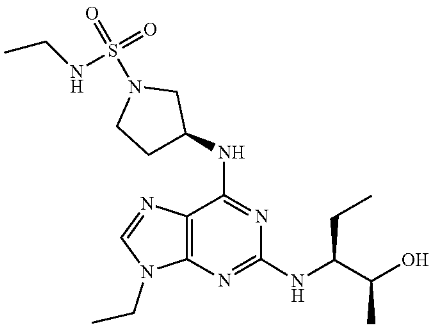

Example 8

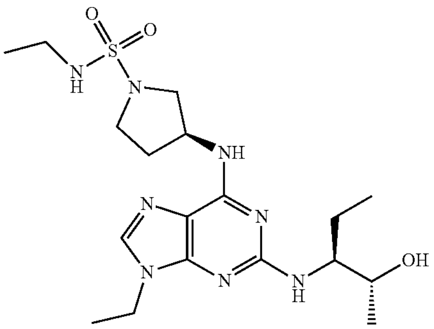

Example 6

(S)—N-ethyl-3-((9-ethyl-2-(((S)-2-oxopentan-3-yl)amino)-9H-purin-6-yl)amino)-pyrrolidine-1-sulfonamide (Example 7, 0.193 g, 0.44 mmol) was dissolved in THF (4.58 ml)/MeOH (0.917 ml) and treated with sodium tetrahydroborate (0.027 g, 0.70 mmol). The reaction mixture was stirred under nitrogen for 45 minutes. The reaction was quenched with saturated aq. ammonium chloride and extracted with DCM. The organic layer was dried over sodium sulfate, filtered, and the filtrate was concentrated under reduced pressure. The resulting residue was coated on silica and purified by flash silica chromatography, elution gradient 0 to 10% MeOH in DCM. Product fractions were concentrated under reduced pressure to afford the crude product (0.152 g, 78%) as a white solid. The solid was purified by chiral SFC (IH 4.6×150 mm, 5 μm column) using 0.2% $NH_4OH$ in MeOH to yield (S)—N-ethyl-3-((9-ethyl-2-(((2S,3S)-2-hydroxypentan-3-yl)amino)-9H-purin-6-yl)amino)pyrrolidine-1-sulfonamide (Example 8, 0.016 g, 8.46%) as the minor regioisomer. $^1H$ NMR (500 MHz, DMSO-$d_6$) 0.88 (3H, t), 1.02-1.09 (6H, m), 1.35 (3H, t), 1.42-1.53 (1H, m), 1.55-1.64 (1H, m), 2.05 (1H, br dd), 2.16-2.25 (1H, m), 2.88-3.04 (2H, m), 3.11 (1H, dd), 3.18-3.29 (1H, m), 3.35-3.41 (1H, m), 3.55 (1H, dd), 3.74-3.82 (2H, m), 4.00 (2H, q), 4.45-4.59 (1H, m), 4.65 (1H, br s), 5.59-5.79 (1H, m), 7.07 (1H, t), 7.21-7.60 (1H, m), 7.75 (1H, br s). m/z ($ES^+$) $[M+H]^+$=441.

Example 9: (S)-3-((9-ethyl-2-(((2R,3S)-2-hydroxypentan-3-yl)amino)-9H-purin-6-yl)amino)pyrrolidine-1-sulfonamide

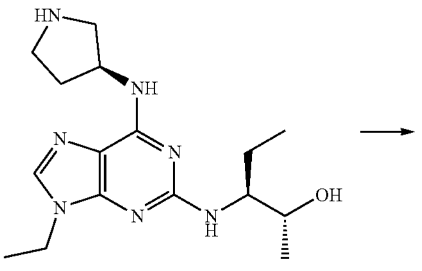

Intermediate 11

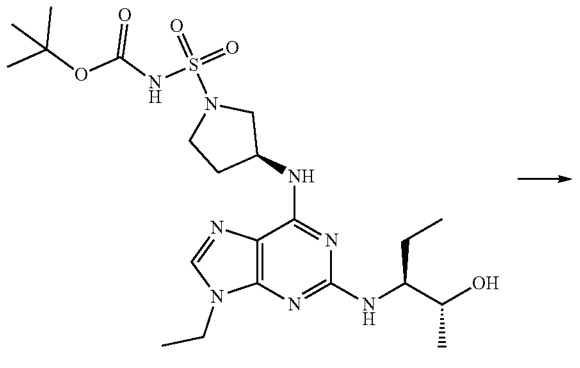

Intermediate 12

-continued

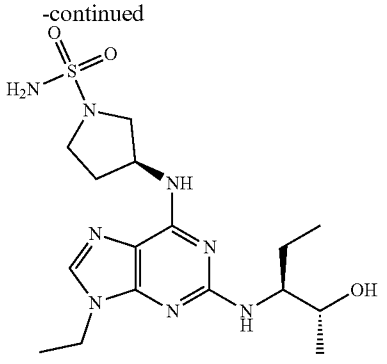

Example 9

Intermediate 12: tert-butyl(((S)-3-((9-ethyl-2-(((2R,3S)-2-hydroxypentan-3-yl)amino)-9H-purin-6-yl)amino)pyrrolidin-1-yl)sulfonyl)carbamate (2R,3S)-3-((9-ethyl-6-(((S)-pyrrolidin-3-yl)amino)-9H-purin-2-yl)amino)pentan-2-ol, HCl (Intermediate 11, 0.520 g, 1.41 mmol) was weighed in a 30 mL scintillation vial, added dichloromethane (12.77 ml) and triethylamine (0.974 ml, 7.03 mmol), reaction was cooled to −40° C. Solution of tert-butyl (chlorosulfonyl)carbamate (0.303 g, 1.41 mmol) in dichloromethane (12.77 ml) (poor solubility) was added to the reaction mixture and stirred for 1 h. The reaction was quenched by addition of aqueous $NaHCO_3$ solution. The organic layer was separated, dried over $Na_2SO_4$ and concentrated under vacuum. The resulting white solid was purified by flash silica chromatography using 0-10% MeOH in DCM to yield tert-butyl (((S)-3-((9-ethyl-2-(((2R,3S)-2-hydroxypentan-3-yl)amino)-9H-purin-6-yl)amino)pyrrolidin-1-yl)sulfonyl)carbamate (Intermediate 12, 0.455 g, 63.1%) as a white solid. $^1H$ NMR (500 MHZ, DMSO-$d_6$) 0.86 (3H, t), 1.06 (3H, d), 1.28-1.45 (13H, m), 1.69 (1H, ttd), 1.96-2.11 (1H, m), 2.11-2.26 (1H, m), 3.22-3.30 (2H, m), 3.35-3.46 (1H, m), 3.54-3.60 (1H, m), 3.62-3.80 (3H, m), 3.99 (2H, q), 4.54-4.76 (1H, m), 5.82-6.03 (1H, m), 7.24-7.56 (1H, m), 7.73 (1H, s), 10.91 (1H, br s). m/z ($ES^+$) $[M+H]^+$=513.

Example 9: (S)-3-((9-ethyl-2-(((2R,3S)-2-hydroxypentan-3-yl)amino)-9H-purin-6-yl)amino)pyrrolidine-1-sulfonamide

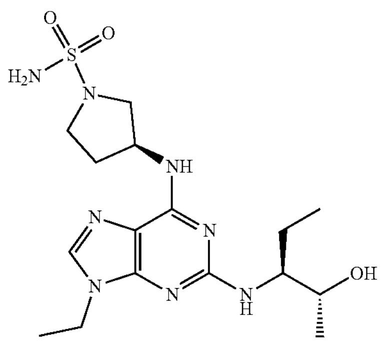 [SMILES: CC[C@H](Nc1nc(N[C@H]2CCN(S(N)(=O)=O)C2)c2ncn(CC)c2n1)[C@@H](C)O]

tert-Butyl (((S)-3-((9-ethyl-2-(((2R,3S)-2-hydroxypentan-3-yl)amino)-9H-purin-6-yl)amino)pyrrolidin-1-yl)

sulfonyl)carbamate (Intermediate 12, 0.121 g, 0.24 mmol) was weighed in a 20 mL scintillation vial, added dichloromethane and hydrochloric acid (0.236 mL, 0.94 mmol) (4 M solution in 1,4-dioxane) and stirred at rt for 1.5 h (LCMS showed no SM remaining). The reaction was concentrated to yield a white foam as HCl salt of the desired product. A part of the solid was dissolved in ethyl acetate and aq. $NaHCO_3$ solution was added. Organic layer was separated, dried and concentrated to yield (S)-3-((9-ethyl-2-(((2R,3S)-2-hydroxypentan-3-yl)amino)-9H-purin-6-yl)amino)pyrrolidine-1-sulfonamide (Example 9, 33 mg, 33.9%) as the free base. $^1$H NMR (500 MHz, DMSO-$d_6$) 0.79-0.93 (3H, m), 0.96-1.16 (3H, m), 1.29-1.44 (4H, m), 1.62-1.84 (1H, m), 2.01 (1H, br dd), 2.12-2.27 (1H, m), 3.05 (1H, br dd), 3.14-3.29 (3H, m), 3.51 (1H, dd), 3.59-3.68 (1H, m), 3.74-3.80 (1H, m), 3.99 (2H, q), 4.66 (1H, br s), 5.88-6.04 (1H, m), 6.77 (2H, s), 7.33 (1H, br s), 7.73 (1H, s). m/z (ES$^+$) $[M+H]^+$ =413.

Example 10: (S)-3-((9-ethyl-2-(((S)-2-oxopentan-3-yl)amino)-9H-purin-6-yl)amino)pyrrolidine-1-sulfonamide

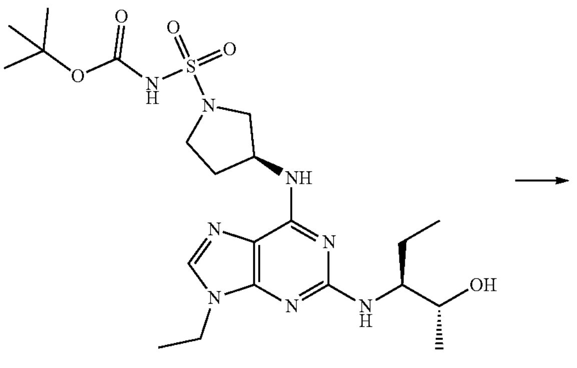

Intermediate 12

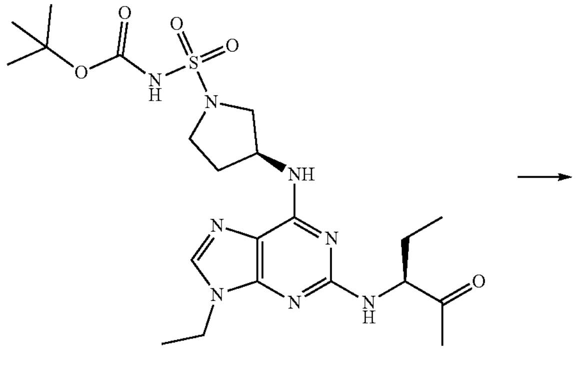

Intermediate 13

-continued

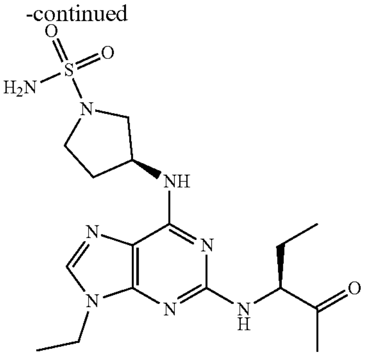

Example 10

Intermediate 13: tert-butyl (((S)-3-((9-ethyl-2-(((S)-2-oxopentan-3-yl)amino)-9H-purin-6-yl)amino)pyrrolidin-1-yl) sulfonyl) carbamate tert-Butyl (((S)-3-((9-ethyl-2-(((2R,3S)-2-hydroxypentan-3-yl)amino)-9H-purin-6-yl)amino)pyrrolidin-1-yl) sulfonyl)carbamate (Intermediate 12, 0.457 g, 0.89 mmol) was suspended in DCM (25.4 ml) and cooled to 0° C. and treated with DMSO (3.35 ml, 47.25 mmol) and DIEA (0.934 ml, 5.35 mmol). The reaction was then treated with pyridine-sulfur trioxide (0.568 g, 3.57 mmol) and stirred at 0° C. for 30 minutes, warmed up to room temperature and stirred for 20 minutes. The reaction was quenched with water, diluted with EtOAc and the organic layer was separated. The organic layer was washed with water, brine, and dried over sodium sulfate. The drying agent was filtered and the filtrate was concentrated under reduced pressure. The resulting residue was purified by flash silica chromatography, elution gradient 0 to 100% EtOAc in hexane followed by 2% MeOH in EtOAc. Product fractions were concentrated under reduced pressure to afford tert-butyl (((S)-3-((9-ethyl-2-(((S)-2-oxopentan-3-yl)amino)-9H-purin-6-yl)amino)pyrrolidin-1-yl)sulfonyl)carbamate (Intermediate 13, 0.326 g, 71.6%) as a white solid. $^1$H NMR (500 MHz, DMSO-$d_6$) δ ppm 0.92 (3H, t), 1.34 (3H, t), 1.43 (9H, s), 1.61-1.77 (2H, m), 1.97-2.17 (5H, m), 3.26-3.30 (1H, m), 3.38-3.44 (1H, m), 3.53-3.59 (1H, m), 3.70 (1H, dd), 3.96-4.13 (3H, m), 4.55 (1H, br s), 6.77 (1H, br s), 7.55 (1H, br s), 7.78 (1H, s), 10.90 (1H, s). m/z (ES$^+$) [M+H]*=511.

Example 10: (S)-3-((9-ethyl-2-(((S)-2-oxopentan-3-yl)amino)-9H-purin-6-yl)amino)pyrrolidine-1-sulfonamide

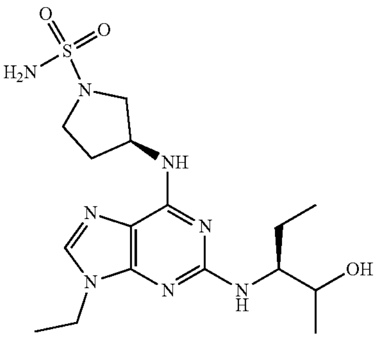 [SMILES: CC[C@H](Nc1nc(N[C@H]2CCN(S(N)(=O)=O)C2)c2ncn(CC)c2n1)C(C)O]

tert-Butyl (((S)-3-((9-ethyl-2-(((S)-2-oxopentan-3-yl) amino)-9H-purin-6-yl)amino)pyrrolidin-1-yl)sulfonyl)carbamate (Intermediate 13, 191 mg, 0.37 mmol) was weighed in a 20 mL scintillation vial, added dichloromethane (5 mL) and hydrochloric acid (0.374 mL, 1.50 mmol) (4 M solution in 1,4-dioxane) and stirred at rt for 1.5 h. The reaction was concentrated to yield a white foam. The solid was purified by flash C18 chromatography using 0-100% ACN in $H_2O$ (0.1% $NH_4OH$ additive) and the product fractions were directly lyophilized to yield (S)-3-((9-ethyl-2-(((S)-2-oxopentan-3-yl)amino)-9H-purin-6-yl)amino)pyrrolidine-1-sulfonamide (Example 10, 60.0 mg, 39.1%). $^1$H NMR (500 MHZ, DMSO-$d_6$) δ ppm 0.93 (3H, t), 1.34 (3H, t), 1.62-1.80 (2H, m), 1.93-2.06 (1H, m), 2.08 (3H, s), 2.11-2.22 (1H, m), 3.00-3.10 (1H, m), 3.12-3.24 (1H, m), 3.41-3.54 (2H, m), 3.96-4.15 (3H, m), 4.58 (1H, br s), 6.70-6.84 (3H, m), 7.47 (1H, br s), 7.80 (1H, s). m/z (ES$^+$) [M+H]$^+$=411.

Example 11: (S)—N-ethyl-3-((9-ethyl-2-(((2S,3R)-2-hydroxypentan-3-yl)amino)-9H-purin-6-yl)amino) pyrrolidine-1-sulfonamide

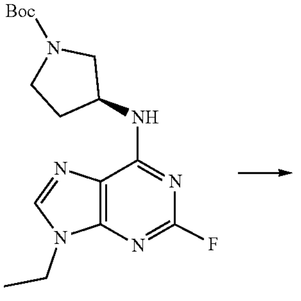

Intermediate 9

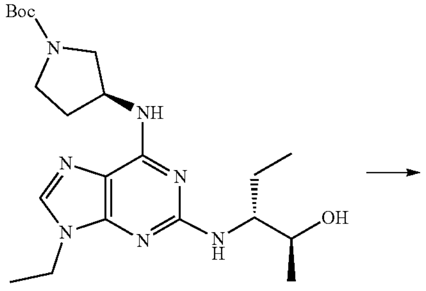

Intermediate 14

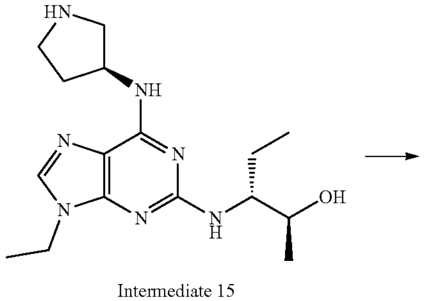

Intermediate 15

-continued

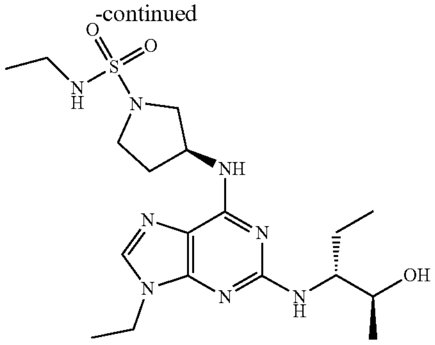

Example 11

Intermediate 14: tert-butyl (S)-3-((9-ethyl-2-(((2S,3R)-2-hydroxypentan-3-yl)amino)-9H-purin-6-yl) amino)pyrrolidine-1-carboxylate tert-Butyl (S)-3-((9-ethyl-2-fluoro-9H-purin-6-yl)amino) pyrrolidine-1-carboxylate (Intermediate 9, 2.5 g, 7.13 mmol), (2S,3R)-3-aminopentan-2-ol (2.94 g, 28.54 mmol), and DIEA (12.46 ml, 71.35 mmol) were dissolved in dimethylsulfoxide (12.31 ml) and the reaction was heated at 140° C. The reaction was stirred at 140° C. for 65 h, cooled, concentrated under vacuum and purified by flash C18 column chromatography using 0-100% acetonitrile in water (0.1% formic acid) to yield tert-butyl (S)-3-((9-ethyl-2-(((2S,3R)-2-hydroxypentan-3-yl)amino)-9H-purin-6-yl) amino)pyrrolidine-1-carboxylate (Intermediate 14, 3.00 g, 97%) as a white solid. $^1$H NMR (500 MHz, DMSO-$d_6$) 0.86 (3H, t), 1.06 (3H, d), 1.32-1.42 (13H, m), 1.65-1.74 (1H, m), 1.95-2.05 (1H, m), 2.05-2.15 (1H, m), 3.15-3.31 (3H, m), 3.41-3.48 (1H, m), 3.57-3.68 (2H, m), 3.73-3.79 (1H, m), 3.99 (2H, q), 4.64 (1H, br s), 5.96 (1H, br s), 7.39 (1H, br s), 7.73 (1H, s); m/z (ES$^+$) [M+H]$^+$=434.

Intermediate 15: (2S,3R)-3-((9-ethyl-6-(((S)-pyrrolidin-3-yl)amino)-9H-purin-2-yl)amino)pentan-2-ol hydrochloride In a reaction flask was added tert-butyl (S)-3-((9-ethyl-2-(((2S,3R)-2-hydroxypentan-3-yl)amino)-9H-purin-6-yl) amino)pyrrolidine-1-carboxylate (Intermediate 14, 3.09 g, 7.13 mmol), dichloromethane (5 mL) and hydrogen chloride (8.91 mL, 35.64 mmol) (4 M in 1,4-dioxane). The reaction was stirred at rt for overnight. The reaction mixture was concentrated under vacuum to obtain a white solid as (2S,3R)-3-((9-ethyl-6-(((S)-pyrrolidin-3-yl)amino)-9H-purin-2-yl)amino)pentan-2-ol hydrochloride (Intermediate 15, 2.65 g, 101%). m/z (ES$^+$) [M+H]$^+$=334.

Example 11: (S)—N-ethyl-3-((9-ethyl-2-(((2S,3R)-2-hydroxypentan-3-yl)amino)-9H-purin-6-yl)amino) pyrrolidine-1-sulfonamide

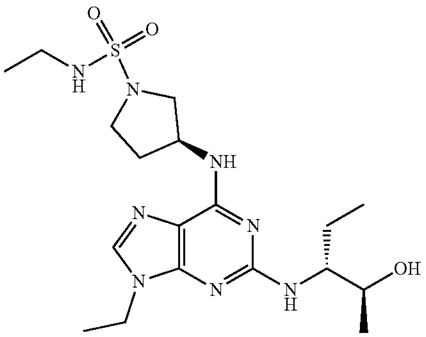 [SMILES: CCNS(=O)(=O)N1CC[C@H](Nc2nc(N[C@H](CC)[C@H](C)O)nc3c2ncn3CC)C1]

(2S,3R)-3-((9-ethyl-6-(((S)-pyrrolidin-3-yl)amino)-9H-purin-2-yl)amino)pentan-2-ol, HCl (Intermediate 15, 1.60 g, 4.33 mmol) was weighed in a reaction flask, added dichloromethane (50 mL) and triethylamine (3.00 mL, 21.63 mmol) and the reaction was cooled to −78° C. Ethylsulfamoyl chloride (0.686 g, 4.54 mmol) was added to the reaction mixture as a solution in DCM and stirred for 2 h. The reaction was quenched with aq. $NaHCO_3$ solution, stirred for 15 mins, extracted with DCM, organic layer was separated, dried over $MgSO_4$ and concentrated to yield a white foam. The solid was purified by flash silica chromatography using 0-20% MeOH in DCM to yield (S)—N-ethyl-3-((9-ethyl-2-(((2S,3R)-2-hydroxypentan-3-yl) amino)-9H-purin-6-yl)amino)pyrrolidine-1-sulfonamide (Example 11, 1.100 g, 57.7%). 1H NMR (500 MHZ, DMSO-$d_6$) 0.86 (3H, t), 1.04-1.08 (6H, m), 1.31-1.44 (4H, m), 1.70 (1H, ddd), 2.05 (1H, br dd), 2.16-2.24 (1H, m), 2.93-2.99 (2H, m), 3.10 (1H, dd), 3.16-3.25 (1H, m), 3.33-3.42 (1H, m), 3.54 (1H, dd), 3.62-3.68 (1H, m), 3.76 (1H, tdd), 3.99 (2H, q), 4.56-4.75 (2H, m), 5.90-6.03 (1H, m), 7.07 (1H, t), 7.27-7.47 (1H, m), 7.73 (1H, s). m/z ($ES^+$) $[M+H]^+$=441.

Example 12: (S)—N-ethyl-3-((9-ethyl-2-(((R)-2-oxopentan-3-yl)amino)-9H-purin-6-yl)amino)pyrrolidine-1-sulfonamide

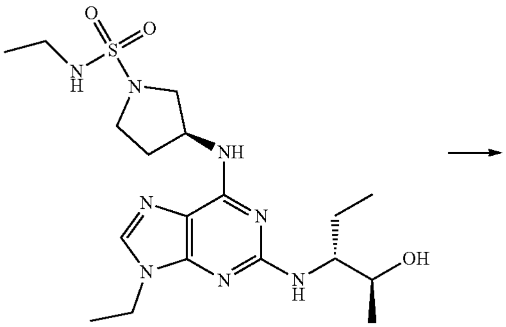

Example 11

-continued

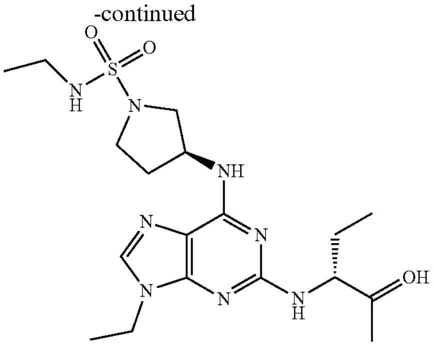

Example 12

(S)—N-ethyl-3-((9-ethyl-2-(((2S,3R)-2-hydroxypentan-3-yl)amino)-9H-purin-6-yl)amino)pyrrolidine-1-sulfonamide (Example 11, 0.873 g, 1.98 mmol) was suspended in DCM (56.5 ml), cooled to 0° C. and treated with DMSO (7.45 ml, 105.02 mmol) and DIEA (2.077 ml, 11.89 mmol). The reaction was treated with pyridine-sulfur trioxide (1.262 g, 7.93 mmol) and stirred at 0° C. for 30 minutes, warmed up to room temperature and stirred for 20 minutes. The reaction was quenched with water, diluted with EtOAc and the layers were separated. The organic was washed with water, brine, and dried over sodium sulfate. The drying agent was filtered and the filtrate was concentrated under reduced pressure. The resulting residue was purified by flash C18 chromatography using 0-100% acetonitrile in $H_2O$ (0.1% formic acid). Product fractions were concentrated under reduced pressure to afford (S)—N-ethyl-3-((9-ethyl-2-(((R)-2-oxopentan-3-yl)amino)-9H-purin-6-yl)amino)pyrrolidine-1-sulfonamide (Example 12, 0.687 g, 79%). $^1H$ NMR (500 MHZ, DMSO-$d_6$) 0.92 (3H, t), 1.07 (3H, t), 1.34 (3H, t), 1.62-1.79 (2H, m), 1.99-2.06 (1H, m), 2.07 (3H, s), 2.15-2.24 (1H, m), 2.97 (2H, quin), 3.07 (1H, br dd), 3.17-3.26 (1H, m), 3.39 (1H, td), 3.44-3.49 (1H, m), 3.99 (2H, q), 4.05-4.12 (1H, m), 4.45-4.79 (1H, m), 6.77 (1H, br s), 7.07 (1H, t), 7.49 (1H, br s), 7.78 (1H, s); m/z ($ES^+$) [M+H]+=439.

Example 13: (S)—N-ethyl-3-((9-ethyl-2-(((2RS, 3R)-2-hydroxypentan-3-yl)amino)-9H-purin-6-yl) amino)pyrrolidine-1-sulfonamide e

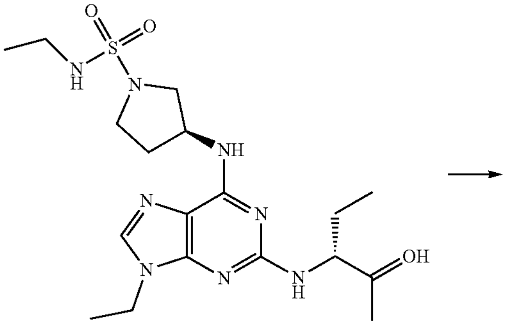

Example 12

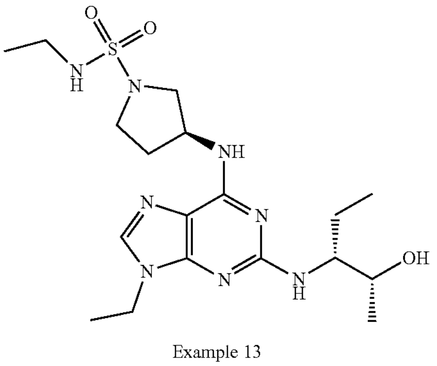

Example 13

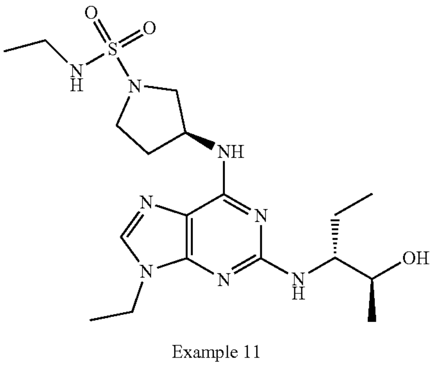

Example 11

(S)—N-ethyl-3-((9-ethyl-2-(((R)-2-oxopentan-3-yl) amino)-9H-purin-6-yl)amino)pyrrolidine-1-sulfonamide (Example 12, 0.200 g, 0.46 mmol) was dissolved in THF (4.75 ml)/MeOH (0.950 ml) and treated with sodium tetrahydroborate (0.028 g, 0.73 mmol). The reaction mixture was stirred under nitrogen for 35 minutes. The reaction was quenched with saturated ammonium chloride and extracted with EtOAc. The organic extracts were dried over sodium sulfate, filtered, and the filtrate was concentrated under reduced pressure to afford a 2.2:1 mixture of diastereomers. The diastereomers were separated by SFC (IH 21×250 mm, 5 μm column) purification using 0.2% $NH_4OH$ in MeOH to yield (S)—N-ethyl-3-((9-ethyl-2-(((2R,3R)-2-hydroxypentan-3-yl)amino)-9H-purin-6-yl)amino)pyrrolidine-1-sulfonamide (Example 13, 28 mg, 0.064 mmol, 13.94%) as the minor isomer. $^1H$ NMR (500 MHz, DMSO-$d_6$) 0.88 (3H, t), 1.02-1.09 (6H, m), 1.35 (3H, t), 1.43-1.52 (1H, m), 1.55-1.63 (1H, m), 2.00-2.08 (1H, m), 2.17-2.24 (1H, m), 2.93-2.99 (2H, m), 3.09 (1H, dd), 3.19-3.29 (1H, m), 3.33-3.40 (1H, m), 3.55 (1H, dd), 3.74-3.81 (2H, m), 3.99 (2H, q), 4.50 (1H, br s), 4.65 (1H, br s), 5.66 (1H, br s), 7.08 (1H, t), 7.38 (1H, br s), 7.74 (1H, s). m/z ($ES^+$) $[M+H]^+$=441.

Example 14: (S)-3-((2-(((R)-1-cyclopropyl-2-hydroxyethyl)amino)-9-(difluoromethyl)-9H-purin-6-yl)amino)-N-ethylpyrrolidine-1-sulfonamide

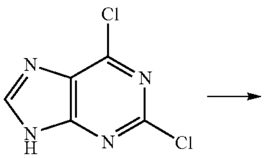

Intermediate 1

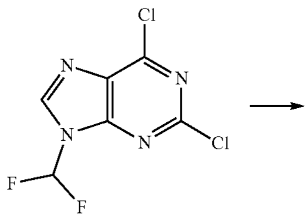

Intermediate 16

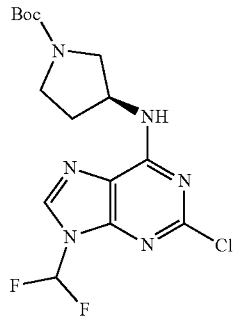

Intermediate 17

-continued

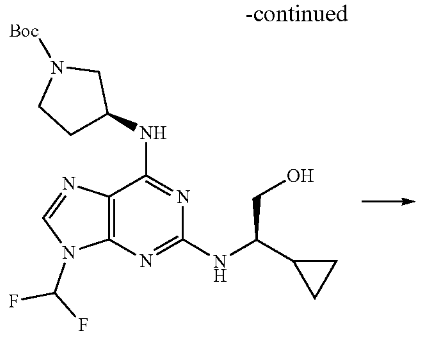

Intermediate 18

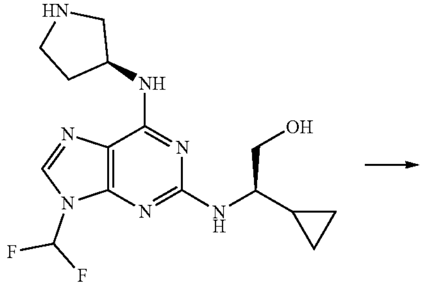

Intermediate 19

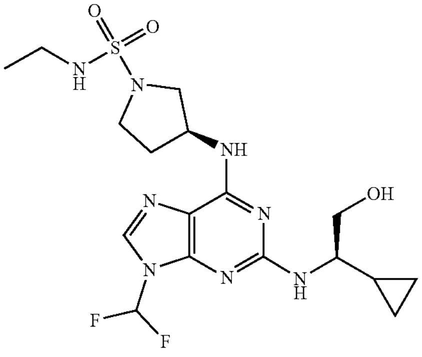

Example 14

Intermediate 16: 2,6-dichloro-9-(difluoromethyl)-9H-purine 2,6-Dichloro-9H-purine (Intermediate 1, 8.18 g, 43.28 mmol), diethyl (bromodifluoromethyl)phosphonate (16.85 g, 60.59 mmol) and potassium fluoride (5.03 g, 86.56 mmol) in MeCN (160 mL) were stirred under nitrogen atmosphere at rt for 16 h. The reaction was quenched with water, extracted with EtOAc, EtOAc layer was dried and concentrated. The colorless liquid was purified by flash silica chromatography using hexane: EtOAc to yield 2,6-dichloro-9-(difluoromethyl)-9H-purine (Intermediate 16, 9.80 g, 95%) contaminated with residual diethyl (bromodifluoromethyl)phosphonate. $^1$H NMR (500 MHZ, Dichloromethane-$d_2$) 7.66 (1H, t), 8.51 (1H, s). m/z (ES$^+$) [M+H]$^+$=239.

Intermediate 17: tert-butyl (S)-3-((2-chloro-9-(difluoromethyl)-9H-purin-6-yl)-amino)pyrrolidine-1-carboxylate 2,6-Dichloro-9-(difluoromethyl)-9H-purine (Intermediate 16, 4.00 g, 4.18 mmol, 25% wt), tert-butyl (S)-3-aminopyrrolidine-1-carboxylate (0.812 g, 4.18 mmol) was dissolved in acetonitrile (30 mL) under $N_2$, added N,N-diisopropylethylamine (2.192 mL, 12.55 mmol), and stirred at rt for 16 h. Added 0.3 equiv additional tert-butyl (S)-3-aminopyrrolidine-1-carboxylate and stirred for 6 h. The solvent was removed under reduced pressure and the residue was dissolved in DCM, washed with aq. $NaHCO_3$ solution. The aqueous layer was re-extracted with DCM, combined organic layers were dried over magnesium sulfate, filtered and concentrated under reduced pressure to obtain a yellow oil which was purified by flash silica chromatography to yield tert-butyl (S)-3-((2-chloro-9-(difluoromethyl)-9H-purin-6-yl)amino)pyrrolidine-1-carboxylate (Intermediate 17, 0.706 g, 43.4%). m/z (ES$^+$) [M+H]$^+$=389.

Intermediate 18: tert-butyl (S)-3-((2-(((R)-1-cyclopropyl-2-hydroxyethyl)amino)-9-(difluoromethyl)-9H-purin-6-yl)amino)pyrrolidine-1-carboxylate tert-Butyl (S)-3-((2-chloro-9-(difluoromethyl)-9H-purin-6-yl)amino)pyrrolidine-1-carboxylate (Intermediate 17, 706 mg, 1.82 mmol), (R)-2-amino-2-cyclopropylethan-1-ol, HCl (500 mg, 3.63 mmol), cesium carbonate (2071 mg, 6.36 mmol), 2-(dicyclohexylphosphino)-3,6-dimethoxy-2'-4'-6'-tri-i-propyl-1,1'-biphenyl (292 mg, 0.54 mmol), and palladium(II) acetate (40.8 mg, 0.18 mmol) were placed in an oven dried vial. The vial was evacuated and filled with nitrogen 2 times then tBuOH (5.19 mL) was added, the reaction was sealed and heated at 90° C. for 16 h. The reaction was concentrated and the resulting residue was purified by flash silica chromatography, elution gradient 0 to 100% EtOAc in hexanes followed by 0-10% MeOH in DCM. Product fractions were concentrated under reduced pressure to afford tert-butyl (3S)-3-((2-((1-cyclopropyl-2-hydroxyethyl)amino)-9-(difluoromethyl)-9H-purin-6-yl) amino)pyrrolidine-1-carboxylate (Intermediate 18, 0.361 g, 43.9%) as a yellow dry film. $^1$H NMR (500 MHZ, Dichloromethane-$d_2$) 0.34-0.46 (2H, m), 0.49-0.61 (2H, m), 1.02 (1H, br s), 1.47 (9H, br s), 1.98 (1H, br s), 2.24 (1H, br s), 3.28-3.37 (1H, m), 3.37-3.53 (3H, m), 3.75 (2H, br dd), 3.92 (1H, br d), 4.23 (1H, br s), 4.56-4.79 (1H, m), 5.43-5.55 (1H, m), 6.22 (1H, br s), 7.36 (1H, t), 7.77 (1H, s). m/z (ES$^+$) [M+H]$^+$=454.

Intermediate 19: (R)-2-cyclopropyl-2-((9-(difluoromethyl)-6-(((S)-pyrrolidin-3-yl)amino)-9H-purin-2-yl)amino)ethan-1-ol hydrochloride In a 30 mL scintillation vial was added tert-butyl (S)-3-((2-(((R)-1-cyclopropyl-2-hydroxyethyl)amino)-9-(difluoromethyl)-9H-purin-6-yl)amino)pyrrolidine-1-carboxylate (Intermediate 18, 0.3612 g, 0.80 mmol), dichloromethane (2 mL) and hydrogen chloride (0.996 ml, 3.98 mmol) (4 M in 1,4-dioxane). The vial was sealed and stirred at rt for 16 h. The reaction mixture was concentrated and dried under vacuum to obtain (R)-2-cyclopropyl-2-((9-(difluoromethyl)-6-(((S)-pyrrolidin-3-yl)amino)-9H-purin-2-yl)amino)ethan-1-ol. 4HCl (Intermediate 19, 0.406 g, 102%) as a white solid.

Example 14: (S)-3-((2-(((R)-1-cyclopropyl-2-hydroxyethyl)amino)-9-(difluoromethyl)-9H-purin-6-yl)amino)-N-ethylpyrrolidine-1-sulfonamide

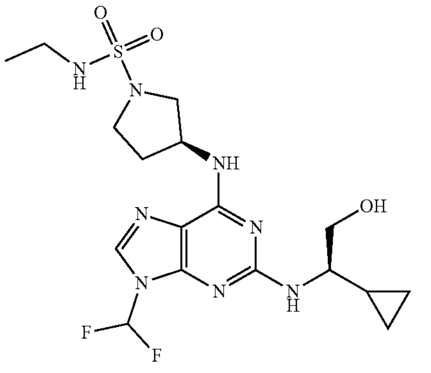 [SMILES: CCNS(=O)(=O)N1CC[C@H](Nc2nc(N[C@@H](CO)C3CC3)nc3c2ncn3C(F)F)C1]

(R)-2-cyclopropyl-2-((9-(difluoromethyl)-6-(((S)-pyrrolidin-3-yl)amino)-9H-purin-2-yl)amino)ethan-1-ol, 4HCl (Intermediate 19, 0.116 g, 0.23 mmol) was weighed in a 20 mL scintillation vial, added dichloromethane (5 mL) and triethylamine (0.129 ml, 0.93 mmol), and the reaction was cooled to −78° C. Ethylsulfamoyl chloride (0.039 g, 0.26 mmol) was added to the reaction mixture and stirred for 60 min. Additional ethylsulfamoyl chloride (5.34 mg, 0.04 mmol) was added and the reaction mixture was stirred for 1 h. The reaction was quenched with aq. $NaHCO_3$ solution, extracted with DCM, the organic layer was dried and concentrated. The crude product was purified by flash silica chromatography using 0-20% MeOH in DCM to yield (S)-3-((2-(((R)-1-cyclopropyl-2-hydroxyethyl)amino)-9-(difluoromethyl)-9H-purin-6-yl)amino)-N-ethylpyrrolidine-1-sulfonamide (Example 14, 0.037 g, 34.6%) as a colorless film. $^1H$ NMR (500 MHZ, Dichloromethane-$d_2$) 0.37-0.46 (2H, m), 0.52-0.67 (2H, m), 0.92-1.08 (1H, m), 1.21 (3H, t), 1.90 (1H, br s), 2.03-2.12 (1H, m), 2.38 (1H, dq), 3.12-3.21 (2H, m), 3.27-3.46 (3H, m), 3.54 (1H, ddd), 3.65-3.80 (2H, m), 3.92 (1H, dd), 4.77 (1H, br s), 4.84 (1H, br s), 5.31-5.35 (1H, m), 6.13 (1H, br s), 7.36 (1H, t), 7.78 (1H, s). 19F NMR (471 MHz, Dichloromethane-$d_2$)-96.02 (2F, s). m/z ($ES^+$) $[M+H]^+$=461.

Example 15: 2-cyclopentyl-2-((9-isopropyl-6-(((S)-1-(methylsulfonyl)pyrrolidin-3-yl)amino)-9H-purin-2-yl)amino)ethan-1-ol

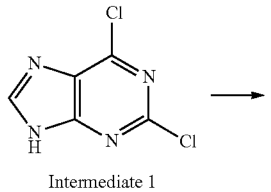

Intermediate 1

-continued

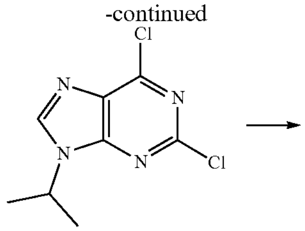

Intermediate 20

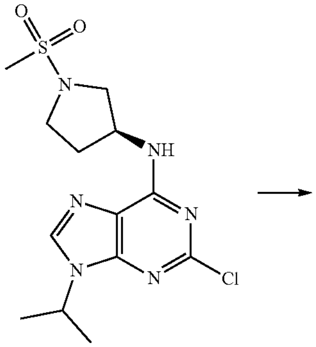

Intermediate 21

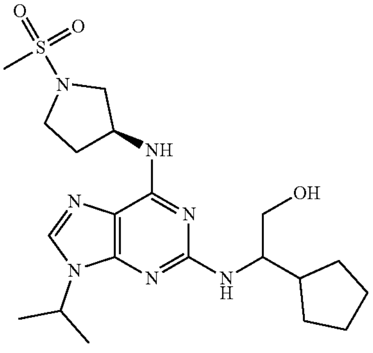

Example 15

Intermediate 20: 2,6-dichloro-9-isopropyl-9H-purine

DIAD (20.57 mL, 105.82 mmol) was added slowly to 2,6-dichloro-9H-purine (Intermediate 1, 10 g, 52.91 mmol), IPA (16.31 mL, 211.64 mmol) and triphenylphosphine (27.8 g, 105.82 mmol) in THF (30 mL). The resulting mixture was stirred at rt for 16 h. The reaction mixture was diluted with EtOAc (500 mL), and washed sequentially with saturated aq. $Na_2CO_3$ solution (300 mL×3) and aq. brine solution (300 mL×2). The organic layer was dried over $Na_2SO_4$, filtered and concentrated under reduced pressure to afford the crude product. The crude product was purified by flash silica chromatography, elution gradient 0 to 50% EtOAc in petroleum ether. Pure fractions were evaporated to dryness to afford 2,6-dichloro-9-isopropyl-9H-purine (Intermediate 20, 7.00 g, 57.3%) as a white solid (contaminated with triphenyl phosphine oxide). This compound was subjected to the next step without further purification. m/z ($ES^+$) $[M+H]^+$=231.

Intermediate 21: (S)-2-chloro-9-isopropyl-N-(1-(methylsulfonyl)pyrrolidin-3-yl)-9H-purin-6-amine DIEA (2.72 mL, 15.58 mmol) was added to 2,6-dichloro-9-isopropyl-9H-purine (Intermediate 20, 1.2 g, 3.12 mmol, 60% wt) and (S)-1-(methylsulfonyl)pyrrolidin-3-amine hydrochloride (0.625 g, 3.12 mmol) in iPrOH (4 mL). The resulting mixture was stirred at 100° C. for 2 hours. The reaction mixture was quenched with saturated $NH_4Cl$ (100 mL), extracted with DCM (3×100 mL), the organic layer was dried over $Na_2SO_4$, filtered and evaporated to afford the crude product. The crude product was purified by flash C18 chromatography, elution gradient 5 to 70% MeCN in water (0.1% $NH_4HCO_3$). Pure fractions were evaporated to dryness to afford (S)-2-chloro-9-isopropyl-N-(1-(methylsulfonyl)pyrrolidin-3-yl)-9H-purin-6-amine (Intermediate 21, 0.750 g, 67.1%) as a white solid. $^1$H NMR (400 MHZ, DMSO-$d_6$) δ 1.50 (6H, d), 2.04 (1H, s), 2.23 (1H, s), 2.92 (3H, s), 3.24 (1H, s), 3.33-3.39 (2H, m), 3.48 (1H, s), 3.60 (1H, s), 4.68 (1H, p), 8.33 (1H, s), 8.52 (1H, s). m/z (ES$^+$) $[M+H]^+$=359.

Example 15: 2-cyclopentyl-2-((9-isopropyl-6-(((S)-1-(methylsulfonyl)pyrrolidin-3-yl)amino)-9H-purin-2-yl)amino)ethan-1-ol

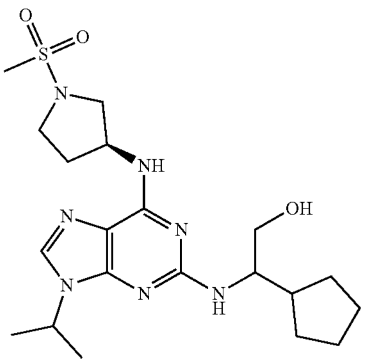 [SMILES: CC(C)n1cnc2c(N[C@H]3CCN(S(C)(=O)=O)C3)nc(NC(CO)C3CCCC3)nc21]

2-Amino-2-cyclopentylethan-1-ol (194 mg, 1.50 mmol) and (S)-2-chloro-9-isopropyl-N-(1-(methylsulfonyl)pyrrolidin-3-yl)-9H-purin-6-amine (Intermediate 21, 360 mg, 1.00 mmol) were placed in a vial and the reaction mixture was dissolved in 1 mL of dry NMP. Then N-ethyl-N-isopropylpropan-2-amine (648 mg, 5.02 mmol) was added. The reaction mixture was heated with stirring for 16 h at 140° C. After cooling to ambient temperature, the mixture was evaporated under vacuum. The residue was purified by flash C18 chromatography using water (contains $NH_3$) and methanol as eluents to afford 2-cyclopentyl-2-((9-isopropyl-6-(((S)-1-(methylsulfonyl)pyrrolidin-3-yl)amino)-9H-purin-2-yl)amino)ethan-1-ol (Example 15, 4.70 mg, 1.037%). m/z (ES$^+$) $[M+H]^+$=452.

Example 16: 2-((9-isopropyl-6-(((S)-1-(methylsulfonyl)pyrrolidin-3-yl)amino)-9H-purin-2-yl)amino)-2-(tetrahydrofuran-2-yl)ethan-1-ol

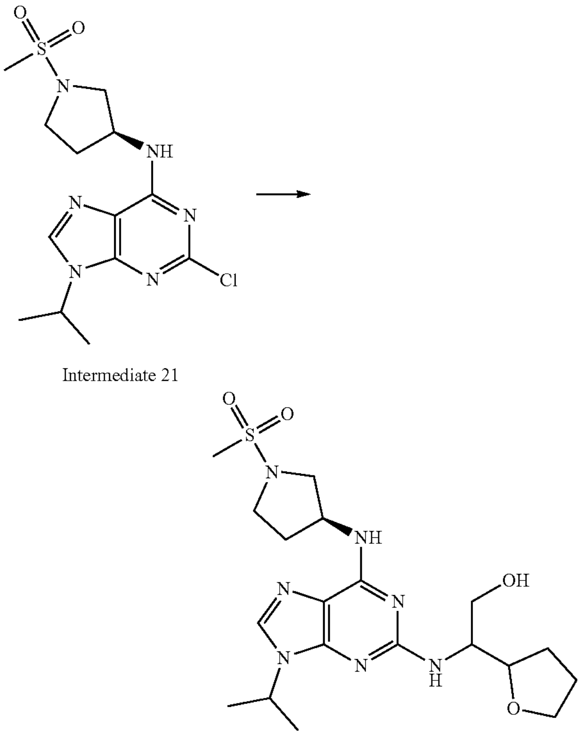

Intermediate 21

Example 16

2-Amino-2-(tetrahydrofuran-2-yl)ethan-1-ol (197 mg, 1.50 mmol) and (S)-2-chloro-9-isopropyl-N-(1-(methylsulfonyl)pyrrolidin-3-yl)-9H-purin-6-amine (Intermediate 21, 360 mg, 1.00 mmol) were placed in a vial and the reaction mixture was dissolved in 1 mL of dry NMP. Then N-ethyl-N-isopropylpropan-2-amine (648 mg, 5.02 mmol) was added. The reaction mixture was heated with stirring for 16 h at 140° C. After cooling to ambient temperature, the mixture was evaporated under vacuum. The residue was purified by flash C18 chromatography using water (contains $NH_3$) and methanol as eluents to afford 2-((9-isopropyl-6-(((S)-1-(methylsulfonyl)pyrrolidin-3-yl)amino)-9H-purin-2-yl)amino)-2-(tetrahydrofuran-2-yl)ethan-1-ol (Example 16, 4.60 mg, 1.011%). m/z (ES$^+$) $[M+H]^+$=454.

Example 17: (R)-2-((6-(((3R*,4R*)-1-((1H-imidazol-2-yl)sulfonyl)-4-fluoropyrrolidin-3-yl)amino)-9-ethyl-9H-purin-2-yl)amino)-2-cyclopropylethan-1-ol

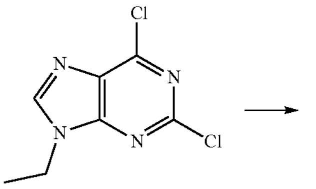

Intermediate 2

-continued

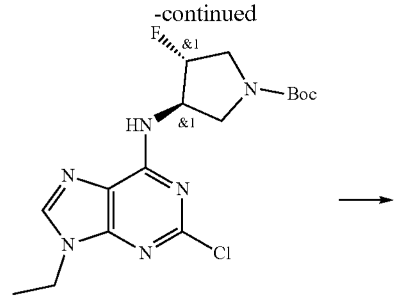

Intermediate 22

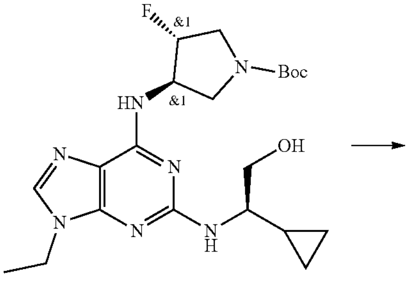

Intermediate 23

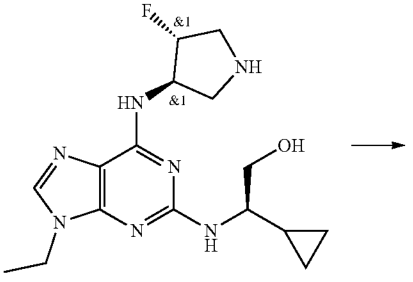

Intermediate 24

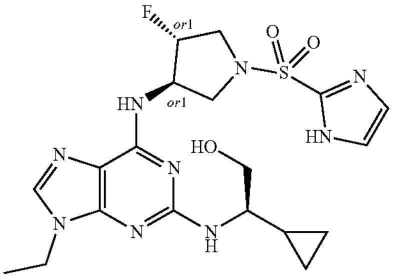

Example 17

Intermediate 22: rac-tert-butyl (3R,4R)-3-((2-chloro-9-ethyl-9H-purin-6-yl)amino)-4-fluoropyrrolidine-1-carboxylate 2,6-Dichloro-9-ethyl-9H-purine (Intermediate 2, 0.32 g, 1.47 mmol) and trans-1-Boc-3-amino-4-fluoropyrrolidine (0.361 g, 1.77 mmol) were placed in a 20 mL reaction vial under nitrogen and dissolved in acetonitrile (8.44 mL). The reaction was treated with DIEA (0.772 ml, 4.42 mmol), sealed and heated at 100° C. for 16 h. The reaction was concentrated at reduced pressure and the resulting residue was purified by flash silica chromatography, elution gradient 0 to 100% EtOAc in hexanes (EtOAc contains 6% MeOH). Product fractions were concentrated under reduced pressure to afford rac-tert-butyl (3R,4R)-3-((2-chloro-9-ethyl-9H-purin-6-yl)amino)-4-fluoropyrrolidine-1-carboxylate (Intermediate 22, 0.529 g, 93%) as a beige foam. $^1$H NMR (DMSO-$d_6$) 1.35-1.44 (12H, m), 3.40-3.78 (4H, m), 4.14 (2H, q), 4.55-4.81 (1H, m), 5.08-5.29 (1H, m), 8.25 (1H, s), 8.68 (1H, br d); m/z (ES$^+$) $[M+H]^+$=385.

Intermediate 23: tert-butyl (3RS, 4RS)-3-((2-(((R)-1-cyclopropyl-2-hydroxyethyl)amino)-9-ethyl-9H-purin-6-yl)amino)-4-fluoropyrrolidine-1-carboxylate Rac-tert-Butyl (3R,4R)-3-((2-chloro-9-ethyl-9H-purin-6-yl)amino)-4-fluoropyrrolidine-1-carboxylate (Intermediate 22, 0.529 g, 1.37 mmol), (R)-2-amino-2-cyclopropylethan-1-ol, HCl (0.378 g, 2.75 mmol), cesium carbonate (1.568 g, 4.81 mmol), 2-(Dicyclohexylphosphino)-3,6-dimethoxy-2'-4'-6'-tri-i-propyl-1,1'-biphenyl (0.221 g, 0.41 mmol), and palladium(II) acetate (0.031 g, 0.14 mmol) were placed in an oven dried and under nitrogen microwave vial. The vial was evacuated and filled with nitrogen 2 times then tBuOH (6.87 mL) was added and the reaction was sealed and heated in an oil bath at 90° C. overnight. LC/MS showed complete reaction. The reaction was diluted with EtOAc/$H_2O$. The layers were separated and the organic was dried over sodium sulfate, filtered, and the filtrate concentrated under reduced pressure. The resulting residue was purified by flash silica chromatography, elution gradient 0 to 100% EtOAc in hexanes (EtOAc contains 7% MeOH). Product fractions were concentrated under reduced pressure to afford tert-butyl (3RS,4RS)-3-((2-(((R)-1-cyclopropyl-2-hydroxyethyl)amino)-9-ethyl-9H-purin-6-yl)amino)-4-fluoropyrrolidine-1-carboxylate (Intermediate 23, 0.308 g, 49.8%) as a beige solid. $^1$H NMR (DMSO-$d_6$) 0.14-0.44 (4H, m), 0.91-1.04 (1H, m), 1.32 (3H, t), 1.41 (9H, s), 3.40-3.73 (7H, m), 3.97 (2H, q), 4.57 (1H, br s), 4.63-4.82 (1H, m), 5.06-5.38 (1H, m), 6.04 (1H, br d), 7.50-7.69 (1H, m), 7.74 (1H, s); m/z (ES$^+$) $[M+H]^+$=450.

Intermediate 24: (R)-2-cyclopropyl-2-((9-ethyl-6-(((3RS,4RS)-4-fluoropyrrolidin-3-yl)amino)-9H-purin-2-yl)amino)ethan-1-ol hydrochloride tert-Butyl (3RS,4RS)-3-((2-(((R)-1-cyclopropyl-2-hydroxyethyl)amino)-9-ethyl-9H-purin-6-yl)amino)-4-fluoropyrrolidine-1-carboxylate (Intermediate 23, 0.308 g, 0.69 mmol) was dissolved in MeOH (2.57 mL) and treated with HCl (4.0 M in Dioxane) (1.713 ml, 6.85 mmol). The reaction was stirred at room temperature for 1.5 h. The reaction was concentrated at reduced pressure to afford (R)-2-cyclopropyl-2-((9-ethyl-6-(((3RS,4RS)-4-fluoropyrrolidin-3-yl)amino)-9H-purin-2-yl)amino)ethan-1-ol. 4HCl (Intermediate 24, 0.315 g, 93%) as a yellow foam; m/z (ES$^+$) $[M+H]^+$=350.

Example 17: (R)-2-((6-(((3R*,4R*)-1-((1H-imidazol-2-yl)sulfonyl)-4-fluoropyrrolidin-3-yl)amino)-9-ethyl-9H-purin-2-yl)amino)-2-cyclopropylethan-1-ol

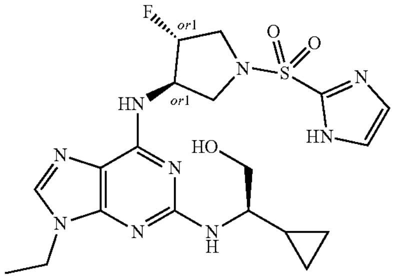 [SMILES: CCn1cnc2c(N[C@@H]3CN(S(=O)(=O)c4ncc[nH]4)C[C@H]3F)nc(N[C@@H](CO)C3CC3)nc21]

(R)-2-cyclopropyl-2-((9-ethyl-6-(((3RS,4RS)-4-fluoropyrrolidin-3-yl)amino)-9H-purin-2-yl)amino)ethan-1-ol, 4HCl (Intermediate 24, 315 mg, 0.64 mmol) was suspended in DCM (15.37 mL) and treated with TEA (532 μl, 3.82 mmol). The reaction was cooled to −78° C. and treated with a suspension of 1H-imidazole-2-sulfonyl chloride (106 mg, 0.64 mmol) in 3 mL of DCM. The reaction was stirred at that temperature for 30 minutes and then allowed to warm up slowly to room temperature. The reaction was concentrated under reduced pressure and the resulting residue was purified by flash silica chromatography, elution gradient 0 to 15% MeOH in DCM followed by preparative SFC (Chiralpak AD column, 5 μm, 21 mm diameter, 250 mm length), 40° C. column temperature, 100 bar outlet pressure, 70 mL/min flow rate), eluting with 15% MeOH containing 0.2% $NH_4OH$ in $CO_2$, to afford (R)-2-((6-(((3R*,4R*)-1-((1H-imidazol-2-yl)sulfonyl)-4-fluoropyrrolidin-3-yl)amino)-9-ethyl-9H-purin-2-yl)amino)-2-cyclopropylethan-1-ol (Example 17, Isomer 1, 0.100 g, 32.8%) as a white dry film, $^1H$ NMR (DMSO-$d_6$) 0.15-0.23 (1H, m), 0.25-0.33 (1H, m), 0.33-0.44 (2H, m), 0.91-1.02 (1H, m), 1.32 (3H, t), 3.43-3.75 (6H, m), 3.81 (1H, br dd), 3.97 (2H, q), 4.57 (1H, br s), 4.65-4.89 (1H, m), 5.07-5.30 (1H, m), 6.07 (1H, br d), 7.38 (2H, s), 7.76 (1H, s), 7.92-8.37 (1H, m), 13.66 (1H, br s); m/z (ES$^+$) $[M+H]^+$=480; and isomer 2 (106 mg, 34.8%) as a dry film.

Example 18: (S)-3-((9-ethyl-2-(((2R,3S)-2-hydroxypentan-3-yl)amino)-9H-purin-6-yl)amino)-N—((R)-tetrahydrofuran-3-yl)pyrrolidine-1-sulfonamide

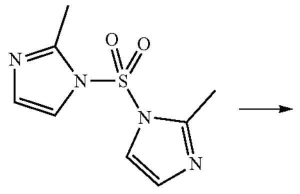

Intermediate 25

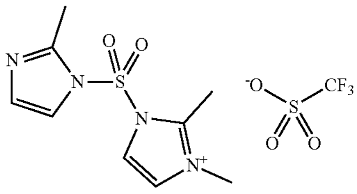

Intermediate 26

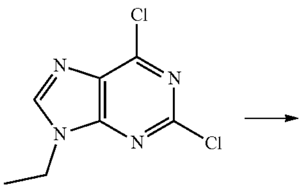

Intermediate 2

-continued

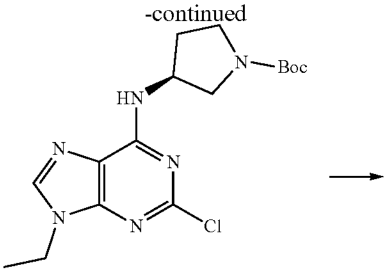

Intermediate 3

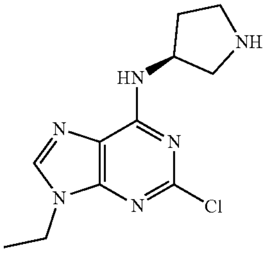

Intermediate 4

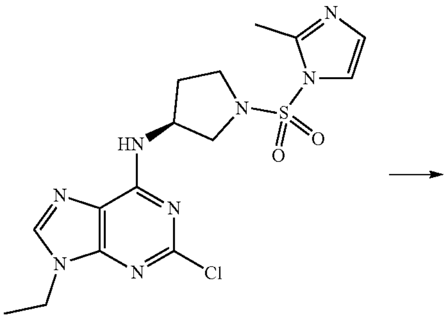

Intermediate 27

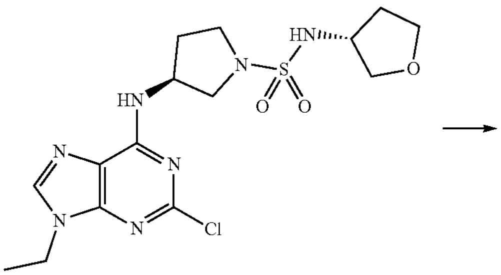

Intermediate 28

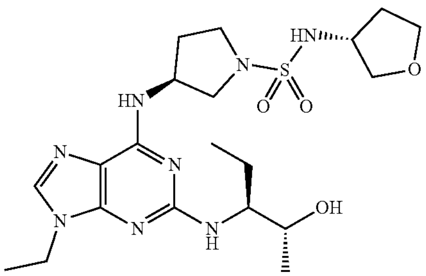

Example 18

Intermediate 26: 2,3-dimethyl-1-((2-methyl-1H-imidazol-1-yl)sulfonyl)-1H-imidazol-3-ium trifluoromethane sulfonate 1,1'-Sulfonylbis(2-methyl-1H-imidazole) (Intermediate 25, 3.00 g, 13.26 mmol) was dissolved in DCM (53.8 mL)

and cooled in dry ice/MeOH bath (−20° C.) under nitrogen. Methyl trifluoromethanesulfonate (1.460 ml, 13.26 mmol) was dissolved in DCM (17.95 mL) and added dropwise to the cold solution. The reaction was allowed to warm up to 20° C. and stir for 1.5 hrs. The white precipitate was allowed to settle down and the supernatant decanted. The solid was washed with 30 mL of DCM and dried under vacuum to afford 2,3-dimethyl-1-((2-methyl-1H-imidazol-1-yl)sulfonyl)-1H-imidazol-3-ium (Intermediate 26, 4.63 g, 89%) as a white solid; $^1$H NMR (Methanol-$d_4$) 2.64 (3H, s), 2.88 (3H, s), 3.89 (3H, s), 7.09 (1H, d), 7.77 (1H, d), 7.90 (1H, d), 8.29 (1H, d).

Intermediate 3: tert-butyl (S)-3-((2-chloro-9-ethyl-9H-purin-6-yl)amino)-pyrrolidine-1-carboxylate 2,6-Dichloro-9-ethyl-9H-purine (Intermediate 2, 2.024 g, 9.32 mmol) and tert-butyl (S)-3-aminopyrrolidine-1-carboxylate (1.628 ml, 9.32 mmol) were dissolved in DMF (10.66 mL) and cooled to 0° C. under nitrogen. The reaction was then treated with DIEA (3.26 ml, 18.65 mmol) and allowed to warm up to room temperature and stirred for 48 hrs. The reaction was diluted with 50% saturated sodium chloride solution and extracted with DCM. The extracts were washed with brine, dried over sodium sulfate, filtered and the filtrate concentrated under reduced pressure. The resulting residue was coated on silica and purified by flash silica chromatography, elution gradient 0 to 100% EtOAc in hexanes then 10% MeOH in EtOAc. Product fractions were concentrated under reduced pressure to afford tert-butyl (S)-3-((2-chloro-9-ethyl-9H-purin-6-yl)amino)pyrrolidine-1-carboxylate (Intermediate 3, 3.56 g, 104%) as a white foam which solidified upon standing. NMR showed presence of residual DMF. $^1$H NMR (DMSO-$d_6$) 1.31-1.50 (12H, m), 1.83-2.27 (2H, m), 3.16-3.29 (2H, m), 3.44 (1H, br s), 3.58 (1H, br dd), 4.13 (2H, q), 4.48-5.44 (1H, m), 8.21 (1H, s), 8.47 (1H, br s); m/z (ES$^+$) [M+H]$^+$=367.

Intermediate 4: (S)-2-chloro-9-ethyl-N-(pyrrolidin-3-yl)-9H-purin-6-amine tert-Butyl (S)-3-((2-chloro-9-ethyl-9H-purin-6-yl)amino) pyrrolidine-1-carboxylate (Intermediate 3, 1.52 g, 4.14 mmol) was dissolved in MeOH (15.52 mL) and treated with HCl (4.0M in Dioxane) (10.34 ml, 41.38 mmol). The reaction was stirred at room temperature for 2 hrs. The reaction was diluted with methanol and concentrated at reduced pressure. The residue was diluted with 20% i-PrOH in DCM and treated with a solution of sodium bicarbonate (1.043 g, 12.41 mmol) in 10 mL of water. The layers were separated and the aqueous was extracted with 20% i-PrOH in DCM. The combined extracts were dried over sodium sulfate, filtered, and the filtrate concentrated under reduced pressure to afford (S)-2-chloro-9-ethyl-N-(pyrrolidin-3-yl)-9H-purin-6-amine (Intermediate 4, 1.08 g, 98%) as a beige solid. 1H NMR (DMSO-$d_6$) 1.37 (3H, t), 1.74-1.93 (1H, m), 2.06-2.20 (1H, m), 2.82-3.03 (2H, m), 3.05-3.16 (1H, m), 3.20 (1H, br dd), 4.13 (2H, q), 4.62 (1H, br s), 6.40-6.78 (1H, m), 8.20 (1H, s), 8.33 (1H, br s); m/z (ES$^+$) [M+H]$^+$=267.

Intermediate 27: (S)-2-chloro-9-ethyl-N-(1-((2-methyl-1H-imidazol-1-yl)sulfonyl)-pyrrolidin-3-yl)-9H-purin-6-amine (S)-2-chloro-9-ethyl-N-(pyrrolidin-3-yl)-9H-purin-6-amine (Intermediate 4, 1.08 g, 4.05 mmol) was suspended in acetonitrile (57.8 mL)/THF (9.64 mL) and treated with 2,3-dimethyl-1-((2-methyl-1H-imidazol-1-yl)sulfonyl)-1H-imidazol-3-ium trifluoromethanesulfonate (Intermediate 26, 2.371 g, 6.07 mmol). The reaction was stirred at room temperature overnight when it became homogeneous. The reaction was concentrated under reduced pressure and the resulting residue was purified by flash silica chromatography, elution gradient 0 to 100% EtOAc in hexanes (EtOAc contains 15% MeOH). Product fractions were concentrated under reduced pressure to afford (S)-2-chloro-9-ethyl-N-(1-((2-methyl-1H-imidazol-1-yl)sulfonyl)pyrrolidin-3-yl)-9H-purin-6-amine (intermediate 27, 1.467 g, 88%) as a beige foam. $^1$H NMR (Methanol-$d_4$) 1.48 (3H, t), 2.08-2.19 (1H, m), 2.32-2.44 (1H, m), 2.56 (3H, s), 3.51-3.66 (2H, m), 3.68-3.85 (2H, m), 4.23 (2H, q), 4.48-4.75 (1H, m), 6.75 (1H, br s), 7.39 (1H, s), 8.07 (1H, s); N—H not observed; m/z (ES$^+$) [M+H]$^+$=411.

Intermediate 28: (S)-3-((2-chloro-9-ethyl-9H-purin-6-yl)amino)-N—((R)-tetrahydrofuran-3-yl)pyrrolidine-1-sulfonamide (S)-2-chloro-9-ethyl-N-(1-((2-methyl-1H-imidazol-1-yl) sulfonyl)pyrrolidin-3-yl)-9H-purin-6-amine (Intermediate 27, 310 mg, 0.75 mmol) was dissolved in DCM (3.07 mL) and cooled in dry ice/MeOH bath (−20° C.) under nitrogen. Methyl trifluoromethanesulfonate (74.8 µl, 0.68 mmol) was dissolved in DCM (1.023 mL) and added dropwise to the cold solution. The reaction was allowed to warm up to 20° C. and stirred for 1 h. The solvent was removed at reduced pressure to afford (S)-1-((3-((2-chloro-9-ethyl-9H-purin-6-yl)amino)pyrrolidin-1-yl)sulfonyl)-2,3-dimethyl-1H-imidazol-3-ium trifluoromethanesulfonate (434 mg, 100%) as a white foam; m/z (ES$^+$) [M]$^+$=425. The (S)-1-((3-((2-chloro-9-ethyl-9H-purin-6-yl)amino)pyrrolidin-1-yl)sulfonyl)-2,3-dimethyl-1H-imidazol-3-ium trifluoromethanesulfonate (216 mg, 0.38 mmol) and (R)-tetrahydrofuran-3-amine (39.3 mg, 0.45 mmol) were dissolved in acetonitrile (6.26 mL) and heated at 70° C. for 16 h. The reaction was concentrated under reduced pressure and purified by flash silica chromatography, elution gradient 0 to 100% EtOAc in hexanes (EtOAc contains 15% MeOH). Product fractions were concentrated under reduced pressure to afford (S)-3-((2-chloro-9-ethyl-9H-purin-6-yl)amino)-N—((R)-tetrahydrofuran-3-yl)pyrrolidine-1-sulfonamide (Intermediate 28, 0.115 g, 73.6%) as a white solid. $^1$H NMR (DMSO-$d_6$) 1.38 (3H, t), 1.80 (1H, dq), 2.01-2.14 (2H, m), 2.15-2.31 (1H, m), 3.07-3.14 (1H, m), 3.21-3.29 (1H, m), 3.36-3.48 (2H, m), 3.49-3.68 (2H, m), 3.74 (2H, q), 3.80-3.91 (1H, m), 4.13 (2H, q), 4.63 (1H, br d), 7.41 (1H, br d), 8.22 (1H, br s), 8.35-8.62 (1H, m); m/z (ES$^+$) [M+H]$^+$=416.

Example 18: (S)-3-((9-ethyl-2-(((2R,3S)-2-hydroxypentan-3-yl)amino)-9H-purin-6-yl)amino)-N—((R)-tetrahydrofuran-3-yl)pyrrolidine-1-sulfonamide

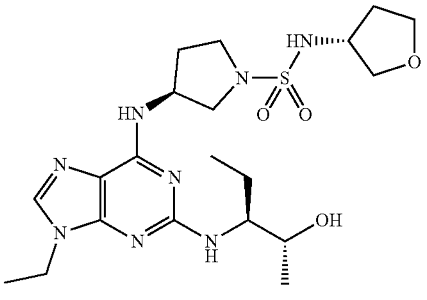 [SMILES: CC[C@H](Nc1nc(N[C@H]2CCN(S(=O)(=O)N[C@@H]3CCOC3)C2)c2ncn(CC)c2n1)[C@@H](C)O]

(S)-3-((2-chloro-9-ethyl-9H-purin-6-yl)amino)-N—((R)-tetrahydrofuran-3-yl)pyrrolidine-1-sulfonamide (Intermediate 28, 114 mg, 0.27 mmol), (2R,3S)-3-aminopentan-2-ol (56.6 mg, 0.55 mmol), cesium carbonate (268 mg, 0.82 mmol), 2-(dicyclohexylphosphino)-3,6-dimethoxy-2'-4'-6'-tri-i-propyl-1,1'-biphenyl (44.1 mg, 0.08 mmol), and palladium(II) acetate (6.15 mg, 0.03 mmol) were placed in an oven dried and under nitrogen microwave vial. The vial was evacuated and filled with nitrogen 2 times then tBuOH (1.371 mL) was added and the reaction was sealed and heated at 100° C. for 3 h. The reaction was diluted with EtOAc/$H_2O$. The layers were separated and the organic was dried over sodium sulfate, filtered, and the filtrate concentrated under reduced pressure. The resulting residue was purified by flash silica chromatography, elution gradient 0 to 20% MeOH in DCM. Product fractions were concentrated under reduced pressure to afford (S)-3-((9-ethyl-2-(((2R,3S)-2-hydroxypentan-3-yl)amino)-9H-purin-6-yl)amino)-N—((R)-tetrahydrofuran-3-yl)pyrrolidine-1-sulfonamide (Example 18, 0.053 g, 40.0%) as a white foam. $^1H$ NMR (DMSO-$d_6$) 0.85 (3H, br t), 1.04 (3H, br d), 1.28-1.48 (4H, m), 1.68 (1H, br s), 1.79 (1H, dq), 1.95-2.13 (2H, m), 2.14-2.27 (1H, m), 3.05-3.16 (1H, m), 3.22 (1H, q), 3.34-3.42 (1H, m), 3.46 (1H, br dd), 3.53 (1H, br t), 3.62 (2H, q), 3.69-3.80 (3H, m), 3.80-3.88 (1H, m), 3.97 (2H, q), 4.42-4.88 (2H, m), 5.95 (1H, br s), 7.22-7.52 (2H, m), 7.72 (1H, s); m/z ($ES^+$) $[M+H]^+$=483.

Example 19: (S)-3-((2-(((R)-1-cyclopropyl-2-hydroxyethyl)amino)-9-methyl-9H-purin-6-yl)amino)-N-ethylpyrrolidine-1-sulfonamide

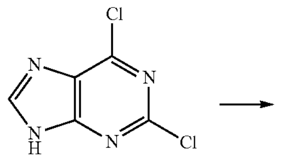

Intermediate 1

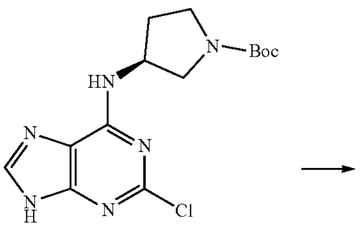

Intermediate 29

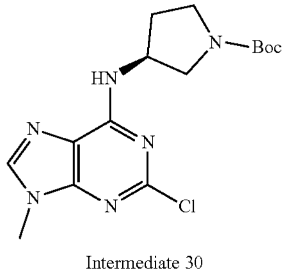

Intermediate 30

-continued

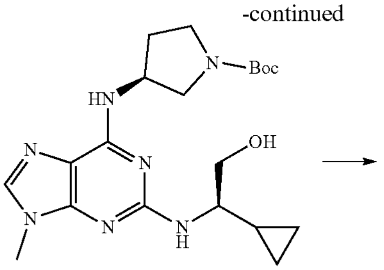

Intermediate 31

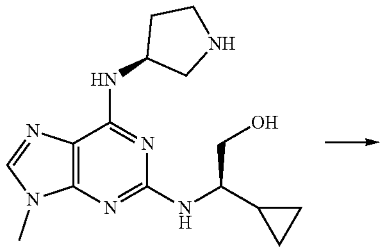

Intermediate 32

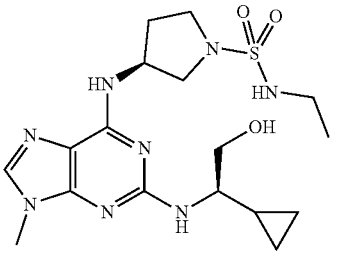

Example 19

Intermediate 29: tert-butyl (S)-3-((2-chloro-9H-purin-6-yl)amino)pyrrolidine-1-carboxylate tert-Butyl (S)-3-aminopyrrolidine-1-carboxylate (10.58 ml, 58.20 mmol) was added to a solution of 2,6-dichloro-9H-purine (Intermediate 1, 10 g, 52.91 mmol) and N,N-diisopropylethylamine (10.17 ml, 58.20 mmol) dissolved in 2-methyl-2-butanol (140 mL) at room temperature under nitrogen. The reaction mixture was heated at 100° C. for 90 minutes. The reaction was cooled and concentrated to obtain an oily solid. Water (200 mL) was added and the product was extracted with ethyl acetate (200 mL), the organic layer was dried over magnesium sulfate, filtered, and concentrated under reduced pressure to afford tert-butyl (S)-3-((2-chloro-9H-purin-6-yl)amino)pyrrolidine-1-carboxylate (Intermediate 29, 17.20 g, 96%) as a yellow solid. $^1H$ NMR (DMSO-$d_6$) 1.32-1.50 (9H, m), 1.95-2.04 (2H, m), 2.06-2.25 (1H, m), 3.15-3.27 (1H, m), 3.42-3.51 (1H, m), 3.61 (1H, br dd), 4.51-4.72 (1H, m), 8.17 (1H, s), 8.26-8.47 (1H, m), 11.80-13.36 (1H, m); m/z ($ES^+$) $[M+H]^+$=339.

Intermediate 30: tert-butyl (S)-3-((2-chloro-9-methyl-9H-purin-6-yl)amino)-pyrrolidine-1-carboxylate Iodomethane (3.48 ml, 55.84 mmol) was added to a stirred suspension of tert-butyl (S)-3-((2-chloro-9H-purin-6-yl)amino)pyrrolidine-1-carboxylate (Intermediate 29, 17.2 g, 50.77 mmol) and potassium carbonate (8.77 g, 63.46 mmol) in DMSO (190 mL) and the reaction stirred for 20 h at room temperature. The reaction mixture was diluted with water, extracted with ethyl acetate, dried over sodium sulfate, filtered, and the filtrate concentrated under reduced pressure. The resulting residue was coated on silica and purified by flash silica chromatography, elution gradient 0 to 100% ethyl acetate in hexanes. Product fractions were concentrated under reduced pressure to afford tert-butyl (S)-3-((2-chloro-9-methyl-9H-purin-6-yl)amino)pyrrolidine-1-carboxylate (Intermediate 30, 8.50 g, 47.5%) as a white solid. $^1$H NMR (DMSO-$d_6$) 1.40 (9H, br d), 1.92-2.05 (1H, m), 2.14 (1H, br d), 3.15-3.25 (1H, m), 3.27-3.35 (1H, m), 3.45 (1H, br s), 3.55-3.67 (1H, m), 3.66-3.76 (3H, m), 4.58-5.29 (1H, m), 8.14 (1H, br s), 8.47 (1H, br s); m/z (ES$^+$) [M+H]$^+$=353.

Intermediate 31: tert-butyl (S)-3-((2-(((R)-1-cyclopropyl-2-hydroxyethyl)amino)-9-methyl-9H-purin-6-yl)amino)pyrrolidine-1-carboxylate tert-Butyl (S)-3-((2-chloro-9-methyl-9H-purin-6-yl)amino)pyrrolidine-1-carboxylate (Intermediate 30, 2 g, 5.67 mmol), (R)-2-amino-2-cyclopropylethan-1-ol, HCl (1.56 g, 11.33 mmol), cesium carbonate (6.47 g, 19.84 mmol), 2-(dicyclohexylphosphino)-3,6-dimethoxy-2'-4'-6'-tri-i-propyl-1,1'-biphenyl (0.913 g, 1.71 mmol), and palladium(II) acetate (0.127 g, 0.57 mmol) were placed in an oven dried and under nitrogen vial. The vial was evacuated and filled with nitrogen 2 times then tBuOH (28 mL) was added and the reaction was heated in an oil bath at 100° C. for 3.5 h. The reaction was diluted with EtOAc/$H_2O$ and the layers were separated. The organic was dried over sodium sulfate, filtered, and the filtrate concentrated under reduced pressure. The resulting residue was purified by flash silica chromatography, elution gradient 0 to 100% EtOAc in hexanes (EtOAc contains 17% MeOH). Product fractions were concentrated under reduced pressure to afford tert-butyl (S)-3-((2-(((R)-1-cyclopropyl-2-hydroxyethyl)amino)-9-methyl-9H-purin-6-yl)amino)pyrrolidine-1-carboxylate (Intermediate 31, 1.408 g, 59%) as a yellow foam. $^1$H NMR (DMSO-$d_6$) 0.11-0.46 (4H, m), 0.91-1.06 (1H, m), 1.38 (8H, br d), 1.85-1.98 (1H, m), 2.02-2.23 (1H, m), 3.11-3.28 (3H, m), 3.36-3.69 (1H, m), 3.39-3.64 (7H, m), 4.35-4.81 (2H, m), 5.94 (1H, br d), 7.21-7.49 (1H, m), 7.66 (1H, s); m/z (ES$^+$) [M+H]$^+$=418.

Intermediate 32: (R)-2-cyclopropyl-2-((9-methyl-6-(((S)-pyrrolidin-3-yl)amino)-9H-purin-2-yl)amino)ethan-1-ol hydrochloride tert-Butyl (S)-3-((2-(((R)-1-cyclopropyl-2-hydroxyethyl)amino)-9-methyl-9H-purin-6-yl)amino)pyrrolidine-1-carboxylate (Intermediate 31, 1.40 g, 3.35 mmol) was dissolved in MeOH (14.7 mL) and treated with HCl (4 M in dioxane) (6.33 ml, 25.15 mmol). The reaction was stirred at room temperature for 3.5 hrs at which time it was concentrated under reduced pressure to afford (R)-2-cyclopropyl-2-((9-methyl-6-(((S)-pyrrolidin-3-yl)amino)-9H-purin-2-yl)amino)ethan-1-ol hydrochloride (Intermediate 32, 1.436 g, 99%) as a beige solid. m/z (ES$^+$) [M+H]$^+$=318.

Example 19: (S)-3-((2-(((R)-1-cyclopropyl-2-hydroxyethyl)amino)-9-methyl-9H-purin-6-yl)amino)-N-ethylpyrrolidine-1-sulfonamide

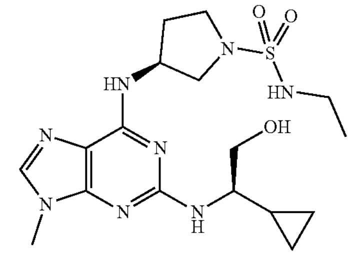 [SMILES: CCNS(=O)(=O)N1CC[C@H](Nc2nc(N[C@@H](CO)C3CC3)nc3c2ncn3C)C1]

(R)-2-cyclopropyl-2-((9-methyl-6-(((S)-pyrrolidin-3-yl)amino)-9H-purin-2-yl)amino)ethan-1-ol, 4HCl (Intermediate 32, 1.229 g, 2.65 mmol) was suspended in DCM (59 mL) and treated with TEA (2.22 ml, 15.91 mmol). The reaction was cooled to −60° C. and treated with a solution of ethylsulfamoyl chloride (0.381 g, 2.65 mmol) in 20 mL of DCM dropwise over 20 minutes. The reaction was allowed to warm up to −35° C. in 3 hrs at which time the reaction was concentrated under reduced pressure and the resulting residue was coated on silica and purified by flash silica chromatography, elution gradient 0 to 100% EtOAc in hexanes (EtOAc contains 20% MeOH). Product fractions were concentrated under reduced pressure to afford (S)-3-((2-(((R)-1-cyclopropyl-2-hydroxyethyl)amino)-9-methyl-9H-purin-6-yl)amino)-N-ethylpyrrolidine-1-sulfonamide (Example 19, 0.500 g, 44.5%) as a white foam. $^1$H NMR (DMSO-$d_6$) 0.15-0.24 (1H, m), 0.26-0.33 (1H, m), 0.34-0.46 (2H, m), 0.91-1.02 (1H, m), 1.05 (3H, t), 1.98-2.08 (1H, m), 2.11-2.26 (1H, m), 2.88-3.00 (2H, m), 3.07 (1H, dd), 3.20 (1H, dt), 3.36 (1H, ddd), 3.42-3.61 (7H, m), 4.36-4.91 (2H, m), 5.95 (1H, br d), 7.07 (1H, t), 7.22-7.47 (1H, m), 7.66 (1H, s); m/z (ES$^+$) [M+H]$^+$=425.

Example 20: (R)-2-((9-isopropyl-6-(((S)-1-(methylsulfonyl)pyrrolidin-3-yl)-amino)-9H-purin-2-yl)amino)-3-methylbutan-1-ol

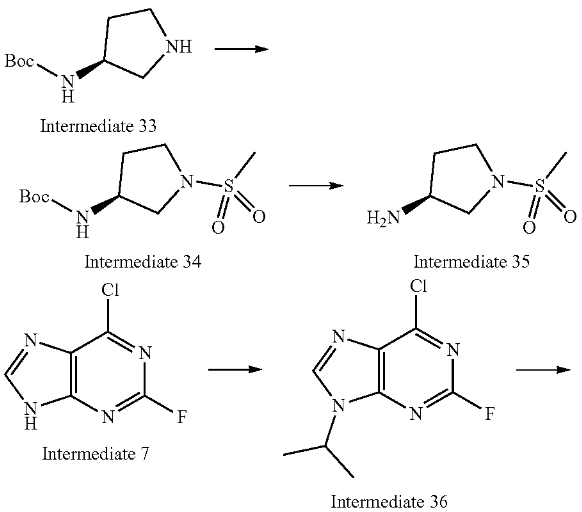

Intermediate 33

Intermediate 34

Intermediate 35

Intermediate 7

Intermediate 36

-continued

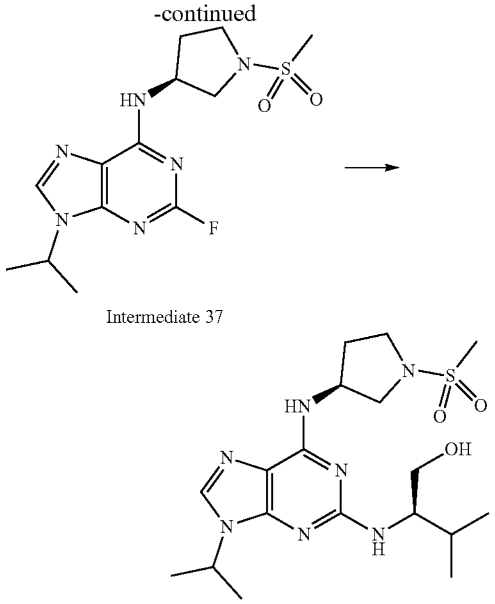

Intermediate 37

Example 20

Intermediate 34: tert-butyl (S)-(1-(methylsulfonyl) pyrrolidin-3-yl)carbamate tert-Butyl (S)-pyrrolidin-3-ylcarbamate (Intermediate 33, 14.17 g, 76.08 mmol) was dissolved in DCM (200 mL) under nitrogen. The solution was treated with DIEA (20 mL, 114.51 mmol) and cooled to 0° C. Methanesulfonyl chloride (5.93 mL, 76.08 mmol) was added dropwise over ca. 5 minutes and the reaction was stirred allowing the cooling bath to expire and reaction to slowly warm to room temperature overnight. The reaction was concentrated under reduced pressure and the mixture diluted with EtOAc and stirred for 5 min. The mixture was filtered and the solids washed liberally with EtOAc. The filtrate was washed with aqueous 1 M HCl (2×100 mL), water and saturated aqueous NaCl. The organic was dried over magnesium sulfate, filtered, and the filtrate concentrated under reduced pressure to afford tert-butyl (S)-(1-(methylsulfonyl)pyrrolidin-3-yl)carbamate (Intermediate 34, 15.91 g, 79%) as an off-white solid. $^1$H NMR (DMSO-$d_6$) 1.38 (9H, s), 1.76 (1H, dq), 2.03 (1H, dq), 2.86 (3H, s), 3.00 (1H, dd), 3.16-3.26 (1H, m), 3.28-3.35 (1H, m), 3.40 (1H, dd), 3.93-4.04 (1H, m), 7.16 (1H, br d); m/z (ES$^+$) [M-Boc]$^+$=165.

Intermediate 35: (S)-1-(methylsulfonyl)pyrrolidin-3-amine

HCl (4.0 M in dioxane) (100 mL, 400.00 mmol) was added slowly via cannula to a stirred solution of tert-butyl (S)-(1-(methylsulfonyl)pyrrolidin-3-yl)carbamate (Intermediate 34, 15.91 g, 60.19 mmol) in 1,4-dioxane (150 mL). The reaction was stirred at room temperature for 18 hrs (reaction became a suspension). The solvent was removed under reduced pressure and the solid residue was washed with $Et_2O$ and filtered to afford the HCl salt of (S)-1-(methylsulfonyl)pyrrolidin-3-amine (Intermediate 35, 11.92 g, 99%) as an off-white solid. $^1$H NMR (DMSO-$d_6$) 1.91-2.03 (1H, m), 2.21 (1H, dq), 2.95 (3H, s), 3.24-3.35 (2H, m), 3.44 (1H, dt), 3.51 (1H, dd), 3.82 (1H, br d), 8.40 (3H, br s).

Intermediate 36: 6-chloro-2-fluoro-9-isopropyl-9H-purine

6-Chloro-2-fluoro-9H-purine (Intermediate 7, 8.00 g, 46.36 mmol) was dissolved in THF (300 mL) in an oven dried 1 L flask under nitrogen. The solution was treated with 2-propanol (14.29 mL, 185.46 mmol), followed by triphenylphosphine (24.32 g, 92.73 mmol), and DIAD (18.03 mL, 92.73 mmol) which was added dropwise over 20 minutes. After the addition, the reaction was allowed to stir at room temperature for 17 hrs. The reaction was poured over water and extracted with EtOAc. The extract was washed with brine, dried over sodium sulfate, filtered, and the filtrate concentrated under reduced pressure. The resulting residue was purified by flash silica chromatography, elution gradient 0 to 80% EtOAc in hexanes. Product fractions were concentrated under reduced pressure to afford 6-chloro-2-fluoro-9-isopropyl-9H-purine (Intermediate 36, 7.40 g, 74.4%) as a white solid. $^1$H NMR (DMSO-$d_6$) 1.54 (6H, d), 4.73-4.84 (1H, m), 8.81 (1H, s); m/z (ES$^+$) [M+H]$^+$=215.

Intermediate 37: (S)-2-fluoro-9-isopropyl-N-(1-(methylsulfonyl)pyrrolidin-3-yl)-9H-purin-6-amine 6-Chloro-2-fluoro-9-isopropyl-9H-purine (Intermediate 36, 6.4 g, 29.82 mmol) and (S)-1-(methylsulfonyl)pyrrolidin-3-amine. HCl (Intermediate 35, 7.18 g, 35.78 mmol) was dissolved in EtOH (150 mL) under nitrogen, cooled in an ice-water bath and treated with N,N-diisopropylethylamine (20.83 mL, 119.28 mmol) in a 500 mL round bottom flask. The reaction was warmed to room temperature and stirred for 4 days (for convenience, usually needs 48 h). The solvent was removed at reduced pressure and the residue was dissolved in DCM, washed with water, dried over sodium sulfate/magnesium sulfate, filtered and concentrated under reduced pressure. The resulting residue was coated on silica and purified by flash silica chromatography, elution gradient 50 to 100% EtOAc in hexanes then 8% MeOH in DCM. Product fractions were concentrated under reduced pressure to afford (S)-2-fluoro-9-isopropyl-N-(1-(methylsulfonyl)pyrrolidin-3-yl)-9H-purin-6-amine (Intermediate 37, 6.46 g, 63.3%) as a beige solid. $^1$H NMR (DMSO-$d_6$) 1.49 (6H, d), 2.05 (1H, br d), 2.15-2.32 (1H, m), 2.91 (3H, s), 3.24 (1H, br s), 3.30-3.38 (1H, m), 3.40-3.52 (1H, m), 3.59 (1H, br s), 4.63 (2H, quin), 8.26 (1H, s), 8.56 (1H, br s); m/z (ES$^+$) [M+H]$^+$=343.

Example 20: (R)-2-((9-isopropyl-6-(((S)-1-(methylsulfonyl)pyrrolidin-3-yl)-amino)9H-purin-2-yl) amino)-3-methylbutan-1-ol

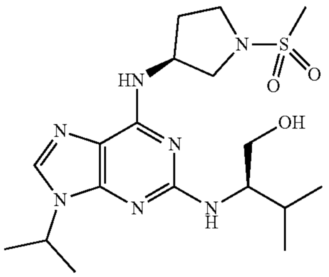 [SMILES: CC(C)[C@H](CO)Nc1nc(N[C@H]2CCN(S(C)(=O)=O)C2)c2ncn(C(C)C)c2n1]

(S)-2-fluoro-9-isopropyl-N-(1-(methylsulfonyl)pyrrolidin-3-yl)-9H-purin-6-amine (Intermediate 37, 3.0 g, 8.76 mmol), (R)-2-amino-3-methylbutan-1-ol (3.24 ml, 29.20 mmol), and DIEA (3.83 ml, 29.20 mmol) were dissolved in n-butanol (18 ml)/dimethylsulfoxide (2.25 ml) and the reaction was placed in preheated oil bath at 140° C. The reaction was heated for 64 h. The reaction was concentrated under reduced pressure and the residue was diluted with EtOAc, washed with water, brine, dried over sodium sulfate/magnesium sulfate, filtered, and concentrated under reduced pressure. The resulting residue was purified by flash silica chromatography, elution gradient 40 to 100% EtOAc in hexanes then 5% MeOH in DCM. Product fractions were concentrated under reduced pressure to afford impure product. The residue was repurified by flash silica chromatography, elution gradient 0 to 10% MeOH in EtOAc. Product fractions were concentrated under reduced pressure to afford (R)-2-((9-isopropyl-6-(((S)-1-(methylsulfonyl)pyrrolidin-3-yl)amino)-9H-purin-2-yl)amino)-3-methylbutan-1-ol (Example 20, 3.09 g, 83%) as a white dry film. $^1H$ NMR (DMSO-$d_6$) 0.89 (6H, t), 1.45 (6H, t), 1.86-2.09 (2H, m), 2.12-2.25 (1H, m), 2.90 (3H, s), 3.14-3.29 (2H, m), 3.40-3.53 (3H, m), 3.58 (1H, dd), 3.73-3.88 (1H, m), 4.36-4.58 (2H, m), 4.59-4.90 (1H, m), 5.79 (1H, br s), 7.39 (1H, br s), 7.79 (1H, s); m/z (ES$^+$) [M+H]$^+$=426.

Example 21: (S)-3-((9-ethyl-2-(((3S*,4R*)-1,1,1-trifluoro-4-hydroxypentan-3-yl)-amino)-9H-purin-6-yl)amino)-N-methylpyrrolidine-1-sulfonamide

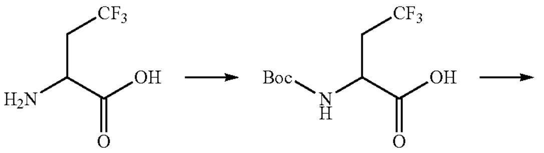

Intermediate 38

Intermediate 39

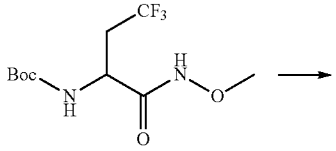

Intermediate 40

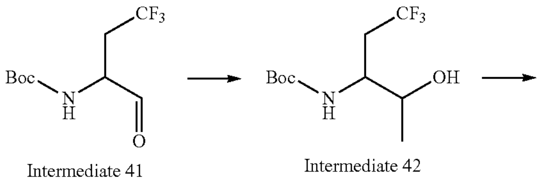

Intermediate 41

Intermediate 42

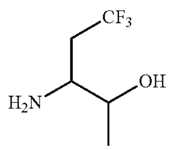

Intermediate 43

-continued

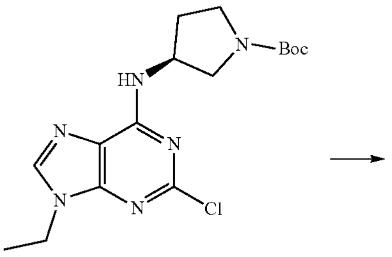

Intermediate 3

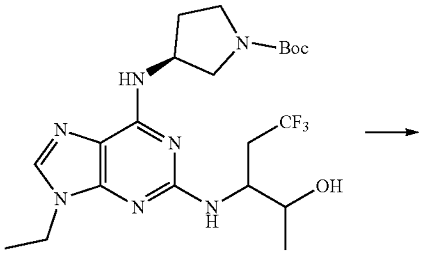

Intermediate 44

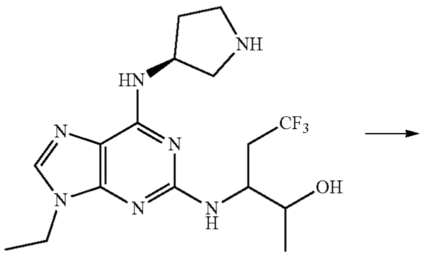

Intermediate 45

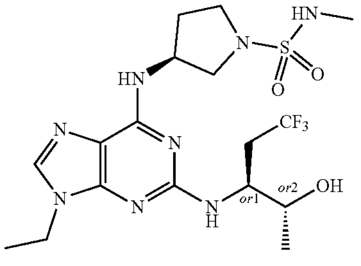

Example 21

Intermediate 39: 2-((tert-butoxycarbonyl)amino)-4,4,4-trifluorobutanoic acid

2-Amino-4,4,4-trifluorobutanoic acid (Intermediate 38, 2.51 g, 15.98 mmol) was suspended in DCM (64.1 mL) and cooled to 0° C. in an ice bath. Boc-anhydride (4.08 ml, 17.58 mmol) and TEA (4.45 ml, 31.96 mmol) was added. The reaction was warmed up to room temperature and stirred overnight. The reaction was extracted with water, the aqueous extract was acidified with 1 N HCl, and extracted with DCM. The combined extracts were washed with brine, dried over sodium sulfate, filtered and the filtrate concentrated under reduced pressure to afford 2-((tert-butoxycarbonyl)amino)-4,4,4-trifluorobutanoic acid (Intermediate 39, 3.19 g, 78%) as a white foam. $^1H$ NMR (DMSO-$d_6$) 1.37 (9H, s), 2.53-2.65 (1H, m), 2.66-2.80 (1H, m), 4.07-4.19 (1H, m), 7.12 (1H, br d), 11.78-13.76 (1H, m).

Intermediate 40: tert-butyl (4,4,4-trifluoro-1-(methoxyamino)-1-oxobutan-2-yl)-carbamate 2-((tert-Butoxycarbonyl)amino)-4,4,4-trifluorobutanoic acid (Intermediate 39, 3.19 g, 12.40 mmol) and HOBt (2.279 g, 14.88 mmol) were dissolved in DCM (31.8 mL)/THF (7.94 mL) and cooled to 0° C. under nitrogen. The reaction was then treated with EDC (2.85 g, 14.88 mmol), N,O-dimethylhydroxylamine. HCl (1.452 g, 14.88 mmol), and N-methylmorpholine (1.636 ml, 14.88 mmol). The reaction was allowed to warm up slowly to room temperature and stir overnight. The reaction was concentrated under reduced pressure and the residue was partitioned between EtOAc and 5% $KHSO_4$ in water (50 mL). The organic layer was then washed with 5% $KHSO_4$ (50 mL), saturated sodium bicarbonate, brine, dried over sodium sulfate, filtered, and the filtrate concentrated under reduced pressure. The resulting residue was purified by flash silica chromatography, elution gradient 0 to 100% EtOAc in hexanes. Product fractions were concentrated under reduced pressure to afford tert-butyl (4,4,4-trifluoro-1-(methoxy(methyl)amino)-1-oxobutan-2-yl)carbamate (Intermediate 40, 2.80 g, 75%) as a white solid. $^1$H NMR (DMSO-$d_6$) 1.36 (9H, s), 2.51-2.60 (2H, m), 3.11 (3H, s), 3.71 (3H, s), 4.73 (1H, br d), 7.35 (1H, br d); m/z ($ES^+$) $[M+H]^+$=301.

Intermediate 41: tert-butyl (4,4,4-trifluoro-1-oxobutan-2-yl)carbamate tert-Butyl (4,4,4-trifluoro-1-(methoxy(methyl)amino)-1-oxobutan-2-yl)carbamate (Intermediate 40, 2.8 g, 9.32 mmol) was dissolved in THF (54.9 mL) in an oven dried flask and under nitrogen. The solution was cooled to 0° C. in an ice bath for 15 minutes at which time it was treated with LAH (2.0 M in THF) (7.23 ml, 14.45 mmol). The reaction was stirred at 0° C. for 1 hour. A solution of potassium hydrogen sulfate (2.54 g, 18.65 mmol) in 28 mL of water was added slowly at 0° C. and allowed to stir for 15 minutes. The organic solvent in the reaction mixture was concentrated under reduced pressure. An additional 28 mL of water was added to the aqueous residue and extracted with DCM (3×). The combined extracts were then washed with 1 N HCl, saturated $NaHCO_3$, brine, dried over sodium sulfate, and filtered. The filtrate was concentrated under reduced pressure to afford tert-butyl (4,4,4-trifluoro-1-oxobutan-2-yl)carbamate (Intermediate 41, 2.150 g, 96%) as a white solid. $^1$H NMR (DMSO-$d_6$) 1.39 (9H, s), 2.38-2.43 (1H, m), 2.73-2.86 (1H, m), 4.15 (1H, br t), 7.62 (1H, br d), 9.36 (1H, s).

Intermediate 42: tert-butyl (1,1,1-trifluoro-4-hydroxypentan-3-yl)carbamate tert-Butyl (4,4,4-trifluoro-1-oxobutan-2-yl)carbamate (Intermediate 41, 2.15 g, 8.91 mmol) was dissolved in DCM (34.2 mL) and cooled in a dry-ice/MeOH bath. The solution was treated with MeMgBr (3.0 M in $Et_2O$) (10.40 ml, 31.20 mmol) and stirred at that temperature for 20 minutes. The reaction was then warmed up to room temperature and stirred overnight at which time it was quenched with saturated ammonium chloride (34 mL, slowly), diluted with EtOAc, and the layers were separated. The organic layer was washed with brine, dried over sodium sulfate, filtered, and the filtrate concentrated under reduced pressure. The resulting residue was purified by flash silica chromatography, elution gradient 0 to 80% EtOAc in hexanes. Product fractions were concentrated under reduced pressure to afford tert-butyl (1,1,1-trifluoro-4-hydroxypentan-3-yl)carbamate (Intermediate 42, 1.510 g, 66.0%) as a colorless oil. $^1$H NMR (DMSO-$d_6$) 0.87-1.07 (3H, m), 1.32-1.42 (9H, m), 2.14-2.46 (2H, m), 3.33-3.82 (2H, m), 4.71-4.97 (1H, m), 6.59-6.87 (1H, m).

Intermediate 43: 3-amino-5,5,5-trifluoropentan-2-ol tert-Butyl (1,1,1-trifluoro-4-hydroxypentan-3-yl)carbamate (Intermediate 42, 1.51 g, 5.87 mmol) was dissolved in 1,4-dioxane (22.01 mL) and treated with HCl (4.0 M in dioxane) (14.67 ml, 58.70 mmol). The reaction was stirred at room temperature overnight. The reaction was concentrated under reduced pressure to afford 3-amino-5,5,5-trifluoropentan-2-ol (Intermediate 43, 1.200 g, 106%) as a light yellow oil and as HCl salt which solidified upon standing in freezer. $^1$H NMR (DMSO-$d_6$) 1.02-1.22 (3H, m), 2.53-2.88 (2H, m), 3.21-3.38 (1H, m), 3.75-3.87 (1H, m), 5.28-5.82 (1H, m), 8.03-8.43 (3H, m).

Intermediate 44: tert-butyl (3S)-3-((9-ethyl-2-((1,1,1-trifluoro-4-hydroxypentan-3-yl)amino)-9H-purin-6-yl)amino)pyrrolidine-1-carboxylate tert-Butyl (S)-3-((2-chloro-9-ethyl-9H-purin-6-yl)amino)pyrrolidine-1-carboxylate (Intermediate 3, 408 mg, 1.11 mmol), 3-amino-5,5,5-trifluoropentan-2-ol. HCl (Intermediate 43, 532 mg, 2.74 mmol), cesium carbonate (1812 mg, 5.56 mmol), 2-(dicyclohexylphosphino)-3,6-dimethoxy-2'-4'-6'-tri-i-propyl-1,1'-biphenyl (179 mg, 0.33 mmol), and palladium(II) acetate (25 mg, 0.11 mmol) were placed in an oven dried and under nitrogen vial. The vial was evacuated and filled with nitrogen then tBuOH (2.009 mL) was added and the reaction was sealed and heated at 100° C. over the weekend. The reaction was diluted with EtOAc/$H_2O$. The layers were separated and the organic was dried over sodium sulfate, filtered, and the filtrate concentrated under reduced pressure. The resulting residue was purified by flash silica chromatography, elution gradient 0 to 100% EtOAc in hexanes (EtOAc contains 6% MeOH). Product fractions were concentrated under reduced pressure to afford tert-butyl (3S)-3-((9-ethyl-2-((1,1,1-trifluoro-4-hydroxypentan-3-yl)amino)-9H-purin-6-yl)amino)pyrrolidine-1-carboxylate (Intermediate 44, 0.434 g, 80%) as a yellow dry film. m/z ($ES^+$) $[M+H]^+$=488.

Intermediate 45: 3-((9-ethyl-6-(((S)-pyrrolidin-3-yl)amino)-9H-purin-2-yl)amino)-5,5,5-trifluoropentan-2-ol tert-Butyl (3S)-3-((9-ethyl-2-((1,1,1-trifluoro-4-hydroxypentan-3-yl)amino)-9H-purin-6-yl)amino)pyrrolidine-1-carboxylate (Intermediate 44, 0.434 g, 0.89 mmol) was dissolved in 1,4-dioxane (3.39 mL) and treated with HCl (4.0 M in 1,4-dioxane) (2.25 ml, 8.90 mmol). The reaction was stirred at room temperature for 16 h to form a gum. The reaction was diluted with methanol until it became homogeneous and then concentrated at reduced pressure. The residue was dissolved in methanol and treated with 1.1 g of MP carbonate (3.12 mmol/g) and stirred gently for 1 h to free base the product. The MP carbonate was filtered and the filtrate concentrated under reduced pressure to afford 3-((9-ethyl-6-(((S)-pyrrolidin-3-yl)amino)-9H-purin-2-yl)amino)-5,5,5-trifluoropentan-2-ol (Intermediate 45, 0.343 g, 99%) as a yellow dry film. m/z ($ES^+$) $[M+H]^+$=388.

Example 21: (S)-3-((9-ethyl-2-(((3S*,4R*)-1,1,1-trifluoro-4-hydroxypentan-3-yl)-amino)-9H-purin-6-yl)amino)-N-methylpyrrolidine-1-sulfonamide

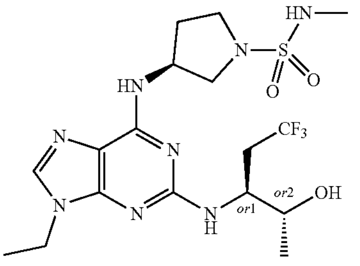 [SMILES: CCn1cnc2c(N[C@H]3CCN(S(=O)(=O)NC)C3)nc(N[C@@H](CC(F)(F)F)[C@@H](C)O)nc21]

3-((9-Ethyl-6-(((S)-pyrrolidin-3-yl)amino)-9H-purin-2-yl)amino)-5,5,5-trifluoropentan-2-ol (Intermediate 45, 0.342 g, 0.88 mmol) was dissolved in DCM (14.10 mL) and treated with TEA (0.615 ml, 4.41 mmol). The reaction was cooled down in dry-ice/MeOH bath and treated with methylsulfamoyl chloride (0.117 g, 0.91 mmol). The reaction was stirred at that temperature for 2 h. The reaction was concentrated under reduced pressure, coated on silica, and the resulting residue was purified by flash silica chromatography, elution gradient 0 to 10% MeOH in DCM. Product fractions were concentrated under reduced pressure and the sample was submitted for chiral separation. Two methods were used to separate the four isomers. Isomers 1 and 2 were purified by preparative SFC (Chiralpak IG column, 5 μm, 21 mm diameter, 250 mm length), 40° C. column temperature, 100 bar outlet pressure, 70 mL/min flow rate), eluting with 17% MeOH containing 0.2% $NH_4OH$ in $CO_2$. Isomers 3 and 4 were purified by preparative SFC (Chiralpak IC column, 5 μm, 21 mm diameter, 250 mm length), 40° C. column temperature, 100 bar outlet pressure, 70 mL/min flow rate), eluting with 20% IPA containing 0.2% $NH_4OH$ in $CO_2$ to afford (S)-3-((9-ethyl-2-(((3S*,4R*)-1,1,1-trifluoro-4-hydroxypentan-3-yl)-amino)-9H-purin-6-yl)amino)-N-methylpyrrolidine-1-sulfonamide (Example 21, Isomer 4, 0.0286 g, 15.0%) as a colorless dry film. $^1H$ NMR (Methanol-$d_4$) 1.23 (3H, d), 1.44 (3H, t), 2.02-2.12 (1H, m), 2.33-2.49 (2H, m), 2.59-2.74 (4H, m), 3.20-3.29 (1H, m), 3.38-3.46 (1H, m), 3.48-3.57 (1H, m), 3.68 (1H, dd), 3.87 (1H, quin), 4.10 (2H, q), 4.30-4.45 (1H, m), 4.73-4.82 (1H, m), 7.73 (1H, br s) N—Hs not observed; m/z ($ES^+$) $[M+H]^+$=481; along with Isomers 1, 2, and 3 as colorless films.

Example 22: (S)-3-((9-ethyl-2-(((2R,3S)-2-hydroxypentan-3-yl)amino)-9H-purin-6-yl)amino)-N—((S)-tetrahydrofuran-3-yl)pyrrolidine-1-sulfonamide

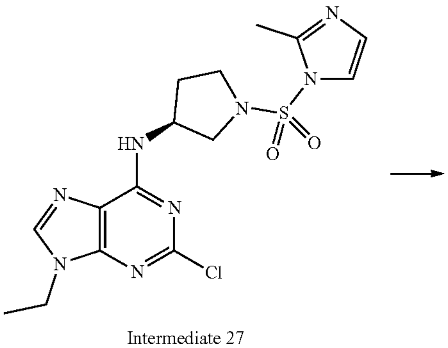

Intermediate 27

-continued

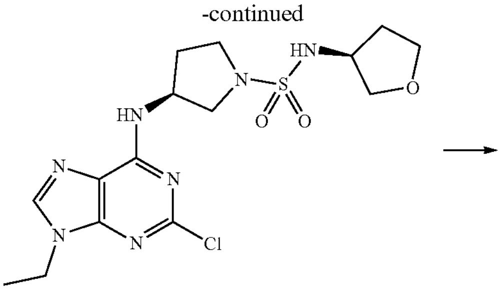

Intermediate 46

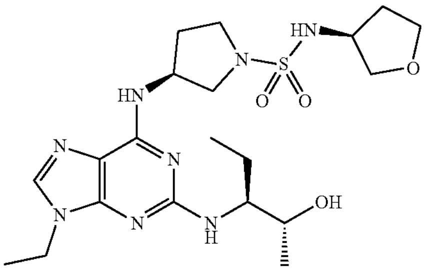

Example 22

Intermediate 46: (S)-3-((2-chloro-9-ethyl-9H-purin-6-yl)amino)-N—((S)-tetrahydrofuran-3-yl)pyrrolidine-1-sulfonamide (S)-2-chloro-9-ethyl-N-(1-((2-methyl-1H-imidazol-1-yl)sulfonyl)pyrrolidin-3-yl)-9H-purin-6-amine (Intermediate 27, 310 mg, 0.75 mmol) was dissolved in DCM (3.07 mL) and cooled in dry ice/MeOH bath (−20° C.) under nitrogen. Methyl trifluoromethanesulfonate (74.8 μl, 0.68 mmol) was dissolved in DCM (1.023 mL) and added dropwise to the cold solution. The reaction was allowed to warm up to 20° C. and stir for 1 hr. The solvent was removed at reduced pressure to afford (S)-1-((3-((2-chloro-9-ethyl-9H-purin-6-yl)amino)pyrrolidin-1-yl)sulfonyl)-2,3-dimethyl-1H-imidazol-3-ium trifluoromethanesulfonate (434 mg, 100%) as a white foam. The (S)-1-((3-((2-chloro-9-ethyl-9H-purin-6-yl)amino)pyrrolidin-1-yl)sulfonyl)-2,3-dimethyl-1H-imidazol-3-ium trifluoromethanesulfonate (216 mg, 0.38 mmol) and (S)-tetrahydrofuran-3-amine (39.3 mg, 0.45 mmol) were dissolved in acetonitrile (6.26 mL) and heated at 70° C. for 16 h. The reaction was concentrated under reduced pressure and purified by flash silica chromatography, elution gradient 0 to 100% EtOAc in hexanes (EtOAc contains 15% MeOH). Product fractions were concentrated under reduced pressure to afford (S)-3-((2-chloro-9-ethyl-9H-purin-6-yl)amino)-N—((S)-tetrahydrofuran-3-yl)pyrrolidine-1-sulfonamide (Intermediate 46, 0.134 g, 86%) as a white solid. $^1H$ NMR (DMSO-$d_6$) 1.38 (3H, t), 1.71-1.82 (1H, m), 1.99-2.16 (2H, m), 2.16-2.30 (1H, m), 3.13 (1H, br s), 3.21-3.28 (1H, m), 3.36-3.44 (1H, m), 3.47 (1H, br dd), 3.50-3.67 (2H, m), 3.67-3.80 (2H, m), 3.81-3.91 (1H, m), 4.13 (2H, q), 4.44-4.85 (1H, m), 7.41 (1H, br d), 8.22 (1H, br s), 8.37-8.58 (1H, m); m/z ($ES^+$) $[M+H]^+$=416.

Example 22: (S)-3-((9-ethyl-2-(((2R,3S)-2-hydroxypentan-3-yl)amino)-9H-purin-6-yl)amino)-N—((S)-tetrahydrofuran-3-yl)pyrrolidine-1-sulfonamide

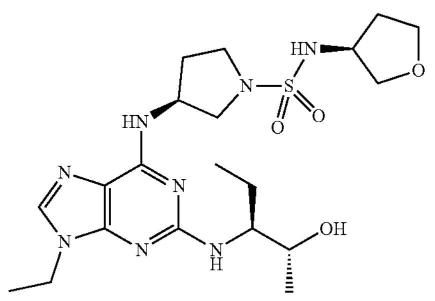 [SMILES: CC[C@H](Nc1nc(N[C@H]2CCN(S(=O)(=O)N[C@H]3CCOC3)C2)c2ncn(CC)c2n1)[C@@H](C)O]

(S)-3-((2-chloro-9-ethyl-9H-purin-6-yl)amino)-N—((S)-tetrahydrofuran-3-yl)pyrrolidine-1-sulfonamide (Intermediate 46, 129 mg, 0.31 mmol), (2R,3S)-3-aminopentan-2-ol (64.0 mg, 0.62 mmol), cesium carbonate (303 mg, 0.93 mmol), 2-(dicyclohexylphosphino)-3,6-dimethoxy-2'-4'-6'-tri-i-propyl-1,1'-biphenyl (49.9 mg, 0.09 mmol), and palladium(II) acetate (6.96 mg, 0.03 mmol) were placed in an oven dried and under nitrogen microwave vial. The vial was evacuated and filled with nitrogen 2 times then tBuOH (1.551 mL) was added and the reaction was sealed and heated at 100° C. for 3 hrs. The reaction was diluted with EtOAc/$H_2O$. The layers were separated and the organic was dried over sodium sulfate, filtered, and the filtrate concentrated under reduced pressure. The resulting residue was purified by flash silica chromatography, elution gradient 0 to 20% MeOH in DCM. Product fractions were concentrated under reduced pressure to afford (S)-3-((9-ethyl-2-(((2R,3S)-2-hydroxypentan-3-yl)amino)-9H-purin-6-yl)amino)-N—((S)-tetrahydrofuran-3-yl)pyrrolidine-1-sulfonamide (Example 22, 0.069 g, 46.4%) as a white foam. $^1$H NMR (DMSO-$d_6$) 0.84 (3H, br t), 1.04 (3H, br d), 1.28-1.44 (4H, m), 1.59-1.73 (1H, m), 1.73-1.83 (1H, m), 1.99-2.10 (2H, m), 2.15-2.24 (1H, m), 3.07-3.15 (1H, m), 3.21 (1H, q), 3.34-3.41 (1H, m), 3.44-3.50 (1H, m), 3.53 (1H, br t), 3.58-3.66 (2H, m), 3.68-3.79 (3H, m), 3.80-3.89 (1H, m), 3.97 (2H, q), 4.41-4.90 (2H, m), 5.95 (1H, br d), 7.25-7.52 (2H, m), 7.72 (1H, s); m/z (ES$^+$) [M+H]$^+$=416.

Example 23: (S)—N—(((S)-1,4-dioxan-2-yl)methyl)-3-((9-ethyl-2-(((2R,3S)-2-hydroxypentan-3-yl)amino)-9H-purin-6-yl)amino)pyrrolidine-1-sulfonamide

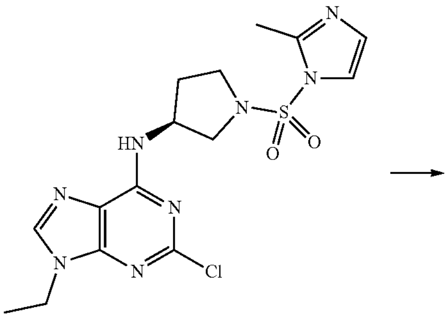

Intermediate 27

-continued

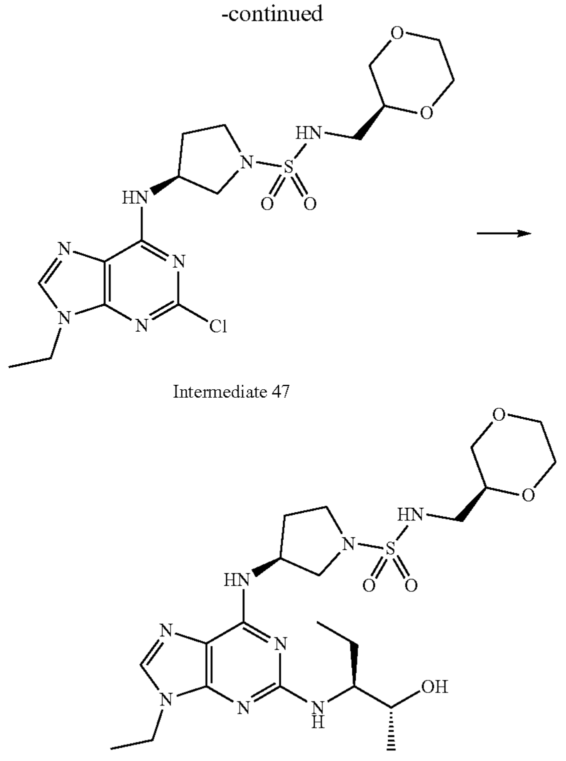

Intermediate 47

Example 23

Intermediate 47: (S)-3-((2-chloro-9-ethyl-9H-purin-6-yl)amino)-N—((S)-tetrahydrofuran-3-yl)pyrrolidine-1-sulfonamide (S)-2-chloro-9-ethyl-N-(1-((2-methyl-1H-imidazol-1-yl)sulfonyl)pyrrolidin-3-yl)-9H-purin-6-amine (Intermediate 27, 154 mg, 0.37 mmol) was dissolved in DCM (1.525 mL) and cooled in dry ice/MeOH bath (−20° C.) under nitrogen. Methyl trifluoromethanesulfonate (37.2 μl, 0.34 mmol) was dissolved in DCM (0.508 mL) and added dropwise to the cold solution. The reaction was allowed to warm up to 20° C. and stir for 1 hr. The solvent was removed at reduced pressure to afford (S)-1-((3-((2-chloro-9-ethyl-9H-purin-6-yl)amino)pyrrolidin-1-yl)sulfonyl)-2,3-dimethyl-1H-imidazol-3-ium trifluoromethanesulfonate (216 mg, 100%) as a white foam. (S)-(1,4-dioxan-2-yl)methanamine, HCl (68.1 mg, 0.44 mmol) was dissolved in acetonitrile (1.675 mL) and treated with TEA (61.8 μl, 0.44 mmol) and the reaction was stirred for 10 minutes. The solution was then added to a solution of (S)-1-((3-((2-chloro-9-ethyl-9H-purin-6-yl)amino)pyrrolidin-1-yl)sulfonyl)-2,3-dimethyl-1H-imidazol-3-ium trifluoromethanesulfonate (216 mg, 0.38 mmol) in acetonitrile (4.52 mL). The reaction was then heated at 70° C. for 16 h. The reaction was concentrated under reduced pressure and purified by flash silica chromatography, elution gradient 0 to 100% EtOAc in hexanes (EtOAc contains 15% MeOH). Product fractions were concentrated under reduced pressure to afford (S)—N—(((S)-1,4-dioxan-2-yl)methyl)-3-((2-chloro-9-ethyl-9H-purin-6-yl)amino)pyrrolidine-1-sulfonamide (Intermediate 47, 0.122 g, 72.8%) as a light yellow solid. $^1$H NMR (DMSO-$d_6$) 1.37 (3H, t), 2.00-2.31 (2H, m), 2.92 (2H, br t), 3.07-3.20 (2H, m), 3.21-3.28 (1H, m), 3.36-3.46 (2H, m), 3.48-3.63 (4H, m), 3.69 (2H, br t), 4.13 (2H, q), 4.39-4.88 (1H, m), 7.24 (1H, br s), 8.21 (1H, s), 8.45 (1H, br s); m/z (ES$^+$) [M+H]$^+$=446.

Example 23: (S)—N—(((S)-1,4-dioxan-2-yl)methyl)-3-((9-ethyl-2-(((2R,3S)-2-hydroxypentan-3-yl)amino)-9H-purin-6-yl)amino)pyrrolidine-1-sulfonamide

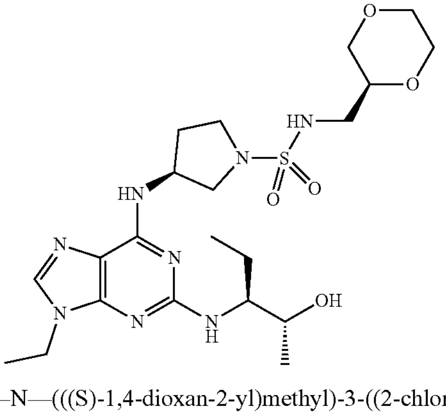

(S)—N—(((S)-1,4-dioxan-2-yl)methyl)-3-((2-chloro-9-ethyl-9H-purin-6-yl)amino)pyrrolidine-1-sulfonamide (Intermediate 47, 118.5 mg, 0.27 mmol), (2R,3S)-3-aminopentan-2-ol (54.8 mg, 0.53 mmol), cesium carbonate (260 mg, 0.80 mmol), 2-(dicyclohexylphosphino)-3,6-dimethoxy-2'-4'-6'-tri-i-propyl-1,1'-biphenyl (42.8 mg, 0.08 mmol), and palladium(II) acetate (5.97 mg, 0.03 mmol) were placed in an oven dried and under nitrogen vial. The vial was evacuated and filled with nitrogen then tBuOH (1.329 mL) was added and the reaction was sealed and heated at 100° C. for 5.5 hrs. The reaction was diluted with EtOAc/$H_2O$. The layers were separated and the organic was dried over sodium sulfate, filtered, and the filtrate concentrated under reduced pressure. The resulting residue was purified by flash silica chromatography, elution gradient 0 to 15% MeOH in DCM. Product fractions were concentrated under reduced pressure to afford (S)—N—(((S)-1,4-dioxan-2-yl)methyl)-3-((9-ethyl-2-(((2R,3S)-2-hydroxypentan-3-yl)amino)-9H-purin-6-yl)amino)pyrrolidine-1-sulfonamide (Example 23, 0.077 g, 56.7%) as a yellow foam. $^1$H NMR (DMSO-$d_6$) 0.85 (3H, br t), 1.04 (3H, br d), 1.30-1.45 (4H, m), 1.57-1.76 (1H, m), 1.94-2.11 (1H, m), 2.11-2.25 (1H, m), 2.86-2.99 (2H, m), 3.06-3.26 (3H, m), 3.33-3.45 (2H, m), 3.48-3.57 (3H, m), 3.57-3.66 (2H, m), 3.66-3.80 (3H, m), 3.97 (2H, q), 4.63 (2H, br s), 5.94 (1H, br s), 7.22 (1H, br t), 7.36 (1H, br s), 7.72 (1H, s); m/z (ES$^+$) [M+H]$^+$=513.

Example 24: (2R,3S)-3-((9-ethyl-6-(((S)-1-((3-fluoroazetidin-1-yl)sulfonyl)pyrrolidin-3-yl)amino)-9H-purin-2-yl)amino)pentan-2-ol

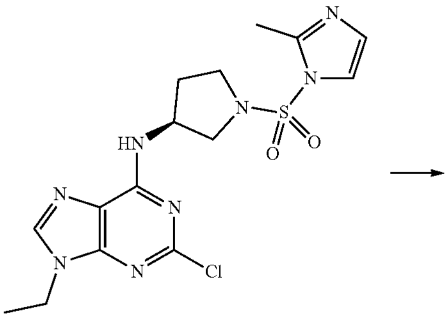

Intermediate 27

-continued

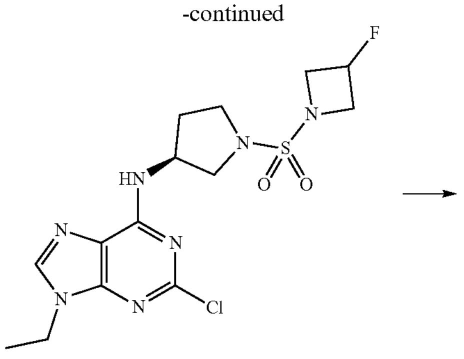

Intermediate 48

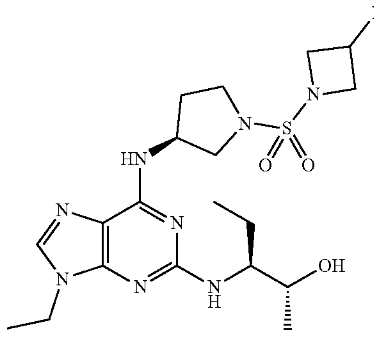

Example 24

Intermediate 48: (S)-2-chloro-9-ethyl-N-(1-((3-fluoroazetidin-1-yl)sulfonyl)pyrrolidin-3-yl)-9H-purin-6-amine (S)-2-chloro-9-ethyl-N-(1-((2-methyl-1H-imidazol-1-yl)sulfonyl)pyrrolidin-3-yl)-9H-purin-6-amine (Intermediate 27, 158 mg, 0.38 mmol) was dissolved in DCM (1.565 mL) and cooled in dry ice/MeOH bath (−20° C.) under nitrogen. methyl trifluoromethanesulfonate (38.1 µl, 0.35 mmol) was dissolved in DCM (0.522 mL) and added dropwise to the cold solution. The reaction was allowed to warm up to 20° C. and stir for 1 hr. The solvent was removed at reduced pressure to afford (S)-1-((3-((2-chloro-9-ethyl-9H-purin-6-yl)amino)pyrrolidin-1-yl)sulfonyl)-2,3-dimethyl-1H-imidazol-3-ium trifluoromethanesulfonate (221 mg, 100%) as a white foam. 3-fluoroazetidine, HCl (60.0 mg, 0.54 mmol) was dissolved in acetonitrile (3.17 mL) and treated with TEA (75 µl, 0.54 mmol) and the reaction was stirred for 10 minutes. A solution of (S)-1-((3-((2-chloro-9-ethyl-9H-purin-6-yl)amino)pyrrolidin-1-yl)sulfonyl)-2,3-dimethyl-1H-imidazol-3-ium trifluoromethanesulfonate (221 mg, 0.38 mmol) in acetonitrile (3.17 mL) was then added and the reaction was then heated at 70° C. for 3 h. The reaction was concentrated under reduced pressure and purified by flash silica chromatography, elution gradient 0 to 100% EtOAc in hexanes (EtOAc contains 15% MeOH). Product fractions were concentrated under reduced pressure to afford (S)-2-chloro-9-ethyl-N-(1-((3-fluoroazetidin-1-yl)sulfonyl)pyrrolidin-3-yl)-9H-purin-6-amine (Intermediate 48, 0.114 g, 73.1%) as a white solid. $^1$H NMR (DMSO-$d_6$) 1.38 (3H, t), 2.00-2.14 (1H, m), 2.16-2.29 (1H, m), 3.17-3.38 (3H, m), 3.43-3.54 (1H, m), 3.54-3.72 (1H, m), 3.83-3.97 (2H, m), 4.07-4.17 (3H, m), 4.46-4.83 (1H, m), 5.24-5.48 (1H, m), 8.22 (1H, s), 8.49 (1H, br d); m/z (ES$^+$) [M+H]$^+$=404.

Example 24: (2R,3S)-3-((9-ethyl-6-(((S)-1-((3-fluoroazetidin-1-yl)sulfonyl)pyrrolidin-3-yl)amino)-9H-purin-2-yl)amino)pentan-2-ol

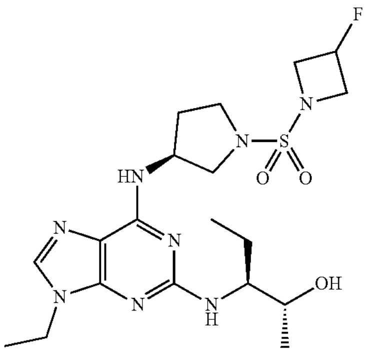 [SMILES: CC[C@H](Nc1nc(N[C@H]2CCN(S(=O)(=O)N3CC(F)C3)C2)c2ncn(CC)c2n1)[C@@H](C)O]

(S)-2-chloro-9-ethyl-N-(1-((3-fluoroazetidin-1-yl)sulfonyl)pyrrolidin-3-yl)-9H-purin-6-amine (Intermediate 48, 105 mg, 0.26 mmol), (2R,3S)-3-aminopentan-2-ol (53.6 mg, 0.52 mmol), cesium carbonate (254 mg, 0.78 mmol), 2-(Dicyclohexylphosphino)-3,6-dimethoxy-2'-4'-6'-tri-i-propyl-1,1'-biphenyl (41.9 mg, 0.08 mmol), and palladium(II) acetate (5.84 mg, 0.03 mmol) were placed in an oven dried and under nitrogen microwave vial. The vial was evacuated and filled with nitrogen then tBuOH (1.300 mL) was added and the reaction was sealed and heated at 100° C. for 5.5 h. The reaction was diluted with EtOAc/$H_2O$. The layers were separated and the organic was dried over sodium sulfate, filtered, and the filtrate concentrated under reduced pressure. The resulting residue was purified by flash silica chromatography, elution gradient 0 to 20% MeOH in DCM. Product fractions were concentrated under reduced pressure to afford (2R,3S)-3-((9-ethyl-6-(((S)-1-((3-fluoroazetidin-1-yl)sulfonyl)pyrrolidin-3-yl)amino)-9H-purin-2-yl)amino)pentan-2-ol (Example 24, 0.099 g, 81%) as a light yellow foam. $^1H$ NMR (DMSO-$d_6$) 0.84 (3H, t), 1.04 (3H, d), 1.30-1.44 (4H, m), 1.63-1.75 (1H, m), 2.00-2.12 (1H, m), 2.14-2.23 (1H, m), 3.20 (1H, br dd), 3.30-3.35 (1H, m), 3.43-3.51 (1H, m), 3.56-3.67 (2H, m), 3.72-3.81 (1H, m), 3.85-4.02 (4H, m), 4.04-4.16 (2H, m), 4.37-4.86 (2H, m), 5.23-5.46 (1H, m), 5.98 (1H, br s), 7.23-7.59 (1H, m), 7.73 (1H, s); m/z ($ES^+$) $[M+H]^+$=471.

Example 25: (S)—N—(((R)-1,4-dioxan-2-yl)methyl)-3-((9-ethyl-2-(((2R,3S)-2-hydroxypentan-3-yl)amino)-9H-purin-6-yl)amino)pyrrolidine-1-sulfonamide

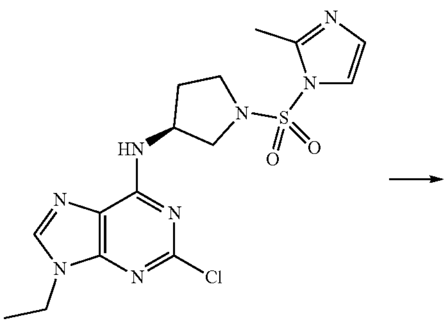

Intermediate 27

-continued

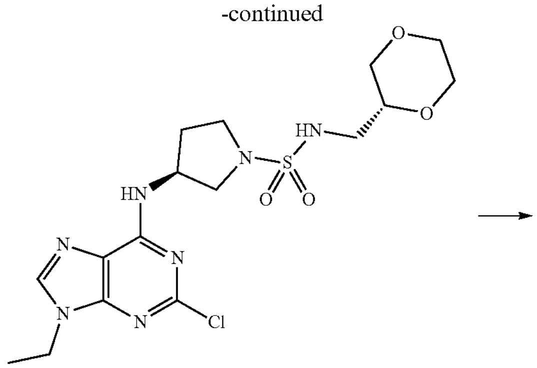

Intermediate 49

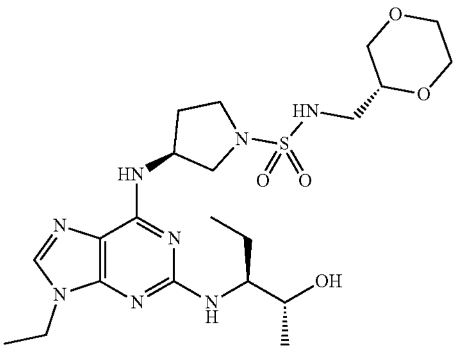

Example 25

Intermediate 49: (S)—N—(((R)-1,4-dioxan-2-yl)methyl)-3-((2-chloro-9-ethyl-9H-purin-6-yl)amino)pyrrolidine-1-sulfonamide (S)-2-chloro-9-ethyl-N-(1-((2-methyl-1H-imidazol-1-yl)sulfonyl)pyrrolidin-3-yl)-9H-purin-6-amine (Intermediate 27, 154 mg, 0.37 mmol) was dissolved in DCM (1.525 mL) and cooled in dry ice/MeOH bath (−20° C.) under nitrogen. Methyl trifluoromethanesulfonate (37.2 μl, 0.34 mmol) was dissolved in DCM (0.508 mL) and added dropwise to the cold solution. The reaction was allowed to warm up to 20° C. and stirred for 1 h. The solvent was removed at reduced pressure to afford (S)-1-((3-((2-chloro-9-ethyl-9H-purin-6-yl)amino)pyrrolidin-1-yl)sulfonyl)-2,3-dimethyl-1H-imidazol-3-ium trifluoromethanesulfonate (216 mg, 100%) as a white foam. (R)-(1,4-dioxan-2-yl)methanamine, HCl (75 mg, 0.49 mmol) was dissolved in acetonitrile (1.720 mL) and treated with TEA (68.1 μl, 0.49 mmol) and the reaction was stirred for 10 minutes. The solution was then added to a solution of (S)-1-((3-((2-chloro-9-ethyl-9H-purin-6-yl)amino)pyrrolidin-1-yl)sulfonyl)-2,3-dimethyl-1H-imidazol-3-ium trifluoromethanesulfonate (216 mg, 0.38 mmol) in acetonitrile (4.47 mL). The reaction was then heated at 70° C. for 16 h. The reaction was concentrated under reduced pressure and purified by flash silica chromatography, elution gradient 0 to 100% EtOAc in hexanes (EtOAc contains 15% MeOH). Product fractions were concentrated under reduced pressure to afford (S)—N—(((R)-1,4-dioxan-2-yl)methyl)-3-((2-chloro-9-ethyl-9H-purin-6-yl)amino)pyrrolidine-1-sulfonamide (Intermediate 49, 0.087 g, 51.9%) as a white foam. $^1H$ NMR (DMSO-$d_6$) 1.37 (3H, t), 1.98-2.32 (2H, m), 2.84-3.01 (2H, m), 3.07-3.20 (2H, m), 3.20-3.28 (1H, m), 3.34-3.45 (2H, m), 3.46-3.64 (4H, m), 3.70 (2H, br d), 4.13 (2H, q), 4.47-4.84 (1H, m), 7.24 (1H, br s), 8.21 (1H, s), 8.45 (1H, br s); m/z ($ES^+$) $[M+H]^+$=446.

Example 25: (S)—N—(((R)-1,4-dioxan-2-yl) methyl)-3-((9-ethyl-2-(((2R,3S)-2-hydroxypentan-3-yl)amino)-9H-purin-6-yl)amino)pyrrolidine-1-sulfonamide

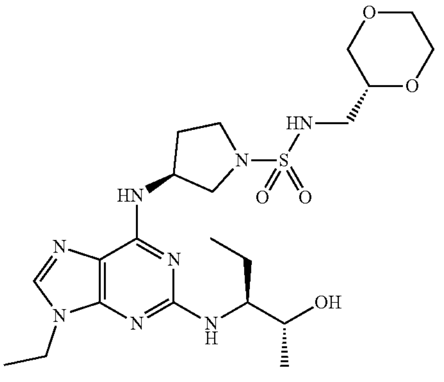 [SMILES: CC[C@H](Nc1nc(N[C@H]2CCN(S(=O)(=O)NC[C@@H]3COCCO3)C2)c2ncn(CC)c2n1)[C@@H](C)O]

(S)—N—(((R)-1,4-dioxan-2-yl)methyl)-3-((2-chloro-9-ethyl-9H-purin-6-yl)amino)pyrrolidine-1-sulfonamide (Intermediate 49, 83.8 mg, 0.19 mmol), (2R,3S)-3-aminopentan-2-ol (38.8 mg, 0.38 mmol), cesium carbonate (184 mg, 0.56 mmol), 2-(dicyclohexylphosphino)-3,6-dimethoxy-2'-4'-6'-tri-i-propyl-1,1'-biphenyl (30.3 mg, 0.06 mmol), and palladium(II) acetate (4.22 mg, 0.02 mmol) were placed in an oven dried vial. The vial was evacuated and filled with nitrogen, then tBuOH (0.940 mL) was added and the reaction was sealed and heated at 100° C. for 5.5 h. The reaction was diluted with EtOAc/$H_2O$. The layers were separated and the organic layer was dried over sodium sulfate, filtered, and the filtrate was concentrated under reduced pressure. The resulting residue was purified by flash silica chromatography, elution gradient 0 to 15% MeOH in DCM. Product fractions were concentrated under reduced pressure to afford (S)—N—(((R)-1,4-dioxan-2-yl)methyl)-3-((9-ethyl-2-(((2R,3S)-2-hydroxypentan-3-yl)amino)-9H-purin-6-yl) amino)pyrrolidine-1-sulfonamide (Example 25, 0.053 g, 54.5%) as a yellow foam. $^1H$ NMR (500 MHz, DMSO-$d_6$) 0.85 (3H, t), 1.04 (3H, d), 1.30-1.45 (4H, m), 1.63-1.75 (1H, m), 1.96-2.08 (1H, m), 2.13-2.23 (1H, m), 2.85-3.00 (2H, m), 3.05-3.25 (3H, m), 3.33-3.45 (2H, m), 3.47-3.56 (3H, m), 3.57-3.66 (2H, m), 3.67-3.82 (3H, m), 3.97 (2H, q), 4.63 (2H, br s), 5.95 (1H, br s), 7.22 (1H, br t), 7.37 (1H, br s), 7.72 (1H, s); m/z ($ES^+$) $[M+H]^+$=513.

Example 26: (3R*,4R*)-3-((2-(((R)-1-cyclopropyl-2-hydroxyethyl)amino)-9-methyl-9H-purin-6-yl) amino)-N-ethyl-4-fluoropyrrolidine-1-sulfonamide

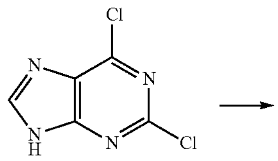

Intermediate 1

-continued

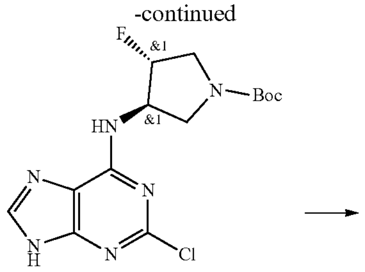

Intermediate 50

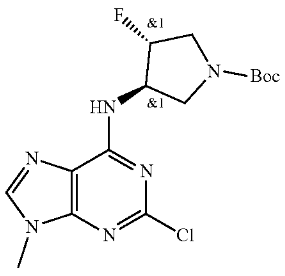

Intermediate 51

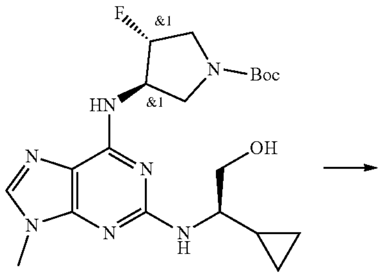

Intermediate 52

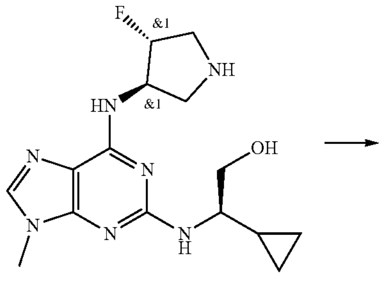

Intermediate 53

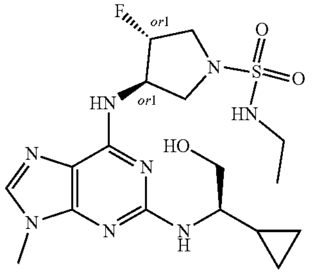

Example 26

Intermediate 50: rac-tert-butyl (3R,4R)-3-((2-chloro-9H-purin-6-yl)amino)-4-fluoropyrrolidine-1-carboxylate DIEA (1.525 mL, 8.73 mmol) was added to a stirred solution of 2,6-dichloro-9H-purine (Intermediate 1, 1.5 g, 7.94 mmol) and rac-tert-butyl (3R,4R)-3-amino-4-fluoropyrrolidine-1-carboxylate (1.783 g, 8.73 mmol) in 2-methylbutan-2-ol (22 mL, 7.94 mmol) and the vial was heated at 100° C. for 1.5 h. The solvent was removed reduced pressure and the resulting residue was purified by flash silica chromatography, elution gradient 0 to 10% MeOH in DCM. Product fractions were concentrated under reduced pressure to afford rac-tert-butyl (3R,4R)-3-((2-chloro-9H-purin-6-yl)amino)-4-fluoropyrrolidine-1-carboxylate (Intermediate 50, 2.260 g, 80%) as a pale yellow solid.

Intermediate 51: rac-tert-butyl (3R,4R)-3-((2-chloro-9-methyl-9H-purin-6-yl)-amino)-4-fluoropyrrolidine-1-carboxylate Iodomethane (0.432 ml, 6.91 mmol) was added to a stirred solution of rac-tert-butyl (3R,4R)-3-((2-chloro-9H-purin-6-yl)amino)-4-fluoropyrrolidine-1-carboxylate (Intermediate 50, 2.24 g, 6.28 mmol) and $K_2CO_3$ (1.085 g, 7.85 mmol) in DMSO (20.50 mL). The resulting solution was stirred at rt for 18 h. The reaction mixture was diluted with water, extracted with ethyl acetate, dried over sodium sulfate, filtered, and the filtrate concentrated under reduced pressure. The resulting residue was coated on silica and purified by flash silica chromatography, elution gradient 0 to 100% ethyl acetate in hexanes. Product fractions were concentrated under reduced pressure to afford rac-tert-butyl (3R,4R)-3-((2-chloro-9-methyl-9H-purin-6-yl)amino)-4-fluoropyrrolidine-1-carboxylate (Intermediate 51, 1.56 g, 67%). $^1$H NMR (DMSO-$d_6$) 1.43 (9H, s), 3.39-3.57 (2H, m), 3.58-3.69 (1H, m), 3.72 (4H, s), 4.56-4.86 (1H, m), 5.08-5.29 (1H, m), 8.18 (1H, br s), 8.53-8.76 (1H, m); one proton not observed.

Intermediate 52: tert-butyl (3RS,4RS)-3-((2-(((R)-1-cyclopropyl-2-hydroxyethyl)amino)-9-methyl-9H-purin-6-yl)amino)-4-fluoropyrrolidine-1-carboxylate rac-tert-Butyl (3R,4R)-3-((2-chloro-9-methyl-9H-purin-6-yl)amino)-4-fluoropyrrolidine-1-carboxylate (Intermediate 51, 800 mg, 2.16 mmol), (R)-2-amino-2-cyclopropylethan-1-ol. HCl (594 mg, 4.31 mmol), cesium carbonate (2460 mg, 7.55 mmol), 2-(dicyclohexylphosphino)-3,6-dimethoxy-2'-4'-6'-tri-i-propyl-1,1'-biphenyl (232 mg, 0.43 mmol), and palladium(II) acetate (48.4 mg, 0.22 mmol) were placed in an oven dried vial. The vial was evacuated and filled with nitrogen 2 times, then tBuOH (6.16 mL) was added and the reaction was sealed and heated at 96° C. for 16 h. The reaction was diluted with EtOAc/$H_2O$. The layers were separated and the organic was dried over sodium sulfate, filtered, and the filtrate was concentrated under reduced pressure. The resulting residue was purified by flash silica chromatography, elution gradient 0 to 100% EtOAc in hexanes (EtOAc contains 6% MeOH). Product fractions were concentrated under reduced pressure to afford tert-butyl (3RS,4RS)-3-((2-(((R)-1-cyclopropyl-2-hydroxyethyl)amino)-9-methyl-9H-purin-6-yl)amino)-4-fluoropyrrolidine-1-carboxylate (Intermediate 52, 0.530 g, 56.4%) as a yellow dry film.

Intermediate 53: (R)-2-cyclopropyl-2-((6-(((3RS,4RS)-4-fluoropyrrolidin-3-yl)-amino)-9-methyl-9H-purin-2-yl)amino)ethan-1-ol hydrochloride HCl (4 M in 1,4-dioxane) (689 µl, 2.76 mmol) was added to a stirred solution of tert-butyl (3RS,4RS)-3-((2-(((R)-1-cyclopropyl-2-hydroxyethyl)amino)-9-methyl-9H-purin-6-yl)amino)-4-fluoropyrrolidine-1-carboxylate (Intermediate 52, 200 mg, 0.46 mmol) in MeOH (0.5 ml) and 1,4-dioxane (1 ml) at 20° C. The resulting solution was stirred at rt for 1 h. Reaction was concentrated to give (R)-2-cyclopropyl-2-((6-(((3RS,4RS)-4-fluoropyrrolidin-3-yl)amino)-9-methyl-9H-purin-2-yl)amino)ethan-1-ol hydrochloride (Intermediate 53, 170 mg, 100%).

Example 26: (3R*, 4R*)-3-((2-(((R)-1-cyclopropyl-2-hydroxyethyl)amino)-9-methyl-9H-purin-6-yl)amino)-N-ethyl-4-fluoropyrrolidine-1-sulfonamide

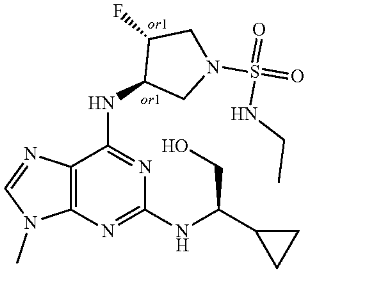 [SMILES: CCNS(=O)(=O)N1C[C@@H](F)[C@H](Nc2nc(N[C@@H](CO)C3CC3)nc3c2ncn3C)C1]

(R)-2-cyclopropyl-2-((6-(((3RS,4RS)-4-fluoropyrrolidin-3-yl)amino)-9-methyl-9H-purin-2-yl)amino)ethan-1-ol. HCl (Intermediate 53, 140 mg, 0.38 mmol) was weighed in a 40 mL scintillation vial, added dichloromethane (5 mL), triethylamine (261 µl, 1.88 mmol) and the reaction mixture was cooled to −78° C. Ethylsulfamoyl chloride (51.2 mg, 0.34 mmol) was added to the reaction mixture and stirred for 2 h. Additional ethylsulfamoyl chloride (17.08 mg, 0.12 mmol) was added to the reaction mixture and stirred for 1 h. The reaction was quenched with aq. $NaHCO_3$ solution, stirred for 15 mins, extracted with DCM, organic layer was separated, dried over $MgSO_4$ and concentrated to yield a white foam. The resulting residue was purified by flash silica chromatography, elution gradient 0 to 20% MeOH in DCM. Product fractions were concentrated under reduced pressure to afford racemic product which was submitted for chiral separation. The product was purified by preparative SFC (AD column, 5 µm, 4.6 mm diameter, 100 mm length), 40° C. column temperature, 120 bar outlet pressure, 4.0 mL/min flow rate), eluting with 10-60% methanol in $CO_2$ to afford (3R*,4R*)-3-((2-(((R)-1-cyclopropyl-2-hydroxyethyl)amino)-9-methyl-9H-purin-6-yl)amino)-N-ethyl-4-fluoropyrrolidine-1-sulfonamide (Example 26, Isomer 1, 33 mg, 20%). $^1$H NMR (DMSO-$d_6$) 0.15-0.24 (m, 1H) 0.32 (dt, 1H) 0.36-0.45 (m, 2H) 1.00 (br d, 1H) 1.07 (t, 3H) 2.93-3.05 (m, 2H) 3.23-3.29 (m, 1H) 3.37-3.46 (m, 1H) 3.49-3.73 (m, 8H) 4.58 (br s, 1H) 4.64-4.85 (m, 1H) 5.22-5.47 (m, 1H) 6.07 (br s, 1H) 7.25 (t, 1H) 7.53 (br s, 1H) 7.71 (s, 1H); m/z (ES$^+$) [M+H]$^+$=443; and Isomer 2 (37 mg, 22.2%).

Example 27: (R)-2-(6-((S)-1-(cyclopropylsulfonyl)pyrrolidin-3-yl)amino)-9-isopropyl-9H-purin-2-ylamino)-3-methylbutan-1-ol

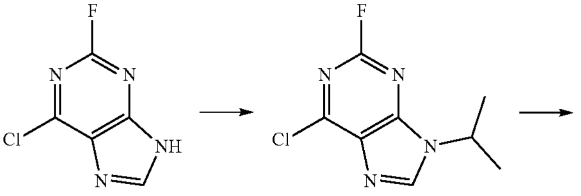

Intermediate 7

Intermediate 36

-continued

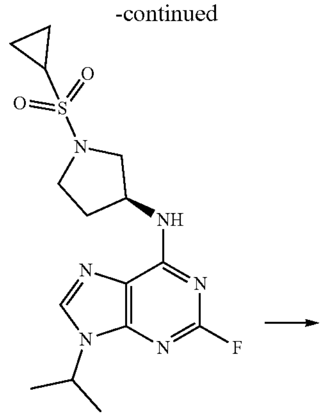

Intermediate 54

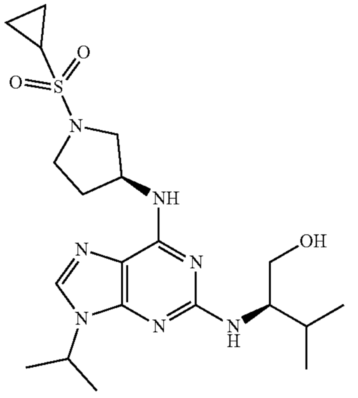

Example 27

Intermediate 36: 6-chloro-2-fluoro-9-isopropyl-9H-purine

DIAD (22.54 mL, 115.91 mmol) was added to 6-chloro-2-fluoro-9H-purine (Intermediate 7, 10 g, 57.96 mmol), IPA (8.93 mL, 115.91 mmol) and $PPh_3$ (30.4 g, 115.91 mmol) in THF (200 mL) at 0° C. over a period of 30 minutes under nitrogen. The resulting mixture was stirred at rt for 16 h. The reaction mixture was quenched with saturated aq. $NaHCO_3$ solution (200 mL), extracted with EtOAc (3×100 mL), the organic layer was dried over $Na_2SO_4$, filtered and evaporated to afford yellow solid. The crude product was purified by flash silica chromatography, elution gradient 0 to 90% EtOAc in petroleum ether. Pure fractions were evaporated to dryness to afford 6-chloro-2-fluoro-9-isopropyl-9H-purine (Intermediate 36, 10.00 g, 80%) as a yellow solid (contains triphenyl phosphine oxide, challenging to separate). 1H NMR (400 MHZ, DMSO-$d_6$) 1.18 (3H, d), 1.55 (3H, d), 4.69-4.85 (1H, m), 8.84 (1H, d); m/z ($ES^+$) $[M+H]^+$=215.

Intermediate 54: (S)—N-(1-(cyclopropylsulfonyl) pyrrolidin-3-yl)-2-fluoro-9-isopropyl-9H-purin-6-amine DIEA (0.488 mL, 2.80 mmol) was added to 6-chloro-2-fluoro-9-isopropyl-9H-purine (200 mg, 0.56 mmol, 60% wt) and (S)-1-(cyclopropylsulfonyl)pyrrolidin-3-amine (Intermediate 36, 213 mg, 1.12 mmol) in MeCN (5 mL). The resulting mixture was stirred at 100° C. for 2 h. The reaction mixture was diluted with EtOAc (20 mL), and washed sequentially with saturated aq. $NH_4Cl$ solution (20 mL×1), saturated aq. $Na_2CO_3$ solution (20 mL), and saturated aq. brine solution (20 mL). The organic layer was dried over $Na_2SO_4$, filtered and evaporated to afford crude product. The residue was purified by preparative TLC (EtOAc), to afford (S)—N-(1-(cyclopropylsulfonyl)pyrrolidin-3-yl)-2-fluoro-9-isopropyl-9H-purin-6-amine (Intermediate 54, 110 mg, 53.4%) as a colourless oil (contains triphenyl phosphine oxide). 1H NMR (300 MHz, DMSO-$d_6$) 0.95 (4H, dq), 1.51 (6H, d), 2.09 (1H, d), 2.24 (1H, d), 2.73 (1H, ddd), 3.29 (1H, s), 3.35-3.50 (1H, m), 3.50-3.62 (1H, m), 3.67 (1H, s), 4.65 (2H, p), 8.28 (1H, s), 8.59 (1H, br s); m/z ($ES^+$) [M+H] *=369.

Example 27: (R)-2-(6-((S)-1-(cyclopropylsulfonyl) pyrrolidin-3-yl)amino)-9-isopropyl-9H-purin-2-ylamino)-3-methylbutan-1-ol

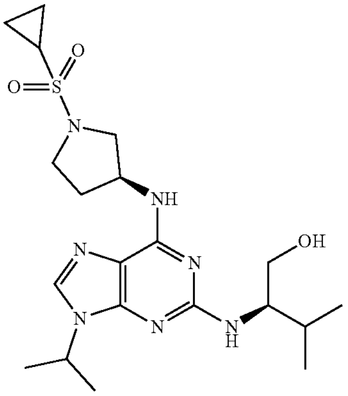 [SMILES: CC(C)[C@H](CO)Nc1nc(N[C@H]2CCN(S(=O)(=O)C3CC3)C2)c2ncn(C(C)C)c2n1]

DIEA (0.474 mL, 2.71 mmol) was added to (S)—N-(1-(cyclopropylsulfonyl)pyrrolidin-3-yl)-2-fluoro-9-isopropyl-9H-purin-6-amine (Intermediate 54, 100 mg, 0.27 mmol) and (R)-2-amino-3-methylbutan-1-ol (140 mg, 1.36 mmol) in NMP (4 mL). The resulting mixture was stirred at 140° C. for 5 days. The reaction mixture was purified by preparative HPLC (Waters XBridge Prep C18 OBD column, 5μ silica, 50 mm diameter, 150 mm length), using decreasingly polar mixtures of water (containing 0.01% $NH_4HCO_3$) and MeCN as eluents. Fractions containing the desired compound were evaporated to dryness to afford (R)-2-((6-(((S)-1-(cyclopropylsulfonyl)pyrrolidin-3-yl)amino)-9-isopropyl-9H-purin-2-yl)amino)-3-methylbutan-1-ol (Example 27, 45.0 mg, 36.7%). $^1H$ NMR (400 MHZ, DMSO-$d_6$) 0.86-1.02 (10H, m), 1.46 (6H, t), 1.96 (1H, dt), 2.07 (1H, p), 2.22 (1H, dq), 2.65-2.73 (1H, m), 3.27 (1H, dd), 3.33-3.39 (1H, m), 3.46-3.56 (3H, m), 3.62-3.67 (1H, m), 3.82 (1H, dq), 4.52 (2H, dq), 4.71 (1H, br s), 5.79 (1H, br s), 7.38 (1H, br s), 7.80 (1H, s); m/z ($ES^+$) $[M+H]^+$=452.

Example 28: (R)-2-(9-ethyl-6-((S)-1-(methylsulfonyl)pyrrolidin-3-yl)amino)-9H-purin-2-yl)amino)-3-methylbutan-1-ol

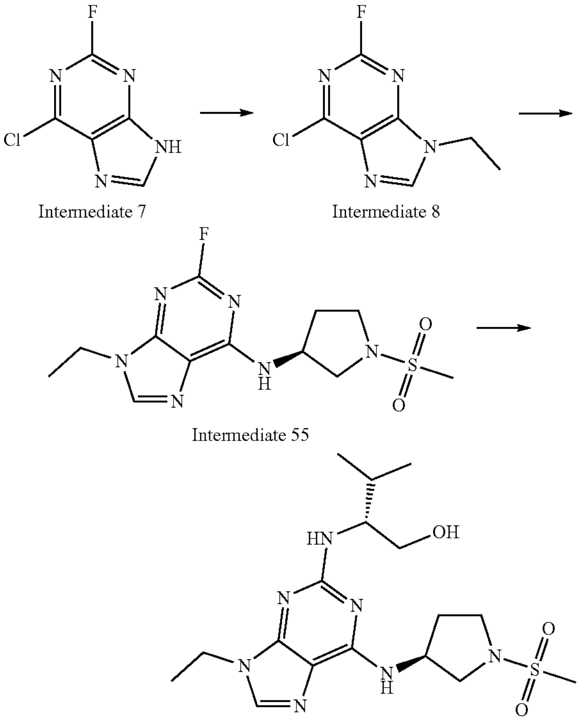

Intermediate 7

Intermediate 8

Intermediate 55

Example 28

Intermediate 8: 6-chloro-9-ethyl-2-fluoro-9H-purine

DIAD (0.845 mL, 4.35 mmol) was added dropwise to 6-chloro-2-fluoro-9H-purine (Intermediate 7, 0.5 g, 2.90 mmol), ethanol (0.400 g, 8.69 mmol) and $PPh_3$ (2.280 g, 8.69 mmol) in THF (5 mL) under nitrogen. The resulting mixture was stirred at rt for 16 h. The solvent was removed under reduced pressure. The crude product was purified by flash silica chromatography, elution gradient 0 to 80% EtOAc in petroleum ether. Pure fractions were evaporated to dryness to afford 6-chloro-9-ethyl-2-fluoro-9H-purine (Intermediate 8, 0.400 g, 68.8%) as a pale yellow solid. $^1H$ NMR (400 MHZ, DMSO-$d_6$) 1.18 (3H, d), 4.72-4.84 (2H, m), 8.86 (1H, s); m/z ($ES^+$) $[M+H]^+$=201.

Intermediate 55: (S)-9-ethyl-2-fluoro-N-(1-(methylsulfonyl)pyrrolidin-3-yl)-9H-purin-6-amine TEA (1.042 mL, 7.48 mmol) was added to 6-chloro-9-ethyl-2-fluoro-9H-purine (0.5 g, 2.49 mmol) and (S)-1-(methylsulfonyl)pyrrolidin-3-amine hydrochloride (Intermediate 8, 0.500 g, 2.49 mmol) in MeCN (20 mL). The resulting mixture was stirred at 80° C. for 2 h. The reaction mixture was poured into saturated aq. $Na_2CO_3$ solution (100 mL), extracted with DCM (3×100 mL), the organic layer was dried over $Na_2SO_4$. The crude product was purified by flash silica chromatography, elution gradient 0 to 80% EtOAc in petroleum ether. Pure fractions were evaporated to dryness to afford (S)-9-ethyl-2-fluoro-N-(1-(methylsulfonyl)pyrrolidin-3-yl)-9H-purin-6-amine (Intermediate 55, 0.400 g, 48.9%) as a pale yellow solid. m/z ($ES^+$) $[M+H]^+$ =329.

Example 28: (R)-2-(9-ethyl-6-((S)-1-(methylsulfonyl)pyrrolidin-3-yl)amino)-9H-purin-2-yl)amino)-3-methylbutan-1-ol

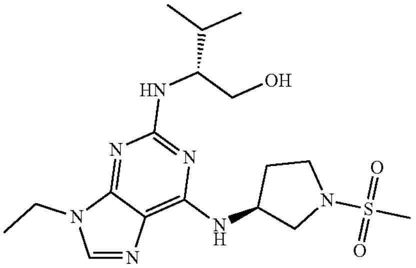 [SMILES: CCn1cnc2c(N[C@H]3CCN(S(C)(=O)=O)C3)nc(N[C@@H](CO)C(C)C)nc21]

(S)-9-ethyl-2-fluoro-N-(1-(methylsulfonyl)pyrrolidin-3-yl)-9H-purin-6-amine (150 mg, 0.46 mmol), (R)-2-amino-3-methylbutan-1-ol (Intermediate 55, 236 mg, 2.28 mmol) and DIEA (0.798 mL, 4.57 mmol) in NMP (5 mL) were stirred under 140° C. for 3 days. The crude product was purified by preparative HPLC, Column: XBridge Shield RP18 OBD Column, 30*150 mm, 5 μm; Mobile Phase A: Water (0.05% $NH_3H_2O$), Mobile Phase B: ACN; Flow rate: 60 mL/min; Gradient: 18 B to 38 B in 7 min. Fractions containing the desired compound were evaporated to dryness to afford (R)-2-((9-ethyl-6-(((S)-1-(methylsulfonyl) pyrrolidin-3-yl)amino)-9H-purin-2-yl)amino)-3-methylbutan-1-ol (Example 28, 123 mg, 65.4%). $^1H$ NMR (400 MHZ, DMSO-$d_6$) 0.86-0.93 (6H, m), 1.34 (3H, t), 1.89-2.10 (2H, m), 2.13-2.26 (1H, m), 2.91 (3H, s), 3.17-3.25 (1H, m), 3.25-3.35 (1H, m), 3.42-3.54 (3H, m), 3.55-3.63 (1H, m), 3.77-3.88 (1H, m), 3.94-4.04 (2H, m), 4.49 (1H, t), 4.71 (1H, br s), 5.84 (1H, br s), 7.41 (1H, br s), 7.74 (1H, s); m/z ($ES^+$) $[M+H]^+$=412.

Example 29: (R)-2-(9-cyclopropyl-6-(((S)-1-(methylsulfonyl)pyrrolidin-3-yl-amino)-9H-purin-2-yl) amino)-3-methylbutan-1-ol

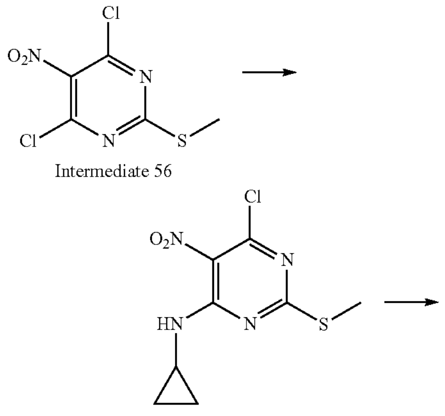

Intermediate 56

Intermediate 57

-continued

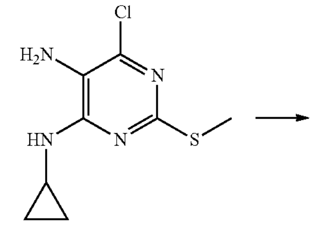

Intermediate 58

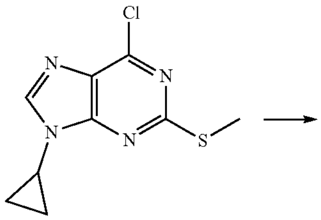

Intermediate 59

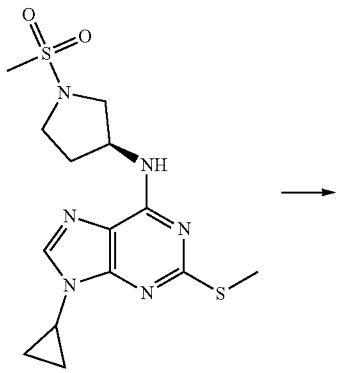

Intermediate 60

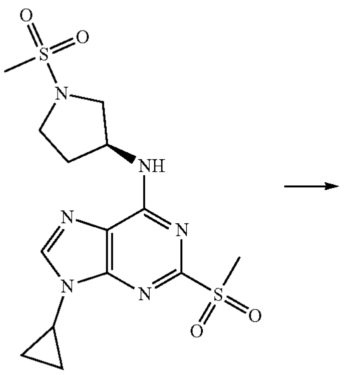

Intermediate 61

-continued

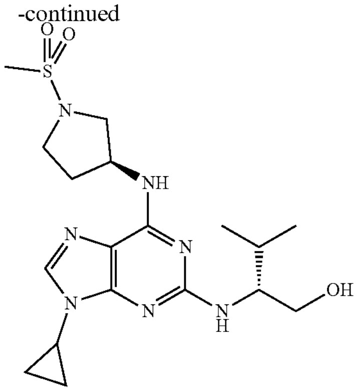

Example 29

Intermediate 57: 6-chloro-N-cyclopropyl-2-(methylthio)-5-nitropyrimidin-4-amine 4,6-Dichloro-2-(methylthio)-5-nitropyrimidine (Intermediate 56, 5 g, 20.83 mmol) was added to cyclopropanamine (1.070 g, 18.75 mmol) and TEA (8.71 mL, 62.48 mmol) in THF (100 mL) at 25° C. The resulting mixture was stirred at 25° C. for 1 day. The crude product was purified by flash silica chromatography, elution gradient 0 to 60% EtOAc in petroleum ether. Pure fractions were evaporated to dryness to afford 6-chloro-N-cyclopropyl-2-(methylthio)-5-nitropyrimidin-4-amine (Intermediate 57, 3.00 g, 55.3%) as a yellow solid. m/z ($ES^+$) $[M+H]^+$=261.

Intermediate 58: 6-chloro-$N^4$-cyclopropyl-2-(methylthio)pyrimidine-4,5-diamine 6-Chloro-N-cyclopropyl-2-(methylthio)-5-nitropyrimidin-4-amine (Intermediate 57, 3 g, 11.51 mmol) was added to iron (3.21 g, 57.54 mmol) in iPrOH (100 mL) and saturated aq. $NH_4Cl$ solution (100 mL) at 25° C. The resulting mixture was stirred at 50° C. for 1 day. The reaction mixture was filtered through celite. The reaction mixture was diluted with DCM (300 mL), and washed sequentially with saturated aq. $NH_4Cl$ solution (200 mL×3) and saturated aq. brine solution (300 mL). The organic layer was dried over $Na_2SO_4$, filtered and evaporated to afford crude product. The crude product was purified by flash silica chromatography, elution gradient 0 to 50% EtOAc in petroleum ether. Pure fractions were evaporated to dryness to afford 6-chloro-N4-cyclopropyl-2-(methylthio)pyrimidine-4,5-diamine (Intermediate 58, 2.000 g, 75%) as a off-white solid. $^1H$ NMR (400 MHZ, DMSO-$d_6$) 0.44-0.53 (2H, m), 0.66-0.80 (2H, m), 2.40 (3H, s), 2.77-2.88 (1H, m), 4.74 (2H, s), 7.07 (1H, d); m/z ($ES^+$) $[M+H]^+$=231.

Intermediate 59: 6-chloro-9-cyclopropyl-2-(methylthio)-9H-purine

Methanesulfonic acid (1.250 g, 13.00 mmol) was added to 6-chloro-N4-cyclopropyl-2-(methylthio)pyrimidine-4,5-diamine (Intermediate 58, 1 g, 4.33 mmol) in triethyl orthoformate (15 mL, 4.33 mmol). The resulting mixture was stirred at 100° C. for 16 hours. The solvent was removed under reduced pressure. The crude product was purified by flash C18 chromatography, elution gradient 5 to 60% MeCN in water (0.1% $NH_4HCO_3$). Pure fractions were evaporated to dryness to afford 6-chloro-9-cyclopropyl-2-(methylthio)-

9H-purine (Intermediate 59, 0.600 g, 57.5%) as a pale yellow solid. $^1$H NMR (400 MHZ, DMSO-$d_6$) 1.06-1.13 (2H, m), 1.13-1.20 (2H, m), 2.60 (3H, s), 3.51-3.61 (1H, m), 8.51 (1H, s); m/z (ES$^+$) [M+H]$^+$=241.

Intermediate 60: (S)-9-cyclopropyl-N-(1-(methylsulfonyl)pyrrolidin-3-yl)-2-(methylthio)-9H-purin-6-amine DIEA (4.35 mL, 24.93 mmol) was added to 6-chloro-9-cyclopropyl-2-(methylthio)-9H-purine (Intermediate 59, 600 mg, 2.49 mmol) and (S)-1-(methylsulfonyl)pyrrolidin-3-amine hydrochloride (750 mg, 3.74 mmol) in iPrOH (60 mL). The resulting mixture was stirred at 100° C. for 2 hours. The reaction mixture was poured into saturated aq. $Na_2CO_3$ solution (100 mL), extracted with DCM (3×100 mL), the organic layer was dried over $Na_2SO_4$, filtered and evaporated to afford pale yellow solid. The crude product was purified by flash silica chromatography, elution gradient 0 to 60% EtOAc in petroleum ether. Pure fractions were evaporated to dryness to afford (S)-9-cyclopropyl-N-(1-(methylsulfonyl)pyrrolidin-3-yl)-2-(methylthio)-9H-purin-6-amine (Intermediate 60, 400 mg, 43.6%) as an off-white solid. 1H NMR (400 MHZ, Methanol-$d_4$) 1.06-1.21 (4H, m), 2.07-2.20 (1H, m), 2.34-2.47 (1H, m), 2.58 (3H, s), 2.90 (3H, s), 3.33-3.42 (1H, m), 3.39-3.54 (2H, m), 3.54-3.64 (1H, m), 3.70-3.78 (1H, m), 4.84 (1H, br s), 7.92 (1H, s); one exchangeable H not shown; m/z (ES$^+$) [M+H]$^+$=369.

Intermediate 61: (S)-9-cyclopropyl-2-(methylsulfonyl)-N-(1-(methylsulfonyl)-pyrrolidin-3-yl)-9H-purin-6-amine mCPBA (562 mg, 3.26 mmol) was added slowly to (S)-9-cyclopropyl-N-(1-(methylsulfonyl)pyrrolidin-3-yl)-2-(methylthio)-9H-purin-6-amine (Intermediate 59, 400 mg, 1.09 mmol) in DCM (1 mL). The resulting mixture was stirred at rt for 1 hour. The crude product was purified by flash silica chromatography, elution gradient 0 to 60% EtOAc in petroleum ether. Pure fractions were evaporated to dryness to afford (S)-9-cyclopropyl-2-(methylsulfonyl)-N-(1-(methylsulfonyl)pyrrolidin-3-yl)-9H-purin-6-amine (Intermediate 61, 160 mg, 36.8%) as a white solid. m/z (ES$^+$) [M+H]$^+$=401.

Example 29: (R)-2-(9-cyclopropyl-6-(((S)-1-(methylsulfonyl)pyrrolidin-3-yl)amino)-9H-purin-2-yl)amino)-3-methylbutan-1-ol

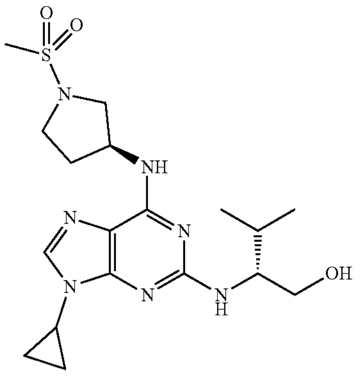 [SMILES: CC(C)[C@H](CO)Nc1nc(N[C@H]2CCN(S(C)(=O)=O)C2)c2ncn(C3CC3)c2n1]

(S)-9-cyclopropyl-2-(methylsulfonyl)-N-(1-(methylsulfonyl)pyrrolidin-3-yl)-9H-purin-6-amine (Intermediate 61, 80 mg, 0.20 mmol) was added to (R)-2-amino-3-methylbutan-1-ol (1 mL, 0.60 mmol). The resulting mixture was stirred at 140° C. for 2 days. The crude product was purified by preparative HPLC, Column: XBridge Shield RP18 OBD Column, 30*150 mm, 5 μm; Mobile Phase A: Water (0.05% $NH_3H_2O$), Mobile Phase B: ACN; Flow rate: 60 mL/min; Gradient: 20 B to 40 B in 7 min. Fractions containing the desired compound were evaporated to dryness to afford (R)-2-((9-cyclopropyl-6-(((S)-1-(methylsulfonyl)pyrrolidin-3-yl)amino)-9H-purin-2-yl)amino)-3-methylbutan-1-ol (Example 29, 70.0 mg, 83%). $^1$H NMR (400 MHZ, DMSO-$d_6$) 0.79-0.93 (6H, m), 0.91-1.06 (4H, m), 1.90-2.09 (2H, m), 2.12-2.25 (1H, m), 2.90 (3H, s), 3.15-3.24 (1H, m), 3.25-3.32 (2H, m), 3.41-3.52 (3H, m), 3.54-3.62 (1H, m), 3.77-3.87 (1H, m), 4.52 (1H, s), 4.68 (1H, br s), 5.95 (1H, br s), 7.43 (1H, br s), 7.68 (1H, s); m/z (ES$^+$) [M+H]$^+$=424.

Example 30: (R)-2-cyclopropyl-2-((9-isopropyl-6-(((S)-1-(methylsulfonyl)-pyrrolidin-3-yl)amino)-9H-purin-2-yl)amino)ethanol

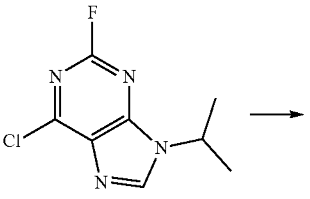

Intermediate 36

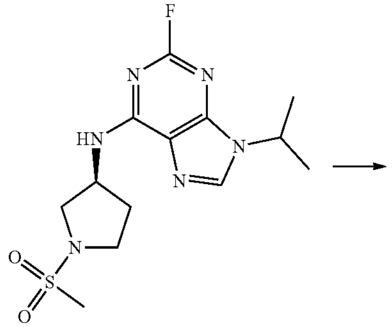

Intermediate 37

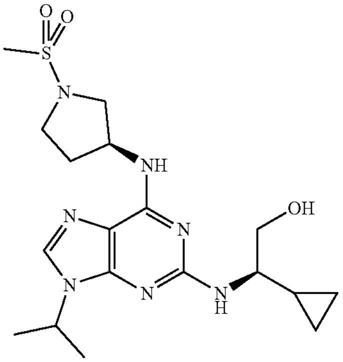 [SMILES: CC(C)n1cnc2c(N[C@H]3CCN(S(C)(=O)=O)C3)nc(N[C@@H](CO)C3CC3)nc21]

Example 30

Intermediate 37: (S)-2-fluoro-9-isopropyl-N-(1-(methylsulfonyl)pyrrolidin-3-yl)-9H-purin-6-amine 6-Chloro-2-fluoro-9-isopropyl-9H-purine (Intermediate 36, 500 mg, 2.33 mmol) was added to (S)-1-(methylsulfonyl)pyrrolidin-3-amine hydrochloride (468 mg, 2.33 mmol), and DIEA (2.034 mL, 11.65 mmol) in EtOH (5 mL) at 80° C. over a period of 2 hours. The resulting mixture was stirred at 80° C. for 2 hours. The solvent was removed under reduced pressure. The residue was purified by preparative TLC (EtOAc:petroleum ether=1:0), to afford (S)-2-fluoro-9-isopropyl-N-(1-(methylsulfonyl)pyrrolidin-3-yl)-9H-purin-6-amine (Intermediate 37, 310 mg, 38.9%) as a white solid. $^1$H NMR (300 MHZ, DMSO-$d_6$) 1.5 (6H, d), 2.1 (1H, br s), 2.2 (1H, br s), 2.9 (3H, s), 3.1-3.3 (2H, m), 3.3-3.4 (1H, m), 3.4-3.5 (1H, m), 3.6 (1H, s), 4.6 (1H, p), 8.3 (1H, s), 8.6 (1H, br s); m/z (ES$^+$) [M+H]$^+$=343.

Example 30: (R)-2-cyclopropyl-2-((9-isopropyl-6-(((S)-1-(methylsulfonyl)-pyrrolidin-3-yl)amino)-9H-purin-2-yl)amino)ethanol

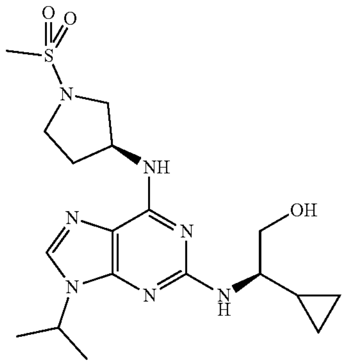

N-ethyl-N-isopropylpropan-2-amine (566 mg, 4.38 mmol) was added to (R)-2-amino-2-cyclopropylethan-1-ol hydrochloride (201 mg, 1.46 mmol) and (S)-2-fluoro-9-isopropyl-N-(1-(methylsulfonyl)pyrrolidin-3-yl)-9H-purin-6-amine (Intermediate 37, 100 mg, 0.29 mmol) in NMP (1 mL). The resulting mixture was stirred at 140° C. for 4 days. The reaction mixture was filtered through celite. The crude product was purified by preparative HPLC, Column: Xselect CSH OBD Column 30*150 mm, 5 μm; Mobile Phase A: Water (0.1% FA), Mobile Phase B: ACN; Flow rate: 60 mL/min; Gradient: 14 B to 24 B in 7 min. Fractions containing the desired compound were evaporated to dryness to afford (R)-2-cyclopropyl-2-((9-isopropyl-6-(((S)-1-(methylsulfonyl)pyrrolidin-3-yl)amino)-9H-purin-2-yl)amino)ethan-1-ol (Example 30, 30.0 mg, 22.77%). $^1$H NMR (400 MHZ, DMSO-$d_6$) 0.18-0.26 (1H, m), 0.29-0.45 (3H, m), 0.95-1.04 (1H, m), 1.46 (6H, d), 1.99-2.08 (1H, m), 2.15-2.24 (1H, m), 2.91 (3H, s), 3.15-3.33 (2H, m), 3.40-3.64 (5H, m), 4.48-4.61 (1H, m), 4.69 (1H, br s), 5.96 (1H, br d), 7.41 (1H, br s), 7.81 (1H, s), 8.17 (1H, s). m/z (ES$^+$) [M+H]$^+$=424.

Example 31: (2R,3S)-3-((9-isopropyl-6-(((S)-1-(1-methyl-1H-pyrazol-4-yl-sulfonyl)pyrrolidin-3-yl)amino)-9H-purin-2-yl)amino)pentan-2-ol

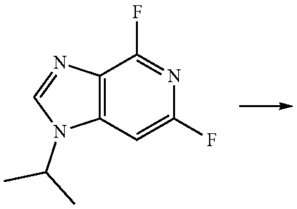

Intermediate 36

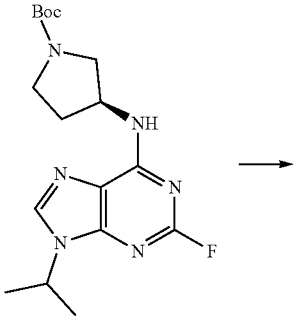

Intermediate 62

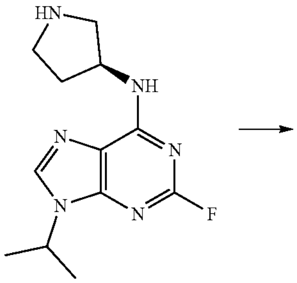

Intermediate 63

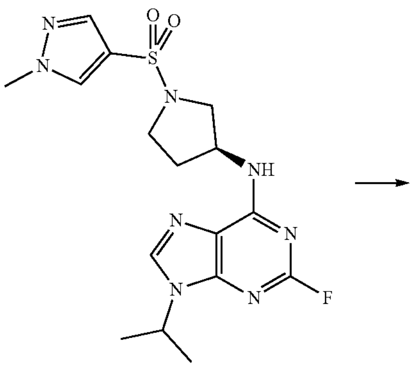

Intermediate 64

-continued

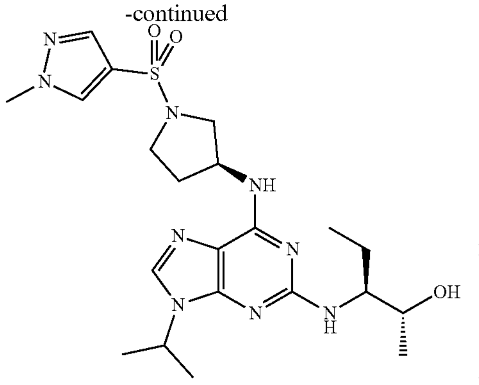

Example 31

Intermediate 62: (S)-tert-butyl 3-(2-fluoro-9-isopropyl-9H-purin-6-ylamino)-pyrrolidine-1-carboxylate DIEA (1.221 mL, 6.99 mmol) was added to 6-chloro-2-fluoro-9-isopropyl-9H-purine (Intermediate 36, 500 mg, 1.40 mmol, 60% wt) and tert-butyl (S)-3-aminopyrrolidine-1-carboxylate (521 mg, 2.80 mmol) in MeCN (5 mL). The resulting mixture was stirred at 100° C. for 2 hours. The crude product was purified by flash silica chromatography, elution gradient 0 to 100% EtOAc in petroleum ether. Pure fractions were evaporated to dryness to afford tert-butyl (S)-3-((2-fluoro-9-isopropyl-9H-purin-6-yl)amino)pyrrolidine-1-carboxylate (Intermediate 62, 200 mg, 39.3%) as a colorless oil. $^1$H NMR (400 MHz, DMSO-$d_6$) 1.40 (9H, br d), 1.50 (6H, d), 1.93-2.07 (1H, m), 2.14 (1H, br d), 3.21-3.29 (2H, m), 3.39-3.50 (1H, m), 3.54-3.66 (1H, m), 4.58-4.70 (2H, m), 8.26 (1H, s), 8.56 (1H, br s); m/z (ES$^+$) [M+H]$^+$=365.

Intermediate 63: (S)-2-fluoro-9-isopropyl-N-(pyrrolidin-3-yl)-9H-purin-6-amine hydrochloride HCl in 1,4-dioxane (3 ml, 98.74 mmol, 4 M) was added dropwise to tert-butyl (S)-3-((2-fluoro-9-isopropyl-9H-purin-6-yl)amino)pyrrolidine-1-carboxylate (Intermediate 62, 200 mg, 0.55 mmol) in MeOH (3 mL). The resulting mixture was stirred at rt for 2 hours. The solvent was removed under reduced pressure to afford (S)-2-fluoro-9-isopropyl-N-(pyrrolidin-3-yl)-9H-purin-6-amine. HCl (Intermediate 63, 190 mg, 115.3%) as a white solid. The product was used in the next step directly without further purification.

Intermediate 64: (S)-2-fluoro-9-isopropyl-N-(1-(1-methyl-1H-pyrazol-4-yl-sulfonyl)pyrrolidin-3-yl)-9H-purin-6-amine A solution of 1-methyl-1H-pyrazole-4-sulfonyl chloride (156 mg, 0.86 mmol) in DCM (2 mL) was added dropwise to a stirred solution of (S)-2-fluoro-9-isopropyl-N-(pyrrolidin-3-yl)-9H-purin-6-amine (Intermediate 63, 190 mg, 0.72 mmol) and TEA (0.301 mL, 2.16 mmol) in DCM (3 mL). The resulting mixture was stirred at rt for 1 hour. The reaction mixture was diluted with DCM (20 mL), and washed sequentially with saturated aq. $NH_4Cl$ solution (20 mL), saturated aq. $NaHCO_3$ solution (20 mL), and saturated aq. brine solution (20 mL). The organic layer was dried over $Na_2SO_4$, filtered and evaporated to afford (S)-2-fluoro-9-isopropyl-N-(1-((1-methyl-1H-pyrazol-4-yl)sulfonyl)pyrrolidin-3-yl)-9H-purin-6-amine (Intermediate 64, 210 mg, 71.5%) as a desired product. m/z (ES$^+$) [M+H]$^+$=409.

Example 31: (2R,3S)-3-((9-isopropyl-6-(((S)-1-(1-methyl-1H-pyrazol-4-ylsulfonyl)-pyrrolidin-3-yl)amino)-9H-purin-2-yl)amino)pentan-2-ol

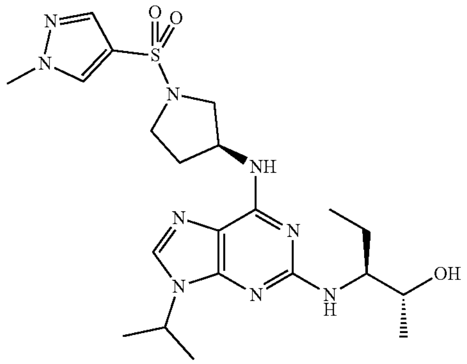 [SMILES: CC[C@H](Nc1nc(N[C@H]2CCN(S(=O)(=O)c3cnn(C)c3)C2)c2ncn(C(C)C)c2n1)[C@@H](C)O]

DIEA (0.812 mL, 4.65 mmol) was added to (S)-2-fluoro-9-isopropyl-N-(1-((1-methyl-1H-pyrazol-4-yl)sulfonyl)pyrrolidin-3-yl)-9H-purin-6-amine (Intermediate 64, 190 mg, 0.47 mmol) and (2R,3S)-3-aminopentan-2-ol. HCl (194.7 mg, 1.41 mmol) in NMP (4 mL). The resulting mixture was stirred at 140° C. for 4 days. The reaction mixture was filtered through celite. The crude product was purified by preparative HPLC, Column: Xselect CSH OBD Column 30*150 mm 5 μm; Mobile Phase A: Water (0.1% FA), Mobile Phase B: ACN; Flow rate: 60 mL/min; Gradient: 16 B to 26 B in 7 min. Fractions containing the desired compound were evaporated to dryness to afford (2R,3S)-3-((9-isopropyl-6-(((S)-1-((1-methyl-1H-pyrazol-4-yl)sulfonyl)pyrrolidin-3-yl)amino)-9H-purin-2-yl)amino)pentan-2-ol (Example 31, 85 mg, 37.2%). $^1$H NMR (300 MHz, DMSO-$d_6$) 0.9 (3H, t), 1.0 (3H, d), 1.5 (7H, d, overlapped), 1.7 (1H, s), 1.9 (1H, s), 2.0-2.1 (1H, m), 3.0-3.1 (1H, m), 3.2 (1H, q), 3.3 (1H, d), 3.5 (1H, m), 3.6-3.7 (2H, m), 3.9 (3H, s), 4.5-4.6 (2H, m), 4.6 (1H, s), 5.9 (1H, br s), 7.3 (1H, br s), 7.8 (2H, d), 8.3 (1H, s); m/z (ES$^+$) [M+H]$^+$=492.

Example 32: (2R,3S)-3-((9-isopropyl-6-(((S)-1-(1-methyl-1H-imidazol-4-yl-sulfonyl)pyrrolidin-3-yl)amino)-9H-purin-2-yl)amino)pentan-2-ol

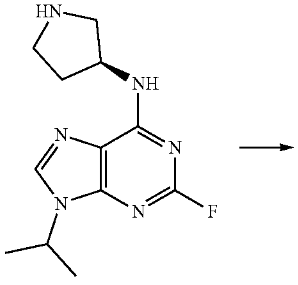

Intermediate 63

-continued

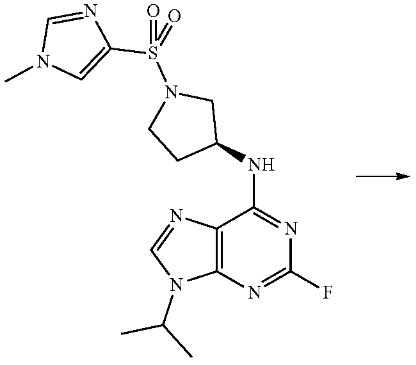

Intermediate 65

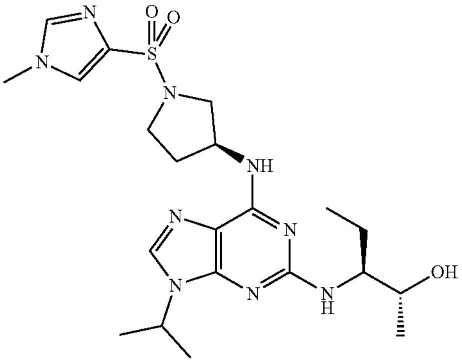

Example 32

Intermediate 65: (S)-2-fluoro-9-isopropyl-N-(1-(1-methyl-1H-imidazol-4-yl-sulfonyl)pyrrolidin-3-yl)-9H-purin-6-amine A solution of 1-methyl-1H-imidazole-4-sulfonyl chloride (353 mg, 1.96 mmol) in DCM (2 mL) was added dropwise to a stirred solution of (S)-2-fluoro-9-isopropyl-N-(pyrrolidin-3-yl)-9H-purin-6-amine hydrochloride (Intermediate 63, 490 mg, 1.63 mmol) and TEA (0.681 mL, 4.89 mmol) in DCM (3 mL). The resulting mixture was stirred at rt for 1 hour. The reaction mixture was diluted with DCM (20 mL), and washed sequentially with saturated aq. $NH_4Cl$ solution (20 mL), saturated aq. $NaHCO_3$ solution (20 mL), and saturated aq. brine solution (20 mL). The organic layer was dried over $Na_2SO_4$, filtered and evaporated to afford (S)-2-fluoro-9-isopropyl-N-(1-((1-methyl-1H-imidazol-4-yl)sulfonyl)pyrrolidin-3-yl)-9H-purin-6-amine (Intermediate 65, 600 mg, 90%) as a white solid. $^1H$ NMR (300 MHz, DMSO-$d_6$) 1.50 (6H, d), 1.92-2.16 (2H, m), 3.26-3.47 (4H, m, overlapped), 3.56-3.65 (1H, m), 3.71-3.82 (2H, m), 4.44 (1H, br d), 4.65 (1H, quin), 7.78 (1H, s), 7.80-7.85 (1H, m), 8.26 (1H, s), 8.42-8.52 (1H, m); m/z (ES$^+$) [M+H]$^+$=409.

Example 32: (2R,3S)-3-((9-isopropyl-6-(((S)-1-(1-methyl-1H-imidazol-4-yl-sulfonyl)pyrrolidin-3-yl)amino)-9H-purin-2-yl)amino)pentan-2-ol

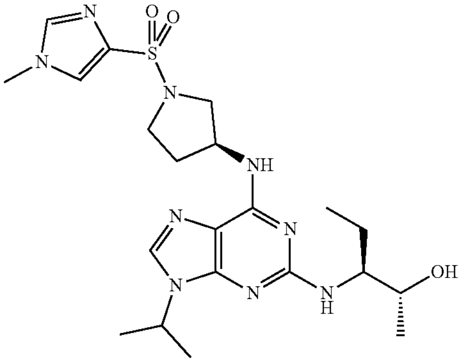 [SMILES: CC[C@H](Nc1nc(N[C@H]2CCN(S(=O)(=O)c3cn(C)cn3)C2)c2ncn(C(C)C)c2n1)[C@@H](C)O]

DIEA (0.641 mL, 3.67 mmol) was added dropwise to (S)-2-fluoro-9-isopropyl-N-(1-((1-methyl-1H-imidazol-4-yl)sulfonyl)pyrrolidin-3-yl)-9H-purin-6-amine (Intermediate 65, 150 mg, 0.37 mmol) and (2R,3S)-3-aminopentan-2-ol (189 mg, 1.84 mmol) in NMP (4 mL). The resulting mixture was stirred at 140° C. for 2 days. The reaction mixture was filtered through celite. The crude product was purified by preparative Column: XBridge Shield RP18 OBD Column, 30*150 mm, 5 μm; Mobile Phase A: Water (0.05% $NH_4OH$), Mobile Phase B: ACN; Flow rate: 60 mL/min; Gradient: 23 B to 63 B in 7 min. Fractions containing the desired compound were evaporated to dryness to afford (2R,3S)-3-((9-isopropyl-6-(((S)-1-((1-methyl-1H-imidazol-4-yl)sulfonyl)pyrrolidin-3-yl)amino)-9H-purin-2-yl)amino)pentan-2-ol (Example 32, 50.0 mg, 27.7%). $^1H$ NMR (600 MHz, DMSO-$d_6$) 0.86 (3H, t), 1.05 (3H, d), 1.36-1.44 (1H, m), 1.46 (6H, dd), 1.71 (1H, ddd), 1.88-1.99 (1H, m), 2.07 (1H, dq), 3.24 (1H, br dd), 3.29-3.33 (1H, m), 3.40-3.45 (1H, m), 3.59-3.66 (2H, m), 3.69 (3H, s), 3.73 (1H, tdd), 4.42-4.56 (2H, m), 4.66 (1H, br s), 5.94 (1H, br s), 7.32 (1H, br s), 7.78-7.83 (3H, m). m/z (ES$^+$) [M+H]+=492.

Example 33: (R)-2-((6-(((3R,4R)-4-fluoro-1-(methylsulfonyl)pyrrolidin-3-yl)-amino)-9-isopropyl-9H-purin-2-yl)amino)-3-methylbutan-1-ol

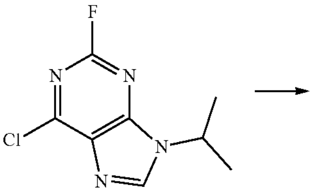

Intermediate 36

-continued

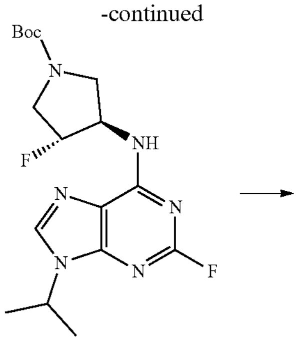

Intermediate 66

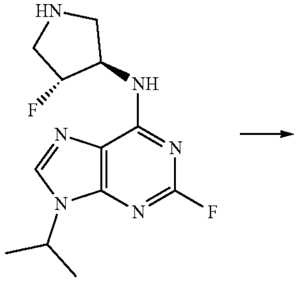

Intermediate 67

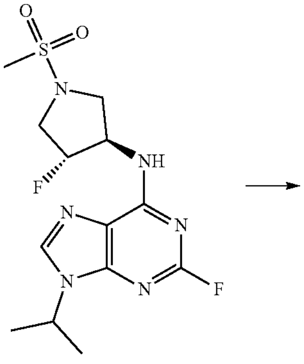

Intermediate 68

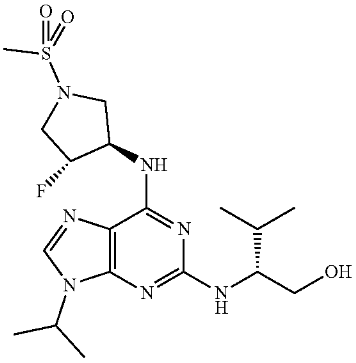 [SMILES: CC(C)[C@H](CO)Nc1nc(N[C@@H]2CN(S(C)(=O)=O)C[C@H]2F)c2ncn(C(C)C)c2n1]

Example 33

Intermediate 66: (3R,4R)-tert-butyl 3-fluoro-4-(2-fluoro-9-isopropyl-9H-purin-6-yl-amino)pyrrolidine-1-carboxylate 6-Chloro-2-fluoro-9-isopropyl-9H-purine (Intermediate 36, 0.300 g, 1.40 mmol) was added to tert-butyl (3R,4R)-3-amino-4-fluoropyrrolidine-1-carboxylate (0.314 g, 1.54 mmol) and DIEA (0.732 mL, 4.19 mmol) in MeCN (3 mL) at 25° C. The resulting mixture was stirred at 80° C. for 1 day. The reaction was concentrated and the crude product was purified by flash silica chromatography, elution gradient 0 to 60% EtOAc in petroleum ether. Pure fractions were evaporated to dryness to afford tert-butyl (3R,4R)-3-fluoro-4-((2-fluoro-9-isopropyl-9H-purin-6-yl)amino)pyrrolidine-1-carboxylate (Intermediate 66, 0.280 g, 52.4%) as a white solid. 1H NMR (400 MHZ, DMSO-$d_6$) 1.41 (9H, s), 1.47-1.53 (6H, m), 3.43-3.76 (4H, m), 4.58-4.74 (2H, m), 5.20 (1H, d), 8.30 (1H, s), 8.77 (1H, br s); m/z ($ES^+$) $[M+H]^+$ =383.

Intermediate 67: 2-fluoro-N-((3R,4R)-4-fluoropyrrolidin-3-yl)-9-isopropyl-9H-purin-6-amine hydrochloride tert-Butyl (3R,4R)-3-fluoro-4-((2-fluoro-9-isopropyl-9H-purin-6-yl)amino)pyrrolidine-1-carboxylate (Intermediate 66, 0.200 g, 0.52 mmol) was added to HCl in 1,4-dioxane (18 mL, 4 M) at 25° C. The resulting mixture was stirred at 25° C. for 1 day. The solvent was removed under reduced pressure. The product 2-fluoro-N-((3R,4R)-4-fluoropyrrolidin-3-yl)-9-isopropyl-9H-purin-6-amine. HCl (Intermediate 67, 0.120 g, 72.1%) as a colourless gum was used in the next step directly without further purification. m/z ($ES^+$) $[M+H]^+$ =283.

Intermediate 68: 2-fluoro-N-((3R,4R)-4-fluoro-1-(methylsulfonyl)pyrrolidin-3-yl)-9-isopropyl-9H-purin-6-amine 2-Fluoro-N-((3R,4R)-4-fluoropyrrolidin-3-yl)-9-isopropyl-9H-purin-6-amine. HCl (Intermediate 67, 0.110 g, 0.35 mmol) was added to methanesulfonic anhydride (0.081 g, 0.47 mmol) and triethylamine (0.118 g, 1.17 mmol) in DCM (20 mL) at 25° C. The resulting mixture was stirred at 25° C. for 2 hours. The reaction was concentrated and the residue was purified by preparative TLC (EtOAc) to afford 2-fluoro-N-((3R,4R)-4-fluoro-1-(methylsulfonyl)pyrrolidin-3-yl)-9-isopropyl-9H-purin-6-amine (Intermediate 68, 0.090 g, 72.3%) as a white solid. 1H NMR (300 MHz, DMSO-$d_6$) 1.50 (6H, d), 2.98 (3H, s), 3.40-3.88 (4H, m), 4.56-4.86 (2H, m), 5.30 (1H, d), 8.32 (1H, s), 8.75 (1H, br s); m/z ($ES^+$) $[M+H]^+$=361.

Example 33: (R)-2-((6-(((3R,4R)-4-fluoro-1-(methylsulfonyl)pyrrolidin-3-yl)amino)-9-isopropyl-9H-purin-2-yl)amino)-3-methylbutan-1-ol

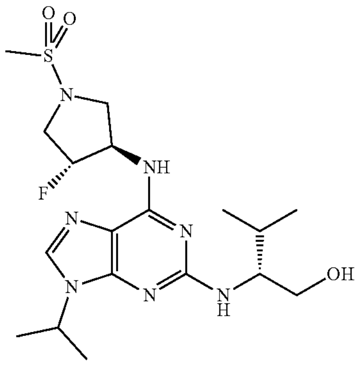

2-Fluoro-N-((3R,4R)-4-fluoro-1-(methylsulfonyl)pyrrolidin-3-yl)-9-isopropyl-9H-purin-6-amine (Intermediate 68, 0.060 g, 0.17 mmol) was added to (R)-2-amino-3-methylbutan-1-ol (0.086 g, 0.83 mmol) and DIEA (0.145 mL, 0.83 mmol) in NMP (2 mL) at 25° C. The resulting mixture was stirred at 140° C. for 1 day. The reaction was concentrated and the crude product was purified by preparative HPLC, Column: XBridge Shield RP18 OBD Column, 30*150 mm, 5 μm; Mobile Phase A: Water (0.05% $NH_3H_2O$), Mobile Phase B: MeOH; Flow rate: 60 mL/min; Gradient: 46 B to 54 B in 7 min. Fractions containing the desired compound were evaporated to dryness to afford (R)-2-((6-(((3R,4R)-4-fluoro-1-(methylsulfonyl)pyrrolidin-3-yl)amino)-9-isopropyl-9H-purin-2-yl)amino)-3-methylbutan-1-ol (Example 33, 0.013 g, 18.25%). $^1$H NMR (400 MHZ, DMSO-$d_6$) 0.89-0.98 (6H, m), 1.45-1.53 (6H, m), 1.91-1.99 (1H, m), 2.98 (3H, s), 3.44-3.53 (3H, m), 3.58 (1H, br d), 3.65-3.69 (1H, m), 3.72-3.78 (1H, m), 3.84-3.89 (1H, m), 4.48-4.57 (2H, m), 4.80-4.85 (1H, m), 5.28 (1H, d), 5.96 (1H, br s), 7.67 (1H, br s), 7.87 (1H, s); 19F NMR (376 MHz, DMSO-$d_6$)-177.52; m/z ($ES^+$) $[M+H]^+$=444.

Example 34: (R)-2-((9-isopropyl-6-(((3S,5R)-5-methyl-1-(methylsulfonyl)-pyrrolidin-3-yl)amino)-9H-purin-2-yl)amino)-3-methylbutan-1-ol

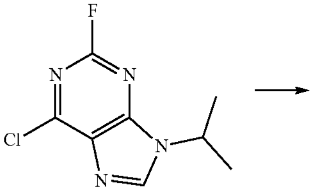

Intermediate 36

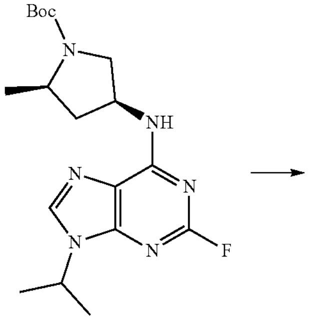

Intermediate 69

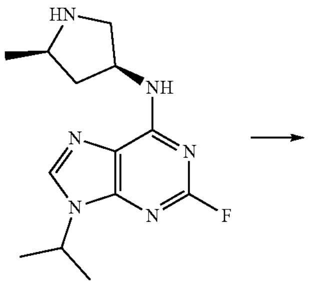

Intermediate 70

-continued

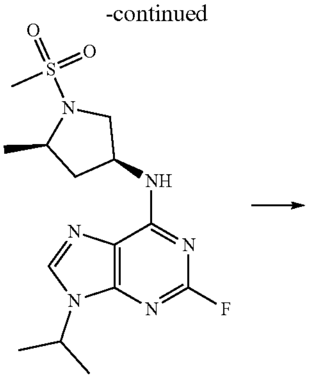

Intermediate 71

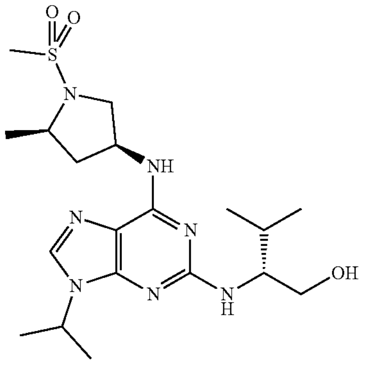 [SMILES: CC(C)[C@H](CO)Nc1nc(N[C@H]2C[C@@H](C)N(S(C)(=O)=O)C2)c2ncn(C(C)C)c2n1]

Example 34

Intermediate 69: (2R,4S)-tert-butyl 4-(2-fluoro-9-isopropyl-9H-purin-6-ylamino)-2-methylpyrrolidine-1-carboxylate 6-Chloro-2-fluoro-9-isopropyl-9H-purine (Intermediate 36, 0.300 g, 1.40 mmol) was added to tert-butyl (2R,4S)-4-amino-2-methylpyrrolidine-1-carboxylate (0.308 g, 1.54 mmol) and DIEA (0.732 mL, 4.19 mmol) in MeCN (5 mL) at 25° C. The resulting mixture was stirred at 100° C. for 1 day. The crude product was purified by flash silica chromatography, elution gradient 0 to 100% EtOAc in petroleum ether. Pure fractions were evaporated to dryness to afford tert-butyl (2R,4S)-4-((2-fluoro-9-isopropyl-9H-purin-6-yl)amino)-2-methylpyrrolidine-1-carboxylate (Intermediate 69, 0.240 g, 45.4%) as a white solid. m/z ($ES^+$) $[M+H]^+$=379.

Intermediate 70: 2-fluoro-9-isopropyl-N-((3S,5R)-5-methylpyrrolidin-3-yl)-9H-purin-6-amine hydrochloride tert-Butyl (2R,4S)-4-((2-fluoro-9-isopropyl-9H-purin-6-yl)amino)-2-methylpyrrolidine-1-carboxylate (Intermediate 69, 0.230 g, 0.61 mmol) was added to HCl in 1,4-dioxane (15 mL, 4 M) at 25° C. The resulting mixture was stirred at 25° C. for 1 day. The reaction mixture was evaporated to afford crude product 2-fluoro-9-isopropyl-N-((3S,5R)-5-methylpyrrolidin-3-yl)-9H-purin-6-amine. HCl (Intermediate 70, 0.140 g, 73.3%). m/z ($ES^+$) $[M+H]^+$=279.

Intermediate 71: 2-fluoro-9-isopropyl-N-((3S,5R)-5-methyl-1-(methylsulfonyl)-pyrrolidin-3-yl)-9H-purin-6-amine 2-Fluoro-9-isopropyl-N-((3S,5R)-5-methylpyrrolidin-3-yl)-9H-purin-6-amine. HCl (Intermediate 70, 0.130 g, 0.41 mmol) was added to TEA (0.195 mL, 1.40 mmol) and methanesulfonic anhydride (0.098 g, 0.56 mmol) in DCM (15 mL) at 20° C. The resulting mixture was stirred at 25° C. for 2 hours. The reaction was concentrated and the residue was purified by preparative TLC (EtOAc:petroleum ether=5:1), to afford 2-fluoro-9-isopropyl-N-((3S,5R)-5-methyl-1-(methylsulfonyl)pyrrolidin-3-yl)-9H-purin-6-amine (Intermediate 71, 0.130 g, 78%) as a white solid. $^1H$ NMR (300 MHz, DMSO-$d_6$) 1.29 (3H, d), 1.50 (6H, d), 1.66-1.80 (1H, m), 1.99 (1H, s), 3.02 (3H, d), 3.64-3.97 (2H, m), 3.99-4.09 (1H, m), 4.41-4.60 (1H, m), 4.60-4.71 (1H, m), 8.31 (1H, br d), 8.53 (1H, d); m/z ($ES^+$) $[M+H]^+$=357.

Example 34: (R)-2-((9-isopropyl-6-(((3S,5R)-5-methyl-1-(methylsulfonyl)-pyrrolidin-3-yl)amino)-9H-purin-2-yl)amino)-3-methylbutan-1-ol

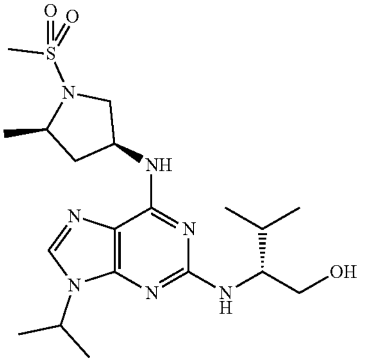

2-Fluoro-9-isopropyl-N-((3S,5R)-5-methyl-1-(methylsulfonyl)pyrrolidin-3-yl)-9H-purin-6-amine (Intermediate 71, 60.0 mg, 0.17 mmol) was added to DIEA (0.147 mL, 0.84 mmol) and (R)-2-amino-3-methylbutan-1-ol (87 mg, 0.84 mmol) in NMP (2 mL) at 20° C. The resulting mixture was stirred at 140° C. for 2 days. The crude product was purified by preparative HPLC, Column: XBridge Shield RP18 OBD Column, 30*150 mm, 5 μm; Mobile Phase A: Water (0.05% $NH_3H_2O$), Mobile Phase B: ACN; Flow rate: 60 mL/min; Gradient: 35 B to 35 B in 6 min. Fractions containing the desired compound were evaporated to dryness to afford (R)-2-((9-isopropyl-6-(((3S,5R)-5-methyl-1-(methylsulfonyl)pyrrolidin-3-yl)amino)-9H-purin-2-yl)amino)-3-methylbutan-1-ol (Example 34, 63.0 mg, 85%). $^1H$ NMR (400 MHZ, DMSO-$d_6$) 0.88-0.93 (6H, m), 1.29 (3H, d), 1.46 (6H, t), 1.72-1.81 (1H, m), 1.95 (1H, dq), 2.41-2.48 (1H, m), 2.98 (3H, br s), 3.10-3.21 (1H, m), 3.31-3.32 (1H, m), 3.46-3.54 (2H, m), 3.73-3.84 (3H, m), 4.46-4.61 (2H, m), 5.76-5.91 (1H, m), 7.28-7.45 (1H, m), 7.82 (1H, br s); m/z ($ES^+$) $[M+H]^+$=440.

Example 35: (R)-2-((9-isopropyl-6-(((3S,5S)-5-methyl-1-(methylsulfonyl)-pyrrolidin-3-yl)amino)-9H-purin-2-yl)amino)-3-methylbutan-1-ol

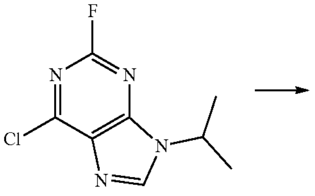

Intermediate 36

-continued

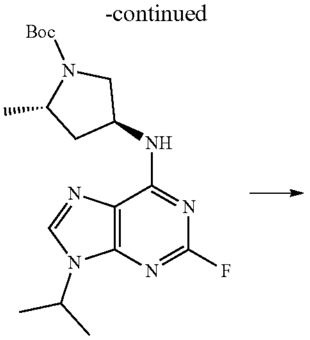

Intermediate 72

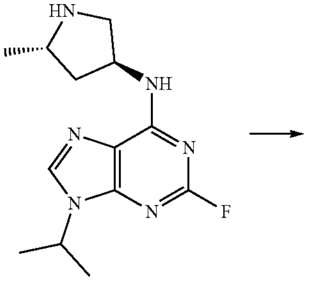

Intermediate 73

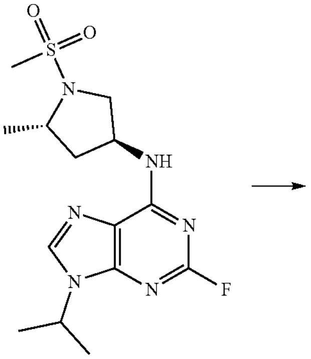

Intermediate 74

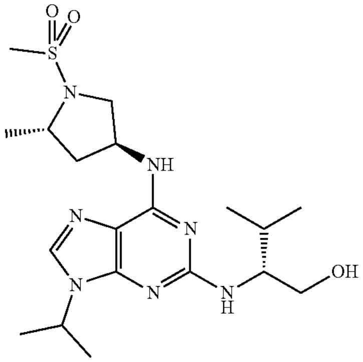 [SMILES: CC(C)[C@H](CO)Nc1nc(N[C@H]2C[C@H](C)N(S(C)(=O)=O)C2)c2ncn(C(C)C)c2n1]

Example 35

Intermediate 72: (2S,4S)-tert-butyl 4-(2-fluoro-9-isopropyl-9H-purin-6-ylamino)-2-methylpyrrolidine-1-carboxylate 6-Chloro-2-fluoro-9-isopropyl-9H-purine (Intermediate 36, 0.300 g, 1.40 mmol) was added to tert-butyl (2S,4S)-4-amino-2-methylpyrrolidine-1-carboxylate (0.308 g, 1.54 mmol) and DIEA (0.732 mL, 4.19 mmol) in MeCN (5 mL) at 25° C. The resulting mixture was stirred at 100° C. for 1 day. The reaction was concentrated and the crude product was purified by flash silica chromatography, elution gradient 0 to 100% EtOAc in petroleum ether. Pure fractions were evaporated to dryness to afford tert-butyl (2S,4S)-4-((2-fluoro-9-isopropyl-9H-purin-6-yl)amino)-2-methylpyrrolidine-1-carboxylate (Intermediate 72, 0.240 g, 45.4%) as a yellow solid. m/z ($ES^+$) $[M+H]^+$=379.

Intermediate 73: 2-fluoro-9-isopropyl-N-((3S,5S)-5-methylpyrrolidin-3-yl)-9H-purin-6-amine hydrochloride tert-Butyl (2S,4S)-4-((2-fluoro-9-isopropyl-9H-purin-6-yl)amino)-2-methylpyrrolidine-1-carboxylate (Intermediate 72, 0.230 g, 0.61 mmol) was added to HCl in 1,4-dioxane (3 mL, 4 M) at 25° C. The resulting mixture was stirred at 25° C. for 1 day. The reaction mixture was filtered and evaporated to afford crude product 2-fluoro-9-isopropyl-N-((3S,5S)-5-methylpyrrolidin-3-yl)-9H-purin-6-amine. HCl (Intermediate 73, 0.140 g, 73.3%); m/z ($ES^+$) $[M+H]^+$=279.

Intermediate 74: 2-fluoro-9-isopropyl-N-((3S,5S)-5-methyl-1-(methylsulfonyl)-pyrrolidin-3-yl)-9H-purin-6-amine 2-Fluoro-9-isopropyl-N-((3S,5S)-5-methylpyrrolidin-3-yl)-9H-purin-6-amine. HCl (Intermediate 73, 0.130 g, 0.41 mmol) was added to TEA (0.195 mL, 1.40 mmol) and methanesulfonic anhydride (0.098 g, 0.56 mmol) in DCM (15 mL) at 20° C. The resulting mixture was stirred at 25° C. for 2 h. The reaction was concentrated and the residue was purified by preparative TLC (EtOAc:petroleum ether=5:1) to afford 2-fluoro-9-isopropyl-N-((3S,5S)-5-methyl-1-(methylsulfonyl)pyrrolidin-3-yl)-9H-purin-6-amine (Intermediate 74, 0.130 g, 88.2%) as a white solid. $^1H$ NMR (300 MHz, DMSO-$d_6$) 1.25 (3H, d), 1.51 (6H, d), 1.88-1.96 (1H, m), 2.19-2.30 (1H, m), 2.88 (3H, s), 3.29-3.30 (1H, m), 3.59-3.68 (1H, m), 3.98-4.07 (1H, m), 4.6-4.65 (2H, m), 8.29 (1H, s), 8.52 (1H, br s); m/z ($ES^+$) $[M+H]^+$=357.

Example 35: (R)-2-((9-isopropyl-6-(((3S,5S)-5-methyl-1-(methylsulfonyl)-pyrrolidin-3-yl)amino)-9H-purin-2-yl)amino)-3-methylbutan-1-ol

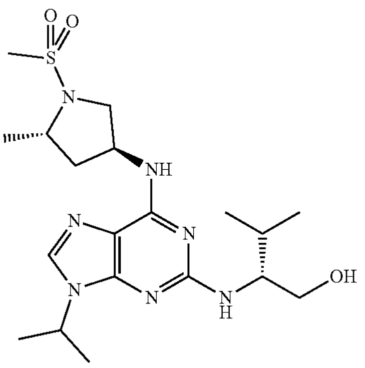

2-Fluoro-9-isopropyl-N-((3S,5S)-5-methyl-1-(methylsulfonyl)pyrrolidin-3-yl)-9H-purin-6-amine (Intermediate 74, 60.0 mg, 0.17 mmol) was added to DIEA (0.147 mL, 0.84 mmol) and (R)-2-amino-3-methylbutan-1-ol (87 mg, 0.84 mmol) in NMP (2 mL) at 20° C. The resulting mixture was stirred at 140° C. for 2 days. The reaction was concentrated and the crude product was purified by preparative HPLC, Column: XBridge Prep OBD C18 Column, 30×150 mm 5 μm; Mobile Phase A: Water (10 mmol/L $NH_4HCO_3$+0.1% $NH_3{\cdot}H_2O$), Mobile Phase B: ACN; Flow rate: 60 mL/min; Gradient: 34 B to 39 B in 7 min. Fractions containing the desired compound were evaporated to dryness to afford (R)-2-((9-isopropyl-6-(((3S,5S)-5-methyl-1-(methylsulfonyl)pyrrolidin-3-yl)amino)-9H-purin-2-yl)amino)-3-methylbutan-1-ol (Example 35, 62.0 mg, 84%). $^1H$ NMR (400 MHZ, DMSO-$d_6$) 0.90 (6H, dd), 1.24 (3H, d), 1.46 (6H, t), 1.83-2.02 (2H, m), 2.20 (1H, dt), 2.87 (3H, s), 3.30-3.32 (1H, m), 3.50 (2H, t), 3.59 (1H, dd), 3.78-3.86 (1H, m), 3.94-4.02 (1H, m), 4.47-4.58 (2H, m), 4.81 (1H, br s), 5.89 (1H, br s), 7.37 (1H, br s), 7.81 (1H, s); m/z ($ES^+$) $[M+H]^+$=440.

Example 36: (R)-2-((9-isopropyl-6-(((3S,4R)-4-methyl-1-(methylsulfonyl)-pyrrolidin-3-yl)amino)-9H-purin-2-yl)amino)-3-methylbutan-1-ol

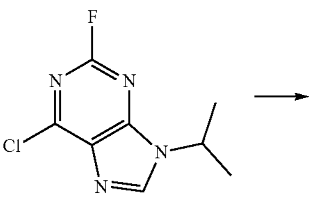

Intermediate 36

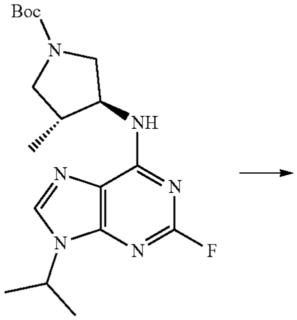

Intermediate 75

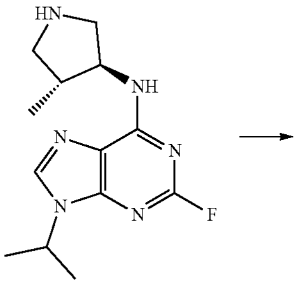

Intermediate 76

-continued

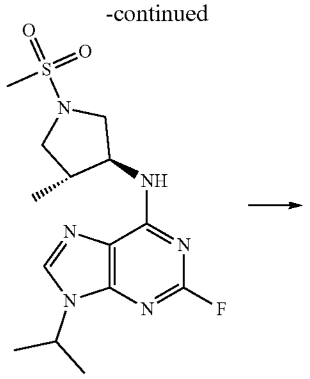

Intermediate 77

Intermediate 77: 2-fluoro-9-isopropyl-N-((3S,4R)-4-methyl-1-(methylsulfonyl)-pyrrolidin-3-yl)-9H-purin-6-amine 2-Fluoro-9-isopropyl-N-((3S,4R)-4-methylpyrrolidin-3-yl)-9H-purin-6-amine, HCl (Intermediate 76, 0.090 g, 0.29 mmol) was added to methanesulfonic anhydride (0.068 g, 0.39 mmol) and TEA (0.225 mL, 1.62 mmol) in DCM (2 mL) at 20° C. The resulting mixture was stirred at 20° C. for 1 day. The reaction was concentrated to obtain the crude product that was purified by preparative TLC (EtOAc:petroleum ether=10:1) to afford 2-fluoro-9-isopropyl-N-((3S,4R)-4-methyl-1-(methylsulfonyl)pyrrolidin-3-yl)-9H-purin-6-amine (Intermediate 77, 0.100 g, 98%) as a white solid. $^1$H NMR (300 MHz, DMSO-$d_6$) 0.93 (3H, t), 1.50 (6H, d), 2.55-2.67 (1H, m), 2.93 (3H, s), 3.20 (1H, t), 3.44-3.46 (1H, m), 3.47 (1H, dd), 3.63 (1H, t), 4.60-4.70 (1H, m), 4.79 (1H, br s), 8.28 (1H, s), 8.51 (1H, d); m/z (ES$^+$) [M+H]$^+$=357.

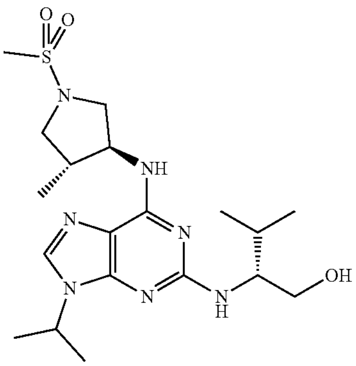 [SMILES: CC(C)[C@H](CO)Nc1nc(N[C@@H]2CN(S(C)(=O)=O)C[C@H]2C)c2ncn(C(C)C)c2n1]

Example 36

Intermediate 75: (3S,4R)-tert-butyl 3-(2-fluoro-9-isopropyl-9H-purin-6-ylamino)-4-methylpyrrolidine-1-carboxylate 6-Chloro-2-fluoro-9-isopropyl-9H-purine (Intermediate 36, 0.300 g, 1.40 mmol) was added to tert-butyl (3S,4R)-3-amino-4-methylpyrrolidine-1-carboxylate (0.308 g, 1.54 mmol) and DIEA (0.732 mL, 4.19 mmol) in MeCN (5 mL) at 20° C. The resulting mixture was stirred at 80° C. for 1 day. The reaction was concentrated and the residue was purified by preparative TLC (EtOAc:petroleum ether=1:1) to afford tert-butyl (3S,4R)-3-((2-fluoro-9-isopropyl-9H-purin-6-yl)amino)-4-methylpyrrolidine-1-carboxylate (Intermediate 75, 0.300 g, 56.7%) as a white gum. m/z (ES$^+$) [M+H]$^+$=379.

Intermediate 76: 2-fluoro-9-isopropyl-N-((3S,4R)-4-methylpyrrolidin-3-yl)-9H-purin-6-amine hydrochloride tert-Butyl (3S,4R)-3-((2-fluoro-9-isopropyl-9H-purin-6-yl)amino)-4-methylpyrrolidine-1-carboxylate (Intermediate 75, 0.280 g, 0.74 mmol) was added to HCl in 1,4-dioxane (15 mL, 4 M) at 20° C. The resulting mixture was stirred at 20° C. for 1 day. The solvent was evaporated to afford crude product 2-fluoro-9-isopropyl-N-((3S,4R)-4-methylpyrrolidin-3-yl)-9H-purin-6-amine. HCl (Intermediate 76, 0.100 g, 43.0%). m/z (ES$^+$) [M+H]$^+$=279.

Example 36: (R)-2-((9-isopropyl-6-(((3S,4R)-4-methyl-1-(methylsulfonyl)-pyrrolidin-3-yl)amino)-9H-purin-2-yl)amino)-3-methylbutan-1-ol

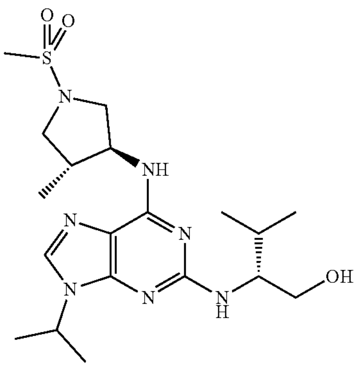

2-Fluoro-9-isopropyl-N-((3S,4R)-4-methyl-1-(methylsulfonyl)pyrrolidin-3-yl)-9H-purin-6-amine (Intermediate 77, 0.050 g, 0.14 mmol) was added to (R)-2-amino-3-methylbutan-1-ol (0.072 g, 0.70 mmol) and DIEA (0.123 mL, 0.70 mmol) in NMP (2 mL) at 25° C. The resulting mixture was stirred at 120° C. for 1 day. The reaction was concentrated and the residue was purified by preparative HPLC, Column: XBridge Shield RP18 OBD Column, 30*150 mm, 5 μm; Mobile Phase A: Water (0.05% $NH_3H_2O$), Mobile Phase B: MeOH; Flow rate: 60 mL/min; Gradient: 48 B to 50 B in 7 min. Fractions containing the desired compound were evaporated to dryness to afford (R)-2-((9-isopropyl-6-(((3S,4R)-4-methyl-1-(methylsulfonyl)pyrrolidin-3-yl)amino)-9H-purin-2-yl)amino)-3-methylbutan-1-ol (Example 36, 0.022 g, 35.2%). $^1$H NMR (300 MHz, DMSO-$d_6$) 0.90 (6H, dd), 1.03 (3H, d), 1.47 (6H, dd), 1.90-2.00 (1H, m), 2.27-2.48 (1H, m), 2.89-2.93 (1H, m), 2.94 (3H, s), 3.05-3.17 (1H, m), 3.45-3.70 (4H, m), 3.78-3.87 (1H, m), 4.33-4.59 (3H, m), 5.83 (1H, br s), 7.42 (1H, br s), 7.83 (1H, s); m/z (ES$^+$) [M+H]$^+$=440.

Example 37: (2R,3S)-3-((9-isopropyl-6-(((3S,5R)-5-methyl-1-(methylsulfonyl)-pyrrolidin-3-yl)amino)-9H-purin-2-yl)amino)pentan-2-ol

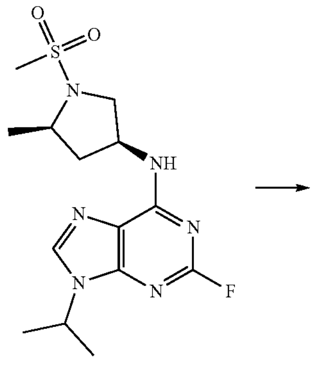

Intermediate 71

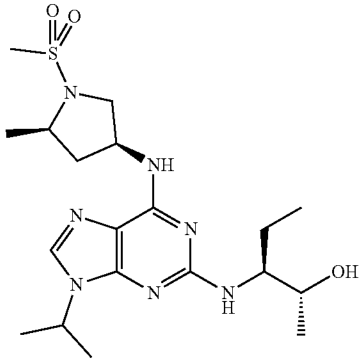

Example 37

2-Fluoro-9-isopropyl-N-((3S,5R)-5-methyl-1-(methylsulfonyl)pyrrolidin-3-yl)-9H-purin-6-amine (Intermediate 71, 60.0 mg, 0.17 mmol) was added to DIEA (147 μl, 0.84 mmol) and (2R,3S)-3-aminopentan-2-ol hydrochloride (118 mg, 0.84 mmol) in NMP (2 mL) at 20° C. The resulting mixture was stirred at 140° C. for 2 days. The reaction mixture was purified by preparative Column: XBridge Shield RP18 OBD Column, 30*150 mm, 5 μm; Mobile Phase A: Water (0.05% $NH_3H_2O$), Mobile Phase B: ACN; Flow rate: 60 mL/min; Gradient: 45 B to 60 B in 7 min. Fractions containing the desired compound were evaporated to dryness to afford (2R,3S)-3-((9-isopropyl-6-(((3S,5R)-5-methyl-1-(methylsulfonyl)pyrrolidin-3-yl)amino)-9H-purin-2-yl)amino)pentan-2-ol (Example 37, 0.040 g, 54.1%). $^1$H NMR (400 MHZ, DMSO-$d_6$) 0.86 (3H, t), 1.06 (3H, d), 1.30 (3H, d), 1.37-1.50 (7H, m, overlapped), 1.63-1.81 (2H, m), 2.41-2.48 (1H, m), 2.98 (3H, br s), 3.07-3.18 (1H, m), 3.61-3.69 (1H, m), 3.74-3.84 (3H, m), 4.40-4.62 (2H, m), 4.68 (1H, br s), 5.97 (1H, br s), 7.39 (1H, br s), 7.82 (1H, br s) m/z (ES$^+$) [M+H]$^+$=440.

Example 38: (R)-2-((9-ethyl-6-(((S)-1-(methylsulfonyl)pyrrolidin-3-yl)amino)-9H-purin-2-yl)amino)butan-1-ol

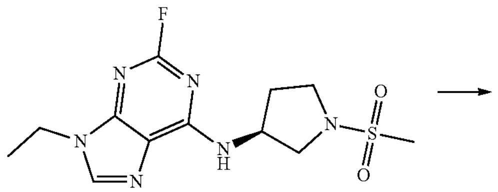

Intermediate 55

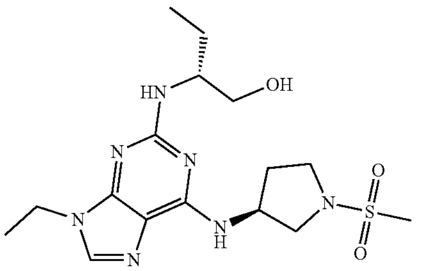

Example 38

DIEA (0.532 mL, 3.05 mmol) was added to (S)-9-ethyl-2-fluoro-N-(1-(methylsulfonyl)pyrrolidin-3-yl)-9H-purin-6-amine (Intermediate 55, 100 mg, 0.30 mmol) and (R)-2-aminobutan-1-ol (136 mg, 1.52 mmol) in NMP (3 mL) under nitrogen. The resulting mixture was stirred at 140° C. for 4 days. The reaction was concentrated and the crude product was purified by preparative Column: XBridge Shield RP18 OBD Column, 30*150 mm, 5 μm; Mobile Phase A: Water (0.05% $NH_3H_2O$), Mobile Phase B: ACN; Flow rate: 60 mL/min; Gradient: 17 B to 37 B in 7 min. Fractions containing the desired compound were evaporated to dryness to afford (R)-2-((9-ethyl-6-(((S)-1-(methylsulfonyl)pyrrolidin-3-yl)amino)-9H-purin-2-yl)amino)butan-1-ol (Example 38, 45.0 mg, 37.2%). $^1$H NMR (400 MHZ, DMSO-$d_6$) 0.88 (3H, t), 1.34 (3H, t), 1.39-1.51 (1H, m), 1.57-1.70 (1H, m), 2.00-2.11 (1H, m), 2.13-2.24 (1H, m), 2.90 (3H, s), 3.15-3.24 (2H, m), 3.35-3.64 (4H, m, overlapped), 3.82 (1H, d), 4.02 (2H, q), 4.57 (1H, s), 4.68 (1H, br s), 5.94 (1H, br s), 7.44 (1H, br s), 7.75 (1H, s); m/z (ES$^+$) [M+H]$^+$=398.

Example 39: (R)-2-cyclopropyl-2-((9-ethyl-6-(((S)-1-(methylsulfonyl)pyrrolidin-3-yl)amino)-9H-purin-2-yl)amino)ethanol

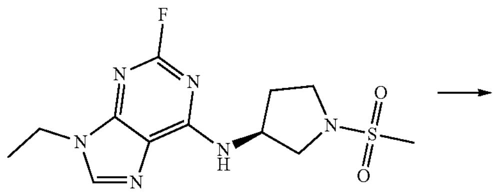

Intermediate 55

-continued

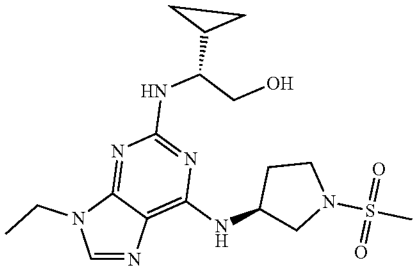

Example 39

(S)-9-ethyl-2-fluoro-N-(1-(methylsulfonyl)pyrrolidin-3-yl)-9H-purin-6-amine (5.60 g, 17.05 mmol) was added to (R)-2-amino-2-cyclopropylethan-1-ol hydrochloride (Intermediate 55, 11.73 g, 85.27 mmol) and DIEA (29.8 ml, 170.54 mmol) in DMSO (6 mL). The resulting mixture was stirred at 140° C. for 2 days. The reaction was concentrated and the crude product was purified by preparative SFC, Column: GreenSep Basic, 30*150 mm 5 μm; Mobile Phase A: $CO_2$, Mobile Phase B: MeOH (0.5% 2M $NH_3$-MeOH); Flow rate: 50 mL/min; Gradient: 30% B. Fractions containing the desired compound were evaporated to dryness to afford (R)-2-cyclopropyl-2-((9-ethyl-6-(((S)-1-(methylsulfonyl)pyrrolidin-3-yl)amino)-9H-purin-2-yl)amino)ethan-1-ol (Example 39, 3.30 g, 47.3%). $^1$H NMR (300 MHz, DMSO-$d_6$) 0.19-0.45 (4H, m), 0.94-1.07 (1H, m), 1.34 (3H, t), 1.98-2.26 (2H, m), 2.91 (3H, s), 3.20 (1H, dd), 3.27-3.35 (1H, m), 3.44-3.53 (2H, m), 3.53-3.61 (3H, m), 3.99 (2H, q), 4.63 (1H, t), 4.70 (1H, br s), 5.99 (1H, br d), 7.42 (1H, s), 7.75 (1H, s); m/z (ES$^+$) [M+H]*=410.

Example 40: (R)-2-((9-ethyl-6-(((S)-1-(2,2,2-trifluoroethylsulfonyl)pyrrolidin-3-yl)amino)-9H-purin-2-yl)amino)-3-methylbutan-1-ol

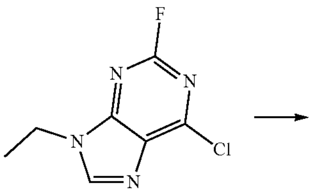

Intermediate 8

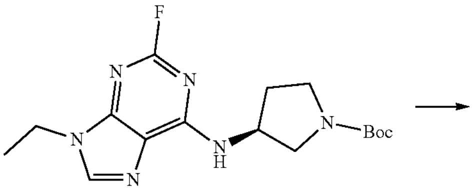

Intermediate 9

-continued

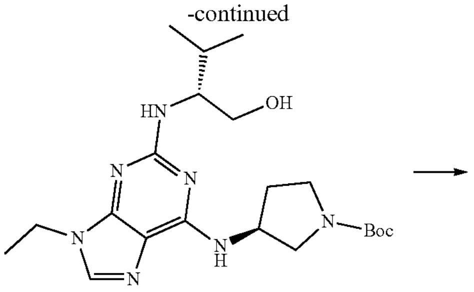

Intermediate 78

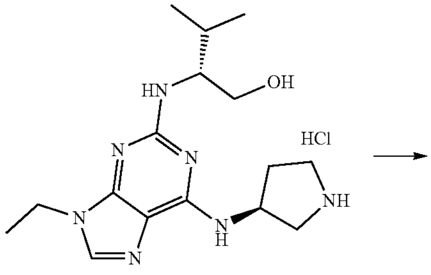

Intermediate 79

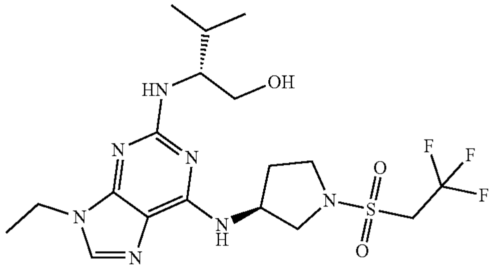

Example 40

Intermediate 9: (S)-tert-butyl 3-(9-ethyl-2-fluoro-9H-purin-6-ylamino)pyrrolidine-1-carboxylate DIEA (5.75 ml, 32.90 mmol) was added to 6-chloro-9-ethyl-2-fluoro-9H-purine (Intermediate 8, 2.200 g, 10.97 mmol) and tert-butyl (S)-3-aminopyrrolidine-1-carboxylate (2.043 g, 10.97 mmol) in IPA (20 mL). The resulting mixture was stirred at 100° C. for 16 hours. The solvent was removed under reduced pressure. The crude product was purified by flash silica chromatography, elution gradient 0 to 100% EtOAc in petroleum ether. Pure fractions were evaporated to dryness to afford tert-butyl (S)-3-((9-ethyl-2-fluoro-9H-purin-6-yl)amino)pyrrolidine-1-carboxylate (Intermediate 9, 3.00 g, 78%) as a white solid. $^1$H NMR (300 MHz, DMSO-$d_6$) 1.40-1.33 (12H, m), 1.97 (1H, br s), 2.12 (1H, br s), 3.19-3.24 (2H, m, overlapped), 3.39-3.47 (1H, m), 3.54-3.60 (1H, m), 4.10 (2H, q), 4.57 (1H, br s), 8.16 (1H, s), 8.46 (1H, br s); m/z (ES$^+$) $[M+H]^+$=351.

Intermediate 78: (S)-tert-butyl 3-(9-ethyl-2-((R)-1-hydroxy-3-methylbutan-2-yl-amino)-9H-purin-6-ylamino)pyrrolidine-1-carboxylate tert-Butyl (S)-3-((9-ethyl-2-fluoro-9H-purin-6-yl)amino)pyrrolidine-1-carboxylate (Intermediate 9, 1.200 g, 3.42 mmol) was added to (R)-2-amino-3-methylbutan-1-ol (3.89 g, 37.67 mmol) in NMP (0.5 mL) at 20° C. The resulting mixture was stirred at 100° C. for 16 hours. The reaction mixture was diluted with DCM (300 mL), and washed sequentially with water (200 mL×3). The organic layer was dried over $Na_2SO_4$, filtered and evaporated to afford crude product. The product tert-butyl (S)-3-((9-ethyl-2-(((R)-1-hydroxy-3-methylbutan-2-yl)amino)-9H-purin-6-yl)amino) pyrrolidine-1-carboxylate (Intermediate 78, 1.200 g, 81%) was used in the next step directly without further purification. $^1$H NMR (400 MHz, DMSO-$d_6$) 0.88-0.92 (6H, m), 1.32-1.42 (12H, m), 1.90-2.04 (2H, m), 2.07-2.13 (1H, m), 3.14-3.28 (2H, m), 3.40-3.53 (3H, m), 3.55-3.63 (1H, m), 3.78-3.86 (1H, m), 3.93-4.04 (2H, m), 4.45 (1H, s), 4.55 (1H, br s), 5.78 (1H, br s), 7.36 (1H, br s), 7.73 (1H, s); m/z (ES$^+$) [M+H]$^+$=434.

Intermediate 79: (R)-2-(9-ethyl-6-((S)-pyrrolidin-3-ylamino)-9H-purin-2-yl-amino)-3-methylbutan-1-ol hydrochloride tert-Butyl (S)-3-((9-ethyl-2-(((R)-1-hydroxy-3-methylbutan-2-yl)amino)-9H-purin-6-yl)amino)pyrrolidine-1-carboxylate (Intermediate 78, 1.200 g, 2.77 mmol) was added to HCl in dioxane (20 mL, 4 M) at 20° C. The resulting mixture was stirred at 20° C. for 16 hours. The reaction mixture was evaporated to afford crude product. The product (R)-2-((9-ethyl-6-(((S)-pyrrolidin-3-yl)amino)-9H-purin-2-yl)amino)-3-methylbutan-1-ol. HCl (Intermediate 79, 0.800 g, 78%) as a solid was used in the next step directly without further purification. m/z (ES$^+$) [M+H]$^+$=334.

Example 40: (R)-2-((9-ethyl-6-(((S)-1-(2,2,2-trifluoroethylsulfonyl)pyrrolidin-3-yl)amino)-9H-purin-2-yl)amino)-3-methylbutan-1-ol

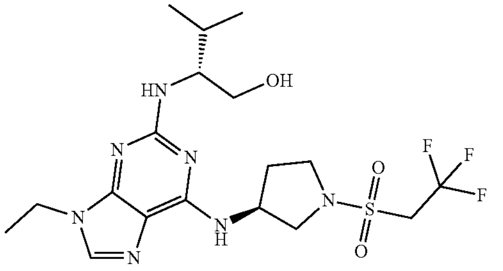 [SMILES: CCn1cnc2c(N[C@H]3CCN(S(=O)(=O)CC(F)(F)F)C3)nc(N[C@@H](CO)C(C)C)nc21]

(R)-2-((9-ethyl-6-(((S)-pyrrolidin-3-yl)amino)-9H-purin-2-yl)amino)-3-methylbutan-1-ol. HCl (Intermediate 79, 150 mg, 0.41 mmol) was added to 2,2,2-trifluoroethane-1-sulfonyl chloride (74 mg, 0.41 mmol) and TEA (170 µl, 1.22 mmol) in DCM (1 mL) at −20° C. The resulting mixture was stirred at −20° C. for 2 hours. The reaction was concentrated and the crude product was purified by preparative HPLC, Column: Sunfire prep C18 column, 30*150, 5 µm; Mobile Phase A: Water (0.1% FA), Mobile Phase B: ACN; Flow rate: 60 mL/min; Gradient: 20 B to 42 B in 7 min. Fractions containing the desired compound were evaporated to dryness to afford (R)-2-((9-ethyl-6-(((S)-1-((2,2,2-trifluoroethyl)sulfonyl)pyrrolidin-3-yl)amino)-9H-purin-2-yl) amino)-3-methylbutan-1-ol (Example 40, 10.00 mg, 5.14%). $^1$H NMR (400 MHZ, DMSO-$d_6$) 0.89-0.92 (6H, m), 1.35 (3H, t), 1.93-1.99 (1H, m), 2.03-2.10 (1H, m), 2.17-2.24 (1H, m), 3.37-3.61 (5H, m), 3.72 (1H, dd), 3.81-3.87 (1H, m), 4.00 (2H, q), 4.49-4.62 (3H, m), 4.71-4.80 (1H, m), 5.87 (1H, br s), 7.47 (1H, br s), 7.76 (1H, s); 19F NMR (376 MHz, DMSO-$d_6$)-60.04; m/z (ES$^+$) [M+H]$^+$=480.

Example 41: (R)-2-((6-(((S)-1-(cyclopropylsulfonyl) pyrrolidin-3-yl)amino)-9-ethyl-9H-purin-2-yl) amino)-3-methylbutan-1-ol

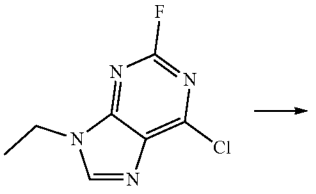

Intermediate 8

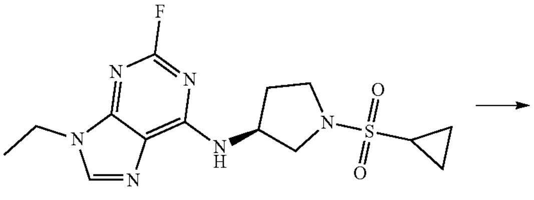

Intermediate 80

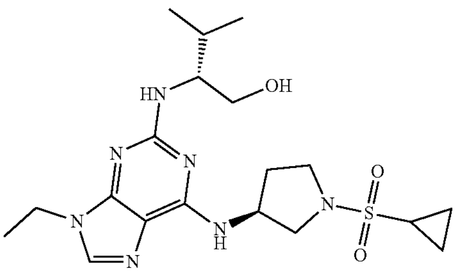

Example 41

Intermediate 80: (S)—N-(1-(cyclopropylsulfonyl) pyrrolidin-3-yl)-9-ethyl-2-fluoro-9H-purin-6-amine DIEA (0.918 mL, 5.26 mmol) was added to 6-chloro-9-ethyl-2-fluoro-9H-purine (Intermediate 8, 300 mg, 1.50 mmol) and (S)-1-(cyclopropylsulfonyl)pyrrolidin-3-amine (0.2 g, 1.05 mmol) in iPrOH (5 mL). The resulting mixture was stirred at 100° C. for 2 hours. The reaction mixture was concentrated under reduced pressure and purified by flash C18 chromatography, elution gradient 20 to 50% MeCN in water (0.1% $NH_4HCO_3$). Pure fractions were evaporated to dryness to afford (S)—N-(1-(cyclopropylsulfonyl)pyrrolidin-3-yl)-9-ethyl-2-fluoro-9H-purin-6-amine (Intermediate 80, 300 mg, 81%) as a brown gum. m/z (ES$^+$) [M+H]+=355.

Example 41: (R)-2-((6-(((S)-1-(cyclopropylsulfonyl) pyrrolidin-3-yl)amino)-9-ethyl-9H-purin-2-yl) amino)-3-methylbutan-1-ol

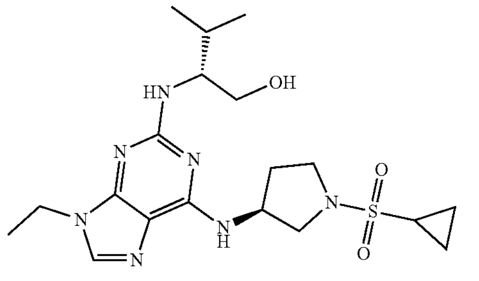 [SMILES: CCn1cnc2c(N[C@H]3CCN(S(=O)(=O)C4CC4)C3)nc(N[C@@H](CO)C(C)C)nc21]

(R)-2-amino-3-methylbutan-1-ol (0.2 mL, 1.80 mmol) was added to (S)—N-(1-(cyclopropylsulfonyl)pyrrolidin-3-yl)-9-ethyl-2-fluoro-9H-purin-6-amine (Intermediate 80, 0.1 g, 0.28 mmol) in NMP (0.5 mL). The resulting mixture was stirred at 120° C. for 16 hours. The reaction mixture was diluted with DCM (50 mL), and washed sequentially with saturated aq. $Na_2CO_3$ solution (50 mL) and saturated brine (50 mL). The organic layer was dried over $Na_2SO_4$, filtered and evaporated to afford crude product. The crude product was purified by preparative HPLC, Column: XBridge Shield RP18 OBD Column, 30*150 mm, 5 μm; Mobile Phase A: Water (0.05% $NH_3H_2O$), Mobile Phase B: ACN; Flow rate: 60 mL/min; Gradient: 25 B to 40 B in 7 min followed by preparative chiral-HPLC, Column: CHIRALPAK IA, 2*25 cm, 5 μm; Mobile Phase A:Hex:DCM=3:1 (10 mM $NH_3$-MeOH), Mobile Phase B: IPA-HPLC; Flow rate: 20 mL/min; Gradient: 10 B to 10 B in 12 min. The fractions containing the desired compound were evaporated to dryness to afford (R)-2-((6-(((S)-1-(cyclopropylsulfonyl)pyrrolidin-3-yl)amino)-9-ethyl-9H-purin-2-yl)amino)-3-methylbutan-1-ol (Example 41, 0.012 g, 9.72%). $^1H$ NMR (400 MHz, DMSO-$d_6$) 0.86-1.02 (10H, m), 1.34 (3H, t), 1.89-2.02 (1H, m), 2.00-2.13 (1H, m), 2.15-2.28 (1H, m), 2.64-2.75 (1H, m), 3.23-3.32 (1H, m), 3.32-3.40 (1H, m), 3.45-3.58 (3H, m), 3.60-3.69 (1H, m), 3.79-3.87 (1H, m), 4.04 (2H, q), 4.49 (1H, s), 4.68 (1H, br s), 5.86 (1H, br s), 7.43 (1H, br s), 7.74 (1H, s); m/z (ES+) $[M+H]^+$=438.

Example 42: (R)-2-((9-ethyl-6-(((S)-1-((2-methoxyethyl)sulfonyl)pyrrolidin-3-yl)-amino)-9H-purin-2-yl)amino)-3-methylbutan-1-ol

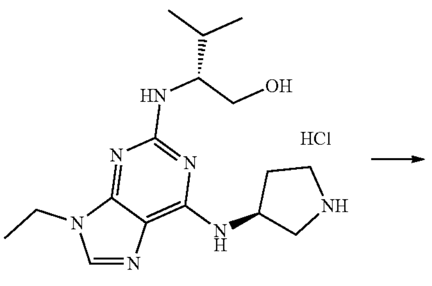

Intermediate 79

-continued

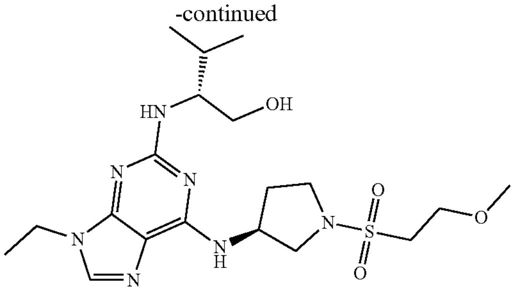

Example 42

(R)-2-((9-ethyl-6-(((S)-pyrrolidin-3-yl)amino)-9H-purin-2-yl)amino)-3-methylbutan-1-ol hydrochloride (Intermediate 79, 60 mg, 0.18 mmol) was added to 2-methoxyethane-1-sulfonyl chloride (14.27 mg, 0.09 mmol) and TEA (0.050 mL, 0.36 mmol) in DCM (5 mL). The resulting mixture was stirred at rt for 4 hours. The solvent was removed under reduced pressure. The crude product was purified by preparative HPLC, Column: XBridge Shield RP18 OBD Column, 19*250 mm, 10 μm; Mobile Phase A: Water (10 mmol/L $NH_4HCO_3$+0.1% $NH_3 \cdot H_2O$), Mobile Phase B: ACN; Flow rate: 20 mL/min; Gradient: 43 B to 48 B in 7 min. Fractions containing the desired compound were evaporated to dryness to afford (R)-2-((9-ethyl-6-(((S)-1-((2-methoxyethyl)sulfonyl)pyrrolidin-3-yl)amino)-9H-purin-2-yl)amino)-3-methylbutan-1-ol (Example 42, 20.67 mg, 25.2%). $^1H$ NMR (400 MHZ, DMSO-$d_6$) 0.89 (6H, dd), 1.34 (3H, t), 1.88-2.08 (2H, m), 2.11-2.24 (1H, m), 3.22 (1H, dd), 3.28 (3H, s), 3.34-3.41 (3H, m), 3.47 (3H, d), 3.56-3.70 (3H, m), 3.76-3.90 (1H, m), 3.99 (2H, q), 4.49 (1H, s), 4.68 (1H, br s), 5.71-5.96 (1H, m), 7.38 (1H, br s), 7.74 (1H, s); m/z (ES+) $[M+H]^+$=456.

Example 43: (R)-2-((9-ethyl-6-(((S)-1-(fluoromethylsulfonyl)pyrrolidin-3-yl)-amino)-9H-purin-2-yl) amino)-3-methylbutan-1-ol

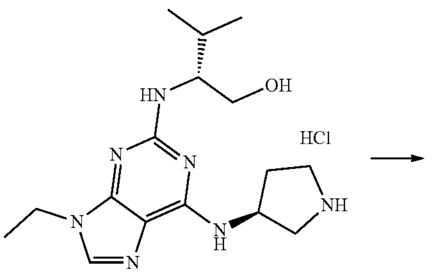

Intermediate 79

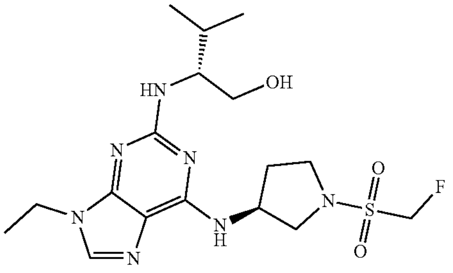

Example 43

Fluoromethanesulfonyl chloride (31.8 mg, 0.24 mmol) was added dropwise to (R)-2-((9-ethyl-6-(((S)-pyrrolidin-3-yl)amino)-9H-purin-2-yl)amino)-3-methylbutan-1-ol hydrochloride (Intermediate 79, 80 mg, 0.24 mmol) and TEA (100 μl, 0.72 mmol) in DCM (1 mL) at 20° C. The resulting mixture was stirred at −20° C. for 75 minutes. The solvent was removed under reduced pressure. The crude product was purified by preparative HPLC, Column: XBridge Prep OBD C18 Column, 30×150 mm 5 μm; Mobile Phase A: Water (10 mmol/L $NH_4HCO_3$+0.1% $NH_3{\cdot}H_2O$), Mobile Phase B: ACN; Flow rate: 60 mL/min; Gradient: 23 B to 30 B in 7 min. Fractions containing the desired compound were evaporated to dryness to afford (R)-2-((9-ethyl-6-(((S)-1-((fluoromethyl)sulfonyl)pyrrolidin-3-yl)amino)-9H-purin-2-yl)amino)-3-methylbutan-1-ol (Example 43, 0.055 g, 53.4%). $^1$H NMR (400 MHZ, DMSO-$d_6$) 0.86-0.94 (6H, m), 1.34 (3H, t), 1.91-2.00 (1H, m), 2.07 (1H, br s), 2.17-2.27 (1H, m), 3.26-3.37 (1H, m), 3.39-3.52 (3H, m), 3.55-3.63 (1H, m), 3.70-3.78 (1H, m), 3.82 (1H, t), 3.98 (2H, q), 4.47 (1H, s), 4.73 (1H, br s), 5.53 (1H, s), 5.65 (1H, s), 5.84 (1H, br s), 7.44 (1H, br s), 7.74 (1H, s); 19F NMR (376 MHz, DMSO-$d_6$)-214.373; m/z (ES$^+$) [M+H]$^+$=430.

Example 44: (S)-3-((9-ethyl-2-(((2R,3S)-2-hydroxypentan-3-yl)amino)-9H-purin-6-yl)amino)-N-methylpyrrolidine-1-sulfonamide

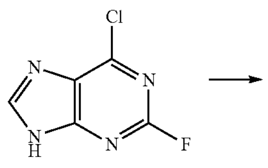

Intermediate 7

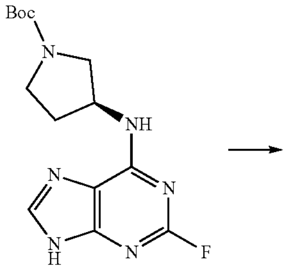

Intermediate 81

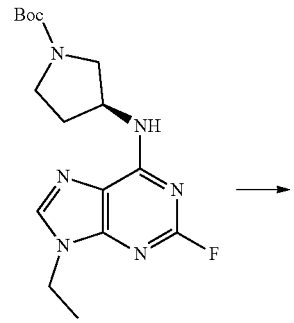

Intermediate 9

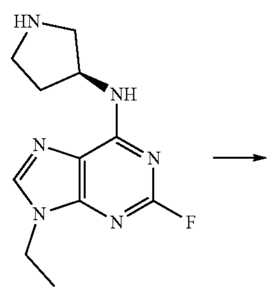

Intermediate 82

-continued

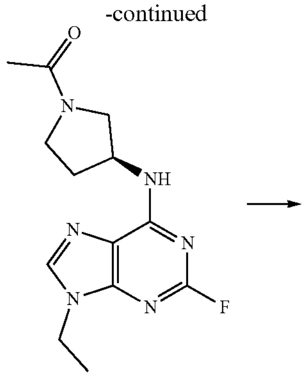

Intermediate 83

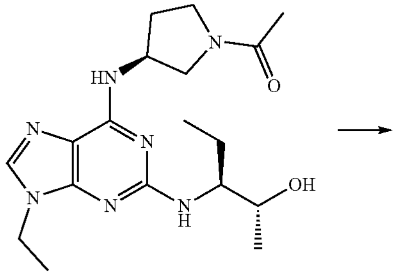

Intermediate 84

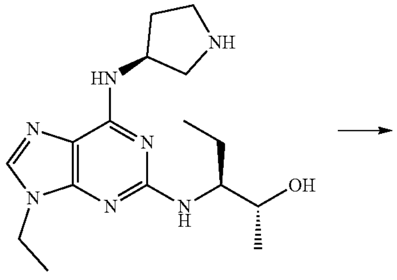

Intermediate 11

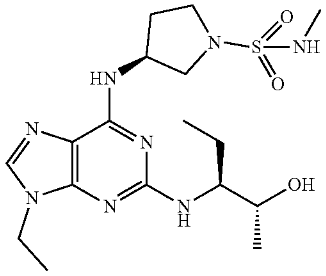

Example 44

Intermediate 81: (S)-tert-butyl 3-(2-fluoro-9H-purin-6-ylamino)pyrrolidine-1-carboxylate 6-Chloro-2-fluoro-9H-purine (Intermediate 7, 50 g, 289.78 mmol) was dissolved in tert-amyl alcohol (1200 mL) at rt under nitrogen and then heated to 100° C. (Solution 1). In a separated vessel was added tert-butyl (S)-3-aminopyrrolidine-1-carboxylate (59.4 g, 318.75 mmol), DIEA (55.7 ml, 318.75 mmol) and tert-amyl alcohol (100 mL) at room temperature under nitrogen (Solution 2). Solution 2 was added dropwise to solution 1 and reaction mixture heated at 100° C. for 90 minutes. LCMS after 1 h indicated reaction complete, displacement Cl:F 13:1. The mixture was poured into ice water (2 L) and the aqueous phase was extracted with EtOAc (2×1 L) and the organic phase was washed with $Na_2SO_4$, filtered and evaporated to give tert-butyl (S)-3-((2-fluoro-9H-purin-6-yl)amino)pyrrolidine-1-carboxylate (Intermediate 81, 105 g, 91%) as a yellow solid. $^1$H NMR (300 MHz, DMSO-$d_6$) 1.41 (9H, s), 1.91-2.07 (1H, m), 2.11-2.29 (1H, m), 3.15-3.73 (5H, m), 8.12 (1H, s), 8.39 (1H, s), 10.39 (1H, br s); (ES$^+$) [M+H]$^+$=323.

Intermediate 9: (S)-tert-butyl 3-(9-ethyl-2-fluoro-9H-purin-6-ylamino)pyrrolidine-1-carboxylate Iodoethane (22.34 ml, 276.41 mmol) was added dropwise to tert-butyl (S)-3-((2-fluoro-9H-purin-6-yl)amino)pyrrolidine-1-carboxylate (Intermediate 81, 100 g, 251.29 mmol, 81% wt) in DMSO (1500 mL) at room temperature. The resulting mixture was stirred at 25° C. for 16 hours. The reaction mixture was poured into ice water. The precipitate was collected by filtration, washed with water and dried under vacuum to afford crude product. The crude product was triturated with MeCN to afford tert-butyl (S)-3-((9-ethyl-2-fluoro-9H-purin-6-yl)amino)pyrrolidine-1-carboxylate (Intermediate 9, 60.0 g, 68%) as a pale yellow solid. $^1$H NMR (400 MHZ, DMSO-$d_6$) 1.32-1.47 (12H, m), 1.90-2.07 (1H, m), 2.08-2.23 (1H, m), 3.16-3.30 (2H, m), 3.38-3.53 (1H, m), 3.55-3.68 (1H, m), 4.13 (2H, q), 4.51-5.30 (1H, m), 8.19 (1H, s), 8.35-8.61 (1H, m); (ES$^+$) [M+H]$^+$=351.

Intermediate 82: (S)-9-ethyl-2-fluoro-N-(pyrrolidin-3-yl)-9H-purin-6-amine hydrochloride tert-Butyl (S)-3-((9-ethyl-2-fluoro-9H-purin-6-yl)amino) pyrrolidine-1-carboxylate (Intermediate 9, 54 g, 154.11 mmol) was added to HCl in 1,4-dioxane (385 ml, 1540.76 mmol, 4 M). The resulting mixture was stirred at 25° C. for 6 hours. The solid formed was collected and washed with MTBE and air dried to give (S)-9-ethyl-2-fluoro-N-(pyrrolidin-3-yl)-9H-purin-6-amine hydrochloride (Intermediate 82, 50.0 g, 100%) as a white solid. (ES$^+$) [M+H]$^+$=251.

Intermediate 83: (S)-1-(3-(9-ethyl-2-fluoro-9H-purin-6-ylamino)pyrrolidin-1-yl)-ethanone $Ac_2O$ (19.70 ml, 208.85 mmol) was added dropwise to (S)-9-ethyl-2-fluoro-N-(pyrrolidin-3-yl)-9H-purin-6-amine hydrochloride (Intermediate 82, 50 g, 139.23 mmol), and TEA (77.6 ml, 556.93 mmol) in DCM (1000 mL) at 0° C. The resulting mixture was stirred at 25° C. for 12 hours. The mixture was poured into saturated aq. $NH_4Cl$ solution (2 L) and the aqueous phase was extracted with DCM (2×1 L). The organic phase was washed with saturated aq. $NaHCO_3$ solution, saturated aq. brine solution then dried over $Na_2SO_4$, filtered and evaporated to give (S)-1-(3-((9-ethyl-2-fluoro-9H-purin-6-yl)amino)pyrrolidin-1-yl)ethan-1-one (Intermediate 83, 39.0 g, 95%) as a light yellow solid. 1H (300 MHZ, DMSO-$d_6$) 1.36 (3H, t), 1.90-2.26 (5H, m), 3.25-3.55 (2H, m), 3.58-3.85 (2H, m), 4.12 (2H, q), 4.54-5.36 (1H, m), 8.18 (1H, s), 8.36-8.65 (1H, m); (ES$^+$) [M+H]$^+$=293.

Intermediate 84: 1-((S)-3-(9-ethyl-2-((2R,3S)-2-hydroxypentan-3-ylamino)-9H-purin-6-ylamino) pyrrolidin-1-yl)ethanone 28 g of Intermediate 83 was divided equally into 4 portions. In each portion, DIEA (25.09 ml, 143.68 mmol) was added to (S)-1-(3-((9-ethyl-2-fluoro-9H-purin-6-yl) amino)pyrrolidin-1-yl)ethan-1-one (Intermediate 83, 7 g, 23.95 mmol), (2R,3S)-3-aminopentan-2-ol hydrochloride (6.69 g, 47.89 mmol) and lithium chloride (2.030 g, 47.89 mmol) in 3-ethyl-3-pentanol (50 mL) and stirred at rt for 20 mins. The resulting mixture was stirred at 160° C. for 96 hours. The 4 batches were combined together. The reaction mixture was poured into DCM/MeOH (10:1) (2.5 L), washed with saturated aq. $NH_4Cl$ solution (300 mL×1), the organic layer was dried over $Na_2SO_4$, filtered, and evaporated to afford crude product. The crude product was purified by flash silica chromatography, elution gradient 0 to 8% MeOH in DCM. Pure fractions were evaporated to dryness to afford 1-((S)-3-((9-ethyl-2-(((2R,3S)-2-hydroxypentan-3-yl)amino)-9H-purin-6-yl)amino)pyrrolidin-1-yl)ethan-1-one (Intermediate 84, 26.0 g, 72.2%) as a brown oil. m/z (ES$^+$) [M+H]$^+$=376.

Intermediate 11: (2R,3S)-3-(9-ethyl-6-((S)-pyrrolidin-3-ylamino)-9H-purin-2-yl-amino)pentan-2-ol hydrochloride 1-((S)-3-((9-ethyl-2-(((2R,3S)-2-hydroxypentan-3-yl) amino)-9H-purin-6-yl)amino)-pyrrolidin-1-yl)ethan-1-one (Intermediate 84, 30 g, 79.91 mmol) was added to LiOH (22.97 g, 958.79 mmol) in EtOH:$H_2O$=1:1 (300 mL). The resulting mixture was stirred at 80° C. for 16 hours. The solvent was removed under reduced pressure. The crude product was purified by flash silica chromatography, elution gradient 0 to 10% MeOH ($NH_3$) in DCM. Pure fractions were evaporated to dryness to afford (2R,3S)-3-((9-ethyl-6-(((S)-pyrrolidin-3-yl)amino)-9H-purin-2-yl)amino)pentan-2-ol (Intermediate 11, 14.50 g, 54.4%) as a pale yellow solid. 1H (300 MHz, DMSO-$d_6$) 0.87 (3H, t), 1.06 (3H, d), 1.34 (3H, t), 1.38-1.49 (1H, m), 1.69 (2H, ddt), 2.02 (1H, dtd), 2.65-2.80 (2H, m), 2.96 (2H, ddd), 3.63-3.68 (1H, m), 3.76-3.80 (1H, m), 3.98 (2H, q), 4.57 (1H, s), 5.82-6.00 (1H, m), 7.08 (1H, s), 7.70 (1H, s), two exchangeable protons were not observed; m/z (ES$^+$) [M+H]$^+$=334.

Example 44: (S)-3-((9-ethyl-2-(((2R,3S)-2-hydroxypentan-3-yl)amino)-9H-purin-6-yl)-amino)-N-methylpyrrolidine-1-sulfonamide

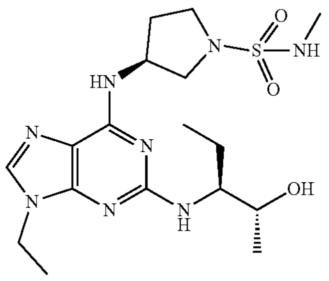 [SMILES: CC[C@H](Nc1nc(N[C@H]2CCN(S(=O)(=O)NC)C2)c2ncn(CC)c2n1)[C@@H](C)O]

Methylsulfamoyl chloride (0.474 g, 3.6 mmol) was added to (2R,3S)-3-((9-ethyl-6-(((S)-pyrrolidin-3-yl)amino)-9H-purin-2-yl)amino)pentan-2-ol (Intermediate 11, 1.2 g, 3.6 mmol) and TEA (1.50 ml, 10.8 mmol) in THF (48 mL). The resulting mixture was stirred at −78° C. for 30 minutes. The reaction mixture was quenched with saturated aq. $NH_4Cl$ solution (75 mL), extracted with DCM (3×75 mL), the organic layer was dried over $Na_2SO_4$, filtered and evaporated to afford pale yellow solid. The crude product was purified by flash silica chromatography, elution gradient 0 to 10% MeOH in DCM. Pure fractions were evaporated and re-purified by flash C18-flash chromatography, elution gradient 2 to 50% MeCN in water (0.1% $NH_4HCO_3$). Pure fractions were evaporated to dryness to afford (S)-3-((9-ethyl-2-(((2R,3S)-2-hydroxypentan-3-yl)amino)-9H-purin-6-yl)amino)-N-methylpyrrolidine-1-sulfonamide (Example 44, 0.760 g, 49.7%). $^1$H NMR (400 Hz, DMSO-$d_6$) 0.86 (3H, t), 1.06 (3H, d), 1.34 (3H, t), 1.38-1.46 (1H, m), 1.65-1.74 (1H, m), 2.01-2.10 (1H, m), 2.17-2.25 (1H, m), 2.55-2.56 (3H, m), 3.10-3.14 (1H, m), 3.20-3.26 (1H, m), 3.37-3.43 (1H, m), 3.53-3.57 (1H, m), 3.61-3.68 (1H, m), 3.74-3.81 (1H, m), 3.98 (2H, q), 4.65 (2H, br s), 5.99 (1H, br s), 7.00 (1H, s), 7.39 (1H, br s), 7.73 (1H, s); m/z (ES$^+$) [M+H]$^+$=427.

Example 45: (S)-3-((9-ethyl-2-(((S)-2-oxopentan-3-yl)amino)-9H-purin-6-yl)-amino)-N-methylpyrrolidine-1-sulfonamide

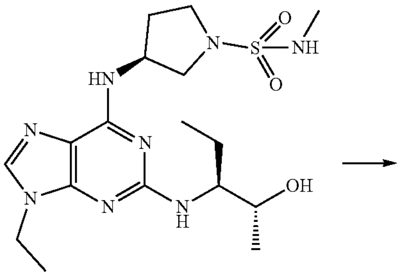

Example 44

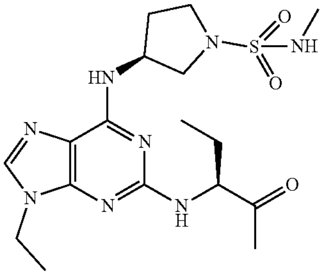

Example 45

Dess-Martin periodinane (497 mg, 1.17 mmol) was added to (S)-3-((9-ethyl-2-(((2R,3S)-2-hydroxypentan-3-yl)amino)-9H-purin-6-yl)amino)-N-methylpyrrolidine-1-sulfonamide (Example 44, 500 mg, 1.17 mmol) in THF (10 mL). The resulting mixture was stirred at 25° C. for 4 hours. The solvent was removed under reduced pressure. The residue was purified by preparative TLC (DCM:MeOH=30:1), to afford the crude product. The crude product was purified by preparative Column: Xselect CSH OBD Column 30*150 mm 5 μm, Mobile Phase A: Water (0.1% FA), Mobile Phase B: ACN; Flow rate: 60 mL/min, 5-35% ACN in water. Fractions containing the desired compound were evaporated to dryness to afford (S)-3-((9-ethyl-2-(((S)-2-oxopentan-3-yl)amino)-9H-purin-6-yl)amino)-N-methylpyrrolidine-1-sulfonamide (Example 45, 0.051 g, 10.25%). $^1$H NMR (400 MHZ, DMSO-$d_6$) 0.92 (3H, t), 1.33 (3H, t), 1.59-1.79 (2H, m), 1.95-2.04 (1H, m), 2.06 (3H, s), 2.16 (1H, br s), 2.55 (3H, d), 3.07-3.16 (1H, m), 3.17-3.27 (1H, m), 3.34-3.44 (1H, m), 3.47-3.56 (1H, m), 3.99 (2H, q), 4.06 (1H, br s), 4.57 (1H, br s), 6.82 (1H, br s), 7.01 (1H, q), 7.54 (1H, br s), 7.78 (1H, s); m/z (ES$^+$) [M+H]$^+$=425.

Example 46: (S)-3-((9-ethyl-2-(((S)-2-hydroxy-2-methylpentan-3-yl)amino)-9H-purin-6-yl)amino)-N-methylpyrrolidine-1-sulfonamide

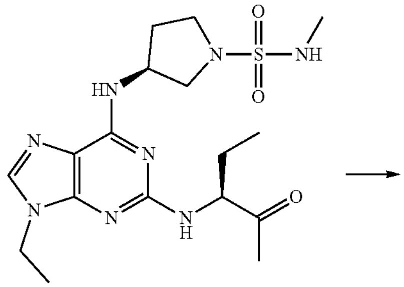

Example 45

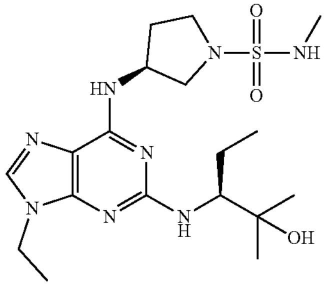

Example 46

Methyl magnesium bromide (1.413 mL, 3.53 mmol) was added to (S)-3-((9-ethyl-2-(((S)-2-oxopentan-3-yl)amino)-9H-purin-6-yl)amino)-N-methylpyrrolidine-1-sulfonamide (Example 45, 150 mg, 0.35 mmol) in THF (3 mL) cooled to 0° C. The resulting mixture was stirred at 0° C. for 5 hours. The reaction mixture was quenched with water (1 mL). The reaction mixture was diluted with DCM (200 mL), and washed sequentially with saturated aq. $NH_4Cl$ solution (250 mL×3) and saturated aq. brine solution (250 mL). The organic layer was dried over $Na_2SO_4$, filtered and evaporated to afford crude product. The crude product was purified by preparative HPLC, Column: Xselect CSH OBD Column 30*150 mm 5 μm; Mobile Phase A: Water (0.1% FA), Mobile Phase B: ACN; Flow rate: 60 mL/min, 12-25% ACN in water. Fractions containing the desired compound were evaporated to dryness to afford (S)-3-((9-ethyl-2-(((S)-2-hydroxy-2-methylpentan-3-yl)amino)-9H-purin-6-yl)amino)-N-methylpyrrolidine-1-sulfonamide (Example 46, 57.0 mg, 36.6%). $^1$H NMR (300 MHz, DMSO-$d_6$) 0.84 (3H, t), 1.08 (6H, d), 1.31-1.36 (4H, m, overlapped), 1.72-1.78 (1H, br m), 2.03-2.09 (1H, br m), 2.12-2.29 (1H, br m), 2.54 (3H, d), 3.06-3.17 (1H, m), 3.17-3.28 (2H, m), 3.50-3.62 (1H, m), 3.78-3.91 (1H, br m), 3.98 (2H, q), 4.32-4.90 (2H, br m), 5.85 (1H, br s), 7.00 (1H, q), 7.40 (1H, br s), 7.73 (1H, s); m/z (ES$^+$) [M+H]$^+$=441.

Example 47: (S)-3-((9-ethyl-2-(((S)-2-hydroxy-2-methylpentan-3-yl)amino)-9H-purin-6-yl)amino)-N-methylpyrrolidine-1-sulfonamide

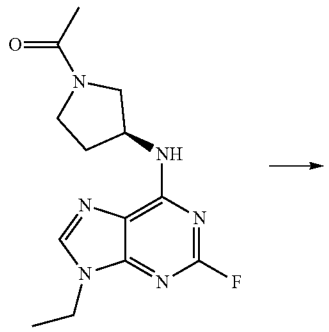

Intermediate 83

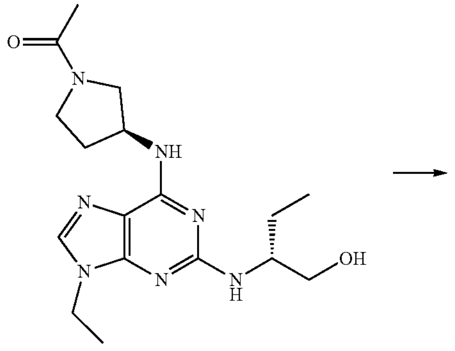

Intermediate 85

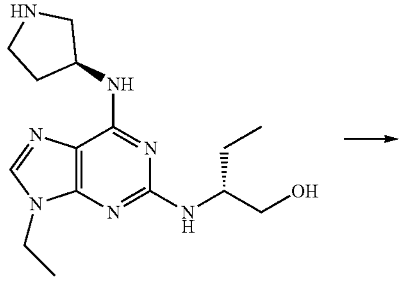

Intermediate 86

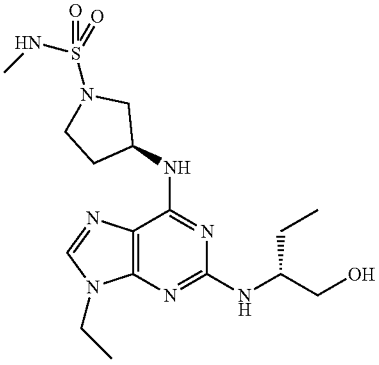

Example 47

Intermediate 85: 1-((S)-3-(9-ethyl-2-((R)-1-hydroxybutan-2-ylamino)-9H-purin-6-ylamino)pyrrolidin-1-yl)ethanone (R)-2-aminobutan-1-ol (229 mg, 2.57 mmol) was added to (S)-1-(3-((9-ethyl-2-fluoro-9H-purin-6-yl)amino)pyrrolidin-1-yl)ethan-1-one (Intermediate 83, 150 mg, 0.51 mmol), DIEA (0.448 mL, 2.57 mmol) and lithium chloride (43.5 mg, 1.03 mmol) in 3-ethylpentan-3-ol (1.5 mL). The resulting mixture was stirred at 160° C. for 16 hours. The reaction mixture was diluted with DCM (100 mL), and washed sequentially with saturated aq. $NH_4Cl$ solution (125 mL×1) and saturated aq. brine solution (125 mL). The organic layer was filtered and evaporated to afford crude product. The crude product was purified by flash C18 chromatography, elution gradient 0 to 50% MeCN in water (0.05% FA). Pure fractions were evaporated to dryness to afford 1-((S)-3-((9-ethyl-2-(((R)-1-hydroxybutan-2-yl)amino)-9H-purin-6-yl)amino)pyrrolidin-1-yl)ethan-1-one (Intermediate 85, 167 mg, 90%) as a yellow gum. $^1$H NMR (300 MHz, DMSO-$d_6$) 0.84-0.93 (3H, m), 1.34 (3H, t), 1.40-1.51 (1H, m), 1.60-1.68 (1H, m), 1.93 (3H, d), 1.98-2.25 (2H, m), 3.42-3.53 (3H, m), 3.59-3.70 (2H, m), 3.76-3.87 (2H, m), 3.99 (2H, q), 4.61 (2H, br s), 5.93 (1H, br s), 7.43 (1H, br s), 7.74 (1H, d); m/z (ES$^+$) [M+H]*=362.

Intermediate 86: (R)-2-(9-ethyl-6-((S)-pyrrolidin-3-ylamino)-9H-purin-2-yl-amino)butan-1-ol LiOH (103 mg, 4.29 mmol) was added to 1-((S)-3-((9-ethyl-2-(((R)-1-hydroxybutan-2-yl)amino)-9H-purin-6-yl)amino)pyrrolidin-1-yl)ethan-1-one (Intermediate 85, 155 mg, 0.43 mmol) in EtOH (4 mL) and water (1 mL). The resulting mixture was stirred at 80° C. for 16 hours. THF was removed under reduced pressure and the resulting residue was diluted with water (100 mL), and extracted with DCM (125 mL×5). The organic layer was dried over $Na_2SO_4$, filtered and evaporated to afford (R)-2-((9-ethyl-6-(((S)-pyrrolidin-3-yl)amino)-9H-purin-2-yl)amino)butan-1-ol (Intermediate 86, 125 mg, 91%) as a white solid. $^1$H NMR (300 MHz, DMSO-$d_6$) 0.86 (3H, t), 1.33 (3H, t), 1.39-1.53 (1H, m), 1.53-1.84 (2H, m), 1.96-2.07 (1H, m), 2.72-2.86 (2H, m), 2.92-3.09 (2H, m), 3.35-3.53 (3H, m), 3.82 (1H, br s), 3.98 (2H, q), 4.45-4.69 (1H, m), 5.87 (1H, br s), 7.15 (1H, br s), 7.71 (1H, s). one proton missing; m/z (ES$^+$) [M+H]$^+$=320.

Example 47: (S)-3-((9-ethyl-2-(((S)-2-hydroxy-2-methylpentan-3-yl)amino)-9H-purin-6-yl)amino)-N-methylpyrrolidine-1-sulfonamide

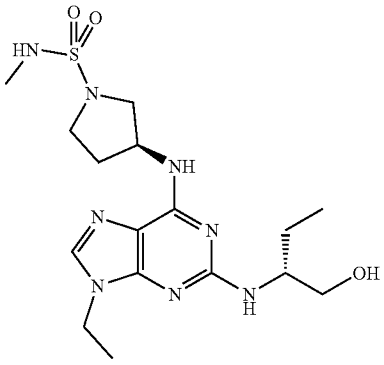 [SMILES: CC[C@H](CO)Nc1nc(N[C@H]2CCN(S(=O)(=O)NC)C2)c2ncn(CC)c2n1]

Methylsulfamoyl chloride (54.8 mg, 0.42 mmol) was added to (R)-2-((9-ethyl-6-(((S)-pyrrolidin-3-yl)amino)-9H-purin-2-yl)amino)butan-1-ol (Intermediate 86, 135 mg, 0.42 mmol) and TEA (0.295 mL, 2.11 mmol) in DCM (10 mL) cooled to −78° C. The resulting mixture was stirred at −78° C. for 3 hours. The reaction mixture was diluted with DCM (125 mL), and washed sequentially with saturated aq. $NH_4Cl$ solution (125 mL×3) and saturated aq. brine solution (125 mL). The organic layer was dried over $Na_2SO_4$, filtered and evaporated to afford crude product. The crude product was purified by preparative Column: XBridge Prep OBD C18 Column, 30×150 mm 5 μm; Mobile Phase A: Water (10 mmol/L $NH_4HCO_3$+0.1% $NH_3 \cdot H_2O$), Mobile Phase B: MeOH; Flow rate: 60 mL/min, 32-52% MeOH in water. Fractions containing the desired compound were evaporated to dryness to afford (S)-3-((9-ethyl-2-(((R)-1-hydroxybutan-2-yl)amino)-9H-purin-6-yl)amino)-N-methylpyrrolidine-1-sulfonamide (Example 47, 30.0 mg, 17.21%). $^1$H NMR (400 MHZ, Methanol-$d_4$) 1.02 (3H, t), 1.45 (3H, t), 1.50-1.66 (1H, m), 1.68-1.81 (1H, m), 2.01-2.14 (1H, m), 2.32-2.45 (1H, m), 2.67 (3H, s), 3.24-3.32 (1H, m), 3.34-3.48 (1H, m), 3.48-3.58 (1H, m), 3.60-3.74 (3H, m), 3.94-4.04 (1H, m), 4.11 (2H, q), 4.78 (1H, br s), 7.73 (1H, s). Four exchangeable protons were not observed; m/z (ES$^+$) [M+H]$^+$=413.

Example 48: (S)-3-((9-ethyl-2-(((S)-1-hydroxybutan-2-yl)amino)-9H-purin-6-yl)-amino)-N-methylpyrrolidine-1-sulfonamide

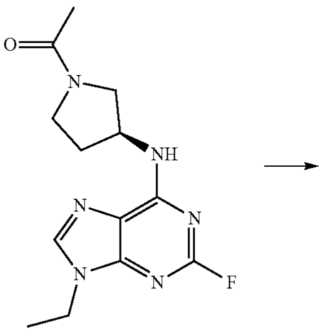

Intermediate 83

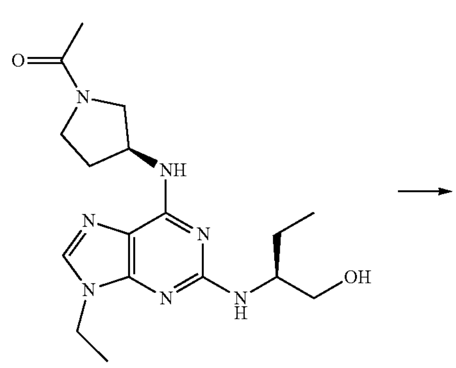

Intermediate 87

-continued

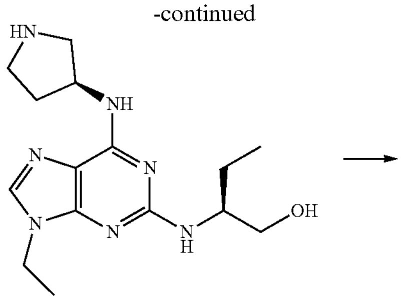

Intermediate 88

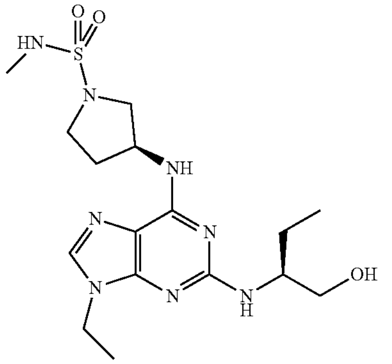

Example 48

Intermediate 87: 1-((S)-3-(9-ethyl-2-((S)-1-hydroxybutan-2-ylamino)-9H-purin-6-ylamino)pyrrolidin-1-yl)ethanone (S)-2-aminobutan-1-ol (110 mg, 1.23 mmol) was added to (S)-1-(3-((9-ethyl-2-fluoro-9H-purin-6-yl)amino)pyrrolidin-1-yl)ethan-1-one (Intermediate 83, 120 mg, 0.41 mmol), DIEA (358 μl, 2.05 mmol) and lithium chloride (34.8 mg, 0.82 mmol) in 3-ethylpentan-3-ol (1 mL). The resulting mixture was stirred at 160° C. for 16 hours. The solvent was removed under reduced pressure. The crude product was purified by flash C18 chromatography, elution gradient 0 to 50% MeCN in water (0.1% FA). Pure fractions were evaporated to dryness to afford 1-((S)-3-((9-ethyl-2-(((S)-1-hydroxybutan-2-yl)amino)-9H-purin-6-yl)amino)pyrrolidin-1-yl)ethan-1-one (Intermediate 87, 0.125 g, 84%) as a pale yellow gum. $^1$H NMR (400 MHZ, DMSO-$d_6$) 0.87 (3H, td), 1.33 (3H, t), 1.38-1.50 (1H, m), 1.58-1.69 (1H, m), 1.92 (3H, d), 2.01-2.25 (2H, m), 3.17-3.39 (2H, m), 3.59-3.70 (1H, m), 3.73-3.86 (2H, m), 3.98 (2H, q), 4.63 (2H, br s), 5.92 (1H, br s), 7.44 (1H, br d), 7.73 (1H, d); Two protons overlapped with the water peak; m/z (ES$^+$) [M+H]$^+$=362.

Intermediate 88: (S)-2-(9-ethyl-6-((S)-pyrrolidin-3-ylamino)-9H-purin-2-yl-amino)butan-1-ol LiOH (114 mg, 4.77 mmol) was added to 1-((S)-3-((9-ethyl-2-(((S)-1-hydroxybutan-2-yl)amino)-9H-purin-6-yl)amino)pyrrolidin-1-yl)ethan-1-one (Intermediate 87, 115 mg, 0.32 mmol) in EtOH (4 mL) and water (4.00 mL). The resulting mixture was stirred at 80° C. for 4 hours. The solvent was removed under reduced pressure. The reaction mixture was diluted with water (50 mL), and extracted with DCM (50 mL×7). The organic layer was dried over $Na_2SO_4$, filtered and evaporated to afford crude (S)-2-((9-ethyl-6-(((S)-pyrrolidin-3-yl)amino)-9H-purin-2-yl)amino)butan-1-ol (Intermediate 88, 0.097 g, 95%) product as a white solid. $^1$H NMR (300 MHz, DMSO-$d_6$) 0.86 (3H, t), 1.32 (3H, t), 1.36-1.49 (1H, m), 1.54-1.79 (2H, m), 1.93-2.10 (1H, m), 2.68-2.82 (2H, m), 2.89-3.05 (2H, m), 3.35 (2H, s), 3.42-3.52 (1H, m), 3.77-3.85 (1H, m), 3.96 (2H, q), 4.54 (2H, br s), 5.86 (1H, br s), 7.14 (1H, br s), 7.69 (1H, s); m/z (ES$^+$) $[M+H]^+$=320.

Example 48: (S)-3-((9-ethyl-2-(((S)-1-hydroxybutan-2-yl)amino)-9H-purin-6-yl)-amino)-N-methylpyrrolidine-1-sulfonamide

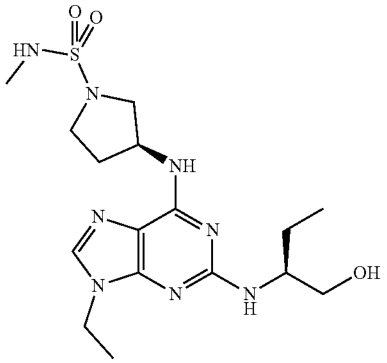 [SMILES: CC[C@@H](CO)Nc1nc(N[C@H]2CCN(S(=O)(=O)NC)C2)c2ncn(CC)c2n1]

Methylsulfamoyl chloride (43.4 mg, 0.33 mmol) was added to (S)-2-((9-ethyl-6-(((S)-pyrrolidin-3-yl)amino)-9H-purin-2-yl)amino)butan-1-ol (Intermediate 88, 107 mg, 0.33 mmol) and TEA (0.233 mL, 1.67 mmol) in DCM (10 mL). The resulting mixture was stirred at −78° C. for 5 hours. The reaction mixture was diluted with DCM (100 mL), and washed sequentially with saturated aq. $NH_4Cl$ solution (125 mL×3) and saturated aq. brine solution (125 mL). The organic layer was dried over $Na_2SO_4$, filtered and evaporated to afford crude product. The crude product was purified by preparative Column: XBridge Shield RP18 OBD Column, 30*150 mm, 5 μm; Mobile Phase A: Water (10 mmol/L $NH_4HCO_3$+0.1% $NH_3 \cdot H_2O$), Mobile Phase B: ACN; Flow rate: 60 mL/min, 20-32% ACN in water. Fractions containing the desired compound were evaporated to dryness to afford (S)-3-((9-ethyl-2-(((S)-1-hydroxybutan-2-yl)amino)-9H-purin-6-yl)amino)-N-methylpyrrolidine-1-sulfonamide (Example 48, 32.0 mg, 23.16%). $^1$H NMR (400 MHZ, DMSO-$d_6$) 0.87 (3H, t), 1.34 (3H, t), 1.38-1.50 (1H, m), 1.57-1.69 (1H, m), 2.06 (1H, s), 2.14-2.25 (1H, m), 2.54 (3H, d), 3.06-3.14 (1H, m), 3.17-3.26 (1H, m), 3.34-3.43 (2H, m), 3.43-3.58 (2H, m), 3.79-3.86 (1H, m), 3.99 (2H, q), 4.53-4.71 (2H, br m), 5.94 (1H, br s), 7.01 (1H, q), 7.42 (1H, br s), 7.74 (1H, s); m/z (ES$^+$) $[M+H]^+$=413.

Example 49 and 50: (S)-3-((9-ethyl-2-(((2R*,3S*)-4,4,4-trifluoro-3-hydroxybutan-2-yl)amino)-9H-purin-6-yl)amino)-N-methylpyrrolidine-1-sulfonamide

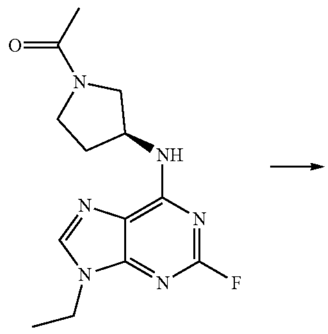

Intermediate 83

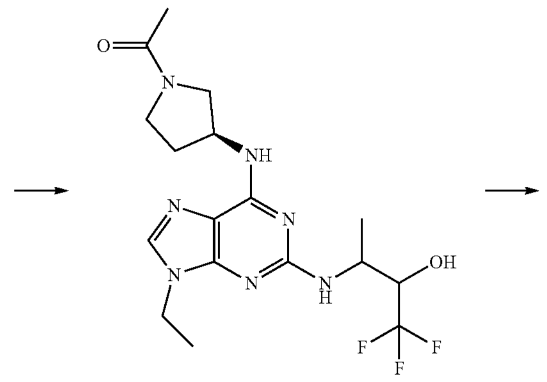

Intermediate 89

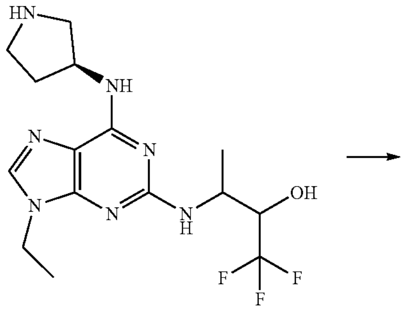

Intermediate 90

-continued

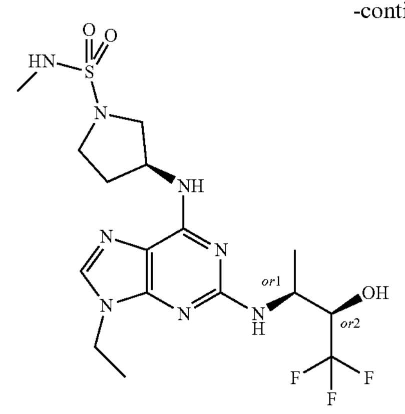

Example 49

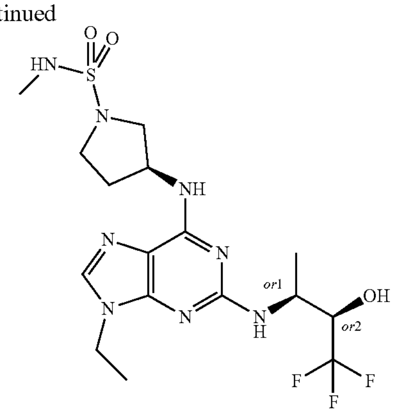

Example 50

Intermediate 89: 1-((S)-3-(9-ethyl-2-(4,4,4-trifluoro-3-hydroxybutan-2-ylamino)-9H-purin-6-ylamino)pyrrolidin-1-yl)ethanone Lithium chloride (87 mg, 2.05 mmol) was added to (S)-1-(3-((9-ethyl-2-fluoro-9H-purin-6-yl)amino)pyrrolidin-1-yl)ethan-1-one (Intermediate 83, 300 mg, 1.03 mmol), rac-(2R,3S)-3-amino-1,1,1-trifluorobutan-2-ol (441 mg, 3.08 mmol) and DIEA (0.896 mL, 5.13 mmol) in 3-methyl-3-pentanol (5 mL). The resulting mixture was stirred at 160° C. for 4 days. The reaction mixture was diluted with DCM (200 mL), and washed sequentially with saturated aq. $NH_4Cl$ solution (250 mL×3) and saturated aq. brine solution (250 mL). The organic layer was dried over $Na_2SO_4$, filtered and evaporated to afford crude product. The crude product was purified by flash C18 chromatography, elution gradient 5 to 100% MeCN in water (0.05% $NH_4HCO_3$). Pure fractions were evaporated to dryness to afford 1-((S)-3-((9-ethyl-2-(((2RS,3SR)-4,4,4-trifluoro-3-hydroxybutan-2-yl)amino)-9H-purin-6-yl)amino)pyrrolidin-1-yl)ethan-1-one (Intermediate 89, 400 mg, 94%) as a white solid. $^1H$ NMR (300 MHz, DMSO-$d_6$) 1.18 (3H, d), 1.32 (3H, t), 1.83-1.94 (3H, m), 1.97-2.21 (2H, m), 3.21-3.28 (1H, m), 3.36-3.50 (2H, m), 3.58-3.64 (1H, m), 3.68-3.81 (1H, m), 3.98 (2H, q), 4.15-4.31 (2H, br m), 4.61 (1H, br s), 6.29 (1H, d), 7.58 (1H, br s), 7.76 (1H, d); m/z ($ES^+$) $[M+H]^+$=416.

Intermediate 90: 3-(9-ethyl-6-((S)-pyrrolidin-3-ylamino)-9H-purin-2-ylamino)-1,1,1-trifluorobutan-2-ol LiOH (450 mg, 18.78 mmol) was added to 1-((S)-3-((9-ethyl-2-(((2RS,3SR)-4,4,4-trifluoro-3-hydroxybutan-2-yl)amino)-9H-purin-6-yl)amino)pyrrolidin-1-yl)ethan-1-one (Intermediate 89, 390 mg, 0.94 mmol) in EtOH (4 mL) and water (1.00 mL). The resulting mixture was stirred at 80° C. for 16 hours. The solvent was removed under reduced pressure. The reaction mixture was diluted with water (25 mL), and washed sequentially with DCM (50 mL×5). The organic layer was dried over $Na_2SO_4$, filtered and evaporated to afford crude (2RS,3SR)-3-((9-ethyl-6-(((S)-pyrrolidin-3-yl)amino)-9H-purin-2-yl)amino)-1,1,1-trifluorobutan-2-ol (Intermediate 90, 320 mg, 91%) product as a white solid. $^1H$ NMR (DMSO-$d_6$, 300 MHz) 1.18 (3H, d), 1.34 (3H, t), 1.62-1.74 (1H, m), 1.99 (1H, s), 2.63-2.78 (2H, m), 2.87-2.99 (2H, m), 3.99 (2H, q), 4.22-4.28 (2H, m), 4.51 (1H, br s), 5.77 (1H, s), 6.27 (1H, br d), 7.22 (1H, br s), 7.74 (1H, s). One proton overlapped with the solvent peak; m/z ($ES^+$) $[M+H]^+$=374.

Example 49 and 50: (S)-3-((9-ethyl-2-(((2R*,3S*)-4,4,4-trifluoro-3-hydroxybutan-2-yl)amino)-9H-purin-6-yl)amino)-N-methylpyrrolidine-1-sulfonamide

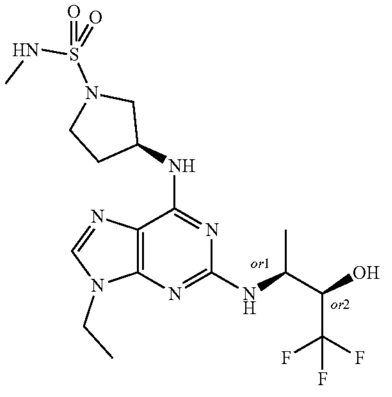 [SMILES: CCn1cnc2c(N[C@H]3CCN(S(=O)(=O)NC)C3)nc(N[C@@H](C)[C@@H](O)C(F)(F)F)nc21]

Methylsulfamoyl chloride (108 mg, 0.83 mmol) was added to (2RS,3SR)-3-((9-ethyl-6-(((S)-pyrrolidin-3-yl)amino)-9H-purin-2-yl)amino)-1,1,1-trifluorobutan-2-ol (Intermediate 90, 310 mg, 0.83 mmol) and TEA (0.579 mL, 4.15 mmol) in DCM (30 mL). The resulting mixture was stirred at −70° C. for 3 hours. The reaction mixture was diluted with DCM (150 mL), and washed sequentially with saturated aq. $NH_4Cl$ solution (200 mL×3) and saturated aq. brine solution (200 mL). The organic layer was dried over $Na_2SO_4$, filtered and evaporated to afford crude product. The crude product was purified by preparative HPLC, Column: YMC-Actus Triart C18 ExRS, 30 mm×150 mm, 5 μm; Mobile Phase A: Water (10 mmol/L $NH_4HCO_3$+0.1% $NH_3 \cdot H_2O$), Mobile Phase B: ACN; Flow rate: 60 mL/min, 18-43% ACN in water to afford mixture of Isomer 1 and Isomer 2 as a white solid and mixture of Isomer 3 and Isomer 4 as a pale yellow solid. The mixture of Isomer 1 and Isomer 2 was purified by preparative chiral-HPLC, Column: CHIRALPAK IG-3, 4.6*50 mm, 3 μm; Mobile Phase A: (Hex: DCM=3:1)(0.3% IPAmine): EtOH=90:10, Flow rate: 1 mL/min. The fractions containing the desired compound were evaporated to dryness to afford Isomer 1 (0.017 g, 4.86%) and (S)-3-((9-ethyl-2-(((2R*,3S*)-4,4,4-trifluoro-3-hydroxybutan-2-yl)amino)-9H-purin-6-yl)amino)-N-methylpyrrolidine-1-sulfonamide (Example 49, Isomer 2, 0.020 g, 5.71%). $^{1}$H NMR (400 MHZ, DMSO-$d_6$) 1.23 (3H, d), 1.35 (3H, t), 2.05 (1H, br s), 2.20 (1H, br s), 2.55 (3H, d), 3.12 (1H, br s), 3.20-3.27 (1H, m), 3.38-3.43 (1H, m), 3.54 (1H, t), 4.01 (2H, q), 4.11 (1H, br s), 4.38 (1H, br s), 4.64 (1H, br s), 5.94 (1H, br s), 6.51 (1H, br s), 7.02 (1H, s), 7.56 (1H, br s), 7.79 (1H, s); 19F NMR (376 MHz, DMSO-$d_6$)-74.089; m/z (ES$^+$) $[M+H]^+$=467. The mixture of Isomer 3 and Isomer 4 was purified by preparative chiral-HPLC, Column: CHIRALPAK ID, 2*25 cm, 5 μm; Mobile Phase A: Hexane:DCM=3:1 (0.3% IPA), Mobile Phase B: IPA; Flow rate: 20 mL/min; Gradient: 7 B to 7 B in 18 min. The fractions containing the desired compound were evaporated to dryness to afford (S)-3-((9-ethyl-2-(((2R*,3S*)-4,4,4-trifluoro-3-hydroxybutan-2-yl)amino)-9H-purin-6-yl)amino)-N-methylpyrrolidine-1-sulfonamide (Example 50, Isomer 3, 0.095 g, 27.1%), $^{1}$H NMR (400 MHZ, DMSO-$d_6$) 1.18 (3H, d), 1.34 (3H, t), 2.04 (1H, s), 2.17 (1H, s), 2.51-2.57 (3H, m), 3.11-3.15 (1H, m), 3.18-3.25 (1H, m), 3.36-3.45 (1H, m), 3.49-3.54 (1H, m), 3.92-4.07 (2H, m), 4.24 (2H, br s), 4.64 (1H, br s), 6.31 (2H, br s), 7.03 (1H, br d), 7.54 (1H, br s), 7.78 (1H, s); 19F NMR (376 MHz, DMSO-$d_6$)-74.279; m/z (ES$^+$) $[M+H]^+$=467; and Isomer 4, (0.086 g, 24.57%).

Example 51: (S)-3-((9-ethyl-2-(((1R,2S)-2-hydroxy-2,3-dihydro-1H-inden-1-yl)-amino)-9H-purin-6-yl)amino)-N-methylpyrrolidine-1-sulfonamide

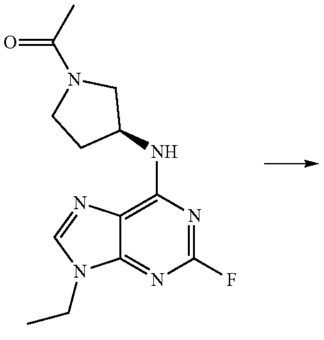

Intermediate 83

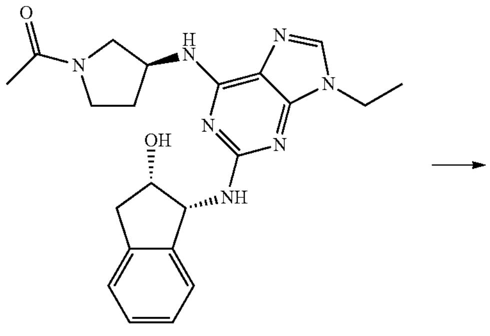

Intermediate 91

-continued

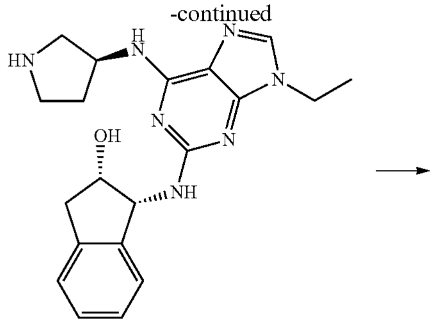

Intermediate 92

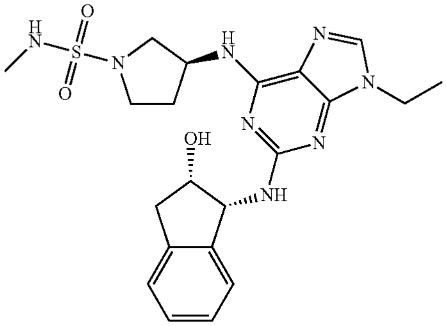

Example 51

Intermediate 91: 1-((S)-3-(9-ethyl-2-((1R,2S)-2-hydroxy-2,3-dihydro-1H-inden-1-ylamino)-9H-purin-6-ylamino)pyrrolidin-1-yl)ethanone (1R,2S)-1-amino-2,3-dihydro-1H-inden-2-ol (561 mg, 3.76 mmol) was added to (S)-1-(3-((9-ethyl-2-fluoro-9H-purin-6-yl)amino)pyrrolidin-1-yl)ethan-1-one (Intermediate 83, 110 mg, 0.38 mmol), DIEA (1314 μl, 7.53 mmol) and lithium chloride (15.95 mg, 0.38 mmol) in 3-ethyl-3-pentanol (2.5 mL). The resulting mixture was stirred at 160° C. for 16 hours. The crude product was purified by flash C18 chromatography, elution gradient 0 to 50% MeCN in water (0.1% $NH_4HCO_3$). Pure fractions were evaporated to dryness to afford 1-((S)-3-((9-ethyl-2-(((1R,2S)-2-hydroxy-2,3-dihydro-1H-inden-1-yl)amino)-9H-purin-6-yl)amino)pyrrolidin-1-yl)ethan-1-one (Intermediate 91, 0.155 g, 98%) as a white solid. $^{1}$H NMR (400 MHZ, DMSO-$d_6$) 1.35 (3H, t), 1.91 (3H, d), 2.05 (2H, br s), 2.84 (1H, d), 3.09 (1H, d), 3.23-3.30 (1H, m), 3.45 (1H, d), 3.58-3.67 (1H, m), 4.02 (2H, q), 4.52 (2H, d), 5.12 (1H, s), 5.41 (1H, s), 5.85 (1H, br s), 7.07-7.30 (5H, m), 7.43-7.71 (1H, m), 7.81 (1H, d); m/z (ES$^+$) $[M+H]^+$=422.

Intermediate 92: (1R,2S)-1-(9-ethyl-6-((S)-pyrrolidin-3-ylamino)-9H-purin-2-yl-amino)-2,3-dihydro-1H-inden-2-ol 1-((S)-3-((9-ethyl-2-(((1R,2S)-2-hydroxy-2,3-dihydro-1H-inden-1-yl)amino)-9H-purin-6-yl)amino)pyrrolidin-1-yl)ethan-1-one (Intermediate 91, 135 mg, 0.32 mmol) was added to LiOH (153 mg, 6.41 mmol) in water (1.5 mL) and EtOH (1.5 mL). The resulting mixture was stirred at 80° C. for 16 hours. The reaction mixture was diluted with DCM (50 mL), and washed sequentially with water (50 mL×3), and saturated aq. brine solution (50 mL). The organic layer was dried over $Na_2SO_4$, filtered and evaporated to afford (1R,2S)-1-((9-ethyl-6-(((S)-pyrrolidin-3-yl)amino)-9H-purin-2-yl)amino)-2,3-dihydro-1H-inden-2-ol (Intermediate 92, 0.103 g, 85%) as pale yellow solid. $^1$H NMR (400 MHZ, DMSO-$d_6$) 1.35 (3H, t), 1.68 (1H, br s), 1.96 (1H, br s), 2.67 (2H, s), 2.89 (2H, d), 3.03-3.20 (3H, m), 4.02 (2H, q), 4.52 (2H, br s), 5.14 (1H, br s), 5.42 (1H, d), 5.79 (1H, br s), 7.09-7.29 (5H, m), 7.78 (1H, s); m/z (ES$^+$) [M+H]$^+$=380.

Example 51: (S)-3-((9-ethyl-2-(((1R,2S)-2-hydroxy-2,3-dihydro-1H-inden-1-yl)amino)-9H-purin-6-yl)amino)-N-methylpyrrolidine-1-sulfonamide

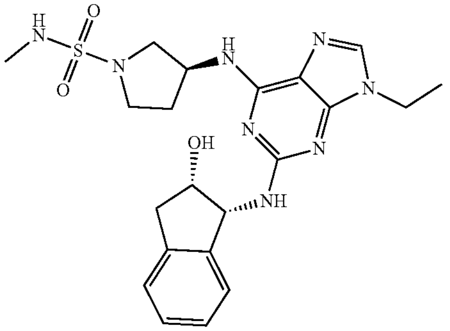 [SMILES: CCn1cnc2c(N[C@H]3CCN(S(=O)(=O)NC)C3)nc(N[C@@H]3c4ccccc4C[C@@H]3O)nc21]

A mixture of methylsulfamoyl chloride (15.88 mg, 0.12 mmol) in DCM (0.5 mL) was added slowly to a stirred mixture of (1R,2S)-1-((9-ethyl-6-(((S)-pyrrolidin-3-yl)amino)-9H-purin-2-yl)amino)-2,3-dihydro-1H-inden-2-ol (Intermediate 92, 93 mg, 0.25 mmol) and TEA (0.171 mL, 1.23 mmol) in DCM (1 mL) at −78° C. The resulting mixture was stirred at −78° C. for 1 hour. The reaction mixture was diluted with DCM (50 mL), and washed sequentially with saturated aq. $Na_2CO_3$ solution (50 mL×3), and saturated aq. brine solution (50 mL×1). The organic layer was dried over $Na_2SO_4$, filtered and evaporated to afford crude product. The crude product was purified by preparative HPLC, Column: YMC-Actus Triart C18 ExRS, 30 mm×150 mm, 5 μm; Mobile Phase A: Water (10 mmol/L $NH_4HCO_3$+0.1% $NH_3·H_2O$), Mobile Phase B: ACN; Flow rate: 60 mL/min, 19-52% ACN in water. Fractions containing the desired compound were evaporated to dryness to afford (S)-3-((9-ethyl-2-(((1R,2S)-2-hydroxy-2,3-dihydro-1H-inden-1-yl)amino)-9H-purin-6-yl)amino)-N-methylpyrrolidine-1-sulfonamide (Example 51, 33.0 mg, 28.5%). $^1$H NMR (300 MHz, Methanol-$d_4$) 1.46 (3H, t), 1.97-2.16 (1H, m), 2.28-2.44 (1H, m), 2.64 (3H, s), 2.97 (1H, d), 3.21-3.30 (2H, m), 3.37-3.45 (1H, m), 3.47-3.58 (1H, m), 3.64-3.75 (1H, m), 4.15 (2H, q), 4.64-4.73 (1H, m), 4.78 (1H, br s), 5.60 (1H, d), 7.16-7.35 (4H, m), 7.79 (1H, s). Four exchangeable protons were not observed; m/z (ES$^+$) [M+H]$^+$=473.

Example 52: (3R*,4R*)-3-((9-ethyl-2-(((2R,3S)-2-hydroxypentan-3-yl)amino)-9H-purin-6-yl)amino)-4-fluoro-N-methylpyrrolidine-1-sulfonamide

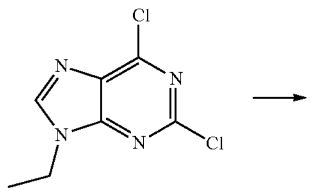

Intermediate 2

-continued

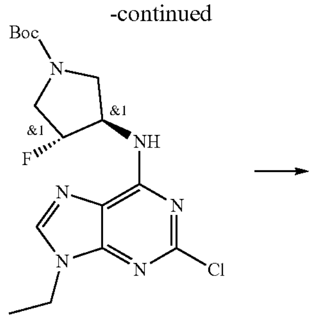

Intermediate 22

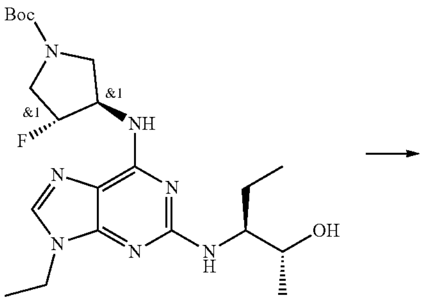

Intermediate 93

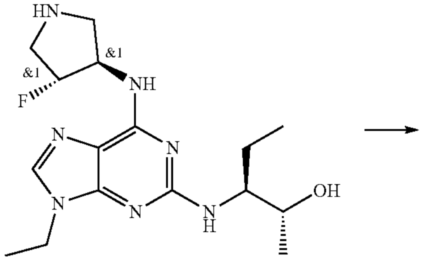

Intermediate 94

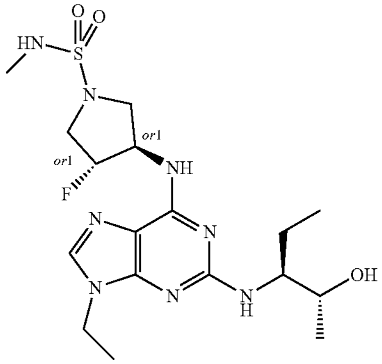

Example 52

Intermediate 22: rac-tert-butyl (3R,4R)-3-((2-chloro-9-ethyl-9H-purin-6-yl)-amino)-4-fluoropyrrolidine-1-carboxylate DIEA (12.07 mL, 69.11 mmol) was added to 2,6-dichloro-9-ethyl-9H-purine (3 g, 13.82 mmol) and rac-tert-butyl (3R,4R)-3-amino-4-fluoropyrrolidine-1-carboxylate (Intermediate 2, 2.82 g, 13.82 mmol) in IPA (45 mL). The resulting mixture was stirred at 100° C. for 2 hours. The reaction mixture was diluted with DCM (500 mL), and washed sequentially with saturated aq. $NH_4Cl$ solution (400 mL×3) and saturated aq. brine solution (400 mL). The organic layer was dried over $Na_2SO_4$, filtered and evaporated to afford crude product. The crude product was purified by flash silica chromatography, elution gradient 0 to 50% EtOAc in petroleum ether. Pure fractions were evaporated to dryness to afford rac-tert-butyl (3R,4R)-3-((2-chloro-9-ethyl-9H-purin-6-yl)amino)-4-fluoropyrrolidine-1-carboxylate (Intermediate 22, 4.70 g, 88%) as a white solid. $^1$H NMR (300 MHz, DMSO-$d_6$) 1.37 (3H, t), 1.40 (9H, s), 3.39-3.58 (2H, m), 3.61-3.72 (2H, m), 4.13 (2H, q), 4.68 (1H, br s), 5.17 (1H, d), 8.25 (1H, s), 8.70 (1H, br s); m/z ($ES^+$) $[M+H]^+$=385.

Intermediate 93: tert-butyl (3RS, 4RS)-3-((9-ethyl-2-(((2R,3S)-2-hydroxypentan-3-yl)amino)-9H-purin-6-yl)amino)-4-fluoropyrrolidine-1-carboxylate t-BuBrettPhos (69.0 mg, 0.14 mmol) was added to t-BuBrettPhos Pd G3 (122 mg, 0.14 mmol), rac-tert-butyl (3R, 4R)-3-((2-chloro-9-ethyl-9H-purin-6-yl)amino)-4-fluoropyrrolidine-1-carboxylate (Intermediate 22, 600 mg, 1.42 mmol), (2R,3S)-3-aminopentan-2-ol. HCl (1988 mg, 14.24 mmol) and $Cs_2CO_3$ (6960 mg, 21.36 mmol) in 3-methyl-3-pentanol (8 mL) under nitrogen. The resulting mixture was stirred at 140° C. for 1 hour. The reaction mixture was diluted with DCM (300 mL), and washed sequentially with saturated aq. $NH_4Cl$ solution (250 mL×3) and saturated aq. brine solution (250 mL×3). The organic layer was dried over $Na_2SO_4$, filtered and evaporated to afford crude product. The crude product was purified by flash silica chromatography, elution gradient 0 to 50% DCM (10% MeOH) in DCM. Pure fractions were evaporated to dryness to afford tert-butyl (3RS,4RS)-3-((9-ethyl-2-(((2R,3S)-2-hydroxypentan-3-yl)amino)-9H-purin-6-yl)amino)-4-fluoropyrrolidine-1-carboxylate (Intermediate 93, 430 mg, 66.9%) as a white solid. m/z ($ES^+$) $[M+H]^+$=452.

Intermediate 94: (2R,3S)-3-((9-ethyl-6-(((3RS,4RS)-4-fluoropyrrolidin-3-yl)-amino)-9H-purin-2-yl)amino)pentan-2-ol tert-Butyl (3RS,4RS)-3-((9-ethyl-2-(((2R,3S)-2-hydroxypentan-3-yl)amino)-9H-purin-6-yl)amino)-4-fluoropyrrolidine-1-carboxylate (Intermediate 93, 420 mg, 0.93 mmol) was treated with HCl in dioxane (5 mL, 4 M). The resulting mixture was stirred at rt for 16 hours. The solvent was removed under reduced pressure to afford (2R,3S)-3-((9-ethyl-6-(((3RS,4RS)-4-fluoropyrrolidin-3-yl)amino)-9H-purin-2-yl)amino)pentan-2-ol. HCl (Intermediate 94, 358 mg, 99%) as a white solid. m/z ($ES^+$) $[M+H]^+$=352.

Example 52: (3R*,4R*)-3-((9-ethyl-2-(((2R,3S)-2-hydroxypentan-3-yl)amino)-9H-purin-6-yl)amino)-4-fluoro-N-methylpyrrolidine-1-sulfonamide

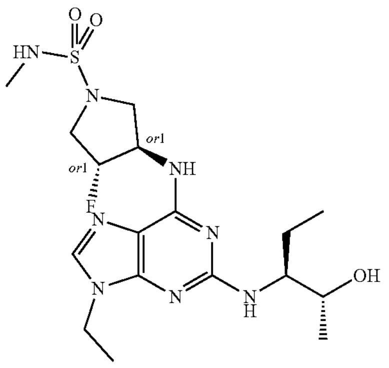 [SMILES: CC[C@H](Nc1nc(N[C@@H]2CN(S(=O)(=O)NC)C[C@H]2F)c2ncn(CC)c2n1)[C@@H](C)O]

Methylsulfamoyl chloride (139 mg, 1.08 mmol) was added to (2R,3S)-3-((9-ethyl-6-(((3RS,4RS)-4-fluoropyrrolidin-3-yl)amino)-9H-purin-2-yl)amino)pentan-2-ol (Intermediate 94, 348 mg, 0.90 mmol) and TEA (0.625 mL, 4.49 mmol) in DCM (10 mL) cooled to −78° C. The resulting mixture was stirred at −78° C. for 4 hours. The reaction mixture was diluted with DCM (200 mL), and washed sequentially with saturated aq. $NH_4Cl$ solution (250 mL×3) and saturated aq. brine solution (250 mL). The organic layer was dried over $Na_2SO_4$, filtered and evaporated to afford crude product. The crude product was purified by preparative HPLC, Column: XBridge Prep OBD C18 Column, 30*150 mm, 5 μm; Mobile Phase A: Water (10 mmol/L $NH_4HCO_3$+0.1% $NH_3 \cdot H_2O$), Mobile Phase B: ACN; Flow rate: 60 mL/min; Gradient: 17% B to 47% B in 8 min. Fractions containing the desired compound were evaporated to dryness to afford the racemic product. The racemic product was purified by preparative chiral-HPLC, Column: CHIRALPAK ID-3, 4.6*50 mm 3 μm; Mobile Phase: Hex (0.3% IPAmine):EtOH=80:20; Flow rate: 1 mL/min. The fractions containing the desired compound were evaporated to dryness to afford (3R*,4R*)-3-((9-ethyl-2-(((2R,3S)-2-hydroxypentan-3-yl)amino)-9H-purin-6-yl)amino)-4-fluoro-N-methylpyrrolidine-1-sulfonamide (Example 52, Isomer 1, 0.085 g, 21.2%), $^1$H NMR (300 MHZ, DMSO-$d_6$) 0.86 (3H, t), 1.06 (3H, d), 1.23-1.54 (4H, m), 1.71 (1H, ddt), 2.58 (3H, d), 3.31 (1H, dd), 3.48 (1H, d), 3.52-3.86 (4H, m), 4.00 (2H, q), 4.62 (2H, s), 5.13-5.51 (1H, m), 6.08 (1H, d), 7.18 (1H, q), 7.56 (1H, s), 7.77 (1H, s); 19F NMR (282 MHz, DMSO-$d_6$)-176.48; m/z ($ES^+$) $[M+H]^+$=445; and Isomer 2 (0.084 g, 21.0%).

Example 53: (S)—N-ethyl-3-((2-(((2R,3S)-2-hydroxypentan-3-yl)amino)-9-methyl-9H-purin-6-yl)amino)pyrrolidine-1-sulfonamide

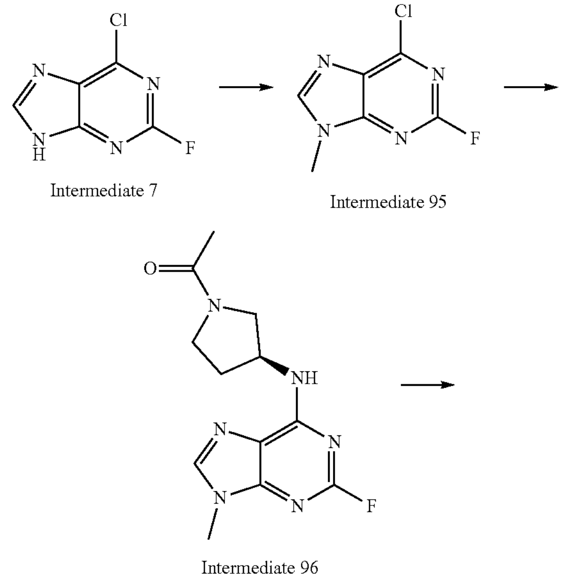
Intermediate 7

Intermediate 95

Intermediate 96

-continued

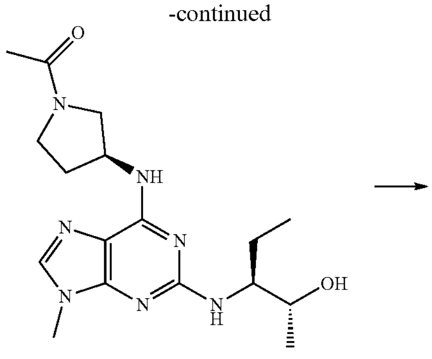

Intermediate 97

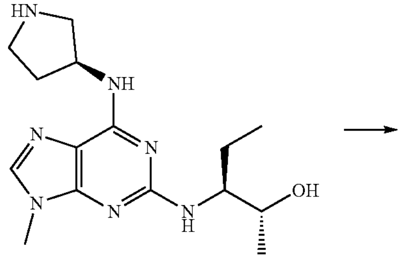

Intermediate 98

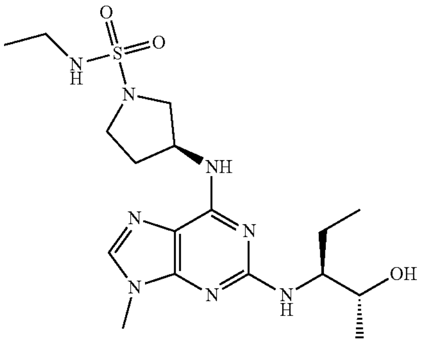

Example 53

Intermediate 95: 6-chloro-2-fluoro-9-methyl-9H-purine

DIAD (16.90 ml, 86.93 mmol) was added dropwise to 6-chloro-2-fluoro-9H-purine (Intermediate 7, 10 g, 57.96 mmol), methanol (5.57 g, 173.87 mmol) and $PPh_3$ (45.6 g, 173.87 mmol) in THF (300 mL) under nitrogen. The resulting mixture was stirred at rt for 16 hours. The solvent was removed under reduced pressure. The crude product was purified by flash C18 chromatography, elution gradient 10 to 50% MeOH in water (0.1% $NH_4HCO_3$). Pure fractions were evaporated to dryness to afford 6-chloro-2-fluoro-9-methyl-9H-purine (Intermediate 95, 4.00 g, 37.0%) as a white solid. $^1H$ NMR (400 MHZ, DMSO-$d_6$) 3.81 (3H, s), 8.65 (1H, s); m/z ($ES^+$) $[M+H]^+$=187.

Intermediate 96: (S)-1-(3-(2-fluoro-9-methyl-9H-purin-6-ylamino)pyrrolidin-1-yl)ethanone 6-Chloro-2-fluoro-9-methyl-9H-purine (Intermediate 95, 1 g, 5.36 mmol), (S)-1-(3-aminopyrrolidin-1-yl)ethan-1-one (0.756 g, 5.90 mmol) and DIEA (2.81 ml, 16.08 mmol) in IPA (10 mL) were stirred under an atmosphere of nitrogen at 80° C. for 2 hours. The solvent was removed under reduced pressure. The mixture was diluted with saturated aq. $NH_4Cl$ solution (25 mL), extracted with DCM (3×25 mL), the organic layer was dried over $Na_2SO_4$, filtered and evaporated to afford yellow oil. The crude product was purified by flash silica chromatography, elution gradient 0 to 10% DCM in MeOH. Pure fractions were evaporated to dryness to afford (S)-1-(3-((2-fluoro-9-methyl-9H-purin-6-yl)amino)pyrrolidin-1-yl)ethan-1-one (Intermediate 96, 1.200 g, 80%) as a white solid; m/z ($ES^+$) $[M+H]^+$=279.

Intermediate 97: 1-((S)-3-(2-((2R,3S)-2-hydroxy-pentan-3-ylamino)-9-methyl-9H-purin-6-ylamino) pyrrolidin-1-yl)ethanone DIEA (2.51 mL, 14.37 mmol), lithium chloride (30.5 mg, 0.72 mmol) and 3-ethyl-3-pentanol (3 mL, 0.72 mmol) were added to (S)-1-(3-((2-fluoro-9-methyl-9H-purin-6-yl) amino)pyrrolidin-1-yl)ethan-1-one (Intermediate 96, 200 mg, 0.72 mmol) and (2R,3S)-3-aminopentan-2-ol (297 mg, 2.87 mmol). The resulting mixture was stirred at 160° C. for 16 hours. The crude product was purified by flash C18 chromatography, elution gradient 20 to 50% MeCN in water (0.05% $NH_4HCO_3$). Pure fractions were evaporated to dryness to afford 1-((S)-3-((2-(((2R,3S)-2-hydroxypentan-3-yl) amino)-9-methyl-9H-purin-6-yl)amino)pyrrolidin-1-yl) ethan-1-one (Intermediate 97, 0.160 g, 61.6%) as a brown solid; m/z ($ES^+$) $[M+H]^+$=362.

Intermediate 98: (2R,3S)-3-(9-methyl-6-((S)-pyrrolidin-3-ylamino)-9H-purin-2-ylamino)pentan-2-ol 1-((S)-3-((2-(((2R,3S)-2-hydroxypentan-3-yl)amino)-9-methyl-9H-purin-6-yl)amino)pyrrolidin-1-yl)ethan-1-one (Intermediate 97, 160 mg, 0.44 mmol) and LiOH (212 mg, 8.85 mmol) were dissolved in EtOH (3 mL) and water (3 mL). The resulting mixture was stirred at 80° C. for 16 hours. The solvent was removed under reduced pressure. The reaction mixture was washed sequentially with saturated aq. $NH_4Cl$ solution (100 mL×2) and DCM (100 mL×4). The organic layer was dried over $Na_2SO_4$, filtered and evaporated to afford desired product. The product (2R, 3S)-3-(9-methyl-6-((S)-pyrrolidin-3-ylamino)-9H-purin-2-ylamino)pentan-2-ol (Intermediate 98, 65 mg, 0.20 mmol, 45%) as a colorless gum that was used in the next step directly without further purification. $^1H$ NMR (300 MHz, DMSO-$d_6$) 0.75-0.89 (3H, m), 1.05 (3H, d), 1.33-1.48 (1H, m), 1.60-1.77 (1H, m), 1.93-2.08 (1H, m), 2.64-2.78 (1H, m), 2.90-3.03 (2H, m), 3.40-3.71 (7H, m), 4.48-4.60 (1H, m), 5.93-6.00 (1H, m), 7.10-7.16 (1H, m), 7.64 (1H, s); Two protons missing; m/z ($ES^+$) $[M+H]^+$=320.

Example 53: (S)—N-ethyl-3-((2-(((2R,3S)-2-hydroxypentan-3-yl)amino)-9-methyl-9H-purin-6-yl) amino)pyrrolidine-1-sulfonamide

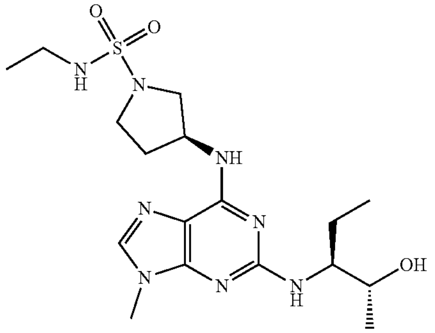 [SMILES: CCNS(=O)(=O)N1CC[C@H](Nc2nc(N[C@@H](CC)[C@@H](C)O)nc3c2ncn3C)C1]

Ethylsulfamoyl chloride (8.77 mg, 0.06 mmol) in DCM (1 mL) was added to (2R,3S)-3-((9-methyl-6-(((S)-pyrrolidin-3-yl)amino)-9H-purin-2-yl)amino)pentan-2-ol (Intermediate 98, 65 mg, 0.20 mmol) and TEA (142 μl, 1.02 mmol) in DCM (1 mL) at −78° C. The resulting mixture was stirred at −78° C. for 30 minutes. The reaction mixture was diluted with saturated aq. $NaHCO_3$ solution (25 mL), extracted with DCM (3×20 mL), the organic layer was dried over $Na_2SO_4$, filtered and evaporated to afford yellow oil. The crude product was purified by preparative HPLC, Column: Xselect CSH F-Phenyl OBD column, 19*250, 5 μm; Mobile Phase A: Water (0.1% FA), Mobile Phase B: ACN; Flow rate: 25 mL/min, 10-20% ACN in water. Fractions containing the desired compound were evaporated to dryness to afford (S)—N-ethyl-3-((2-(((2R,3S)-2-hydroxypentan-3-yl)amino)-9-methyl-9H-purin-6-yl)amino)pyrrolidine-1-sulfonamide (Example 53, 0.014 g, 16.13%). $^1H$ NMR (300 MHz, DMSO-$d_6$) 0.78-0.96 (3H, m), 1.00-1.12 (6H, m), 1.29-1.48 (1H, m), 1.61-1.79 (1H, m), 1.98-2.31 (2H, m), 2.90-3.27 (5H, m), 3.50-3.76 (6H, m), 4.52-4.83 (2H, m), 6.03 (1H, s), 7.05-7.15 (1H, m), 7.41 (1H, br s), 7.68 (1H, s); m/z ($ES^+$) $[M+H]^+$=427.

Example 54: (S)-3-((9-(fluoromethyl)-2-(((2R,3S)-2-hydroxypentan-3-yl)amino)-9H-purin-6-yl)amino)-N-methylpyrrolidine-1-sulfonamide

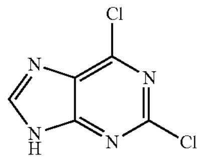

Intermediate 1

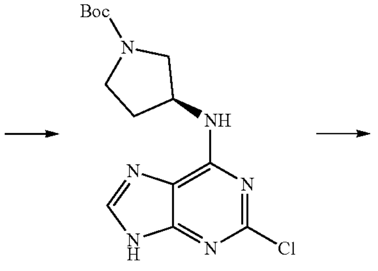

Intermediate 29

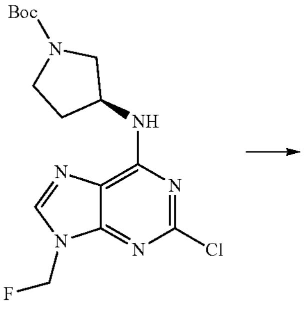

Intermediate 99

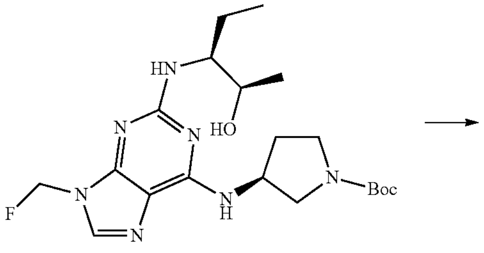

Intermediate 100

-continued

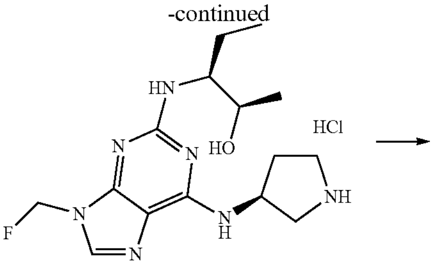

Intermediate 101

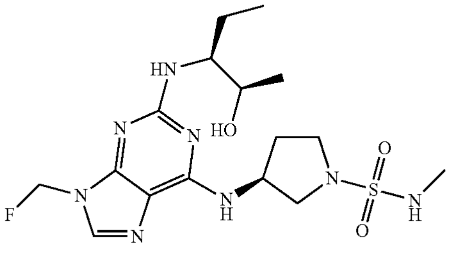

Example 54

Intermediate 29: (S)-tert-butyl 3-(2-chloro-9H-purin-6-ylamino)pyrrolidine-1-carboxylate 2,6-Dichloro-9H-purine (Intermediate 1, 1 g, 5.29 mmol) was added to tert-butyl (S)-3-aminopyrrolidine-1-carboxylate (1.478 g, 7.94 mmol) and DIEA (2.77 ml, 15.87 mmol) in IPA (10 mL). The resulting mixture was stirred at 100° C. for 2 hours. The crude product was purified by flash C18 chromatography, elution gradient 0 to 50% MeCN in water (0.05% FA). Pure fractions were evaporated to dryness to afford tert-butyl (S)-3-((2-chloro-9H-purin-6-yl)amino)pyrrolidine-1-carboxylate (Intermediate 29, 1.500 g, 84%) as a white solid. $^1H$ NMR (400 MHZ, DMSO-$d_6$) 1.39 (9H, d), 1.98 (1H, br s), 2.15 (1H, br s), 3.08-3.26 (2H, m), 3.44 (1H, br s), 3.55-3.64 (1H, m), 4.59 (1H, d), 8.16 (1H, s), 8.38 (1H, s), 13.07 (1H, br s); m/z ($ES^+$) $[M+H]^+$=339.

Intermediate 99: (S)-tert-butyl 3-(2-chloro-9-(fluoromethyl)-9H-purin-6-yl-amino)pyrrolidine-1-carboxylate NaH (0.633 g, 15.82 mmol) was added to tert-butyl (S)-3-((2-chloro-9H-purin-6-yl)amino)pyrrolidine-1-carboxylate (Intermediate 29, 1.34 g, 3.96 mmol) in DMF (30 mL). The resulting mixture was stirred at rt for 30 minutes. Then the chlorofluoromethane (0.271 g, 3.96 mmol) was added to the mixture and the mixture stirred at 80° C. for 3 hours. The reaction mixture was quenched with water (100 mL), extracted with DCM (3×150 mL) and saturated aq. brine solution (5×150 mL), the organic layer was dried over $Na_2SO_4$, filtered and evaporated to afford yellow gum. The crude product was purified by flash silica chromatography, elution gradient 0 to 80% EtOAc in petroleum ether. Pure fractions were evaporated to dryness to afford tert-butyl (S)-3-((2-chloro-9-(fluoromethyl)-9H-purin-6-yl)amino)pyrrolidine-1-carboxylate (0.186 g, 12.68%) as a yellow gum. The crude product was purified by flash C18 chromatography, elution gradient 3 to 80% MeCN in water (0.05% FA). Pure fractions were evaporated to dryness to afford tert-butyl (S)-3-((2-chloro-9-(fluoromethyl)-9H-purin-6-yl)amino)pyrrolidine-1-carboxylate (Intermediate 99, 0.186 g, 12.68%) as a yellow gum. 1H NMR (400 MHZ, DMSO-$d_6$)

1.39-1.42 (9H, m), 1.93-2.09 (1H, m), 2.13-2.28 (1H, m), 3.45-3.71 (4H, m), 4.55-4.60 (1H, m), 6.56 (2H, d), 7.17 (1H, d), 8.61 (1H, s); 19F NMR (376 MHZ, DMSO-$d_6$)-165.58 (1F, s); m/z ($ES^+$) $[M+H]^+$=371.

Intermediate 100: (S)-tert-butyl 3-(9-(fluoromethyl)-2-((2R,3S)-2-hydroxypentan-3-ylamino)-9H-purin-6-ylamino)pyrrolidine-1-carboxylate tert-Butyl (S)-3-((2-chloro-9-(fluoromethyl)-9H-purin-6-yl)amino)pyrrolidine-1-carboxylate (Intermediate 99, 170 mg, 0.46 mmol) was added to (2R,3S)-3-aminopentan-2-ol. HCl (192 mg, 1.38 mmol), $Cs_2CO_3$ (747 mg, 2.29 mmol), tBuBrettPhos Pd 3G (39.2 mg, 0.05 mmol) and tBuBrettPhos (22.22 mg, 0.05 mmol) in 3-ethyl-3-pentanol (5 mL) under nitrogen. The resulting mixture was stirred at 140° C. for 1 hour. The reaction was concentrated and the crude product was purified by flash C18 chromatography, elution gradient 5 to 80% MeCN in water (0.1% $NH_4HCO_3$). Pure fractions were evaporated to dryness to afford tert-butyl (S)-3-((9-(fluoromethyl)-2-(((2R,3S)-2-hydroxypentan-3-yl)amino)-9H-purin-6-yl)amino)pyrrolidine-1-carboxylate (Intermediate 100, 0.060 g, 29.9%) as a yellow solid. $^1H$ NMR (300 MHz, DMSO-$d_6$) 0.83-0.89 (3H, m), 1.05 (3H, d), 1.41 (9H, s), 1.72 (1H, br s), 2.11 (2H, br s), 3.15-3.25 (4H, m), 3.43 (1H, br s), 3.62 (2H, br s), 3.79 (1H, br s), 4.57 (1H, s), 6.07 (2H, d), 6.33 (1H, s), 7.58-7.74 (1H, m), 7.97 (1H, s); m/z ($ES^+$) $[M+H]^+$=438.

Intermediate 101: (2R,3S)-3-(9-(fluoromethyl)-6-((S)-pyrrolidin-3-ylamino)-9H-purin-2-ylamino)pentan-2-ol hydrochloride Hydrogen chloride solution 4.0 M in 1,4-dioxane (2 mL, 8.00 mmol) was added to tert-butyl (S)-3-((9-(fluoromethyl)-2-(((2R,3S)-2-hydroxypentan-3-yl)amino)-9H-purin-6-yl)amino)pyrrolidine-1-carboxylate (Intermediate 100, 50 mg, 0.11 mmol) in EtOAc (0.5 mL). The resulting mixture was stirred at rt for 16 hours. The product (2R,3S)-3-((9-(fluoromethyl)-6-(((S)-pyrrolidin-3-yl)amino)-9H-purin-2-yl)amino)pentan-2-ol (Intermediate 101, 65 mg, 0.16 mmol) as a colorless gum that was used in the next step directly without further purification; m/z ($ES^+$) $[M+H]^+$=338.

Example 54: (S)-3-((9-(fluoromethyl)-2-(((2R,3S)-2-hydroxypentan-3-yl)amino)-9H-purin-6-yl)amino)-N-methylpyrrolidine-1-sulfonamide

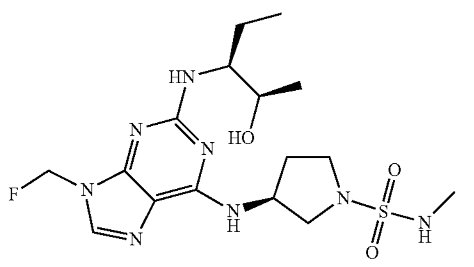 [SMILES: CC[C@H](Nc1nc(N[C@H]2CCN(S(=O)(=O)NC)C2)c2ncn(CF)c2n1)[C@@H](C)O]

Methylsulfamoyl chloride (10.61 mg, 0.08 mmol) was added to (2R,3S)-3-((9-(fluoromethyl)-6-(((S)-pyrrolidin-3-yl)amino)-9H-purin-2-yl)amino)pentan-2-ol (Intermediate 101, 65 mg, 0.16 mmol) and TEA (228 µl, 1.64 mmol) in DCM (2 mL). The resulting mixture was stirred at −70° C. for 30 minutes. The reaction mixture was quenched with water (25 mL), extracted with DCM (3×50 mL), the organic layer was dried over $Na_2SO_4$, filtered and evaporated to afford the crude product. The crude product was purified by preparative HPLC, Column: XBridge Prep OBD C18 Column, 30×150 mm 5 µm; Mobile Phase A: Water (10 mmol/L $NH_4HCO_3$+0.1% $NH_3 \cdot H_2O$), Mobile Phase B: ACN; Flow rate: 60 mL/min; Gradient: 13% B to 33% B in 8 min. Fractions containing the desired compound were evaporated to dryness to afford (S)-3-((9-(fluoromethyl)-2-(((2R,3S)-2-hydroxypentan-3-yl)amino)-9H-purin-6-yl)amino)-N-methylpyrrolidine-1-sulfonamide (Example 54, 0.015 g, 21.28%). $^1H$ NMR (400 MHz, DMSO-$d_6$) 0.86 (3H, t), 1.06 (3H, d), 1.29-1.49 (1H, m), 1.72 (1H, ddd), 2.01-2.14 (1H, m), 2.16-2.29 (1H, m), 2.53-2.56 (3H, m), 3.10-3.32 (2H, m), 3.37-3.44 (1H, m), 3.49-3.67 (2H, m), 3.74-3.83 (1H, m), 4.52-4.74 (2H, m), 6.07 (2H, d), 6.18-6.38 (1H, m), 7.02 (1H, dd), 7.65 (1H, br s), 7.97 (1H, s); 19F NMR (376 MHz, DMSO-$d_6$)-163.51; m/z ($ES^+$) $[M+H]^+$=431.

Example 55: (S)-3-((9-(difluoromethyl)-2-(((2R,3S)-2-hydroxypentan-3-yl)amino)-9H-purin-6-yl)amino)-N-methylpyrrolidine-1-sulfonamide

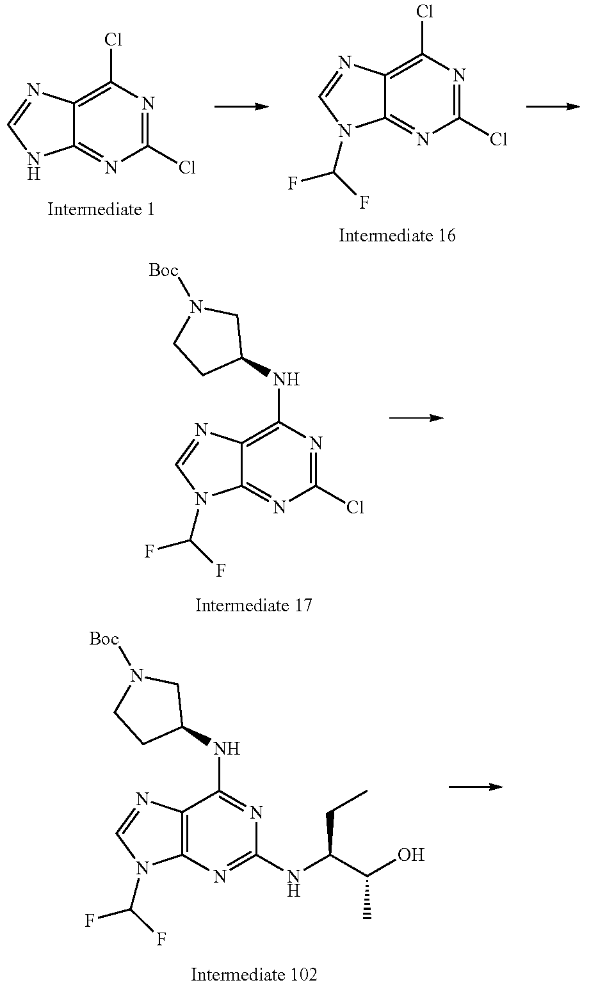
Intermediate 1
Intermediate 16
Intermediate 17
Intermediate 102

-continued

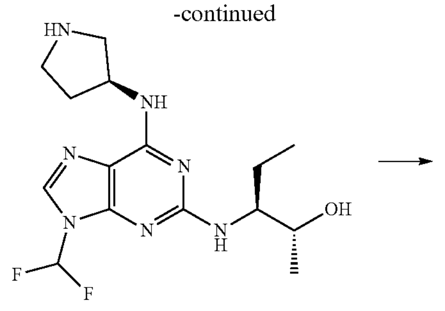

Intermediate 103

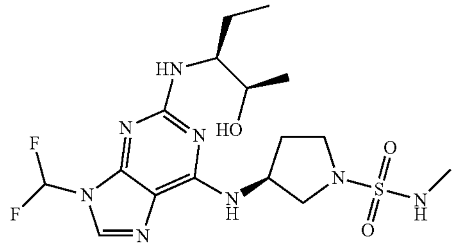

Example 55

Intermediate 16: 2,6-dichloro-9-(difluoromethyl)-9H-purine 2,6-Dichloro-9H-purine (Intermediate 1, 2 g, 10.58 mmol), diethyl (bromodifluoromethyl)phosphonate (2.83 g, 10.58 mmol) and potassium fluoride (1.230 g, 21.16 mmol) in MeCN (40 mL) were stirred under an atmosphere of nitrogen at rt for 16 hours. The solvent was removed under reduced pressure. The crude product was purified by flash C18 chromatography, elution gradient 5 to 80% MeCN in water (0.1% $NH_4HCO_3$). Pure fractions were evaporated to dryness to afford 2,6-dichloro-9-(difluoromethyl)-9H-purine (Intermediate 16, 1.000 g, 39.5%) as a white solid. $^1$H NMR (DMSO-$d_6$, 400 MHZ) 8.12 (1H, t), 9.09 (1H, s); m/z ($ES^+$) $[M+H]^+$=239.

Intermediate 17: (S)-tert-butyl 3-(2-chloro-9-(difluoromethyl)-9H-purin-6-yl-amino)pyrrolidine-1-carboxylate DIEA (1885 µl, 10.79 mmol) was added to 2,6-dichloro-9-(difluoromethyl)-9H-purine (Intermediate 16, 860 mg, 3.60 mmol) and tert-butyl (S)-3-aminopyrrolidine-1-carboxylate (737 mg, 3.96 mmol) in IPA (5 mL). The resulting mixture was stirred at 80° C. for 16 hours. The reaction mixture was quenched with saturated aq. $NH_4Cl$ solution (150 mL×1) and extracted with DCM (100 mL×3). The organic layer was dried over $Na_2SO_4$, filtered and evaporated to afford crude product. The crude product was purified by flash C18 chromatography, elution gradient 25 to 50% MeCN in water (0.05% $NH_4HCO_3$). Pure fractions were evaporated to dryness to afford tert-butyl (S)-3-((2-chloro-9-(difluoromethyl)-9H-purin-6-yl)amino)-pyrrolidine-1-carboxylate (Intermediate 17, 1.100 g, 79%) as a white solid. $^1$H NMR (400 MHZ, DMSO-$d_6$) 1.39 (9H, d), 1.87-2.25 (2H, m), 3.24 (2H, dd), 3.45 (1H, br s), 3.60 (1H, dd), 4.53-4.72 (1H, br m), 7.96 (1H, t), 8.60 (1H, s), 8.75-8.92 (1H, br m); m/z ($ES^+$) $[M+H]^+$=389.

Intermediate 102: (S)-tert-butyl 3-(9-(difluoromethyl)-2-((2R,3S)-2-hydroxypentan-3-ylamino)-9H-purin-6-ylamino)pyrrolidine-1-carboxylate tert-Butyl (S)-3-((2-chloro-9-(difluoromethyl)-9H-purin-6-yl)amino)pyrrolidine-1-carboxylate (Intermediate 17, 400 mg, 1.03 mmol), $Cs_2CO_3$ (1508 mg, 4.63 mmol), 2-(di-tert-butylphosphino)-2',4',6'-triisopropyl-3,6-dimethoxy-1,1'-biphenyl (100 mg, 0.21 mmol), (2R,3S)-3-aminopentan-2-ol, HCl (215 mg, 1.54 mmol) and tBuBrettPhos 3G Pd (88 mg, 0.10 mmol) were added to 3-Methyl-3-pentanol (2 mL, 1.03 mmol) under nitrogen. The resulting mixture was stirred at 140° C. for 3 hours. The crude product was purified by flash C18 chromatography, elution gradient 5 to 60% MeCN in water (1% $NH_4HCO_3$). Pure fractions were evaporated to dryness to afford tert-butyl (S)-3-((9-(difluoromethyl)-2-(((2R,3S)-2-hydroxypentan-3-yl)amino)-9H-purin-6-yl)amino)pyrrolidine-1-carboxylate (Intermediate 102, 0.120 g, 25.6%) as a yellow solid. $^1$H NMR (400 MHZ, DMSO-$d_6$) 0.85 (3H, t), 1.06 (3H, d), 1.39 (9H, d), 1.74 (1H, d), 1.96-2.19 (2H, m), 3.23 (2H, br s), 3.44 (1H, br d), 3.62 (2H, br s), 3.78 (1H, br s), 4.11 (1H, q), 4.56 (2H, br d), 6.41 (1H, br s), 7.52-7.90 (2H, br m), 8.08 (1H, br s); m/z ($ES^+$) $[M+H]^+$=456.

Intermediate 103: (2R,3S)-3-(9-(difluoromethyl)-6-((S)-pyrrolidin-3-ylamino)-9H-purin-2-ylamino)pentan-2-ol hydrochloride tert-Butyl (S)-3-((9-(difluoromethyl)-2-(((2R,3S)-2-hydroxypentan-3-yl)amino)-9H-purin-6-yl)amino)pyrrolidine-1-carboxylate (Intermediate 102, 80 mg, 0.18 mmol) in HCl in 1,4-dioxane (2 ml, 8.00 mmol, 4 M) was stirred at rt for 3 hours. The solvent was removed under reduced pressure to afford (2R,3S)-3-((9-(difluoromethyl)-6-(((S)-pyrrolidin-3-yl)amino)-9H-purin-2-yl)amino)pentan-2-ol. HCl (Intermediate 103, 0.060 g, 87%) as a yellow solid. The product was used in the next step directly without further purification. m/z ($ES^+$) $[M+H]^+$=356.

Example 55: (S)-3-((9-(difluoromethyl)-2-(((2R,3S)-2-hydroxypentan-3-yl)amino)-9H-purin-6-yl)amino)-N-methylpyrrolidine-1-sulfonamide

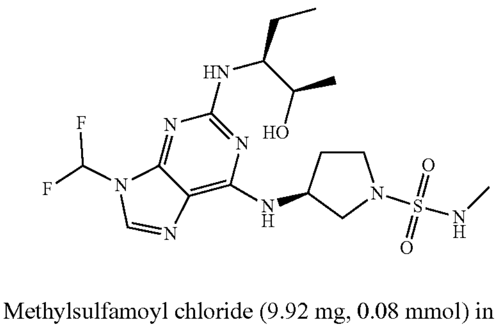

Methylsulfamoyl chloride (9.92 mg, 0.08 mmol) in DCM (1 mL) was added to (2R,3S)-3-((9-(difluoromethyl)-6-(((S)-pyrrolidin-3-yl)amino)-9H-purin-2-yl)amino)pentan-2-ol. HCl (Intermediate 103, 50 mg, 0.13 mmol) and TEA (178 µl, 1.28 mmol) in DCM (1 mL) at −78° C. The resulting mixture was stirred at −78° C. for 1 hour. The reaction mixture was diluted with saturated aq. $Na_2CO_3$ solution (20 mL), extracted with DCM (3×20 mL), the organic layer was dried over $Na_2SO_4$, filtered and evaporated to afford yellow solid. The crude product was purified by preparative HPLC, Column: XBridge Prep OBD C18 Column, 30×150 mm 5 μm; Mobile Phase A: Water (10 mmol/L $NH_4HCO_3$+0.1% $NH_3 \cdot H_2O$), Mobile Phase B: MeOH; Flow rate: 60 mL/min; 33-53% MeOH in water. Fractions containing the desired compound were evaporated to dryness to afford (S)-3-((9-(difluoromethyl)-2-(((2R,3S)-2-hydroxypentan-3-yl) amino)-9H-purin-6-yl)amino)-N-methylpyrrolidine-1-sulfonamide (Example 55, 0.036 g, 62.9%). $^1$H NMR (400 MHZ, DMSO-$d_6$) 0.85 (3H, t), 1.06 (3H, d), 1.33-1.46 (1H, m), 1.66-1.78 (1H, m), 2.07 (1H, br s), 2.23 (1H, dt), 2.55 (3H, s), 3.12-3.17 (1H, m), 3.24 (1H, dt), 3.38-3.45 (1H, m), 3.60 (2H, dt), 3.78 (1H, qd), 4.56 (2H, d), 6.40 (1H, br s), 7.03 (1H, q), 7.54-7.89 (2H, br m), 8.09 (1H, s); m/z (ES$^+$) [M+H]$^+$=449.

Example 56: (2R,3S)-3-((6-(((3R*,4R*)-1-((1H-imidazol-2-yl)sulfonyl)-4-fluoropyrrolidin-3-yl) amino)-9-methyl-9H-purin-2-yl)amino)pentan-2-ol

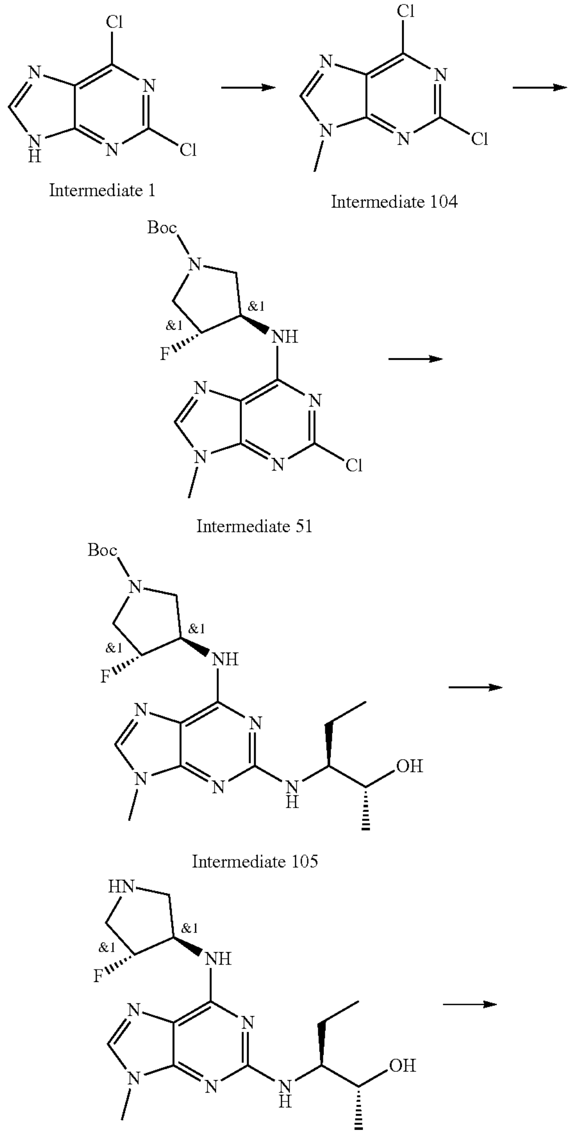

Intermediate 1

Intermediate 104

Intermediate 51

Intermediate 105

Intermediate 106

-continued

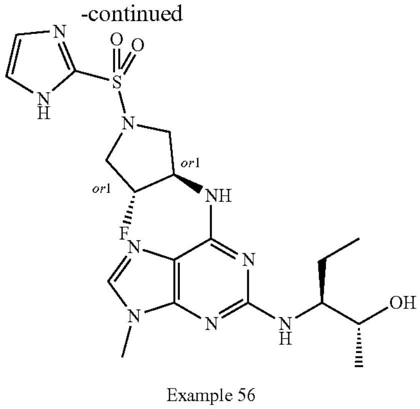

Example 56

Intermediate 104: 2,6-dichloro-9-methyl-9H-purine

DIAD (12.34 ml, 63.49 mmol) was added to 2,6-dichloro-9H-purine (Intermediate 1, 10 g, 52.91 mmol), MeOH (6.42 ml, 158.73 mmol) and $PPh_3$ (20.82 g, 79.37 mmol) in THF (150 mL) at 19° C. over a period of 10 minutes under nitrogen. The resulting mixture was stirred at rt for 16 hours. The reaction mixture was diluted with DCM (200 mL), and washed sequentially with saturated aq. $NH_4Cl$ solution (200 mL×1), saturated aq. $NaHCO_3$ solution (200 mL×1). The organic layer was dried over $Na_2SO_4$, filtered and evaporated to afford crude product. The crude product was purified by flash C18 chromatography, elution gradient 5 to 50% MeCN in water. Pure fractions were evaporated to dryness to afford 2,6-dichloro-9-methyl-9H-purine (Intermediate 104, 5.00 g, 46.5%) as a white solid. $^1$H NMR (400 MHZ, DMSO-$d_6$) 3.84 (3H, s), 8.68 (1H, s); m/z (ES$^+$) [M+H]$^+$ =202.

Intermediate 51: tert-butyl (3RS, 4RS)-3-((2-chloro-9-methyl-9H-purin-6-yl)-amino)-4-fluoropyrrolidine-1-carboxylate 2,6-Dichloro-9-methyl-9H-purine (Intermediate 104, 1 g, 4.93 mmol) was added to rac-tert-butyl (3RS,4RS)-3-amino-4-fluoropyrrolidine-1-carboxylate (1.207 g, 5.91 mmol) and DIEA (4.30 ml, 24.63 mmol) in IPA (10 mL) at 19° C. over a period of 10 minutes under air. The resulting mixture was stirred at 80° C. for 16 hours. The reaction mixture was diluted with DCM (20 mL), and washed sequentially with saturated aq. $NH_4Cl$ solution (20 mL×3), saturated aq. brine solution (20 mL×1). The organic layer was dried over $Na_2SO_4$, filtered and evaporated to afford crude product. The crude product was purified by flash C18 chromatography, elution gradient 5 to 50% MeCN in water. Pure fractions were evaporated to dryness to afford tert-butyl (3RS,4RS)-3-((2-chloro-9-methyl-9H-purin-6-yl)amino)-4-fluoropyrrolidine-1-carboxylate (Intermediate 51, 0.430 g, 23.54%) as a white solid. $^1$H NMR (300 MHz, DMSO-$d_6$) 1.42 (9H, s), 3.40-3.70 (4H, m), 3.71 (3H, s), 4.71 (1H, br s), 5.19 (1H, br d), 8.19 (1H, s), 8.68 (1H, br s); m/z (ES$^+$) [M+H]$^+$=369.

Intermediate 105: tert-butyl (3RS, 4RS)-3-fluoro-4-((2-(((2R,3S)-2-hydroxypentan-3-yl)amino)-9-methyl-9H-purin-6-yl)amino)pyrrolidine-1-carboxylate 2-(Di-tert-butylphosphino)-2',4',6'-triisopropyl-3,6-dimethoxy-1,1'-biphenyl (36.6 mg, 0.08 mmol), tBuBrettphos G3

(64.6 mg, 0.08 mmol) were added to tert-butyl (3RS,4RS)-3-((2-chloro-9-methyl-9H-purin-6-yl)amino)-4-fluoropyrrolidine-1-carboxylate (Intermediate 51, 280 mg, 0.76 mmol), (2R,3S)-3-aminopentan-2-ol hydrochloride (527 mg, 3.78 mmol) and $Cs_2CO_3$ (2460 mg, 7.55 mmol) in 3-methyl-3-pentanol (3 mL) at 10° C. over a period of 16 minutes. The resulting mixture was stirred at 140° C. for 30 minutes. The solid was dried in an oven under reduced pressure. The crude product was purified by flash C18 chromatography, elution gradient 5 to 50% MeCN in water. Pure fractions were evaporated to dryness to afford tert-butyl (3RS,4RS)-3-fluoro-4-((2-(((2R,3S)-2-hydroxypentan-3-yl)amino)-9-methyl-9H-purin-6-yl)amino)pyrrolidine-1-carboxylate (Intermediate 105, 0.180 g, 54.5%) as a brown gum. 1H NMR (300 MHz, DMSO-$d_6$) 0.86 (3H, t), 0.99-1.19 (4H, m), 1.21-1.36 (1H, m), 1.39-1.44 (10H, m, overlapped), 1.56-1.81 (1H, m), 3.18 (1H, s), 3.41-3.52 (1H, m), 3.55 (3H, s), 3.65 (1H, dd), 3.74-3.83 (1H, m), 5.03-5.37 (2H, m), 6.06 (1H, br d), 7.63 (1H, br s), 7.71 (1H, s), 8.27 (1H, br s); m/z ($ES^+$) $[M+H]^+$=438.

Intermediate 106: (2R,3S)-3-((6-(((3RS,4RS)-4-fluoropyrrolidin-3-yl)amino)-9-methyl-9H-purin-2-yl)amino)pentan-2-ol hydrochloride Hydrochloric acid solution (1029 μl, 4.11 mmol, 4 M in 1,4-dioxane) was added to tert-butyl (3RS,4RS)-3-fluoro-4-((2-(((2R,3S)-2-hydroxypentan-3-yl)amino)-9-methyl-9H-purin-6-yl)amino)pyrrolidine-1-carboxylate (Intermediate 105, 180 mg, 0.41 mmol) in 1,4-dioxane (5 mL) at 19° C. over a period of 13 minutes under air. The resulting mixture was stirred at rt for 16 hours. The reaction was concentrated and the solid was dried in an oven under reduced pressure to afford (2R,3S)-3-((6-(((3RS,4RS)-4-fluoropyrrolidin-3-yl)amino)-9-methyl-9H-purin-2-yl)amino)pentan-2-ol hydrochloride (Intermediate 106, 160 mg) as a yellow solid. The crude product was used directly for next step without any further purification; m/z ($ES^+$) $[M+H]^+$=338.

Example 56: (2R,3S)-3-((6-(((3R*,4R*)-1-((1H-imidazol-2-yl)sulfonyl)-4-fluoropyrrolidin-3-yl)amino)-9-methyl-9H-purin-2-yl)amino)pentan-2-ol

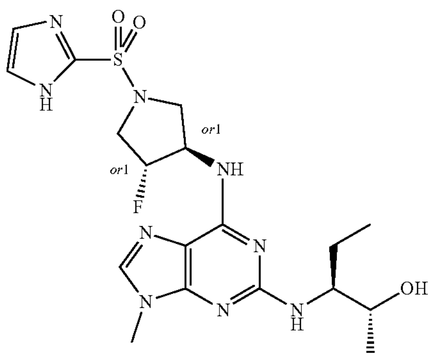 [SMILES: CC[C@H](Nc1nc(N[C@@H]2CN(S(=O)(=O)c3ncc[nH]3)C[C@H]2F)c2ncn(C)c2n1)[C@@H](C)O]

1H-Imidazole-2-sulfonyl chloride (35.6 mg, 0.21 mmol) was added to (2R,3S)-3-((6-(((3RS,4RS)-4-fluoropyrrolidin-3-yl)amino)-9-methyl-9H-purin-2-yl)amino)pentan-2-ol hydrochloride (Intermediate 106, 160 mg, 0.43 mmol) and TEA (298 μl, 2.14 mmol) in DCM (2 mL) at 10° C. over a period of 16 minutes under air. The resulting mixture was stirred at −70° C. for 16 minutes. The reaction was concentrated and the solid was dried in an oven under reduced pressure. The crude product was purified by preparative SFC, Column: CHIRAL ART Cellulose-SB, 3*25 cm, 5 μm; Mobile Phase A: $CO_2$, Mobile Phase B: IPA (0.5% 2M $NH_3$-MeOH); Flow rate: 80 mL/min; Gradient: isocratic 50% B; Column) Temperature (° C.: 35; Back Pressure (bar): 100. Fractions containing the desired compound were evaporated to dryness to afford (2R,3S)-3-((6-(((3RS,4RS)-1-((1H-imidazol-2-yl)sulfonyl)-4-fluoropyrrolidin-3-yl)amino)-9-methyl-9H-purin-2-yl)amino)pentan-2-ol as a white solid. The crude product was purified by preparative SFC, Column: CHIRAL ART Cellulose-SB, 3*25 cm, 5 μm; Mobile Phase A: $CO_2$, Mobile Phase B: IPA (0.5% 2M $NH_3$-MeOH); Flow rate: 80 mL/min; Gradient: isocratic 50% B; Column Temperature (° C.): 35; Back Pressure (bar): 100. Fractions containing the desired compound were evaporated to dryness to afford (2R,3S)-3-((6-(((3R*,4R*)-1-((1H-imidazol-2-yl)sulfonyl)-4-fluoropyrrolidin-3-yl)amino)-9-methyl-9H-purin-2-yl)amino)pentan-2-ol (0.020 g, 28.6%). Fractions containing the desired compound were evaporated to dryness to afford (2R,3S)-3-((6-(((3R*,4R*)-1-((1H-imidazol-2-yl)sulfonyl)-4-fluoropyrrolidin-3-yl)amino)-9-methyl-9H-purin-2-yl)amino)pentan-2-ol (Example 56, Isomer 1, 0.020 g, 20.4%), $^1H$ NMR (300 MHz, DMSO-$d_6$) 0.86 (3H, t), 1.06 (3H, d), 1.39 (1H, dq), 1.72 (1H, ddd), 3.47-3.89 (9H, m), 4.57 (1H, br s), 4.76 (1H, br s), 5.22 (1H, d), 6.08 (1H, d), 7.39 (2H, s), 7.72 (1H, s), 8.11 (1H, s), 13.51 (1H, br s); 19F NMR (282 MHZ, DMSO-$d_6$)-178.27; m/z ($ES^+$) $[M+H]^+$=468; and Isomer 2 (0.015 g, 21.43%).

Example 57: (2R,3S)-3-((6-(((3R*,4R*)-1-((1H-imidazol-2-yl)sulfonyl)-4-fluoropyrrolidin-3-yl)amino)-9-(difluoromethyl)-9H-purin-2-yl)amino)-1,1,1-trifluorobutan-2-ol

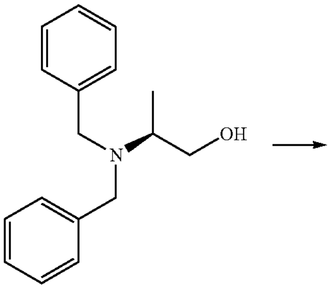

Intermediate 107

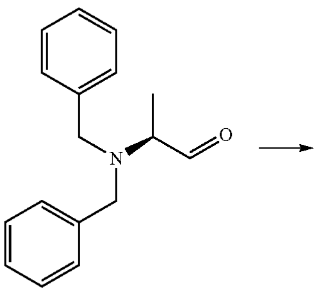

Intermediate 108

-continued

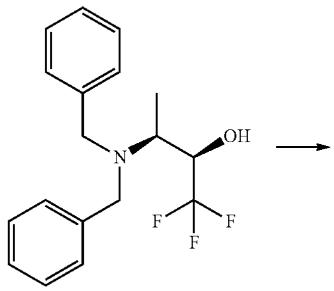

Intermediate 109

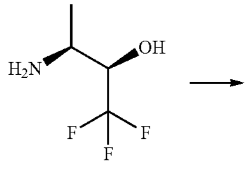

Intermediate 110

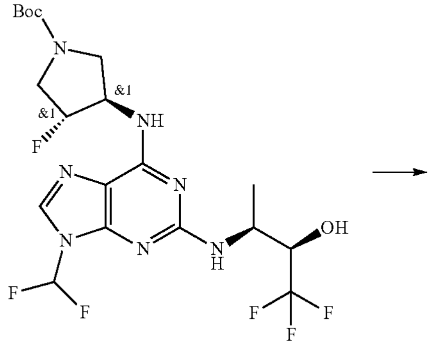

Intermediate 111

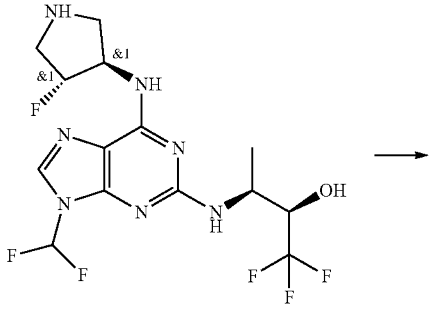

Intermediate 112

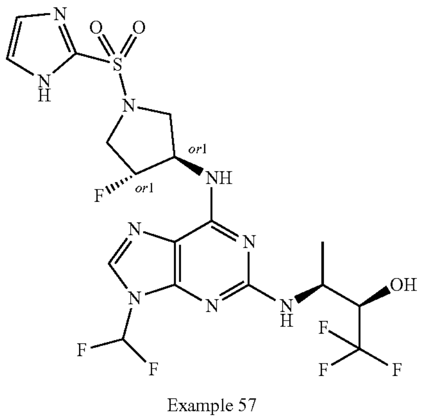

Example 57

Intermediate 108: (S)-2-(dibenzylamino)propanal

DMSO (9.73 ml, 137.06 mmol) was added dropwise to oxalyl chloride (8.45 g, 66.57 mmol) in DCM (30 mL) and cooled to −78° C. over a period of 15 minutes under argon. A solution of (S)-2-(dibenzylamino)propan-1-ol (Intermediate 107, 10 g, 39.16 mmol) in DCM (70 mL) was added to the cooled mixture at −78° C., over a period of 30 minutes followed by TEA (15.61 ml, 112.00 mmol). The resulting mixture was warmed up to rt and stirred for 45 minutes. The reaction mixture was diluted with DCM (300 mL), and washed sequentially with saturated aq. $Na_2CO_3$ solution (100 mL×3) and saturated aq. brine solution (100 mL×1). The organic layer was dried over $Na_2SO_4$, filtered and evaporated to afford (S)-2-(dibenzylamino)propanal (Intermediate 108, 9.85 g, 99%) as yellow oil. $^1$H NMR (400 MHZ, Chloroform-d) 1.21 (3H, d), 3.32-3.40 (1H, m), 3.60 (2H, d), 3.76 (2H, d), 7.26-7.43 (10H, m), 9.75 (1H, s); m/z ($ES^+$) $[M+H]^+$=254.

Intermediate 109: (2R,3S)-3-(dibenzylamino)-1,1,1-trifluorobutan-2-ol

Trifluoromethyltrimethylsilane in THF (48.6 ml, 97.20 mmol) was added slowly to TBAF in THF (1.944 ml, 1.94 mmol) and (S)-2-(dibenzylamino)propanal (Intermediate 108, 9.85 g, 38.88 mmol) in THF (100 mL). The resulting mixture was stirred at 0° C. for 1 hour. Then TBAF in THF (11.66 ml, 11.66 mmol) was added to the reaction mixture, and the reaction stirred at rt for 1 hour. The reaction mixture was diluted with diethyl ether (300 mL), and washed sequentially with saturated aq. $NH_4Cl$ solution (150 mL×3), and saturated aq. brine solution (100 mL×1). The organic layer was dried over $Na_2SO_4$, filtered and evaporated to afford crude product. The crude product was purified by flash silica chromatography, elution gradient 0 to 70% petroleum ether:EtOAc (20:1) in petroleum ether. Pure fractions were evaporated to dryness to afford (2R,3S)-3-(dibenzylamino)-1,1,1-trifluorobutan-2-ol (Intermediate 109, 2.400 g, 19.09%) as a pale yellow oil; $^1$H NMR (400 MHZ, Chloroform-d) 1.23 (3H, dd), 3.04 (1H, dq), 3.42 (2H, d), 3.73-3.79 (1H, m), 3.82 (2H, d), 5.11 (1H, s), 7.26-7.38 (10H, m); m/z ($ES^+$) $[M+H]^+$=324; optical rotation [α]D+58.50 (c 1.0, $CHCl_3$); and (2S,3S)-3-(dibenzylamino)-1,1,1-trifluorobutan-2-ol (7.70 g, 61.2%) as a pale yellow oil.

Intermediate 110: (2R,3S)-3-amino-1,1,1-trifluorobutan-2-ol $Pd(OH)_2$ (0.261 g, 1.86 mmol) was added to (2R,3S)-3-(dibenzylamino)-1,1,1-trifluorobutan-2-ol (Intermediate 109, 1.2 g, 3.71 mmol) in MeOH (10 mL). The resulting mixture was stirred at rt for 4 days. The reaction mixture was filtered through celite. The solvent was removed under reduced pressure and afford (2R,3S)-3-amino-1,1,1-trifluorobutan-2-ol (Intermediate 110, 0.520 g, 98%) as a brown oil. $^1$H NMR (400 MHZ, Methanol-$d_4$) 1.25 (3H, d), 3.21-3.30 (1H, m), 3.79 (1H, qd); 3 exchangeable protons were not observed; m/z ($ES^+$) $[M+H]^+$=144.

Intermediate 111: tert-butyl (3RS, 4RS)-3-((9-(difluoromethyl)-2-(((2S,3R)-4,4,4-trifluoro-3-hydroxybutan-2-yl)amino)-9H-purin-6-yl)amino)-4-fluoropyrrolidine-1-carboxylate rac-tert-Butyl (3R,4R)-3-((2-chloro-9-(difluoromethyl)-9H-purin-6-yl)amino)-4-fluoropyrrolidine-1-carboxylate (Intermediate 113, 200 mg, 0.49 mmol) was added to (2R,3S)-3-amino-1,1,1-trifluorobutan-2-ol (Intermediate 110, 141 mg, 0.98 mmol), $Cs_2CO_3$ (481 mg, 1.47 mmol), 2-(di-tert-butylphosphino)-2',4',6'-triisopropyl-3,6-dimethoxy-1,1'-biphenyl (23.83 mg, 0.05 mmol) and tBuBrettPhos Pd G3 (42.1 mg, 0.05 mmol) in 3-methyl-3-pentanol (2 mL) under nitrogen. The resulting mixture was stirred at 140° C. for 1 hour. The reaction was concentrated and the crude product was purified by flash C18 chromatography, elution gradient 5 to 70% MeCN in water (0.1% $NH_4HCO_3$). Pure fractions were evaporated to dryness to afford tert-butyl (3RS,4RS)-3-((9-(difluoromethyl)-2-(((2S,3R)-4,4,4-trifluoro-3-hydroxybutan-2-yl)amino)-9H-purin-6-yl)amino)-4-fluoropyrrolidine-1-carboxylate (Intermediate 111, 0.240 g, 95%) as a yellow solid. $^1H$ NMR (400 MHZ, DMSO-$d_6$) 1.23 (3H, d), 1.42 (9H, d), 3.41-3.47 (1H, m), 3.47-3.59 (2H, m), 3.60-3.76 (2H, m), 4.11 (1H, q), 4.44 (1H, br s), 4.67 (1H, br s), 5.20 (1H, d), 6.34 (2H, d), 7.75 (1H, t), 8.16 (1H, s); m/z ($ES^+$) $[M+H]^+$=514.

Intermediate 112: (2R,3S)-3-((9-(difluoromethyl)-6-(((3RS,4RS)-4-fluoropyrrolidin-3-yl)amino)-9H-purin-2-yl)amino)-1,1,1-trifluorobutan-2-ol hydrochloride tert-Butyl (3RS,4RS)-3-((9-(difluoromethyl)-2-(((2S,3R)-4,4,4-trifluoro-3-hydroxybutan-2-yl)amino)-9H-purin-6-yl)amino)-4-fluoropyrrolidine-1-carboxylate (Intermediate 111, 220 mg, 0.43 mmol) was added to HCl in dioxane (5 ml, 20.00 mmol, 4 M) in EtOAc (2 mL). The resulting mixture was stirred at rt for 16 hours. Then EtOAc (200 ml) was added to the reaction mixture, and the reaction stirred at rt for 30 minutes. The precipitate was collected by filtration, washed with EtOAc (20 mL) and dried under vacuum to afford (2R,3S)-3-((9-(difluoromethyl)-6-(((3RS,4RS)-4-fluoropyrrolidin-3-yl)amino)-9H-purin-2-yl)amino)-1,1,1-trifluorobutan-2-ol. HCl (Intermediate 112, 170 mg, 88%) as a yellow solid, which was used without further purification. m/z ($ES^+$) $[M+H]^+$=414.

Example 57: (2R,3S)-3-(6-(((3R*,4R*)-1-(1H-imidazol-2-yl)sulfonyl)-4-fluoropyrrolidin-3-yl)amino)-9-(difluoromethyl)-9H-purin-2-yl)amino)-1,1,1-trifluorobutan-2-ol

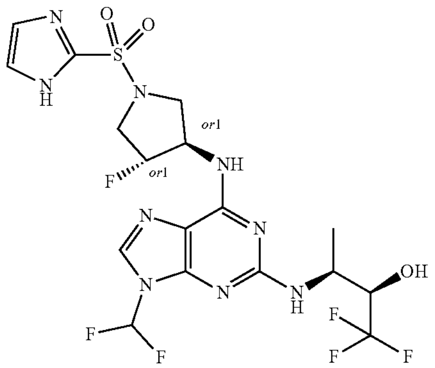 [SMILES: C[C@H](Nc1nc(N[C@@H]2CN(S(=O)(=O)c3ncc[nH]3)C[C@H]2F)c2ncn(C(F)F)c2n1)[C@@H](O)C(F)(F)F]

A solution of 1H-imidazole-2-sulfonyl chloride (160 mg, 0.96 mmol) in DCM (0.5 mL) was added slowly to a stirred mixture of (2R,3S)-3-((9-(difluoromethyl)-6-(((3R,4R)-4-fluoropyrrolidin-3-yl)amino)-9H-purin-2-yl)amino)-1,1,1-trifluorobutan-2-ol (Intermediate 112, 160 mg, 0.36 mmol) and TEA (0.992 mL, 7.11 mmol) in DCM (2.5 mL) at −78° C. The resulting mixture was stirred at −78° C. for 30 minutes. The solvent was removed under reduced pressure. The crude product was purified by preparative HPLC, Column: YMC-Actus Triart C18 ExRS, 20*250 mm, 5 μm; Mobile Phase A: Water (10 mmol/L $NH_4HCO_3$+0.1% $NH_3 \cdot H_2O$), Mobile Phase B: ACN; Flow rate: 60 mL/min; Gradient: 24% B to 54% B in 8 min. Fractions containing the desired compound were evaporated to dryness to afford the crude product. The crude product was purified by preparative chiral-HPLC, Column: OptiChiral-C9-5, 3*25 cm, 5 μm; Mobile Phase A: $CO_2$, Mobile Phase B: MeOH (0.1% 2M $NH_3$-MeOH); Flow rate: 100 mL/min; Gradient: isocratic 20% B; Column Temperature (C): 35; Back Pressure (bar): 100. The fractions containing the desired compound were evaporated to dryness afford Isomer 1 (26.0 mg, 13.3%) and (2R,3S)-3-((6-(((3R*,4R*)-1-((1H-imidazol-2-yl)sulfonyl)-4-fluoropyrrolidin-3-yl)amino)-9-(difluoromethyl)-9H-purin-2-yl)amino)-1,1,1-trifluorobutan-2-ol (Example 57, Isomer 2, 25.00 mg, 12.8%). $^1H$ NMR (400 MHZ, DMSO-$d_6$) 1.23 (3H, d), 3.51-3.87 (4H, m), 4.09 (1H, br s), 4.43 (1H, br s), 4.72 (1H, br s), 5.21 (1H, d), 6.22-6.42 (2H, m), 7.38 (2H, br s), 7.74 (1H, t), 8.17 (1H, s), 8.54 (1H, br s), 13.67 (1H, br s); m/z ($ES^+$) $[M+H]^+$=544.

Example 58: (S)-3-((2-(((R*)-1-cyclopropyl-3-hydroxypropan-2-yl)amino)-9-ethyl-9H-purin-6-yl)amino)-N-ethylpyrrolidine-1-sulfonamide

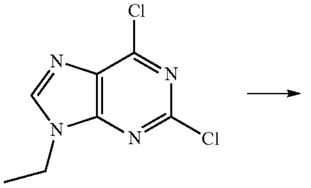

Intermediate 1

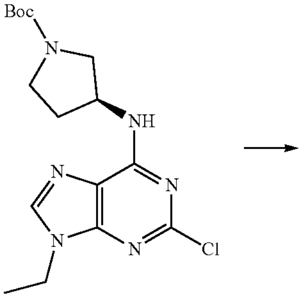

Intermediate 3

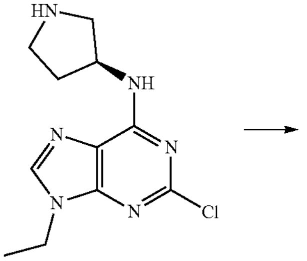

Intermediate 4

-continued

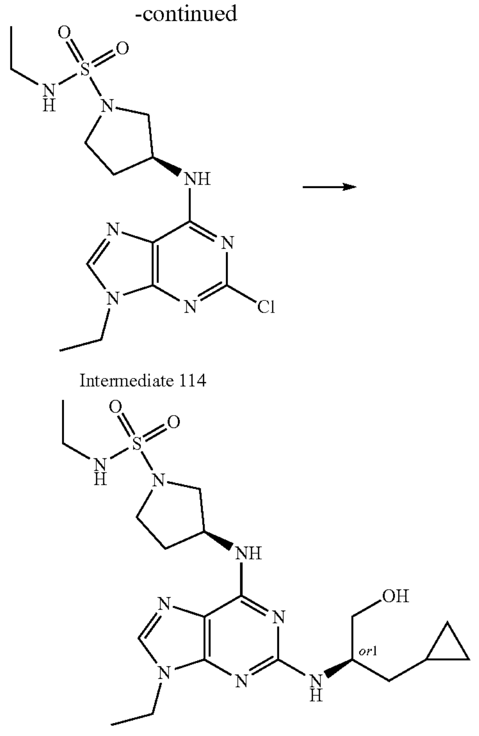

Intermediate 114

Example 58

Intermediate 3: (S)-tert-butyl 3-(2-chloro-9-ethyl-9H-purin-6-ylamino)pyrrolidine-1-carboxylate Five batches of the following reaction were set up separately: tert-butyl (S)-3-aminopyrrolidine-1-carboxylate (3.78 g, 20.27 mmol) was added to 2,6-dichloro-9-ethyl-9H-purine (Intermediate 1, 4 g, 18.43 mmol) and DIEA (9.66 mL, 55.29 mmol) in IPA (15 mL). The resulting mixture was stirred at 100° C. for 2 hours. The five reactions were combined and the solvent removed under reduced pressure. The crude product was purified by flash silica chromatography, elution gradient 0 to 20% MeOH in DCM. Pure fractions were evaporated to dryness to afford tert-butyl (S)-3-((2-chloro-9-ethyl-9H-purin-6-yl)amino)pyrrolidine-1-carboxylate (Intermediate 3, 39.0 g, 98%) as a yellow gum containing 0.5 eq DIEA. $^1$H NMR (300 MHz, DMSO-$d_6$) 1.35-1.44 (12H, m), 2.07 (2H, br d), 3.09-3.23 (1H, m), 3.46 (2H, ddd), 3.62 (1H, dt), 4.14 (2H, q), 4.61 (1H, br s), 8.22 (1H, s), 8.50 (1H, br d); m/z (ES$^+$) [M+H]*=367.

Intermediate 4: (S)-2-chloro-9-ethyl-N-(pyrrolidin-3-yl)-9H-purin-6-amine hydrochloride HCl in 1,4-dioxane (50 mL, 200.00 mmol, 4 M) was added to tert-butyl (S)-3-((2-chloro-9-ethyl-9H-purin-6-yl)amino)pyrrolidine-1-carboxylate (Intermediate 3, 10 g, 27.26 mmol) in EtOAc (200 mL). The resulting mixture was stirred at rt for 2 hours. The precipitate was collected by filtration, washed with EtOAc (50 mL) and dried under vacuum to afford (S)-2-chloro-9-ethyl-N-(pyrrolidin-3-yl)-9H-purin-6-amine. HCl (Intermediate 4, 8.00 g, 97%) as a white solid, which was used without further purification. m/z (ES$^+$) [M+H]$^+$=267.

Intermediate 114: (S)-3-(2-chloro-9-ethyl-9H-purin-6-ylamino)-N-ethylpyrrolidine-1-sulfonamide A solution of ethylsulfamoyl chloride (5.30 g, 36.94 mmol) in DCM (40 mL) was added dropwise to a stirred mixture of (S)-2-chloro-9-ethyl-N-(pyrrolidin-3-yl)-9H-purin-6-amine hydrochloride (Intermediate 4, 8 g, 26.39 mmol) and DIEA (13.83 mL, 79.16 mmol) in DCM (100 mL) at −78° C. The resulting mixture was stirred at −78° C. for 1 hour. The reaction mixture was diluted with DCM (200 mL), and washed sequentially with saturated aq. $NH_4Cl$ solution (100 mL), saturated aq. $NaHCO_3$ solution (100 mL×3), and saturated aq. brine solution (150 mL). The organic layer was dried over $Na_2SO_4$, filtered and evaporated to afford crude product. The crude product was purified by crystallisation from EtOAc to afford (S)-3-((2-chloro-9-ethyl-9H-purin-6-yl)amino)-N-ethylpyrrolidine-1-sulfonamide (Intermediate 114, 6.70 g, 67.9%) as a yellow solid. $^1$H NMR (300 MHz, DMSO-$d_6$) 1.06 (3H, t), 1.39 (3H, t), 2.08 (1H, br s), 2.24 (1H, br s), 2.96 (2H, qd), 3.13 (1H, dd), 3.25 (1H, dt), 3.41 (1H, td), 3.55 (1H, t), 4.15 (2H, q), 4.64 (1H, br s), 7.13 (1H, t), 8.23 (1H, s), 8.47 (1H, br s); m/z (ES$^+$) [M+H]*=374.

Example 58: (S)-3-((2-(((R*)-1-cyclopropyl-3-hydroxypropan-2-yl)amino)-9-ethyl-9H-purin-6-yl)amino)-N-ethylpyrrolidine-1-sulfonamide

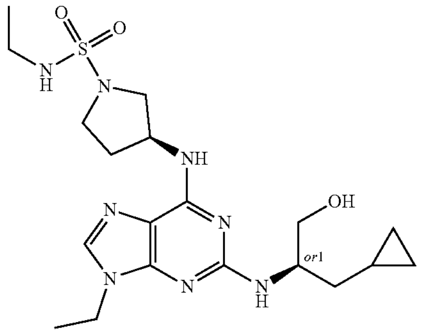 [SMILES: CCNS(=O)(=O)N1CC[C@H](Nc2nc(N[C@@H](CO)CC3CC3)nc3c2ncn3CC)C1]

Pd-PEPPSI-IPentCl o-picoline (2-methylpyridine) pre-catalyst (67.4 mg, 0.08 mmol) was added to (S)-3-((2-chloro-9-ethyl-9H-purin-6-yl)amino)-N-ethylpyrrolidine-1-sulfonamide (Intermediate 114, 300 mg, 0.80 mmol), rac-(R)-2-amino-3-cyclopropylpropan-1-ol hydrochloride (146 mg, 0.96 mmol) and sodium 2-methylpropan-2-olate (231 mg, 2.41 mmol) in dioxane (3 mL) under nitrogen. The resulting mixture was stirred at 90° C. for 4 hours. The reaction mixture was diluted with DCM (50 mL), and washed sequentially with water (50 mL), and saturated aq. brine solution (50 mL×1). The organic layer was dried over $Na_2SO_4$, filtered and evaporated to afford crude product. The crude product was purified by preparative HPLC, Column: YMC-Actus Triart C18, 30*150 mm, 5 μm; Mobile Phase A: Water (10 mmol/L $NH_4HCO_3$+0.1% $NH_3 \cdot H_2O$), Mobile Phase B: ACN; Flow rate: 60 mL/min; Gradient: 28% B to 43% B in 10 min. Fractions containing the desired compound were evaporated to dryness to afford the racemic product. The racemic product was purified by preparative chiral-HPLC, Column: CHIRALPAK IC-3, 4.6*50 mm, 3 μm; Mobile Phase A: (Hex:DCM=3:1) (0.1% DEA): EtOH=70:30; Flow rate: 1 mL/min. The fractions containing the desired compound were evaporated to dryness to afford (S)-3-((2-(((R*)-1-cyclopropyl-3-hydroxypropan-2-yl)amino)-9-ethyl-9H-purin-6-yl)amino)-N-ethylpyrrolidine-1-sulfonamide (Example 58, Isomer 1, 34.0 mg, 9.37%), $^1$H NMR (400 MHz, DMSO-$d_6$) 0.00-0.05 (1H, m), 0.05-0.13 (1H, m), 0.32-0.42 (2H, m), 0.68-0.81 (1H, m), 1.06 (3H, t), 1.34 (3H, t), 1.44 (2H, td), 1.98-2.10 (1H, m), 2.14-2.25 (1H, m), 2.90-3.01 (2H, m), 3.05-3.13 (1H, m), 3.16-3.27 (1H, m), 3.34-3.42 (1H, m), 3.43-3.60 (3H, m), 3.90-4.05 (3H, m), 4.57 (1H, br t), 4.69 (1H, s), 5.91 (1H, br s), 7.08 (1H, t), 7.38 (1H, br s), 7.74 (1H, s); m/z (ES$^+$) [M+H]$^+$=453; and Isomer 2 (58.0 mg, 19.33%).

Example 59: (S)—N-ethyl-3-((9-ethyl-2-(((R*)-3-hydroxy-3-methylbutan-2-yl)-amino)-9H-purin-6-yl)amino)pyrrolidine-1-sulfonamide

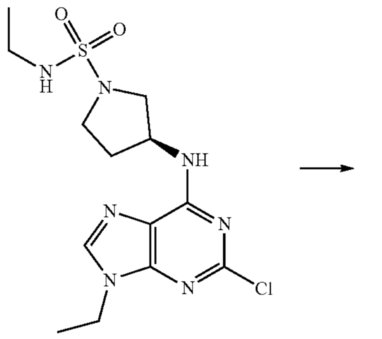

Intermediate 114

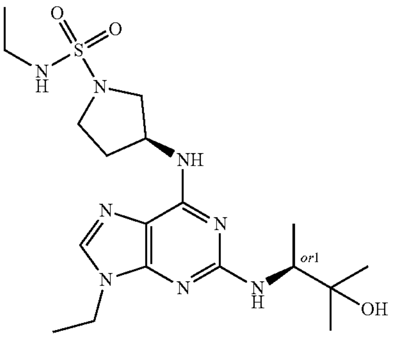

Example 59

(S)-3-((2-chloro-9-ethyl-9H-purin-6-yl)amino)-N-ethylpyrrolidine-1-sulfonamide (Intermediate 114, 300 mg, 0.80 mmol) was added to rac-(R)-3-amino-2-methylbutan-2-ol (124 mg, 1.20 mmol), sodium tert-butoxide (231 mg, 2.41 mmol) and Pd-PEPPSI-IPentCl o-picoline (2-methylpyridine) precatalyst (67.4 mg, 0.08 mmol) in dioxane (3 mL) under nitrogen. The resulting mixture was stirred at 90° C. for 5 hours. The reaction mixture was concentrated and diluted with DCM (100 mL), and washed sequentially with water (75 mL×1) and saturated aq. brine solution (100 mL×1). The organic layer was dried over $Na_2SO_4$, filtered and evaporated to afford crude product. The crude product was purified by preparative HPLC, Column: XBridge Shield RP18 OBD Column, 30*150 mm, 5 μm; Mobile Phase A: Water (10 mmol/L $NH_4HCO_3$+0.1% $NH_3 \cdot H_2O$), Mobile Phase B: ACN; Flow rate: 60 mL/min; 14-67% ACN in water. Fractions containing the desired compound were evaporated to dryness to afford the racemic product. The racemic product was purified by preparative chiral-HPLC, Column: CHIRALPAK IA-3, 4.6*50 mm, 3 μm; Mobile Phase A: (Hex:DCM=3:1) (0.1% DEA):EtOH=90:10; Flow rate: 1 mL/min. The fractions containing the desired compound were evaporated to dryness to afford (S)—N-ethyl-3-((9-ethyl-2-(((R*)-3-hydroxy-3-methylbutan-2-yl)amino)-9H-purin-6-yl)amino)pyrrolidine-1-sulfonamide (Isomer 1, 76 mg, 21.50%) and (S)—N-ethyl-3-((9-ethyl-2-(((R*)-3-hydroxy-3-methylbutan-2-yl)amino)-9H-purin-6-yl)amino)pyrrolidine-1-sulfonamide (Example 59, Isomer 2, 5.50 mg, 1.56%). $^1$H NMR (400 MHz, DMSO-$d_6$) 1.02-1.13 (13H, m), 1.34 (3H, t), 2.04 (1H, s), 2.15-2.23 (1H, m), 2.90-3.01 (2H, m), 3.05-3.14 (1H, m), 3.14-3.27 (1H, m), 3.34-3.42 (1H, m), 3.50-3.58 (1H, m), 3.89-4.00 (3H, m), 4.01 (1H, d), 4.52 (1H, s), 5.77 (1H, br s), 7.08 (1H, br t), 7.74 (1H, s); m/z (ES$^+$) [M+H]$^+$=441.

Example 60: (S)—N-ethyl-3-((3-ethyl-5-(((2R,3S)-2-hydroxypentan-3-yl)amino)-3H-imidazo[4,5-b]pyridin-7-yl)amino)pyrrolidine-1-sulfonamide

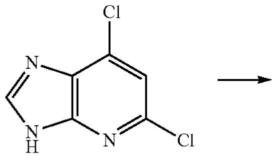

Intermediate 115

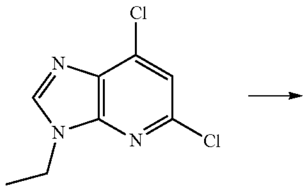

Intermediate 116

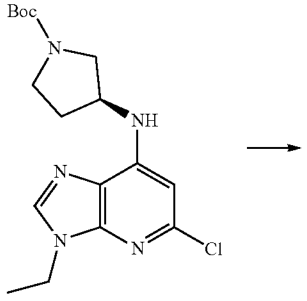

Intermediate 117

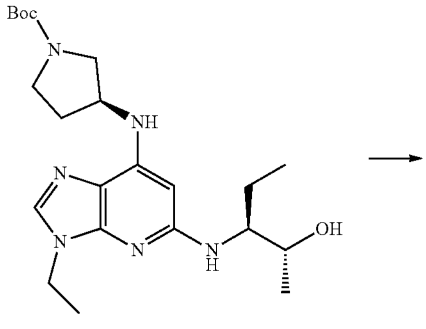

Intermediate 118

-continued

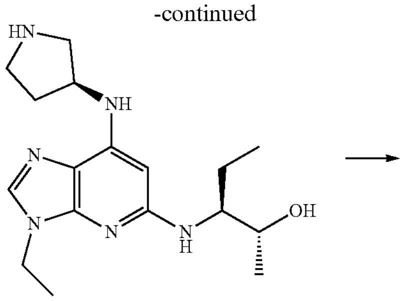

Intermediate 119

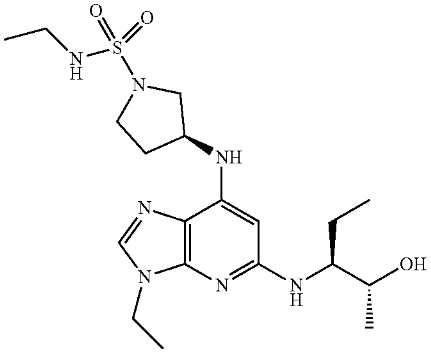

Example 60

Intermediate 116: 5,7-dichloro-3-ethyl-3H-imidazo[4,5-b]pyridine

DIAD (9.31 mL, 47.87 mmol) was added to ethanol (4.41 g, 95.74 mmol), triphenylphosphine (16.74 g, 63.83 mmol) and 5,7-dichloro-3H-imidazo[4,5-b]pyridine (Intermediate 115, 6 g, 31.91 mmol) in THF (40 mL) at 0° C. under nitrogen. The resulting mixture was warmed up and stirred at 25° C. for 2 hours. The solvent was removed under reduced pressure. The crude product was purified by preparative chiral SFC, Column: GreenSep Naphthyl, 3*25 cm, 5 μm; Mobile Phase A: $CO_2$, Mobile Phase B: MeOH (0.1% 2 M $NH_3$-MeOH); Flow rate: 60 mL/min; Gradient: isocratic 20% B; Column Temperature (° C.): 35; Back Pressure (bar): 100. The fractions containing the desired compound were evaporated to dryness to afford 5,7-dichloro-3-ethyl-3H-imidazo[4,5-b]pyridine (Intermediate 116, 3.50 g, 50.8%) as a yellow solid. $^1$H NMR (400 MHz, DMSO-$d_6$) 1.43 (3H, t), 4.27 (2H, q), 7.53 (1H, d), 8.61 (1H, d); m/z ($ES^+$) $[M+H]^+$=216.

Intermediate 117: (S)-tert-butyl 3-(5-chloro-3-ethyl-3H-imidazo[4,5-b]pyridin-7-ylamino)pyrrolidine-1-carboxylate 5,7-Dichloro-3-ethyl-3H-imidazo[4,5-b]pyridine (Intermediate 116, 800 mg, 3.70 mmol) was added to tert-butyl (S)-3-aminopyrrolidine-1-carboxylate (3448 mg, 18.51 mmol) and DIEA (6.47 mL, 37.03 mmol) in n-butanol (6 mL). The resulting mixture was stirred at 140° C. for 3 days. The reaction mixture was concentrated and diluted with EtOAc (150 mL), and washed sequentially with saturated aq. $NH_4Cl$ solution (100 mL×1) and saturated aq. brine solution (100 mL×1). The organic layer was dried over $Na_2SO_4$, filtered and evaporated to afford crude product. The crude product was purified by flash C18 chromatography, elution gradient 10 to 70% MeCN in $NH_4HCO_3$ (0.1% in water). Pure fractions were evaporated to dryness to afford tert-butyl (S)-3-((5-chloro-3-ethyl-3H-imidazo[4,5-b]pyridin-7-yl)amino)pyrrolidine-1-carboxylate (Intermediate 117, 2000 mg, 148%, contains residual solvent) as a brown solid. m/z ($ES^+$) $[M+H]^+$=366.

Intermediate 118: (S)-tert-butyl 3-(3-ethyl-5-((2R,3S)-2-hydroxypentan-3-yl-amino)-3H-imidazo[4,5-b]pyridin-7-ylamino)pyrrolidine-1-carboxylate tert-Butyl (S)-3-((5-chloro-3-ethyl-3H-imidazo[4,5-b]pyridin-7-yl)amino)pyrrolidine-1-carboxylate (Intermediate 117, 400 mg, 1.09 mmol) was added to (2R,3S)-3-aminopentan-2-ol (338 mg, 3.28 mmol), cesium carbonate (2137 mg, 6.56 mmol) and 2-(di-tert-butylphosphino)-2',4',6'-triisopropyl-3,6-dimethoxy-1,1'-biphenyl (53.0 mg, 0.11 mmol) and tBuBrettPhos Pd G3 (104 mg, 0.11 mmol) in 3-methyl-3-pentanol (4 mL) under nitrogen. The resulting mixture was stirred at 140° C. for 2 hours. The reaction mixture was filtered through activated charcoal and concentrated. The crude product was purified by flash C18 chromatography, elution gradient 10 to 70% MeCN in $NH_4HCO_3$ (0.1% in water). Pure fractions were evaporated to dryness to afford tert-butyl (S)-3-((3-ethyl-5-(((2R,3S)-2-hydroxypentan-3-yl)amino)-3H-imidazo[4,5-b]pyridin-7-yl)amino)pyrrolidine-1-carboxylate (Intermediate 118, 350 mg, 74.0%) as a brown solid. $^1$H NMR (400 MHZ, DMSO-$d_6$) 0.89 (3H, t), 1.05 (3H, d), 1.30-1.45 (13H, m), 1.57-1.72 (1H, m), 1.93-2.05 (1H, m), 2.08-2.18 (1H, m), 3.20 (1H, br dd), 3.26-3.32 (1H, m), 3.40-3.49 (1H, m), 3.55-3.74 (3H, m), 4.01 (2H, q), 4.19-4.35 (1H, m), 5.12 (1H, br s), 5.61 (1H, s), 5.82 (1H, br t), 6.29 (1H, br t), 7.69 (1H, s); m/z ($ES^+$) $[M+H]^+$=433.

Intermediate 119: (2R,3S)-3-(3-ethyl-7-((S)-pyrrolidin-3-ylamino)-3H-imidazo[4,5-b]pyridin-5-ylamino)pentan-2-ol hydrochloride tert-Butyl (S)-3-((3-ethyl-5-(((2R,3S)-2-hydroxypentan-3-yl)amino)-3H-imidazo[4,5-b]pyridin-7-yl)amino)pyrrolidine-1-carboxylate (Intermediate 118, 300 mg, 0.69 mmol) was added to HCl in MeOH (5 mL, 30.00 mmol, 6 M). The resulting mixture was stirred at 25° C. for 16 hours. The solvent was removed under reduced pressure and afford (2R,3S)-3-((3-ethyl-7-(((S)-pyrrolidin-3-yl)amino)-3H-imidazo[4,5-b]pyridin-5-yl)amino)pentan-2-ol. HCl (Intermediate 119, 200 mg, 78%) as a yellow solid. m/z ($ES^+$) $[M+H]^+$=333.

Example 60: (S)—N-ethyl-3-((3-ethyl-5-(((2R,3S)-2-hydroxypentan-3-yl)amino)-3H-imidazo[4,5-b]pyridin-7-yl)amino)pyrrolidine-1-sulfonamide

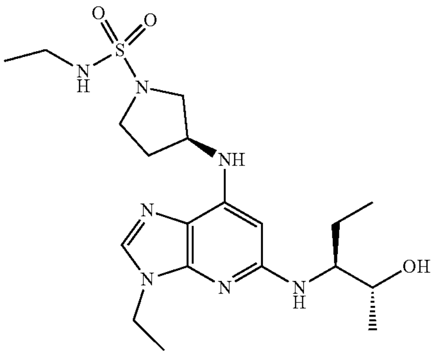 [SMILES: CCNS(=O)(=O)N1CC[C@H](Nc2cc(N[C@@H](CC)[C@@H](C)O)nc3c2ncn3CC)C1]

Ethylsulfamoyl chloride (14.04 mg, 0.10 mmol) was added to (2R,3S)-3-((3-ethyl-7-(((S)-pyrrolidin-3-yl)amino)-3H-imidazo[4,5-b]pyridin-5-yl)amino)pentan-2-ol. HCl (Intermediate 119, 65 mg, 0.18 mmol) and DIEA (0.341 mL, 1.96 mmol) in DCM (3 mL). The resulting mixture was stirred at −78° C. for 15 minutes. The reaction mixture was concentrated and diluted with DCM (100 mL), and washed sequentially with saturated aq. $NH_4Cl$ solution (50 mL×2) and saturated aq. brine solution (100 mL×1). The organic layer was dried over $Na_2SO_4$, filtered and evaporated to afford crude product. The crude product was purified by preparative HPLC, Column: Xselect CSH C18 OBD Column 30*150 mm 5 μm; Mobile Phase A: Water (0.1% FA), Mobile Phase B: ACN; Flow rate: 60 mL/min; Gradient: 5-25% ACN in water. Fractions containing the desired compound were evaporated to dryness to afford (S)—N-ethyl-3-((3-ethyl-5-(((2R,3S)-2-hydroxypentan-3-yl)amino)-3H-imidazo[4,5-b]pyridin-7-yl)amino)pyrrolidine-1-sulfonamide (Example 60, 7.00 mg, 9.01%). $^1H$ NMR (400 MHZ, DMSO-$d_6$) 0.88 (3H, t), 1.00-1.10 (6H, m), 1.30-1.45 (4H, m), 1.65 (1H, ddd), 2.02 (1H, dt), 2.24 (1H, dq), 2.89-3.01 (2H, m), 3.09 (1H, dd), 3.23 (1H, dt), 3.37 (1H, m), 3.52 (1H, dd), 3.61-3.73 (2H, m), 4.00 (2H, q), 4.36 (1H, br s), 5.15 (1H, br s), 5.59 (1H, s), 5.82 (1H, d), 6.29 (1H, d), 7.09 (1H, t), 7.69 (1H, s); m/z (ES$^+$) [M+H]$^+$=440.

Example 61: (R)-2-((6-(((3R*,4R*)-1-((1H-imidazol-2-yl)sulfonyl)-4-fluoro-pyrrolidin-3-yl)amino)-9-(difluoromethyl)-9H-purin-2-yl)amino)-2-cyclopropylethan-1-ol

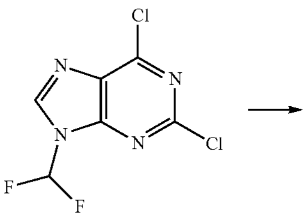

Intermediate 16

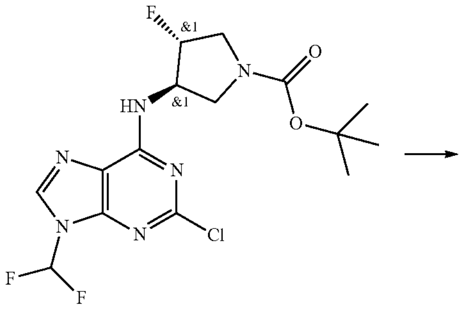

Intermediate 113

-continued

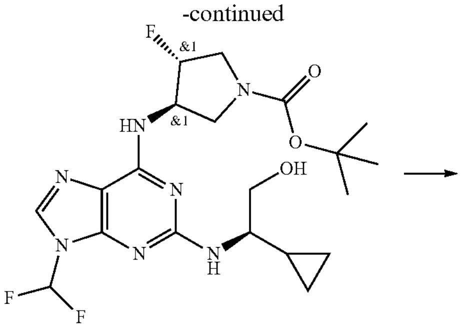

Intermediate 120

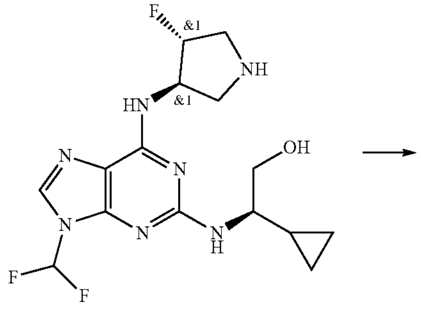

Intermediate 121

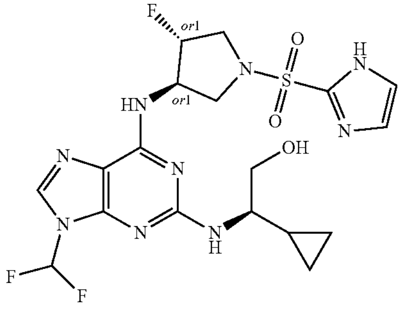

Example 61

Intermediate 113: rac-tert-butyl (3R,4R)-3-((2-chloro-9-(difluoromethyl)-9H-purin-6-yl)amino)-4-fluoropyrrolidine-1-carboxylate rac-tert-Butyl (3R,4R)-3-amino-4-fluoropyrrolidine-1-carboxylate (1.025 g, 5.02 mmol) was added to 2,6-dichloro-9-(difluoromethyl)-9H-purine (Intermediate 16, 1.00 g, 4.18 mmol) in acetonitrile (10 mL), N,N-diisopropylethylamine (2.186 ml, 12.55 mmol) was added and the reaction mixture was stirred and heated at 90° C. in a reaction vial for 3 h. The crude mixture was diluted with dichloromethane (50 mL) and washed with water (50 mL×2), then brine (50 mL×1) and the organic layer was dried over sodium sulfate. The crude mixture was purified by flash silica chromatography (Biotage®Sfär Silica HC), elution gradient 5-100% ethyl acetate in hexanes to yield rac-tert-butyl (3R,4R)-3-((2-chloro-9-(difluoromethyl)-9H-purin-6-yl)amino)-4-fluoro-pyrrolidine-1-carboxylate (Intermediate 113, 0.673 g, 39.5%) contaminated with the diethyl (bromodifluoromethyl)phosphonate from the previous reaction (~30% by $^1H$ NMR integration). $^1H$ NMR (500 MHz, DMSO-$d_6$) 1.41 (9H, s), 3.38-3.76 (4H, overlapped), 4.60-4.80 (1H, m), 5.19 (1H, d), 7.97 (1H, t), 8.62 (1H, s), 8.93-9.13 (1H, m); m/z (ES$^-$) [M−H]$^-$=405.

Intermediate 120: tert-butyl (3RS, 4RS)-3-((2-(((R)-1-cyclopropyl-2-hydroxyethyl)-amino)-9-(difluoromethyl)-9H-purin-6-yl)amino)-4-fluoropyrrolidine-1-carboxylate rac-tert-Butyl (3R,4R)-3-((2-chloro-9-(difluoromethyl)-9H-purin-6-yl)amino)-4-fluoropyrrolidine-1-carboxylate (Intermediate 113, 673 mg, 1.65 mmol), (R)-2-amino-2-cyclopropylethan-1-ol hydrochloride (455 mg, 3.31 mmol), cesium carbonate (1887 mg, 5.79 mmol), 2-(dicyclohexylphosphino)-3,6-dimethoxy-2'-4'-6'-tri-i-propyl-1,1'-biphenyl (266 mg, 0.50 mmol), and palladium(II) acetate (37.1 mg, 0.17 mmol) were added to a reaction vial under nitrogen. The vial was evacuated and filled with nitrogen 2 times then tert-butanol (4.73 mL) was added, and the reaction was sealed, and heated at 90° C. for 16 h with stirring. The reaction was diluted with ethyl acetate (50 mL) and washed with water (50 mL×2). The organic layer was dried over sodium sulfate, filtered and the filtrate concentrated in vacuo. The resulting residue was purified by flash silica chromatography (Biotage®Sfär Silica HC), elution gradient 0 to 100% ethyl acetate in hexanes. Product fractions were concentrated in vacuo to afford tert-butyl (3RS,4RS)-3-((2-(((R)-1-cyclopropyl-2-hydroxyethyl)amino)-9-(difluoromethyl)-9H-purin-6-yl)amino)-4-fluoropyrrolidine-1-carboxylate (Intermediate 120, 278 mg, 36%). $^1$H NMR (500 MHz, DMSO-$d_6$) 0.12-0.48 (5H, overlapped), 0.93-1 (1H, m), 1.41 (9H, s), 3.40-3.76 (7H, overlapped), 4.50-4.84 (2H, overlapped), 5.05-5.34 (1H, m), 6.44 (1H, br s), 7.69 (1H, t), 8.09 (1H, s); m/z (ES$^+$) [M+H]$^+$=472.

Intermediate 121: (R)-2-cyclopropyl-2-((9-(difluoromethyl)-6-(((3RS, 4RS)-4-fluoropyrrolidin-3-yl)amino)-9H-purin-2-yl)amino)ethan-1-ol A 4 M solution of hydrogen chloride in 1,4-dioxane (0.884 mL, 3.54 mmol) was added to a stirred solution of tert-butyl (3RS,4RS)-3-((2-(((R)-1-cyclopropyl-2-hydroxyethyl)amino)-9-(difluoromethyl)-9H-purin-6-yl)amino)-4-fluoropyrrolidine-1-carboxylate (Intermediate 120, 278 mg, 0.59 mmol) in 1,4-dioxane (5 ml) at rt and the resulting solution was stirred at rt for 16 h. The reaction mixture was concentrated in vacuo and dried to afford (R)-2-cyclopropyl-2-((9-(difluoromethyl)-6-(((3RS,4RS)-4-fluoropyrrolidin-3-yl)amino)-9H-purin-2-yl)amino)ethan-1-ol hydrochloride (Intermediate 121, 231 mg, 96%). This compound was subjected to the next step without further purification. m/z (ES$^-$) [M−H]$^-$=370.

Example 61: (R)-2-((6-(((3R*,4R*)-1-((1H-imidazol-2-yl)sulfonyl)-4-fluoropyrrolidin-3-yl)amino)-9-(difluoromethyl)-9H-purin-2-yl)amino)-2-cyclopropylethan-1-ol

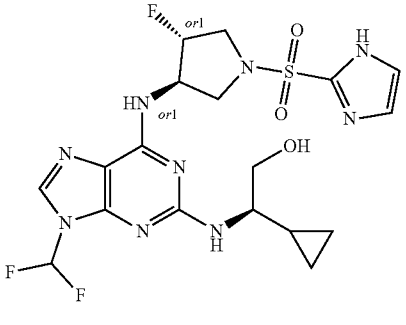 [SMILES: O=S(=O)(c1ncc[nH]1)N1C[C@@H](F)[C@H](Nc2nc(N[C@@H](CO)C3CC3)nc3c2ncn3C(F)F)C1]

Triethylamine (0.359 mL, 2.83 mmol) was added to a stirred solution of (R)-2-cyclopropyl-2-((9-(difluoromethyl)-6-(((3RS,4RS)-4-fluoropyrrolidin-3-yl)amino)-9H-purin-2-yl)amino)ethan-1-ol hydrochloride (Intermediate 121, 231 mg, 0.57 mmol) in dichloromethane (5 mL) and the reaction mixture was cooled to −78° C. 1H-imidazole-2-sulfonyl chloride, hydrochloride (125 mg, 0.62 mmol) was added in solid portions of 25 mg over the course of 1 hour at −78° C. while monitoring by UPLC (reaction complete in about 1 h). The reaction mixture was quenched with saturated sodium bicarbonate solution (10 mL) and stirred for 15 minutes at rt. The reaction mixture was extracted with dichloromethane (10 mL×3) and the combined organic layers dried over magnesium sulfate. Solvent was removed in vacuo and the resulting crude material was purified by flash silica chromatography (Biotage®Sfär Silica HC), elution gradient 0 to 20% methanol in dichloromethane. Product fractions were concentrated in vacuo to afford a mixture of diastereomers which were purified by SFC (Chiralpak AD 4.6 mm×100 mm 3 μM $CO_2$/methanol with 0.2% $NH_4OH$) to yield (R)-2-((6-(((3R*,4R*)-1-((1H-imidazol-2-yl)sulfonyl)-4-fluoropyrrolidin-3-yl)amino)-9-(difluoromethyl)-9H-purin-2-yl)amino)-2-cyclopropylethan-1-ol (Example 61, Isomer 1, 43 mg, 15.1%); $^1$H NMR (500 MHZ, DMSO-$d_6$) 0.08-0.44 (4H, overlapped), 0.84-1.05 (1H, m), 3.40-3.89 (7H, overlapped), 4.42-4.93 (2H, overlapped), 5.19 (1H, d), 6.48 (1H, br s), 7.38 (2H, s), 7.70 (1H, t), 8.11 (1H, s), 8.46 (1H, br s), 13.68 (1H, br s); m/z (ES$^+$) [M+H]$^+$=502; and Isomer 2 (46 mg, 16.2%).

Example 62: (2R,3S)-3-((6-(((S)-1-((1H-pyrazol-5-yl)sulfonyl)pyrrolidin-3-yl)amino)-9-ethyl-9H-purin-2-yl)amino)pentan-2-ol

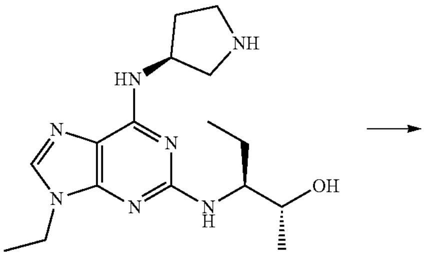

Intermediate 11

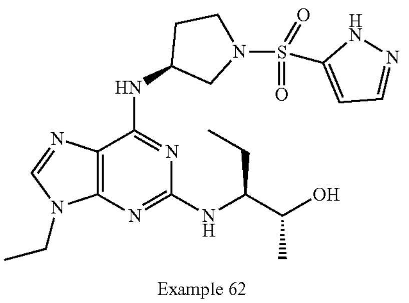

Example 62

1H-pyrazole-3-sulfonyl fluoride (19.48 mg, 0.13 mmol) in 1 mL of dichloromethane was added dropwise to a stirring solution of (2R,3S)-3-((9-ethyl-6-(((S)-pyrrolidin-3-yl)amino)-9H-purin-2-yl)amino)pentan-2-ol hydrochloride (Intermediate 11, 48 mg, 0.13 mmol) and triethylamine (36.2 μl, 0.26 mmol) in dichloromethane (5 mL) at −10° C. The reaction was warmed to room temperature and stirred over the weekend at which point the reaction showed ~60% conversion to desired product. The reaction mixture was diluted with dichloromethane (25 mL) and washed with water (25 mL×1) and brine (25 mL×1). The organic layer was dried over sodium sulfate, filtered and concentrated in vacuo. The crude mixture was purified by flash silica chromatography (Biotage®Sfär Silica HC), elution gradient 1-100% methanol in dichloromethane to yield (2R,3S)-3-((6-(((S)-1-((1H-pyrazol-5-yl)sulfonyl)pyrrolidin-3-yl)amino)-9-ethyl-9H-purin-2-yl)amino)pentan-2-ol (Example 62, 0.021 g, 34.9%). $^1$H NMR (500 MHZ, DMSO-$d_6$) 0.84 (3H, t), 1.03 (3H, d), 1.30-1.40 (4H, overlapped), 1.66-1.72 (1H, m), 1.88-1.97 (1H, m), 2.01-2.09 (1H, m), 3.12-3.15 (1H, m), 3.24-3.29 (1H, overlapped with solvent peak), 3.42-3.46 (1H, m), 3.57-3.67 (2H, m), 3.71-3.76 (1H, m), 3.96 (2H, q), 4.31-4.85 (2H, overlapped), 5.94 (1H, br s), 6.70 (1H, d), 7.38 (1H, br s), 7.70 (1H, s), 7.98 (1H, s), 13.73 (1H, br s); m/z ($ES^+$) $[M+H]^+$=464.

C. Biological Data

Example 63: CDK1, CDK2, and CDK4 Activity (NanoBRET Assay in MCF-7 Cells)

Compounds were tested in breast cancer cell line MCF-7 to assess inhibition of CDK1, CDK2, and CDK4 activity. MCF-7 cells transiently transfected with CDK1:CCNB1, CDK2:CCNE1, or CDK4:CCND1 were harvested at a density of 1E5 cells/mL in complete media, seeded 20 µL/well into 384-well Greiner 784080 plates using a Multidrop Combi, and incubated overnight at 37° C. and 5% $CO_2$. The next day media were evacuated from the wells using the Bluewasher centrifugal plate washer (Bluecatbio) and 10 µL/well phenol red free OptiMEM was then added using a Multidrop Combi. Test compounds were then dispensed into the wells using an Echo instrument (555/655, Beckman Coulter). Immediately after compound addition, a Tecan HP300 dispenser was used to dispense the relevant NanoBRET™ tracer to the CDK1 wells (12.5 nl, 400 µM, NanoBRET™ TE Tracer K-9), the CDK2 wells (12.5 nl, 200 µM, NanoBRET™ TE Tracer K-9), and the CDK4 wells (8 nl, 100 µM, NanoBRET™ TE Tracer K-7) and the plates were incubated for 2 hours at 37° C. and 5% $CO_2$. The plates were allowed to cool for 10 minutes at room temperature and 5 µL/well of TE Nano-Glo® Substrate/Inhibitor at 2.4 µM and 1:500 respectively (N2162 Promega) was added. The plates were incubated in subdued lighting for 10 minutes and then read on a Pherastar FS plate reader (BMG Technologies) using a NanoBRET™ filter module (460±80 nm/610 nm-LP). The ratio values were normalized to controls and the IC50 values of test compounds determined using Genedata Screener software.

$IC_{50}$ values for the compounds tested are reported in Table 2. The data confirm that the compounds have nanomolar potency against CDK2 and are selective for CDK2 relative to CDK1 and CDK4.

TABLE 2

| Example | CDK2 $IC_{50}$[1] (µM) | CDK1 $IC_{50}$[1] (µM) | CDK4 $IC_{50}$[1] (µM) |
|---|---|---|---|
| 1 | 0.017 | 0.236 | 11.9 |
| 2 | 0.029 | 0.904 | 17.8 |
| 3 | 0.018 | 0.636 | 12.8 |
| 4 | 0.020 | 1.166 | 17.7 |
| 5 | 0.018 | 0.900 | 18.5 |
| 6 | 0.009 | 0.528 | 9.4 |
| 7 | 0.013 | 0.591 | 19.1 |
| 8 | 0.114 | 8.095 | >29.7 |
| 9 | 0.100 | 2.213 | 20.2 |
| 10 | 0.100 | 4.616 | >23.1 |
| 11 | 0.079 | 1.535 | 10.1 |
| 12 | 0.088 | 7.484 | >29.7 |
| 13 | 0.013 | 0.660 | 11.2 |
| 14 | 0.006 | 0.098 | 1.0 |
| 15 | 0.022 | 1.216 | 2.6 |
| 16 | 0.093 | 1.602 | 17.2 |
| 17 | 0.009 | 0.114 | 1.2 |
| 18 | 0.019 | 0.641 | 11.0 |
| 19 | 0.027 | 0.342 | 5.8 |
| 20 | 0.013 | 0.566 | 5.0 |
| 21 | 0.049 | 3.830 | >29.7 |
| 22 | 0.047 | 2.191 | 17.8 |
| 23 | 0.057 | 2.598 | >29.7 |
| 24 | 0.038 | 5.207 | 19.9 |
| 25 | 0.069 | 3.993 | >29.7 |
| 26 | 0.039 | 0.651 | 8.1 |
| 27 | 0.011 | 1.418 | 3.4 |
| 28 | 0.020 | 0.419 | 6.1 |
| 29 | 0.090 | 3.703 | >29.7 |
| 30 | 0.019 | 0.746 | 5.7 |
| 31 | 0.039 | 6.288 | >29.7 |
| 32 | 0.082 | 2.214 | 28.0 |
| 33 | 0.026 | 5.754 | 8.1 |
| 34 | 0.012 | 0.844 | 11.8 |
| 35 | 0.052 | 6.083 | 11.2 |
| 36 | 0.050 | 2.021 | >29.7 |
| 37 | 0.061 | 4.593 | >29.7 |
| 38 | 0.021 | 1.038 | 6.0 |
| 39 | 0.033 | 0.562 | 4.0 |
| 40 | 0.024 | 0.587 | 4.3 |
| 41 | 0.019 | 0.663 | 7.7 |
| 42 | 0.027 | 0.875 | 4.5 |
| 43 | 0.011 | 0.557 | 5.2 |
| 44 | 0.026 | 1.011 | 18.4 |
| 45 | 0.039 | 1.886 | >29.7 |
| 46 | 0.192 | 8.373 | 23.7 |
| 47 | 0.035 | 0.562 | 7.4 |
| 48 | 0.123 | 5.550 | >23.8 |
| 49 | 0.013 | 0.907 | 4.4 |
| 50 | 0.064 | 2.347 | 14.2 |
| 51 | 0.032 | 0.532 | 1.9 |
| 52 | 0.021 | 1.204 | 16.8 |
| 53 | 0.043 | 1.796 | >29.7 |
| 54 | 0.075 | 2.189 | >27.4 |
| 55 | 0.017 | 0.680 | 8.4 |
| 56 | 0.069 | 1.504 | 22.0 |
| 57 | 0.011 | 0.186 | 1.5 |
| 58 | 0.017 | 0.671 | 1.7 |
| 59 | 0.037 | 1.686 | 11.4 |
| 60 | 0.014 | 0.426 | 2.5 |
| 61 | 0.005 | 0.115 | 0.8 |
| 62 | 0.019 | 3.261 | >29.7 |
| Comparative Example A[2] | 0.011 | 5.723 | 2.6 |

[1]$IC_{50}$ is reported after a single measurement (n = 1) or as an average for multiple measurements (n > 1).
[2]Comparative Example A is fadraciclib (CYC065).

Example 64: NPM Phosphorylation (Imaging Assay in MCF-7 Cells)

Compounds were tested to assess the effects of CDK2 inhibition in a cellular context. Specifically, phosphorylation of nucleophosmin (NPM) was measured to determine whether the compounds downregulated NPM phosphorylation in MCF-7 cells. During the cell cycle, the CDK2-cyclin E complex phosphorylates NPM at Thr199 which is a prerequisite step for initiation of centrosome duplication.

MCF-7 cells at a density of 2.5E5 cells/mL in complete media were seeded 40 µL/well into 384-well Greiner 781090 plates using a Multidrop Combi and incubated overnight at 37° C. and 5% $CO_2$. Test compounds were then dispensed into the wells using an Echo instrument (555/655, Beckman Coulter) and the plates were incubated for 2 hours at 37° C. and 5% $CO_2$. The cells were fixed by addition of 40 μL/well of 8% paraformaldehyde and incubated at room temperature for 10 minutes. The plates were washed three times with 50 L/well PBS using a Biotek EL406 plate washer and then permeabilized for 10 minutes at room temperature in 0.3% Triton X100 in PBS. After washing as before, the plates were blocked using 30 μL/well of 2% BSA (w/v) in PBS-T for at least 30 minutes at room temperature. Following aspiration of the blocking solution, the plates were sealed and incubated overnight at 4° C. in 20 μL/well primary antibody (CST #3541, 1/400 in PBS-T with 0.05% BSA). The plates were washed three times with 50 μL/well PBS-T, and then incubated in 20 μL/well of secondary antibody solution (1/500 AlexaFluor488 goat anti-rabbit IgG, (Invitrogen A11008) and 1/10000 Hoechst 33342 (Invitrogen H21492) in 0.05% BSA in PBS-T) for one hour at room temperature, shielded from light. After washing in PBS as before, leaving each well in 40 μL PBS, the plates were sealed and imaged on a Cell Insight imaging system (Thermo) with a 10× objective and 6 fields of view per well. Cells containing 4N DNA were selected using the Hoechst staining. Phospho-NPM levels were normalized to controls and the $IC_{50}$ values of test compounds determined using Genedata Screener software.

$IC_{50}$ values for the compounds tested are reported in Table 3.

TABLE 3

| Example | $IC_{50}{}^1$ (μM) |
|---|---|
| 1 | 0.551 |
| 2 | 0.301 |
| 3 | 0.233 |
| 4 | 0.164 |
| 5 | 0.204 |
| 6 | 0.061 |
| 7 | 0.086 |
| 8 | 0.655 |
| 9 | 0.432 |
| 10 | 0.481 |
| 11 | 0.607 |
| 12 | 1.078 |
| 13 | 0.173 |
| 14 | 0.041 |
| 15 | 0.231 |
| 16 | 0.368 |
| 17 | 0.011 |
| 18 | 0.108 |
| 19 | 0.133 |
| 20 | 0.194 |
| 21 | 0.326 |
| 22 | 0.453 |
| 23 | 0.484 |
| 24 | 0.528 |
| 25 | 0.624 |
| 26 | 0.435 |
| 27 | 0.267 |
| 28 | 0.181 |
| 29 | 2.194 |
| 30 | 0.198 |
| 31 | 1.047 |
| 32 | 0.607 |
| 33 | 0.752 |
| 34 | 0.381 |
| 35 | 1.220 |
| 36 | 1.230 |
| 37 | 0.879 |
| 38 | 0.392 |
| 39 | 0.180 |
| 40 | 0.253 |
| 41 | 0.182 |
| 42 | 0.310 |
| 43 | 0.150 |
| 44 | 0.132 |
| 45 | 0.296 |
| 46 | 1.166 |
| 47 | 0.152 |
| 48 | 1.296 |
| 49 | 0.144 |
| 50 | 0.412 |
| 51 | 0.157 |
| 52 | 0.151 |
| 53 | 0.241 |
| 54 | 0.334 |
| 55 | 0.142 |
| 56 | 0.299 |
| 57 | 0.055 |
| 58 | 0.137 |
| 59 | 0.337 |
| 60 | 0.064 |
| 61 | 0.017 |
| 62 | 0.453 |
| Comparative Example A[2] | 0.228 |

[1] $IC_{50}$ is reported after a single measurement (n = 1) or as an average for multiple measurements (n > 1).
[2] Comparative Example A is fadraciclib (CYC065).

Example 65: POLR2A Ser2 Phosphorylation (Imaging Assay in MCF-7 Cells)

Compounds were tested to assess their effect on CDK9 activity in a cellular context. Specifically, phosphorylation of POLR2A Ser2 was measured to determine whether the compounds downregulated POLR2A Ser2 phosphorylation in MCF-7 cells. During the cell cycle, CDK9 is a component of a multiprotein complex that phosphorylates POLR2A Ser2 which results in transcription elongation.

MCF-7 cells at a density of 1.25E5 cells/mL in complete media were seeded, 40 μL/well, into 384-well Greiner 781090 plates using a Multidrop Combi and incubated overnight at 37° C. and 5% $CO_2$. Test compounds were then dispensed using an Echo instrument (555/655, Beckman Coulter) and the plates were incubated for 2 hours at 37° C. and 5% $CO_2$. T cells were fixed by addition of 40 μL/well of 8% paraformaldehyde and incubated for 10 minutes at room temperature. The plates were washed three times with 50 μL/well PBS using a Biotek EL406 plate washer and then permeabilized for 10 minutes at room temperature in 0.3% Triton X100 in PBS. After washing as before, the plates were blocked using 30 μL/well of 2% BSA (w/v) in PBS-T for over 30 minutes at room temperature. Following aspiration of the blocking solution, the plates were sealed and incubated overnight at 4° C. in 20 μL/well of primary antibody (CST #13499, 1/1000 in PBS-T with 0.05% BSA). The plates were washed three times with 50 μL/well of PBS-T, and then incubated in 20 μL/well of secondary antibody solution (1/500 AlexaFluor488 goat anti-rabbit IgG, (Invitrogen A11008) and 1/10000 Hoechst 33342 (Invitrogen H21492) in 0.05% BSA in PBS-T) for one hour at room temperature, shielded from light. After washing in PBS as before, leaving each well in 40 μL of PBS, the plates were sealed and imaged on a Cell Insight imaging system (Thermo) with a 10× objective and 2 fields of view per well. POLR2A Ser2 levels were normalized to controls and the $IC_{50}$ values of test compounds determined using Genedata Screener software.

$IC_{50}$ values for the compounds tested are reported in Table 4. The data confirm that the compounds are selective for CDK2 relative to CDK9.

TABLE 4

| Example | $IC_{50}$[1] (μM) |
|---|---|
| 1 | 13.3 |
| 2 | 15.4 |
| 3 | 6.5 |
| 4 | >30.0 |
| 5 | >30.0 |
| 6 | >19.3 |
| 7 | 24.2 |
| 8 | >30.0 |
| 9 | >30.0 |
| 10 | >30.0 |
| 11 | >30.0 |
| 12 | >30.0 |
| 13 | >30.0 |
| 14 | 4.2 |
| 15 | >30.0 |
| 16 | >30.0 |
| 17 | 3.9 |
| 18 | 23.6 |
| 19 | 17.6 |
| 20 | >30.0 |
| 21 | >30.0 |
| 22 | >30.0 |
| 23 | >30.0 |
| 24 | >30.0 |
| 25 | >30.0 |
| 26 | 11.4 |
| 27 | >30.0 |
| 28 | >30.0 |
| 29 | >30.0 |
| 30 | >30.0 |
| 31 | >30.0 |
| 32 | >30.0 |
| 33 | >30.0 |
| 34 | >30.0 |
| 35 | >30.0 |
| 36 | >30.0 |
| 37 | >30.0 |
| 38 | >30.0 |
| 39 | >30.0 |
| 40 | >30.0 |
| 41 | >30.0 |
| 42 | >30.0 |
| 43 | >30.0 |
| 44 | >29.1 |
| 45 | >26.7 |
| 46 | >30.0 |
| 47 | >30.0 |
| 48 | >30.0 |
| 49 | 20.2 |
| 50 | >30.0 |
| 51 | 7.4 |
| 52 | 11.1 |
| 53 | >30.0 |
| 54 | >30.0 |
| 55 | 14.4 |
| 56 | 23.9 |
| 57 | 4.4 |
| 58 | >30.0 |
| 59 | >30.0 |
| 60 | 6.1 |
| 61 | 1.7 |
| 62 | >30.0 |
| Comparative Example A[2] | 0.6 |

[1]$IC_{50}$ is reported after single measurement (n = 1) or as an average for multiple measurements (n > 1).

[2]Comparative Example A is fadraciclib (CYC065).

Example 66: Cellular Proliferation in MCF-7 and OVCAR3 Cell Lines (EdU Assay)

Compounds were tested to assess inhibition of cellular proliferation in the breast cancer cell line MCF-7 and the CCNE1-amplified ovarian cell line OVCAR3.

MCF-7 and OVCAR3 cells in RPMI supplemented with 10% Fetal bovine serum were seeded into 384-well plates (Greiner, Kremsmunster, Austria; 781091), 30 μL/well, using a WellMate. The MCF7 and OVCAR3 cells were seeded at 800 and 1200 cells/well, respectively. Test compounds were added to the wells using an Echo 555 liquid handler and the plates were placed in incubator maintained at 37° C. and 5% $CO_2$ and incubated for two days. On Day 2, an EdU assay was performed following the manufacturer's protocol (Thermo Fisher, C10351). The cells were read on an Acumen eX3 instrument. The $IC_{50}$ values of test compounds were determined in Genedata by assessing the ratio of signal intensity at 488 nm to the area of signal at 405 nm.

$IC_{50}$ values for the compounds tested are reported in Table 5.

TABLE 5

| Example | MCF-7 $IC_{50}$[1] (μM) | OVCAR3 $IC_{50}$[1] (μM) |
|---|---|---|
| 1 | 2.001 | 0.270 |
| 2 | 1.361 | 0.404 |
| 3 | 0.969 | 0.457 |
| 4 | 0.685 | 0.294 |
| 5 | 0.917 | 0.154 |
| 6 | 0.278 | 0.066 |
| 7 | 0.486 | 0.203 |
| 8 | 4.773 | 1.579 |
| 9 | 1.056 | 0.486 |
| 10 | 2.942 | 1.300 |
| 11 | 3.305 | 1.403 |
| 12 | 3.402 | 1.563 |
| 13 | 0.490 | 0.202 |
| 14 | 0.111 | 0.051 |
| 15 | 0.918 | 0.568 |
| 16 | 2.515 | 0.964 |
| 17 | — | 0.044 |
| 18 | 0.482 | 0.169 |
| 19 | 0.538 | 0.276 |
| 20 | 0.665 | 0.224 |
| 21 | 1.452 | 0.578 |
| 22 | 1.437 | 0.298 |
| 23 | 1.954 | 0.495 |
| 24 | 2.930 | 0.856 |
| 25 | 1.427 | 0.642 |
| 26 | 0.960 | 0.496 |
| 27 | 0.839 | 0.337 |
| 28 | 0.699 | 0.186 |
| 29 | 2.415 | 1.376 |
| 30 | 0.785 | 0.191 |
| 31 | 3.161 | 0.964 |
| 32 | 3.009 | 0.688 |
| 33 | 2.972 | 0.880 |
| 34 | 1.147 | 0.487 |
| 35 | 3.326 | 1.622 |
| 36 | 3.013 | 1.246 |
| 37 | 2.792 | 1.296 |
| 38 | 2.309 | 0.782 |
| 39 | 0.658 | 0.288 |
| 40 | 2.714 | 6.719 |
| 41 | 0.746 | 0.327 |
| 42 | 0.925 | 0.428 |
| 43 | 0.328 | 0.291 |
| 44 | 0.592 | 0.242 |
| 45 | 0.944 | 0.359 |
| 46 | 3.171 | 1.373 |
| 47 | 0.705 | 0.185 |
| 48 | 3.330 | 2.354 |

TABLE 5-continued

| Example | MCF-7 $IC_{50}$[1] (μM) | OVCAR3 $IC_{50}$[1] (μM) |
|---|---|---|
| 49 | 0.775 | 0.383 |
| 50 | 2.764 | 1.218 |
| 51 | 0.536 | 0.324 |
| 52 | 1.020 | 0.252 |
| 53 | 1.427 | 0.616 |
| 54 | 1.370 | 0.756 |
| 55 | 0.514 | 0.147 |
| 56 | 1.179 | 0.519 |
| 57 | 0.200 | 0.155 |
| 58 | 0.874 | 0.431 |
| 59 | 1.775 | 0.950 |
| 60 | 0.637 | 0.089 |
| 61 | | 0.053 |
| 62 | 1.396 | 0.441 |
| Comparative Example A[3] | 0.294 | 0.316 |

[1]$IC_{50}$ is reported after a single measurement (n = 1) or as an average for multiple measurements (n > 1).
[2]Comparative Example A is fadraciclib (CYC065).

Example 67: Effect on Cell Cycle in OVCAR3 Cell Line (24 Hours Compound Dosing)

Compounds were tested in the CCNE1-amplified ovarian cell line OVCAR3 to assess their effect on cell cycle phases G1 and S and potential off-target effects on cell cycle phases G2 and M.

OVCAR3 cells were seeded at 60,000 cells per well in 24 well plates, 4 wells per sample, in RPMI with 10% Fetal bovine serum. Test compounds were diluted in 96 well plates in dimethyl sulfoxide (DMSO) and then added to the wells containing the cells. The 24 well plates were placed in an incubator maintained at 37° C. and 5% $CO_2$ and incubated for 20 to 24 hours. The next day an EdU assay was performed following the manufacturer's protocol (Thermo Fisher, C10425 EdU Alexa Fluor 488). Antibody staining was carried out using PE Mouse Anti-Cleaved PARP (BD Biosciences Catalog No. 552933) and 4',6-diamidino-2-phenylindole (DAPI). Cells were then analyzed by flow cytometry.

Figure 1B:
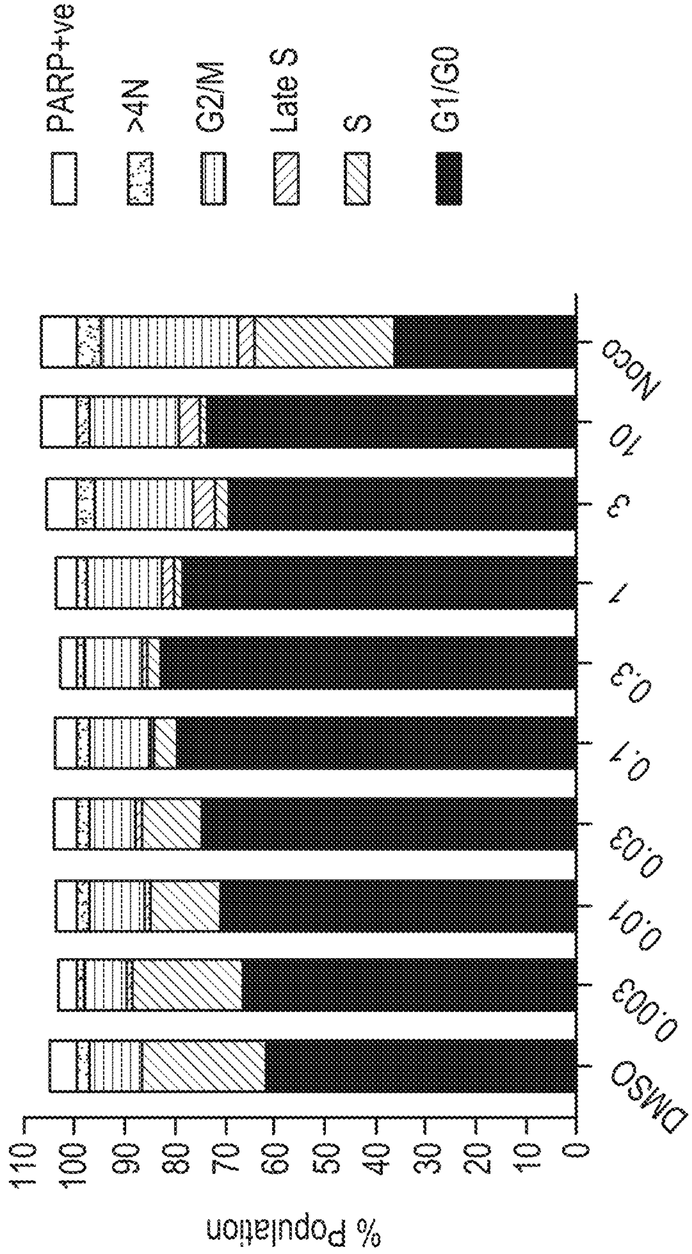

The compounds tested induced G1/S cell cycle arrest, inhibited pRB phosphorylation, and inhibited cell proliferation. FIGS. 1A and 1B illustrate the effect on cell cycle phase in OVCAR3 cells after treatment with control (DMSO), nocodazole, or the compounds of Example 6 (FIG. 1A) and Example 20 (FIG. 1B) at test compound concentrations of 0.003, 0.01, 0.03, 0.1, 0.3, 1, and 3 μM. For convenience, the compounds of Example 6 and Example 20 are subsequently referred to as Compound 6 and Compound 20, respectively, in this Example and the following Examples. Treatment of the OVCAR3 cells with Compound 6 and Compound 20 at concentrations of 0.03, 0.1, 0.3, 1, and 3 μM increased the population of cells in the G0 and G1 phases.

Example 68: pRB Phosphorylation in OVCAR3 Cell Line (Western Blot Analysis)

Compounds were analyzed by Western blot to assess inhibition of pRB phosphorylation in the CCNE1-amplified ovarian cell line OVCAR3. pRB is a tumor suppressor protein that inhibits cell cycle progression. Once hyperphosphorylated, however, pRB is inactivated and the cell cycle can proceed.

On Day 1, OVCAR3 cells were seeded at 60K cells per well in 24 well plates in RPMI with 10% Fetal bovine serum. Test compounds were diluted in 96 well plates in DMSO and then added to the cells. The treated cells were placed in an incubator maintained at 37° C. and 5% $CO_2$ and incubated for 20 to 24 hours. On Day 2, the cells were rinsed once with phosphate buffer saline (PBS) and scraped to 1% SDS lysing buffer. The protein lysate was quantified using a Pierce™ BCA Protein Assay Kit (Thermo Fisher 23225). An equal microgram of proteins was diluted in 1× Novex LDS Sample Buffer (Thermo Fisher NP0008) supplemented with reducing agent (Thermo Fisher NP0009). The gel samples were loaded into NuPAGE 4 to 12% Bis-Tris buffer and electrophoresis run at 200 volts. The samples were then transferred to Nitrocellulose by standard Wet Transfer method in 1× NuPAGE transfer buffer 10% MeOH. The membranes were blocked for one hour in blocking buffer containing 5% milk in PBST (0.2% Tween in PBS). The blots were incubated with primary antibody Anti-Rb (phospho S780) antibody (Abcam ab 173289) in blocking buffer for overnight at 4° C. After washing three times in PBST, the membranes were incubated into secondary antibody (CST Anti-rabbit IgG, HRP-linked Antibody #7074) in blocking buffer at room temperature for one hour. After washing three times in PBST, the signals were developed using SuperSignal™ West Dura Extended Duration Substrate (Thermo Fisher 3707) and imaged in chemiluminescence imager.

Figure 2A:
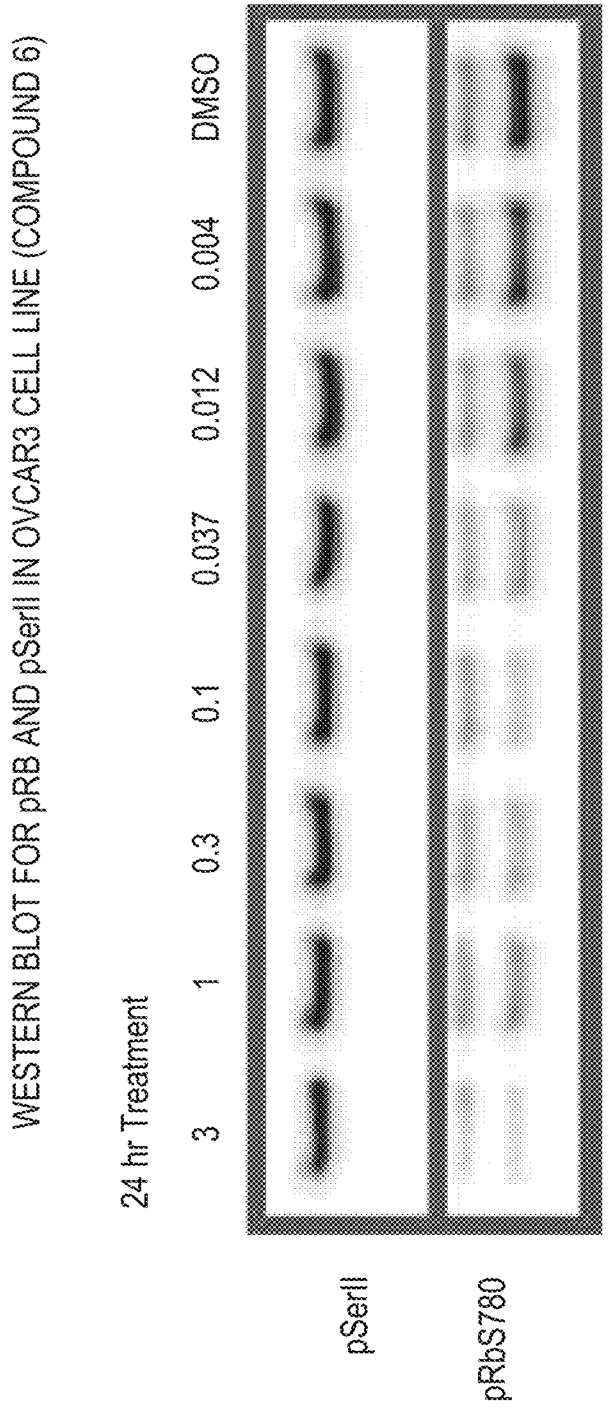
FIG. 2A corresponds to treatment with the compound of Example 6.
Figure 2B:
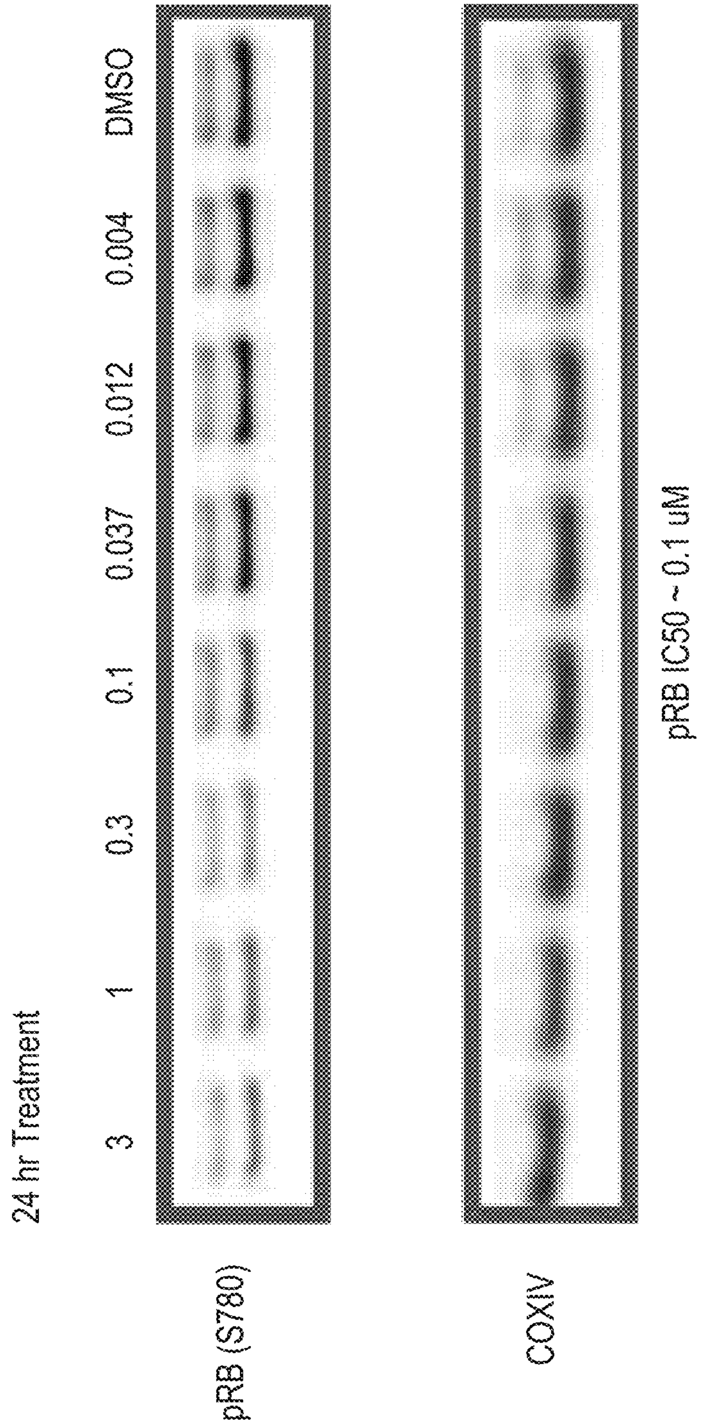
FIG. 2B corresponds to treatment with the compound of Example 20.

The Western blots showed that the compounds tested downregulate pRB phosphorylation in the OVCAR3 cell line and provided further confirmation of the cell cycle effects reported in Example 67. FIGS. 2A and 2B illustrate Western blots for OVCAR3 cells after treatment with Compound 6 and Compound 20, respectively, at concentrations of 0.004, 0.012, 0.037, 0.1, 0.3, 1, and 3 μM.

Compound 6 was similarly analyzed by Western blot to assess modulation of pSer2 of RNAPII, a CDK9 phosphosubstrate. No modulation of pSer2 of RNAPII was observed for Compound 6 indicating that Compound 6 was not impacting CDK9 activity. COXIV shown in FIG. 2B was a loading control.

Example 69: Cell Proliferation in OVCAR3 and SKOV3 Cell Lines (CyQUANT™ Assay)

An imaging-based assay was used to investigate changes in cell number in OVCAR3 cells (CCNE1-amplified ovarian cancer cell line) and SKOV3 cells (non-amplified ovarian cancer cell line) treated with test compounds.

Cells were plated in 384 well plates (Perkin-Elmer 6057300) in RPMI-1640/10% FBS/1× L-Glu at 500 cells per well in 30 μL and incubated with test compound at 37° C. and 5% $CO_2$ for 7 days. Cells were then stained using the CyQuant Direct Cell Proliferation Assay Kit (Thermo Cat #C7026) in accordance with the kit protocol. The stained cells were imaged using an Operetta high content imager to generate cell counts and $IC_{50}$ values were calculated relative to DMSO controls.

$IC_{50}$ values for the compounds tested are reported in Table 6. The compounds inhibited cellular proliferation in the CCNE-1 amplified OVCAR3 cells more potently than in the non-amplified SKOV3 cell line.

TABLE 6

| Example | OVCAR3 $IC_{50}$[1] (μM) | SKOV3 $IC_{50}$[1] (μM) |
|---|---|---|
| 6 | 0.077 | 1.965 |
| 17 | 0.053 | 1.163 |

TABLE 6-continued

| Example | OVCAR3 $IC_{50}$[1] (μM) | SKOV3 $IC_{50}$[1] (μM) |
|---|---|---|
| 19 | 0.201 | 4.043 |
| 20 | 0.188 | 2.523 |
| 44 | 0.133 | 9.151 |
| 53 | 0.373 | 10.697 |
| 61 | 0.034 | 0.514 |

Example 70: Cellular Proliferation in Palbociclib Resistant MCF-7 Cell Line (EdU Assay)

Compounds were tested alone or in combination with a CDK4/6 inhibitor to assess inhibition of cellular proliferation in a palbociclib resistant breast cancer cell line (MCF7-PC1). MCF-7 cells were generated to be resistant to palbociclib through chronic treatment with palbociclib over the course of about three months with increasing concentrations up to 1 μM. The resulting cells (MCF7-PC1) were then banked for use in subsequent experiments.

MCF7-PC1 cells were seeded at 750 cells per well in RPMI supplemented with 10% fetal bovine serum. Cells were plated 30 μL/well into 384-well plates (Greiner 781091) using a WellMate. Test compound (0, 0.017, 0.033, 0.167, 0.333, and 1 μM), alone or in combination with palbociclib or abemaciclib (0, 0.017, 0.033, 0.167, 0.333, or 1 μM), was added using an Echo 555 in combination matrix format, placed in incubator maintained at 37° C. and 5% $CO_2$, and incubated for 2 days. On Day 2, an EdU assay was performed following the manufacturer's protocol (Thermo Fisher, C10351). The plates were read on the Acumen eX3 instrument (SPT LabTech). The percent inhibition relative to DMSO was determined in Genedata (Genedata AG) by assessing the ratio of signal intensity at 488 nm to the area of signal at 405 nm (DAPI).

The compounds tested inhibited cellular proliferation in palbociclib resistant MCF7-PC1 cells. FIG. 3A illustrates a combination signal heatmap (% inhibition of growth signal) for palbociclib resistant MCF7-PC1 cells after treatment with Compound 6, palbociclib, or Compound 6 in combination with palbociclib. FIG. 3B illustrates a combination signal heatmap (% inhibition of growth signal) for palbociclib resistant MCF7-PC1 cells after treatment with Compound 6, abemaciclib, or Compound 6 in combination with abemaciclib. FIG. 3C illustrates a combination signal heatmap (% inhibition of growth signal) for palbociclib resistant MCF7-PC1 cells after treatment with Compound 20, palbociclib, or Compound 20 in combination with palbociclib.

Example 71: Senescence in MCF-7, MCF7-PC1, and OVCAR3 Cell Lines Galactosidase Assay)

Induction of senescence was assessed in MCF-7, MCF7-PC1, and OVCAR3 cell lines treated with test compound alone or in combination with a CDK4/6 inhibitor.

Test compound was dispensed using an Echo acoustic liquid handler into 96-well plates (PerkinElmer 96-well Cell Carrier Ultra) in a six-by-six dose response matrix to assess the combination effects of CDK2 inhibition together with CDK4/6 inhibition (palbociclib or abemaciclib) at the following concentrations after subsequent cell seeding in 200 μl of growth media: 1 μM, 0.3 μM, 0.1 μM, 0.03 μM, 0.01 μM, and vehicle (DMSO). Cells were seeded at 2000 cells per well (MCF-7) or 1200 cells per well (for MCF7-PC1 and OVCAR3) and incubated at 37° C. and 5% $CO_2$. MCF-7 and MCF7-PC1 were grown in DMEM supplemented with 10% FBS. OVCAR3 was grown in RPMI supplemented with 10% FBS. After 4 days (MCF-7) or 5 days (MCF7-PC1 and OVCAR3) of compound treatment, samples were fixed with 4% paraformaldehyde at room temperature for 15 minutes and washed three times with PBS. Cells were then stained with a fluorescent dye to detect senescence-associated ß-galactosidase (CellEvent Senescence Green detection kit, Thermo #C10850), diluted 1:1000 in the provided buffer, and incubated at 37° C. for 2 hours without $CO_2$ in accordance with the manufacturer's instructions. DNA staining was performed using Hoechst 33342, diluted 1:2500 in PBS, for 15 minutes at room temperature, followed by two washes with PBS. Sample imaging was performed on a PerkinElmer Operetta CLS at 10× magnification to detect Hoechst 33342 (nuclei) and Alexa488 (senescence stain). Image analysis was performed in Harmony 4.1 software (PerkinElmer) to identify cells based on nuclear staining. Mean Alexa488 fluorescence intensity was measured within each cell, and the average was taken across all cells observed within each well. Data were normalized for each plate so that the average of control wells (DMSO) was set to 0%, and the maximum observed value across the plate was set as 100%. Data fitting was performed using Genedata Screener (Genedata AG) and combination effect was assessed using the highest single agent (HSA) model.

Combination benefit was seen in both parental MCF-7 and palbociclib resistant MCF7-PC1 cells. An in vitro combination effect was not observed in the CCNE1-amplified OVCAR3 cell line. Senescence was induced by the test compound alone, but no effect was observed with palbociclib alone.

FIG. 4A illustrates a combination signal heatmap (% induction of senescence) for palbociclib resistant MCF7-PC1 cells after treatment with Compound 6, palbociclib, or Compound 6 in combination with palbociclib. FIG. 4B illustrates a combination signal heatmap (% induction of senescence) for palbociclib resistant MCF7-PC1 cells after treatment with Compound 6, abemaciclib, or Compound 6 in combination with abemaciclib.

FIG. 5A illustrates a combination signal heatmap (% induction of senescence) for palbociclib resistant MCF7 cells after treatment with Compound 6, palbociclib, or Compound 6 in combination with palbociclib. FIG. 5B illustrates a combination signal heatmap (% induction of senescence) for palbociclib resistant MCF7 cells after treatment with Compound 6, abemaciclib, or Compound 6 in combination with abemaciclib.

FIG. 6 illustrates a combination signal heatmap (% induction of senescence) for OVCAR3 cells after treatment with Compound 6, palbociclib, or Compound 6 in combination with palbociclib.

Example 72: Tolerability in CCNE1 Amplified Ovarian Tumor Xenograft Model OVCAR3

A tolerability study was conducted to evaluate long-term dosing of a CDK2 inhibitor in mice bearing OVCAR3 xenografts as a monotherapy or in combination with palbociclib.

A. Materials

OVCAR3 cells were grown in RPMI 1640 supplemented with 10% fetal bovine serum. Cells were harvested with 0.25% trypsin and resuspended in PBS/Matrigel (50/50).

Test compounds were formulated in Methocel E4M (hydroxypropyl methylcellulose (HPMC))/Tween 80 0.5/0.1% and adjusted to a pH between 6.0 and 8.0 to achieve a uniform suspension.

Palbociclib was formulated in water and adjusted to a pH between 3.0 and 3.5 to achieve a clear to hazy solution and dosed once daily by oral gavage.

B. Procedure

15 Million OVCAR3 human ovarian cells were implanted subcutaneously in the right flank of female CB17 SCID mice. Dosing was initiated when the average tumor volume reached approximately 200 $mm^3$ and lasted 14 days. A dose escalation approach was instituted assessing test compound dosing at 30 and 100 mg/kg with and without palbociclib compared to the vehicle (0.5% HPMC/0.1% Tween 80). This was followed by test compound dosing at 150 mg/kg with and without palbociclib compared to the vehicle. Body weight was recorded on a daily basis and reported as % change from baseline. Test compound was dosed orally twice daily 10 hours apart. Palbociclib was dosed orally once daily 4 hours after the morning dose of test compound.

Figure 7A:
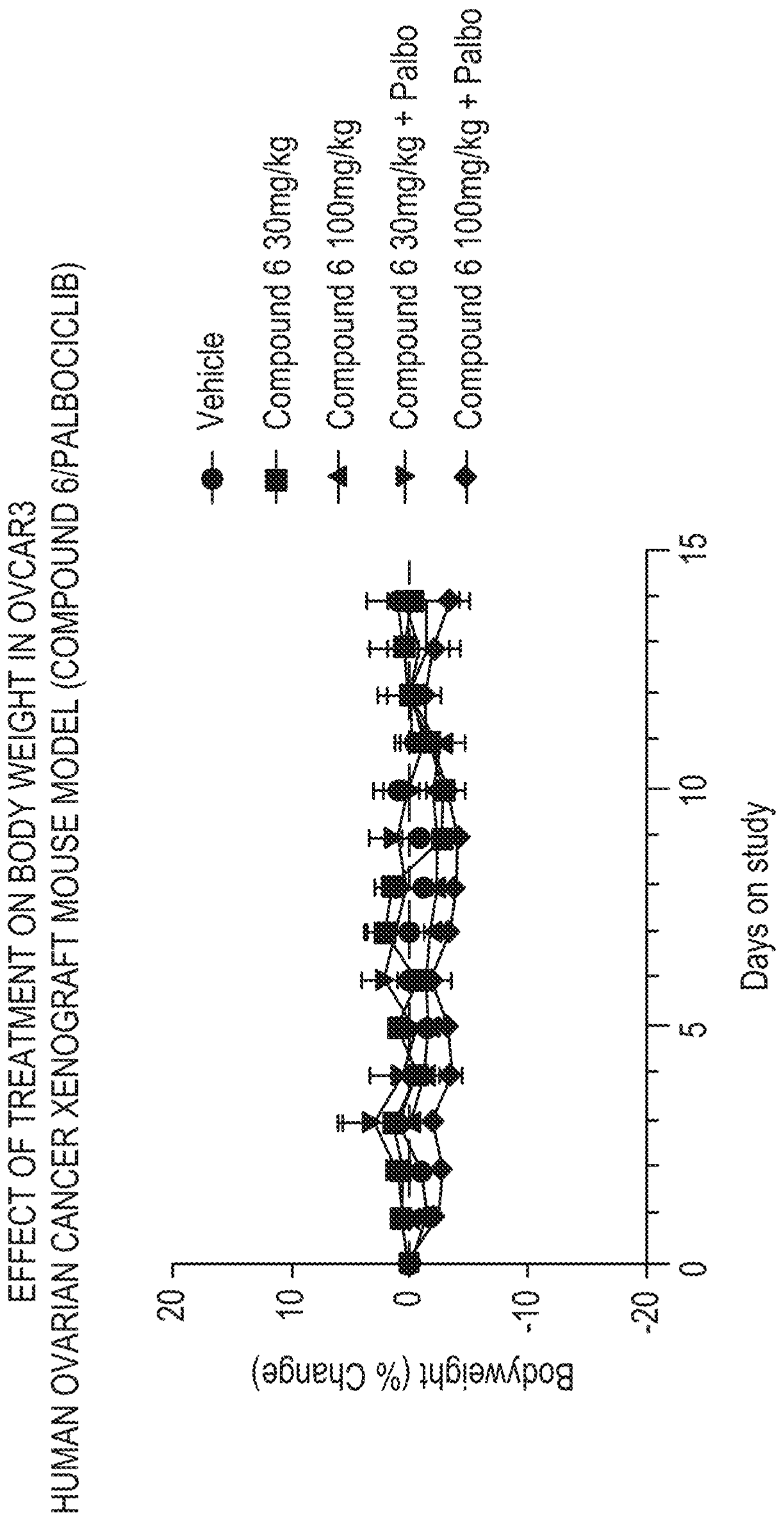
FIGS. 7A and 7B collectively illustrate the effect of treatment with a CDK2 inhibitor (the compound of Example 6) or a combination of a CDK2 inhibitor (the compound of Example 6) and a CDK4/6 inhibitor (palbociclib) on body weight in an OVCAR3 human ovarian cancer xenograft mouse model.
Figure 7B:
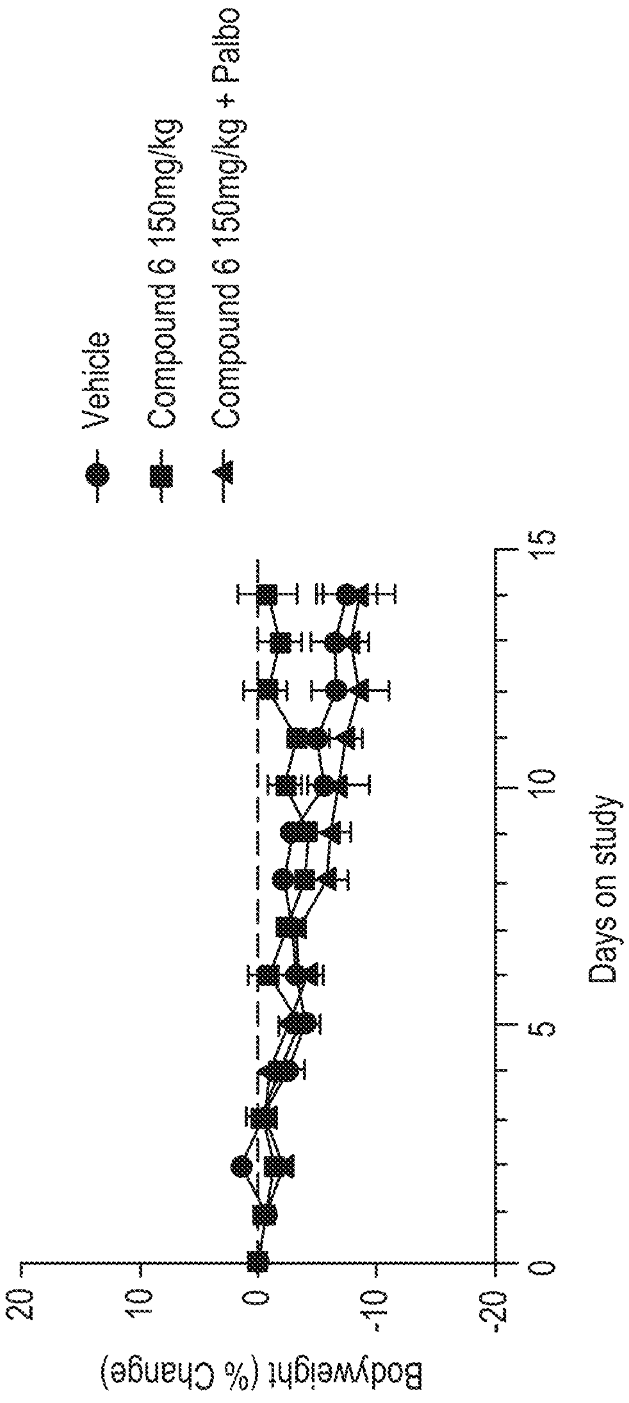

FIGS. 7A and 7B collectively illustrate the effect of treatment with Compound 6 or a combination of Compound 6 and palbociclib on body weight in this OVCAR3 human ovarian cancer xenograft mouse model. No significant body weight loss compared to the vehicle control was observed when Compound 6 was dosed alone or in combination with palbociclib.

Example 73: Anti-Tumor Effect in CCNE1 Amplified Ovarian Xenograft Model OVCAR3

A study was conducted to evaluate the in vivo efficacy of monotherapy with a CDK2 inhibitor and combination therapy with a CDK2 inhibitor and palbociclib in a human CCNE1 amplified and overexpressed ovarian xenograft model.

A. Materials

The OVCAR3 cells, test compound formulations, and palbociclib formulation used in this study were prepared as described in Example 72.

B. Procedure

15 Million OVCAR3 human ovarian cells were implanted subcutaneously in the right flank of female CB17 SCID mice. Mice were randomized into groups of 8 when average tumor volume reached approximately 160 $mm^3$. Mice were treated for 28 days with vehicle (0.5% HPMC/0.1% Tween 80), palbociclib at 50 mg/kg, test compound at 30, 100, or 150 mg/kg, or the combination of test compound and palbociclib. Test compound was dosed orally twice daily 10 hours apart. Palbociclib was dosed orally once daily. When administered in combination with test compound, palbociclib was dosed 4 hours after the morning dose of test compound each day.

Data for Compound 6 are reported in Table 7.

TABLE 7

| DOSE | % INHIBITION |
|---|---|
| Palbociclib at 50 mg/kg | 9% |
| Compound 6 at 30 mg/kg | 31% |
| Compound 6 at 100 mg/kg | 94% |
| Compound 6 at 150 mg/kg | >100% |
| Compound 6 at 30 mg/kg + Palbociclib at 50 mg/kg | 57% |
| Compound 6 at 100 mg/kg + Palbociclib at 50 mg/kg | >100% |

Figure 8:
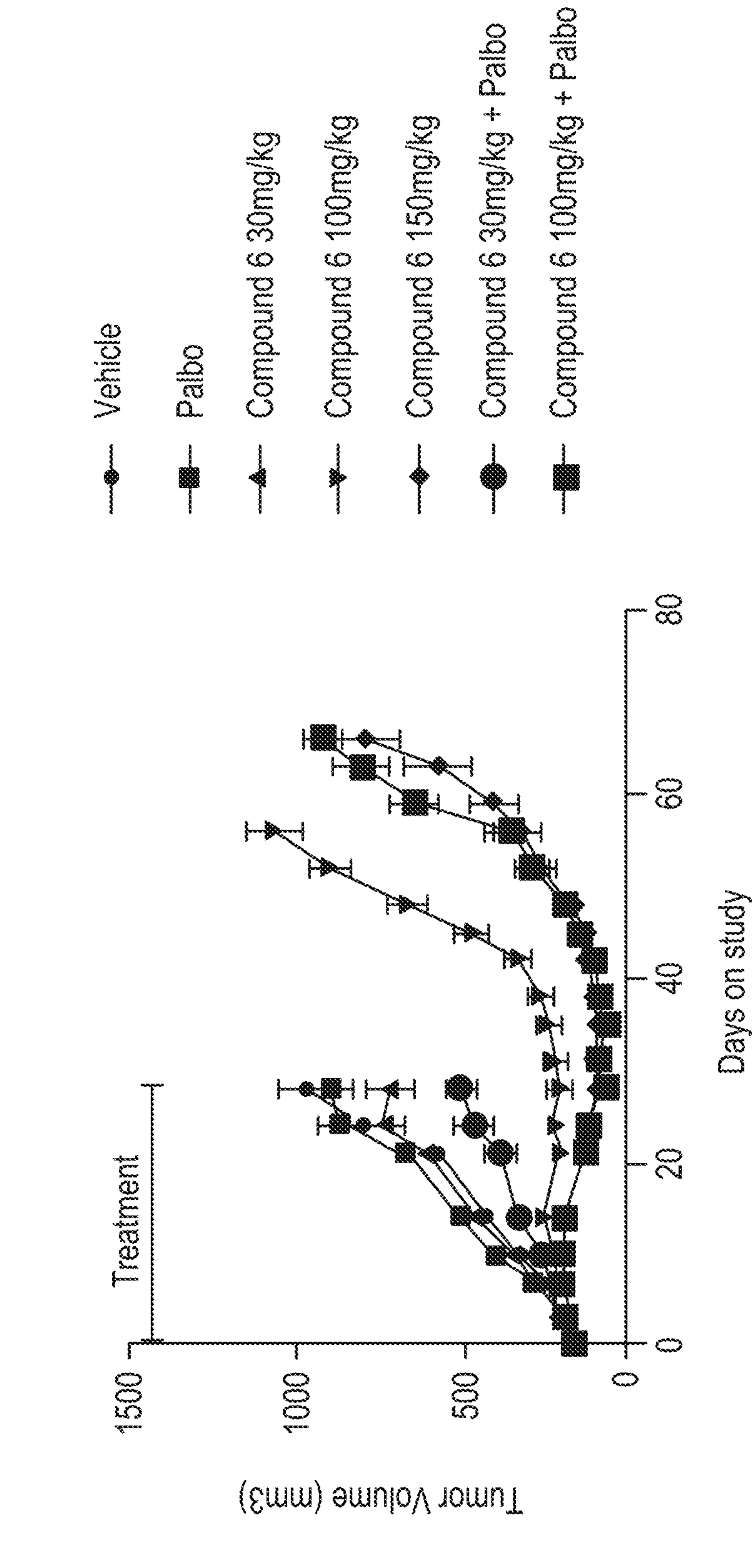
FIG. 8 illustrates the effect of treatment with a CDK2 inhibitor (the compound of Example 6) or a combination of a CDK2 inhibitor (the compound of Example 6) and a CDK4/6 inhibitor (palbociclib) on tumor volume in an OVCAR3 human ovarian cancer xenograft mouse model.

The group administered Compound 6 at 100 mg/kg with and without palbociclib and the group administered Compound 6 at 150 mg/kg were monitored for regrowth. The Compound 6 at 100 mg/kg+palbociclib at 50 mg/kg group and the Compound 6 at 150 mg/kg group showed increased durability compared to the Compound 6 at 100 mg/kg group. FIG. 8 further illustrates the effect of treatment with Compound 6 or a combination of Compound 6 and palbociclib on tumor volume in this OVCAR3 human ovarian cancer xenograft mouse model.

Compound 20 was also tested in this xenograft model. Although Compound 20 was active and well tolerated, further data interpretation was challenging because compound clearance and half-life required high doses that resulted in saturation of clearance mechanisms.

Example 74: Pharmacodynamic Effect in CCNE1 Amplified Ovarian Xenograft Model OVCAR3

A study was conducted to evaluate the in vivo pharmacodynamic response of monotherapy with a CDK2 inhibitor and combination therapy with a CDK2 inhibitor and palbociclib in a human CCNE1 amplified and overexpressed ovarian xenograft model.

A. Materials

The OVCAR3 cells, test compound formulations, and palbociclib formulation used in this study were prepared as described in Example 72.

B. Procedure

15 Million OVCAR3 human ovarian cells were implanted subcutaneously in the right flank of female CB17 SCID mice. Mice were randomized into groups of 9 to 12 mice when average tumor volume reached approximately 350 $mm^3$. Mice were treated for 3 days with vehicle (0.5% HPMC/0.1% Tween 80), palbociclib at 50 mg/kg, test compound at 30, 100, or 150 mg/kg, or the combination of test compound and palbociclib. Test compound was dosed orally twice daily 10 hours apart on day one and two and a single dose in the morning on day 3. Palbociclib was dosed orally once daily. When administered in combination with test compound, palbociclib was dosed 4 hours after the morning dose of test compound on days one and two and 15 minutes after the morning dose of test compound on day 3. The time course of sample collection was as follows: (i) the test compound at 30 mg/kg groups with and without palbociclib treatment were collected at 2, 4, 6, and 8 hours; (ii) the test compound at 150 mg/kg group was collected at 6, 8 and 24 hours; and (iii) all other groups were collected at 2, 8, and 24 hours. pRB (S780) was evaluated by western blotting.

Figure 9:
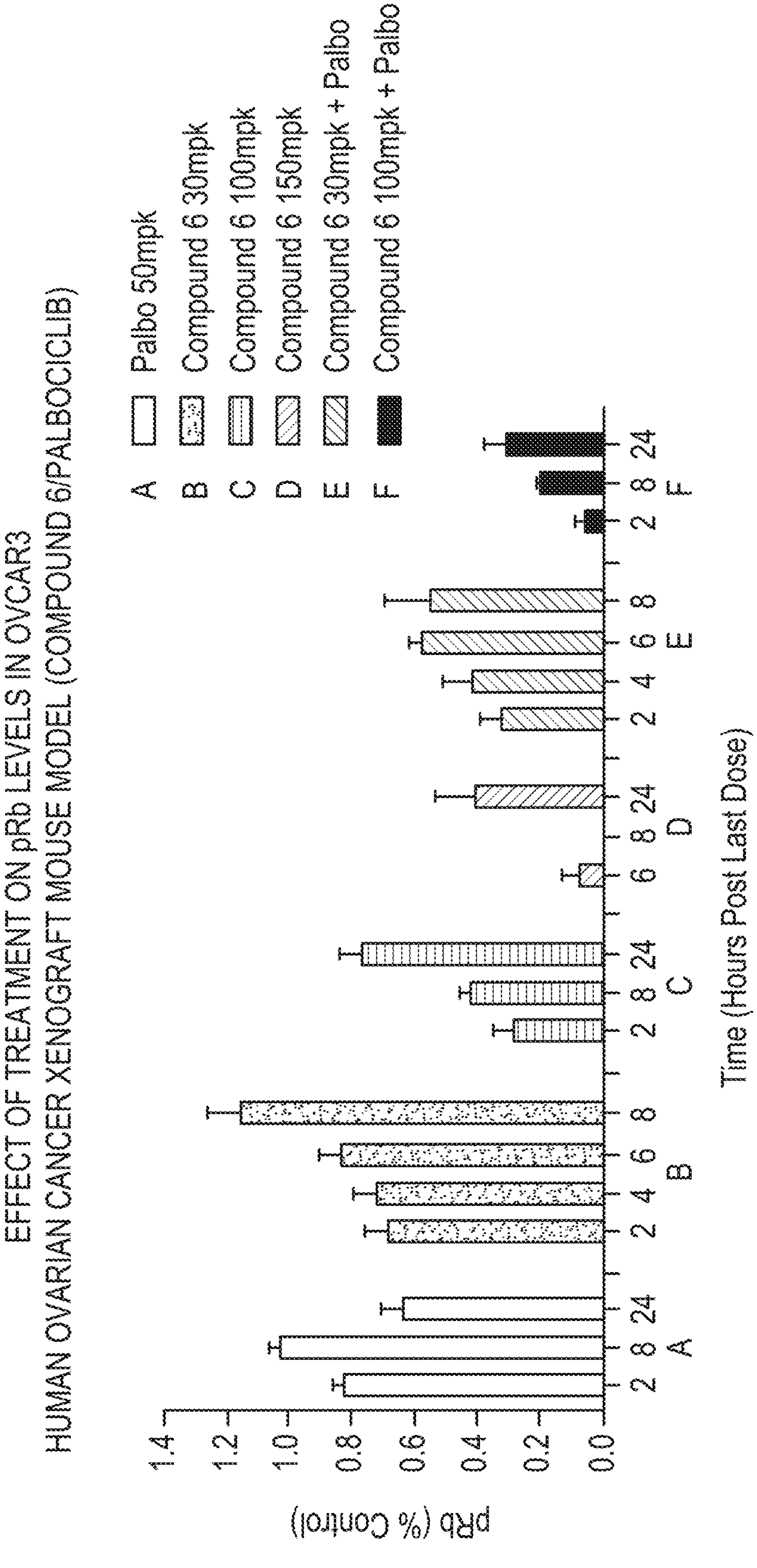
FIG. 9 illustrates the effect of treatment with a CDK2 inhibitor (the compound of Example 6) or a combination of a CDK2 inhibitor (the compound of Example 6) and a CDK4/6 inhibitor (palbociclib) on pRB levels in an OVCAR3 human ovarian cancer xenograft mouse model.

FIG. 9 illustrates the effect of treatment with Compound 6 or a combination of Compound 6 and palbociclib on pRB levels in this OVCAR3 human ovarian cancer xenograft mouse model. A time dependent inhibition of pRB was observed with increasing doses of Compound 6. In addition, the combination of Compound 6 and palbociclib led to further reduction of pRB when compared to Compound 6 alone.

Example 75: Pharmacodynamic Effect in MCF7-PC1 Palbociclib Resistant ER+ Breast Cancer Xenograft Mouse Model A study was conducted to evaluate the in vivo pharmacodynamic response of monotherapy with a CDK2 inhibitor and combination therapy with a CDK2 inhibitor and palbociclib in an MCF7-PC1 human palbociclib resistant ER+ breast cancer xenograft mouse model.

A. Materials

MCF7-PC1 cells were generated as described in Example 70. MCF7-PC1 cells were grown in phenol red free RPMI 1640 supplemented with 10% fetal bovine serum and 1 μM palbociclib. Cells were harvested with 0.25% trypsin and resuspended in PBS/phenol red free Matrigel (50/50). The test compound formulations and palbociclib formulation used in this study were prepared as described in Example 72.

B. Procedure

10 Million MCF7-PC1 cells were implanted orthotopically into the #3 mammary fat pad of female NSG mice. 0.5 mg 90-day release 17B-estradiol pellets from Innovative Research of America were implanted subcutaneously three days prior to cell implant. Palbociclib 50 mg/kg was dosed once daily excluding weekends three weeks on/one week off to maintain palbociclib resistance during tumor engraftment phase to all mice beginning on approximately day 14 post engraftment. A 2-day washout period was given before randomization into groups. Mice were randomized into groups of 9 to 12 mice when average tumor volume reached approximately 300 $mm^3$. Mice were treated for 3 days with vehicle (0.5% HPMC/0.1% Tween 80), palbociclib at 50 mg/kg, test compound at 30, 100, or 150 mg/kg, or the combination of test compound and palbociclib. Test compound was dosed orally twice daily 10 hours apart on day one and two and a single dose in the morning on day 3. Palbociclib was dosed orally once daily. When administered in combination with test compound, palbociclib was dosed 4 hours after the morning dose of test compound on days one and two and 15 minutes after the morning dose of test compound on day 3. The time course of sample collection was as follows: (i) the test compound at 30 mg/kg groups with and without palbociclib treatment were collected at 2, 4, 6, and 8 hours; (ii) the test compound at 150 mg/kg group was collected at 6, 8, and 24 hours; and (iii) all other groups were collected at 2, 8 and 24 hours. pRB (S780) was evaluated by western blotting.

Figure 10:
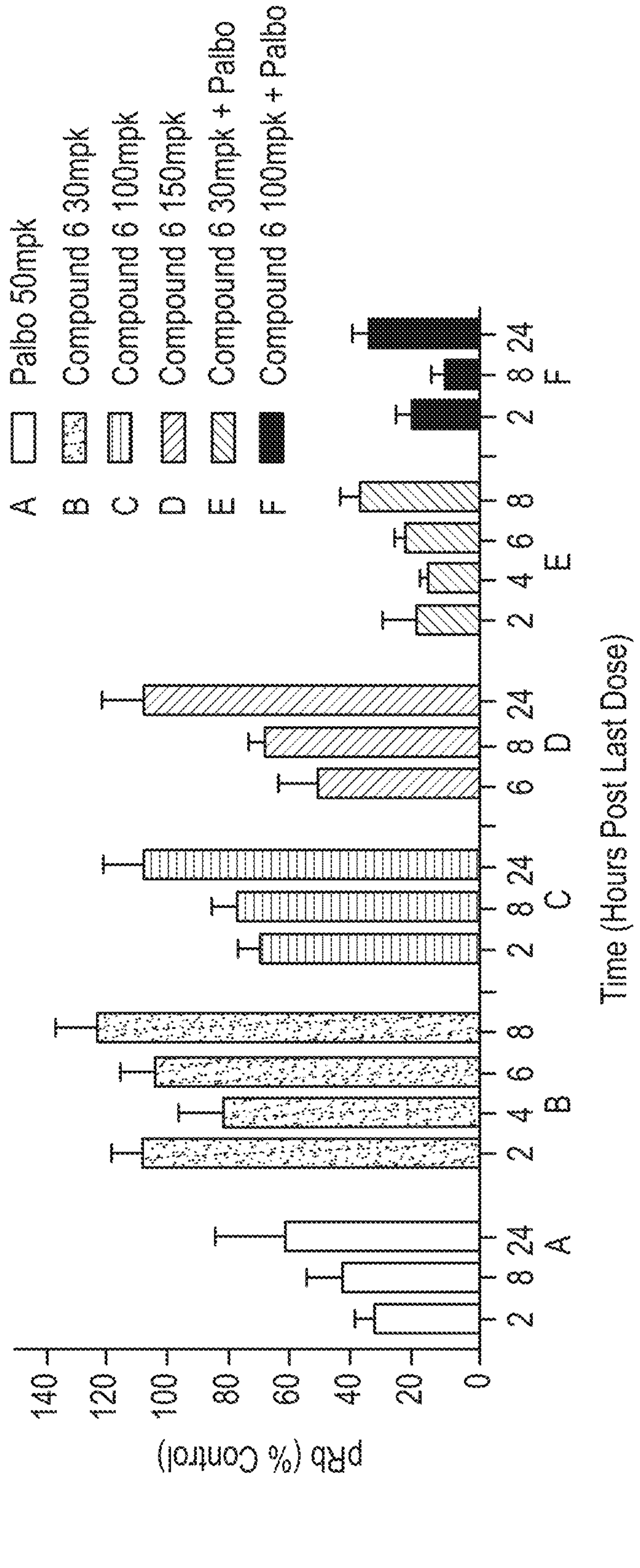
FIG. 10 illustrates the effect of treatment with a CDK2 inhibitor (the compound of Example 6) or a combination of a CDK2 inhibitor (the compound of Example 6) and a CDK4/6 inhibitor (palbociclib) on pRB levels in an MCF7-PC1 human palbociclib resistant ER+ breast cancer xenograft mouse model.

FIG. 10 illustrates the effect of treatment with Compound 6 or a combination of Compound 6 and palbociclib on pRB levels in this MCF7-PC1 human palbociclib resistant ER+ breast cancer xenograft mouse model. A time dependent inhibition of pRB was observed with increasing doses of Compound 6. In addition, the combination of Compound 6 and palbociclib led to further reduction of pRB compared to Compound 6 alone.

Example 76: Anti-Tumor Effect in CTG-3298 CDK4/6 Resistant ER+ Breast Cancer Xenograft Model A study was conducted to evaluate the in vivo efficacy of monotherapy with a CDK2 inhibitor and combination therapy with a CDK2 inhibitor and palbociclib in a CTG-3298 human CDK4/6 resistant ER+ breast cancer xenograft model.

A. Materials

CTG-3298 ER+ breast xenograft tumors were harvested from donor mice and cut into fragments approximately 50 $mm^3$ in volume and then reimplanted adjacent to the #3 mammary fat pad. 0.18 mg 90-day release 17B-estradiol pellets from Innovative Research of America were implanted subcutaneously three days prior to fragment implant.

Test compounds were formulated in Methocel E4M (hydroxypropyl methyl-cellulose (HPMC))/Tween 80 0.5/0.1% and adjusted to a pH between 6.0 and 8.0 to achieve a uniform suspension.

Palbociclib was formulated in water and adjusted to a pH between 3.0 and 3.5 to achieve a clear to hazy solution and dosed once daily by oral gavage.

B. Procedure

CTG-3298 ER+ Breast PDX fragments were implanted orthotopically adjacent to the #3 mammary fat pad using a 10-gauge trocar in female NSG mice. Mice were randomized into groups of 8 when average tumor volume reached approximately 200 $mm^3$. Mice were treated for 28 days with vehicle (0.5% HPMC/0.1% Tween 80), palbociclib at 50 mg/kg, test compound at 30 or 60 mg/kg, or the combination of test compound and palbociclib. Test compound was dosed orally twice daily 10 hours apart. Palbociclib was dosed orally once daily. When administered in combination with test compound, palbociclib was dosed 4 hours after the morning dose of test compound each day Data for Compound 6 are reported in Table 8.

TABLE 8

| DOSE | % INHIBITION (end of dosing) |
|---|---|
| Palbociclib at 50 mg/kg | 49% |
| Compound 6 at 30 mg/kg | 82% |
| Compound 6 at 60 mg/kg | 87% |
| Compound 6 at 30 mg/kg + Palbociclib at 50 mg/kg | >100% |
| Compound 6 at 100 mg/kg + Palbociclib at 50 mg/kg | >100% |

Figure 11:
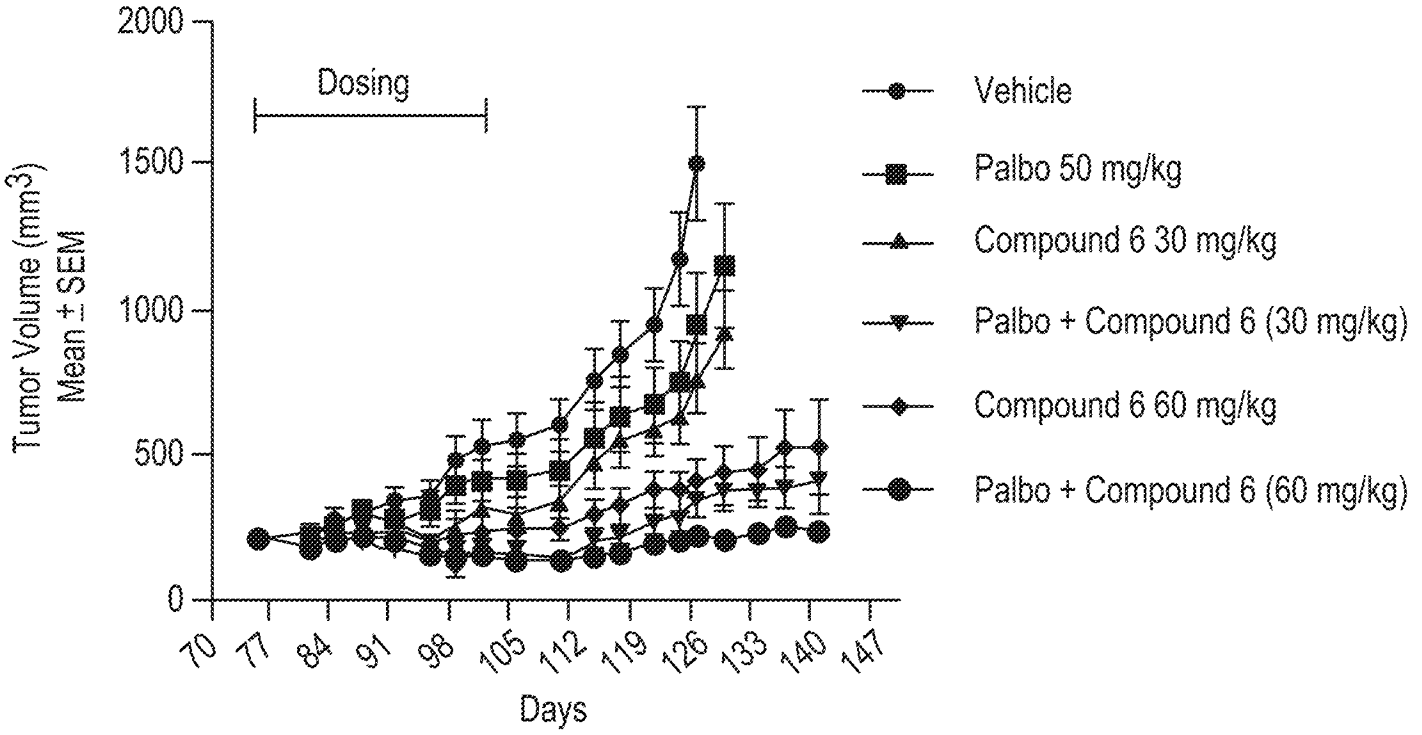
FIG. 11 illustrates the effect of treatment with a CDK2 inhibitor (the compound of Example 6) or a combination of a CDK2 inhibitor (the compound of Example 6) and a CDK4/6 inhibitor (palbociclib) on tumor volume in a CTG-3298 human CDK4/6 resistant ER+ breast cancer xenograft mouse model.

The groups administered Compound 6 at 60 mg/kg with and without palbociclib and the group administered Compound 6 at 30 mg/kg with palbociclib had a more durable response. Greater tumor growth inhibition was achieved with the combining palbociclib with Compound 6 than when dosed alone. FIG. 11 further illustrates the effect of treatment with Compound 6 or a combination of Compound 6 and palbociclib on tumor volume in this CTG-3298 human CDK4/6 resistant ER+ breast cancer xenograft model.

Example 77: Pharmacodynamic Effect (pRB) in CTG-3298 CDK4/6 Resistant ER+ Breast Xenograft Model A study was conducted to evaluate the in vivo pharmacodynamic response of monotherapy with a CDK2 inhibitor and combination therapy with a CDK2 inhibitor and palbociclib in a CTG-3298 human CDK4/6 resistant ER+ breast cancer xenograft model.

A. Materials

CTG-3298 fragments, test compound formulations, and palbociclib formulation used in this study were prepared as described in Example 76.

B. Procedure

CTG-3298 fragments were implanted adjacent to the #3 mammary fat pad of female NSG mice. Mice were randomized into groups of 9 to 12 mice when average tumor volume reached approximately 350 $mm^3$. Mice were treated for 3 days with vehicle (0.5% HPMC/0.1% Tween 80), palbociclib at 50 mg/kg, test compound at 30 or 60 mg/kg, or the combination of test compound and palbociclib. Test compound was dosed orally twice daily 10 hours apart on day one and two and a single dose in the morning on day 3. Palbociclib was dosed orally once daily. When administered in combination with test compound, palbociclib was dosed 4 hours after the morning dose of test compound on days one and two and 15 minutes after the morning dose of test compound on day 3. The time course of sample collection was as follows: (i) the test compound at 30 mg/kg groups with and without palbociclib treatment were collected at 2, 4 and 8 hours; (ii) all other groups were collected at 2, 8, and 24 hours. pRB (S780) was evaluated by western blotting.

Figure 12:
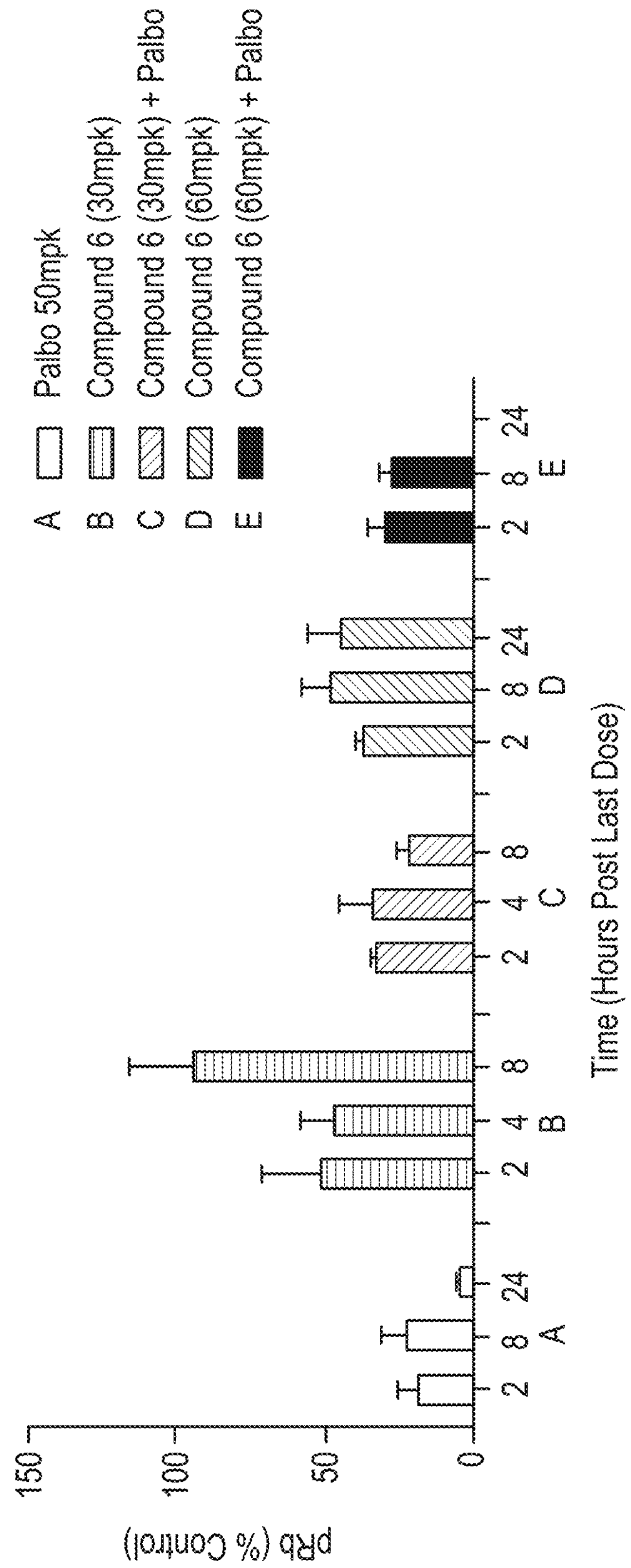
FIG. 12 illustrates the effect of treatment with a CDK2 inhibitor (the compound of Example 6) or a combination of a CDK2 inhibitor (the compound of Example 6) and a CDK4/6 inhibitor (palbociclib) on pRB levels in a CTG-3298 human CDK4/6 resistant ER+ breast cancer xenograft mouse model.

FIG. 12 illustrates the effect of treatment with Compound 6 or a combination of Compound 6 and palbociclib on pRB in this CTG-3298 human CDK4/6 resistant ER+ breast cancer xenograft model. A dose dependent inhibition of pRB was observed with increasing doses of Compound 6. In addition, the combination of Compound 6 and palbociclib led to further reduction of pRB when compared to Compound 6 alone.

Example 78: Pharmacodynamic Effect (pHH3) in CTG-3298 CDK4/6 Resistant ER+ Breast Xenograft Model A study was conducted to evaluate the in vivo pharmacodynamic response of monotherapy with a CDK2 inhibitor and combination therapy with a CDK2 inhibitor and palbociclib in a CTG-3298 human CDK4/6 resistant ER+ breast cancer xenograft model.

A. Materials

CTG-3298 fragments, test compound formulations, and palbociclib formulation used in this study were prepared as described in Example 76.

B. Procedure

CTG-3298 fragments were implanted adjacent to the #3 mammary fat pad of female NSG mice. Mice were randomized into groups of 9 to 12 mice when average tumor volume reached approximately 350 $mm^3$. Mice were treated for 3 days with vehicle (0.5% HPMC/0.1% Tween 80), palbociclib at 50 mg/kg, test compound at 30 or 60 mg/kg, or the combination of test compound and palbociclib. Test compound was dosed orally twice daily 10 hours apart on day one and two and a single dose in the morning on day 3. Palbociclib was dosed orally once daily. When administered in combination with test compound, palbociclib was dosed 4 hours after the morning dose of test compound on days one and two and 15 minutes after the morning dose of test compound on day 3. The time course of sample collection was as follows: (i) the test compound at 30 mg/kg groups with and without palbociclib treatment were collected at 2, 4 and 8 hours; (ii) all other groups were collected at 2, 8, and 24 hours. pHH3 was evaluated by western blotting.

Figure 13:
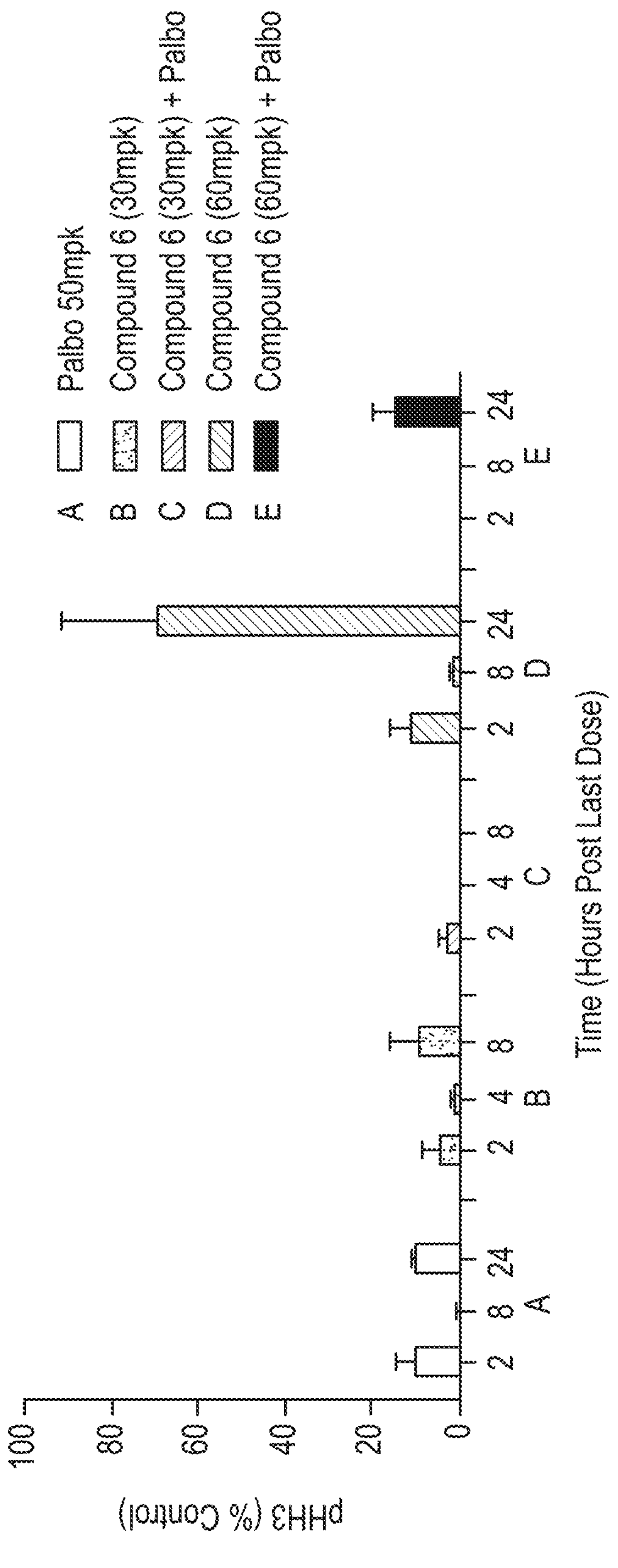
FIG. 13 illustrates the effect of treatment with a CDK2 inhibitor (the compound of Example 6) or a combination of a CDK2 inhibitor (the compound of Example 6) and a CDK4/6 inhibitor (palbociclib) on pHH3 levels in a CTG-3298 human CDK4/6 resistant ER+ breast cancer xenograft mouse model.

FIG. 13 illustrates the effect of treatment with Compound 6 or a combination of Compound 6 and palbociclib on pHH3 levels in this CTG-3298 human CDK4/6 resistant ER+ breast cancer xenograft model. The combination of Compound 6 and palbociclib led to greater reduction of pHH3 when compared to Compound 6 alone Example 79: Pharmacodynamic Effect in T47D P1 Palbociclib Resistant ER+ Breast Cell Line A study was conducted to evaluate the in vivo pharmacodynamic response of monotherapy with a CDK2 inhibitor and combination therapy with a CDK2 inhibitor and palbociclib in a T47D P1 human palbociclib resistant ER+ breast cancer xenograft model.

A. Materials

T47D P1 cells were generated to be resistant to palbociclib through chronic treatment with palbociclib over the course of about three months with increasing concentrations up to 3 μM. The resulting cells (T47D P1) were then banked for use in subsequent experiments. T47D P1 cells were grown in phenol red free RPMI 1640 supplemented with 10% fetal bovine serum and 3 μM palbociclib. Cells were harvested with 0.25% trypsin and resuspended in PBS/phenol red free Matrigel (50/50). The test compound formulations and palbociclib formulation used in this study were prepared as described in Example 72.

B. Procedure

10 Million T47D P1 cells were implanted orthotopically into the #3 mammary fat pad of female NSG mice. 0.5 mg 90 day release 17B-estradiol pellets from Innovative Research of America were implanted subcutaneously three days prior to cell implant. Palbociclib 50 mg/kg was dosed once daily excluding weekends three weeks on/one week off to maintain Palbociclib resistance during tumor engraftment phase to all mice beginning on approximately day 14 post engraftment A 2 day washout period was given before randomization into groups. Mice were randomized into groups of 9 to 12 mice when average tumor volume reached approximately 300 $mm^3$. Mice were treated for 3 days with vehicle (0.5% HPMC/0.1% Tween 80), palbociclib at 50 mg/kg, test compound at 30 or 100 mg/kg, or the combination of test compound and palbociclib. Test compound was dosed orally twice daily 10 hours apart on day one and two and a single dose in the morning on day 3. Palbociclib was dosed orally once daily. When administered in combination with test compound, palbociclib was dosed 4 hours after the morning dose of test compound on days one and two and 15 minutes after the morning dose of test compound on day 3. The time course of sample collection was as follows: (i) the test compound at 30 mg/kg groups with and without palbociclib treatment were collected at 2, 4 and 8 hours; and (ii) all other groups were collected at 2, 8 and 24 hours. pHH3 was evaluated by western blotting.

Figure 14:
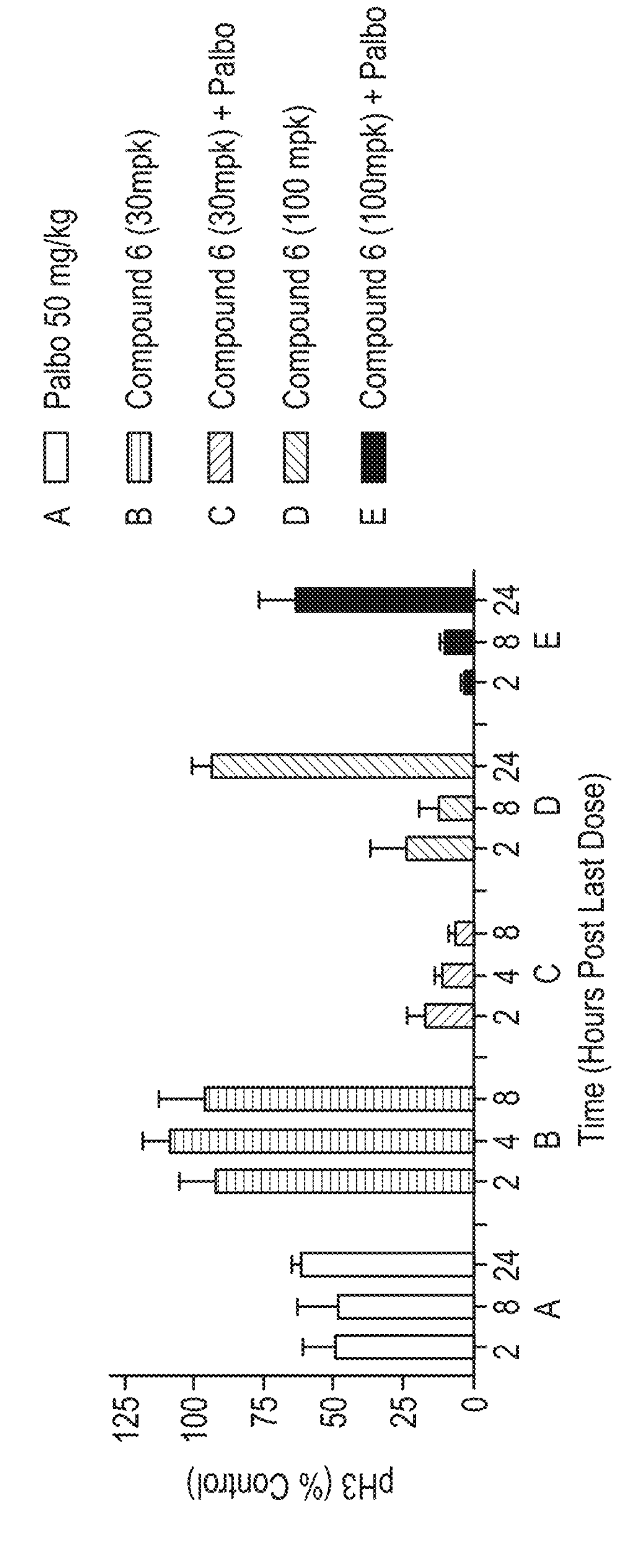
FIG. 14 illustrates the effect of treatment with a CDK2 inhibitor (the compound of Example 6) or a combination of a CDK2 inhibitor (the compound of Example 6) and a CDK4/6 inhibitor (palbociclib) on pRB levels in a T47D P1 human CDK4/6 resistant ER+ breast cancer xenograft mouse model.

FIG. 14 illustrates the effect of treatment with Compound 6 or a combination of Compound 6 and palbociclib on pHH3 levels in this T47D P1 human palbociclib resistant ER+ breast cancer xenograft model. A time dependent inhibition of pHH3 was observed with increasing doses of Compound 6. In addition, the combination of Compound 6 and palbociclib led to further reduction of pHH3 compared to Compound 6 alone.

Example 80: Kinase Profiling

Test compounds were profiled against a broad panel of kinases at ThermoFisher Scientific using the SelectScreen Kinase Profiling Services. Each kinase assay used one of the following assay technology protocols:

1) Z-LYTE™ Screening Protocol and Assay Conditions (Revised 23 Jan. 2018 version) available at http://assets.thermofisher.com/TFS-Assets/BID/Methods-&-Protocols/20180123_SSBK_Customer_Protocol_and_Assay_Conditions.pdf;
2) Adapta™ Screening Protocol and Assay Conditions (Revised 23 Jan. 2018 version) available at http://assets.thermofisher.com/TFS-Assets/BID/Methods-&-Protocols/20180123_SSBK_Adapta_Customer_Protocol_and_Assay_Conditions.pdf; or
3) LanthaScreen™ Eu Kinase Binding Assay Screening Protocol and Assay Conditions (Revised 23 Jan. 2018 version) available at http://assets.thermofisher.com/TFS-Assets/BID/Methods-&-Protocols/20180123_SSBK_LanthaScreen_Binding_Customer_Protocol_and_Assay_Conditions.pdf.

The kinase panel included 379 non-CDK kinase (or corresponding non-CDK kinase-complex) targets. Compound 6 showed less than 20% inhibition at 1 μM for all non-CDK kinases tested. The compounds of Examples 3, 19, 20, 28, 39, 44, 53, and 62 also showed broadly similar kinase inhibition profiles to Compound 6.

Example 81: Secondary Pharmacology

Secondary pharmacology assays were performed at Eurofins CEREP using standard experimental techniques. Specifically, radioligand binding assays were used to assess the ability of test compounds to interact with G-protein coupled receptors (GPCRs), ion channels, and transmembrane transporters. Assays measuring substrate turnover or phosphorylation by isolated proteins were used for enzyme and kinase targets, allowing direct determination of the mode of action of the tested compounds. Where a binding activity was observed at a GPCR target, mode of action was determined using cell based functional assays with secondary messenger read outs. Assays were run either in eight-point concentration response mode with half log dilutions, with $IC_{50}$, $EC_{50}$ or Ki (Cheng and Prusoff, 1973) values determined or using an initial single concentration of 10 μM with concentration-response curves generated as follow up where >25% activity was detected. Details of the GPCR, ion channel, and transmembrane transporter assays including experimental protocols can be found on the Eurofins website located at https://www.eurofinsdiscoveryservices.com.

Compounds were profiled against 97 targets. Compound 6 had an $IC_{50}$ value greater than 10 μM for 94 out of 97 targets and greater than 4 μM for 96 out of 97 targets. The sole target having an $IC_{50}$ value less than 1 μM was CDK1. The compounds of Examples 3, 6, 19, 20, 28, 39, 44, 53, and 62 also showed broadly similar secondary pharmacology to Compound 6.

Example 82: Caco-2 Cell Permeability

Test compounds were evaluated for gastrointestinal permeability and potential bioavailability in a Caco-2 cell permeability assay. Detailed description of the methodology was previously published in "Evaluation of the Disconnect between Hepatocyte and Microsome Intrinsic Clearance and In Vitro In Vivo Extrapolation Performance"; Williamson Beth, Harlfinger Steffanie, McGinnity F. Dermot; Drug Metab Dispos 48:1137-1146, November 2020. In brief, Caco-2 cells were plated at $6.86 \times 10^5$ cells/mL and were cultured for 14 to 18 days with culture medium replaced every other day. Test compound (10 μM) was added to the donor well and the appearance in the receiver well measured after 2 hours incubation at 37° C. When determining the rate of compound transport in the apical to basolateral (A-B) direction, the donor well was the apical (A) compartment and the receiver was the basolateral (B) compartment. Similarly, when determining the rate of compound transport in the basolateral to apical (B-A) direction, the donor well was the basolateral (B) compartment and the receiver was the apical (A) compartment. Samples were analyzed by liquid chromatography (LC)-mass spectrometry (MS)/MS.

The permeability coefficient ($1 \times 10^{-6}$ cm/s) was calculated using the following equation:

$$P_{app} = (dC_r/dt) \times V_r/(A \times C_0),$$

and the efflux ratio (ER) was calculated using the following equation:

$$\text{Efflux ratio} = P_{app}(B \text{ to } A)/P_{app}(A \text{ to } B),$$

where:

$dC_r/dt$ is the cumulative concentration of the compound in the receiver chamber as a function of time (in μM/s);

$V_r$ is the solution volume in the receiver chamber (0.1 ml on the apical side and 0.3 ml on the basolateral side);

A is the surface area for the transport (i.e., 0.11 $cm^2$ for the area of the monolayer); and $C_0$ is the initial concentration in the donor chamber (in μM).

Data for the compounds tested are reported in Table 9.

TABLE 9

| Example | Caco-2 Intrinsic Permeability [1] (1E−6 · cm/s) | Caco-2 Efflux Ratio |
|---|---|---|
| 6 | 13.5 | 40.9 |
| 19 | 7.8 | 63.4 |
| 20 | 29.7 | 11.7 |
| 28 | 4.2 | 41.7 |
| 33 | 22.3 | 25.8 |
| 38 | 1.9 | 89.5 |
| 39 | 2.9 | 106 |
| 44 | 13.2 | 48 |
| 45 | 18.8 | 15.3 |
| 53 | 6.8 | 40.1 |
| 61 | 27.8 | 23.5 |
| Comparative Example A[2] | 60.1 | 1.6 |

[1] Papp is reported aftfer single measurement (n = 1) or as an average for multiple measurements (n > 1).
[2] Comparative Example A is fadraciclib (CYC065).

Example 83: Metabolic Stability Assays

A. $Cl_{int}$ Assessment in Human Hepatocytes (HH)

Test compound was prepared (10 mM in 100% DMSO) and further diluted to 100 μM in 100% acetonitrile. The hepatocyte incubations were prepared in Leibovitz's L-15 Medium (pH 7.4) containing 1 million hepatocytes/ml and a final compound concentration of 1 μM. Cell viability was determined using a Cellometer Vision and greater than 80% cell viability was required to proceed with the compound incubation. The compound/cell solution (250 ml) was incubated for 2 hours at 37° C. and shaken at 900 rpm on an Eppendorf Thermomixer Comfort plate shaker. Samples (20 μl) were taken at 0.5, 5, 15, 30, 45, 60, 80, 100, and 120 minutes and quenched with 100 μl of 100% ice-cold acetonitrile. Samples were shaken at 800 rpm for 2 minutes and centrifuged at 4000 rpm for 20 minutes at 4° C. to pellet precipitated protein. The supernatant fraction was diluted 1:5 with deionized water, shaken at 1000 rpm for 2 minutes, and further diluted 1:1 with deionized water. Samples were analyzed by LC-MS/MS.

B. $Cl_{int}$ Assessment in Human Liver Microsomes (HLMs)

Test compound was prepared (10 mM in 100% DMSO) and further diluted to 100 μM in 100% acetonitrile. The microsomal incubations were prepared in phosphate buffered solution (pH 7.4) containing 1 mg/ml microsomal protein, 1 mM NADPH, and a final compound concentration of 1 μM. After a preincubation with NADPH for 8 minutes, reactions were initiated through the addition of the test compound (final volume 250 μl) and incubated at 37° C. in a water bath for 30 minutes. At each time point (0.5, 5, 10, 15, 20, 30 minutes), 20 μl of incubation mixture was quenched with 100 μl of 100% ice-cold acetonitrile. Samples were shaken at 800 rpm for 2 minutes and centrifuged at 4000 rpm for 20 minutes at 4° C. to pellet precipitated protein. The supernatant fraction was diluted 1:5 with deionized water, shaken at 1000 rpm for 2 minutes, and further diluted 1:1 with deionized water. Samples were analyzed by LC-MS/MS.

C. $Cl_{int}$ Assessment in HμREL (Co-Culture of Human Hepatocyte and Stromal Cells)

Test compound was dissolved in DMSO at 10 mM, then diluted to 2 μM in dosing medium using Echo dispense. All steps were performed at room temperature, while the 2 μM test compound was preheated at 37° C. before start of incubation. Prior to assay, maintenance medium was removed from the cells, followed by a washing step with 100 μL of preheated blank dosing medium without serum. Compound incubation was initiated by addition of 50 μL of dosing medium and 50 μL of dosing medium containing 2 μM test compound. The final test concentration was 1 μM. Plates were kept without shaking in the incubator during the experiments, at 37° C. in humidified atmosphere containing 95% air and 5% $CO_2$. 70 μL aliquots of sample duplicates were taken at 0, 1, 3, 5, 24, 48 and 72 hours and quenched with 70 μL of ice-cold acetonitrile stop solution. Quenched samples were diluted with 140 μL of 0.1% formic acid in water and analyzed on a mass spectrometer.

D. Data Analysis

The $t_{1/2}$ and the $CL_{int}$ of the compounds incubated in the HH, HLM, and HμREL assays as described above were calculated according to the following equations:

$$t_{1/2}(\text{min}) = \ln(2)/-\text{slope},$$

and $$Cl_{int}(\mu\text{l/min}/10^6 \text{ cells or mg protein}) = \ln(2) * V/(t_{1/2}),$$

where V (μl/×$10^6$ cells or mg protein) is the incubation volume (μl) divided by the number of cells (×$10^6$) or microsomal protein content (mg) in the incubation.

Data for the compounds tested are reported in Table 10.

TABLE 10

| Example | HH $CL_{int}$[1] (μL/min/mg) | HLM $CL_{int}$[2] (μL/min/1E6) | HμREL $CL_{int}$[3] (μL/min/1E6) |
|---|---|---|---|
| 1 | — | >300 | — |
| 2 | — | 61.6 | — |
| 3 | — | 45.2 | — |
| 4 | — | 85.2 | — |
| 5 | | 46 | |
| 6 | <1.1 | 39 | 1.5 |
| 7 | — | 63.6 | — |
| 8 | — | 28.9 | — |
| 9 | — | 13.4 | — |
| 10 | — | 17.6 | — |
| 11 | — | 116 | — |
| 12 | — | 66.8 | — |
| 13 | — | 66.8 | — |
| 14 | — | 38 | — |
| 15 | — | >300 | — |
| 16 | — | 96.5 | — |
| 17 | — | 46 | — |
| 18 | — | 35.1 | — |
| 19 | <1 | 8.5 | 0.23 |
| 20 | — | >300 | — |
| 21 | — | 34.1 | — |
| 22 | — | 32.7 | — |
| 23 | — | 57.5 | — |
| 24 | — | 63.8 | — |
| 25 | — | 61.6 | — |
| 26 | — | 15.2 | — |
| 27 | — | >300 | — |
| 28 | 2 | 41.2 | — |
| 29 | — | 90.5 | — |
| 30 | — | 191 | — |
| 31 | — | 154 | — |
| 32 | — | 73 | — |
| 33 | — | 175 | — |
| 34 | — | >300 | — |
| 35 | — | >300 | — |
| 36 | — | >300 | — |
| 37 | — | 143 | — |
| 38 | <1 | 13 | — |
| 39 | <1 | 13.9 | — |
| 40 | — | >300 | — |
| 41 | — | 177 | — |
| 42 | — | 196 | — |
| 43 | — | 148 | — |
| 44 | <1 | 21 | 0.29 |
| 45 | — | 30.5 | — |
| 46 | — | 76.6 | — |
| 47 | <1 | 26 | — |
| 48 | — | 13.3 | — |
| 49 | — | 19.5 | — |
| 50 | — | 36.3 | — |
| 51 | — | 212 | — |
| 52 | — | 21.1 | — |
| 53 | — | 12.2 | — |
| 54 | — | 38.9 | — |
| 55 | — | 22.7 | — |
| 56 | — | 39.8 | — |
| 57 | — | 33.5 | — |
| 58 | — | 202 | — |
| 59 | — | 35.9 | — |
| 60 | — | 65.6 | — |
| 61 | 3.8 | 35.6 | — |

TABLE 10-continued

| Example | HH $CL_{int}$[1] (μL/min/mg) | HLM $CL_{int}$[2] (μL/min/1E6) | HμREL $CL_{int}$[3] (μL/min/1E6) |
|---|---|---|---|
| 62 | — | 29.6 | — |
| Comparative Example A[4] | 8.3 | 130 | — |

[1] $CL_{int}$ is reported after single measurement (n = 1) or as an average for multiple measurements (n > 1).
[2] $CL_{int}$ is reported after single measurement (n = 1) or as geometric mean for multiple measurements (n > 1).
[3] $CL_{int}$ is reported after single measurement (n = 1) or as geometric mean for multiple measurements (n = 2).
[4] Comparative Example A is fadraciclib (CYC065).

Example 84: Aqueous Solubility

The thermodynamic solubility of the test compounds was measured in a shake-flask approach starting from 10 mM DMSO solutions. The DMSO was evaporated and the dried compounds were equilibrated in glass vials in aqueous phosphate buffer (0.1 M, pH 7.4) for 24 hours at 25° C. under constant stirring. The portion with the dissolved compound was then separated from the remainder through a double centrifugation with a tip wash in between to ensure that no residues of the dried compound were interfering. The solutions were diluted with purified water before quantification using UPLC/MS/MS. The aqueous solubilities measured for the compounds tested are reported in Table 11.

TABLE 11

| EXAMPLE | AQUEOUS SOLUBILITY (μM) |
|---|---|
| 1 | 7 |
| 2 | 55 |
| 3 | 48 |
| 4 | 57 |
| 5 | >1000 |
| 6 | >882 |
| 7 | 220 |
| 8 | 957 |
| 9 | >1000 |
| 10 | >904 |
| 11 | 654 |
| 12 | 955 |
| 13 | 762 |
| 14 | 320 |
| 15 | 132 |
| 16 | >1000 |
| 17 | 280 |
| 18 | 726 |
| 19 | 1,600 |
| 20 | 93 |
| 21 | 606 |
| 22 | >1000 |
| 23 | 814 |
| 24 | 466 |
| 25 | 912 |
| 26 | 101 |
| 27 | 39.8 |
| 28 | 114 |
| 29 | 71.2 |
| 30 | 276 |
| 31 | >1000 |
| 32 | >1000 |
| 33 | 18.7 |
| 34 | 59.9 |
| 35 | 26.4 |
| 36 | 11.1 |
| 37 | 414 |
| 38 | >976 |
| 39 | 165 |
| 40 | 1.79 |
| 41 | 39.2 |
| 42 | 167 |
| 43 | 97.2 |
| 44 | 382 |
| 45 | >1000 |
| 46 | >1000 |
| 47 | 253 |
| 48 | >1000 |
| 49 | 120 |
| 50 | 23.1 |
| 51 | 35 |
| 52 | 300 |
| 53 | >930 |
| 54 | 593 |
| 55 | >1,000 |
| 56 | >1,000 |
| 57 | 884 |
| 58 | 51.9 |
| 59 | >1000 |
| 60 | 51.3 |
| 61 | 8 |
| 62 | >1,000 |
| Comparative Example A[1] | 740 |

[1] Comparative Example A is fadraciclib (CYC065).

Example 85: Anti-Tumor Effect in CTG-3283 CDK4/6 Resistant ER+ Breast Cancer Xenograft Model A study was conducted to evaluate the in vivo efficacy of monotherapy with a CDK2 inhibitor and combination therapy with a CDK2 inhibitor and palbociclib in a CTG-3283 human CDK4/6 resistant ER+ breast cancer xenograft model.

A. Materials

CTG-3283 ER+ breast xenograft tumors were harvested from donor mice and cut into fragments approximately 50 $mm^3$ in volume and then reimplanted adjacent to the #3 mammary fat pad. 0.18 mg 90-day release 17B-estradiol pellets from Innovative Research of America were implanted subcutaneously three days prior to fragment implant.

Test compounds were formulated in Methocel E4M (hydroxypropyl methyl-cellulose (HPMC))/Tween 80 0.5/0.1% and adjusted to a pH between 6.0 and 8.0 to achieve a uniform suspension.

Palbociclib was formulated in water and adjusted to a pH between 3.0 and 3.5 to achieve a clear to hazy solution and dosed once daily by oral gavage.

B. Procedure

CTG-3283 ER+ Breast PDX fragments were implanted orthotopically adjacent to the #3 mammary fat pad using a 10-gauge trocar in female NSG mice. Mice were randomized into groups of 8 when average tumor volume reached approximately 200 $mm^3$. Mice were treated for 28 days with vehicle (0.5% HPMC/0.1% Tween 80), palbociclib at 50 mg/kg, test compound at 30 or 60 mg/kg, or the combination of test compound and palbociclib. Test compound was dosed orally twice daily 10 hours apart. Palbociclib was dosed orally once daily. When administered in combination with test compound, palbociclib was dosed 4 hours after the morning dose of test compound each day.

Data for Compound 6 are reported in Table 12.

TABLE 12

| DOSE | % INHIBITION (end of dosing) |
|---|---|
| Palbociclib at 50 mg/kg | 46% |
| Compound 6 at 30 mg/kg | 28% |
| Compound 6 at 60 mg/kg | 21% |
| Compound 6 at 30 mg/kg + Palbociclib at 50 mg/kg | 86% |
| Compound 6 at 60 mg/kg + Palbociclib at 50 mg/kg | 91% |

Figure 15:
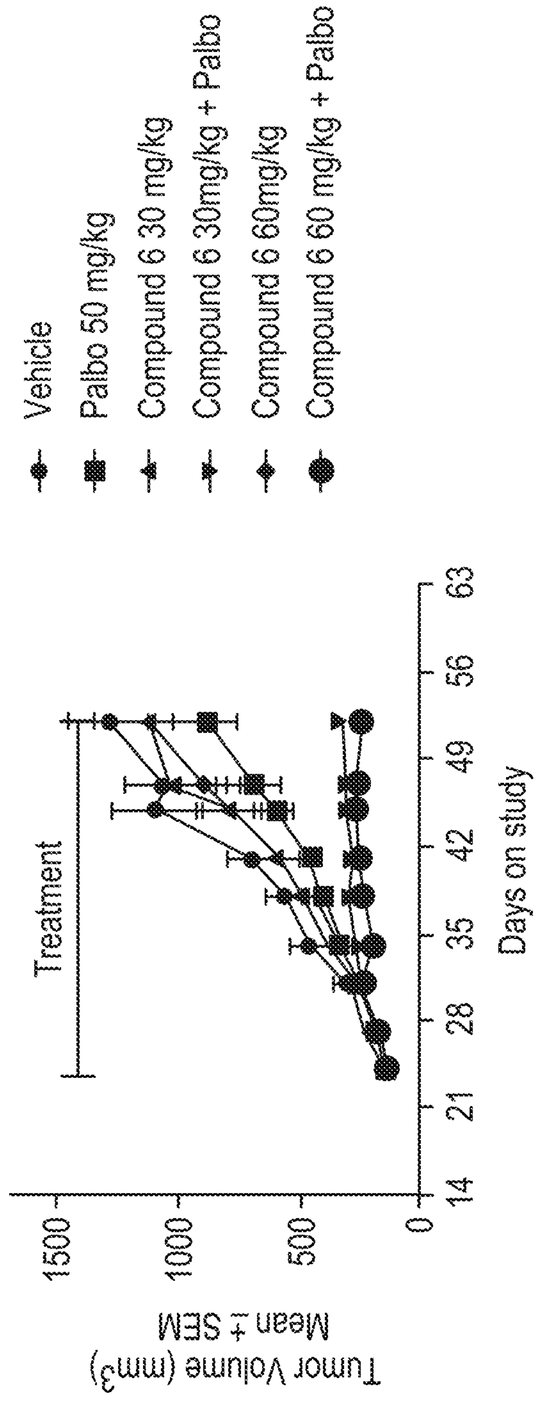
FIG. 15 illustrates the effect of treatment with a CDK2 inhibitor (the compound of Example 6) or a combination of a CDK2 inhibitor (the compound of Example 6) and a CDK4/6 inhibitor (palbociclib) on tumor volume in a CTG-3283 human CDK4/6 resistant ER+ breast cancer xenograft mouse model.

Significant tumor growth inhibition was achieved with the combination of Compound 6 and palbociclib. Treatment with Compound 6 at 30 and 60 mg/kg monotherapy resulted in lower inhibition of tumor growth. FIG. 15 further illustrates the effect of treatment with Compound 6 or a combination of Compound 6 and palbociclib on tumor volume in this CTG-3283 human CDK4/6 resistant ER+ breast cancer xenograft model.

Example 86: Pharmacodynamic Effect (pRB) in CTG-3283 CDK4/6 Resistant ER+ Breast Xenograft Model A study was conducted to evaluate the in vivo pharmacodynamic response of monotherapy with a CDK2 inhibitor and combination therapy with a CDK2 inhibitor and palbociclib in a CTG-3283 human CDK4/6 resistant ER+ breast cancer xenograft model.

A. Materials

CTG-3283 fragments, test compound formulations, and palbociclib formulation used in this study were prepared as described in Example 85.

B. Procedure

CTG-3283 fragments were implanted adjacent to the #3 mammary fat pad of female NSG mice. Mice were randomized into groups of 9 to 12 mice when average tumor volume reached approximately 350 $mm^3$. Mice were treated for 3 days with vehicle (0.5% HPMC/0.1% Tween 80), palbociclib at 50 mg/kg, test compound at 30 or 60 mg/kg, or the combination of test compound and palbociclib. Test compound was dosed orally twice daily 10 hours apart on day one and two and a single dose in the morning on day 3. Palbociclib was dosed orally once daily. When administered in combination with test compound, palbociclib was dosed 4 hours after the morning dose of test compound on days one and two and 15 minutes after the morning dose of test compound on day 3. The time course of sample collection was as follows: (i) the test compound at 30 mg/kg groups with and without palbociclib treatment were collected at 2, 4, and 8 hours; (ii) all other groups were collected at 2, 8, and 24 hours. pRB (S780) was evaluated by western blotting.

Figure 16:
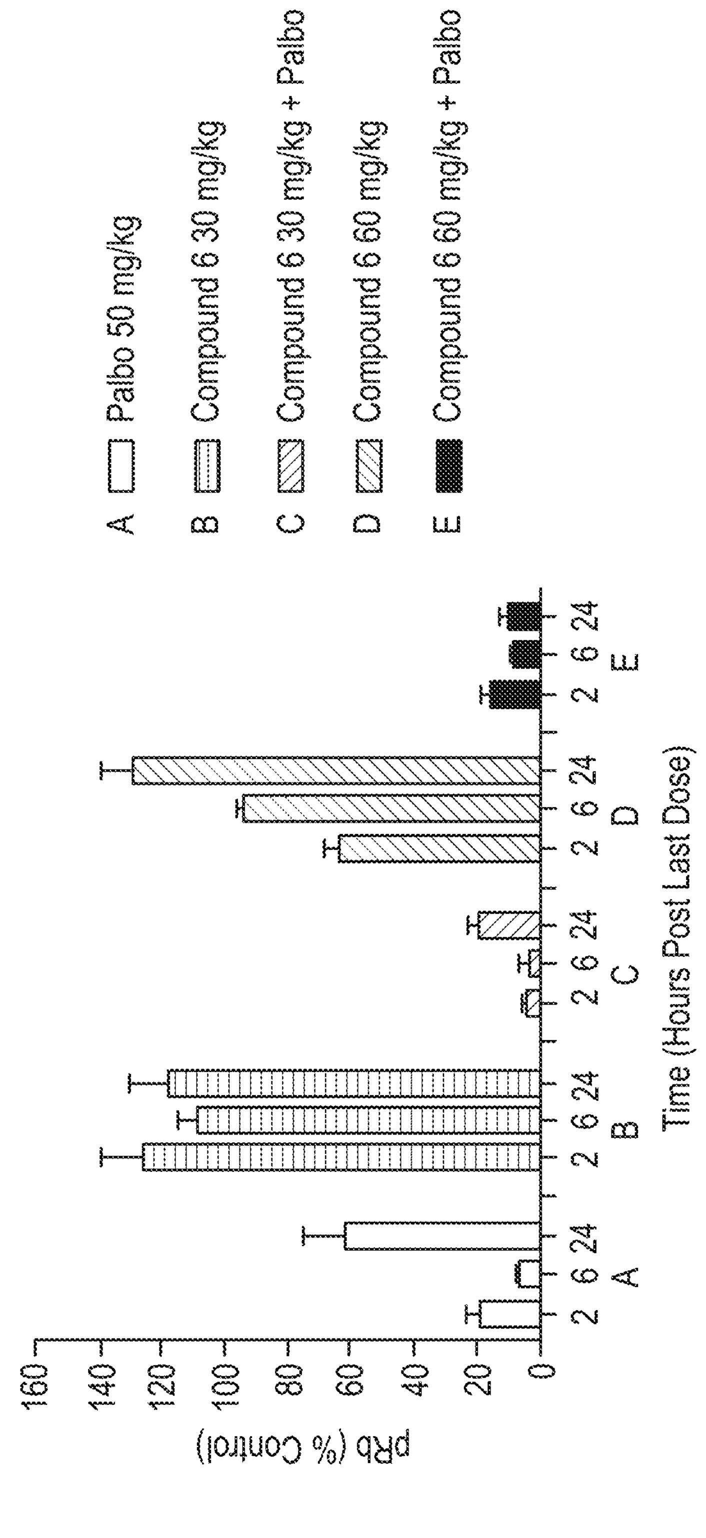
FIG. 16 illustrates the effect of treatment with a CDK2 inhibitor (the compound of Example 6) or a combination of a CDK2 inhibitor (the compound of Example 6) and a CDK4/6 inhibitor (palbociclib) on pRB levels in a CTG-3283 human CDK4/6 resistant ER+ breast cancer xenograft mouse model.

FIG. 16 illustrates the effect of treatment with Compound 6 or a combination of Compound 6 and palbociclib on pRB in this CTG-3283 human CDK4/6 resistant ER+ breast cancer xenograft model. A dose dependent inhibition of pRB was observed with increasing doses of Compound 6. In addition, the combination of Compound 6 and palbociclib led to further reduction of pRB when compared to Compound 6 alone.

IX. Additional Embodiments

Embodiment 1. A compound having the structure of Formula (I):

(I)

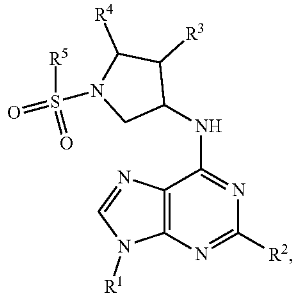

or a pharmaceutically acceptable salt thereof, wherein:

$R^1$ is selected from the group consisting of $C_{1-6}$-alkyl, halo-$C_{1-6}$-alkyl, and cyclopropyl;

$R^2$ is selected from the group consisting of —$NHR^6$,

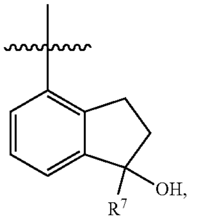

and

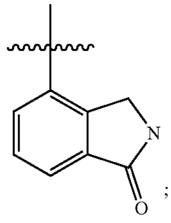

;

one of $R^3$ and $R^4$ is hydrogen and the other of $R^3$ and $R^4$ is selected from the group consisting of hydrogen, halogen, $C_{1-3}$-alkyl, halo-$C_{1-3}$-alkyl, and $C_{1-3}$-alkoxy;

$R^5$ is selected from the group consisting of $C_{1-6}$-alkyl, $C_{3-6}$-cycloalkyl, —$NR^8R^9$, pyrazolyl, and imidazolyl; wherein the $C_{1-6}$-alkyl and $C_{3-6}$-cycloalkyl are optionally substituted with one or more substituents independently selected from halogen and $C_{1-3}$-alkoxy; and the pyrazolyl and imidazolyl are optionally substituted with one or more substituents independently selected from $C_{1-3}$-alkyl;

$R^6$ is $C_{1-10}$-alkyl or

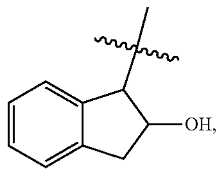 [SMILES: *C1c2ccccc2CC1O]

wherein the $C_{1-10}$-alkyl is substituted with hydroxy or oxo, and is optionally substituted with one or more substituents independently selected from the group consisting of halogen, $C_{3-6}$-cycloalkyl, and tetrahydrofuranyl;

$R^7$ is hydrogen or $C_{1-3}$-alkyl;

$R^8$ is hydrogen; and $R^9$ is selected from the group consisting of hydrogen, $C_{1-6}$-alkyl, $C_{3-6}$-cycloalkyl, $C_{1-6}$-alkoxy-$C_{1-6}$-alkyl, tetrahydrofuranyl, and 1,4-dioxanyl-$C_{1-3}$-alkyl; wherein the $C_{1-6}$-alkyl, $C_{3-6}$-cycloalkyl, $C_{1-6}$-alkoxy-$C_{1-6}$-alkyl, tetrahydrofuranyl, and 1,4-dioxanyl-$C_{1-3}$-alkyl are optionally substituted with one or more substituents independently selected from halogen; or $R^8$ and $R^9$ together with the nitrogen atom to which they are attached form a 4-, 5-, or 6-membered saturated monocyclic ring wherein the remaining ring atoms are carbon atoms, and wherein the monocyclic ring is optionally substituted with one or more substituents independently selected from halogen.

Embodiment 2. The compound of Embodiment 1, or a pharmaceutically acceptable salt thereof, wherein the compound has the structure of Formula (I-A):

(I-A)

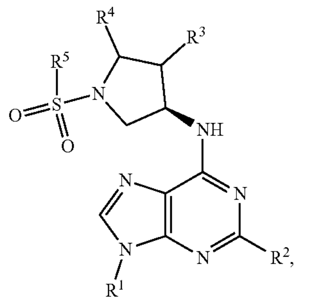

and wherein $R^1$, $R^2$, $R^3$, $R^4$, and $R^5$ are as defined in Embodiment 1.

Embodiment 3. The compound of Embodiment 1, or a pharmaceutically acceptable salt thereof, wherein $R^1$ is selected from the group consisting of $C_{1-3}$-alkyl, halo-$C_{1-3}$-alkyl, and cyclopropyl.

Embodiment 4. The compound of Embodiment 3, or a pharmaceutically acceptable salt thereof, wherein $R^1$ is selected from the group consisting of $C_{1-3}$-alkyl and halo-$C_{1-3}$-alkyl.

Embodiment 5. The compound of Embodiment 3, or a pharmaceutically acceptable salt thereof, wherein $R^1$ is selected from the group consisting of methyl, ethyl, isopropyl, fluoromethyl, and difluoromethyl.

Embodiment 6. The compound of Embodiment 3, or a pharmaceutically acceptable salt thereof, wherein $R^1$ is selected from the group consisting of ethyl and isopropyl.

Embodiment 7. The compound of Embodiment 3, or a pharmaceutically acceptable salt thereof, wherein $R^1$ is $C_{1-3}$-alkyl.

Embodiment 8. The compound of Embodiment 3, or a pharmaceutically acceptable salt thereof, wherein $R^1$ is methyl.

Embodiment 9. The compound of Embodiment 3, or a pharmaceutically acceptable salt thereof, wherein $R^1$ is ethyl.

Embodiment 10. The compound of Embodiment 3, or a pharmaceutically acceptable salt thereof, wherein $R^1$ is n-propyl.

Embodiment 11. The compound of Embodiment 3, or a pharmaceutically acceptable salt thereof, wherein $R^1$ is isopropyl.

Embodiment 12. The compound of Embodiment 3, or a pharmaceutically acceptable salt thereof, wherein $R^1$ is halo-$C_{1-3}$-alkyl.

Embodiment 13. The compound of Embodiment 3, or a pharmaceutically acceptable salt thereof, wherein $R^1$ is fluoro-$C_{1-3}$-alkyl.

Embodiment 14. The compound of Embodiment 3, or a pharmaceutically acceptable salt thereof, wherein $R^1$ is selected from the group consisting of fluoromethyl and difluoromethyl.

Embodiment 15. The compound of Embodiment 3, or a pharmaceutically acceptable salt thereof, wherein $R^1$ is fluoromethyl.

Embodiment 16. The compound of Embodiment 3, or a pharmaceutically acceptable salt thereof, wherein $R^1$ is difluoromethyl.

Embodiment 17. The compound of Embodiment 3, or a pharmaceutically acceptable salt thereof, wherein $R^1$ is cyclopropyl.

Embodiment 18. The compound of any of Embodiments 1 to 17, or a pharmaceutically acceptable salt thereof, wherein $R^2$ is —$NHR^6$.

Embodiment 19. The compound of Embodiment 18, or a pharmaceutically acceptable salt thereof, wherein $R^6$ is $C_{1-10}$-alkyl, wherein the $C_{1-10}$-alkyl is substituted with hydroxy, and is optionally substituted with one or more substituents independently selected from the group consisting of halogen, $C_{3-6}$-cycloalkyl, and tetrahydrofuranyl.

Embodiment 20. The compound of Embodiment 18, or a pharmaceutically acceptable salt thereof, wherein $R^6$ is $C_{2-6}$-alkyl, wherein the $C_{2-6}$-alkyl is substituted with hydroxy, and is optionally substituted with one or more substituents independently selected from the group consisting of halogen, $C_{3-6}$-cycloalkyl, and tetrahydrofuranyl.

Embodiment 21. The compound of Embodiment 18, or a pharmaceutically acceptable salt thereof, wherein $R^6$ is $C_{1-10}$-alkyl, wherein the $C_{1-10}$-alkyl is substituted with hydroxy, and is optionally substituted with one or more substituents independently selected from the group consisting of fluoro, cyclopropyl, and tetrahydrofuranyl.

Embodiment 22. The compound of Embodiment 18, or a pharmaceutically acceptable salt thereof, wherein $R^6$ is $C_{2-6}$-alkyl, wherein the $C_{2-6}$-alkyl is substituted with hydroxy, and is optionally substituted with one or more substituents independently selected from the group consisting of fluoro, cyclopropyl, and tetrahydrofuranyl.

Embodiment 23. The compound of Embodiment 18, or a pharmaceutically acceptable salt thereof, wherein $R^6$ is $C_{1-10}$-alkyl, wherein the $C_{1-10}$-alkyl is substituted with hydroxy, and is optionally substituted with one or more substituents independently selected from the group consisting of fluoro and cyclopropyl.

Embodiment 24. The compound of Embodiment 18, or a pharmaceutically acceptable salt thereof, wherein $R^6$ is $C_{2-6}$-alkyl, wherein the $C_{2-6}$-alkyl is substituted with hydroxy, and is optionally substituted with one or more substituents independently selected from the group consisting of fluoro and cyclopropyl.

Embodiment 25. The compound of Embodiment 18, or a pharmaceutically acceptable salt thereof, wherein $R^6$ is $C_{1-10}$-alkyl, wherein the $C_{1-10}$-alkyl is substituted with hydroxy.

Embodiment 26. The compound of Embodiment 18, or a pharmaceutically acceptable salt thereof, wherein $R^6$ is $C_{2-6}$-alkyl, wherein the $C_{2-6}$-alkyl is substituted with hydroxy.

Embodiment 27. The compound of Embodiment 18, or a pharmaceutically acceptable salt thereof, wherein $R^6$ is $C_4$-alkyl, wherein the $C_4$-alkyl is substituted with hydroxy.

Embodiment 28. The compound of Embodiment 18, or a pharmaceutically acceptable salt thereof, wherein $R^6$ is $C_5$-alkyl, wherein the $C_5$-alkyl is substituted with hydroxy.

Embodiment 29. The compound of Embodiment 18, or a pharmaceutically acceptable salt thereof, wherein $R^6$ is $C_6$-alkyl, wherein the $C_6$-alkyl is substituted with hydroxy.

Embodiment 30. The compound of Embodiment 18, or a pharmaceutically acceptable salt thereof, wherein $R^6$ is

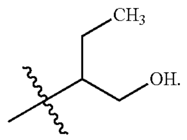 [SMILES: *C(CC)CO]

Embodiment 31. The compound of Embodiment 18, or a pharmaceutically acceptable salt thereof, wherein $R^6$ is selected from the group consisting of

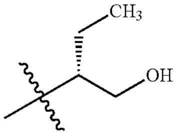

and

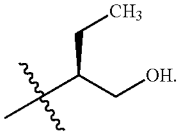

Embodiment 32. The compound of Embodiment 18, or a pharmaceutically acceptable salt thereof, wherein $R^6$ is

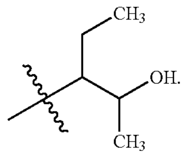

Embodiment 33. The compound of Embodiment 18, or a pharmaceutically acceptable salt thereof, wherein $R^6$ is selected from the group consisting of

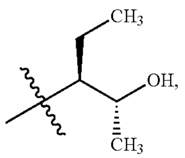

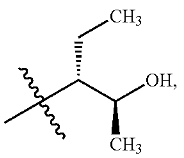

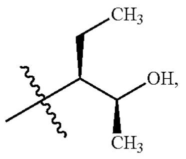

and

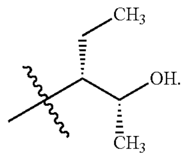

Embodiment 34. The compound of Embodiment 18, or a pharmaceutically acceptable salt thereof, wherein $R^6$ is

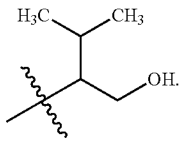 [SMILES: *C(CO)C(C)C]

Embodiment 35. The compound of Embodiment 18, or a pharmaceutically acceptable salt thereof, wherein $R^6$ is selected from the group consisting of

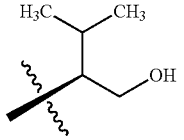

and

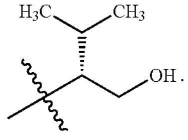

Embodiment 36. The compound of Embodiment 18, or a pharmaceutically acceptable salt thereof, wherein $R^6$ is $C_{1-10}$-alkyl, wherein the $C_{1-10}$-alkyl is substituted with hydroxy and one or more halogen.

Embodiment 37. The compound of Embodiment 18, or a pharmaceutically acceptable salt thereof, wherein $R^6$ is $C_{2-6}$-alkyl, wherein the $C_{2-6}$-alkyl is substituted with hydroxy and one or more halogen.

Embodiment 38. The compound of Embodiment 18, or a pharmaceutically acceptable salt thereof, wherein $R^6$ is $C_4$-alkyl, wherein the $C_4$-alkyl is substituted with hydroxy and one or more halogen.

Embodiment 39. The compound of Embodiment 18, or a pharmaceutically acceptable salt thereof, wherein $R^6$ is $C_5$-alkyl, wherein the $C_5$-alkyl is substituted with hydroxy and one or more halogen.

Embodiment 40. The compound of Embodiment 18, or a pharmaceutically acceptable salt thereof, wherein $R^6$ is $C_6$-alkyl, wherein the $C_6$-alkyl is substituted with hydroxy and one or more halogen.

Embodiment 41. The compound of any of Embodiments 36 to 40, or a pharmaceutically acceptable salt thereof, wherein the halogen is fluoro.

Embodiment 42. The compound of Embodiment 18, or a pharmaceutically acceptable salt thereof, wherein $R^6$ is

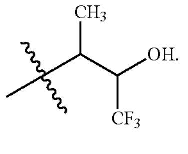

Embodiment 43. The compound of Embodiment 18, or a pharmaceutically acceptable salt thereof, wherein $R^6$ is

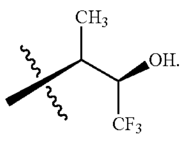

Embodiment 44. The compound of Embodiment 18, or a pharmaceutically acceptable salt thereof, wherein $R^6$ is

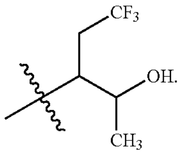

Embodiment 45. The compound of Embodiment 18, or a pharmaceutically acceptable salt thereof, wherein $R^6$ is

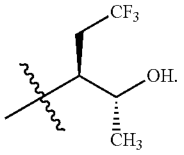

Embodiment 46. The compound of Embodiment 18, or a pharmaceutically acceptable salt thereof, wherein $R^6$ is $C_{1-10}$-alkyl, wherein the $C_{1-10}$-alkyl is substituted with hydroxy and $C_{3-6}$-cycloalkyl.

Embodiment 47. The compound of Embodiment 18, or a pharmaceutically acceptable salt thereof, wherein $R^6$ is $C_{2-6}$-alkyl, wherein the $C_{2-6}$-alkyl is substituted with hydroxy and $C_{3-6}$-cycloalkyl.

Embodiment 48. The compound of Embodiment 18, or a pharmaceutically acceptable salt thereof, wherein $R^6$ is $C_2$-alkyl, wherein the $C_2$-alkyl is substituted with hydroxy and $C_{3-6}$-cycloalkyl.

Embodiment 49. The compound of Embodiment 18, or a pharmaceutically acceptable salt thereof, wherein $R^6$ is $C_3$-alkyl, wherein the $C_3$-alkyl is substituted with hydroxy and $C_{3-6}$-cycloalkyl.

Embodiment 50. The compound of Embodiment 18, or a pharmaceutically acceptable salt thereof, wherein $R^6$ is $C_{1-10}$-alkyl, wherein the $C_{1-10}$-alkyl is substituted with hydroxy and cyclopropyl.

Embodiment 51. The compound of Embodiment 18, or a pharmaceutically acceptable salt thereof, wherein $R^6$ is $C_{2-6}$-alkyl, wherein the $C_{2-6}$-alkyl is substituted with hydroxy and cyclopropyl.

Embodiment 52. The compound of Embodiment 18, or a pharmaceutically acceptable salt thereof, wherein $R^6$ is $C_2$-alkyl, wherein the $C_2$-alkyl is substituted with hydroxy and cyclopropyl.

Embodiment 53. The compound of Embodiment 18, or a pharmaceutically acceptable salt thereof, wherein $R^6$ is $C_3$-alkyl, wherein the $C_3$-alkyl is substituted with hydroxy and cyclopropyl.

Embodiment 54. The compound of Embodiment 18, or a pharmaceutically acceptable salt thereof, wherein $R^6$ is

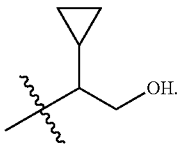 [SMILES: *C(CO)C1CC1]

Embodiment 55. The compound of Embodiment 18, or a pharmaceutically acceptable salt thereof, wherein $R^6$ is selected from the group consisting of:

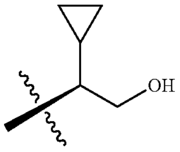 and 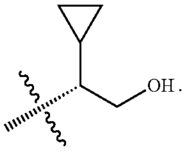

Embodiment 56. The compound of Embodiment 18, or a pharmaceutically acceptable salt thereof, wherein $R^6$ is

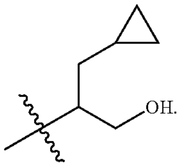 [SMILES: *C(CO)CC1CC1]

Embodiment 57. The compound of Embodiment 18, or a pharmaceutically acceptable salt thereof, wherein $R^6$ is selected from the group consisting of:

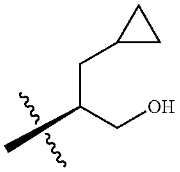 and 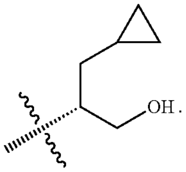

Embodiment 58. The compound of Embodiment 18, or a pharmaceutically acceptable salt thereof, wherein $R^6$ is $C_{1-10}$-alkyl, wherein the $C_{1-10}$-alkyl is substituted with hydroxy and cyclopentyl.

Embodiment 59. The compound of Embodiment 18, or a pharmaceutically acceptable salt thereof, wherein $R^6$ is $C_{2-6}$-alkyl, wherein the $C_{2-6}$-alkyl is substituted with hydroxy and cyclopentyl.

Embodiment 60. The compound of Embodiment 18, or a pharmaceutically acceptable salt thereof, wherein $R^6$ is $C_2$-alkyl, wherein the $C_2$-alkyl is substituted with hydroxy and cyclopentyl.

Embodiment 61. The compound of Embodiment 18, or a pharmaceutically acceptable salt thereof, wherein $R^6$ is $C_3$-alkyl, wherein the $C_3$-alkyl is substituted with hydroxy and cyclopentyl.

Embodiment 62. The compound of Embodiment 18, or a pharmaceutically acceptable salt thereof, wherein $R^6$ is

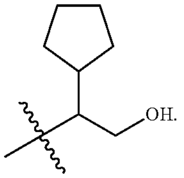 [SMILES: *C(CO)C1CCCC1]

Embodiment 63. The compound of Embodiment 18, or a pharmaceutically acceptable salt thereof, wherein $R^6$ is

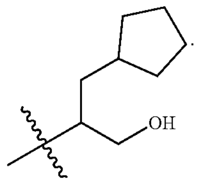 [SMILES: *C(CO)CC1CCCC1]

Embodiment 64. The compound of Embodiment 18, or a pharmaceutically acceptable salt thereof, wherein $R^6$ is $C_{1-10}$-alkyl, wherein the $C_{1-10}$-alkyl is substituted with hydroxy and tetrahydrofuranyl.

Embodiment 65. The compound of Embodiment 18, or a pharmaceutically acceptable salt thereof, wherein $R^6$ is $C_{2-6}$-alkyl, wherein the $C_{2-6}$-alkyl is substituted with hydroxy and tetrahydrofuranyl.

Embodiment 66. The compound of Embodiment 18, or a pharmaceutically acceptable salt thereof, wherein $R^6$ is $C_2$-alkyl, wherein the $C_2$-alkyl is substituted with hydroxy and tetrahydrofuranyl.

Embodiment 67. The compound of Embodiment 18, or a pharmaceutically acceptable salt thereof, wherein $R^6$ is $C_3$-alkyl, wherein the $C_3$-alkyl is substituted with hydroxy and tetrahydrofuranyl.

Embodiment 68. The compound of Embodiment 18, or a pharmaceutically acceptable salt thereof, wherein $R^6$ is

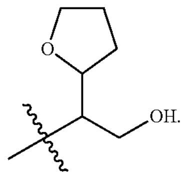 [SMILES: *C(CO)C1CCCO1]

Embodiment 69. The compound of Embodiment 18, or a pharmaceutically acceptable salt thereof, wherein $R^6$ is

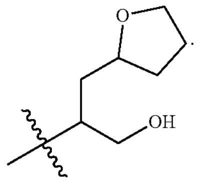 [SMILES: *C(CO)CC1CCCO1]

Embodiment 70. The compound of Embodiment 18, or a pharmaceutically acceptable salt thereof, wherein $R^6$ is

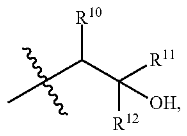

wherein:

$R^{10}$ is selected from the group consisting of $C_{1-3}$-alkyl, halo-$C_{1-3}$-alkyl, $C_{3-6}$-cycloalkyl, $C_{3-6}$-cycloalkyl-$C_{1-3}$-alkyl, and tetrahydrofuranyl;

$R^{11}$ is selected from the group consisting of hydrogen and $C_{1-3}$-alkyl; and $R^{12}$ is selected from the group consisting of hydrogen, $C_{1-3}$-alkyl, and halo-$C_{1-3}$-alkyl.

Embodiment 71. The compound of Embodiment 70, or a pharmaceutically acceptable salt thereof, wherein:

$R^{10}$ is selected from the group consisting of $C_{1-3}$-alkyl and halo-$C_{1-3}$-alkyl;

$R^{11}$ is selected from the group consisting of hydrogen and $C_{1-3}$-alkyl; and $R^{12}$ is selected from the group consisting of hydrogen, $C_{1-3}$-alkyl, and halo-$C_{1-3}$-alkyl.

Embodiment 72. The compound of Embodiment 70, or a pharmaceutically acceptable salt thereof, wherein:

$R^{10}$ is selected from the group consisting of $C_{3-6}$-cycloalkyl, $C_{3-6}$-cycloalkyl-$C_{1-3}$-alkyl, and tetrahydrofuranyl;

$R^{11}$ is selected from the group consisting of hydrogen and $C_{1-3}$-alkyl; and $R^{12}$ is selected from the group consisting of hydrogen, $C_{1-3}$-alkyl, and halo-$C_{1-3}$-alkyl.

Embodiment 73. The compound of Embodiment 70, or a pharmaceutically acceptable salt thereof, wherein:

$R^{10}$ is selected from the group consisting of methyl, ethyl, fluoroethyl, cyclopropyl, cyclopropylmethyl, cyclopentyl, and tetrahydrofuranyl;

$R^{11}$ is selected from the group consisting of hydrogen and methyl; and $R^{12}$ is selected from the group consisting of hydrogen, methyl, and trifluoromethyl.

Embodiment 74. The compound of Embodiment 70, or a pharmaceutically acceptable salt thereof, wherein:

$R^{10}$ is selected from the group consisting of methyl, ethyl, and fluoroethyl;

$R^{11}$ is selected from the group consisting of hydrogen and methyl; and $R^{12}$ is selected from the group consisting of hydrogen, methyl, and trifluoromethyl.

Embodiment 75. The compound of Embodiment 70, or a pharmaceutically acceptable salt thereof, wherein:

$R^{10}$ is methyl;

$R^{11}$ is selected from the group consisting of hydrogen and methyl; and $R^{12}$ is selected from the group consisting of hydrogen, methyl, and trifluoromethyl.

Embodiment 76. The compound of Embodiment 70, or a pharmaceutically acceptable salt thereof, wherein:

$R^{10}$ is ethyl;

$R^{11}$ is selected from the group consisting of hydrogen and methyl; and $R^{12}$ is selected from the group consisting of hydrogen, methyl, and trifluoromethyl.

Embodiment 77. The compound of Embodiment 70, or a pharmaceutically acceptable salt thereof, wherein:

$R^{10}$ is fluoroethyl;

$R^{11}$ is selected from the group consisting of hydrogen and methyl; and $R^{12}$ is selected from the group consisting of hydrogen, methyl, and trifluoromethyl.

Embodiment 78. The compound of Embodiment 70, or a pharmaceutically acceptable salt thereof, wherein:

$R^{10}$ is selected from the group consisting of cyclopropyl and cyclopropylmethyl;

$R^{11}$ is selected from the group consisting of hydrogen and methyl; and $R^{12}$ is selected from the group consisting of hydrogen and methyl.

Embodiment 79. The compound of Embodiment 70, or a pharmaceutically acceptable salt thereof, wherein:

$R^{10}$ is cyclohexyl;

$R^{11}$ is selected from the group consisting of hydrogen and methyl; and $R^{12}$ is selected from the group consisting of hydrogen and methyl.

Embodiment 80. The compound of Embodiment 70, or a pharmaceutically acceptable salt thereof, wherein:

$R^{10}$ is tetrahydrofuranyl;

$R^{11}$ is selected from the group consisting of hydrogen and methyl; and $R^{12}$ is selected from the group consisting of hydrogen and methyl.

Embodiment 81. The compound of Embodiment 18, or a pharmaceutically acceptable salt thereof, wherein $R^6$ is

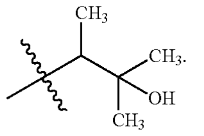

Embodiment 82. The compound of Embodiment 18, or a pharmaceutically acceptable salt thereof, wherein $R^6$ is selected from the group consisting of:

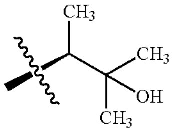
and
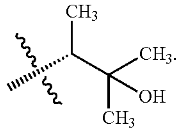

Embodiment 83. The compound of Embodiment 18, or a pharmaceutically acceptable salt thereof, wherein $R^6$ is

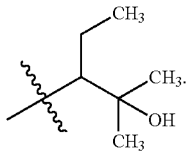

Embodiment 84. The compound of Embodiment 18, or a pharmaceutically acceptable salt thereof, wherein $R^6$ is selected from the group consisting of:

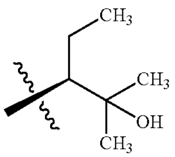
and
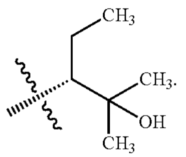

Embodiment 85. The compound of Embodiment 18, or a pharmaceutically acceptable salt thereof, wherein $R^6$ is $C_{1-10}$-alkyl, wherein the $C_{1-10}$-alkyl is substituted with oxo, and is optionally substituted with one or more substituents independently selected from the group consisting of halogen, $C_{3-6}$-cycloalkyl, and tetrahydrofuranyl.

Embodiment 86. The compound of Embodiment 85, or a pharmaceutically acceptable salt thereof, wherein $R^6$ is $C_{2-5}$-alkyl, wherein the $C_{2-5}$-alkyl is substituted with oxo, and is optionally substituted with one or more substituents independently selected from the group consisting of halogen, $C_{3-6}$-cycloalkyl, and tetrahydrofuranyl.

Embodiment 87. The compound of Embodiment 85, or a pharmaceutically acceptable salt thereof, wherein $R^6$ is $C_{1-10}$-alkyl, wherein the $C_{1-10}$-alkyl is substituted with oxo.

Embodiment 88. The compound of Embodiment 85, or a pharmaceutically acceptable salt thereof, wherein $R^6$ is $C_{1-5}$-alkyl, wherein the $C_{2-5}$-alkyl is substituted with oxo.

Embodiment 89. The compound of Embodiment 18, or a pharmaceutically acceptable salt thereof, wherein $R^6$ is

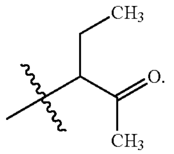

Embodiment 90. The compound of Embodiment 18, or a pharmaceutically acceptable salt thereof, wherein $R^6$ is selected from the group consisting of:

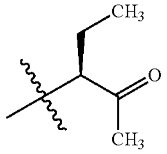
and
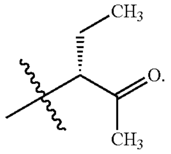

Embodiment 91. The compound of Embodiment 18, or a pharmaceutically acceptable salt thereof, wherein $R^6$ is

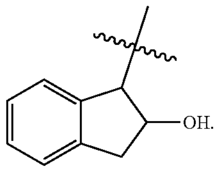 [SMILES: *C1c2ccccc2CC1O]

Embodiment 92. The compound of any of Embodiments 1 to 17, or a pharmaceutically acceptable salt thereof, wherein $R^2$ is

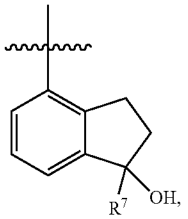

wherein $R^7$ is hydrogen or $C_{1-3}$-alkyl.

Embodiment 93. The compound of Embodiment 92, or a pharmaceutically acceptable salt thereof, wherein $R^7$ is hydrogen or methyl.

Embodiment 94. The compound of Embodiment 92, or a pharmaceutically acceptable salt thereof, wherein $R^7$ is hydrogen.

Embodiment 95. The compound of Embodiment 92, or a pharmaceutically acceptable salt thereof, wherein $R^7$ is methyl.

Embodiment 96. The compound of Embodiment 1, or a pharmaceutically acceptable salt thereof, wherein $R^2$ is

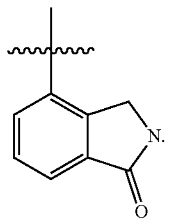

Embodiment 97. The compound of any of Embodiments 1 to 96, or a pharmaceutically acceptable salt thereof, wherein $R^3$ is hydrogen and $R^4$ is selected from the group consisting of hydrogen, halogen, $C_{1-3}$-alkyl, halo-$C_{1-3}$-alkyl, and $C_{1-3}$-alkoxy.

Embodiment 98. The compound of any of Embodiments 1 to 96, or a pharmaceutically acceptable salt thereof, wherein $R^3$ is selected from the group consisting of hydrogen, halogen, $C_{1-3}$-alkyl, halo-$C_{1-3}$-alkyl, and $C_{1-3}$-alkoxy, and $R^4$ is hydrogen.

Embodiment 99. The compound of any of Embodiments 1 to 96, or a pharmaceutically acceptable salt thereof, wherein $R^3$ is hydrogen and $R^4$ is selected from the group consisting of hydrogen, fluoro, methyl, and methoxy.

Embodiment 100. The compound of any of Embodiments 1 to 96, or a pharmaceutically acceptable salt thereof, wherein $R^3$ is selected from the group consisting of hydrogen, fluoro, methyl, and methoxy, and $R^4$ is hydrogen.

Embodiment 101. The compound of any of Embodiments 1 to 96, or a pharmaceutically acceptable salt thereof, wherein $R^3$ is selected from the group consisting of hydrogen, methyl, and fluoro, and $R^4$ is hydrogen.

Embodiment 102. The compound of any of Embodiments 1 to 96, or a pharmaceutically acceptable salt thereof, wherein $R^3$ is hydrogen and $R^4$ is selected from the group consisting of hydrogen and methyl.

Embodiment 103. The compound of any of Embodiments 1 to 96, or a pharmaceutically acceptable salt thereof, wherein $R^3$ and $R^4$ are each hydrogen.

Embodiment 104. The compound of any of Embodiments 1 to 96, or a pharmaceutically acceptable salt thereof, wherein $R^3$ is fluoro and $R^4$ is hydrogen.

Embodiment 105. The compound of any of Embodiments 1 to 96, or a pharmaceutically acceptable salt thereof, wherein $R^3$ is methyl and $R^4$ is hydrogen.

Embodiment 106. The compound of any of Embodiments 1 to 96, or a pharmaceutically acceptable salt thereof, wherein $R^3$ is hydrogen and $R^4$ is methyl.

Embodiment 107. The compound of any of Embodiments 1 to 106, or a pharmaceutically acceptable salt thereof, wherein $R^5$ is selected from the group consisting of $C_1$-6-alkyl, $C_{3-6}$-cycloalkyl, and —$NR^8R^9$; wherein the $C_{1-6}$-alkyl and $C_{3-6}$-cycloalkyl are optionally substituted with one or more substituents independently selected from halogen and $C_{1-3}$-alkoxy.

Embodiment 108. The compound of Embodiment 107, or a pharmaceutically acceptable salt thereof, wherein $R^5$ is selected from the group consisting of $C_{1-3}$-alkyl, $C_{3-6}$-cycloalkyl, and —$NR^8R^9$; wherein the $C_{1-3}$-alkyl and $C_{3-6}$-cycloalkyl are optionally substituted with one or more substituents independently selected from halogen and $C_{1-3}$-alkoxy.

Embodiment 109. The compound of Embodiment 107, or a pharmaceutically acceptable salt thereof, wherein $R^5$ is selected from the group consisting of $C_{1-6}$-alkyl and $C_{3-6}$-cycloalkyl; wherein the $C_{1-6}$-alkyl and $C_{3-6}$-cycloalkyl are optionally substituted with one or more substituents independently selected from halogen and $C_{1-3}$-alkoxy.

Embodiment 110. The compound of Embodiment 107, or a pharmaceutically acceptable salt thereof, wherein $R^5$ is $C_{1-6}$-alkyl, wherein the $C_{1-6}$-alkyl is optionally substituted with one or more substituents independently selected from halogen and $C_{1-3}$-alkoxy.

Embodiment 111. The compound of Embodiment 107, or a pharmaceutically acceptable salt thereof, wherein $R^5$ is $C_{1-3}$-alkyl, wherein the $C_{1-3}$-alkyl is optionally substituted with one or more substituents independently selected from halogen and $C_{1-3}$-alkoxy.

Embodiment 112. The compound of Embodiment 107, or a pharmaceutically acceptable salt thereof, wherein $R^5$ is methyl, wherein the methyl is optionally substituted with one or more substituents independently selected from halogen and $C_{1-3}$-alkoxy.

Embodiment 113. The compound of Embodiment 107, or a pharmaceutically acceptable salt thereof, wherein $R^5$ is ethyl, wherein the ethyl is optionally substituted with one or more substituents independently selected from halogen and $C_{1-3}$-alkoxy.

Embodiment 114. The compound of Embodiment 107, or a pharmaceutically acceptable salt thereof, wherein $R^5$ is propyl, wherein the propyl is optionally substituted with one or more substituents independently selected from halogen and $C_{1-3}$-alkoxy.

Embodiment 115. The compound of Embodiment 107, or a pharmaceutically acceptable salt thereof, wherein $R^5$ is $C_{3-6}$-cycloalkyl, wherein the $C_{3-6}$-cycloalkyl is optionally substituted with one or more substituents independently selected from halogen and $C_{1-3}$-alkoxy.

Embodiment 116. The compound of Embodiment 107, or a pharmaceutically acceptable salt thereof, wherein $R^5$ is cyclopropyl, wherein the cyclopropyl is optionally substituted with one or more substituents independently selected from halogen and $C_{1-3}$-alkoxy.

Embodiment 117. The compound of Embodiment 107, or a pharmaceutically acceptable salt thereof, wherein $R^5$ is cyclobutyl, wherein the cyclobutyl is optionally substituted with one or more substituents independently selected from halogen and $C_{1-3}$-alkoxy.

Embodiment 118. The compound of Embodiment 107, or a pharmaceutically acceptable salt thereof, wherein $R^5$ is cyclopentyl, wherein the cyclopentyl is optionally substituted with one or more substituents independently selected from halogen and $C_{1-3}$-alkoxy.

Embodiment 119. The compound of Embodiment 107, or a pharmaceutically acceptable salt thereof, wherein $R^5$ is cyclohexyl, wherein the cyclohexyl is optionally substituted with one or more substituents independently selected from halogen and $C_{1-3}$-alkoxy.

Embodiment 120. The compound of any of Embodiments 107 to 119, or a pharmaceutically acceptable salt thereof, wherein the halogen is fluoro.

Embodiment 121. The compound of any of Embodiments 107 to 119, or a pharmaceutically acceptable salt thereof, wherein the $C_{1-3}$-alkoxy is methoxy.

Embodiment 122. The compound of any of Embodiments 107 to 119, or a pharmaceutically acceptable salt thereof, wherein the halogen is fluoro and the $C_{1-3}$-alkoxy is methoxy.

Embodiment 123. The compound of Embodiment 107, or a pharmaceutically acceptable salt thereof, wherein $R^5$ is selected from the group consisting of pyrazolyl and imidazolyl, wherein the pyrazolyl and imidazolyl are optionally substituted with one or more substituents independently selected from $C_{1-3}$-alkyl.

Embodiment 124. The compound of Embodiment 107, or a pharmaceutically acceptable salt thereof, wherein $R^5$ is selected from the group consisting of pyrazolyl and imidazolyl, wherein the pyrazolyl and imidazolyl are optionally substituted with one or more methyl.

Embodiment 125. The compound of Embodiment 107, or a pharmaceutically acceptable salt thereof, wherein $R^5$ is pyrazolyl, wherein the pyrazolyl is optionally substituted with one or more substituents independently selected from $C_{1-3}$-alkyl.

Embodiment 126. The compound of Embodiment 107, or a pharmaceutically acceptable salt thereof, wherein $R^5$ is pyrazolyl, wherein the pyrazolyl is optionally substituted with one or more methyl.

Embodiment 127. The compound of Embodiment 107, or a pharmaceutically acceptable salt thereof, wherein $R^5$ is imidazolyl, wherein the imidazolyl is optionally substituted with one or more substituents independently selected from $C_{1-3}$-alkyl.

Embodiment 128. The compound of Embodiment 107, or a pharmaceutically acceptable salt thereof, wherein $R^5$ is imidazolyl, wherein the imidazolyl is optionally substituted with one or more methyl.

Embodiment 129. The compound of Embodiment 107, or a pharmaceutically acceptable salt thereof, wherein $R^5$ is selected from the group consisting of methyl, fluoromethyl, trifluoromethyl, methoxyethyl, cyclopropyl, imidazolyl, pyrazolyl, methylimidazolyl, and methylpyrazolyl.

Embodiment 130. The compound of Embodiment 107, or a pharmaceutically acceptable salt thereof, wherein $R^5$ is —$NR^8R^9$; $R^8$ is hydrogen; and $R^9$ is selected from the group consisting of hydrogen, $C_{1-6}$-alkyl, $C_{3-6}$-cycloalkyl, $C_{1-6}$-alkoxy-$C_{1-6}$-alkyl, tetrahydrofuranyl, and 1,4-dioxanyl-$C_{1-3}$-alkyl; wherein the $C_{1-6}$-alkyl, $C_{3-6}$-cycloalkyl, $C_{1-6}$-alkoxy-$C_{1-6}$-alkyl, tetrahydrofuranyl, and 1,4-dioxanyl-$C_{1-3}$-alkyl are optionally substituted with one or more substituents independently selected from halogen.

Embodiment 131. The compound of Embodiment 130, or a pharmaceutically acceptable salt thereof, wherein $R^9$ is selected from the group consisting of hydrogen, $C_{1-3}$-alkyl, $C_{3-6}$-cycloalkyl, $C_{1-3}$-alkoxy-$C_{1-3}$-alkyl, tetrahydrofuranyl, and 1,4-dioxanyl-$C_{1-3}$-alkyl; wherein the $C_{1-3}$-alkyl, $C_{3-6}$-cycloalkyl, $C_{1-3}$-alkoxy-$C_{1-3}$-alkyl, tetrahydrofuranyl, and 1,4-dioxanyl-$C_{1-3}$-alkyl are optionally substituted with one or more substituents independently selected from halogen.

Embodiment 132. The compound of Embodiment 130, or a pharmaceutically acceptable salt thereof, wherein $R^9$ is selected from the group consisting of hydrogen, $C_{1-3}$-alkyl, tetrahydrofuranyl, and 1,4-dioxanyl-$C_{1-3}$-alkyl; wherein the $C_{1-3}$-alkyl is optionally substituted with one or more substituents independently selected from halogen.

Embodiment 133. The compound of Embodiment 130, or a pharmaceutically acceptable salt thereof, wherein $R^9$ is hydrogen.

Embodiment 134. The compound of Embodiment 130, or a pharmaceutically acceptable salt thereof, wherein $R^9$ is $C_{1-6}$-alkyl, wherein the $C_{1-6}$-alkyl is optionally substituted with one or more substituents independently selected from halogen.

Embodiment 135. The compound of Embodiment 130, or a pharmaceutically acceptable salt thereof, wherein $R^9$ is $C_{1-3}$-alkyl, wherein the $C_{1-3}$-alkyl is optionally substituted with one or more substituents independently selected from halogen.

Embodiment 136. The compound of Embodiment 130, or a pharmaceutically acceptable salt thereof, wherein $R^9$ is methyl, wherein the methyl is optionally substituted with one or more substituents independently selected from halogen.

Embodiment 137. The compound of Embodiment 130, or a pharmaceutically acceptable salt thereof, wherein $R^9$ is ethyl, wherein the ethyl is optionally substituted with one or more substituents independently selected from halogen.

Embodiment 138. The compound of Embodiment 130, or a pharmaceutically acceptable salt thereof, wherein $R^9$ is propyl, wherein the propyl is optionally substituted with one or more substituents independently selected from halogen.

Embodiment 139. The compound of Embodiment 130, or a pharmaceutically acceptable salt thereof, wherein $R^9$ is $C_{3-6}$-cycloalkyl, wherein the $C_{3-6}$-cycloalkyl is optionally substituted with one or more substituents independently selected from halogen.

Embodiment 140. The compound of Embodiment 130, or a pharmaceutically acceptable salt thereof, wherein $R^9$ is cyclopropyl, wherein the cyclopropyl is optionally substituted with one or more substituents independently selected from halogen.

Embodiment 141. The compound of Embodiment 130, or a pharmaceutically acceptable salt thereof, wherein $R^9$ is cyclobutyl, wherein the cyclobutyl is optionally substituted with one or more substituents independently selected from halogen.

Embodiment 142. The compound of Embodiment 130, or a pharmaceutically acceptable salt thereof, wherein $R^9$ is cyclopentyl, wherein the cyclopentyl is optionally substituted with one or more substituents independently selected from halogen.

Embodiment 143. The compound of Embodiment 130, or a pharmaceutically acceptable salt thereof, wherein $R^9$ is cyclohexyl, wherein the cyclohexyl is optionally substituted with one or more substituents independently selected from halogen.

Embodiment 144. The compound of any of Embodiments 130 to 143, or a pharmaceutically acceptable salt thereof, wherein the halogen is fluoro.

Embodiment 145. The compound of Embodiment 130, or a pharmaceutically acceptable salt thereof, wherein $R^9$ is $C_{1-6}$-alkoxy-$C_{1-6}$-alkyl, wherein the $C_{1-6}$-alkoxy-$C_{1-6}$-alkyl is optionally substituted with one or more substituents independently selected from halogen.

Embodiment 146. The compound of Embodiment 130, or a pharmaceutically acceptable salt thereof, wherein $R^9$ is $C_{1-3}$-alkoxy-$C_{1-3}$-alkyl, wherein the $C_{1-3}$-alkoxy-$C_{1-3}$-alkyl is optionally substituted with one or more substituents independently selected from halogen.

Embodiment 147. The compound of Embodiment 130, or a pharmaceutically acceptable salt thereof, wherein $R^9$ is methoxy-$C_{1-3}$-alkyl, wherein the methoxy-$C_{1-3}$-alkyl is optionally substituted with one or more substituents independently selected from halogen.

Embodiment 148. The compound of Embodiment 130, or a pharmaceutically acceptable salt thereof, wherein $R^9$ is methoxymethyl, wherein the methoxymethyl is optionally substituted with one or more substituents independently selected from halogen.

Embodiment 149. The compound of Embodiment 130, or a pharmaceutically acceptable salt thereof, wherein $R^9$ is methoxyethyl, wherein the methoxyethyl is optionally substituted with one or more substituents independently selected from halogen.

Embodiment 150. The compound of any of Embodiments 145 to 149, or a pharmaceutically acceptable salt thereof, wherein the halogen is fluoro.

Embodiment 151. The compound of Embodiment 130, or a pharmaceutically acceptable salt thereof, wherein $R^9$ is selected from the group consisting of tetrahydrofuranyl and 1,4-dioxanyl-$C_{1-3}$-alkyl; wherein the tetrahydrofuranyl, and 1,4-dioxanyl-$C_{1-3}$-alkyl are optionally substituted with one or more substituents independently selected from halogen.

Embodiment 152. The compound of Embodiment 130, or a pharmaceutically acceptable salt thereof, wherein $R^9$ is tetrahydrofuranyl.

Embodiment 153. The compound of Embodiment 130, or a pharmaceutically acceptable salt thereof, wherein $R^9$ is 1,4-dioxanyl-$C_{1-3}$-alkyl.

Embodiment 154. The compound of Embodiment 130, or a pharmaceutically acceptable salt thereof, wherein $R^9$ is 1,4-dioxanyl-methyl.

Embodiment 155. The compound of any of Embodiments 151 to 154, or a pharmaceutically acceptable salt thereof, wherein the halogen is fluoro.

Embodiment 156. The compound of Embodiment 107, or a pharmaceutically acceptable salt thereof, wherein $R^8$ and $R^9$ together with the nitrogen atom to which they are attached form a 4-, 5-, or 6-membered saturated monocyclic ring wherein the remaining ring atoms are carbon atoms, and wherein the monocyclic ring is optionally substituted with one or more substituents independently selected from halogen.

Embodiment 157. The compound of Embodiment 156, or a pharmaceutically acceptable salt thereof, wherein $R^8$ and $R^9$ together with the nitrogen atom to which they are attached form a 4-membered saturated monocyclic ring wherein the remaining ring atoms are carbon atoms, and wherein the monocyclic ring is optionally substituted with one or more substituents independently selected from halogen.

Embodiment 158. The compound of Embodiment 156, or a pharmaceutically acceptable salt thereof, wherein $R^8$ and $R^9$ together with the nitrogen atom to which they are attached form a 5-membered saturated monocyclic ring wherein the remaining ring atoms are carbon atoms, and wherein the monocyclic ring is optionally substituted with one or more substituents independently selected from halogen.

Embodiment 159. The compound of Embodiment 156, or a pharmaceutically acceptable salt thereof, wherein $R^8$ and $R^9$ together with the nitrogen atom to which they are attached form a 6-membered saturated monocyclic ring wherein the remaining ring atoms are carbon atoms, and wherein the monocyclic ring is optionally substituted with one or more substituents independently selected from halogen.

Embodiment 160. The compound of Embodiment 107, or a pharmaceutically acceptable salt thereof, wherein $R^9$ is selected from the group consisting of hydrogen, methyl, ethyl, difluoroethyl, trifluoroethyl, tetrahydrofuranyl, and 1,4-dioxanylmethyl; or $R^8$ and $R^9$ together with the nitrogen atom to which they are attached form an azetidinyl ring, and wherein the azetidinyl ring is optionally substituted with one or more substituents independently selected from halogen.

Embodiment 161. The compound of any of Embodiments 156 to 160, or a pharmaceutically acceptable salt thereof, wherein the halogen is fluoro.

Embodiment 162. The compound of Embodiment 1, or a pharmaceutically acceptable salt thereof, wherein the compound has a structure selected from the group consisting of:

(I-1)

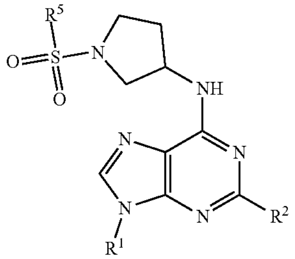

(I-2)

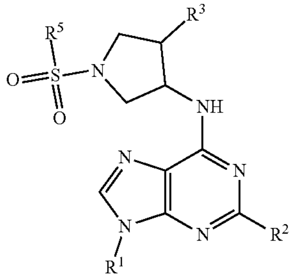

(I-3)

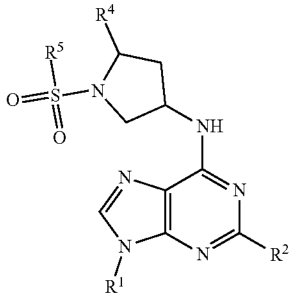

(I-4)

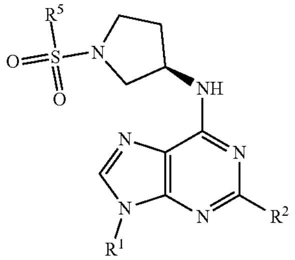

(I-5)

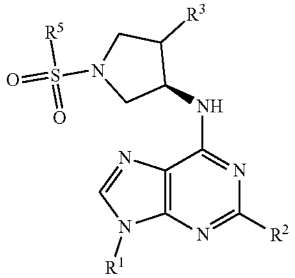

-continued
(I-6)
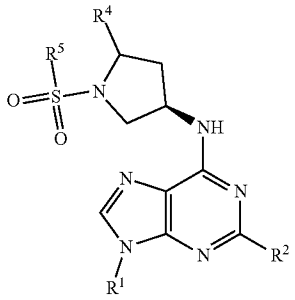
(I-7)
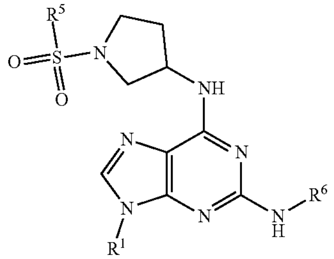
(I-8)
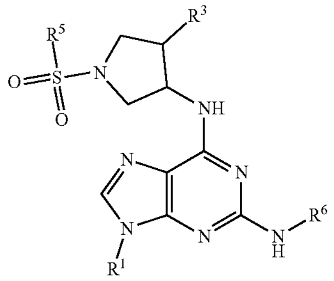
(I-9)
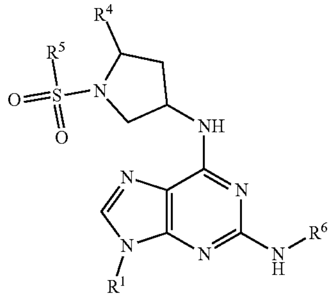
(I-10)
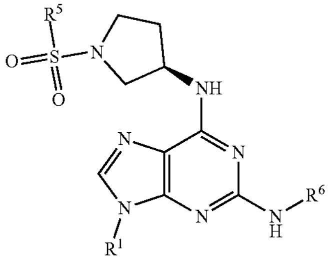
-continued
(I-11)
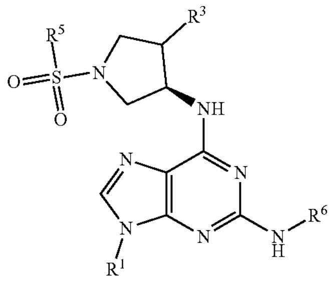
(I-12)
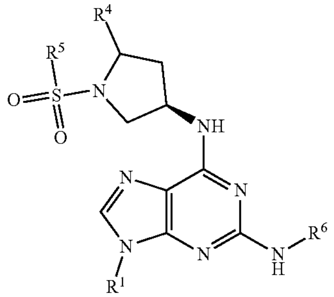
(I-13)
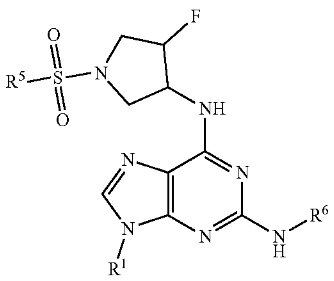
(I-14)
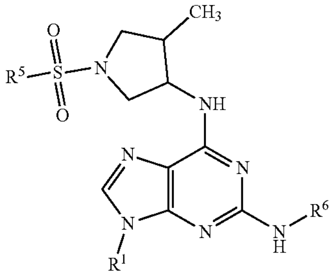
(I-15)
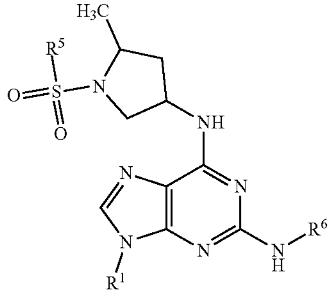

-continued
(I-16)
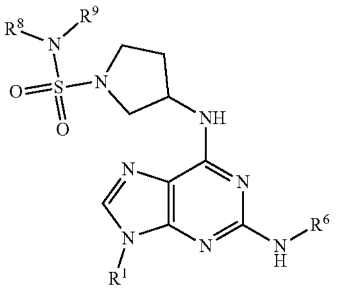
(I-17)
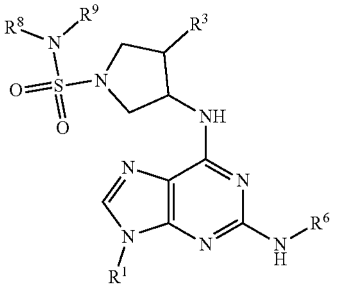
(I-18)
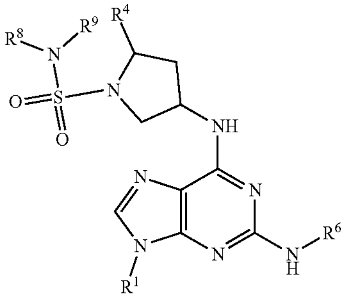
(I-19)
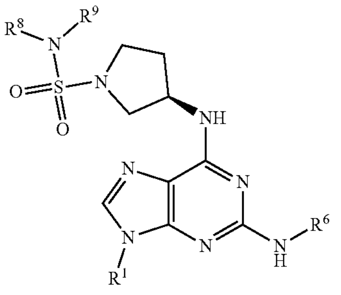
(I-20)
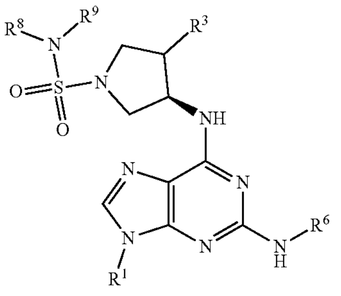
-continued
(I-21)
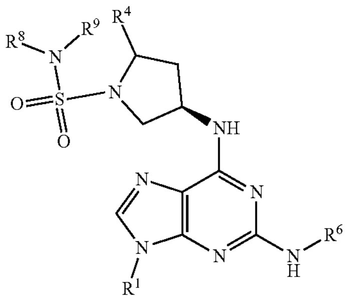
(I-22)
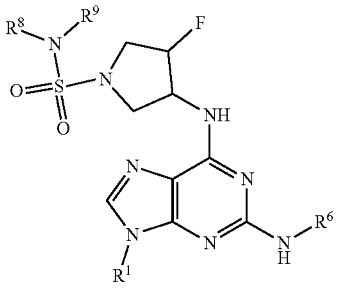
(I-23)
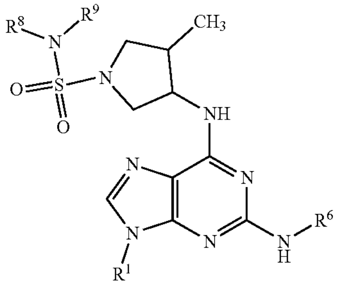
(I-24)
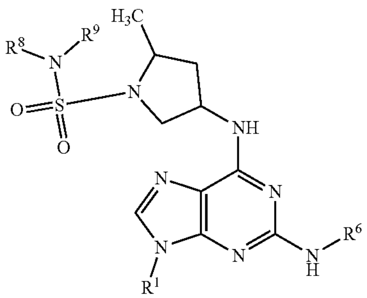
(I-25)
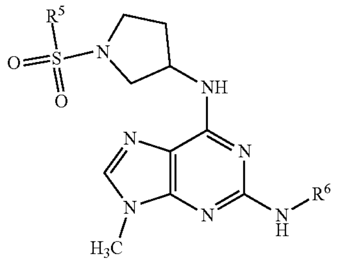

-continued
(I-26)
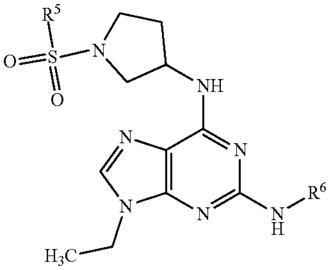
(I-27)
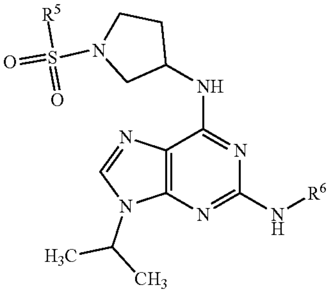
(I-28)
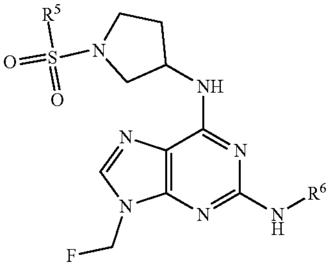
(I-29)
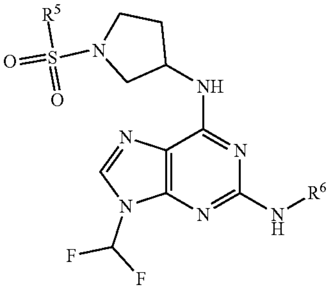
(I-30)
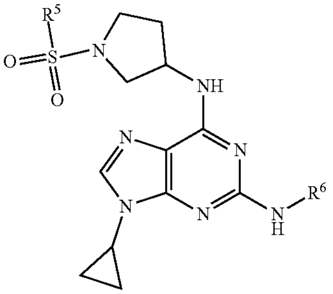
-continued
(I-31)
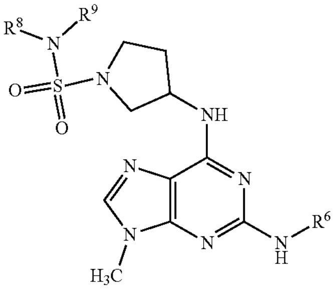
(I-32)
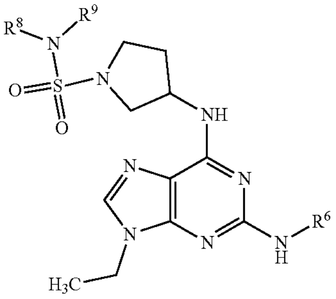
(I-33)
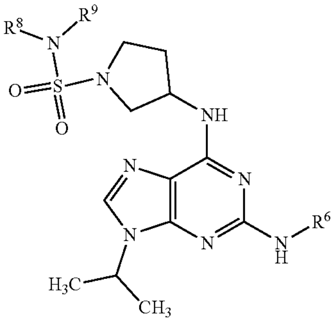
(I-34)
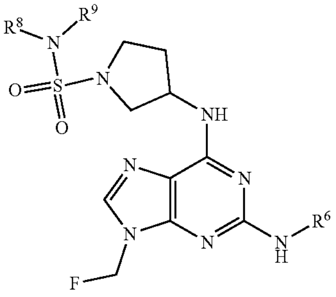
(I-35)
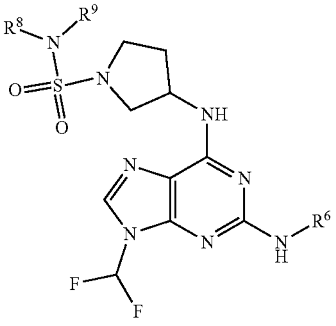

-continued
(I-36)
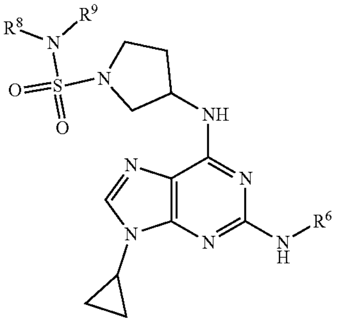
(I-37)
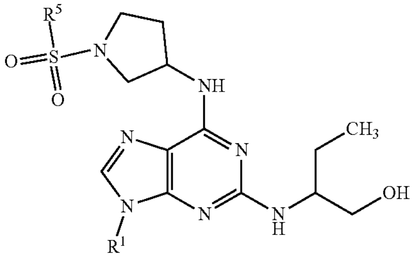
(I-38)
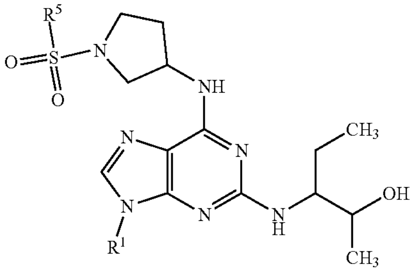
(I-39)
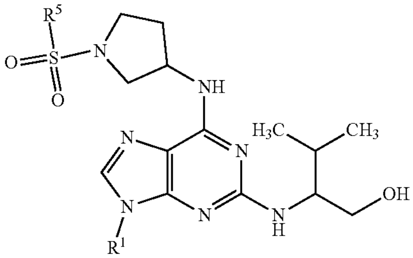
(I-40)
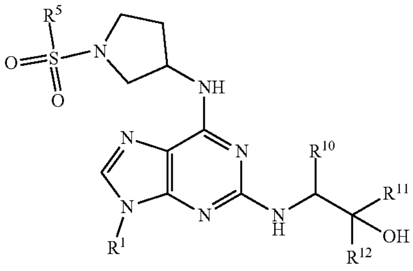
-continued
(I-41)
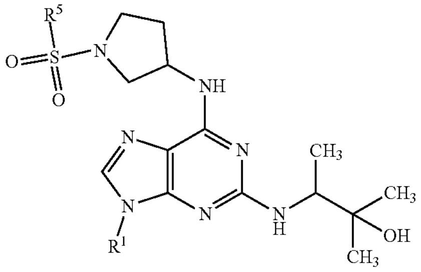
(I-42)
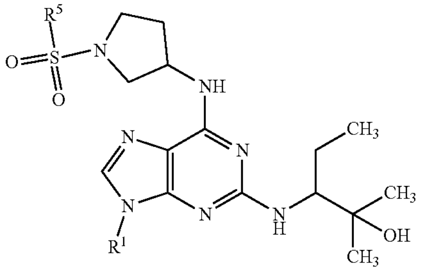
(I-43)
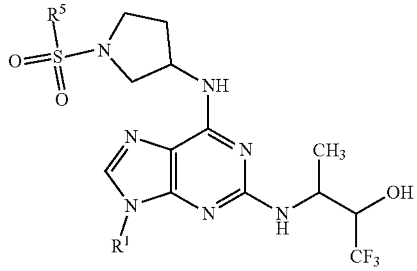
(I-44)
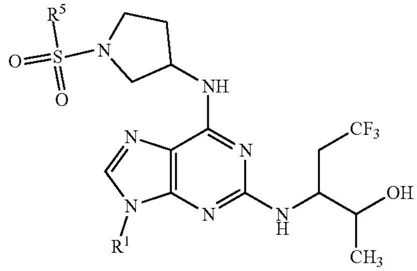
(I-45)
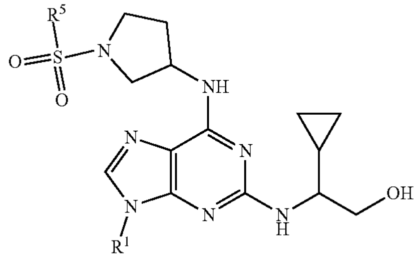
(I-46)
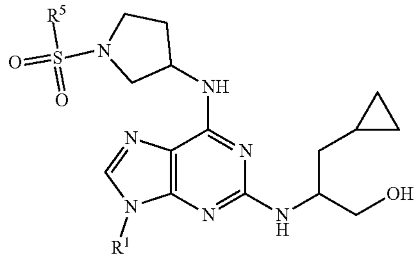

-continued
(I-47)
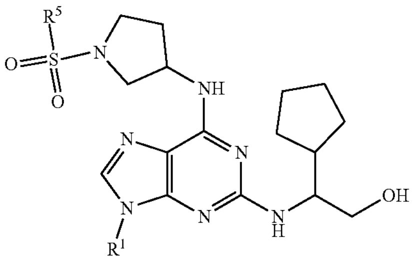
(I-48)
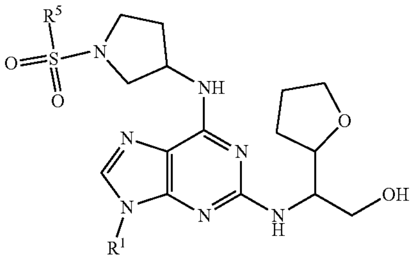
(I-49)
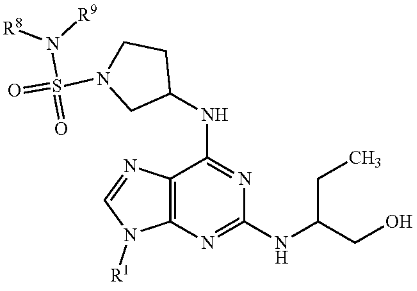
(I-50)
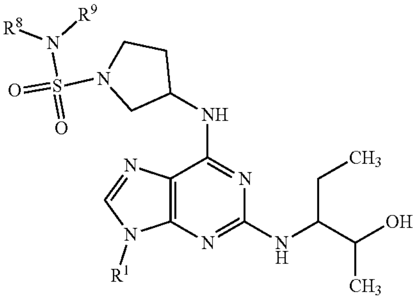
(I-51)
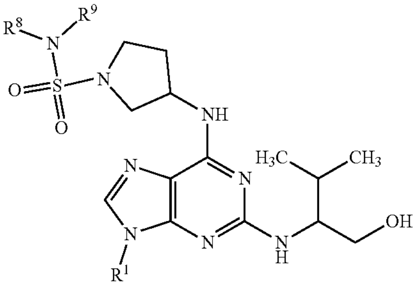
-continued
(I-52)
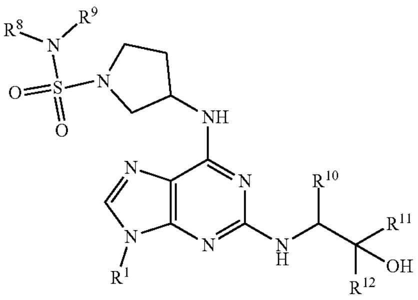
(I-53)
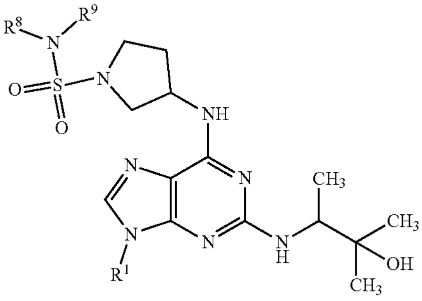
(I-54)
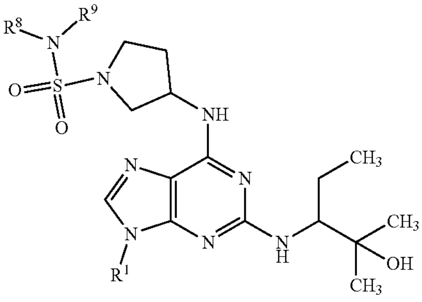
(I-55)
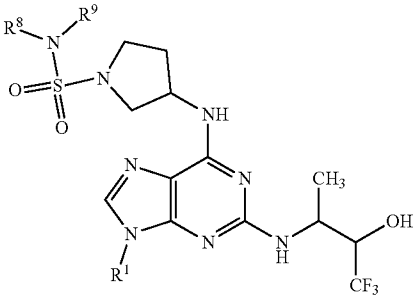
(I-56)
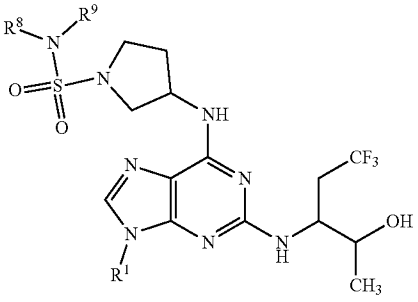

-continued
(I-57)
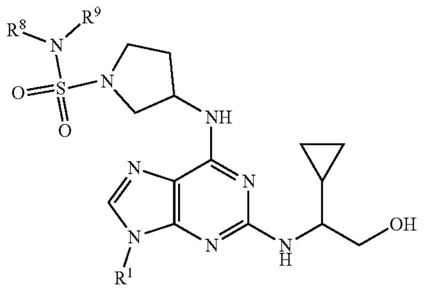
(I-58)
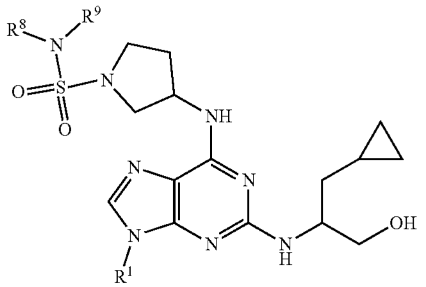
(I-59)
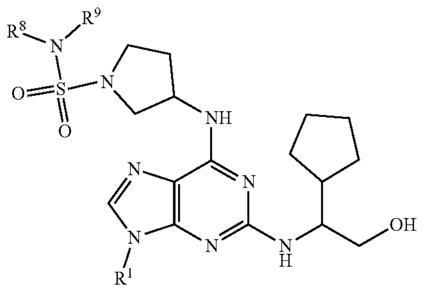
(I-60)
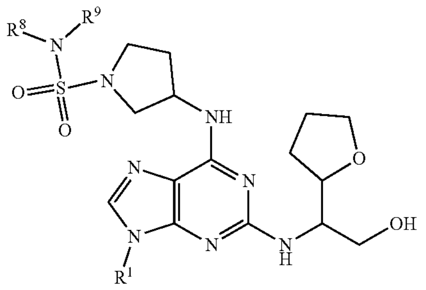
(I-61)
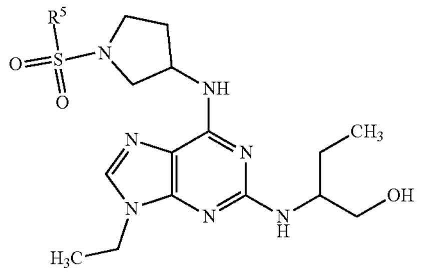
-continued
(I-62)
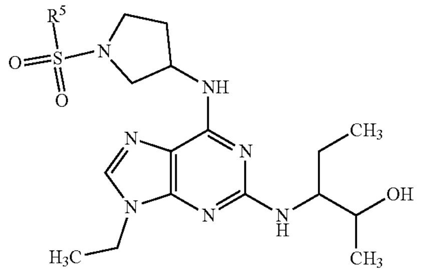
(I-63)
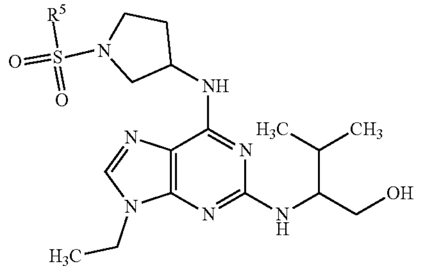
(I-64)
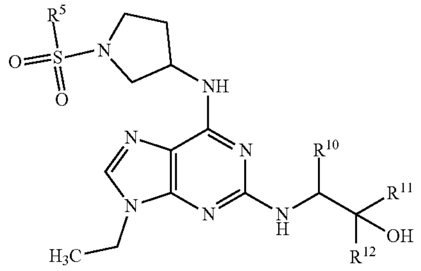
(I-65)
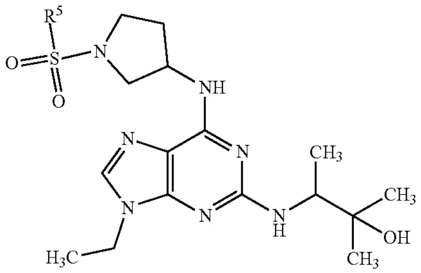
(I-66)
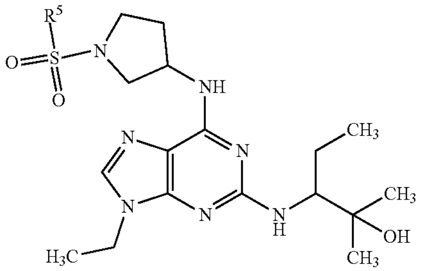

-continued
(I-67)
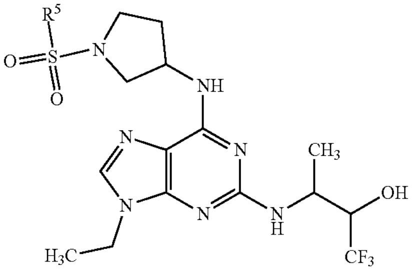
(I-68)
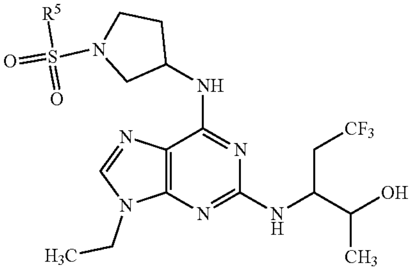
(I-69)
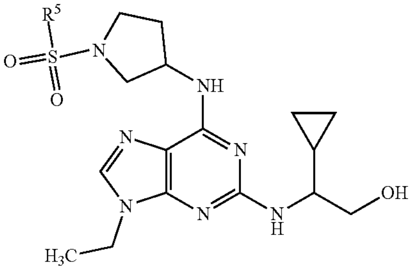
(I-70)
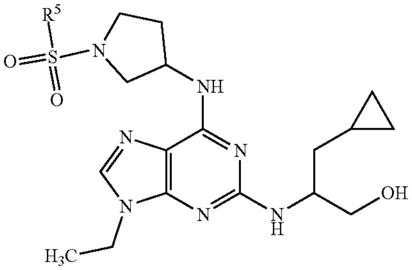
(I-71)
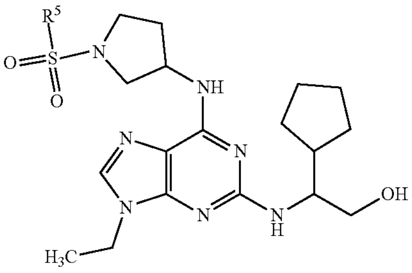
-continued
(I-72)
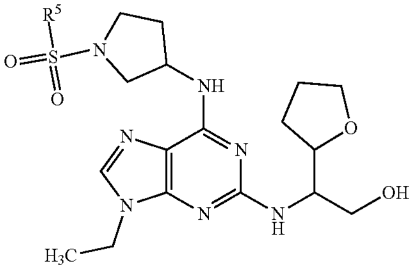
(I-73)
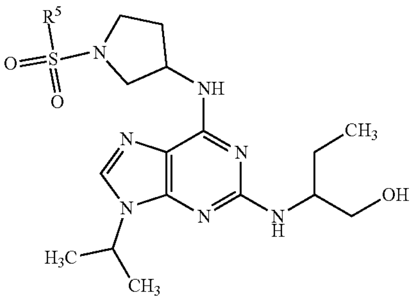
(I-74)
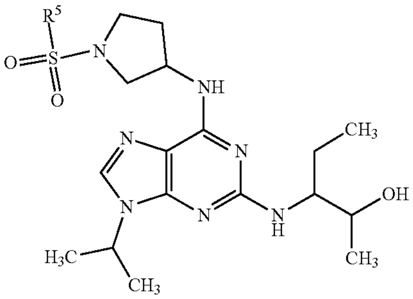
(I-75)
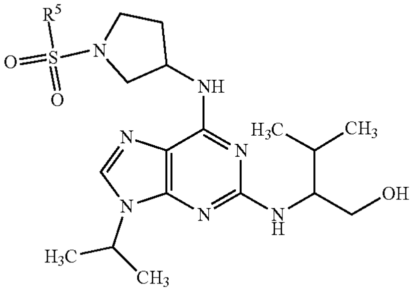
(I-76)
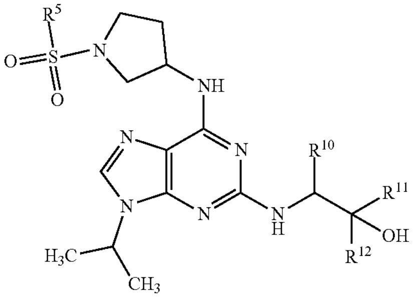

-continued
(I-77)
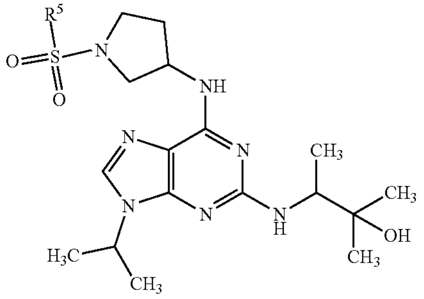
(I-78)
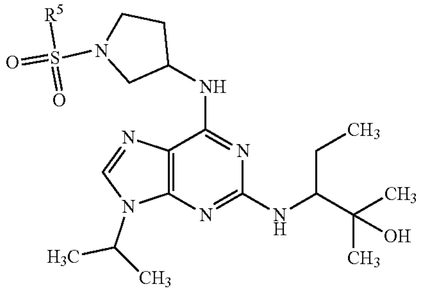
(I-79)
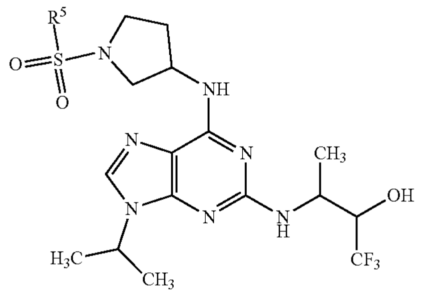
(I-80)
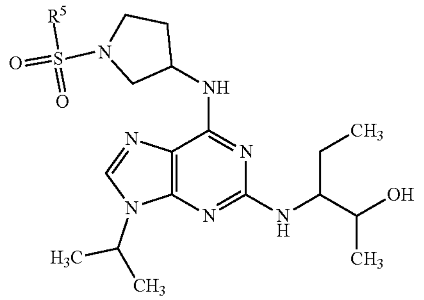
(I-81)
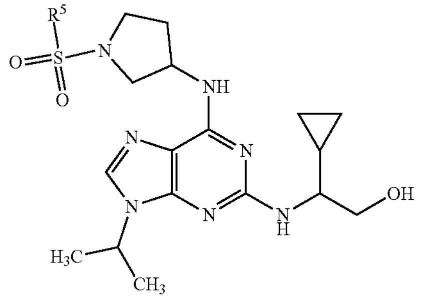
-continued
(I-82)
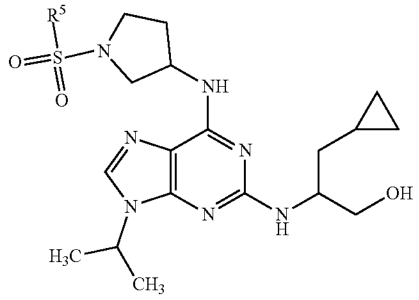
(I-83)
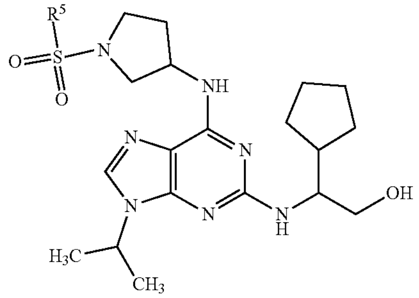
(I-84)
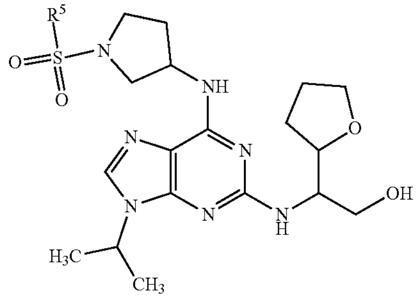
(I-85)
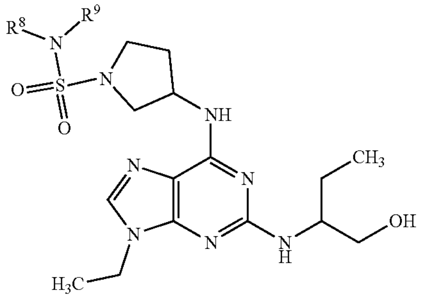
(I-86)
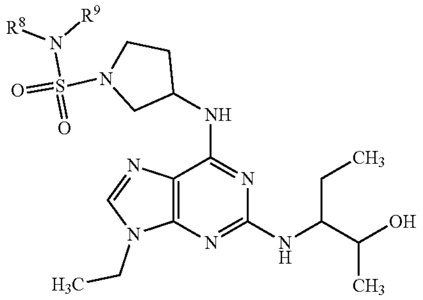

-continued
(I-87)
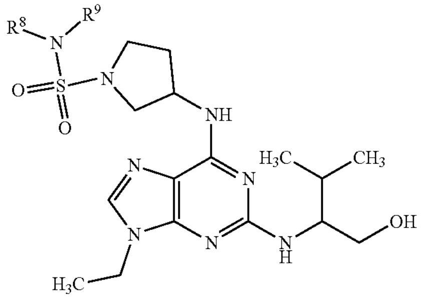
(I-88)
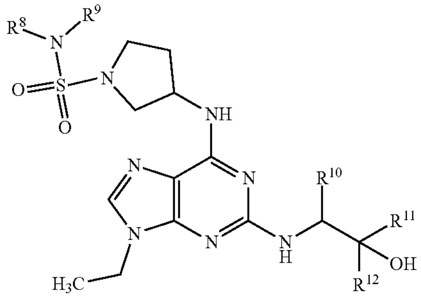
(I-89)
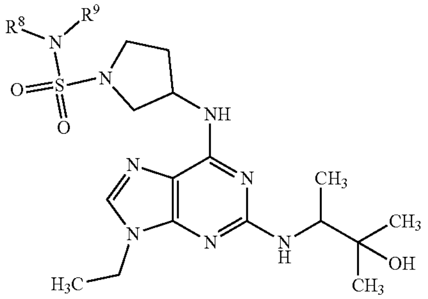
(I-90)
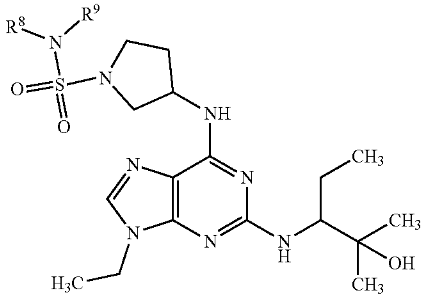
(I-91)
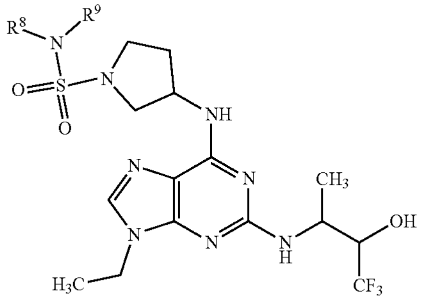
-continued
(I-92)
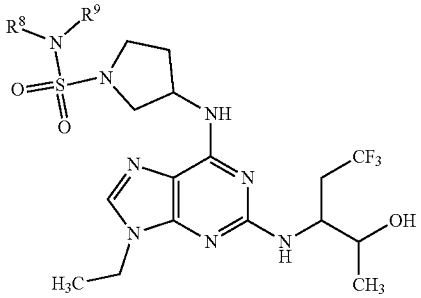
(I-93)
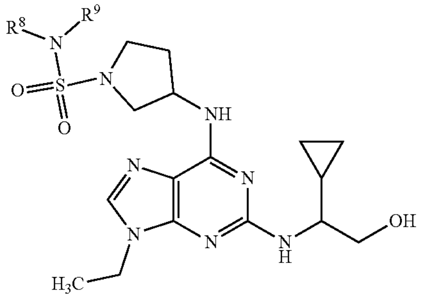
(I-94)
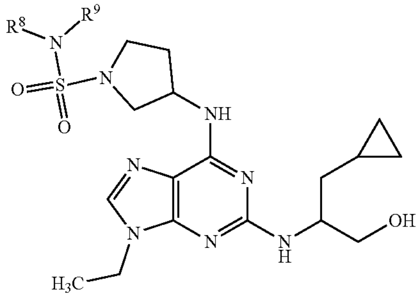
(I-95)
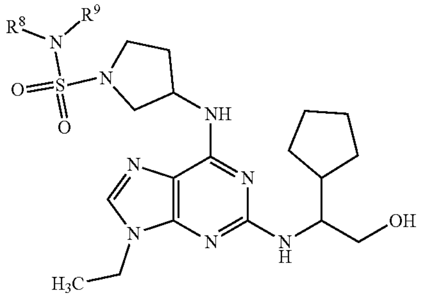
(I-96)
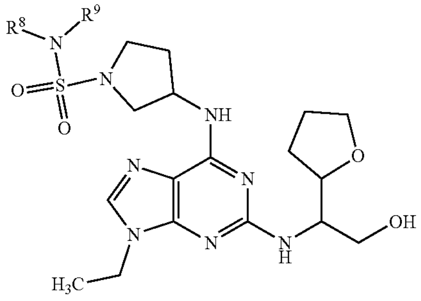

-continued
(I-97)
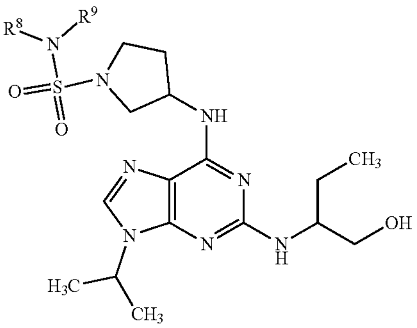
(I-98)
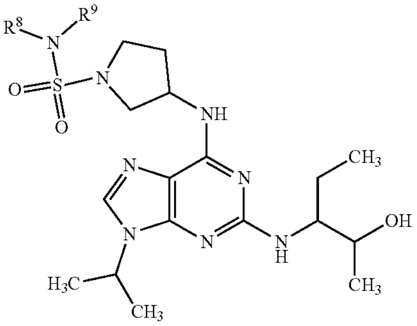
(I-99)
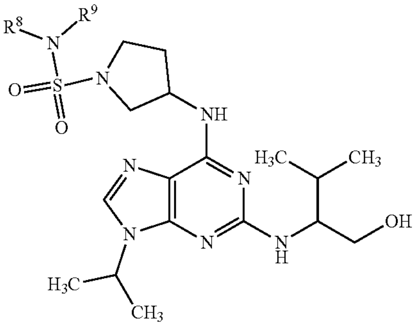
(I-100)
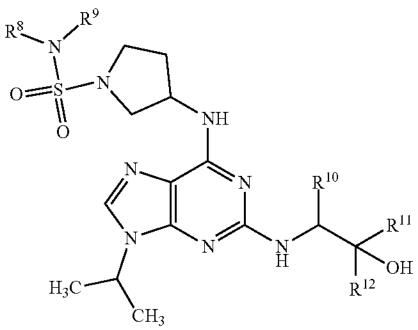
-continued
(I-101)
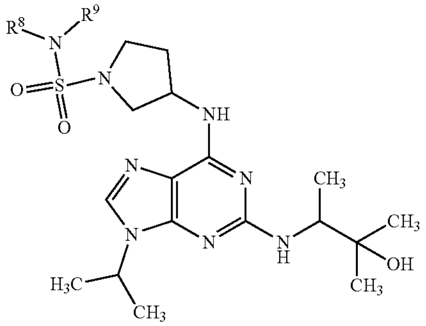
(I-102)
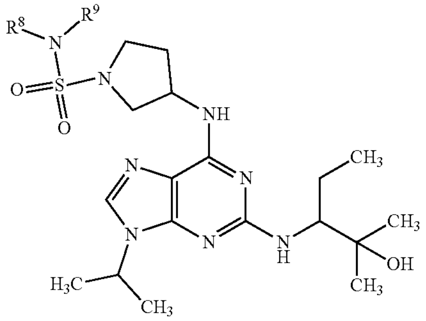
(I-103)
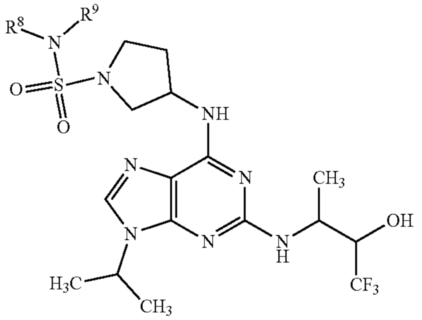
(I-104)
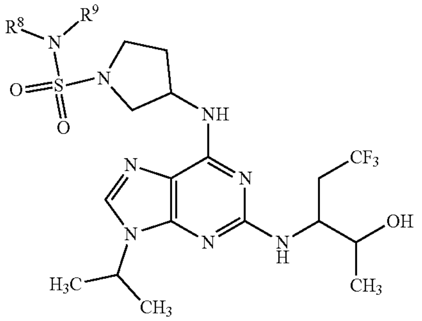
(I-105)
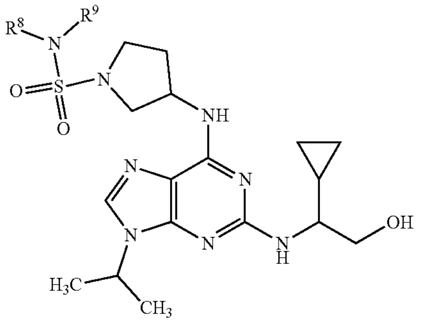

-continued
(I-106)
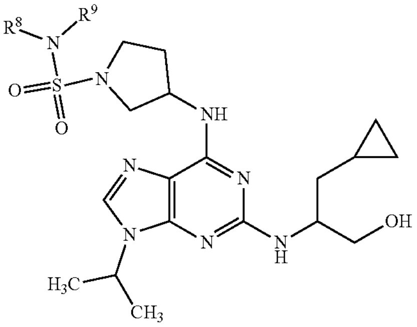
(I-107)
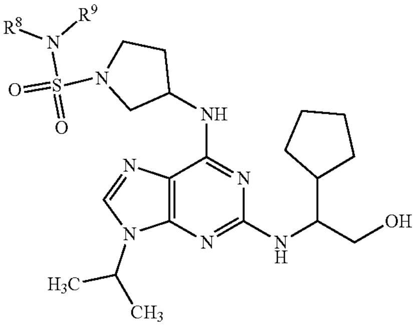
(I-108)
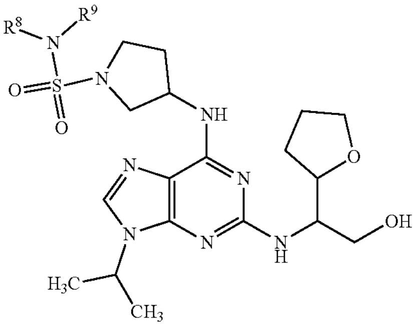
(I-109)
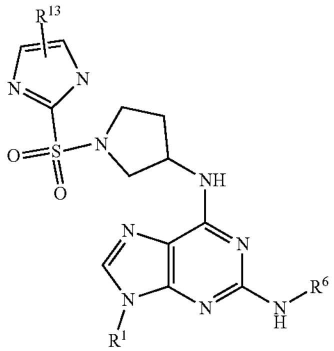
-continued
(I-110)
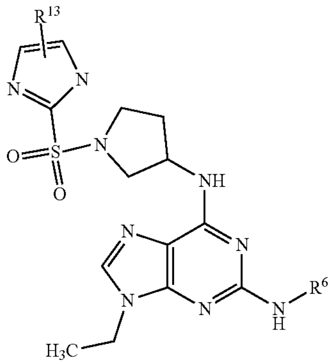
(I-111)
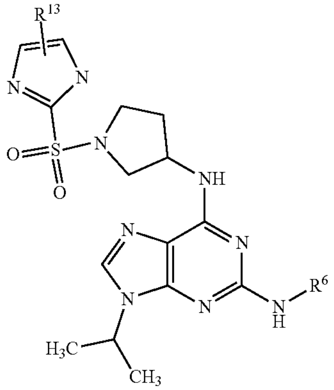
(I-112)
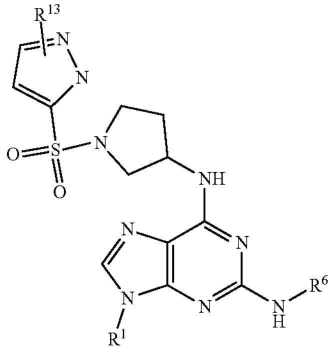
(I-113)
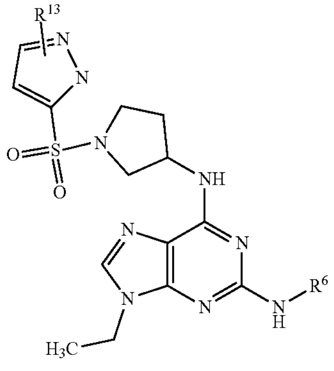

-continued (I-114)

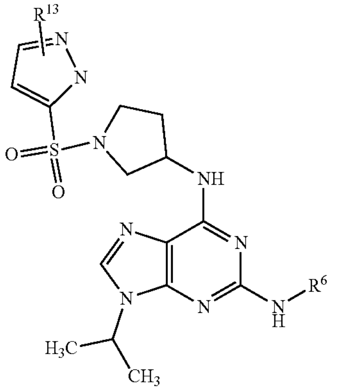

(I-115)

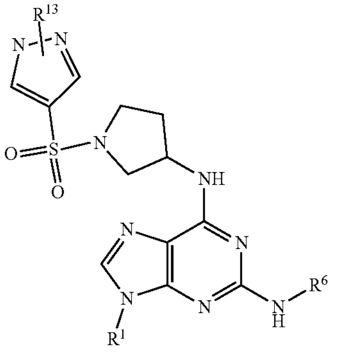

(I-116)

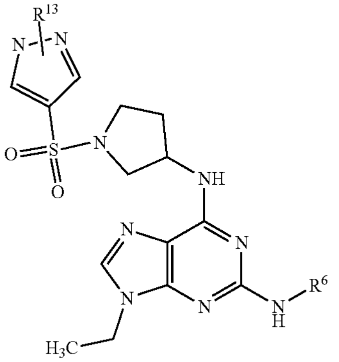

(I-117)

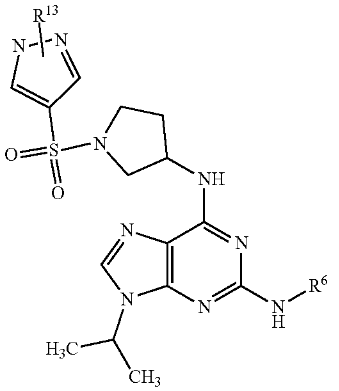

wherein, as applicable:

$R^1$ is selected from the group consisting of $C_{1-6}$-alkyl, halo-$C_{1-6}$-alkyl, and cyclopropyl;

$R^2$ is selected from the group consisting of —$NHR^6$,

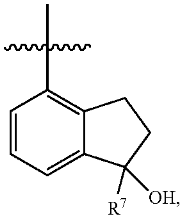

and

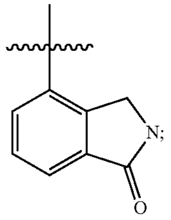

one of $R^3$ and $R^4$ is hydrogen and the other of $R^3$ and $R^4$ is selected from the group consisting of hydrogen, halogen, $C_{1-3}$-alkyl, halo-$C_{1-3}$-alkyl, and $C_{1-3}$-alkoxy;

$R^5$ is selected from the group consisting of $C_{1-6}$-alkyl, $C_{3-6}$-cycloalkyl, —$NR^8R^9$, pyrazolyl, and imidazolyl; wherein the $C_{1-6}$-alkyl and $C_{3-6}$-cycloalkyl are optionally substituted with one or more substituents independently selected from halogen and $C_{1-3}$-alkoxy; and the pyrazolyl and imidazolyl are optionally substituted with one or more substituents independently selected from $C_{1-3}$-alkyl;

$R^6$ is $C_{1-10}$-alkyl or

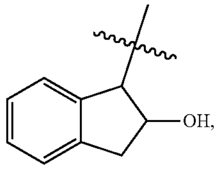 [SMILES: *C1c2ccccc2CC1O]

wherein the $C_{1-10}$-alkyl is substituted with hydroxy or oxo, and is optionally substituted with one or more substituents independently selected from the group consisting of halogen, $C_{3-6}$-cycloalkyl, and tetrahydrofuranyl;

$R^7$ is hydrogen or $C_{1-3}$-alkyl;

$R^8$ is hydrogen;

$R^9$ is selected from the group consisting of hydrogen, $C_{1-6}$-alkyl, $C_{3-6}$-cycloalkyl, $C_{1-6}$-alkoxy-$C_{1-6}$-alkyl, tetrahydrofuranyl, and 1,4-dioxanyl-$C_{1-3}$-alkyl; wherein the $C_{1-6}$-alkyl, $C_{3-6}$-cycloalkyl, $C_{1-6}$-alkoxy-$C_{1-6}$-alkyl, tetrahydrofuranyl, and 1,4-dioxanyl-$C_{1-3}$-alkyl are optionally substituted with one or more substituents independently selected from halogen; or $R^8$ and $R^9$ together with the nitrogen atom to which they are attached form a 4-, 5-, or 6-membered saturated monocyclic ring wherein the remaining ring atoms are carbon atoms, and wherein the monocyclic ring is optionally substituted with one or more substituents independently selected from halogen;

$R^{10}$ is selected from the group consisting of $C_{1-3}$-alkyl, halo-$C_{1-3}$-alkyl, $C_{3-6}$-cycloalkyl, $C_{3-6}$-cycloalkyl-$C_{1-3}$-alkyl, and tetrahydrofuranyl;

$R^{11}$ is selected from the group consisting of hydrogen and $C_{1-3}$-alkyl;

$R^{12}$ is selected from the group consisting of hydrogen, $C_{1-3}$-alkyl, and halo-$C_{1-3}$-alkyl; and $R^{13}$ is selected from the group consisting of hydrogen and $C_{1-3}$-alkyl.

Embodiment 163. The compound of Embodiment 162, or a pharmaceutically acceptable salt thereof, wherein, as applicable:

$R^1$ is selected from the group consisting of $C_{1-3}$-alkyl, halo-$C_{1-3}$-alkyl, and cyclopropyl;

$R^2$ is —$NHR^6$;

$R^3$ is hydrogen and $R^4$ is selected from the group consisting of hydrogen and $C_{1-3}$-alkyl; or $R^4$ is hydrogen and $R^3$ is selected from the group consisting of hydrogen, halogen, and $C_{1-3}$-alkyl;

$R^5$ is selected from the group consisting of $C_{1-6}$-alkyl, $C_{3-6}$-cycloalkyl, —$NR^8R^9$, pyrazolyl, and imidazolyl; wherein the $C_{1-6}$-alkyl and $C_{3-6}$-cycloalkyl are optionally substituted with one or more substituents independently selected from halogen and $C_{1-3}$-alkoxy; and the pyrazolyl and imidazolyl are optionally substituted with one or more substituents independently selected from $C_{1-3}$-alkyl;

$R^6$ is $C_{1-10}$-alkyl, wherein the $C_{1-10}$-alkyl is substituted with hydroxy, and is optionally substituted with one or more substituents independently selected from the group consisting of halogen, $C_{3-6}$-cycloalkyl, and tetrahydrofuranyl;

$R^8$ is hydrogen;

$R^9$ is selected from the group consisting of hydrogen, $C_{1-3}$-alkyl, tetrahydrofuranyl, and 1,4-dioxanyl-$C_{1-3}$-alkyl; wherein the $C_{1-3}$-alkyl, tetrahydrofuranyl, and 1,4-dioxanyl-$C_{1-3}$-alkyl are optionally substituted with one or more substituents independently selected from halogen; or or $R^8$ and $R^9$ together with the nitrogen atom to which they are attached form an azetidinyl ring, and wherein the azetidinyl ring is optionally substituted with one or more substituents independently selected from halogen;

$R^{10}$ is selected from the group consisting of $C_{1-3}$-alkyl, halo-$C_{1-3}$-alkyl, $C_{3-6}$-cycloalkyl, $C_{3-6}$-cycloalkyl-$C_{1-3}$-alkyl, and tetrahydrofuranyl;

$R^{11}$ is selected from the group consisting of hydrogen and $C_{1-3}$-alkyl;

$R^{12}$ is selected from the group consisting of hydrogen, $C_{1-3}$-alkyl, and halo-$C_{1-3}$-alkyl; and $R^{13}$ is selected from the group consisting of hydrogen and $C_{1-3}$-alkyl.

Embodiment 164. The compound of Embodiment 162, or a pharmaceutically acceptable salt thereof, wherein, as applicable:

$R^1$ is selected from the group consisting of $C_{1-3}$-alkyl and fluoro-$C_{1-3}$-alkyl;

$R^2$ is —$NHR^6$;

$R^3$ is hydrogen and $R^4$ is selected from the group consisting of hydrogen and methyl; or $R^4$ is hydrogen and $R^3$ is selected from the group consisting of hydrogen, fluoro, and methyl;

$R^5$ is selected from the group consisting of $C_{1-3}$-alkyl, $C_{3-6}$-cycloalkyl, —$NR^8R^9$, pyrazolyl, and imidazolyl; wherein the $C_{1-6}$-alkyl and $C_{3-6}$-cycloalkyl are optionally substituted with one or more substituents independently selected from fluoro and methoxy; and the pyrazolyl and imidazolyl are optionally substituted with one or more methyl;

$R^6$ is $C_{2-6}$-alkyl, wherein the $C_{2-6}$-alkyl is substituted with hydroxy, and is optionally substituted with one or more substituents independently selected from the group consisting of fluoro, $C_{3-6}$-cycloalkyl, and tetrahydrofuranyl;

$R^8$ is hydrogen;

$R^9$ is selected from the group consisting of hydrogen, $C_{1-3}$-alkyl, tetrahydrofuranyl, and 1,4-dioxanylmethyl; wherein the $C_{1-3}$-alkyl, tetrahydrofuranyl, and 1,4-dioxanylmethyl are optionally substituted with one or more substituents independently selected from halogen;

$R^{10}$ is selected from the group consisting of $C_{1-3}$-alkyl, fluoro-$C_{1-3}$-alkyl, $C_{3-6}$-cycloalkyl, $C_{3-6}$-cycloalkylmethyl, and tetrahydrofuranyl;

$R^{11}$ is selected from the group consisting of hydrogen and $C_{1-3}$-alkyl;

$R^{12}$ is selected from the group consisting of hydrogen, $C_{1-3}$-alkyl, and halo-$C_{1-3}$-alkyl; and $R^{13}$ is selected from the group consisting of hydrogen and $C_{1-3}$-alkyl.

Embodiment 165. The compound of Embodiment 162, or a pharmaceutically acceptable salt thereof, wherein, as applicable:

$R^1$ is selected from the group consisting of $C_{1-3}$-alkyl and fluoro-$C_{1-3}$-alkyl;

$R^2$ is —$NHR^6$;

$R^3$ is selected from the group consisting of hydrogen and fluoro;

$R^4$ is hydrogen;

$R^5$ is selected from the group consisting of $C_{1-3}$-alkyl, cyclopropyl, —$NR^8R^9$, pyrazolyl, and imidazolyl; wherein the $C_{1-6}$-alkyl and cyclopropyl are optionally substituted with one or more substituents independently selected from fluoro and methoxy; and the pyrazolyl and imidazolyl are optionally substituted with one or more methyl;

$R^6$ is $C_{2-6}$-alkyl, wherein the $C_{2-6}$-alkyl is substituted with hydroxy, and is optionally substituted with one or more substituents independently selected from the group consisting of fluoro, $C_{3-6}$-cycloalkyl, and tetrahydrofuranyl;

$R^8$ is hydrogen;

$R^9$ is selected from the group consisting of hydrogen, $C_{1-3}$-alkyl, tetrahydrofuranyl, and 1,4-dioxanylmethyl; wherein the $C_{1-3}$-alkyl, tetrahydrofuranyl, and 1,4-dioxanylmethyl are optionally substituted with one or more fluoro;

$R^{10}$ is selected from the group consisting of methyl, ethyl, fluoroethyl, cyclopropyl, cyclopropylmethyl, cyclopentyl, and tetrahydrofuranyl;

$R^{11}$ is selected from the group consisting of hydrogen and methyl; and $R^{12}$ is selected from the group consisting of hydrogen, methyl, and fluoromethyl.

Embodiment 166. The compound of Embodiment 162, or a pharmaceutically acceptable salt thereof, wherein, as applicable:

$R^1$ is selected from the group consisting of methyl, ethyl, isopropyl, fluoromethyl, and difluoromethyl;

$R^2$ is —$NHR^6$;

$R^3$ and $R^4$ are hydrogen;

$R^5$ is selected from the group consisting of methyl, fluoromethyl, trifluoromethyl, methoxyethyl, cyclopropyl, —$NR^8R^9$, imidazolyl, pyrazolyl, methylimidazolyl, and methylpyrazolyl;

$R^6$ is $C_{2-6}$-alkyl, wherein the $C_{2-6}$-alkyl is substituted with hydroxy, and is optionally substituted with one or more substituents independently selected from the group consisting of fluoro, $C_{3-6}$-cycloalkyl, and tetrahydrofuranyl;

$R^8$ is hydrogen;

$R^9$ is selected from the group consisting of hydrogen, methyl, ethyl, difluoroethyl, trifluoroethyl, tetrahydrofuranyl, and 1,4-dioxanylmethyl;

$R^{10}$ is selected from the group consisting of methyl, ethyl, fluoroethyl, cyclopropyl, cyclopropylmethyl, cyclopentyl, and tetrahydrofuranyl;

$R^{11}$ is selected from the group consisting of hydrogen and methyl; and $R^{12}$ is selected from the group consisting of hydrogen, methyl, and fluoromethyl.

Embodiment 167. The compound of Embodiment 162, or a pharmaceutically acceptable salt thereof, wherein the compound has the structure of Formula (I-61):

(I-61)

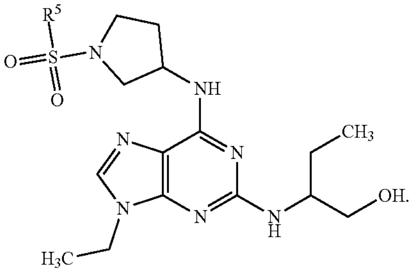

Embodiment 168. The compound of Embodiment 162, or a pharmaceutically acceptable salt thereof, wherein the compound has the structure of Formula (I-62):

(I-62)

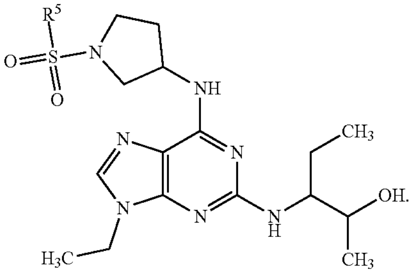

Embodiment 169. The compound of Embodiment 162, or a pharmaceutically acceptable salt thereof, wherein the compound has the structure of Formula (I-63):

(I-63)

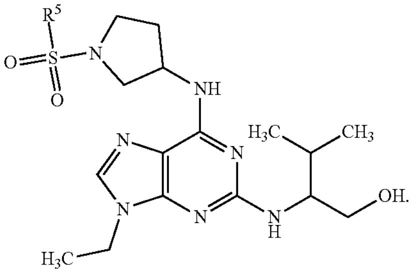

Embodiment 170. The compound of Embodiment 162, or a pharmaceutically acceptable salt thereof, wherein the compound has the structure of Formula (I-64):

(I-64)

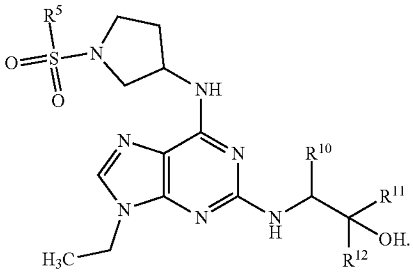

Embodiment 171. The compound of Embodiment 162, or a pharmaceutically acceptable salt thereof, wherein the compound has the structure of Formula (I-65):

(I-65)

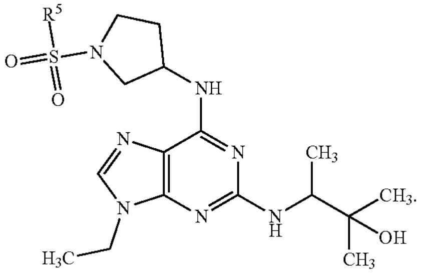

Embodiment 172. The compound of Embodiment 162, or a pharmaceutically acceptable salt thereof, wherein the compound has the structure of Formula (I-66):

(I-66)

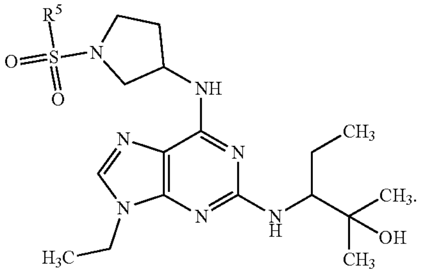

Embodiment 173. The compound of Embodiment 162, or a pharmaceutically acceptable salt thereof, wherein the compound has the structure of Formula (I-67):

(I-67)

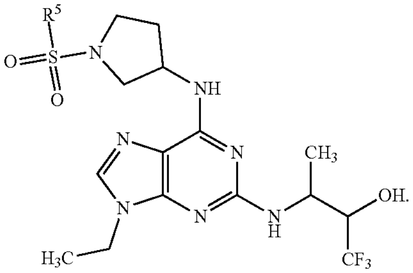

Embodiment 174. The compound of Embodiment 162, or a pharmaceutically acceptable salt thereof, wherein the compound has the structure of Formula (I-68):

(I-68)

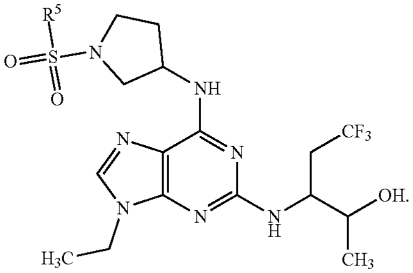

Embodiment 175. The compound of Embodiment 162, or a pharmaceutically acceptable salt thereof, wherein the compound has the structure of Formula (I-69):

(I-69)

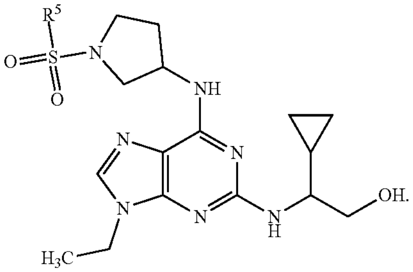

Embodiment 176. The compound of Embodiment 162, or a pharmaceutically acceptable salt thereof, wherein the compound has the structure of Formula (I-70):

(I-70)

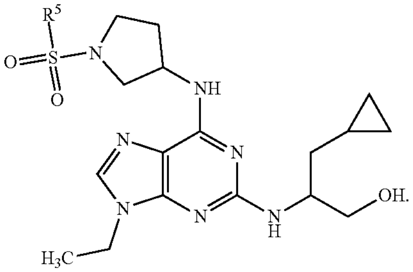

Embodiment 177. The compound of Embodiment 162, or a pharmaceutically acceptable salt thereof, wherein the compound has the structure of Formula (I-71):

(I-71)

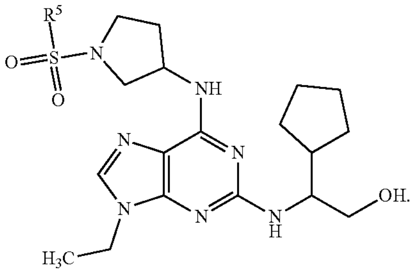

Embodiment 178. The compound of Embodiment 162, or a pharmaceutically acceptable salt thereof, wherein the compound has the structure of Formula (I-72):

(I-72)

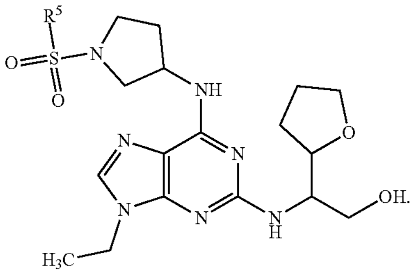

Embodiment 179. The compound of Embodiment 162, or a pharmaceutically acceptable salt thereof, wherein the compound has the structure of Formula (I-73):

(I-73)

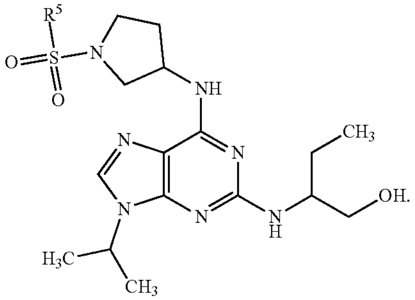

Embodiment 180. The compound of Embodiment 162, or a pharmaceutically acceptable salt thereof, wherein the compound has the structure of Formula (I-74):

(I-74)

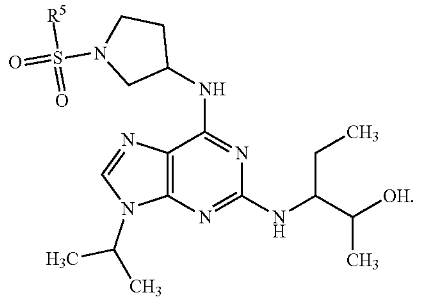

Embodiment 181. The compound of Embodiment 162, or a pharmaceutically acceptable salt thereof, wherein the compound has the structure of Formula (I-75):

(I-75)

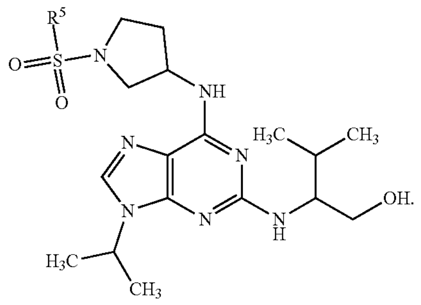

Embodiment 182. The compound of Embodiment 162, or a pharmaceutically acceptable salt thereof, wherein the compound has the structure of Formula (I-76):

(I-76)

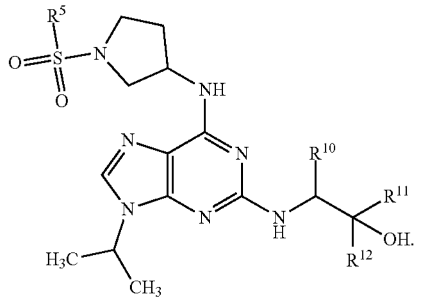

Embodiment 183. The compound of Embodiment 162, or a pharmaceutically acceptable salt thereof, wherein the compound has the structure of Formula (I-77):

(I-77)

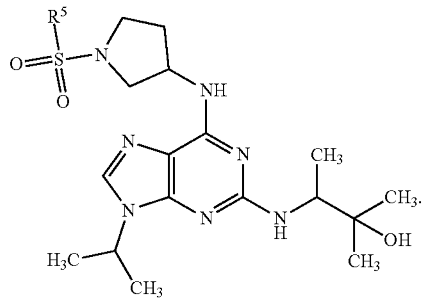

Embodiment 184. The compound of Embodiment 162, or a pharmaceutically acceptable salt thereof, wherein the compound has the structure of Formula (I-78):

(I-78)

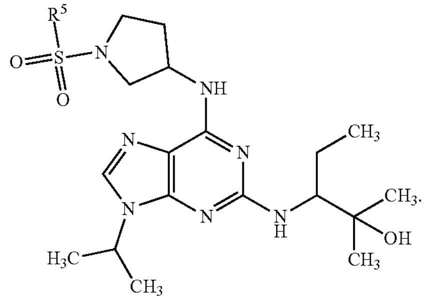

Embodiment 185. The compound of Embodiment 162, or a pharmaceutically acceptable salt thereof, wherein the compound has the structure of Formula (I-79):

(I-79)

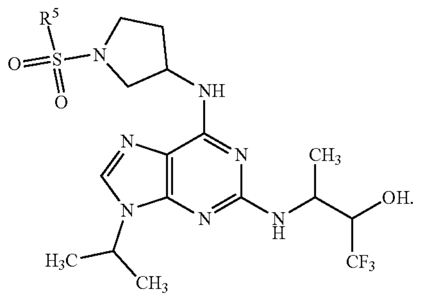

Embodiment 186. The compound of Embodiment 162, or a pharmaceutically acceptable salt thereof, wherein the compound has the structure of Formula (I-80):

(I-80)

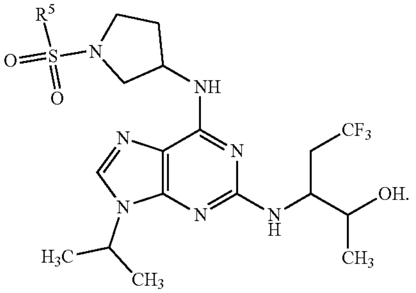

Embodiment 187. The compound of Embodiment 162, or a pharmaceutically acceptable salt thereof, wherein the compound has the structure of Formula (I-81):

(I-81)

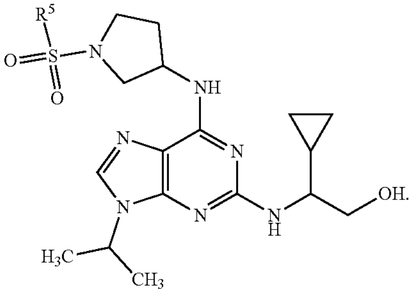

Embodiment 188. The compound of Embodiment 162, or a pharmaceutically acceptable salt thereof, wherein the compound has the structure of Formula (1-82):

(I-82)

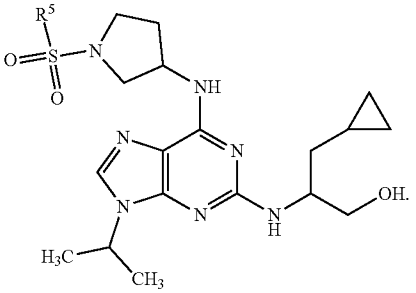

Embodiment 189. The compound of Embodiment 162, or a pharmaceutically acceptable salt thereof, wherein the compound has the structure of Formula (I-83):

(I-83)

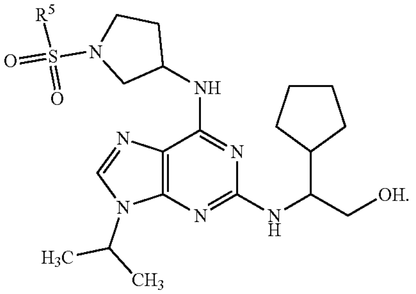

Embodiment 190. The compound of Embodiment 162, or a pharmaceutically acceptable salt thereof, wherein the compound has the structure of Formula (I-84):

(I-84)

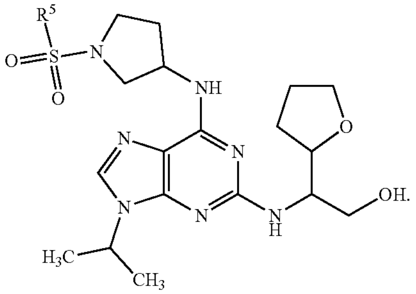

Embodiment 191. The compound of Embodiment 162, or a pharmaceutically acceptable salt thereof, wherein $R^5$ is $C_{1-3}$-alkyl, wherein the $C_{1-3}$-alkyl is optionally substituted with one or more substituents independently selected from fluoro and $C_{1-3}$-alkoxy.

Embodiment 192. The compound of Embodiment 162, or a pharmaceutically acceptable salt thereof, wherein $R^5$ is cyclopropyl, wherein the cyclopropyl is optionally substituted with one or more fluoro substituents.

Embodiment 193. The compound of Embodiment 162, or a pharmaceutically acceptable salt thereof, wherein $R^5$ is cyclobutyl, wherein the cyclobutyl is optionally substituted with one or more fluoro substituents.

Embodiment 194. The compound of Embodiment 162, or a pharmaceutically acceptable salt thereof, wherein $R^5$ is pyrazolyl, wherein the pyrazolyl is optionally substituted with one or more substituents independently selected from $C_{1-3}$-alkyl.

Embodiment 195. The compound of Embodiment 162, or a pharmaceutically acceptable salt thereof, wherein $R^5$ is pyrazolyl, wherein the pyrazolyl is optionally substituted with one or more methyl.

Embodiment 196. The compound of Embodiment 162, or a pharmaceutically acceptable salt thereof, wherein $R^5$ is imidazolyl, wherein the imidazolyl is optionally substituted with one or more substituents independently selected from $C_{1-3}$-alkyl.

Embodiment 197. The compound of Embodiment 162, or a pharmaceutically acceptable salt thereof, wherein $R^5$ is imidazolyl, wherein the imidazolyl is optionally substituted with one or more methyl.

Embodiment 198. The compound of Embodiment 162, or a pharmaceutically acceptable salt thereof, wherein $R^5$ is $—NR^8R^9$.

Embodiment 199. The compound of Embodiment 198, or a pharmaceutically acceptable salt thereof, wherein $R^9$ is $C_{1-3}$-alkyl, wherein the $C_{1-3}$-alkyl is optionally substituted with one or more fluoro substituents.

Embodiment 200. The compound of Embodiment 198, or a pharmaceutically acceptable salt thereof, wherein $R^9$ is tetrahydrofuranyl.

Embodiment 201. The compound of Embodiment 198, or a pharmaceutically acceptable salt thereof, wherein $R^9$ is 1,4-dioxanyl-$C_{1-3}$-alkyl.

Embodiment 202. The compound of Embodiment 198, or a pharmaceutically acceptable salt thereof, wherein $R^9$ is 1,4-dioxanylmethyl.

Embodiment 203. The compound of Embodiment 1, or a pharmaceutically acceptable salt thereof, wherein the compound is selected from the group consisting of:

(S)-3-((9-ethyl-2-(1-oxoisoindolin-4-yl)-9H-purin-6-yl)amino)-N-methylpyrrolidine-1-sulfonamide [Example 1];

(S)-3-((9-ethyl-2-((R)-1-hydroxy-2,3-dihydro-1H-inden-4-yl)-9H-purin-6-yl)amino)-N-methylpyrrolidine-1-sulfonamide [Example 2];

(S)-3-((9-ethyl-2-((R*)-1-hydroxy-1-methyl-2,3-dihydro-1H-inden-4-yl)-9H-purin-6-yl)-amino)-N-methylpyrrolidine-1-sulfonamide [Example 3];

(S)-3-((9-ethyl-2-(((2R,3S)-2-hydroxypentan-3-yl)amino)-9H-purin-6-yl)amino)-N-(2,2,2-trifluoroethyl)pyrrolidine-1-sulfonamide [Example 4];

(S)—N-(2,2-difluoroethyl)-3-((9-ethyl-2-(((2R,3S)-2-hydroxypentan-3-yl)amino)-9H-purin-6-yl)amino)pyrrolidine-1-sulfonamide [Example 5];

(S)—N-ethyl-3-((9-ethyl-2-(((2R,3S)-2-hydroxypentan-3-yl)amino)-9H-purin-6-yl)amino)pyrrolidine-1-sulfonamide [Example 6];

(S)—N-ethyl-3-((9-ethyl-2-(((S)-2-oxopentan-3-yl)amino)-9H-purin-6-yl)amino)-pyrrolidine-1-sulfonamide [Example 7];

(S)—N-ethyl-3-((9-ethyl-2-(((2S,3S)-2-hydroxypentan-3-yl)amino)-9H-purin-6-yl)-amino)pyrrolidine-1-sulfonamide [Example 8];

(S)-3-((9-ethyl-2-(((2R,3S)-2-hydroxypentan-3-yl)amino)-9H-purin-6-yl)amino)pyrrolidine-1-sulfonamide [Example 9];

(S)-3-((9-ethyl-2-(((S)-2-oxopentan-3-yl)amino)-9H-purin-6-yl)amino)pyrrolidine-1-sulfonamide [Example 10];

(S)—N-ethyl-3-((9-ethyl-2-(((2S,3R)-2-hydroxypentan-3-yl)amino)-9H-purin-6-yl)-amino)pyrrolidine-1-sulfonamide [Example 11];

(S)—N-ethyl-3-((9-ethyl-2-(((R)-2-oxopentan-3-yl)amino)-9H-purin-6-yl)amino)pyrrolidine-1-sulfonamide [Example 12];

(S)—N-ethyl-3-((9-ethyl-2-(((2R,3R)-2-hydroxypentan-3-yl)amino)-9H-purin-6-yl)-amino)pyrrolidine-1-sulfonamide [Example 13];

(S)-3-((2-(((R)-1-cyclopropyl-2-hydroxyethyl)amino)-9-(difluoromethyl)-9H-purin-6-yl)-amino)-N-ethylpyrrolidine-1-sulfonamide [Example 14];

2-cyclopentyl-2-((9-isopropyl-6-(((S)-1-(methylsulfonyl)pyrrolidin-3-yl)amino)-9H-purin-2-yl)amino)ethan-1-ol [Example 15];

2-((9-isopropyl-6-(((S)-1-(methylsulfonyl)pyrrolidin-3-yl)amino)-9H-purin-2-yl)amino)-2-(tetrahydrofuran-2-yl)ethan-1-ol [Example 16];

(R)-2-((6-(((3R*,4R*)-1-((1H-imidazol-2-yl)sulfonyl)-4-fluoropyrrolidin-3-yl)amino)-9-ethyl-9H-purin-2-yl)amino)-2-cyclopropylethan-1-ol [Example 17];

(S)-3-((2-(((2S,3R)-1,3-dihydroxybutan-2-yl)amino)-9-ethyl-9H-purin-6-yl)amino)-N—((R)-tetrahydrofuran-3-yl)pyrrolidine-1-sulfonamide [Example 18];

(S)-3-((2-(((R)-1-cyclopropyl-2-hydroxyethyl)amino)-9-methyl-9H-purin-6-yl)amino)-N-ethylpyrrolidine-1-sulfonamide [Example 19];

(R)-2-((9-isopropyl-6-(((S)-1-(methylsulfonyl)pyrrolidin-3-yl)-amino)-9H-purin-2-yl)-amino)-3-methylbutan-1-ol [Example 20];

(S)-3-((9-ethyl-2-(((3S,4R)-1,1,1-trifluoro-4-hydroxypentan-3-yl-)-amino)-9H-purin-6-yl)amino)-N-methylpyrrolidine-1-sulfonamide [Example 21];

(S)-3-((9-ethyl-2-(((2R,3S)-2-hydroxypentan-3-yl)amino)-9H-purin-6-yl)amino)-N—((S)-tetrahydrofuran-3-yl)pyrrolidine-1-sulfonamide [Example 22];

(S)—N—(((S)-1,4-dioxan-2-yl)methyl)-3-((9-ethyl-2-(((2R,3S)-2-hydroxypentan-3-yl)-amino)-9H-purin-6-yl)amino)pyrrolidine-1-sulfonamide [Example 23];

(2R,3S)-3-((9-ethyl-6-(((S)-1-((3-fluoroazetidin-1-yl)sulfonyl)pyrrolidin-3-yl)amino)-9H-purin-2-yl)amino)pentan-2-ol [Example 24];

(S)—N—(((R)-1,4-dioxan-2-yl)methyl)-3-((9-ethyl-2-(((2R,3S)-2-hydroxypentan-3-yl)-amino)-9H-purin-6-yl)amino)pyrrolidine-1-sulfonamide [Example 25];

(3R*,4R*)-3-((2-(((R)-1-cyclopropyl-2-hydroxyethyl)amino)-9-methyl-9H-purin-6-yl)-amino)-N-ethyl-4-fluoropyrrolidine-1-sulfonamide [Example 26];

(R)-2-(6-((S)-1-(cyclopropylsulfonyl)pyrrolidin-3-yl)amino)-9-isopropyl-9H-purin-2-ylamino)-3-methylbutan-1-ol [Example 27];

(R)-2-(9-ethyl-6-((S)-1-(methylsulfonyl)pyrrolidin-3-yl)amino)-9H-purin-2-yl)amino)-3-methylbutan-1-ol [Example 28];

(R)-2-(9-cyclopropyl-6-(((S)-1-(methylsulfonyl)pyrrolidin-3-yl-amino)-9H-purin-2-yl)amino)-3-methylbutan-1-ol [Example 29];

(R)-2-cyclopropyl-2-((9-isopropyl-6-(((S)-1-(methylsulfonyl)-pyrrolidin-3-yl)amino)-9H-purin-2-yl)amino)ethanol [Example 30];

(2R,3S)-3-((9-isopropyl-6-(((S)-1-(1-methyl-1H-pyrazol-4-yl-sulfonyl)pyrrolidin-3-yl)amino)-9H-purin-2-yl)amino)pentan-2-ol [Example 31];

(2R,3S)-3-((9-isopropyl-6-(((S)-1-(1-methyl-1H-imidazol-4-yl-sulfonyl)pyrrolidin-3-yl)amino)-9H-purin-2-yl)amino)pentan-2-ol [Example 32];

(R)-2-((6-(((3R,4R)-4-fluoro-1-(methylsulfonyl)pyrrolidin-3-yl)amino)-9-isopropyl-9H-purin-2-yl)amino)-3-methylbutan-1-ol [Example 33];

(R)-2-((9-isopropyl-6-(((3S,5R)-5-methyl-1-(methylsulfonyl)-pyrrolidin-3-yl)amino)-9H-purin-2-yl)amino)-3-methylbutan-1-ol [Example 34];

(R)-2-((9-isopropyl-6-(((3S,5S)-5-methyl-1-(methylsulfonyl)-pyrrolidin-3-yl)amino)-9H-purin-2-yl)amino)-3-methylbutan-1-ol [Example 35];

(R)-2-((9-isopropyl-6-(((3S,4R)-4-methyl-1-(methylsulfonyl)-pyrrolidin-3-yl)amino)-9H-purin-2-yl)amino)-3-methylbutan-1-ol [Example 36];

(2R,3S)-3-((9-isopropyl-6-(((3S,5R)-5-methyl-1-(methylsulfonyl)-pyrrolidin-3-yl)amino)-9H-purin-2-yl)amino)pentan-2-ol [Example 37];

(R)-2-((9-ethyl-6-(((S)-1-(methylsulfonyl)pyrrolidin-3-yl)amino)-9H-purin-2-yl)amino)butan-1-ol [Example 38];

(R)-2-cyclopropyl-2-((9-ethyl-6-(((S)-1-(methylsulfonyl)pyrrolidin-3-yl)amino)-9H-purin-2-yl)amino)ethanol [Example 39];

(R)-2-((9-ethyl-6-(((S)-1-(2,2,2-trifluoroethylsulfonyl)pyrrolidin-3-yl)amino)-9H-purin-2-yl)amino)-3-methylbutan-1-ol [Example 40];

(R)-2-((6-(((S)-1-(cyclopropylsulfonyl)pyrrolidin-3-yl)amino)-9-ethyl-9H-purin-2-yl)amino)-3-methylbutan-1-ol [Example 41];

(R)-2-((9-ethyl-6-(((S)-1-((2-methoxyethyl)sulfonyl)pyrrolidin-3-yl)amino)-9H-purin-2-yl)amino)-3-methylbutan-1-ol [Example 42];

(R)-2-((9-ethyl-6-(((S)-1-(fluoromethylsulfonyl)pyrrolidin-3-yl)amino)-9H-purin-2-yl)amino)-3-methylbutan-1-ol [Example 43];

(S)-3-((9-ethyl-2-(((2R,3S)-2-hydroxypentan-3-yl)amino)-9H-purin-6-yl)amino)-N-methylpyrrolidine-1-sulfonamide [Example 44];

(S)-3-((9-ethyl-2-(((S)-2-oxopentan-3-yl)amino)-9H-purin-6-yl)amino)-N-methylpyrrolidine-1-sulfonamide [Example 45];

(S)-3-((9-ethyl-2-(((S)-2-hydroxy-2-methylpentan-3-yl)amino)-9H-purin-6-yl)amino)-N-methylpyrrolidine-1-sulfonamide [Example 46];

(S)-3-((9-ethyl-2-(((S)-2-hydroxy-2-methylpentan-3-yl)amino)-9H-purin-6-yl)amino)-N-methylpyrrolidine-1-sulfonamide [Example 47];

(S)-3-((9-ethyl-2-(((S)-1-hydroxybutan-2-yl)amino)-9H-purin-6-yl)amino)-N-methylpyrrolidine-1-sulfonamide [Example 48];

(S)-3-((9-ethyl-2-(((2R*,3S*)-4,4,4-trifluoro-3-hydroxybutan-2-yl)amino)-9H-purin-6-yl)amino)-N-methylpyrrolidine-1-sulfonamide [Examples 49/50];

(S)-3-((9-ethyl-2-(((1R,2S)-2-hydroxy-2,3-dihydro-1H-inden-1-yl)amino)-9H-purin-6-yl)amino)-N-methylpyrrolidine-1-sulfonamide [Example 51];

(3R*,4R*)-3-((9-ethyl-2-(((2R,3S)-2-hydroxypentan-3-yl)amino)-9H-purin-6-yl)amino)-4-fluoro-N-methylpyrrolidine-1-sulfonamide [Example 52];

(S)—N-ethyl-3-((2-(((2R,3S)-2-hydroxypentan-3-yl)amino)-9-methyl-9H-purin-6-yl)amino)pyrrolidine-1-sulfonamide [Example 53];

(S)-3-((9-(fluoromethyl)-2-(((2R,3S)-2-hydroxypentan-3-yl)amino)-9H-purin-6-yl)amino)-N-methylpyrrolidine-1-sulfonamide [Example 54];

(S)-3-((9-(difluoromethyl)-2-(((2R,3S)-2-hydroxypentan-3-yl)amino)-9H-purin-6-yl)amino)-N-methylpyrrolidine-1-sulfonamide [Example 55];

(2R,3S)-3-((6-(((3R*,4R*)-1-((1H-imidazol-2-yl)sulfonyl)-4-fluoropyrrolidin-3-yl)-amino)-9-methyl-9H-purin-2-yl)amino)pentan-2-ol [Example 56];

(2R,3S)-3-((6-(((3R*,4R*)-1-((1H-imidazol-2-yl)sulfonyl)-4-fluoropyrrolidin-3-yl)-amino)-9-(difluoromethyl)-9H-purin-2-yl)amino)-1,1,1-trifluorobutan-2-ol [Example 57];

(S)-3-((2-(((R*)-1-cyclopropyl-3-hydroxypropan-2-yl)amino)-9-ethyl-9H-purin-6-yl)-amino)-N-ethylpyrrolidine-1-sulfonamide [Example 58];

(S)—N-ethyl-3-((9-ethyl-2-(((R*)-3-hydroxy-3-methylbutan-2-yl)-amino)-9H-purin-6-yl)amino)pyrrolidine-1-sulfonamide [Example 59];

(S)—N-ethyl-3-((3-ethyl-5-(((2R,3S)-2-hydroxypentan-3-yl)amino)-3H-imidazo[4,5-b]pyridin-7-yl)amino)pyrrolidine-1-sulfonamide [Example 60];

(R)-2-((6-(((3R*,4R*)-1-((1H-imidazol-2-yl)sulfonyl)-4-fluoro-pyrrolidin-3-yl)amino)-9-(difluoromethyl)-9H-purin-2-yl)amino)-2-cyclopropylethan-1-ol [Example 61]; and (2R,3S)-3-((6-(((S)-1-((1H-pyrazol-5-yl)sulfonyl)pyrrolidin-3-yl)amino)-9-ethyl-9H-purin-2-yl)amino)pentan-2-ol [Example 62].

Embodiment 204. A pharmaceutical composition comprising a compound of any of Embodiments 1 to 203, or a pharmaceutically acceptable salt thereof, and one or more pharmaceutically acceptable excipients.

Embodiment 205. A method of treating cancer in a subject suffering from or susceptible to the cancer, the method comprising administering to the subject a therapeutically effective amount of a compound of any of Embodiments 1 to 203, or a pharmaceutically acceptable salt thereof.

Embodiment 206. The method of Embodiment 205, wherein the cancer is mediated, in whole or in part, by CDK2.

Embodiment 207. The method of Embodiment 206, wherein the cancer is characterized by amplification or overexpression of the cyclin E1 (CCNE1) gene.

Embodiment 208. The method of Embodiment 206, wherein the cancer is characterized by amplification or overexpression of the cyclin E2 (CCNE2) gene.

Embodiment 209. The method of Embodiment 206, wherein the cancer is selected from the group consisting of breast cancer, ovarian cancer, endometrial cancer, cervical cancer, uterine cancer, gastric cancer, prostate cancer, bladder cancer, lung cancer, esophageal cancer, head and neck cancer, kidney cancer, liver cancer, pancreatic cancer, thyroid cancer, colorectal cancer, and skin cancer.

Embodiment 210. The method of Embodiment 206, wherein the cancer is selected from the group consisting of breast cancer, ovarian cancer, endometrial cancer, and lung cancer.

Embodiment 211. The method of Embodiment 206, wherein the cancer is breast cancer.

Embodiment 212. The method of Embodiment 211, wherein the breast cancer is selected from the group consisting of hormone receptor positive (HR+) breast cancer, hormone receptor negative (HR−) breast cancer, and triple negative breast cancer.

Embodiment 212. The method of Embodiment 206, wherein the cancer is ovarian cancer.

Embodiment 213. The method of Embodiment 206, wherein the cancer is endometrial cancer.

Embodiment 214. The method of Embodiment 206, wherein the cancer is lung cancer.

Embodiment 215. The method of any of Embodiments 205 to 214, wherein the method further comprises administering to the subject a therapeutically effective amount of a CDK4/6 inhibitor.

Embodiment 216. The method of Embodiment 215, wherein the CDK4/6 inhibitor selected from the group consisting of palbociclib, abemaciclib, ribociclib, and dalpiciclib.

Embodiment 217. The use of a compound of any of Embodiments 1 to 203, or a pharmaceutically acceptable salt thereof, for the manufacture of a medicament for treating cancer.

Although specific embodiments and examples have been described above, these embodiments and examples are only illustrative and do not limit the scope of the disclosure. Changes and modifications can be made in accordance with ordinary skill in the art without departing from the disclosure in its broader aspects as defined in the following claims. For example, any embodiment described herein can be combined with any other suitable embodiment described herein to provide additional embodiments.

As will be understood by the skilled artisan, all numbers, including those expressing quantities of ingredients, properties such as molecular weight, reaction conditions, and so forth, are approximations and understood as being modified in all instances by the term "about." These values can vary depending upon the desired properties sought to be obtained by those skilled in the art utilizing the present teachings of the present disclosure. It is also understood that such values inherently contain variability necessarily resulting from the standard deviations found in their respective testing measurements.

One skilled in the art will also readily recognize that where members are grouped together in a common manner, such as in a Markush group, the present disclosure encompasses not only the entire group listed as a whole, but each member of the group individually and all possible subgroups of the main group. Additionally, for all purposes, the present disclosure encompasses not only the main group, but also the main group absent one or more of the group members. The present disclosure also envisages the explicit exclusion or disclaimer of one or more of any of the group members in the claimed disclosure.

As will be understood by one skilled in the art, for any and all purposes, particularly in terms of providing a written description, all ranges disclosed herein also encompass any and all possible subranges and combinations of subranges thereof as well as the individual values making up the range, particularly integer values. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. For example, the range $C_{(1-6)}$, includes the subranges $C_{(2-6)}$, $C_{(3-6)}$, $C_{(3-5)}$, $C_{(4-6)}$, etc., as well as $C_1$ (methyl), $C_2$ (ethyl), $C_3$ (propyl), $C_4$ (butyl), $C_5$ (pentyl) and $C_6$ (hexyl) individually. As will also be understood by one skilled in the art, all language such as "up to," "at least," "greater than," "less than," "more than," "or more" and the like include the number recited and refer to ranges which can be subsequently broken down into subranges as discussed above. In the same manner, all ratios disclosed herein also include all subratios falling within the broader ratio.

Reference to a "step" in this disclosure is used for convenience purposes only and does not categorize, define or limit the disclosure as set forth herein.

What is claimed is:

1. A compound having the structure of Formula (I):

(I)

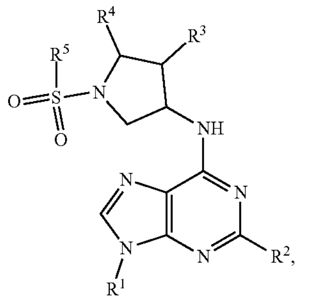

or a pharmaceutically acceptable salt thereof, wherein:

$R^1$ is selected from the group consisting of $C_{1-6}$-alkyl, halo-$C_{1-6}$-alkyl, and cyclopropyl;

$R^2$ is selected from the group consisting of —$NHR^6$,

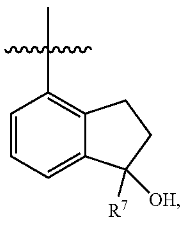

and

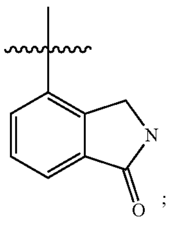

;

one of $R^3$ and $R^4$ is hydrogen and the other of $R^3$ and $R^4$ is selected from the group consisting of hydrogen, halogen, $C_{1-3}$-alkyl, halo-$C_{1-3}$-alkyl, and $C_{1-3}$-alkoxy;

$R^5$ is selected from the group consisting of $C_{1-6}$-alkyl, $C_{3-6}$-cycloalkyl, —$NR^8R^9$, pyrazolyl, and imidazolyl; wherein the $C_{1-6}$-alkyl and $C_{3-6}$-cycloalkyl are optionally substituted with one or more substituents independently selected from halogen and $C_{1-3}$-alkoxy; and the pyrazolyl and imidazolyl are optionally substituted with one or more substituents independently selected from $C_{1-3}$-alkyl;

$R^6$ is $C_{1-10}$-alkyl or

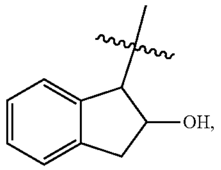

wherein the $C_{1-10}$-alkyl is substituted with hydroxy or oxo, and is optionally substituted with one or more substituents independently selected from the group consisting of halogen, $C_{3-6}$-cycloalkyl, and tetrahydrofuranyl;

$R^7$ is hydrogen or $C_{1-3}$-alkyl;

$R^8$ is hydrogen; and $R^9$ is selected from the group consisting of hydrogen, $C_{1-6}$-alkyl, $C_{3-6}$-cycloalkyl, $C_{1-6}$-alkoxy-$C_{1-6}$-alkyl, tetrahydrofuranyl, and 1,4-dioxanyl-$C_{1-3}$-alkyl; wherein the $C_{1-6}$-alkyl, $C_{3-6}$-cycloalkyl, $C_{1-6}$-alkoxy-$C_{1-6}$-alkyl, tetrahydrofuranyl, and 1,4-dioxanyl-$C_{1-3}$-alkyl are optionally substituted with one or more substituents independently selected from halogen; or $R^8$ and $R^9$ together with the nitrogen atom to which they are attached form a 4-, 5-, or 6-membered saturated monocyclic ring wherein the remaining ring atoms are carbon atoms, and wherein the monocyclic ring is optionally substituted with one or more substituents independently selected from halogen.

2. The compound of claim 1, or a pharmaceutically acceptable salt thereof, wherein the compound has the structure of Formula (I-A):

(I-A)

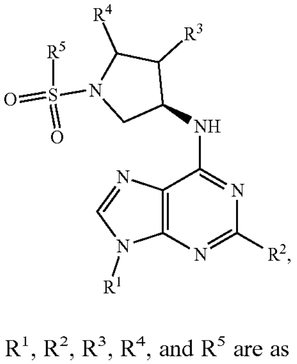

and wherein $R^1$, $R^2$, $R^3$, $R^4$, and $R^5$ are as defined in claim 1.

3. The compound of claim 2, or a pharmaceutically acceptable salt thereof, wherein $R^1$ is selected from the group consisting of $C_{1-3}$-alkyl and halo-$C_{1-3}$-alkyl.

4. The compound of claim 2, or a pharmaceutically acceptable salt thereof, wherein $R^2$ is —$NHR^6$.

5. The compound of claim 4, or a pharmaceutically acceptable salt thereof, wherein $R^6$ is $C_{1-10}$-alkyl, wherein the $C_{1-10}$-alkyl is substituted with hydroxy, and is optionally substituted with one or more substituents independently selected from the group consisting of halogen, $C_{3-6}$-cycloalkyl, and tetrahydrofuranyl.

6. The compound of claim 4, or a pharmaceutically acceptable salt thereof, wherein $R^6$ is $C_{2-6}$-alkyl, wherein the $C_{2-6}$-alkyl is substituted with hydroxy.

7. The compound of claim 4, or a pharmaceutically acceptable salt thereof, wherein $R^6$ is

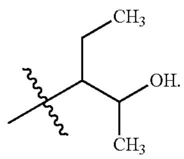

8. The compound of claim 4, or a pharmaceutically acceptable salt thereof, wherein $R^6$ is selected from the group consisting of

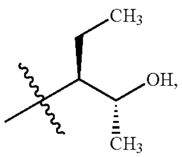

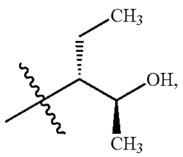

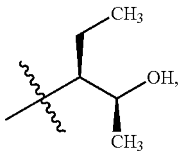

and

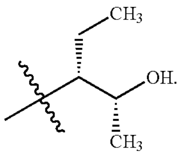

9. The compound of claim 4, or a pharmaceutically acceptable salt thereof, wherein $R^6$ is

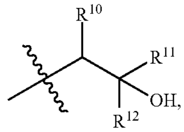

wherein:

$R^{10}$ is selected from the group consisting of $C_{1-3}$-alkyl, halo-$C_{1-3}$-alkyl, $C_{3-6}$-cycloalkyl, $C_{3-6}$-cycloalkyl-$C_{1-3}$-alkyl, and tetrahydrofuranyl;

$R^{11}$ is selected from the group consisting of hydrogen and $C_{1-3}$-alkyl; and $R^{12}$ is selected from the group consisting of hydrogen, $C_{1-3}$-alkyl, and halo-$C_{1-3}$-alkyl.

10. The compound of claim 2, or a pharmaceutically acceptable salt thereof, wherein $R^3$ and $R^4$ are each hydrogen.

11. The compound of claim 2, or a pharmaceutically acceptable salt thereof, wherein $R^5$ is —$NR^8R^9$; $R^8$ is hydrogen; and $R^9$ is selected from the group consisting of hydrogen, $C_{1-6}$-alkyl, $C_{3-6}$-cycloalkyl, $C_{1-6}$-alkoxy-$C_{1-6}$-alkyl, tetrahydrofuranyl, and 1,4-dioxanyl-$C_{1-3}$-alkyl; wherein the $C_{1-6}$-alkyl, $C_{3-6}$-cycloalkyl, $C_{1-6}$-alkoxy-$C_{1-6}$-alkyl, tetrahydrofuranyl, and 1,4-dioxanyl-$C_{1-3}$-alkyl are optionally substituted with one or more substituents independently selected from halogen.

12. The compound of claim 11, or a pharmaceutically acceptable salt thereof, wherein $R^9$ is $C_{1-6}$-alkyl, wherein the $C_{1-6}$-alkyl is optionally substituted with one or more substituents independently selected from halogen.

13. The compound of claim 1, or a pharmaceutically acceptable salt thereof, wherein the compound has a structure selected from the group consisting of:

(I-1)

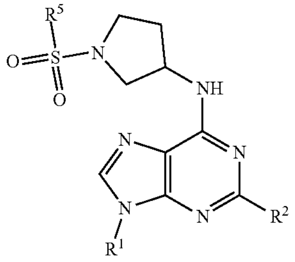

(I-2)

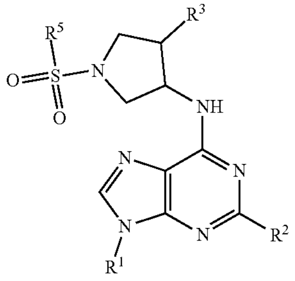

(I-3)

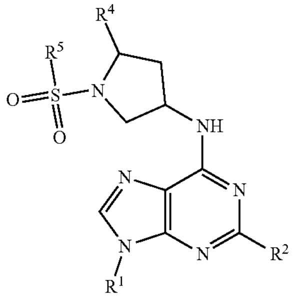

(I-4)

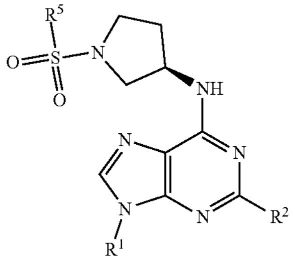

(I-5)

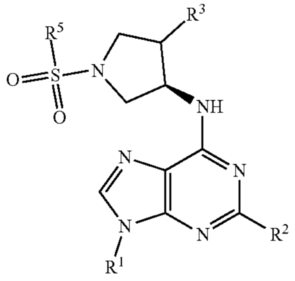

-continued
(I-6)
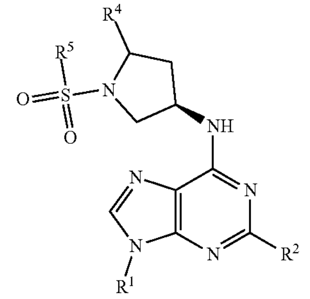
(I-7)
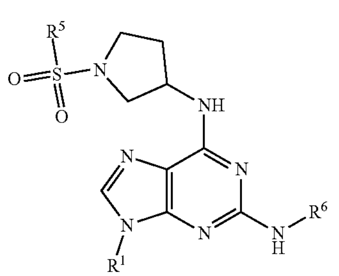
(I-8)
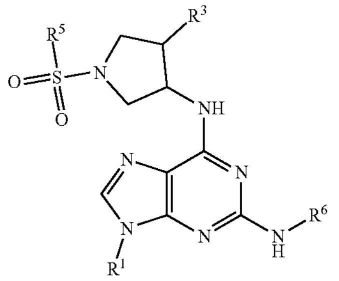
(I-9)
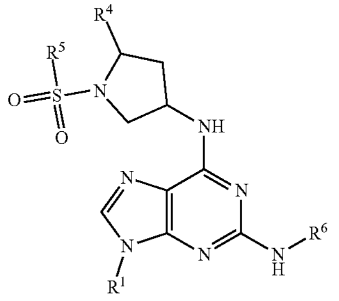
(I-10)
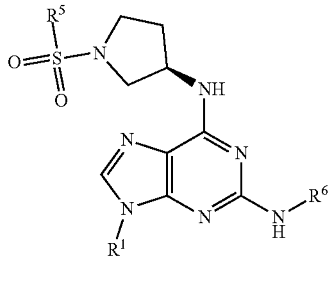
-continued
(I-11)
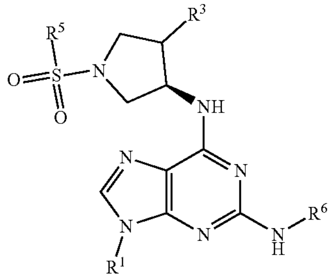
(I-12)
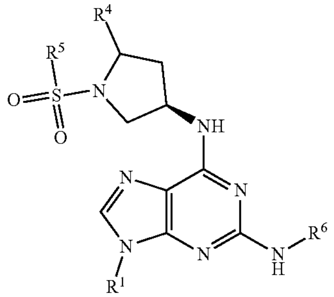
(I-13)
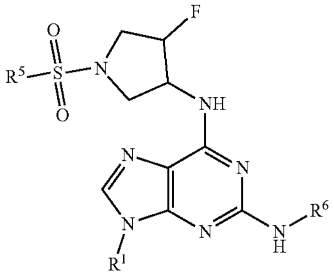
(I-14)
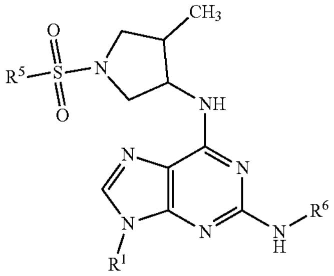
(I-15)
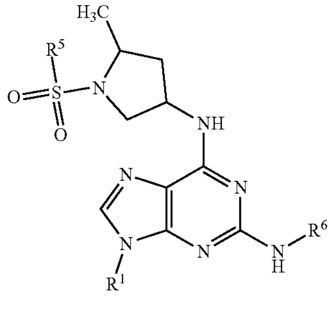

-continued
(I-16)
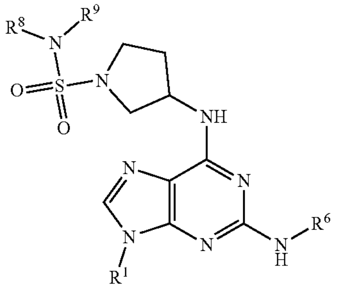
(I-17)
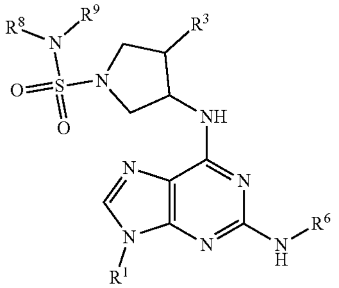
(I-18)
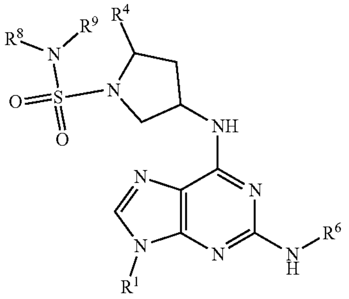
(I-19)
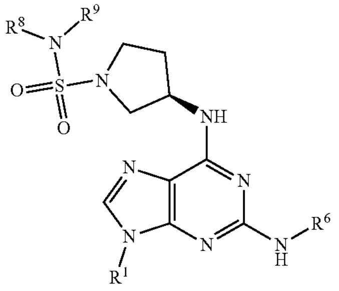
(I-20)
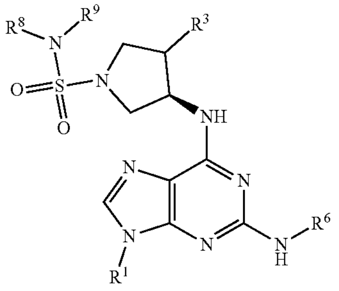
-continued
(I-21)
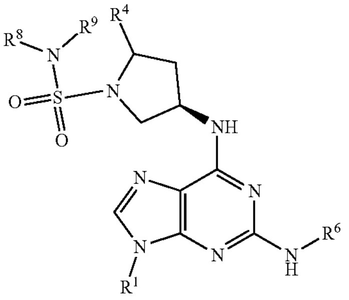
(I-22)
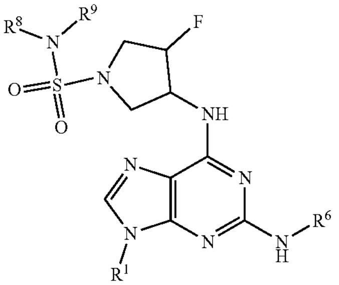
(I-23)
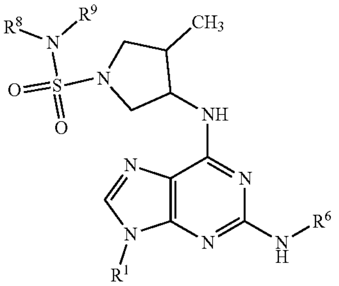
(I-24)
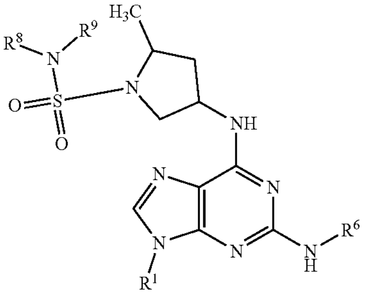
(I-25)
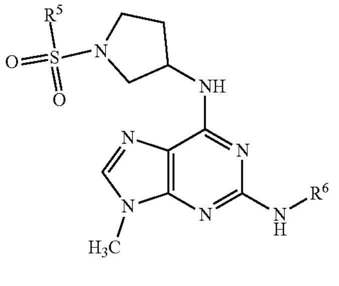

-continued
(I-26)
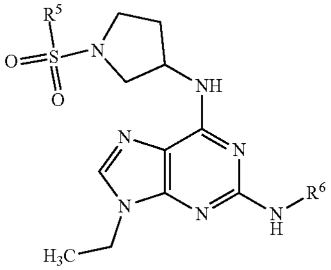
(I-27)
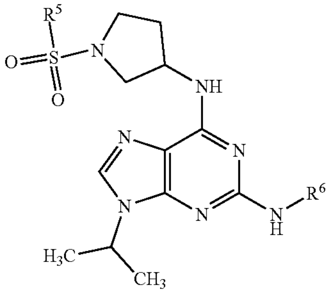
(I-28)
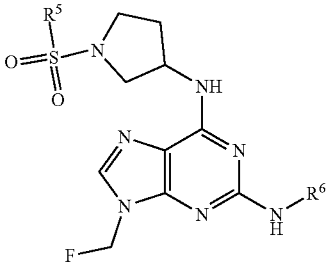
(I-29)
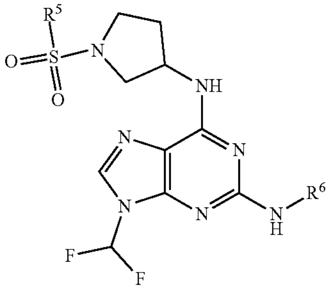
(I-30)
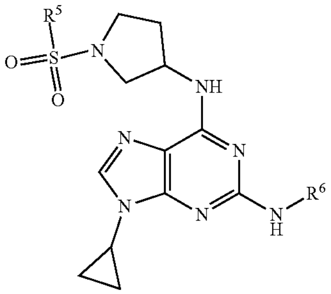
-continued
(I-31)
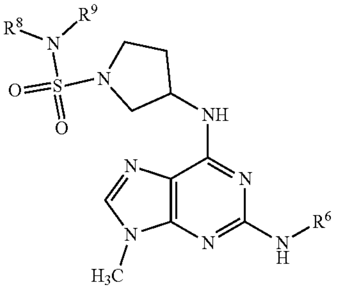
(I-32)
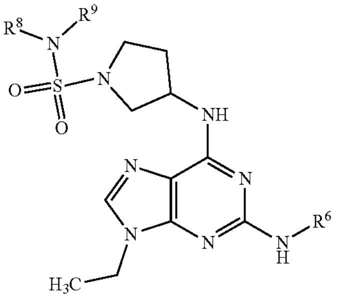
(I-33)
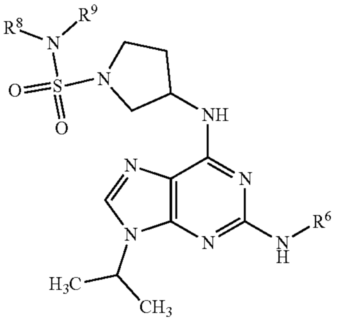
(I-34)
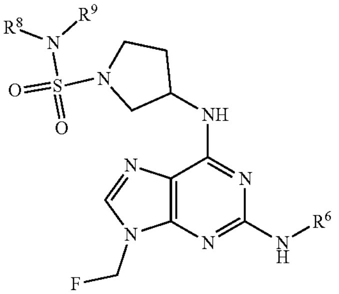
(I-35)
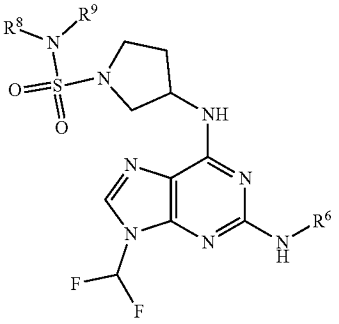

-continued
(I-36)
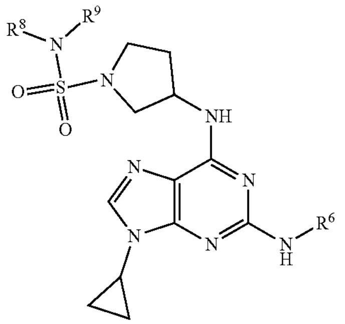
(I-37)
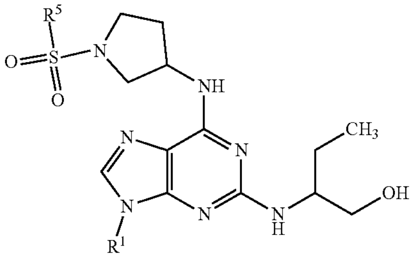
(I-38)
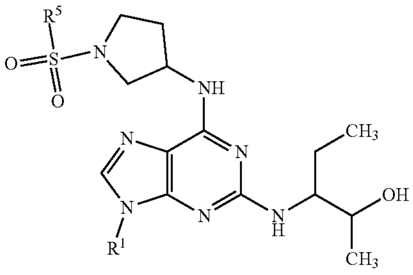
(I-39)
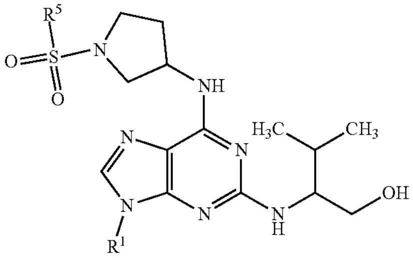
(I-40)
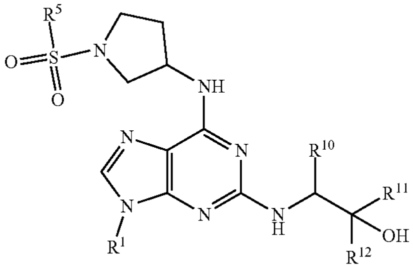
-continued
(I-41)
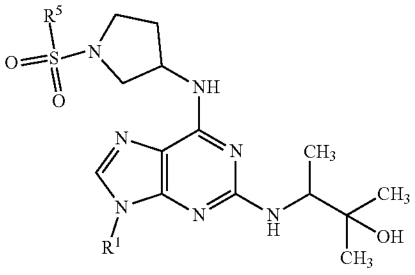
(I-42)
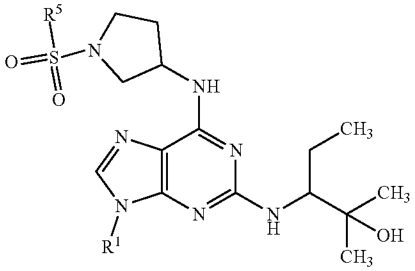
(I-43)
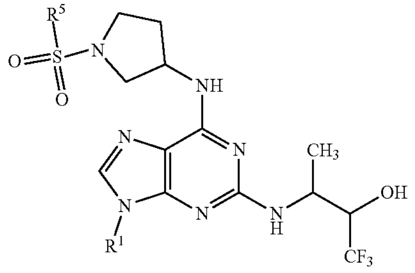
(I-44)
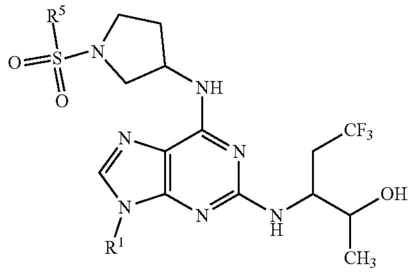
(I-45)
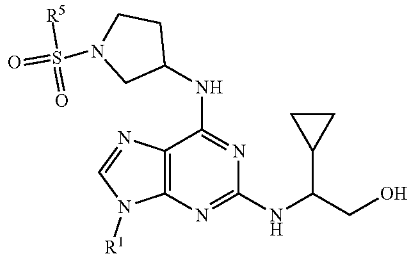
(I-46)
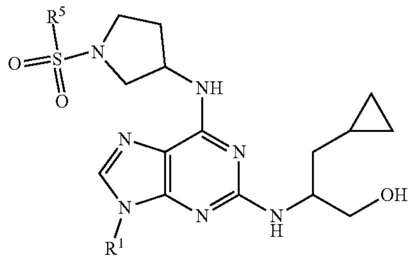

-continued
(I-47)
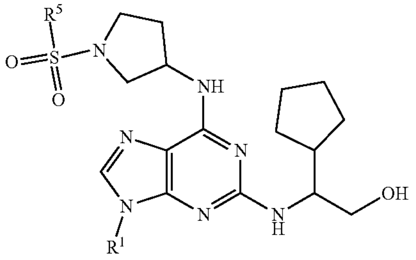
(I-48)
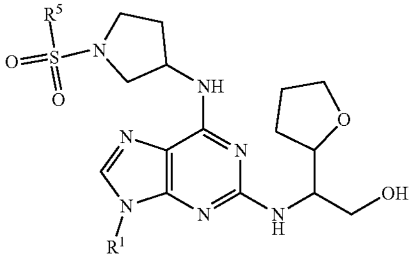
(I-49)
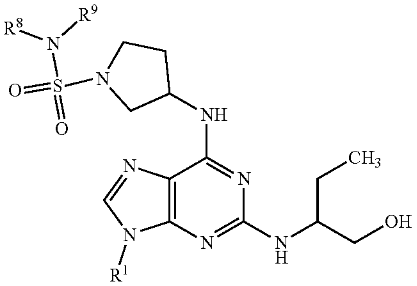
(I-50)
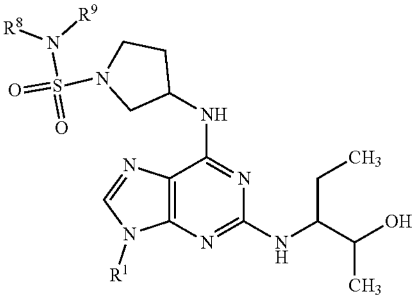
(I-51)
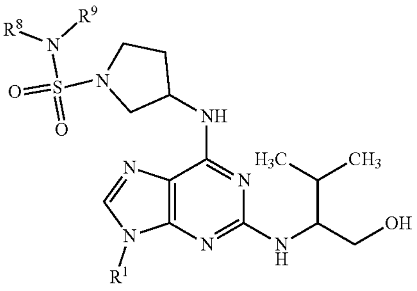
-continued
(I-52)
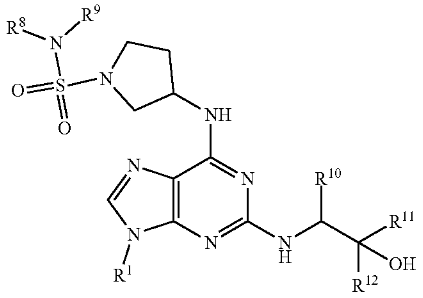
(I-53)
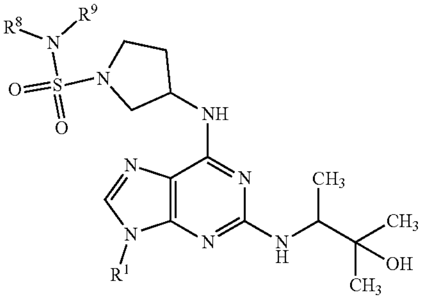
(I-54)
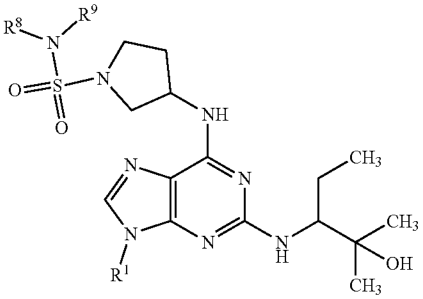
(I-55)
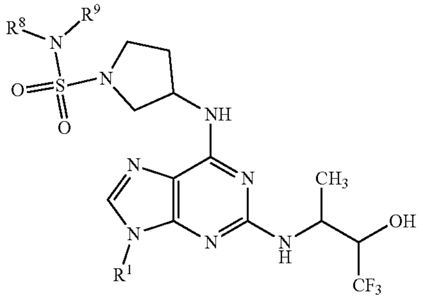
(I-56)
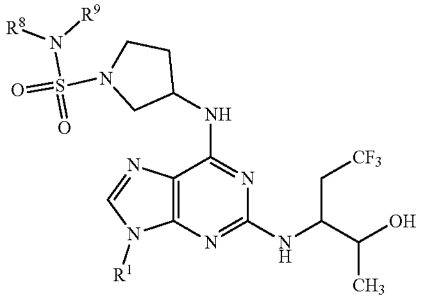

-continued
(I-57)
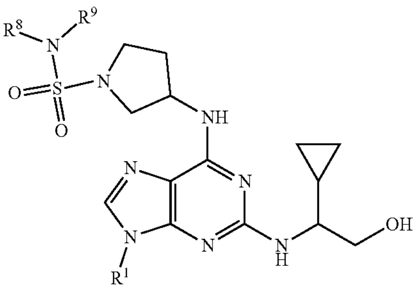
(I-58)
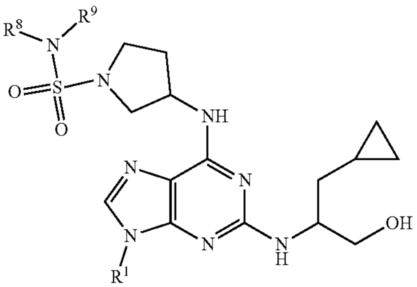
(I-59)
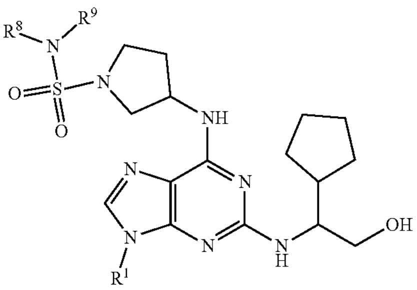
(I-60)
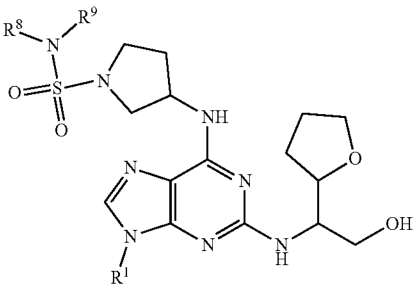
(I-61)
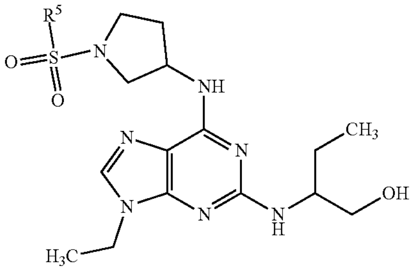
-continued
(I-62)
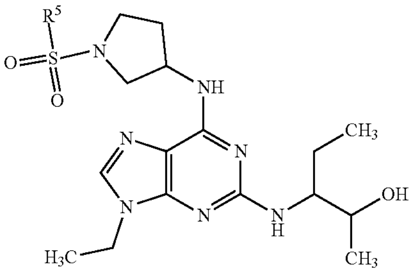
(I-63)
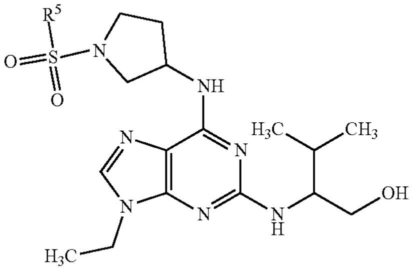
(I-64)
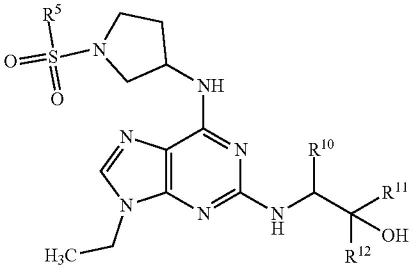
(I-65)
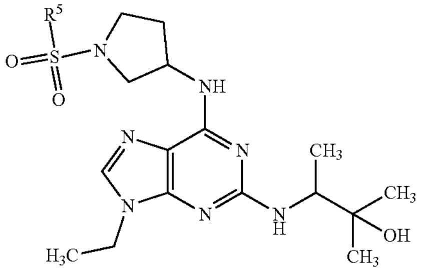
(I-66)
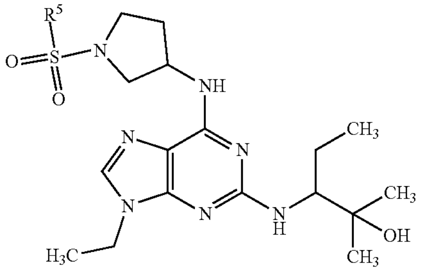

-continued
(I-67)
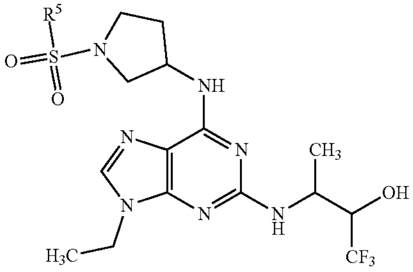
(I-68)
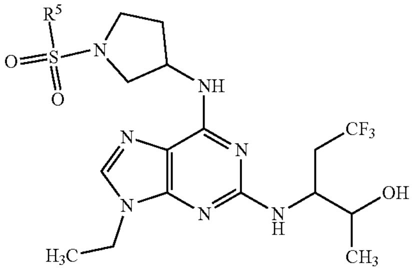
(I-69)
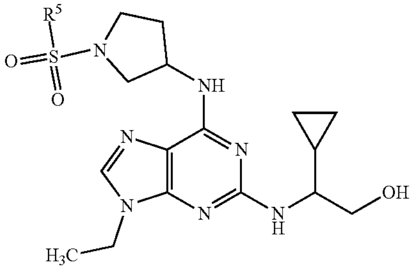
(I-70)
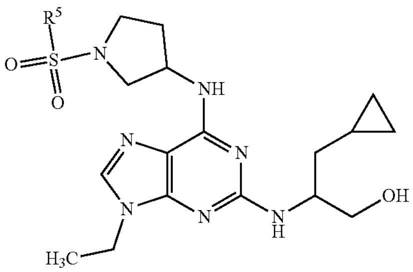
(I-71)
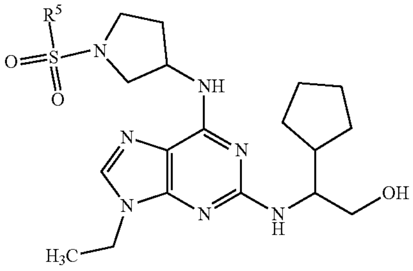
-continued
(I-72)
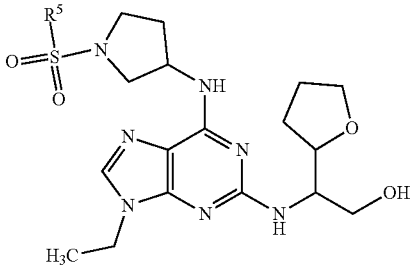
(I-73)
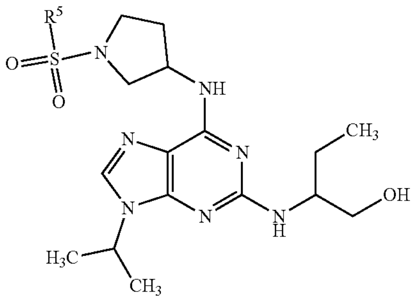
(I-74)
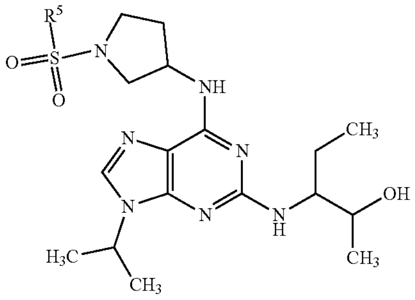
(I-75)
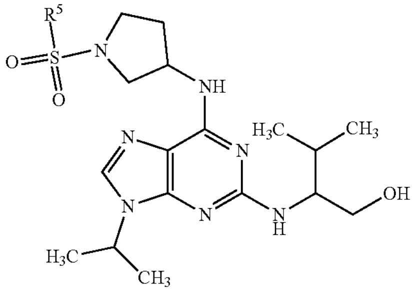
(I-76)
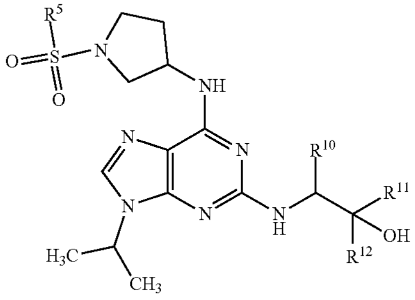

-continued
(I-77)
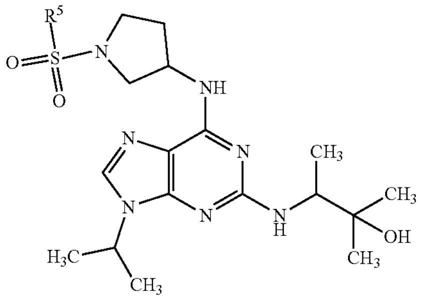
(I-78)
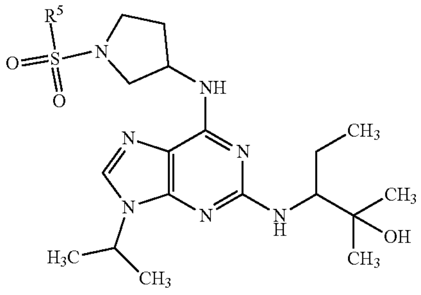
(I-79)
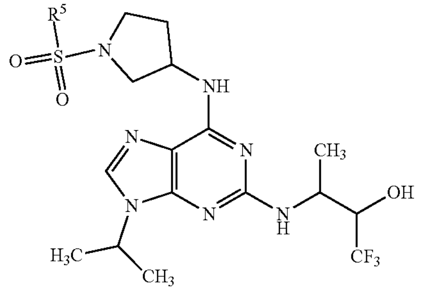
(I-80)
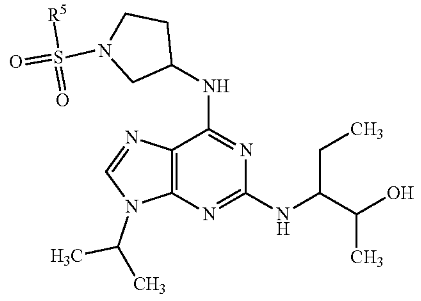
(I-81)
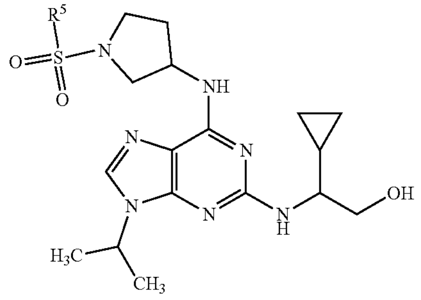
-continued
(I-82)
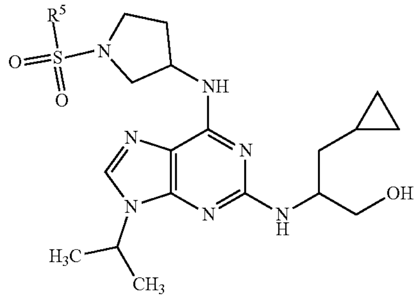
(I-83)
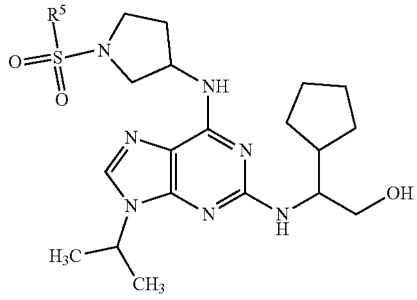
(I-84)
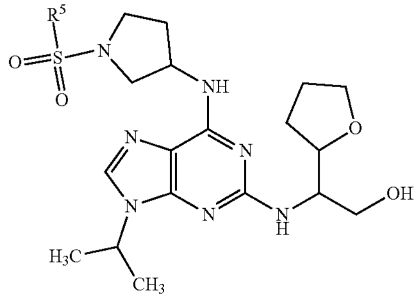
(I-85)
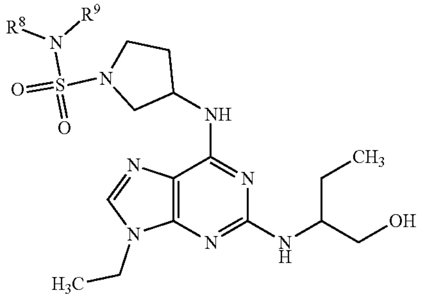
(I-86)
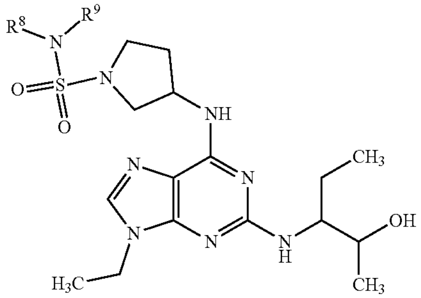

-continued
(I-87)
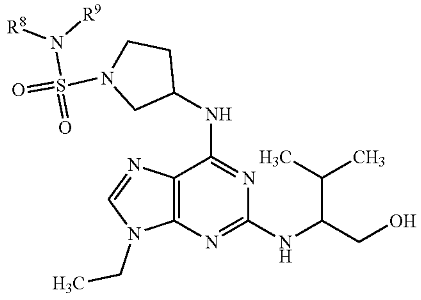
(I-88)
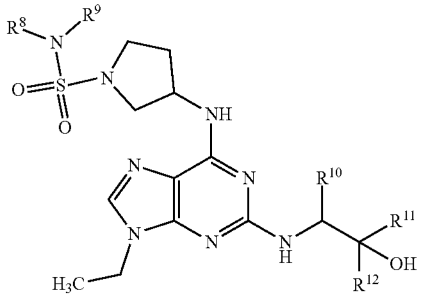
(I-89)
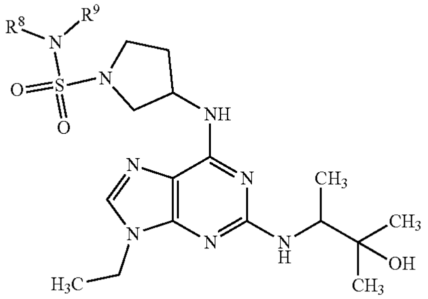
(I-90)
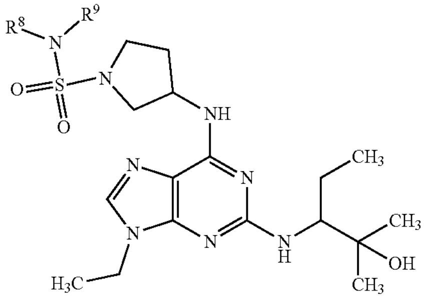
(I-91)
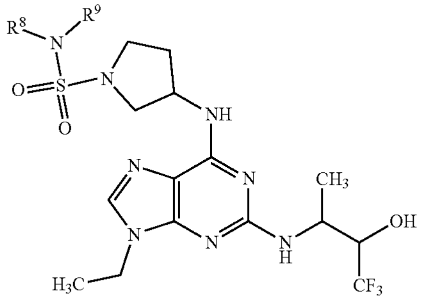
-continued
(I-92)
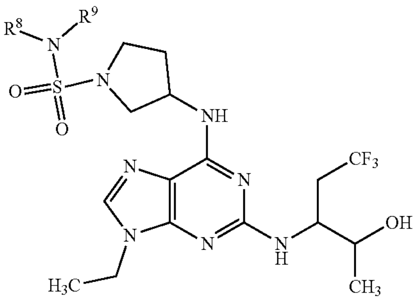
(I-93)
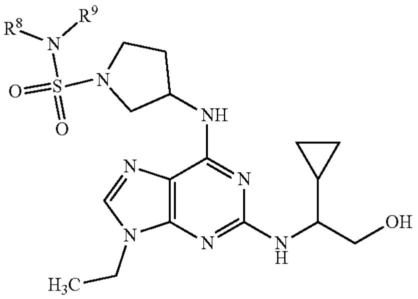
(I-94)
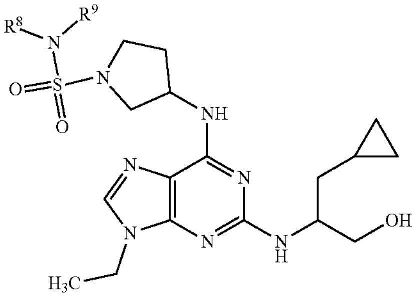
(I-95)
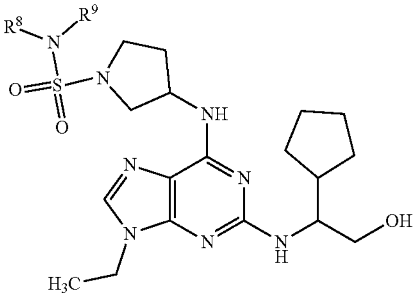
(I-96)
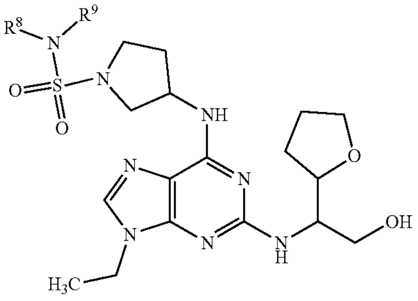

-continued
(I-97)
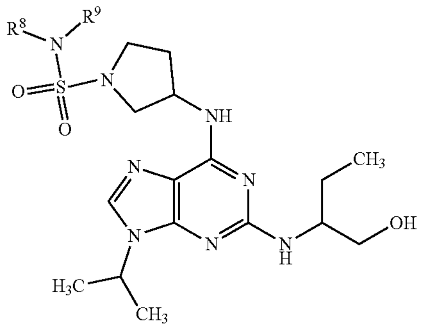
(I-98)
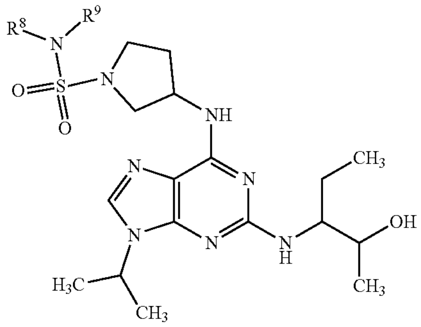
(I-99)
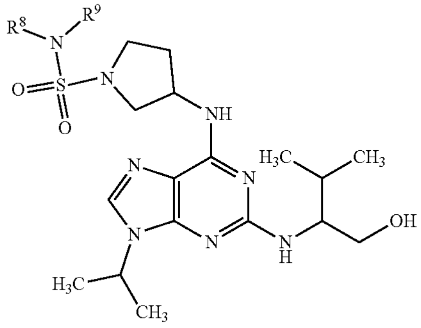
(I-100)
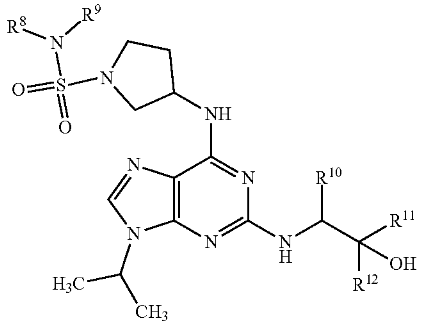
-continued
(I-101)
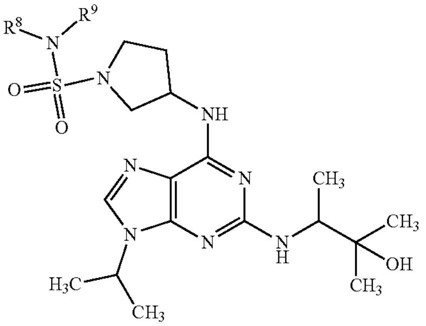
(I-102)
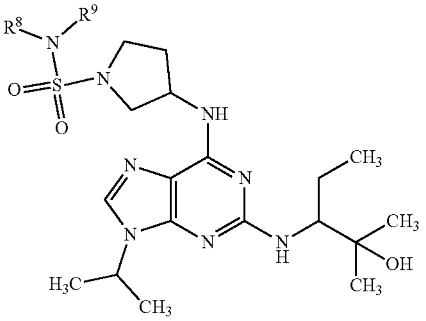
(I-103)
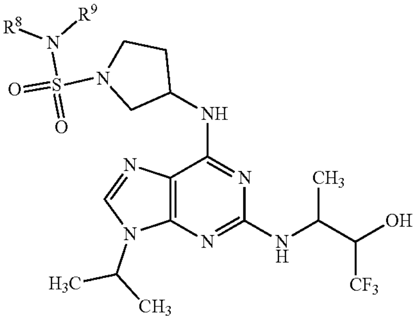
(I-104)
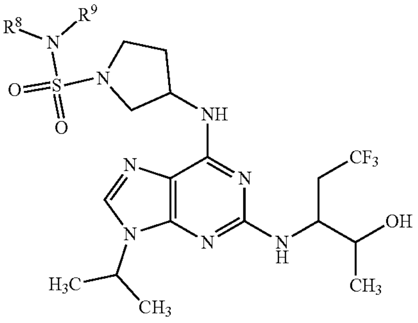
(I-105)
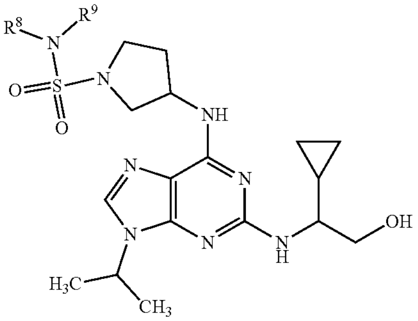

-continued
(I-106)
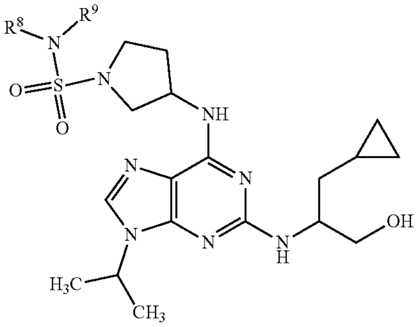
(I-107)
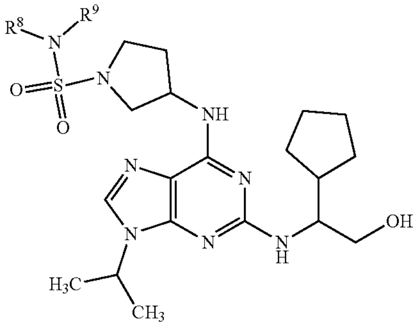
(I-108)
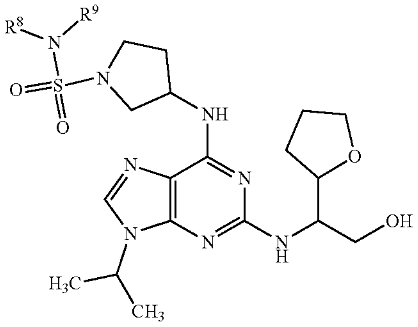
(I-109)
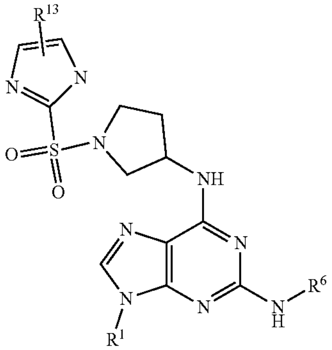
-continued
(I-110)
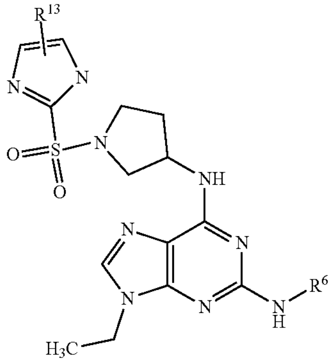
(I-111)
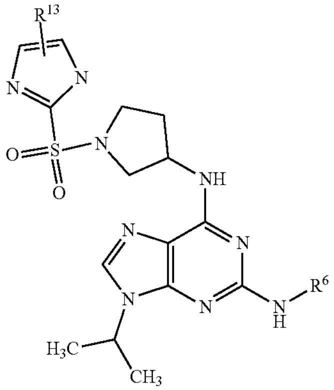
(I-112)
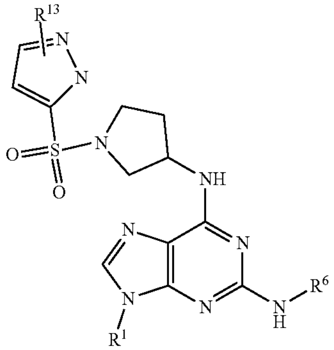
(I-113)
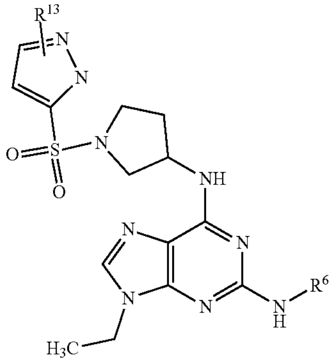

-continued (I-114)

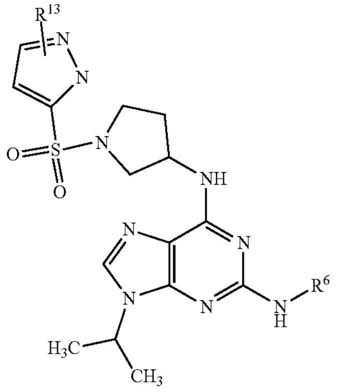

(I-115)

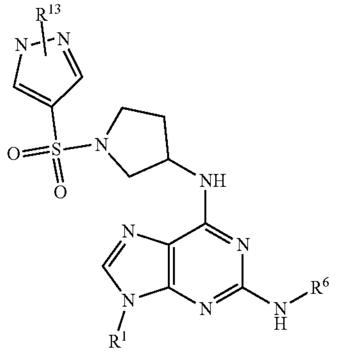

(I-116)

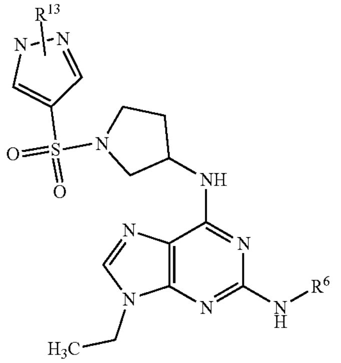

(I-117)

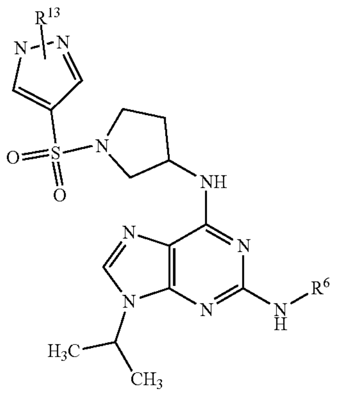

wherein, as applicable:

$R^1$ is selected from the group consisting of $C_{1-6}$-alkyl, halo-$C_{1-6}$-alkyl, and cyclopropyl;

$R^2$ is selected from the group consisting of —$NHR^6$,

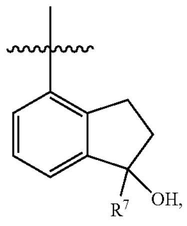

and

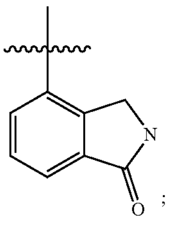

;

one of $R^3$ and $R^4$ is hydrogen and the other of $R^3$ and $R^4$ is selected from the group consisting of hydrogen, halogen, $C_{1-3}$-alkyl, halo-$C_{1-3}$-alkyl, and $C_{1-3}$-alkoxy;

$R^5$ is selected from the group consisting of $C_{1-6}$-alkyl, $C_{3-6}$-cycloalkyl, —$NR^8R^9$, pyrazolyl, and imidazolyl; wherein the $C_{1-6}$-alkyl and $C_{3-6}$-cycloalkyl are optionally substituted with one or more substituents independently selected from halogen and $C_{1-3}$-alkoxy; and the pyrazolyl and imidazolyl are optionally substituted with one or more substituents independently selected from $C_{1-3}$-alkyl;

$R^6$ is $C_{1-10}$-alkyl or

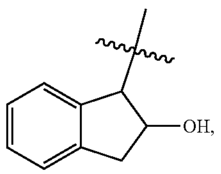 [SMILES: *C1c2ccccc2CC1O]

wherein the $C_{1-10}$-alkyl is substituted with hydroxy or oxo, and is optionally substituted with one or more substituents independently selected from the group consisting of halogen, $C_{3-6}$-cycloalkyl, and tetrahydrofuranyl;

$R^7$ is hydrogen or $C_{1-3}$-alkyl;

$R^8$ is hydrogen;

$R^9$ is selected from the group consisting of hydrogen, $C_{1-6}$-alkyl, $C_{3-6}$-cycloalkyl, $C_{1-6}$-alkoxy-$C_{1-6}$-alkyl, tetrahydrofuranyl, and 1,4-dioxanyl-$C_{1-3}$-alkyl; wherein the $C_{1-6}$-alkyl, $C_{3-6}$-cycloalkyl, $C_{1-6}$-alkoxy-$C_{1-6}$-alkyl, tetrahydrofuranyl, and 1,4-dioxanyl-$C_{1-3}$-alkyl are optionally substituted with one or more substituents independently selected from halogen; or $R^8$ and $R^9$ together with the nitrogen atom to which they are attached form a 4-, 5-, or 6-membered saturated monocyclic ring wherein the remaining ring atoms are carbon atoms, and wherein the monocyclic ring is optionally substituted with one or more substituents independently selected from halogen;

$R^{10}$ is selected from the group consisting of $C_{1-3}$-alkyl, halo-$C_{1-3}$-alkyl, $C_{3-6}$-cycloalkyl, $C_{3-6}$-cycloalkyl-$C_{1-3}$-alkyl, and tetrahydrofuranyl;

$R^{11}$ is selected from the group consisting of hydrogen and $C_{1-3}$-alkyl;

$R^{12}$ is selected from the group consisting of hydrogen, $C_{1-3}$-alkyl, and halo-$C_{1-3}$-alkyl; and $R^{13}$ is selected from the group consisting of hydrogen and $C_{1-3}$-alkyl.

14. The compound of claim 13, or a pharmaceutically acceptable salt thereof, wherein, as applicable:

$R^1$ is selected from the group consisting of $C_{1-3}$-alkyl, halo-$C_{1-3}$-alkyl, and cyclopropyl;

$R^2$ is —$NHR^6$;

$R^3$ is hydrogen and $R^4$ is selected from the group consisting of hydrogen and $C_{1-3}$-alkyl;

or $R^4$ is hydrogen and $R^3$ is selected from the group consisting of hydrogen, halogen, and $C_{1-3}$-alkyl;

$R^5$ is selected from the group consisting of $C_{1-6}$-alkyl, $C_{3-6}$-cycloalkyl, —$NR^8R^9$, pyrazolyl, and imidazolyl; wherein the $C_{1-6}$-alkyl and $C_{3-6}$-cycloalkyl are optionally substituted with one or more substituents independently selected from halogen and $C_{1-3}$-alkoxy; and the pyrazolyl and imidazolyl are optionally substituted with one or more substituents independently selected from $C_{1-3}$-alkyl;

$R^6$ is $C_{1-10}$-alkyl, wherein the $C_{1-10}$-alkyl is substituted with hydroxy, and is optionally substituted with one or more substituents independently selected from the group consisting of halogen, $C_{3-6}$-cycloalkyl, and tetrahydrofuranyl;

$R^8$ is hydrogen;

$R^9$ is selected from the group consisting of hydrogen, $C_{1-3}$-alkyl, tetrahydrofuranyl, and 1,4-dioxanyl-$C_{1-3}$-alkyl; wherein the $C_{1-3}$-alkyl, tetrahydrofuranyl, and 1,4-dioxanyl-$C_{1-3}$-alkyl are optionally substituted with one or more substituents independently selected from halogen; or or $R^8$ and $R^9$ together with the nitrogen atom to which they are attached form an azetidinyl ring, and wherein the azetidinyl ring is optionally substituted with one or more substituents independently selected from halogen;

$R^{10}$ is selected from the group consisting of $C_{1-3}$-alkyl, halo-$C_{1-3}$-alkyl, $C_{3-6}$-cycloalkyl, $C_{3-6}$-cycloalkyl-$C_{1-3}$-alkyl, and tetrahydrofuranyl;

$R^{11}$ is selected from the group consisting of hydrogen and $C_{1-3}$-alkyl;

$R^{12}$ is selected from the group consisting of hydrogen, $C_{1-3}$-alkyl, and halo-$C_{1-3}$-alkyl; and $R^{13}$ is selected from the group consisting of hydrogen and $C_{1-3}$-alkyl.

15. The compound of claim 13, or a pharmaceutically acceptable salt thereof, wherein, as applicable:

$R^1$ is selected from the group consisting of $C_{1-3}$-alkyl and fluoro-$C_{1-3}$-alkyl;

$R^2$ is —$NHR^6$;

$R^3$ is hydrogen and $R^4$ is selected from the group consisting of hydrogen and methyl; or $R^4$ is hydrogen and $R^3$ is selected from the group consisting of hydrogen, fluoro, and methyl;

$R^5$ is selected from the group consisting of $C_{1-3}$-alkyl, $C_{3-6}$-cycloalkyl, —$NR^8R^9$, pyrazolyl, and imidazolyl; wherein the $C_{1-6}$-alkyl and $C_{3-6}$-cycloalkyl are optionally substituted with one or more substituents independently selected from fluoro and methoxy; and the pyrazolyl and imidazolyl are optionally substituted with one or more methyl;

$R^6$ is $C_{2-6}$-alkyl, wherein the $C_{2-6}$-alkyl is substituted with hydroxy, and is optionally substituted with one or more substituents independently selected from the group consisting of fluoro, $C_{3-6}$-cycloalkyl, and tetrahydrofuranyl;

$R^8$ is hydrogen;

$R^9$ is selected from the group consisting of hydrogen, $C_{1-3}$-alkyl, tetrahydrofuranyl, and 1,4-dioxanylmethyl; wherein the $C_{1-3}$-alkyl, tetrahydrofuranyl, and 1,4-dioxanylmethyl are optionally substituted with one or more substituents independently selected from halogen;

$R^{10}$ is selected from the group consisting of $C_{1-3}$-alkyl, fluoro-$C_{1-3}$-alkyl, $C_{3-6}$-cycloalkyl, $C_{3-6}$-cycloalkylmethyl, and tetrahydrofuranyl;

$R^{11}$ is selected from the group consisting of hydrogen and $C_{1-3}$-alkyl;

$R^{12}$ is selected from the group consisting of hydrogen, $C_{1-3}$-alkyl, and halo-$C_{1-3}$-alkyl; and $R^{13}$ is selected from the group consisting of hydrogen and $C_{1-3}$-alkyl.

16. The compound of claim 13, or a pharmaceutically acceptable salt thereof, wherein, as applicable:

$R^1$ is selected from the group consisting of $C_{1-3}$-alkyl and fluoro-$C_{1-3}$-alkyl;

$R^2$ is —$NHR^6$;

$R^3$ is selected from the group consisting of hydrogen and fluoro;

$R^4$ is hydrogen;

$R^5$ is selected from the group consisting of $C_{1-3}$-alkyl, cyclopropyl, —$NR^8R^9$, pyrazolyl, and imidazolyl; wherein the $C_{1-6}$-alkyl and cyclopropyl are optionally substituted with one or more substituents independently selected from fluoro and methoxy; and the pyrazolyl and imidazolyl are optionally substituted with one or more methyl;

$R^6$ is $C_{2-6}$-alkyl, wherein the $C_{2-6}$-alkyl is substituted with hydroxy, and is optionally substituted with one or more substituents independently selected from the group consisting of fluoro, $C_{3-6}$-cycloalkyl, and tetrahydrofuranyl;

$R^8$ is hydrogen;

$R^9$ is selected from the group consisting of hydrogen, $C_{1-3}$-alkyl, tetrahydrofuranyl, and 1,4-dioxanylmethyl; wherein the $C_{1-3}$-alkyl, tetrahydrofuranyl, and 1,4-dioxanylmethyl are optionally substituted with one or more fluoro;

$R^{10}$ is selected from the group consisting of methyl, ethyl, fluoroethyl, cyclopropyl, cyclopropylmethyl, cyclopentyl, and tetrahydrofuranyl;

$R^{11}$ is selected from the group consisting of hydrogen and methyl; and $R^{12}$ is selected from the group consisting of hydrogen, methyl, and fluoromethyl.

17. The compound of claim 13, or a pharmaceutically acceptable salt thereof, wherein, as applicable:

$R^1$ is selected from the group consisting of methyl, ethyl, isopropyl, fluoromethyl, and difluoromethyl;

$R^2$ is —$NHR^6$;

$R^3$ and $R^4$ are hydrogen;

$R^5$ is selected from the group consisting of methyl, fluoromethyl, trifluoromethyl, methoxyethyl, cyclopropyl, —$NR^8R^9$, imidazolyl, pyrazolyl, methylimidazolyl, and methylpyrazolyl;

$R^6$ is $C_{2-6}$-alkyl, wherein the $C_{2-6}$-alkyl is substituted with hydroxy, and is optionally substituted with one or more substituents independently selected from the group consisting of fluoro, $C_{3-6}$-cycloalkyl, and tetrahydrofuranyl;

$R^8$ is hydrogen;

$R^9$ is selected from the group consisting of hydrogen, methyl, ethyl, difluoroethyl, trifluoroethyl, tetrahydrofuranyl, and 1,4-dioxanylmethyl;

$R^{10}$ is selected from the group consisting of methyl, ethyl, fluoroethyl, cyclopropyl, cyclopropylmethyl, cyclopentyl, and tetrahydrofuranyl;

$R^{11}$ is selected from the group consisting of hydrogen and methyl; and $R^{12}$ is selected from the group consisting of hydrogen, methyl, and fluoromethyl.

18. The compound of claim 1, or a pharmaceutically acceptable salt thereof, wherein the compound is selected from the group consisting of:

(S)-3-((9-ethyl-2-(1-oxoisoindolin-4-yl)-9H-purin-6-yl)amino)-N-methylpyrrolidine-1-sulfonamide;

(S)-3-((9-ethyl-2-((R)-1-hydroxy-2,3-dihydro-1H-inden-4-yl)-9H-purin-6-yl)amino)-N-methylpyrrolidine-1-sulfonamide;

(S)-3-((9-ethyl-2-((R*)-1-hydroxy-1-methyl-2,3-dihydro-H-inden-4-yl)-9H-purin-6-yl)-amino)-N-methylpyrrolidine-1-sulfonamide;

(S)-3-((9-ethyl-2-(((2R,3S)-2-hydroxypentan-3-yl)amino)-9H-purin-6-yl)amino)-N-(2,2,2-trifluoroethyl)pyrrolidine-1-sulfonamide;

(S)—N-(2,2-difluoroethyl)-3-((9-ethyl-2-(((2R,3S)-2-hydroxypentan-3-yl)amino)-9H-purin-6-yl)amino)pyrrolidine-1-sulfonamide;

(S)—N-ethyl-3-((9-ethyl-2-(((2R,3S)-2-hydroxypentan-3-yl)amino)-9H-purin-6-yl)amino)pyrrolidine-1-sulfonamide;

(S)—N-ethyl-3-((9-ethyl-2-(((S)-2-oxopentan-3-yl)amino)-9H-purin-6-yl)amino)-pyrrolidine-1-sulfonamide;

(S)—N-ethyl-3-((9-ethyl-2-(((2S,3S)-2-hydroxypentan-3-yl)amino)-9H-purin-6-yl)-amino)pyrrolidine-1-sulfonamide;

(S)-3-((9-ethyl-2-(((2R,3S)-2-hydroxypentan-3-yl)amino)-9H-purin-6-yl)amino)pyrrolidine-1-sulfonamide;

(S)-3-((9-ethyl-2-(((S)-2-oxopentan-3-yl)amino)-9H-purin-6-yl)amino)pyrrolidine-1-sulfonamide;

(S)—N-ethyl-3-((9-ethyl-2-(((2S,3R)-2-hydroxypentan-3-yl)amino)-9H-purin-6-yl)-amino)pyrrolidine-1-sulfonamide;

(S)—N-ethyl-3-((9-ethyl-2-(((R)-2-oxopentan-3-yl)amino)-9H-purin-6-yl)amino)pyrrolidine-1-sulfonamide;

(S)—N-ethyl-3-((9-ethyl-2-(((2R,3R)-2-hydroxypentan-3-yl)amino)-9H-purin-6-yl)amino)pyrrolidine-1-sulfonamide;

(S)-3-((2-(((R)-1-cyclopropyl-2-hydroxyethyl)amino)-9-(difluoromethyl)-9H-purin-6-yl)-amino)-N-ethylpyrrolidine-1-sulfonamide;

2-cyclopentyl-2-((9-isopropyl-6-(((S)-1-(methylsulfonyl)pyrrolidin-3-yl)amino)-9H-purin-2-yl)amino)ethan-1-ol;

2-((9-isopropyl-6-(((S)-1-(methylsulfonyl)pyrrolidin-3-yl)amino)-9H-purin-2-yl)amino)-2-(tetrahydrofuran-2-yl)ethan-1-ol;

(R)-2-((6-(((3R*,4R*)-1-((1H-imidazol-2-yl)sulfonyl)-4-fluoropyrrolidin-3-yl)amino)-9-ethyl-9H-purin-2-yl)amino)-2-cyclopropylethan-1-ol;

(S)-3-((2-(((R)-1-cyclopropyl-2-hydroxyethyl)amino)-9-methyl-9H-purin-6-yl)amino)-N-ethylpyrrolidine-1-sulfonamide;

(R)-2-((9-isopropyl-6-(((S)-1-(methylsulfonyl)pyrrolidin-3-yl)-amino)-9H-purin-2-yl)-amino)-3-methylbutan-1-ol;

(S)-3-((9-ethyl-2-(((3S,4R)-1,1,1-trifluoro-4-hydroxypentan-3-yl-)-amino)-9H-purin-6-yl)amino)-N-methylpyrrolidine-1-sulfonamide;

(S)-3-((9-ethyl-2-(((2R,3S)-2-hydroxypentan-3-yl)amino)-9H-purin-6-yl)amino)-N—((S)-tetrahydrofuran-3-yl)pyrrolidine-1-sulfonamide;

(S)—N—(((S)-1,4-dioxan-2-yl)methyl)-3-((9-ethyl-2-(((2R,3S)-2-hydroxypentan-3-yl)-amino)-9H-purin-6-yl)amino)pyrrolidine-1-sulfonamide;

(2R,3S)-3-((9-ethyl-6-(((S)-1-((3-fluoroazetidin-1-yl)sulfonyl)pyrrolidin-3-yl)amino)-9H-purin-2-yl)amino)pentan-2-ol;

(S)—N—(((R)-1,4-dioxan-2-yl)methyl)-3-((9-ethyl-2-(((2R,3S)-2-hydroxypentan-3-yl)-amino)-9H-purin-6-yl)amino)pyrrolidine-1-sulfonamide;

(3R*,4R*)-3-((2-(((R)-1-cyclopropyl-2-hydroxyethyl)amino)-9-methyl-9H-purin-6-yl)-amino)-N-ethyl-4-fluoropyrrolidine-1-sulfonamide;

(R)-2-(6-((S)-1-(cyclopropylsulfonyl)pyrrolidin-3-yl)amino)-9-isopropyl-9H-purin-2-ylamino)-3-methylbutan-1-ol;

(R)-2-(9-ethyl-6-((S)-1-(methylsulfonyl)pyrrolidin-3-yl)amino)-9H-purin-2-yl)amino)-3-methylbutan-1-ol;

(R)-2-(9-cyclopropyl-6-(((S)-1-(methylsulfonyl)pyrrolidin-3-yl-amino)-9H-purin-2-yl)amino)-3-methylbutan-1-ol;

(R)-2-cyclopropyl-2-((9-isopropyl-6-(((S)-1-(methylsulfonyl)-pyrrolidin-3-yl)amino)-9H-purin-2-yl)amino)ethanol;

(2R,3S)-3-((9-isopropyl-6-(((S)-1-(1-methyl-1H-pyrazol-4-yl-sulfonyl)pyrrolidin-3-yl)amino)-9H-purin-2-yl)amino)pentan-2-ol;

(2R,3S)-3-((9-isopropyl-6-(((S)-1-(1-methyl-1H-imidazol-4-yl-sulfonyl)pyrrolidin-3-yl)amino)-9H-purin-2-yl)amino)pentan-2-ol;

(R)-2-((6-(((3R,4R)-4-fluoro-1-(methylsulfonyl)pyrrolidin-3-yl)amino)-9-isopropyl-9H-purin-2-yl)amino)-3-methylbutan-1-ol;

(R)-2-((9-isopropyl-6-(((3S,5R)-5-methyl-1-(methylsulfonyl)-pyrrolidin-3-yl)amino)-9H-purin-2-yl)amino)-3-methylbutan-1-ol;

(R)-2-((9-isopropyl-6-(((3S,5S)-5-methyl-1-(methylsulfonyl)-pyrrolidin-3-yl)amino)-9H-purin-2-yl)amino)-3-methylbutan-1-ol;

(R)-2-((9-isopropyl-6-(((3S,4R)-4-methyl-1-(methylsulfonyl)-pyrrolidin-3-yl)amino)-9H-purin-2-yl)amino)-3-methylbutan-1-ol;

(2R,3S)-3-((9-isopropyl-6-(((3S,5R)-5-methyl-1-(methylsulfonyl)-pyrrolidin-3-yl)amino)-9H-purin-2-yl)amino)pentan-2-ol;

(R)-2-((9-ethyl-6-(((S)-1-(methylsulfonyl)pyrrolidin-3-yl)amino)-9H-purin-2-yl)amino)butan-1-ol;

(R)-2-cyclopropyl-2-((9-ethyl-6-(((S)-1-(methylsulfonyl)pyrrolidin-3-yl)amino)-9H-purin-2-yl)amino)ethanol;

(R)-2-((9-ethyl-6-(((S)-1-(2,2,2-trifluoroethylsulfonyl)pyrrolidin-3-yl)amino)-9H-purin-2-yl)amino)-3-methylbutan-1-ol;

(R)-2-((6-(((S)-1-(cyclopropylsulfonyl)pyrrolidin-3-yl)amino)-9-ethyl-9H-purin-2-yl)amino)-3-methylbutan-1-ol;

(R)-2-((9-ethyl-6-(((S)-1-((2-methoxyethyl)sulfonyl)pyrrolidin-3-yl)amino)-9H-purin-2-yl)amino)-3-methylbutan-1-ol;

(R)-2-((9-ethyl-6-(((S)-1-(fluoromethylsulfonyl)pyrrolidin-3-yl)amino)-9H-purin-2-yl)amino)-3-methylbutan-1-ol;

(S)-3-((9-ethyl-2-(((2R,3S)-2-hydroxypentan-3-yl)amino)-9H-purin-6-yl)amino)-N-methylpyrrolidine-1-sulfonamide;

(S)-3-((9-ethyl-2-(((S)-2-oxopentan-3-yl)amino)-9H-purin-6-yl)amino)-N-methylpyrrolidine-1-sulfonamide;

(S)-3-((9-ethyl-2-(((S)-2-hydroxy-2-methylpentan-3-yl)amino)-9H-purin-6-yl)amino)-N-methylpyrrolidine-1-sulfonamide;

(S)-3-((9-ethyl-2-(((S)-2-hydroxy-2-methylpentan-3-yl)amino)-9H-purin-6-yl)amino)-N-methylpyrrolidine-1-sulfonamide;

(S)-3-((9-ethyl-2-(((S)-1-hydroxybutan-2-yl)amino)-9H-purin-6-yl)amino)-N-methylpyrrolidine-1-sulfonamide;

(S)-3-((9-ethyl-2-(((2R*,3S*)-4,4,4-trifluoro-3-hydroxybutan-2-yl)amino)-9H-purin-6-yl)amino)-N-methylpyrrolidine-1-sulfonamide;

(S)-3-((9-ethyl-2-(((1R,2S)-2-hydroxy-2,3-dihydro-1H-inden-1-yl)amino)-9H-purin-6-yl)amino)-N-methylpyrrolidine-1-sulfonamide;

(3R*,4R*)-3-((9-ethyl-2-(((2R,3S)-2-hydroxypentan-3-yl)amino)-9H-purin-6-yl)amino)-4-fluoro-N-methylpyrrolidine-1-sulfonamide;

(S)—N-ethyl-3-((2-(((2R,3S)-2-hydroxypentan-3-yl)amino)-9-methyl-9H-purin-6-yl)amino)pyrrolidine-1-sulfonamide;

(S)-3-((9-(fluoromethyl)-2-(((2R,3S)-2-hydroxypentan-3-yl)amino)-9H-purin-6-yl)amino)-N-methylpyrrolidine-1-sulfonamide;

(S)-3-((9-(difluoromethyl)-2-(((2R,3S)-2-hydroxypentan-3-yl)amino)-9H-purin-6-yl)amino)-N-methylpyrrolidine-1-sulfonamide;

(2R,3S)-3-((6-(((3R*,4R*)-1-((1H-imidazol-2-yl)sulfonyl)-4-fluoropyrrolidin-3-yl)-amino)-9-methyl-9H-purin-2-yl)amino)pentan-2-ol;

(2R,3S)-3-((6-(((3R*,4R*)-1-((1H-imidazol-2-yl)sulfonyl)-4-fluoropyrrolidin-3-yl)-amino)-9-(difluoromethyl)-9H-purin-2-yl)amino)-1,1,1-trifluorobutan-2-ol;

(S)-3-((2-(((R*)-1-cyclopropyl-3-hydroxypropan-2-yl)amino)-9-ethyl-9H-purin-6-yl)-amino)-N-ethylpyrrolidine-1-sulfonamide;

(S)—N-ethyl-3-((9-ethyl-2-(((R*)-3-hydroxy-3-methylbutan-2-yl)-amino)-9H-purin-6-yl)amino)pyrrolidine-1-sulfonamide;

(R)-2-((6-(((3R*,4R*)-1-((1H-imidazol-2-yl)sulfonyl)-4-fluoro-pyrrolidin-3-yl)amino)-9-(difluoromethyl)-9H-purin-2-yl)amino)-2-cyclopropylethan-1-ol; and (2R,3S)-3-((6-(((S)-1-((1H-pyrazol-5-yl)sulfonyl)pyrrolidin-3-yl)amino)-9-ethyl-9H-purin-2-yl)amino)pentan-2-ol.

19. A pharmaceutical composition comprising a compound of claim 2, or a pharmaceutically acceptable salt thereof, and one or more pharmaceutically acceptable excipients.

20. A method of treating cancer in a subject suffering from or susceptible to the cancer, the method comprising administering to the subject a therapeutically effective amount of a compound of claim 2, or a pharmaceutically acceptable salt thereof wherein the cancer is selected from the group consisting of breast cancer, ovarian cancer, endometrial cancer, cervical cancer, uterine cancer, gastric cancer, prostate cancer, bladder cancer, lung cancer, esophageal cancer, head and neck cancer, kidney cancer, liver cancer, pancreatic cancer, thyroid cancer, colorectal cancer, and skin cancer.

21. The method of claim 20, wherein the method further comprises administering to the subject a therapeutically effective amount of a CDK4/6 inhibitor.

* * * * *